(12) United States Patent
Wang et al.

(10) Patent No.: US 7,807,676 B2
(45) Date of Patent: *Oct. 5, 2010

(54) DIKETO-PIPERAZINE AND PIPERIDINE DERIVATIVES AS ANTIVIRAL AGENTS

(75) Inventors: Tao Wang, Farmington, CT (US); John F. Kadow, Wallingford, CT (US); Zhongxing Zhang, Madison, CT (US); Zhiwei Yin, Glastonbury, CT (US); Nicholas A. Meanwell, East Hampton, CT (US); Alicia Regueiro-Ren, Middletown, CT (US); Jacob Swidorski, Southington, CT (US); Ying Han, Cheshire, CT (US); David J. Carini, Wallingford, CT (US); Lawrence G. Hamann, North Grafton, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 189 days.

This patent is subject to a terminal disclaimer.

(21) Appl. No.: 11/877,001

(22) Filed: Oct. 23, 2007

(65) Prior Publication Data

US 2008/0139572 A1 Jun. 12, 2008

Related U.S. Application Data

(63) Continuation-in-part of application No. 11/733,283, filed on Apr. 10, 2007.

(60) Provisional application No. 60/794,700, filed on Apr. 25, 2006, provisional application No. 60/794,703, filed on Apr. 25, 2006.

(51) Int. Cl.
*A61K 31/437* (2006.01)
*A61K 31/501* (2006.01)
*A61K 31/506* (2006.01)
*C07D 471/04* (2006.01)

(52) U.S. Cl. ............... 514/252.02; 514/252.18; 514/253.04; 544/238; 544/296; 544/362

(58) Field of Classification Search ............. None
See application file for complete search history.

(56) References Cited

U.S. PATENT DOCUMENTS

| | | | |
|---|---|---|---|
| 3,135,794 A | 6/1964 | Archer | |
| 4,791,104 A | 12/1988 | Picciola et al. | |
| 5,023,265 A | 6/1991 | Scherlock et al. | |
| 5,124,327 A | 6/1992 | Greenlee et al. | |
| 5,192,770 A | 3/1993 | Clark et al. | |
| 5,413,999 A | 5/1995 | Vacca et al. | |
| 5,424,329 A | 6/1995 | Boschelli et al. | |
| 5,811,432 A | 9/1998 | Marfat et al. | |
| 6,008,231 A | 12/1999 | Lebaut et al. | |
| 6,172,085 B1 | 1/2001 | Ohkawa et al. | |
| 6,232,327 B1 | 5/2001 | Nickel et al. | |
| 6,469,006 B1 | 10/2002 | Blair et al. | |
| 6,476,034 B2 | 11/2002 | Wang et al. | |
| 6,573,262 B2 | 6/2003 | Wallace et al. | |
| 6,632,819 B1 | 10/2003 | Wang et al. | |
| 6,825,201 B2 | 11/2004 | Wang et al. | |
| 6,900,206 B2 | 5/2005 | Kadow et al. | |
| 7,037,913 B2 | 5/2006 | Wang et al. | |
| 7,087,610 B2 | 8/2006 | Wang et al. | |
| 7,504,399 B2 * | 3/2009 | Wang et al. ............ | 514/253.04 |
| 7,572,810 B2 * | 8/2009 | Wang et al. ............ | 514/314 |
| 2002/0061892 A1 | 5/2002 | Wang et al. | |
| 2003/0069266 A1 | 4/2003 | Wang et al. | |
| 2003/0207910 A1 | 11/2003 | Wang et al. | |
| 2003/0236277 A1 | 12/2003 | Kadow et al. | |
| 2004/0063744 A1 | 4/2004 | Wang et al. | |
| 2004/0063746 A1 | 4/2004 | Regueiro-Ren et al. | |
| 2004/0110785 A1 | 6/2004 | Wang et al. | |
| 2004/0186292 A1 | 9/2004 | Wang et al. | |
| 2005/0075364 A1 | 4/2005 | Yeung et al. | |
| 2005/0090522 A1 | 4/2005 | Wang et al. | |
| 2005/0124623 A1 | 6/2005 | Bender et al. | |
| 2005/0209246 A1 | 9/2005 | Ueda et al. | |
| 2005/0215543 A1 | 9/2005 | Lin et al. | |
| 2005/0215544 A1 | 9/2005 | Lin et al. | |
| 2005/0215545 A1 | 9/2005 | Lin et al. | |
| 2005/0267130 A1 | 12/2005 | Ruediger et al. | |
| 2006/0100209 A1 | 5/2006 | Gu et al. | |

(Continued)

FOREIGN PATENT DOCUMENTS

EP 0379314 A1 7/1990

(Continued)

OTHER PUBLICATIONS

Heimbach, et al, "Absorption Rate Limit Considerations for Oral Phosphate Prodrugs," Pharmaceutical Research, 20(6), pp. 848-856, 2003.

(Continued)

*Primary Examiner*—Emily Bernhardt
(74) *Attorney, Agent, or Firm*—John F. Levis

(57) ABSTRACT

This disclosure provides compounds having drug and bio-affecting properties, their pharmaceutical compositions and method of use. In particular, the disclosure is concerned with diketo piperazine and piperadine derivatives that possess unique antiviral activity. More particularly, the present disclosure relates to compounds useful for the treatment of HIV and AIDS.

22 Claims, No Drawings

U.S. PATENT DOCUMENTS

| | | | |
|---|---|---|---|
| 2006/0100432 | A1 | 5/2006 | Matiskella et al. |
| 2006/0142298 | A1 | 6/2006 | Kadow et al. |
| 2007/0078141 | A1 | 4/2007 | Wang et al. |
| 2007/0249579 | A1 | 10/2007 | Wang et al. |
| 2007/0249624 | A1 | 10/2007 | Bachand et al. |

FOREIGN PATENT DOCUMENTS

| | | | |
|---|---|---|---|
| EP | 0484071 | A2 | 5/1992 |
| EP | 0530907 | A1 | 3/1993 |
| EP | 1069111 | A1 | 1/2001 |
| WO | WO 93/01181 | | 1/1993 |
| WO | WO 95/04742 | | 2/1995 |
| WO | WO 96/11929 | | 4/1996 |
| WO | WO 97/24350 | | 7/1997 |
| WO | WO 98/28292 | | 7/1998 |
| WO | WO 99/24065 | | 5/1999 |
| WO | WO 9967237 | | 12/1999 |
| WO | WO 00/00201 | | 1/2000 |
| WO | WO 00/12074 | | 3/2000 |
| WO | WO 00/51984 | | 9/2000 |
| WO | WO 00/71535 | | 11/2000 |
| WO | WO 00/76521 | A1 | 12/2000 |
| WO | WO 01/62255 | | 8/2001 |
| WO | WO 02/04440 | | 1/2002 |
| WO | WO 02/10152 | A2 | 2/2002 |
| WO | WO 02/62423 | | 8/2002 |
| WO | WO 02/085301 | A2 | 10/2002 |
| WO | WO 03/041644 | | 5/2003 |
| WO | WO 03/068221 | A1 | 8/2003 |
| WO | WO 03/082881 | A | 10/2003 |
| WO | WO 03/092695 | | 11/2003 |
| WO | WO 03/000210 | A2 | 12/2003 |
| WO | WO 03/103607 | | 12/2003 |
| WO | WO 2004/011425 | A2 | 2/2004 |
| WO | WO 2004/043337 | A2 | 5/2004 |
| WO | WO 2005/016344 | | 2/2005 |
| WO | WO 2005/121094 | | 12/2005 |

OTHER PUBLICATIONS

Stella, et al, Pharmacokinetics of Drug Targeting: Specific Implications for Targeting Via Prodrugs, Handbook of Experimental Pharmacology, Chapter 4, pp. 71-103, 1991.

Zhu, et al, "A One-Pot Synthesis of Nitrogen-Containing Heteroaryl α-Keto Amides from Heteroaryl Halides," Tetrahedron Letters, 46(20), pp. 3587-3589, 2005.

Yin, et al., "Simulated PXRD Patterns in Studies of the Phase Composition and Thermal Behavior of Bulk Crystalline Solids," American Pharmaceutical Review, 2003, 6, 2, pp. 80-85.

Hotoda, "Small-Molecule Inhibitors of HIV-1 Entry Via Chemokine Receptors," Drugs of the Future, 24(12), pp. 1355-1362, 1999.

Sodroski, "HIV-1 Entry Inhibitors in the Side Pocket," Cell, 9, pp. 243-246, 1999.

Blair, et al, "HIV-1 Entry-An Expanding Portal for Drug Discovery," Drug Discovery Today, 5(5), pp. 183-194, 2000.

Font, et al, "Indoles and Pyridazinol[4,5-b]lndoles as Nonnucleoside Analog Inhibitors of HIV-1 Reverse Transcriptase," Eur. J. Med. Chem., 30, pp. 963-971, 1995.

Romero, et al, J. Med. Chem., 36, pp. 1505-1508, 1993.

Young, et al, "2-Heterocyclic Indole-3-Sulfones as Inhibitors of HIV-1 Reverse Transcriptase," Bioorg. Med. Chem. Lett., 5(5), pp. 491-496, 1995.

Genin, et al, "Synthesis and Bioactivity of Novel Bis(Heteroaryl)Piperazine (BHAP) Reverse Transcriptase Inhibitors: Structure-Activity Relationships and Increased Metabolic Stability of Novel Substituted Pyridine Analogs," J. Med. Chem., 39, pp. 5267-5275, 1996.

Silvestri, et al, Antiviral Chem. Chemother., 9, pp. 139-148, 1998.

Fredenhagen, et al, "Semicochliodinol A and B: Inhibitors of HIV-1 Protease and EGF-R Protein Tyrosine Kinase Related to Asterriquinones Produced by the Fungus Chrysosporium Merdarium," J. Of Antibiotics, 50, pp. 395-401, 1997.

Wang, et al., Org. Biol. Chem., 2005, 3, pp. 1781-1786.

Meanwell et al., Current Opinion in Drug Discovery and Development, 2003, 6, 4, pp. 451-461.

Dueweke, et al, "The Binding of a Novel Bisheteroarylpiperazine Mediates Inhibition of Human Immunodeficiency Virus Type 1 Reverse Transcriptase," J. Biol. Chem., 267(1), pp. 27-30, 1992.

Dueweke, et al, "U-90152, a Potent Inhibitor of Human Immunodeficiency Virus Type 1 Replication," Antimicrob. Agent, Chemother., 37(5), pp. 1127-1131, 1993.

Kato, et al, "New 5-HT$_3$ (Serotonin-3) Receptor Antagonists. IV. Synthesis and Structure-Activity Relationships of Azabicycloalkaneacetamide Derivatives," Chem. Pharm. Bull., 43(8), pp. 1351-1357, 1995.

Levacher, et al, "Broadening in the Scope of NADH Models by Using Chiral and Non Chiral Pyrrolo [2,3-b]Pyridine Derivatives," Tetrahedron, 47(3), pp. 429-440, 1991.

Resnyanskaya, et al, "A Simple Synthesis of 1-Acyl-3-Aryl-3H-Pyrrolo[2',3':4,5]Pyrimido[6,1-b]Benzothiazol-6-ium-2-olates: Betainic Derivates of a Novel Heterocyclic System," Synthesis, 18, pp. 2717-2724, 2002.

* cited by examiner

DIKETO-PIPERAZINE AND PIPERIDINE DERIVATIVES AS ANTIVIRAL AGENTS

RELATED APPLICATIONS

This application is a continuation-in-part of pending U.S. patent application Ser. No. 11/733,283 filed Apr. 10, 2007 which claims priority to U.S. provisional application Ser. No. 60/794,700 filed on Apr. 25, 2006 and to U.S. provisional application Ser. No. 60/794,703 filed on Apr. 25, 2006.

FIELD OF THE DISCLOSURE

This disclosure provides compounds having drug and bio-affecting properties, their pharmaceutical compositions and method of use.

In particular, the disclosure is concerned with diketo piperazine and piperidine derivatives that possess unique antiviral activity. More particularly, the present disclosure relates to compounds useful for the treatment of HIV and AIDS.

BACKGROUND ART

HIV-1 (human immunodeficiency virus-1) infection remains a major medical problem, with an estimated 40 million people infected worldwide at the end of 2005. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), emtricitabine (or FTC), Combivir® (contains –3TC plus AZT), Trizivir® (contains abacavir, lamivudine, and zidovudine), Epzicom® (contains abacavir and lamivudine), Truvada® (contains Viread® and emtricitabine); non-nucleoside reverse transcriptase inhibitors: nevirapine (or Viramune®), delavirdine (or Rescriptor®) and efavirenz (or Sustiva®), and peptidomimetic protease inhibitors or approved formulations: saquinavir, indinavir, ritonavir, nelfinavir, amprenavir, lopinavir, and Kaletra® (lopinavir and Ritonavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents currently being studied by a number of investigators.

The properties of a class of HIV entry inhibitors called HIV attachment inhibitors has been improved in an effort to obtain compounds with maximized utility and efficacy as antiviral agents. A disclosure describing indoles of which the structure shown below for BMS-705 is representative has been disclosed [Antiviral Indoleoxoacetyl Piperazine Derivatives].

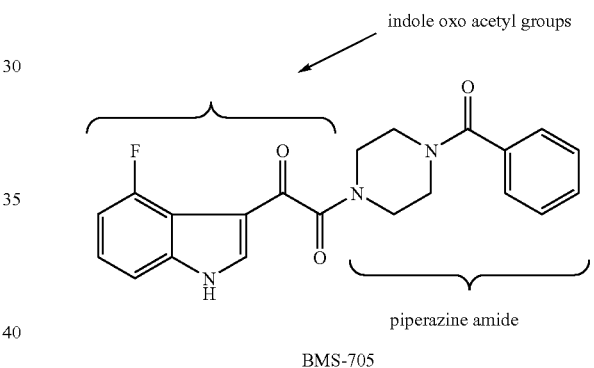

BMS-705

Two other compounds, referred to in the literature as BMS-806 and BMS-043 have been described in both the academic and patent art:

BMS-806

BMS-043

Some description of their properties in human clinical trials have been disclosed in literature.

It should be noted that in all three of these structures, a piperazine amide (In these three structures a piperazine phenyl amide) is present and this group is directly attached to an oxoacetyl moiety. The oxoacetyl group is attached at the 3-position of 4-Fluoro indole in BMS-705 and to the 3 position of substituted azaindoles in BMS-806 and BMS-043.

In an effort to obtain improved anti-HIV compounds, later publications described in part, modified substitution patterns on the indoles and azaindoles. Examples of such effort include: (1) novel substituted indoleoxoacetic piperazine derivatives, (2) substituted piperazinyloxoacetylindole derivatives, and (3) substituted azaindoleoxoacetic piperazine derivatives.

Replacement of these groups with other heteroaromatics or substituted heteroaromatics or bicyclic hydrocarbons was also shown to be feasible. Examples include: (1) indole, azaindole and related heterocyclic amidopiperazine derivatives; (2) bicyclo 4.4.0 antiviral derivatives; and (3) diazaindole derivatives.

A select few replacements for the piperazine amide portion of the molecules have also been described in the art and among these examples are (1) some piperidine alkenes; (2) some pyrrolidine amides; (3) some N-aryl or heteroaryl piperazines; (4) some piperazinyl ureas; and (5) some carboline containing compounds.

Method(s) for preparing prodrugs for this class of compounds was disclosed in Prodrugs of piperazine and Substituted Piperidine Antiviral Agents (Ueda et al., U.S. non-provisional application Ser. No. 11/066,745, filed Feb. 25, 2005 or US20050209246A1 or WO2005090367A1).

A published PCT patent application WO2003103607A1 (Jun. 11, 2003) disclosures an assay useful for assaying some HIV inhibitors.

Several published patent applications describe combination studies with piperazine benzamide inhibitors, for example, US20050215543 (WO2005102328A1), US20050215544 (WO2005102391A1), and US20050215545 (WO2005102392A2).

A publication on new compounds in this class of attachment inhibitors (Jinsong Wang et. al. Org. Biol. Chem. 2005, 3, 1781-1786.) and a patent application on some more remotely related compounds have appeared WO2005/016344 published on Feb. 24, 2005.

Published patent applications WO2005/016344 and WO2005/121094 also describe piperazine derivatives which are HIV inhibitors. The compounds described in these applications are structurally distinct from the compounds of the present disclosure.

Nothing in these references can be construed to disclose or suggest the novel compounds of this disclosure and their use to inhibit HIV infection.

SUMMARY OF THE DISCLOSURE

The present disclosure relates to compounds of Formula I, the pharmaceutically acceptable salts and/or solvates (e.g., hydrates) thereof, their pharmaceutical formulations, and their use in patients suffering from or susceptible to a virus such as HIV. The compounds of Formula I, their pharmaceutically acceptable salts and/or solvate are effective antiviral agents, particularly as inhibitors of HIV. They are useful for the treatment of HIV and AIDS.

One embodiment of the present disclosure is directed to a compound of Formula I, or pharmaceutically acceptable salts thereof,

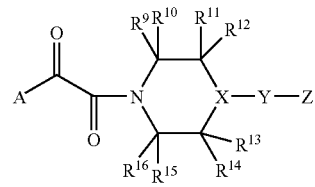

wherein:

A is selected from the group consisting of:

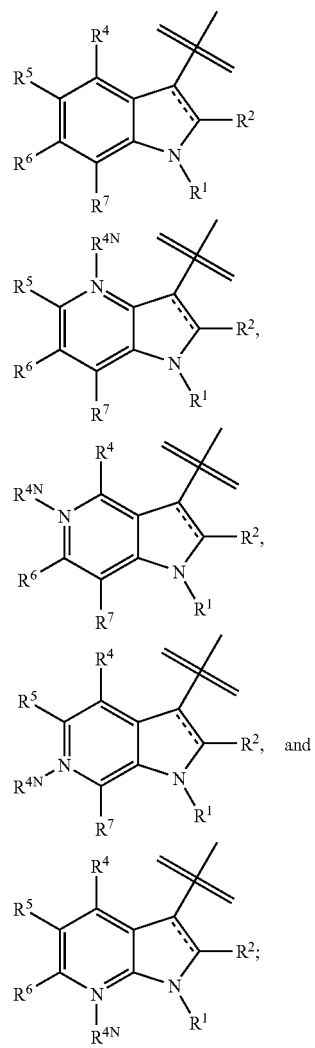

wherein

- - represents a carbon-carbon bond or does not exist;

$R^1$ is hydrogen, $C_1$-$C_4$ alkyl, or $C_1$-$C_4$ fluoroalkyl;

$R^2$ is hydrogen;

$R^4$, $R^5$, $R^6$ and $R^7$ are each independently selected from the group consisting of hydrogen, hydroxy, halogen, cyano, nitro, $C_1$-$C_4$ alkyl, $C_1$-$C_4$ fluoroalkyl, $OR_a$, $NR_aR_b$, $COOR_a$, and Group B;

$R_a$ and $R_b$ are each independently selected from the group consisting of hydrogen, $C_1$-$C_4$ alkyl, and Group B;

$R^{4N}$ is O or does not exist;

Y is selected from the group consisting of phenyl, $C_5$-$C_7$ monocyclic heteroaryl, $C_9$-$C_{10}$ bicyclic aryl, $C_9$-$C_{10}$ bicyclic heteroaryl, $C_4$-$C_7$ heteroalicyclic, and $C_5$-$C_7$ cycloalkyl wherein said heteroaryl or heteroalicyclic contains from 1 to 4 heteroatoms selected from O, N, and S and with the proviso when Y is a bicyclic heteroaryl both X and Y are attached to a common ring wherein said aryl, heteroaryl, and heteroalicyclic are optionally substituted with one to three same or different halogens or from one to three same or different substituents selected from oxo, hydroxyl, $C_1$-$C_6$ alkyl, —$NR^{55}R^{56}$, —$OC_1$-$C_3$ alkyl, —S—$R_1$, —$S(O)_2R_1$, $CF_3$, CN, wherein said $C_1$-$C_6$ alkyl can be optionally substituted with Group B;

Z is selected from the group consisting of $C_{1-6}$ alkyl, $C_{1-6}$ alkoxy, $C_{3-7}$ cycloalkyl, —$COOR_3$, 4, 5, or 6 membered ring cyclic N-lactam, —$C(O)NR^{42}R^{43}$, —$C(O)R^{57}$ wherein $R^{57}$ is optionally substituted with CN or Group B; —$NR^{55}R^{56}$, aryl and heteroaryl; in which said aryl is phenyl; said heteroaryl is selected from the group consisting of pyridinyl, pyrimidinyl, pyrazinyl, furanyl, thienyl, pyrrolyl, imidazolyl, thiazolyl, isothiazolyl, oxazolyl, isoxazolyl and $C_9$-$C_{10}$ bicyclic heteroaryl with 1-4 heteroatom(s); said aryl or heteroaryl is optionally substituted with one or two of the same or different members selected from the group consisting of amino, nitro, cyano, hydroxy, $C_{1-6}$ alkoxy, —$C(O)NH_2$, $C_{1-6}$ alkyl, —$NHC(O)CH_3$, halogen, trifluoromethyl and Group B;

Group B is selected from the group consisting of —$C(O)NR^{40}R^{41}$, aryl, heteroaryl, heteroalicyclic, $C(O)R^3$, $C(=N-O-R^1)R^3$, acetal, $UR^{8a}$, $(C_{1-6})$alkyl$NR^{40}R^{41}$, $(C_{1-6})$alkyl$COOR^{8b}$; wherein said aryl, heteroaryl, and heteroalicyclic are optionally substituted with one to three same or different halogens or from one to three same or different substituents selected from the group F; wherein aryl is napthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may be partially unsaturated and may be substituted by 1 or two oxo groups and may contain from 1 to 2 heteroatoms in the ring skeleton and which may be fused to a benzene or pyridine ring;

or Group B is $(C_{1-6})$alkyl and $(C_{2-6})$alkenyl; wherein said $(C_{1-6})$alkyl and $(C_{2-6})$alkenyl are independently optionally substituted with a member selected from the group consisting of phenyl, heteroaryl or —$C(O)NR^{55}R^{56}$; or with from one to three same or different halogens; wherein heteroaryl is a monocyclic system which contains from 3 to 7 ring atoms, including from 1 to 4 heteroatoms;

Group F is selected from the group consisting of oxo, $(C_{1-6})$alkyl, $(C_{3-7})$cycloalkyl, aryl, heteroaryl, heteroalicyclic, hydroxy, $(C_{1-6})$alkoxy, aryloxy, $(C_{1-6})$thioalkoxy, cyano, halogen, nitro, —$C(O)R^{57}$, benzyl, —$NR^{42}C(O)$—$(C_{1-6})$alkyl, —$NR^{42}C(O)$—$(C_{3-6})$cycloalkyl, —$NR^{42}C(O)$-aryl, —$NR^{42}C(O)$-heteroaryl, —$NR^{42}C(O)$-heteroalicyclic, a 4, 5, or 6 membered ring cyclic N-lactam, —$NR^{42}S(O)_2$—$(C_{1-6})$alkyl, —$NR^{42}S(O)_2$—$(C_{3-6})$cycloalkyl, —$NR^{42}S(O)_2$-aryl, —$NR^{42}S(O)_2$-heteroaryl, —$NR^{42}S(O)_2$-heteroalicyclic, $S(O)_2(C_{1-6})$alkyl, $S(O)_2$aryl, —$S(O)_2$ $NR^{42}R^{43}$, $NR^{42}R^{43}$, $(C_{1-6})$alkyl$C(O)NR^{42}R^{43}$, $C(O)NR^{42}R^{43}$, NHC(O)$NR^{42}R^{43}$, OC(O)$NR^{42}R^{43}$, NHC(O)$OR^{54}$, $(C_{1-6})$alkyl$NR^{42}R^{43}$, $COOR^{54}$, and $(C_{1-6})$alkyl$COOR^{54}$; wherein said $(C_{1-6})$alkyl, $(C_{3-7})$cycloalkyl, aryl, heteroaryl, heteroalicyclic, $(C_{1-6})$alkoxy, and aryloxy, are optionally substituted with one to nine same or different halogens or from one to five same or different substituents selected from the Group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

Group G is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, cyano, halogen, nitro, —$C(O)R^{57}$, benzyl, non-aromatic heterocyclic with 1-2 hetero atoms, —$NR^{48}C(O)$—$(C_{1-6})$alkyl, —$NR^{48}C(O)$—$(C_{3-6})$cycloalkyl, —$NR^{48}C(O)$-aryl, —$NR^{48}C(O)$-heteroaryl, —$NR^{48}C(O)$-heteroalicyclic, a 4, 5, or 6 membered ring cyclic N-lactam, —$NR^{48}S(O)_2$—$(C_{1-6})$alkyl, —$NR^{48}S(O)_2$, —$(C_{3-6})$cycloalkyl, —$NR^{48}S(O)_2$-aryl, —$NR^{43}S(O)_2$-heteroaryl, —$NR^{48}S(O)_2$-heteroalicyclic, sulfinyl, sulfonyl, sulfonamide, $NR^{48}R^{49}$, $(C_{1-6})$alkyl $C(O)NR^{48}R^{49}$, $C(O)NR^{48}R^{49}$, NHC(O)$NR^{48}R^{49}$, OC(O)$NR^{48}R^{49}$, NHC(O)$OR^{54'}$, $(C_{1-6})$alkyl$NR^{48}R^{49}$, $COOR^{54}$, and $(C_{1-6})$alkyl$COOR^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

$R^3$ is selected from the group consisting of $C_1$-$C_4$ alkyl, aryl, heteroaryl, and heteroalicyclic; wherein said $C_1$-$C_4$ alkyl, aryl, heteroaryl, and heteroalicyclic are optionally substituted with one to three same or different halogens or with from one to three same or different substituents selected from the group F;

wherein for $R^3$, $R^8$, $R^{8a}$, $R^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

$R^8$ is selected from the group consisting of hydrogen, $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic; wherein said $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic are optionally substituted with one to six same or different halogens or from one to five same or different substituents selected from the group F;

$R^{8a}$ is a member selected from the group consisting of aryl, heteroaryl, and heteroalicyclic; wherein each member is independently optionally substituted with one to six same or different halogens or from one to five same or different substituents selected from the group F;

$R^{8b}$ is selected from the group consisting of hydrogen, $(C_{1-6})$alkyl and phenyl;

$R^9$, $R^{10}$, $R^{11}$, $R^{12}$, $R^{13}$, $R^{14}$, $R^{15}$, $R^{16}$, are each independently selected from the group consisting of hydrogen and $(C_{1-6})$alkyl; wherein said $(C_{1-6})$alkyl is optionally substituted with one to three same or different halogens or one hydroxy or one O $(C_{1-6})$alkyl or one $NR^{55}R^{56}$; or one of $R^9$, $R^{10}$ or one of $R^{11}$, $R^{12}$ may form respectively with one of $R^{15}$, $R^{16}$ or one of $R^{13}$, $R^{14}$ a one, two or three atom bridged comprised of alkyl or nitrogen atoms;

X is N or CH, (when X is CH the configuration at the center X may be racemic or pure (R) or pure (S) configuration);

U is selected from the group consisting of NH or $NCH_3$, O, and S;

$R^{40}$ and $R^{41}$ are independently selected from the group consisting of (a) hydrogen; (b) $(C_{1-6})$alkyl substituted with one to three same or different halogens (c) $(C_{1-6})$alkoxy, aryl, heteroaryl or heteroalicyclic; or $R^{40}$ and $R^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to two same or different substituents selected from $C_1$-$C_3$alkyl, halogen, hydroxyl, —$OR^{55}$, —$NR^{55}R^{56}$; —$C(O)NR^{55}R^{56}$; wherein for $R^{40}$ and $R^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

$R^{42}$ and $R^{43}$ are independently selected from the group consisting of hydrogen, $(C_{1-6})$alkyl, allyl, $(C_{1-6})$alkoxy, $(C_{3-7})$ cycloalkyl, aryl, heteroaryl and heteroalicyclic; or $R^{42}$ and $R^{43}$ taken together with the nitrogen to which they are attached form a member selected from the group consisting of aziridine, azetidine, pyrrolidine, piperazine (optionally substituted with Group B), 4-NMe piperazine, piperidine, azepine, and morpholine; and wherein said $(C_{1-6})$alkyl, $(C_{1-6})$alkoxy, $(C_{3-7})$cycloalkyl, aryl, heteroaryl, and heteroalicyclic are optionally substituted with one to three same or different halogens or from one to two same or different substituents selected from the Group G; wherein for $R^{42}$ and $R^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

$R^{46}$ is selected from the group consisting of H, $OR^{57}$, and $NR^{55}R^{56}$;

$R^{47}$ is selected from the group consisting of H, amino, halogen, phenyl, and $(C_{1-6})$alkyl;

$R^{48}$ and $R^{49}$ are independently selected from the group consisting of hydrogen, $(C_{1-6})$alkyl and phenyl;

$R^{50}$ is selected from the group consisting of H, $(C_{1-6})$alkyl, $(C_{3-6})$cycloalkyl, and benzyl; wherein each of said $(C_{1-6})$ alkyl, $(C_{3-7})$cycloalkyl and benzyl are optionally substituted with one to three same or different halogen, amino, OH, CN or $NO_2$;

$R^{54}$ is selected from the group consisting of hydrogen and $(C_{1-6})$alkyl;

$R^{54'}$ is $(C_{1-6})$alkyl;

$R^{55}$ and $R^{56}$ are independently selected from the group consisting of hydrogen and $(C_{1-6})$alkyl; and $R^{57}$ is selected from the group consisting of hydrogen, $(C_{1-6})$ alkyl and phenyl; and with the proviso that the compound of Formula (I) is not

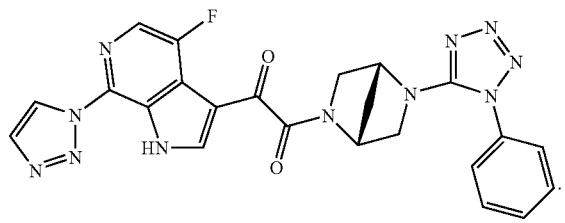

In a preferred embodiment, $R^1$ is H.
In a preferred embodiment, $R^5$ is H.
In a preferred embodiment, $R^{4N}$ does not exist.
In a preferred embodiment, $R^4$ is halogen or $OR^a$.
In a preferred embodiment, $R^9$, $R^{10}$, $R^{11}$, $R^{12}$, $R^{13}$, $R^{14}$, $R^{15}$, $R^{16}$ are each independently selected from the group consisting of hydrogen, $C_1$-$C_4$ alkyl and $C_1$-$C_4$ fluoroalkyl.

In a preferred embodiment, A is

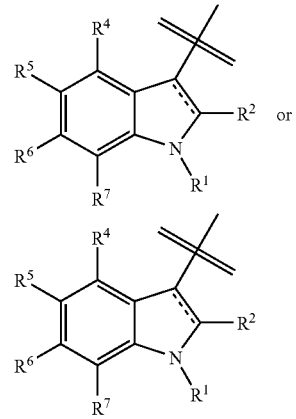

In a preferred embodiment, Y is phenyl.
In a preferred embodiment, Y is $C_5$-$C_7$ monocyclic heteroaryl.
In a preferred embodiment, Y is $C_9$-$C_{10}$ bicyclic aryl.
In a preferred embodiment, Y is $C_9$-$C_{10}$ bicyclic heteroaryl.
In a preferred embodiment, Y is $C_4$-$C_7$ heteroalicyclic.
In a preferred embodiment, Y is $C_5$-$C_7$ cycloalkyl.
In a preferred embodiment, Y is tetrazole, triazole, pyrazole, imidazole, pyridine, pyrazine, pyrimidine, or pyridazine.

Another embodiment of the present disclosure is a method for treating mammals infected with a virus, especially wherein said virus is HIV, comprising administering to said mammal an antiviral effective amount of a compound of Formula I, and one or more pharmaceutically acceptable carriers, excipients or diluents. Optionally, the compound of Formula I can be administered in combination with an antiviral effective amount of an AIDS treatment agent selected from the group consisting of: (a) an AIDS antiviral agent; (b) an anti-infective agent; (c) an immunomodulator; and (d) HIV entry inhibitors.

Another embodiment of the present disclosure is a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE DISCLOSURE

Since the compounds of the present disclosure, may possess asymmetric centers and therefore occur as mixtures of diastereomers and enantiomers, the present disclosure includes the individual diastereoisomeric and enantiomeric forms of the compounds of Formula I in addition to the mixtures thereof.

DEFINITIONS

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompliash systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $Z_3CC(=O)$— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS(=O)_2$— groups with Z as defined above.

A "trihalomethanesulfonamido" group refers to a $Z_3CS(=O)_2NR^x$— group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —$S(=O)_2$R" group with R" being $(C_{1-6})$alkyl.

A "S-sulfonamido" group refers to a —$S(=O)_2NR^XR^Y$, with $R^X$ and $R^Y$ independently being H or $(C_{1-6})$alkyl.

A "N-Sulfonamido" group refers to a R"$S(=O)_2NR_X$— group, with $R_x$ being H or $(C_{1-6})$alkyl.

A "O-carbamyl" group refers to a —OC(=O)$NR^xR^y$ group, with $R^X$ and $R^Y$ independently being H or $(C_{1-6})$alkyl.

A "N-carbamyl" group refers to a $R^xOC(=O)NR^y$ group, with $R^x$ and $R^y$ independently being H or $(C_{1-6})$alkyl.

A "O-thiocarbamyl" group refers to a —OC(=S)$NR^xR^y$ group, with $R^x$ and $R^y$ independently being H or $(C_{1-6})$alkyl.

A "N-thiocarbamyl" group refers to a $R^xOC(=S)NR^y$— group, with $R^x$ and $R^y$ independently being H or $(C_{1-6})$alkyl.

An "amino" group refers to an —$NH_2$ group.

A "C-amido" group refers to a —C(=O)$NR^xR^y$ group, with $R^x$ and $R^y$ independently being H or $(C_{1-6})$alkyl.

A "C-thioamido" group refers to a —C(=S)$NR^xR^y$ group, with $R^x$ and $R^y$ independently being H or $(C_{1-6})$alkyl.

A "N-amido" group refers to a $R^xC(=O)NR^y$— group, with $R^x$ and $R^y$ independently being H or $(C_{1-6})$alkyl.

An "ureido" group refers to a —$NR^xC(=O)NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "guanyl" group refers to a $R^xR^yNC(=N)$— group, with $R^x$ and $R^y$ independently being H or $(C_{1-6})$alkyl.

A "cyano" group refers to a —CN group.

A "silyl" group refers to a —$Si(R")_3$, with R" being $(C_{1-6})$alkyl or phenyl.

A "phosphonyl" group refers to a $P(=O)(OR^x)_2$ with $R^x$ being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

A "4, 5, or 6 membered ring cyclic N-lactam" group refers to

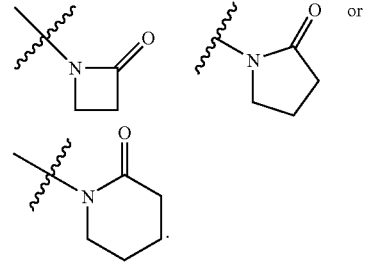

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Physiologically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris (hydroxymethyl)-aminomethane), or with bases such as piperidine or morpholine.

In the method of the present disclosure, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present disclosure is also directed to combinations of the compounds with one or more agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |

-continued

| Drug Name | Manufacturer | Indication |
| --- | --- | --- |
| ddC<br>Dideoxycytidine | Hoffman-La Roche | HIV infection, AIDS, ARC |
| ddI<br>Dideoxyinosine | Bristol-Myers Squibb | HIV infection, AIDS, ARC; combination with AZT/d4T |
| DMP-450 | AVID<br>(Camden, NJ) | HIV infection, AIDS, ARC<br>(protease inhibitor) |
| Efavirenz<br>(DMP 266, Sustiva ®)<br>(-)6-Chloro-4-(S)-<br>cyclopropylethynyl-<br>4(S)-trifluoro-<br>methyl-1,4-dihydro-<br>2H-3,1-benzoxazin-<br>2-one, STOCRINE | Bristol Myers Squibb | HIV infection, AIDS, ARC<br>(non-nucleoside RT inhibitor) |
| EL10 | Elan Corp, PLC<br>(Gainesville, GA) | HIV infection |
| Famciclovir | Smith Kline | herpes zoster, herpes simplex |
| FTC | Emory University | HIV infection, AIDS, ARC<br>(reverse transcriptase inhibitor) |
| GS 840 | Gilead | HIV infection, AIDS, ARC<br>(reverse transcriptase inhibitor) |
| HBY097 | Hoechst Marion Roussel | HIV infection, AIDS, ARC<br>(non-nucleoside reverse transcriptase inhibitor) |
| Hypericin | VIMRx Pharm. | HIV infection, AIDS, ARC |
| Recombinant Human Interferon Beta | Triton Biosciences<br>(Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC<br>(reverse transcriptase inhibitor); also with AZT |
| Lobucavir | Bristol-Myers Squibb | CMV infection |
| Nelfinavir | Agouron Pharmaceuticals | HIV infection, AIDS, ARC<br>(protease inhibitor) |
| Nevirapine | Boeheringer Ingleheim | HIV infection, AIDS, ARC<br>(RT inhibitor) |
| Novapren | Novaferon Labs, Inc.<br>(Akron, OH) | HIV inhibitor |
| Peptide T<br>Octapeptide<br>Sequence | Peninsula Labs<br>(Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC<br>(protease inhibitor) |
| Probucol | Vyrex | HIV infection, AIDS |
| RBC-CD4 | Sheffield Med.<br>Tech (Houston, TX) | HIV infection, AIDS, ARC |
| Ritonavir | Abbott | HIV infection, AIDS, ARC<br>(protease inhibitor) |

-continued

| Drug Name | Manufacturer | Indication |
|---|---|---|
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Emtriva ® (Emtricitabine) | Gilead | HIV infection, AIDS, (reverse transcriptase inhibitor) |
| Combivir ® | GSK | HIV infection, AIDS, (reverse transcriptase inhibitor) |
| Abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (or T-20) | Roche/Trimeris | HIV infection AIDs, viral Fusion inhibitor |
| Lexiva ® (or Fosamprenavir calcium) | GSK/Vertex | HIV infection AIDs, viral protease inhibitor |
| Maraviroc; (UK 427857) | Pfizer | HIV infection AIDs, (CCR5 antagonist, in development) |
| Trizivir ® | GSK | HIV infection AIDs, (three drug combination) |
| PA-457 | Panacos | HIV infection AIDs, (maturation Inhibitor, in development) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| BMS-707035 | Bristol-Myers Squibb | HIV infection AIDs, (viral integrase Inhibitor) |
| Integrase Inhibitor MK-0518 | Merck | HIV infection AIDs, viral integrase inhibitor in development |
| Truvada ® | Gilead | Combination of Tenofovir disoproxil fumarate salt (Viread ®) and Emtriva ® (Emtricitabine) |
| Integrase Inhibitor GS917/JTK-303 | Gilead/Japan Tobacco | HIV Infection AIDs, viral integrase inhibitor in development |
| Triple drug combination | Gilead/Bristol-Myers Squibb | Combination of Tenofovir disoproxil fumarate salt (Viread ®), Emtriva |

-continued

| Drug Name | Manufacturer | Indication |
|---|---|---|
| | | (Emtricitabine), and Sustiva ® (Efavirenz) |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |

-continued

| Drug Name | Manufacturer | Indication |
| --- | --- | --- |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this disclosure with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is Reyataz® (active ingredient Atazanavir). Typically a dose of 300 to 600 mg is administered once a day. This may be co-administered with a low dose of Ritonavir (50 to 500 mgs). Another preferred inhibitor of HIV protease is Kaletra®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present disclosure and other active agents may be administered separately or in conjunction. In addition, the administration of one element may be prior to, concurrent to, or subsequent to the administration of other agent(s).

Preferred combinations are simultaneous or alternating treatments of with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present disclosure and other active agents may be administered separately or in conjunction. In addition, the administration of one element may be prior to, concurrent to, or subsequent to the administration of other agent(s).

ABBREVIATIONS

The following abbreviations, most of which are conventional abbreviations well known to those skilled in the art, are used throughout the description of the disclosure and the examples. Some of the abbreviations used are as follows:
h=hour(s)
rt=room temperature
mol=mole(s)
mmol=millimole(s)
g=gram(s)
mg=milligram(s)
mL=milliliter(s)
TFA=trifluoroacetic Acid
DCE=1,2-Dichloroethane
$CH_2Cl_2$=dichloromethane
TPAP=tetrapropylammonium perruthenate
THF=tetrahydrofuran
DEPBT=3-(diethoxyphosphoryloxy)-1,2,3-benzotriazin-4(3H)-one
DMAP=4-dimethylaminopyridine
P-EDC=polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-diisopropylethylamine
MCPBA=meta-chloroperbenzoic Acid
azaindole=1H-pyrrolo-pyridine
4-azaindole=1H-pyrrolo[3,2-b]pyridine
5-azaindole=1H-pyrrolo[3,2-c]pyridine
6-azaindole=1H-pyrrolo[2,3-c]pyridine
7-azaindole=1H-pyrrolo[2,3-b]pyridine
PMB=4-methoxybenzyl
DDQ=2,3-dichloro-5,6-dicyano-1,4-benzoquinone
OTf=trifluoromethanesulfonoxy
NMM=4-methylmorpholine
PIP-COPh=1-benzoylpiperazine
NaHMDS=sodium hexamethyldisilazide
EDAC=1-(3-dimethylaminopropyl)-3-ethylcarbodiimide
TMS=trimethylsilyl
DCM=dichloromethane
DCE=dichloroethane
MeOH=methanol
THF=tetrahydrofuran
EtOAc=ethyl acetate
LDA=lithium diisopropylamide
TMP-Li=2,2,6,6-tetramethylpiperidinyl lithium
DME=dimethoxyethane
DIBALH=diisobutylaluminum hydride
HOBT=1-hydroxybenzotriazole
CBZ=benzyloxycarbonyl
PCC=pyridinium chlorochromate The compounds of the present disclosure may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present disclosure, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present disclosure.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this disclosure can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Chemistry

The present disclosure comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes.

Chemistry Schemes:

Preparation of Compounds of Formula I

The preparation of template A-CO—CO—Cl and A-CO—CO—OH has been described in detail in U.S. Pat. No. 6,469,006B1, U.S. Pat. No. 6,573,262B2, U.S. Pat. No. 6,900,323B2, US20050090522A1, U.S. Pat. No. 6,825,201, US20050261296A1, US20040186292A1, US20050267130A1, U.S. Pat. No. 6,900,206B2, US20040063746, WO-00076521, WO-00162255, WO-00204440, WO-02062423, WO-02085301, WO-03068221 and US-2004/0063744.

A chemist skilled in the art is aware of many standard conditions for reacting an amine with an acyl halide 1 (Scheme 1) and carboxyl acid 4 (Scheme 2) that could be used to convert the acid chloride or acid to the desired amide products. Some general references of these methodologies and directions for use are contained in "Comprehensive Organic Transformation" by Richard C. Larock, Wiley-VCH, New York, 1989, 972 (Carboxylic acids to amides), 979 (Acid halides to amides).

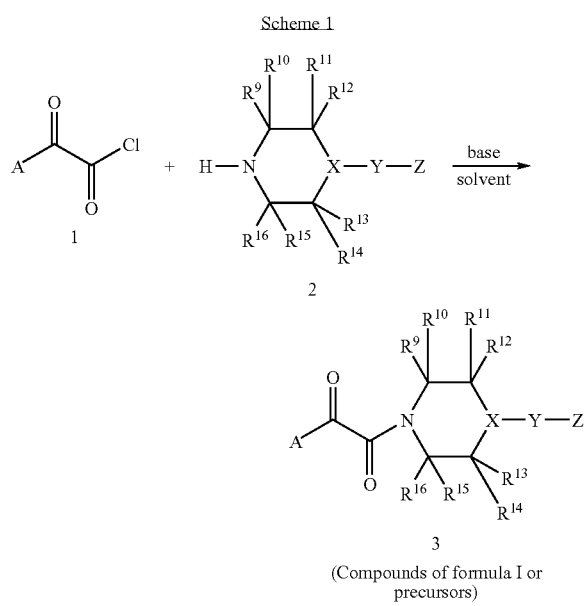

(Compounds of formula I or precursors)

Scheme 1 depicts a general method for forming an amide from piperazine amidine 2 and acyl chloride 1. An appropriate base (from catalytic to an excess amount) selected from sodium hydride, potassium carbonate, triethylamine, DBU, pyridine, DMAP or di-isopropyl ethyl amine was added into a solution of agent 2 and acyl chloride in an appropriate solvent selected from dichloromethane, chloroform, benzene, toluene, THF, diethyl ether, dioxane, acetone, N,N-dimethylformamide or pyridine at room temperature. The reaction was carried out at either room temperature or experimentally determined optimum temperature up to 150° C. over a period of time (30 minutes to 16 hours) to afford compounds 3 which may either be compounds of formula I or precursors. Some selected references involving such reactions include a) *Indian J. Chem., Sect B* 1990, 29, 1077; 2) *Chem. Sci.* 1998, 53, 1216; 3) *Chem. Pharm. Bull* 1992, 40, 1481; 4) *Chem. Heterocycl. Compd.* 2002, 38, 539.

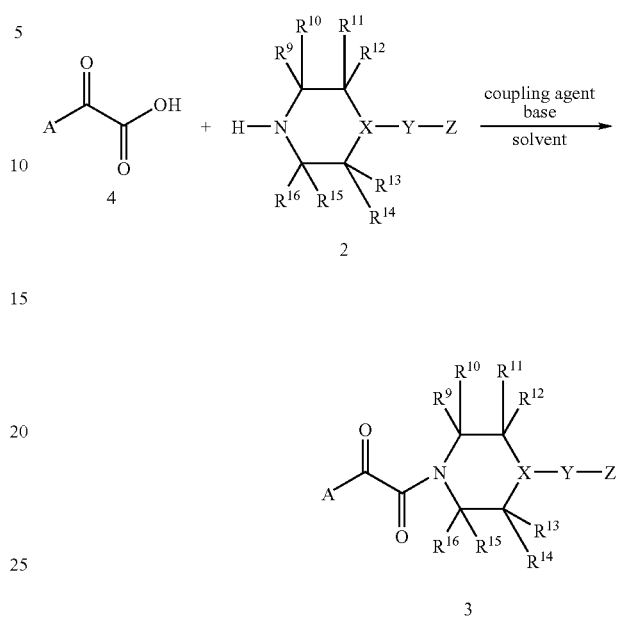

Alternatively, as shown in Scheme 2, structure 2 can be coupled with an acid 4 using standard amide bond or peptide bond forming coupling reagents. Many reagents for amide bond couplings are known by an organic chemist skilled in the art and nearly all of these are applicable for realizing coupled amide products. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU ((a) *J. Chem. Soc. Chem. Comm.* 1994, 201; (b) *J. Am. Chem. Soc.* 1994, 116, 11580). Additionally, DEPBT (3-(diethoxyphosphoryloxy)-1,2,3-benzotriazin-4(3H)-one) and N,N-diisopropylethylamine, commonly known as Hunig's base, represents another efficient method to form the amide bond and provide compounds of Formula I. DEPBT is either purchased from Adrich or prepared according to the procedure described in *Organic Lett.*, 1999, 1, 91. Typically an inert solvent such as DMF or THF is used but other aprotic solvents could be used.

The general agent 2 that's use are exemplified in Schemes 1 and 2, are either commercially available or may be prepared by the general methods described in the experimental section. A few nonlimiting examples of either commercially available or synthesized reagents 2 is listed below:

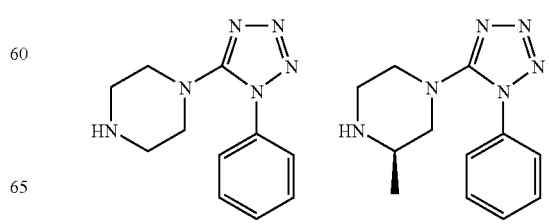

-continued
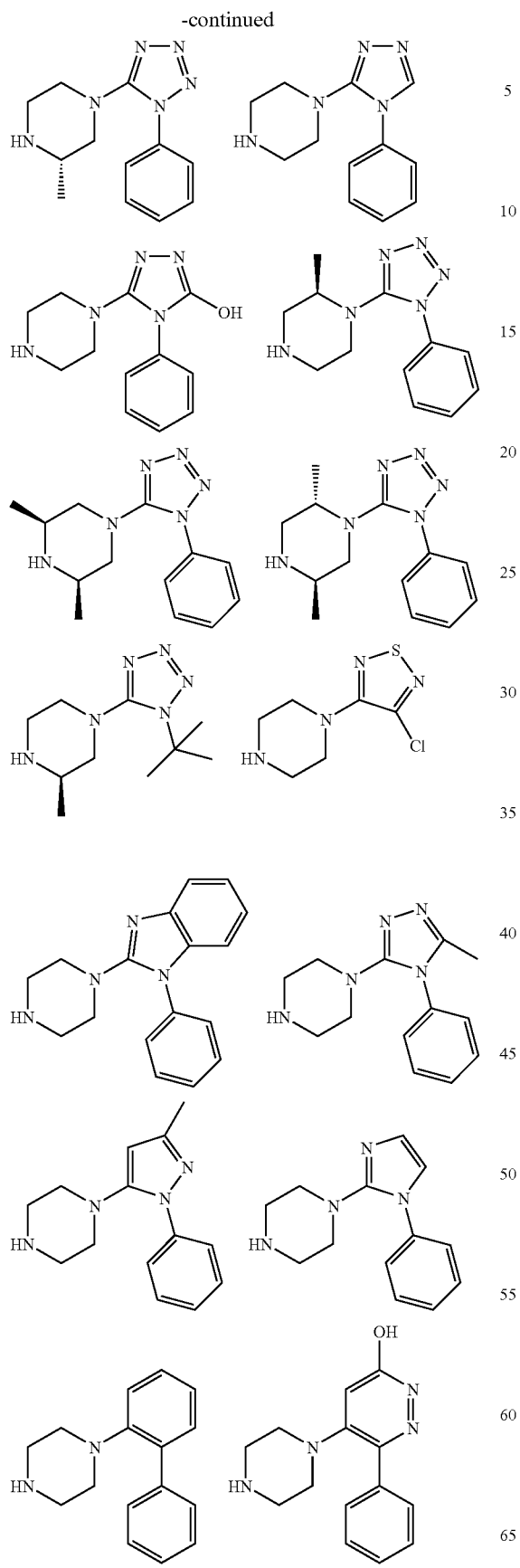
-continued
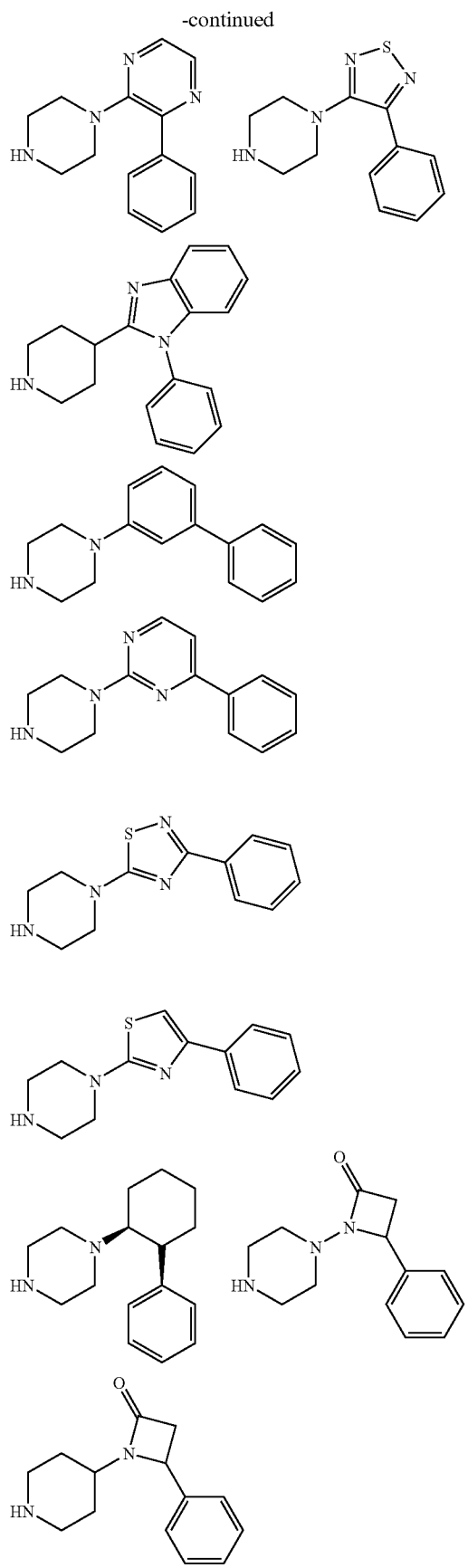

-continued
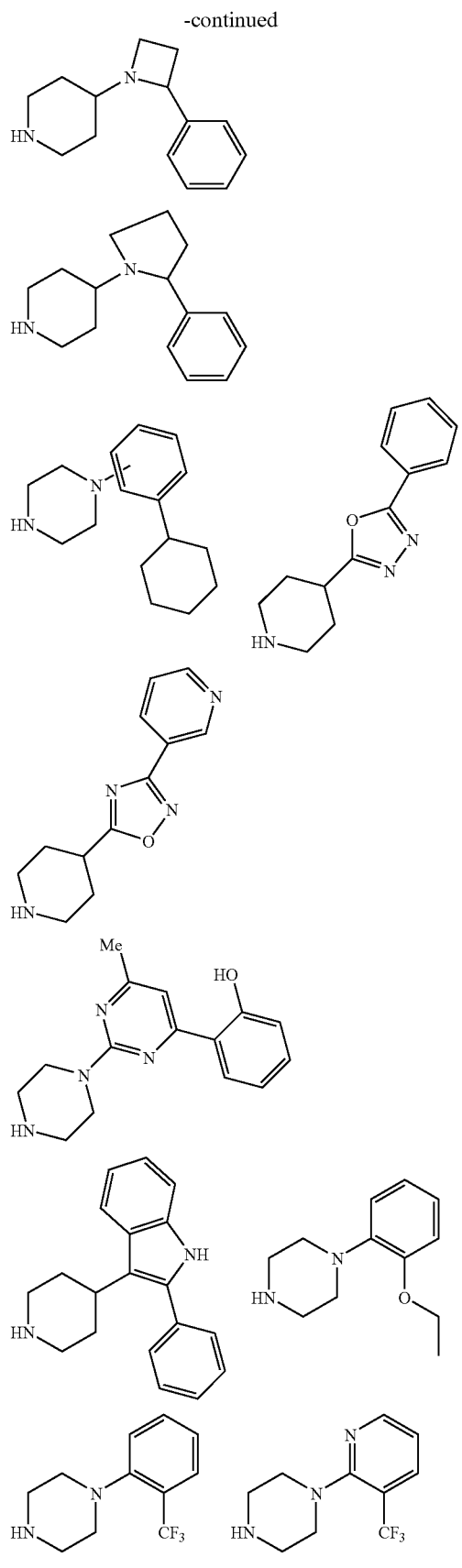
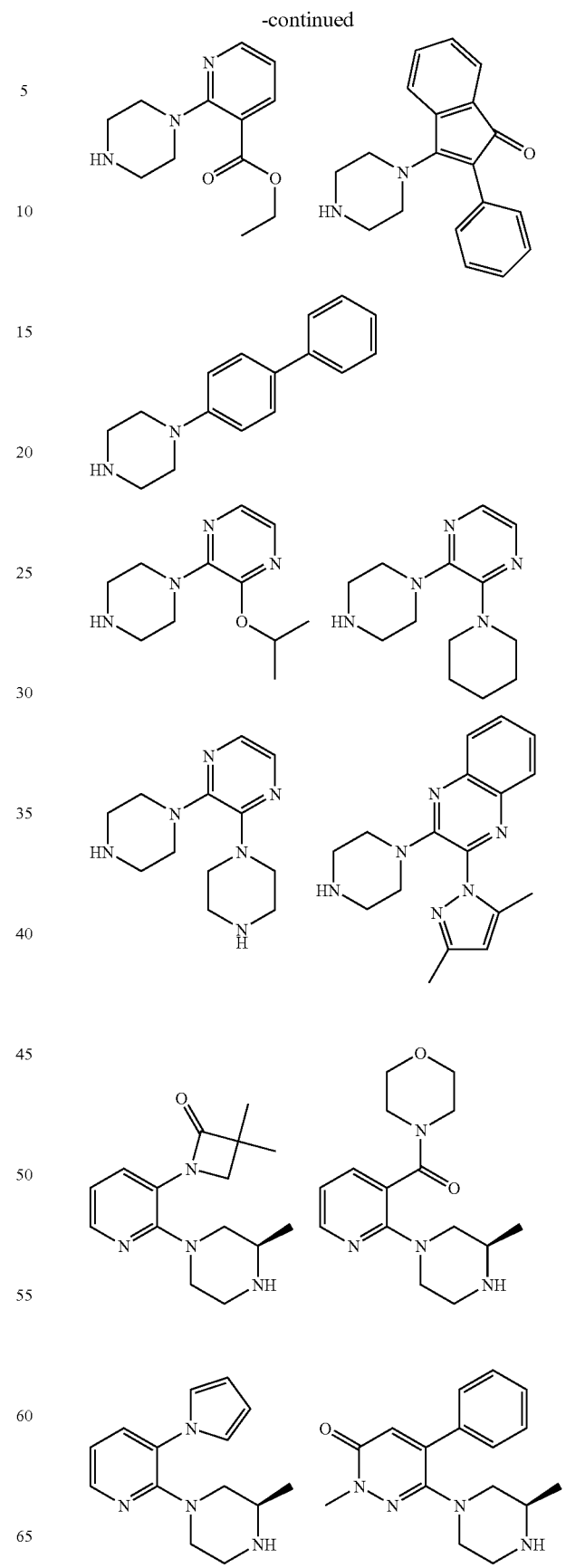

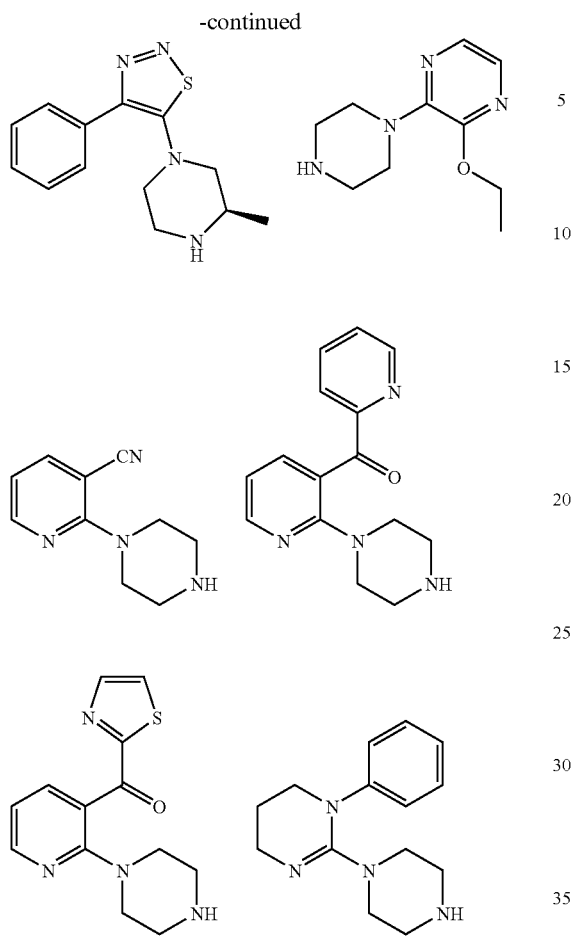

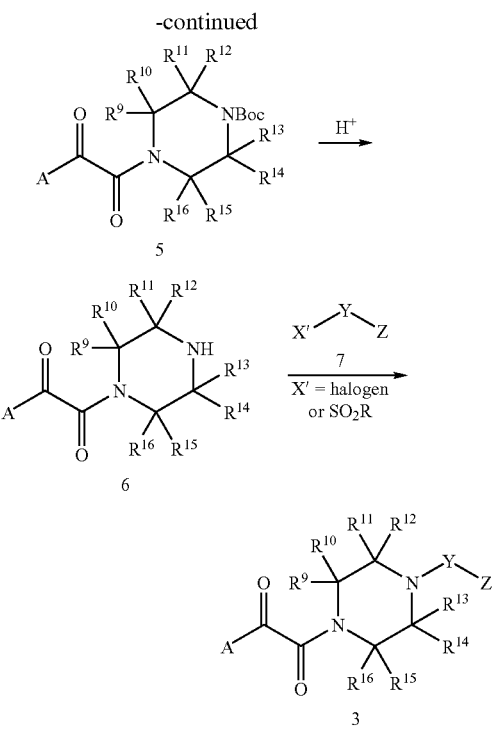

When X is N in Formula I, it can be also prepared by coupling acyl chloride 1 or acid 4 with Boc-protected piperazine under the conditions described in Scheme 1 and 2, to furnish compound 5. The following well established deprotection of Boc group under acidic conditions would provide piperazine amide 6. TFA and aqueous HCl are the typical acids used to effect removal of the Boc group, while the most commonly used solvents are either ether or dichloromethane. TFA may be employed as both reagent and solvent in some instances. Other acidic agents such as formic acid and solvents could also be used to effect BOC removal. The amide 6 could react with halide under $S_N2$, $S_NAr$ and metal-mediated cross coupling to provide compound 3 (compounds of formula I or precursors).

Scheme 3

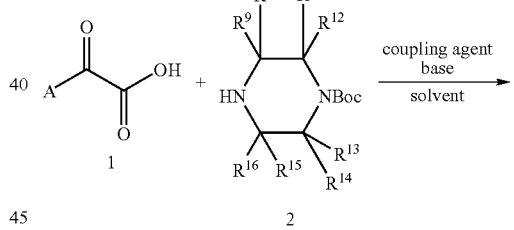

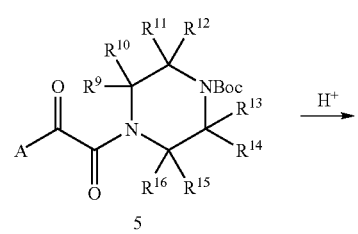

Scheme 4

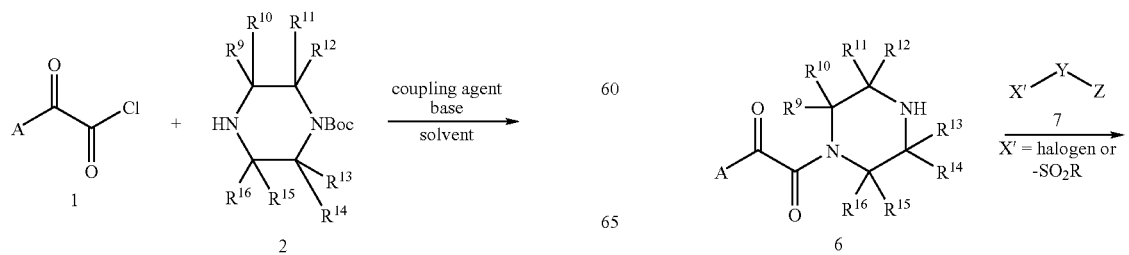

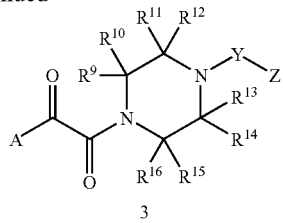

For $S_N2$ and $S_NAr$ reaction, in an aprotic (e.g., THF, DMF, DMSO, benzene) or protic solvent (e.g., MeOH, EtOH, PrOH, BuOH), at temperature from room temperature to 150° C., in the absence or presence of base such as NaH, pyridine, Et₃N, di-Pr₂NEt, Na₂CO₃, K₂CO₃, piperazine amide 6 can react with halide or heteroaryl sulfone 7 to give compound 3.

For metal-mediated cross coupling, temperature could vary from room temperature to 150° C. and solvents prefer to be aprotic solvents such as THF, dioxane, DME, DMF and DMSO. Bases can be selected from NaH, KH, pyridine, Et₃N, di-Pr₂NEt, Na₂CO₃, K₂CO₃, NaHMDS, LiHMDS, KHMDS, Na₃PO₄, Na₂HPO₄ and NaH₂PO₄. Pd, Rh, Ru, Ni or Pt agents can be utilized as catalysts.

EXAMPLES

The following examples illustrate typical syntheses of the compounds of Formula I as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). ¹H NMR spectra were recorded on Bruker DRX-500f at 500 MHz (or Bruker DPX-300B or Varian Gemini 300 at 300 MHz as stated). The chemical shifts were reported in ppm on the δ scale relative to δTMS=0. The following internal references were used for the residual protons in the following solvents: CDCl₃ ($\delta_H$ 7.26), CD₃OD ($\delta_H$ 3.30), and DMSO-d6 ($\delta_H$ 2.50). Standard acronyms were employed to describe the multiplicity patterns: s (singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

The preparation of templates A-CO—CO—Cl and A-CO—CO—OH unless specifically noted has been described in detail in U.S. Pat. No. 6,469,006B1, U.S. Pat. No. 6,573,262B2, U.S. Pat. No. 6,900,323B2, US20050090522A1, U.S. Pat. No. 6,825,201, US20050261296A1, US20040186292A1, US20050267130A1, U.S. Pat. No. 6,900,206B2, US20040063746, WO-00076521, WO-00162255, WO-00204440, WO-02062423, WO-02085301, WO-03068221 or US-2004/0063744. More specifically, the preparation of 7-bromo-4-fluoro-1H-pyrrolo[2,3-c]pyridine, 2-(4-fluoro-7-(1H-1,2,3-triazol-1-yl)-1H-pyrrolo[2,3-c]pyridin-3-yl)-2-oxoacetic acid, 2-(4-methoxy-7-(1H-1,2,3-triazol-1-yl)-1H-pyrrolo[2,3-c]pyridin-3-yl)-2-oxoacetic acid, 2-(7-chloro-4-methoxy-1H-pyrrolo[2,3-c]pyridin-3-yl)-2-oxoacetic acid, and 2-(4-methoxy-7-(3-methyl-1H-1,2,4-triazol-1-yl)-1H-pyrrolo[2,3-c]pyridin-3-yl)-2-oxoacetic acid were prepared as described in US20050090522A1.

Example Chemistry Section A

The following general methods apply to Example Chemistry Section A:

LC/MS Methods (i.e., Compound Identification)
Column A: Xterra MS C18 5 um 4.6×30 mm column
Column B: Phenomenex 5 u C18 4.6×30 mm column
Column C: Xterra MS C18 4.6×30 mm column
Column D: Phenomenex 4.6×50 mm C18 5 um column
Column E: Xterra 4.6×30 mm S5 column
Column F: Phenomenex-Luna 4.6×50 mm S10 column
Column G: Phenomenex 10 u 3.0×50 mm column
Column H: Phenomenex-Luna 4.6×30 mm S5 column
Column I: Phenomenex 4.6×30 mm 10 u column
Column J: Phenomenex C18 10 u 3.0×50 mm column
Column K: Phenomenex, Onyx Monolithic C18 50×4.6 mm column
Gradient: 100% Solvent A/0% Solvent B to 0% Solvent A/100% Solvent B
Gradient time All the LC-MS, except which are specified otherwise, use 2 minutes of gradient time.
Hold time: 1 minute
Flow rate: a. 5 ml/min
b. 4 ml/min
(All the LC-MS, except which are specified using flow rate b, were obtained by using flow rate a.)
Detector Wavelength: 220 nm Solvent System I
Solvent A: 10% MeOH/90% H₂O/0.1% Trifluoroacetic Acid
Solvent B: 10% H₂O/90% MeOH/0.1% Trifluoroacetic Acid Solvent System II
Solvent A: 5% MeCN/95% H₂O/10 mm ammonium acetate
Solvent B: 95% MeCN/5% H₂O/10 mm ammonium acetate
(All the LC-MS in the following sections, except which are specified using solvent system II, were obtained by using solvent system I.)

Compounds purified by preparative HPLC were diluted in methanol (1.2 ml) and purified using the following methods on a Shimadzu LC-10A automated preparative HPLC system.

Preparative HPLC Method (i.e., Compound Purification)
Purification Method Initial gradient (40% B, 60% A) ramp to final gradient (100% B, 0% A) over 20 minutes, hold for 3 minutes (100% B, 0% A)

Solvent A: 10% MeOH/90% H₂O/0.1% Trifluoroacetic Acid

Solvent B: 10% H₂O/90% MeOH/0.1% Trifluoroacetic Acid

Column: YMC C18 S5 20×100 mm column

Detector Wavelength: 220 nm

Typical Procedures and Characterization of Selected Examples:

Preparation of Agent 2

Method A

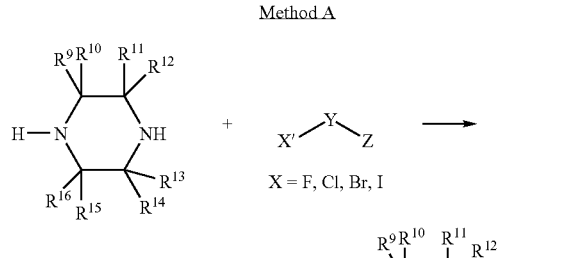

An excess of piperazine (5-10 eq.) was added to a solution of electrophile in THF, dioxane or DMF. The reaction was stirred for 17 hours at room temperature or 115° C., then was quenched with saturated aqueous NaHCO₃. The aqueous phase was extracted with EtOAc. The combined organic layer was washed with water and dried over MgSO₄, filtered, and the filtrate concentrated to a residue, which was used in the further reactions without purification, or purified by silica gel column chromatography or Shimadzu automated preparative HPLC System.

Method B

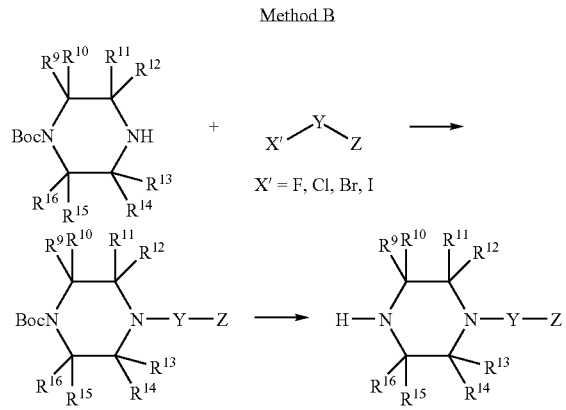

An excess of base (1-20 eq., such as Et₃N, iPr₂NEt or NaH), was added to a solution of N-Boc piperazine (2-5 eq.) in THF, dioxane or DMF, followed by addition of electrophile (1 eq.). The reaction was stirred for 17 hours at room temperature or 115° C., then was quenched with saturated aqueous NaHCO₃. The aqueous phase was extracted with EtOAc. The combined organic layer was dried over MgSO₄, filtered, and the filtrate concentrated to a residue, which was used in the further reactions without purification, or purified by silica gel column chromatography or Shimadzu automated preparative HPLC System.

N-Boc piperazine derivative was dissolved in an acidic solution of TFA or HCl in CH₂Cl₂, ether, dioxane or alcohol. After 0.5 to 17 hours, the solution was concentrated under vacuum to give an salt residue, which was partitioned between aqueous NaHCO₃ and EtOAc. The aqueous phase was extracted with EtOAc. The combined organic layer was dried over MgSO₄, filtered, and the filtrate concentrated to a residue, which was used in the further reactions without purification, or purified by silica gel column chromatography or Shimadzu automated preparative HPLC System.

Method C

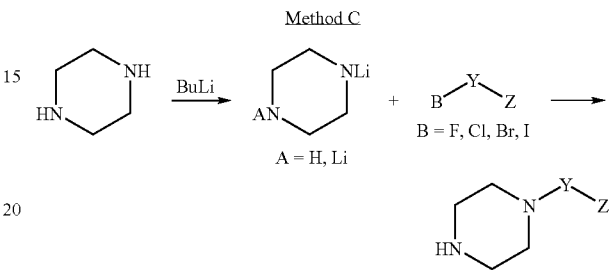

To a stirred solution of piperazine (2 eq.) in dry THF was added n-BuLi (2 to 4 eq.) in THF at room temperature. After stirring for 0.5 hour at room temperature, aryl halide (1 eq.) was added to the solution of anion and the reaction mixture was stirred for an additional 1 to 17 hours at room temperature to 115° C. The reaction mixture was quenched with MeOH, and the solvents evaporated. The residue was partitioned between EtOAc and sat. NaHCO₃. The aqueous layer was extracted with EtOAc. The organic layer was dried over MgSO₄ and concentrated to afford the crude product, which was purified by silica gel column chromatography or Shimadzu automated preparative HPLC System.

Method D

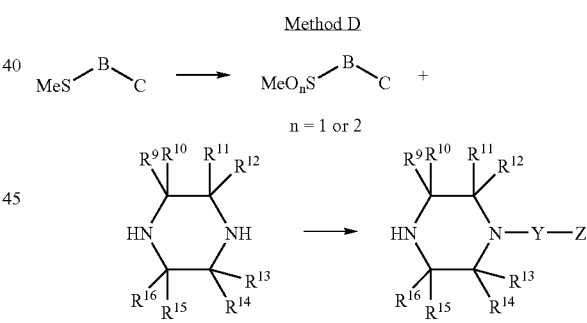

To a solution of methyl thio derivative (1 eq.) in dry CH₂Cl₂ or HOAc was added mCPBA (2-5 eq.) at room temperature. After stirring for 17 hours at room temperature, the reaction mixture was quenched with NaHSO₃, and the solvents evaporated. The residue was partitioned between EtOAc and sat. NaHCO₃. The aqueous layer was extracted with EtOAc. The organic layer was dried over MgSO₄ and concentrated to afford the crude product, which was purified by silica gel column chromatography or Shimadzu automated preparative HPLC System.

An excess of piperazine (5-10 eq.) was added to a solution of sulfone or sulfoxide derivative in 1-butanol or 1-pentanol. The reaction was refluxed for 17 hours. After cooling down, the reaction was quenched with saturated aqueous NaHCO₃. The aqueous phase was extracted with EtOAc. The combined organic layer was washed with water and dried over MgSO₄, filtered, and the filtrate concentrated to a residue, which was used in the further reactions without purification, or purified by silica gel column chromatography or Shimadzu automated preparative HPLC System.

Method E

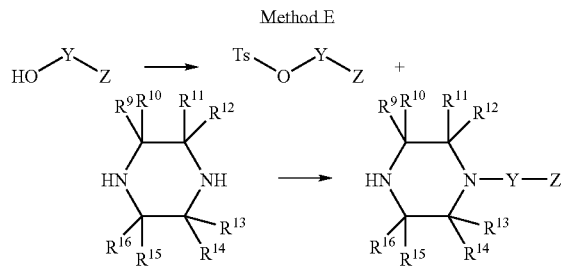

To a solution of alcohol derivative (1 eq.) in dry pyridine was added Ts-Cl (1-2 eq.) at room temperature. After stirring for 17 hours at room temperature, the solvents were evaporated. The residue was partitioned between EtOAc and sat. NaHCO$_3$. The aqueous layer was extracted with EtOAc. The organic layer was dried over MgSO$_4$ and concentrated to afford the crude product, which was purified by silica gel column chromatography or Shimadzu automated preparative HPLC System.

A mixture of an excess of piperazine (5-10 eq.) and tosylate (1 eq.) in sealed tube was heated at 115° C. to 170° C. for 1 to 17 hours. After cooling down, the reaction was quenched with saturated aqueous NaHCO$_3$. The aqueous phase was extracted with EtOAc. The combined organic layer was washed with water and dried over MgSO$_4$, filtered, and the filtrate concentrated to a residue, which was used in the further reactions without purification, or purified by silica gel column chromatography or Shimadzu automated preparative HPLC System.

Method F

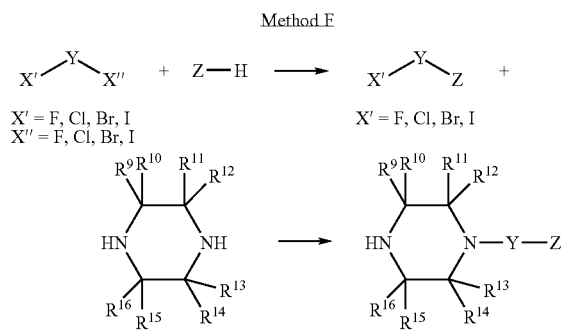

To a solution of dihalide derivative (1 eq.) in dry THF or dioxane or DMF was added amine (1-1.5 eq.) alone or alcohol (1-1.5 eq.) with NaH (1-5 eq.) at room temperature. After stirring for 17 hours at room temperature or 115° C., piperazine derivative (1-5 eq.) was added and the resulting mixture was heated up to 115° C. for 1 hour to 1 week. Then, the solvents were evaporated. The residue was partitioned between EtOAc and sat. NaHCO$_3$. The aqueous layer was extracted with EtOAc. The organic layer was washed with water, dried over MgSO$_4$ and concentrated to afford the crude product, which was purified by silica gel column chromatography or Shimadzu automated preparative HPLC System.

Method G

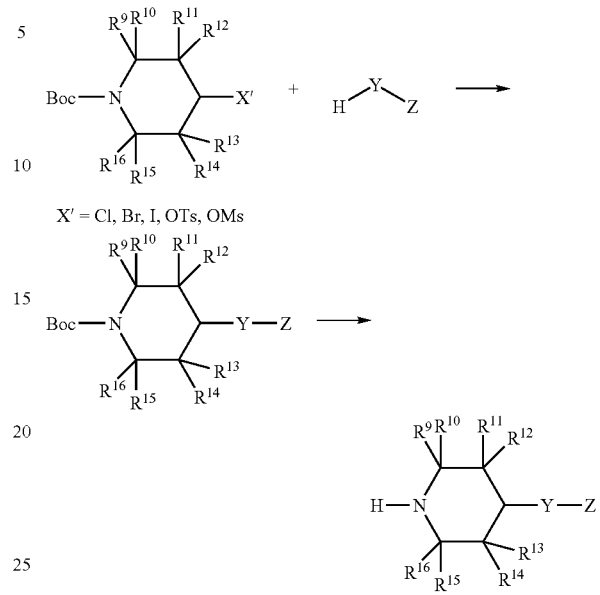

To a solution of N-Boc piperidine derivative (1 eq.) and a nucleophile such as an amine (1-5 eq.) in dry THF or dioxane or DMF was added iPr$_2$Net (1-10 eq.) in a sealed tube. The reaction was heated to 115° C. to 170° C. for 1-17 hours before cooling down. Then, the reaction mixture was quenched with NaHCO$_3$. The aqueous layer was extracted with EtOAc. The organic layer was dried over MgSO$_4$ and concentrated to afford the crude product, which was purified by silica gel column chromatography or Shimadzu automated preparative HPLC System.

N-Boc piperidine derivative was dissolved in an acidic solution of TFA or HCl in CH$_2$Cl$_2$, ether, dioxane or alcohol. After 0.5 to 17 hours, the solution was concentrated under vacuum to give an salt residue, which was partitioned between aqueous NaHCO$_3$ and EtOAc. The aqueous phase was extracted with EtOAc. The combined organic layer was dried over MgSO$_4$, filtered, and the filtrate concentrated to a residue, which was used in the further reactions without purification, or purified by silica gel column chromatography or Shimadzu automated preparative HPLC System.

Method H

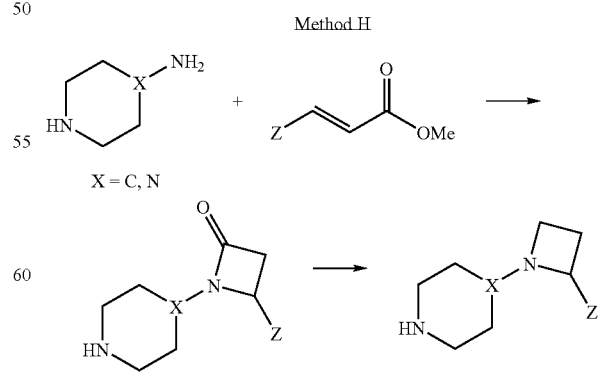

To a solution of piperidine or piperazine amine derivative (1-2 eq.) and a unsaturated ester (1 eq.) in dry THF or dioxane was added NaOMe (1-10 eq.). The reaction was stirred at room temperature or 120° C. for 1-17 hours. The solvents were removed under vacuum and the residue was partioned between NaHCO$_3$ and EtOAc. The aqueous layer was extracted with EtOAc. The organic layer was dried over MgSO$_4$ and concentrated to afford the crude lactam product, which was purified by silica gel column chromatography or Shimadzu automated preparative HPLC System.

LiAlH$_4$ (1-5 eq.) was added into a solution of lactam derivative (1 eq.) in dry THF at 0° C. The reaction was stirred at room temperature for 17 hours before being quenched by MeOH. The solvents were removed under vacuum and the residue was partioned between NaHCO$_3$ and EtOAc. The aqueous layer was extracted with EtOAc. The organic layer was dried over MgSO$_4$ and concentrated to afford the crude lactam product, which was purified by silica gel column chromatography or Shimadzu automated preparative HPLC System.

Sulfone or sulfoxide derivative (1 eq.) was added into the THF solution of piperazine anion (5-10 eq.) which was prepared from piperazine and BuLi (eq. of BuLi/eq. of piperazine=1 to 2) at room temperature in dry THF. The reaction was stirred at room temperature or refluxed for 17 hours. After cooling down, the reaction was quenched with saturated aqueous NaHCO$_3$. The aqueous phase was extracted with EtOAc. The combined organic layer was washed with water and dried over MgSO$_4$, filtered, and the filtrate concentrated to a residue, which was used in the further reactions without purification, or purified by silica gel column chromatography or Shimadzu automated preparative HPLC System.

Method I

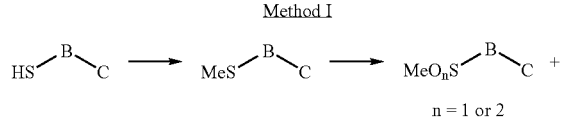

n = 1 or 2

Method J

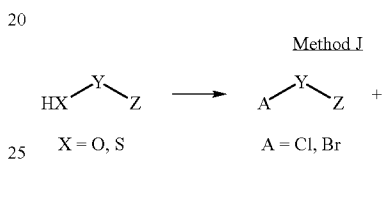

X = O, S         A = Cl, Br

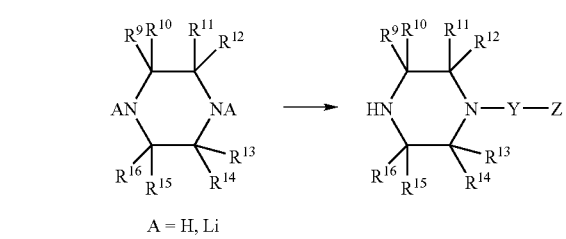

A = H, Li

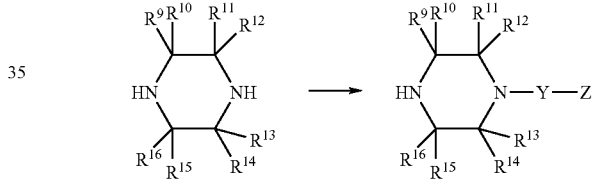

At room temperature, MeI (1-5 eq.) was added into a solution of thio derivative (1 eq.) with KOH (5-10 eq.) in water or with NaH (5-10 eq.) in THF, dioxane or DMF. The reaction was stirred at room temperature for 1 to 17 hours. The solvents were removed under vacuum and the residue was partioned between NaHCO$_3$ and EtOAc. The aqueous layer was extracted with EtOAc. The organic layer was dried over MgSO$_4$ and concentrated to afford the crude methyl thio product, which was purified by silica gel column chromatography or Shimadzu automated preparative HPLC System.

To a solution of methyl thio derivative (1 eq.) in dry CH$_2$Cl$_2$ or HOAc was added mCPBA (2-5 eq.) at room temperature. After stirring for 17 hours at room temperature, the reaction mixture was quenched with NaHSO$_3$, and the solvents evaporated. The residue was partitioned between EtOAc and sat. NaHCO$_3$. The aqueous layer was extracted with EtOAc. The organic layer was dried over MgSO$_4$ and concentrated to afford the crude product(s), sulfone or/and sulfoxide derivative, which was purified by silica gel column chromatography or Shimadzu automated preparative HPLC System.

Hydroxyl or thio derivative (1 eq.) was added into the POCl$_3$ or POBr$_3$ with or without DMF. The reaction was heated to 100° C. to 170° C. for 1 to 17 hours. After cooling down, the reaction was quenched with saturated aqueous NaHCO$_3$. The aqueous phase was extracted with EtOAc. The combined organic layer was washed with water and dried over MgSO$_4$, filtered, and the filtrate concentrated to a residue, which was used in the further reactions without purification, or purified by silica gel column chromatography or Shimadzu automated preparative HPLC System.

A mixture of an excess of piperazine (5-10 eq.) and halide (1 eq.) in BuOH, PnOH, THF, dioxane or DMF was stirred at room temperature or heated at 170° C. for 1 to 17 hours. Cu or Pd catalyst may be utilized. The reaction was quenched with saturated aqueous NaHCO$_3$. The aqueous phase was extracted with EtOAc. The combined organic layer was washed with water and dried over MgSO$_4$, filtered, and filtrate concentrated to a residue, which was used in the further reactions without purification, or purified by silica gel column chromatography or Shimadzu automated preparative HPLC System.

TABLE A-1
| Intermediate | Structure | Method Used | Starting Comercially Available Materials | MS (M + H)+ Calcd. | MS (M + H)+ Observ. And Retention Time and NMR |
|---|---|---|---|---|---|
| I-01 | 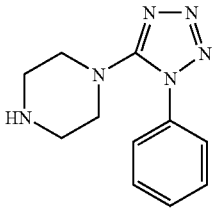 | A | 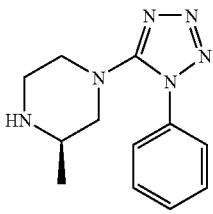 | 231.14 | 231.21 Rf = 0.83 min (column H, flow rate b) |
| I-02 | 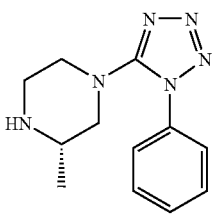 | A | 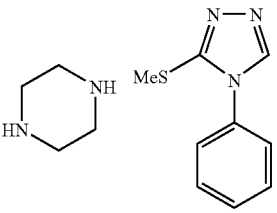 | 245.15 | 245.38 Rf = 0.83 min (column H, flow rate b) |
| I-03 | 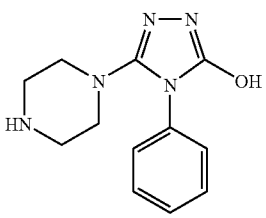 | A | 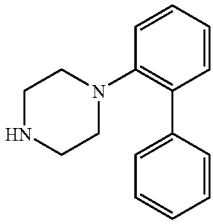 | 245.15 | 245.39 Rf = 0.83 min (column H, flow rate b) |
| I-04 | 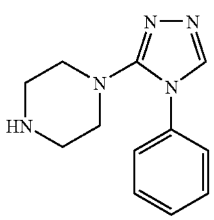 | D |  | 230.14 | 230.06 Rf = 0.65 min (column F, flow rate b) |
| I-05 | 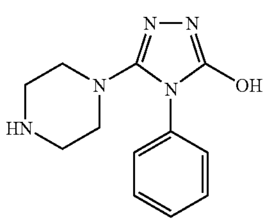 | A |  | 246.14 | 246.28 Rf = 0.32 min (column H, flow rate b) |
| I-06 | 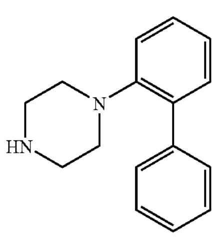 | | From commercial supplier | | |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-07 | 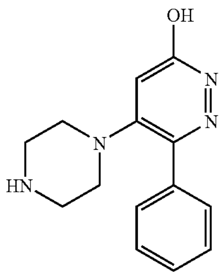 | | From commercial supplier | | |
| I-08 | 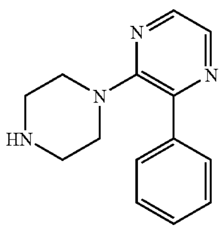 | A | | 241.15 | 241.15 Rf = 0.70 min (column J) ¹H NMR (500 MHz, CD₃OD) δ 8.22 (s, 2 H), 7.85 (d, 2 H, J = 10 Hz), 7.51 (m, 3 H), 3.38 (m, 4 H), 3.19 (m, 4 H); ¹³C NMR (125 MHz, CD₃OD) δ 156.11, 146.47, 141.52, 139.56, 138.06, 130.50, 130.03, 128.88, 46.50, 44.13. |
| I-09 | 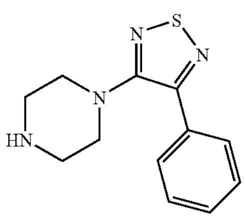 | A | | 247.10 | 247.20 Rf = 1.98 min (column I) ¹H NMR (500 MHz, CD₃OD) δ 7.96 (m, 2 H), 7.54 (m, 3 H), 3.51-3.33 (m, 8H); ¹³C NMR (125 MHz, CD₃OD) δ 161.1, 152.1, 133.6, 129.9, 129.1, 127.7, 46.7, 43.0. HRMS: 247.1023 (calc. 247.1017) |
| I-10 | 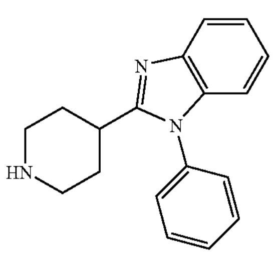 | | From commercial supplier | | |
| I-11 | 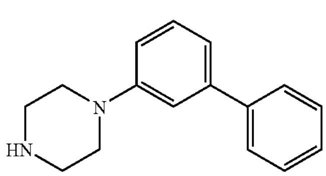 | | From commercial supplier | | |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-12 | 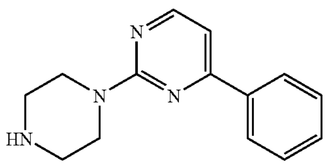 | A | | 241.15 | 241.21 Rf = 1.37 min (column H, flow rate b) |
| I-13 | 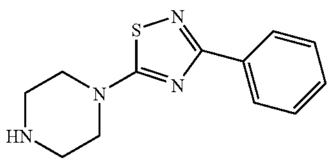 | | From commercial supplier | | |
| I-14 | 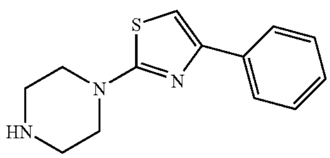 | A | | 246.11 | 246.17 Rf = 1.40 min (column H, flow rate b) |
| I-15 | 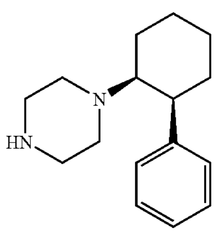 | E | | 245.20 | 245.34 Rf = 0.92 min (column I) |
| I-16 | 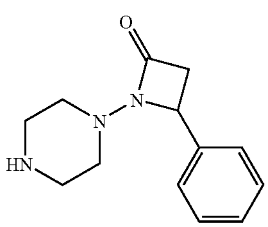 | H | | 232.14 | 232.29 Rf = 1.11 min (column H, flow rate b) |
| I-17 | 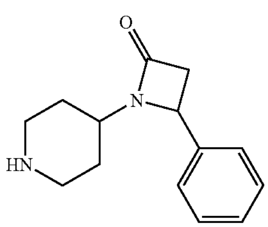 | H | | 231.15 | 231.32 Rf = 1.11 min (column H, flow rate b) |
| I-18 | 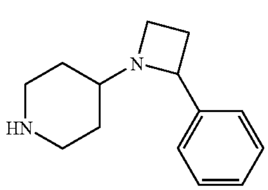 | H | | 217.17 | 217.30 Rf = 1.07 min (column F, flow rate b) |

TABLE A-1-continued
| Intermediate | Structure | Method Used | Starting Comercially Available Materials | MS (M + H)+ Calcd. | MS (M + H)+ Observ. And Retention Time and NMR |
|---|---|---|---|---|---|
| I-19 | 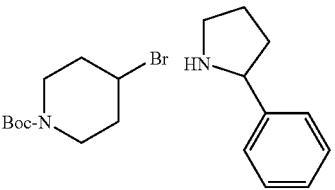 | G | 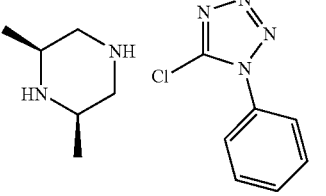 | 230.18 | 231.25 Rf = 0.46 min (column I) |
| I-20 | 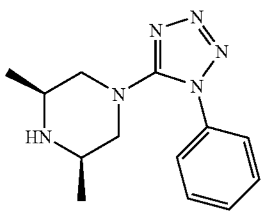 | A | | 259.17 | 259.33 Rf = 1.01 min (column E, flow rate b, gradient time 4 min) |
| I-21 | 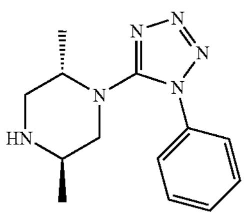 | A | | 259.17 | 259.36 Rf = 1.04 min (column H, flow rate b) |
| I-22 | 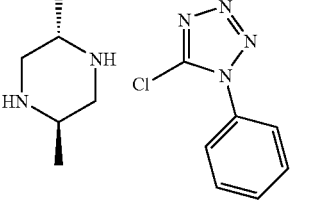 | C | 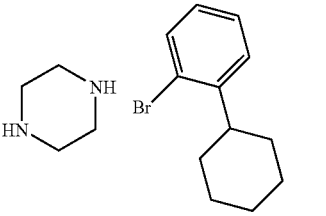 | 245.20 | 245.39 Rf = 1.79 min (column H, flow rate b) |
| I-23 | 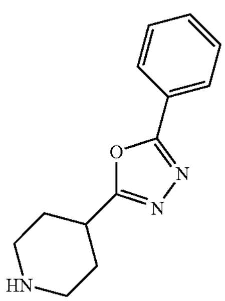 | | From commercial supplier | | |
| I-24 | 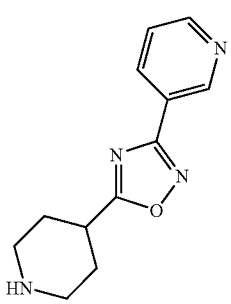 | | From commercial supplier | | |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-25 | 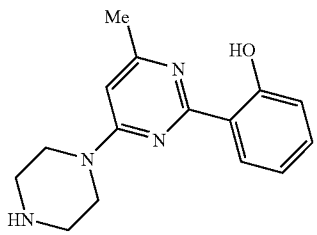 | | From commercial supplier | | |
| I-26 | 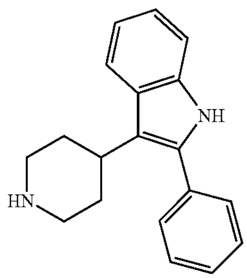 | | From commercial supplier | | |
| I-27 | 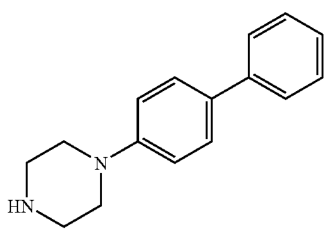 | | From commercial supplier | | |
| I-28 | 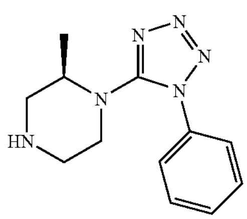 | B | | 245.15 | 245.29 Rf = 0.99 min (column F, flow rate b) |
| I-29 | 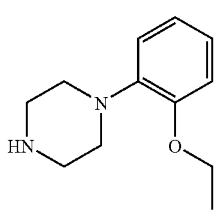 | | From commercial supplier | | |
| I-30 | 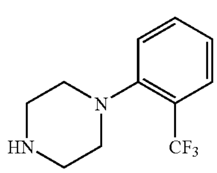 | | From commercial supplier | | |
| I-31 | 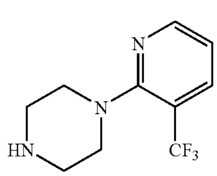 | | From commercial supplier | | |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-32 | 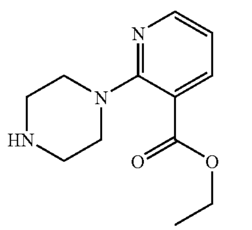 | A | | 236.14 | 236.30 Rf = 1.15 min (column H, rate b) |
| I-33 | 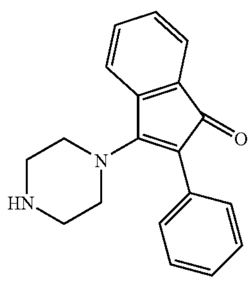 | A | | 291.15 | 291.31 Rf = 1.22 min (column H, flow rate b) |
| I-34 | 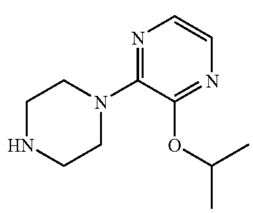 | F | | 223.16 | 223.30 Rf = 1.13 min (column H, flow rate b) |
| I-35 | 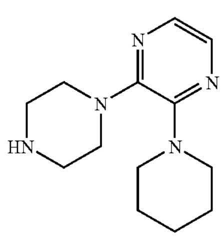 | F | | 248.19 | 248.34 Rf = 1.16 min (column H, flow rate b) |
| I-36 | 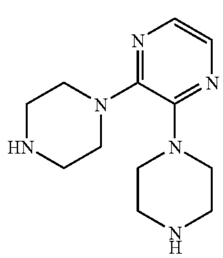 | F | | 249.18 | 249.33 Rf = 0.37 min (column H, flow rate b) |

TABLE A-1-continued

| Intermediate Structure | Method Used | Starting Comercially Available Materials | MS (M + H)+ Calcd. | MS (M + H)+ Observ. And Retention Time and NMR |
|---|---|---|---|---|
| I-37 | A | | 309.18 | 309.37 Rf = 1.53 min (column H, flow rate b) |
| I-38 | A | | 275.19 | 275.36 Rf = 1.09 min (column H, flow rate b) |
| I-39 | A | | 291.18 | 291.37 Rf = 0.76 (column H, flow rate b) |
| I-40 | A | | 243.16 | 243.33 Rf = 1.30 min (column H, flow rate b) |
| I-41 | A | | 285.17 | 285.36 Rf = 1.25 min (column H, flow rate b) |

TABLE A-1-continued
| Intermediate | Structure | Method Used | Starting Comercially Available Materials | MS (M + H)+ Calcd. | MS (M + H)+ Observ. And Retention Time and NMR |
|---|---|---|---|---|---|
| I-42 | 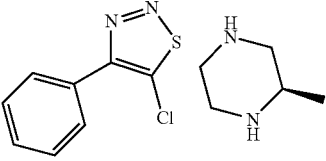 | A | 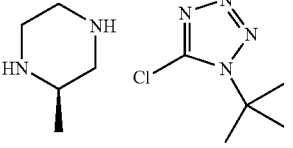 | 261.12 | 261.29 Rf = 1.18 min (column H, flow rate b) |
| I-43 | 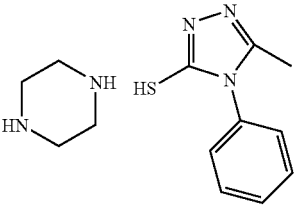 | A | 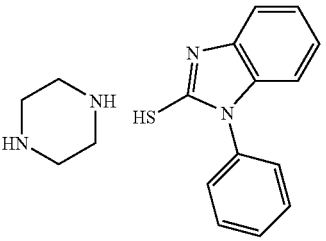 | 225.18 | 225.32 Rf = 0.87 min (column H, flow rate b) |
| I-44 | 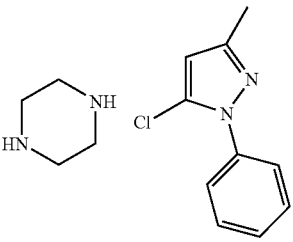 | J | 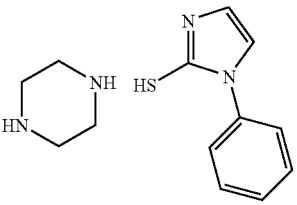 | 244.16 | 244.33 Rf = 0.65 min (column F, flow rate b) |
| I-45 | 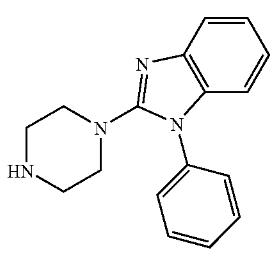 | I | | 279.16 | 279.19 Rf = 0.88 min (column F, flow rate b) |
| I-46 | 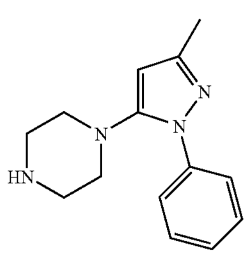 | C | | 243.16 | 243.36 Rf = 0.96 min (column F, flow rate b) |
| I-47 | 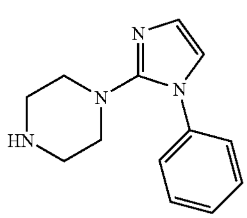 | I | | 229.15 | 229.30 Rf = 0.28 min (column F, flow rate b) |

TABLE A-1-continued
| Intermediate | Structure | Method Used | Starting Comercially Available Materials | MS (M + H)+ Calcd. | MS (M + H)+ Observ. And Retention Time and NMR |
|---|---|---|---|---|---|
| I-48 | 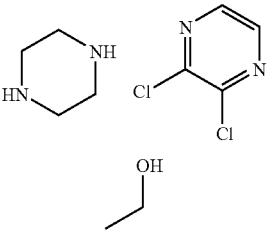 | F | | 209.14 | 209.18 Rf = 1.06 min (column H, flow rate b) |
| I-49 | 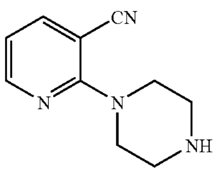 | A | | 189.11 | 189.13 Rf = 0.63 (column H, flow rate b) |
| I-50 | 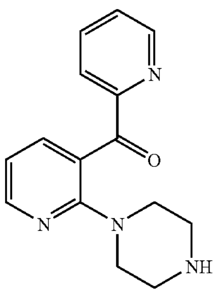 | A | | 269.14 | 269.32 Rf = 0.86 (column H, flow rate b) |
| I-51 | 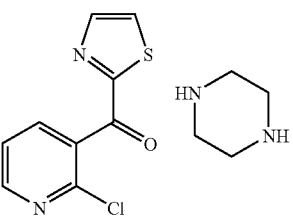 | A | | 275.10 | 275.28 Rf = 0.98 (column H, flow rate b) |
| I-52 | 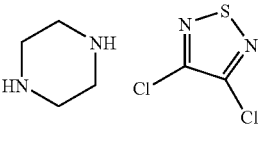 | A | | 205.03 | 205.20 Rf = 1.68 (column H, flow rate b) |
| I-53 | 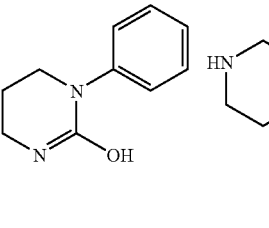 | J | | 245.18 | 245.19 Rf = 0.69 (column F, flow rate b) |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-54 | 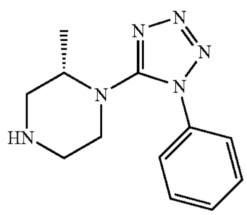 | B | | 245.15 | 245.29 Rf = 0.99 min (column F, flow rate b) |
| I-55 | 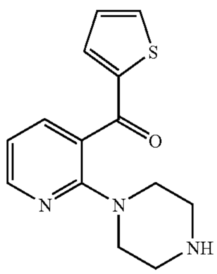 | A | | 274.10 | 273.98 Rf = 1.18 (column H, flow rate b) |
| I-56 | 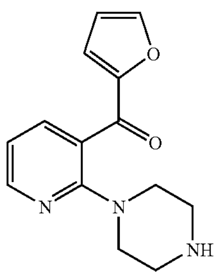 | A | | 258.12 | 258.02 Rf = 0.96 (column H, flow rate b) |
| I-57 | 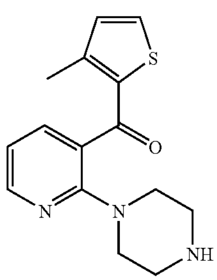 | A | | 288.12 | 287.98 Rf = 1.27 (column H, flow rate b) |
| I-58 | 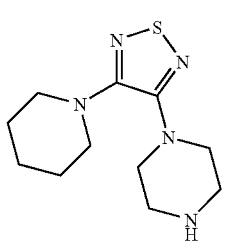 | A | | 254.14 | 254.41 Rf = 1.56 (column H, flow rate b) |
| I-59 | 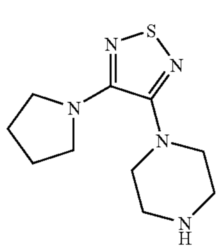 | A | | 240.13 | 240.40 Rf = 1.33 (column H, flow rate b) |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-60 | 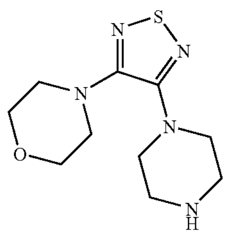 | A | | 256.12 | 256.39 Rf = 1.10 (column H, flow rate b) |
| I-61 | 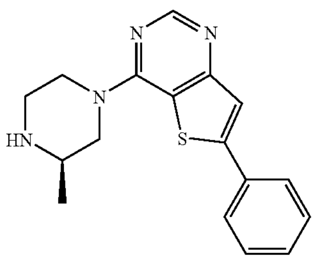 | A | | 311.13 | 311.30 Rf = 1.14 (column H, flow rate b) |
| I-62 | 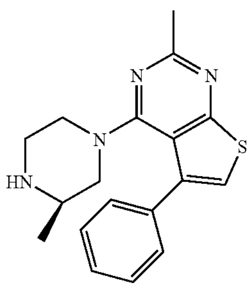 | A | | 325.15 | 325.32 Rf = 1.49 (column H, flow rate b) |
| I-63 | 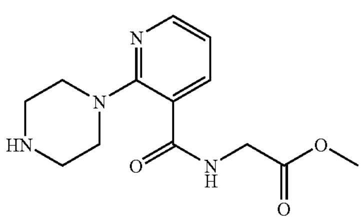 | A | | 279.15 | 279.31 Rf = 0.61 (column H, flow rate b) |
| I-64 | 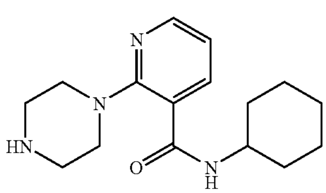 | A | | 289.20 | 289.37 Rf = 1.16 (column H, flow rate b) |
| I-65 | 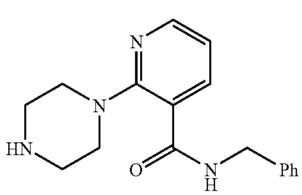 | A | | 297.17 | 297.34 Rf = 1.05 (column H, flow rate b) |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-66 | 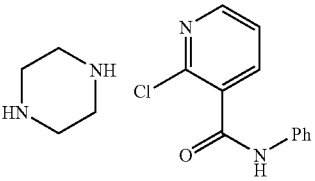 | A | | 283.16 | 283.33<br>Rf = 1.13<br>(column H, flow rate b) |
| I-67 | 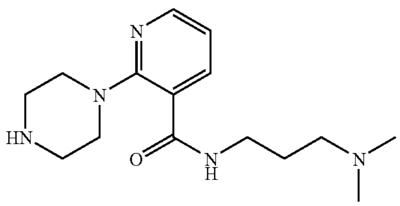 | A | | 292.21 | 292.42<br>Rf = 0.28<br>(column H, flow rate b) |
| I-68 | 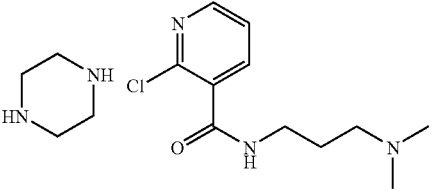 | A | | 293.16 | 293.45<br>Rf = 0.57<br>(column H, flow rate b) |
| I-69 | 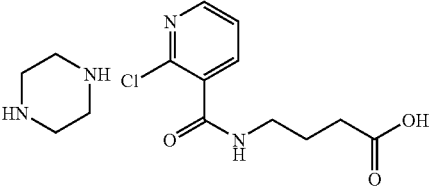 | A | | 352.21 | 352.24<br>Rf = 1.31<br>(column H, flow rate b) |
| I-70 | 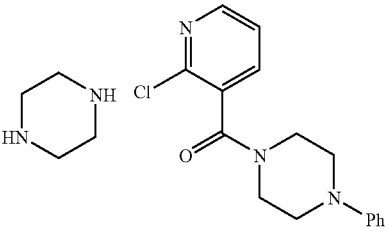 | A | | 288.15 | 288.39<br>Rf = 1.03<br>(column H, flow rate b) |
| I-71 | 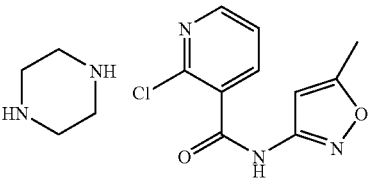 | A | 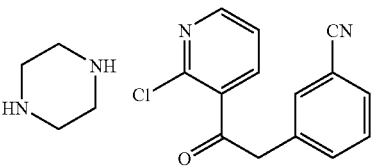 | 307.16 | 307.43<br>Rf = 1.22<br>(column H, flow rate b) |
| I-72 | 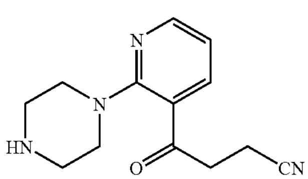 | A | 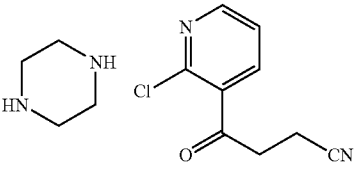 | 245.14 | 245.38<br>Rf = 0.67<br>(column H, flow rate b) |

TABLE A-1-continued

| Intermediate | Structure | Method Used | Starting Commercially Available Materials | MS (M + H)+ Calcd. | MS (M + H)+ Observ. And Retention Time and NMR |
|---|---|---|---|---|---|
| I-73 | 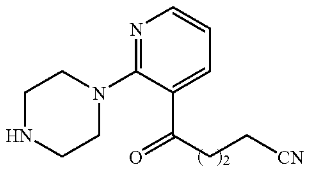 | A | | 259.16 | 259.41 Rf = 0.83 (column H, flow rate b) |
| I-74 | 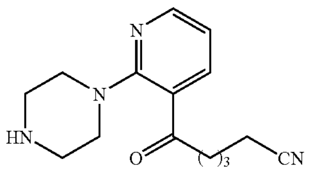 | A | | 273.17 | 273.42 Rf = 0.94 (column H, flow rate b) |
| I-75 | 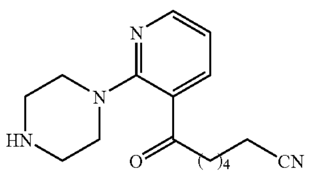 | A | | 287.19 | 287.44 Rf = 1.11 (column H, flow rate b) |
| I-76 | 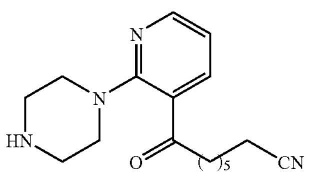 | A | | 301.20 | 301.46 Rf = 1.25 (column H, flow rate b) |
| I-77 | 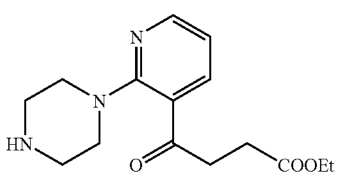 | A | | 292.17 | 292.46 Rf = 1.13 (column H, flow rate b) |
| I-78 | 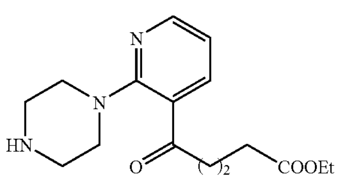 | A | | 306.18 | 306.46 Rf = 1.26 (column H, flow rate b) |
| I-79 | 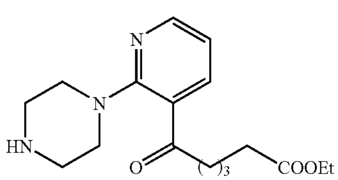 | A | | 320.20 | 320.48 Rf = 1.36 (column H, flow rate b) |
| I-80 | 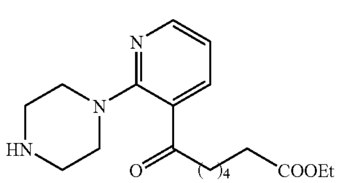 | A | | 334.21 | 334.50 Rf = 1.48 (column H, flow rate b) |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-81 | 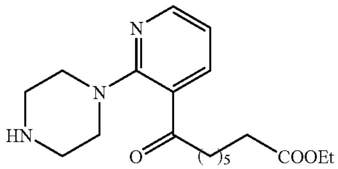 | A | | 348.23 | 348.50 Rf = 1.61 (column H, flow rate b) |
| I-82 | 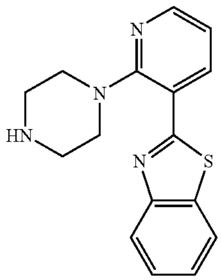 | A | | 297.12 | 297.30 Rf = 1.49 (column H, flow rate b) |
| I-83 | 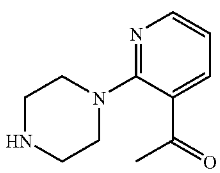 | A | | 206.13 | 206.29 Rf = 0.58 (column H, flow rate b) |
| I-84 | 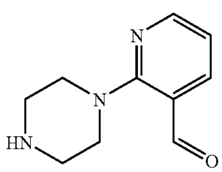 | A | | 192.11 | 301.46 Rf = 1.25 (column H, flow rate b) |
| I-85 | 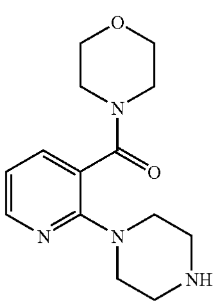 | A | | 277.17 | 277.34 Rf = 0.63 (column H, flow rate b) |
| I-86 | 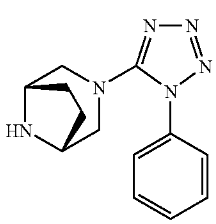 | A | | 257.15 | 257.21 Rf = 1.05 min (column E, flow rate b, gradient time 4 min) |

TABLE A-1-continued

| Intermediate | Structure | Method Used | Starting Comercially Available Materials | MS (M + H)+ Calcd. | MS (M + H)+ Observ. And Retention Time and NMR |
|---|---|---|---|---|---|
| I-87 | 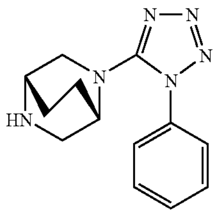 | B | | 257.15 | 257.18<br>Rf = 0.97 min<br>(column E, flow rate b, gradient time 4 min) |
| I-88 | 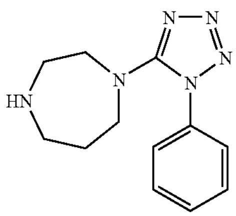 | A | | 245.15 | 245.15<br>Rf = 0.83 min<br>(column E, flow rate b, gradient time 4 min) |
| I-89 | 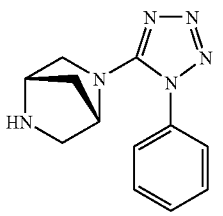 | A | | 243.14 | 243.29<br>Rf = 0.92 min<br>(column E, flow rate b, gradient time 4 min) |

Preparation of Compound 3

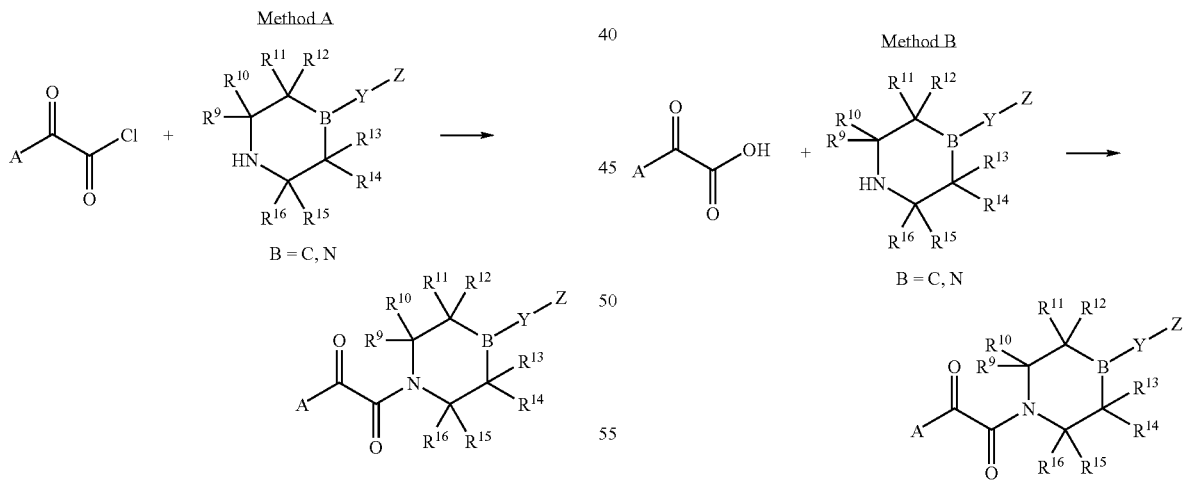

Et$_3$N or iPr$_2$NEt (1-100 eq.) was added into a solution of 2-keto acyl chloride (1 eq.) and piperazine or piperidine derivative (1-5 eq.) in an aprotic solvent (such as THF, DMF, dioxane, ether, acetonitrile) and reaction was stirred at room temperature or 50° C. or 80° C. or 115° C. for 17 hours before quenched with saturated aqueous NaHCO$_3$ solution. The aqueous layer was extracted with ethyl acetate. The organic phase combined and dried over anhydrous MgSO$_4$. Concentration in vacuo provided a crude product, which was purified by tritaration, or recrystallization, or silica gel column chromatography, or Shimadzu automated preparative HPLC System.

2-Keto acid (1 eq.), piperazine (1-5 eq.), 3-(diethoxyphosphoryloxy)-1,2,3-benzotriazin-4(3H)-one (DEPBT) or O-(1H-benzotriazol-1-yl)-N,N,N',N'-tetramethyluronium tetrafluoroborate (TBTU) (1-5 eq.) and Hunig's Base or N-methyl morpholine (1-100 eq.) were combined in THF or DMF. The mixture was stirred at room temperature for 17 hours. THF or DMF was removed via evaporation at reduced pressure and the residue was partitioned between ethyl acetate and 5-10% Na$_2$CO$_3$ aqueous solution. The aqueous layer was extracted with ethyl acetate. The organic phase combined and dried over anhydrous MgSO$_4$. Concentration in vacuo provided a crude product, which was purified by tritaration, or recrystallization, or silica gel column chromatography, or Shimadzu automated preparative HPLC System.

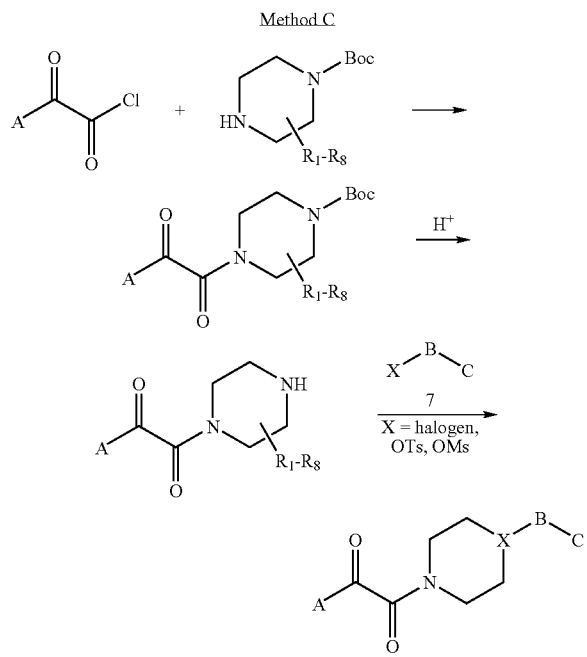

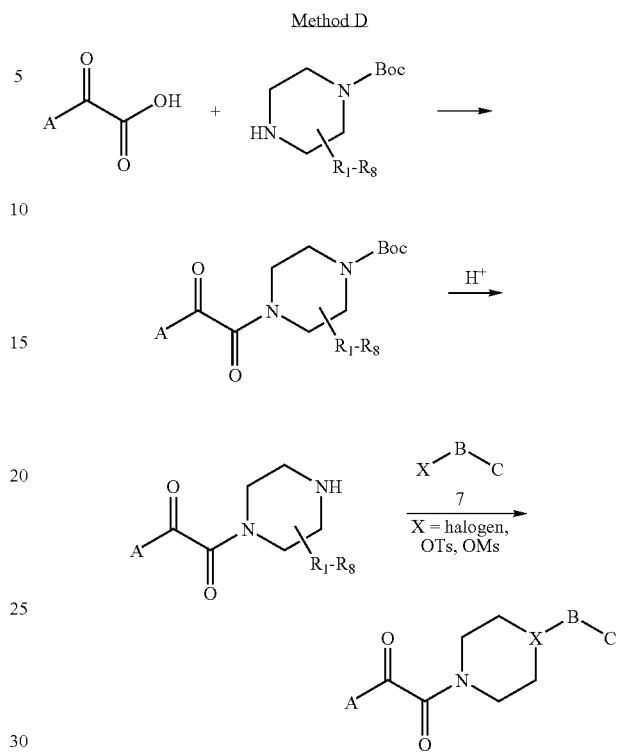

Et$_3$N or iPr$_2$NEt (1-100 eq.) was added into a solution of 2-keto acyl chloride (1 eq.) and Boc-piperazine (1-5 eq.) in an aprotic solvent (such as THF, DMF, dioxane, ether, acetonitrile) and reaction was stirred at room temperature or 50° C. or 80° C. or 115° C. for 17 hours before quenched with saturated aqueous NaHCO$_3$ solution. The aqueous layer was extracted with ethyl acetate. The organic phase combined and dried over anhydrous MgSO$_4$. Concentration in vacuo provided a crude product, which was purified by tritaration, or recrystallization, or silica gel column chromatography, or Shimadzu automated preparative HPLC System.

N-Boc piperazine keto amide derivative was dissolved in an acidic solution of TFA or HCl in CH$_2$Cl$_2$, ether, dioxane or alcohol. After 0.5 to 17 hours, the solution was concentrated under vacuum to give an salt residue, which was used in the next step without purification. Or, salt precipitated out from solution, which was washed with CH$_2$Cl$_2$, ether, dioxane or alcohol before further use.

An excess of base (1-20 eq., such as Et$_3$N, iPr$_2$NEt or NaH), was added to a solution of 2-keto acyl piperazine (1 eq.) in THF or DMF, followed by addition of electrophile (1 to 10 eq.). The reaction was stirred for 17 hours at room temperature or 115° C., then was quenched with saturated aqueous NaHCO$_3$. The aqueous phase was extracted with EtOAc. The combined organic layer was dried over MgSO$_4$, filtered, and the filtrate concentrated to a residue, which was used in the further reactions without purification, or purified by silica gel column chromatography or Shimadzu automated preparative HPLC System.

2-Keto acid (1 eq.), N-Boc piperazine (1-5 eq.), 3-(diethoxyphosphoryloxy)-1,2,3-benzotriazin-4(3H)-one (DEPBT) or O-(1H-benzotriazol-1-yl)-N,N,N',N'-tetramethyluronium tetrafluoroborate (TBTU) (1-5 eq.) and Hunig's Base (1-100 eq.) were combined in THF or DMF. The mixture was stirred at room temperature for 17 hours. THF or DMF was removed via evaporation at reduced pressure and the residue was partitioned between ethyl acetate and 5-10% Na$_2$CO$_3$ aqueous solution. The aqueous layer was extracted with ethyl acetate. The organic phase combined and dried over anhydrous MgSO$_4$. Concentration in vacuo provided a crude product, which was purified by tritaration, or recrystallization, or silica gel column chromatography, or Shimadzu automated preparative HPLC System.

N-Boc piperazine keto amide derivative was dissolved in an acidic solution of TFA or HCl in CH$_2$Cl$_2$, ether, dioxane or alcohol. After 0.5 to 17 hours, the solution was concentrated under vacuum to give an salt residue, which was used in the next step without purification. Or, salt precipitated out from solution, which was washed with CH$_2$Cl$_2$, ether, dioxane or alcohol before further use.

An excess of base (1-20 eq., such as Et$_3$N, iPr$_2$NEt or NaH), was added to a solution of 2-keto acyl piperazine (1 eq.) in THF or DMF, followed by addition of electrophile (1 to 10 eq.). The reaction was stirred for 17 hours at room temperature or 115° C., then was quenched with saturated aqueous NaHCO$_3$. The aqueous phase was extracted with EtOAc. The combined organic layer was dried over MgSO$_4$, filtered, and the filtrate concentrated to a residue, which was used in the further reactions without purification, or purified by silica gel column chromatography or Shimadzu automated preparative HPLC System.

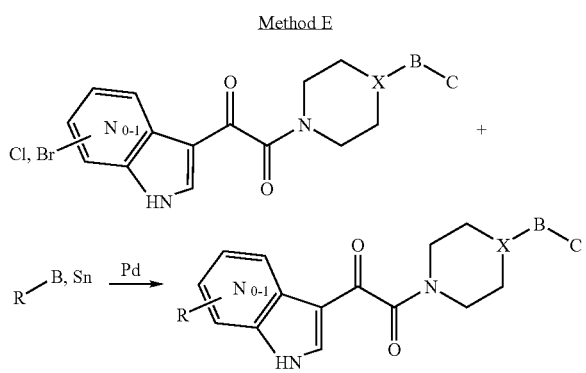

Method E

To a sealed tube, azaindole or indole halide (bromide or chloride), boron or stannane agent (1-20 eq.), Pd catalyst (including but not limited to Pd(PPh$_3$)$_4$, Pd(PPh$_3$)$_2$Cl$_2$, Pd(OAc)$_2$, Pd$_2$(dba)$_3$, PdCl$_2$(dppf)$_2$, 0.05-2 eq.), base (including but not limited to Na$_2$CO$_3$, K$_2$CO$_3$, Cs$_2$CO$_3$, Na$_2$HPO$_3$, NaH$_2$PO$_3$, Na$_3$PO$_4$, NaOAc, NaOEt, NaOtBu, Et$_3$N, iPr$_2$NEt, NaH, K$_2$HPO$_3$, KH$_2$PO$_3$, K$_3$PO$_4$, KOAc, KOEt, KOtBu, 1-20 eq.) were combined in dioxane, toluene or DMF in the presence of or in the absence of water, with or without using a ligand (including but not limited to BINOL, BINAP, 2,2'-bipyridyl, tri-alkylphosphine, dppe, dppf, AsPh$_3$, 1-2 eq.). The reaction was heated at 50-170° C. for 2-17 h. After the mixture cooled down to rt, it was poured into water. The solution was extracted with EtOAc or dichloromethane. The combined extract was concentrated to give a residue which was purified by silica gel column chromatography or Shimadzu automated preparative HPLC System.

TABLE A-2

| Compd # | Structure | Method Used | MS (M + H)$^+$ Calcd. | MS (M + H)$^+$ Observ. And Retention Time and NMR |
|---|---|---|---|---|
| A-1 | 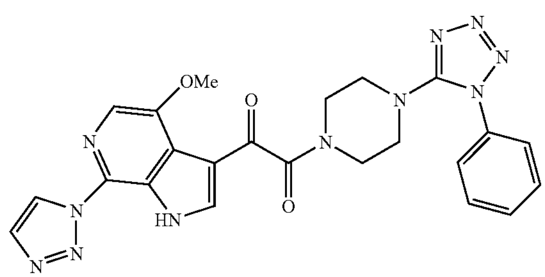 | D | 500.19 | 500.18<br>Rf = 1.78 min (column F, flow rate b) |
| A-2 | 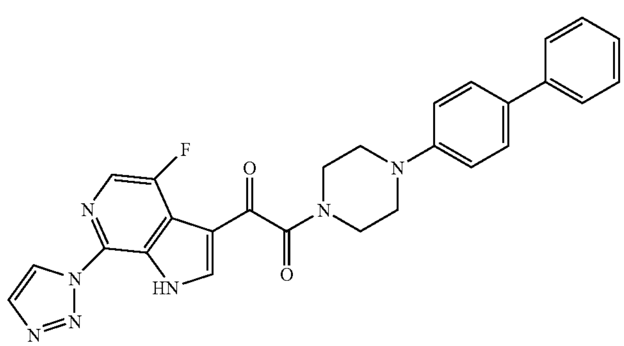 | B | 496.19 | 495.95<br>Rf = 2.30 min (column F, flow rate b)<br>HRMS: 496.1917 (calc. 496.1897) |
| A-3 | 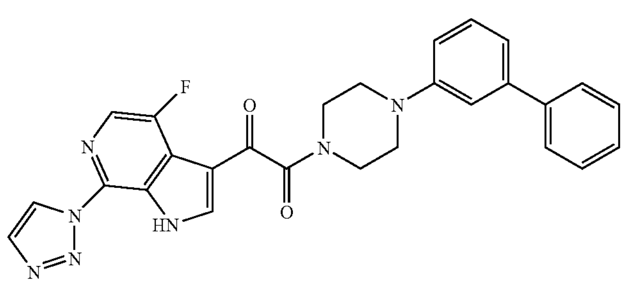 | B | 496.19 | 495.96<br>Rf = 2.24 min (column F, flow rate b)<br>HRMS: 496.1909 (calc. 496.1897) |

TABLE A-2-continued

| Compd # | Structure | Method Used | MS (M + H)+ Calcd. | MS (M + H)+ Observ. And Retention Time and NMR |
|---|---|---|---|---|
| A-4 | 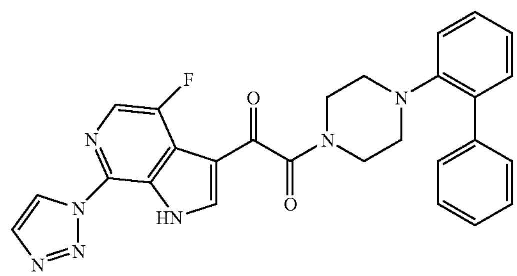 | B | 496.19 | 495.96<br>Rf = 2.40 min (column F, flow rate b)<br>HRMS: 496.1917 (calc. 496.1897) |
| A-5 | 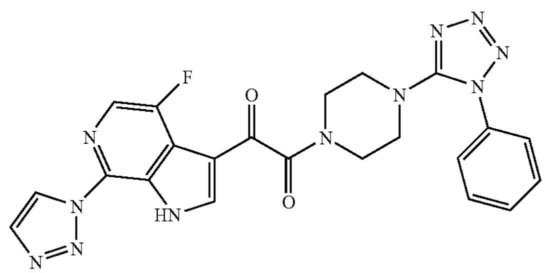 | B | 488.17 | 488.17<br>Rf = 1.56 min (column I)<br>$^1$H NMR (500 MHz, DMSO-d$_6$) δ9.00 (s, 1H), 8.36 (s, 1H), 8.31 (d, 1H, J = 2 Hz), 8.1 (d,, 1H, J = 1.5 Hz), 7.64 (m, 5H), 3.72 (m, 2H), 3.48 (m, 2H), 3.34 (m, 2H), 3.18 (m, 2H); $^{13}$C NMR (125 MHz, DMSO-d$_6$) δ183.9, 165.4, 156.9, 153.2, 151.1, 141.6, 134.3, 134.0, 131.4, 130.0, 125.8, 124.3, 122.9, 121.9, 121.8, 113.0, 48.1, 47.5, 44.3.<br>HRMS: 488.1725 (calc. 488.1707) |
| A-6 | 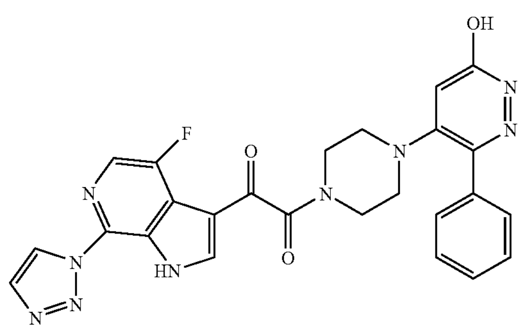 | B | 514.18 | 514.20<br>Rf = 1.61 min (column I)<br>$^1$H NMR (500 MHz, DMSO-d$_6$) δ8.98 (s, 1H), 8.32 (s, 1H), 8.29 (s, 1H), 8.10 (s, 1H), 7.69 (m, 2H), 7.43 (m, 3H), 6.16 (s, 1H), 3.60-2.83 (m, 8H); $^{13}$C NMR (125 MHz, DMSO-d$_6$) δ183.9, 165.3, 161.4, 152.9, 151.1, 141.8, 141.4, 136.1, 133.9, 131.4, 128.6, 128.4, 127.6, 125.9, 125.7, 122.8, 113.0, 110.2, 49.1, 48.5, 44.4.<br>HRMS: 514.1765 (calc. 514.1751) |
| A-7 | 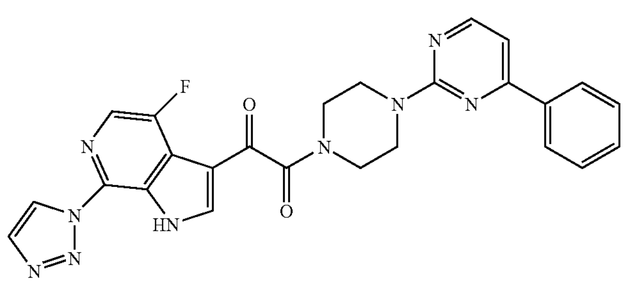 | B | 498.18 | 498.23<br>Rf = 1.81 min (column I)<br>HRMS: 498.1818 (calc. 498.1802) |

TABLE A-2-continued

| Compd # | Structure | Method Used | MS (M + H)+ Calcd. | MS (M + H)+ Observ. And Retention Time and NMR |
|---|---|---|---|---|
| A-8 | 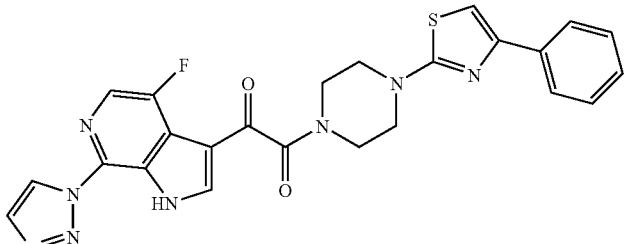 | B | 503.14 | 502.89<br>Rf = 2.13 min (column F, flow rate b)<br>$^1$H NMR (500 MHz, DMSO-d$_6$) δ9.01 (s, 1H), 8.41 (s, 1H), 8.37 (s, 1H), 8.12 (s, 1H), 7.86 (m, 2H), 7.39 (m, 4H), 3.84-3.52 (m, 8H), 2.45 (s, 3H); $^{13}$C NMR (125 MHz, DMSO-d$_6$) δ183.8, 170.0, 165.4, 153.1, 151.1, 150.5, 141.3, 134.4, 133.9, 131.3, 128.3, 127.4, 125.6, 122.7, 121.8, 121.7, 113.0, 102.9, 48.0, 47.4, 44.5.<br>HRMS: 503.1401 (calc. 503.1414) |
| A-9 | 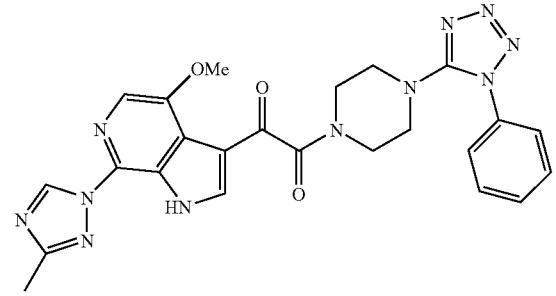 | B | 513.20 | 513.96<br>Rf = 1.78 min (column F, flow rate b)<br>$^1$H NMR (500 MHz, DMSO-d$_6$) δ9.22 (s, 1H), 8.23 (s, 1H), 7.88 (s, 1H), 7.64 (m, 5H), 3.98 (s, 3H), 3.71-3.17 (m, 8H), 2.45 (s, 3H); $^{13}$C NMR (125 MHz, DMSO-d$_6$) δ185.3, 166.2, 161.3, 156.9, 149.2, 142.1, 138.6, 134.3, 123.0, 129.9, 129.6, 124.3, 123.7, 122.8, 121.2, 114.1, 56.8, 47.9, 47.6, 44.2, 13.7.<br>HRMS: 514.2039 (calc. 514.2064) |
| A-10 | 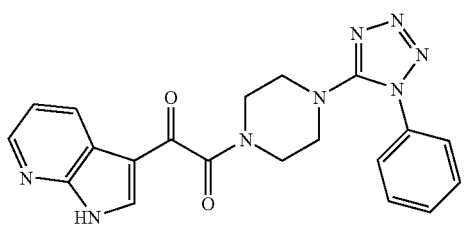 | B | 403.16 | 403.11<br>Rf = 1.60 min (column F, flow rate b)<br>$^1$H NMR (500 MHz, DMSO-d$_6$) δ8.47 (m, 3H), 7.63 (m, 5H), 7.31 (m, 1H), 3.91-3.15 (m, 8H); $^{13}$C NMR (125 MHz, DMSO-d$_6$) δ185.7, 165.4, 156.9, 149.1, 144.8, 137.4, 134.3, 129.9, 129.8, 129.3, 124.3, 118.6, 117.3, 111.7, 48.1, 47.5, 44.3.<br>HRMS: 403.1651 (calc. 433.1631) |
| A-11 | 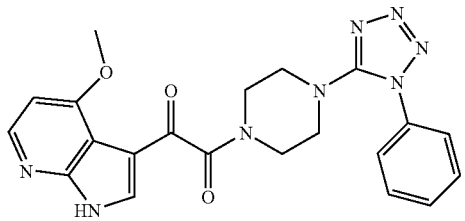 | B | 433.17 | 433.19<br>Rf = 1.33 min (column F, flow rate b)<br>$^1$H NMR (500 MHz, DMSO-d$_6$) δ8.23 (d, 1H, J = 5.5 Hz), 8.18 (s, 1H), 7.63 (m, 5H), 6.87 (d, 1H, J = 5.5 Hz), 3.92 (s, 3H), 3.67-3.15 (m, 8H); $^{13}$C NMR (125 MHz, DMSO-d$_6$) δ185.0, 166.6, 160.2, 156.9, 151.1, 146.7, 135.3, 134.3, 129.9, 129.8, 124.3, 112.5, 106.3, 100.8, 55.7, 48.0, 47.5, 44.2, 40.2.<br>HRMS: 433.1752 (calc. 433.1737) |

TABLE A-2-continued

| Compd # | Structure | Method Used | MS (M + H)+ Calcd. | MS (M + H)+ Observ. And Retention Time and NMR |
|---|---|---|---|---|
| A-12 | 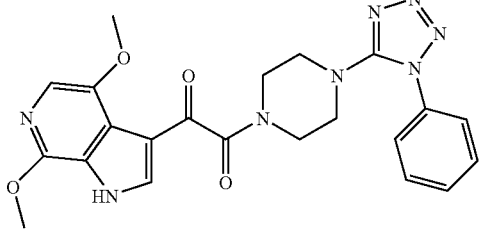 | B | 463.18 | 463.22<br>Rf = 1.55 min (column F, flow rate b)<br>$^1$H NMR (500 MHz, DMSO-$d_6$) δ8.15 (s, 1H), 7.64 (m, 5H), 7.47 (m, 1H), 4.02 (s, 3H), 3.83 (s, 3H), 3.66 (m, 2H), 3.39 (m, 2H), 3.31 (m, 2H), 3.17 (m, 2H); $^{13}$C NMR (125 MHz, DMSO-$d_6$) δ185.4, 166.5, 156.9, 146.3, 145.8, 136.5, 134.3, 129.9, 129.8, 124.3, 122.4, 122.2, 119.6, 114.4, 57.0, 52.9, 47.9, 47.5, 44.2. HRMS: 463.1853 (calc. 463.1842) |
| A-13 | 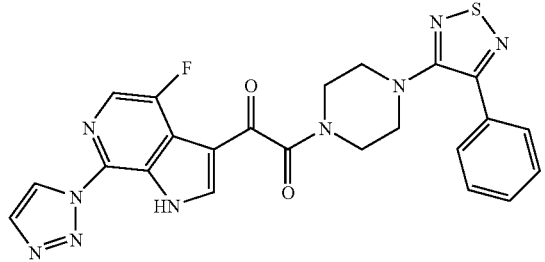 | B | 504.14 | 504.17<br>Rf = 2.23 min (column F, flow rate b)<br>$^1$H NMR (500 MHz, DMSO-$d_6$) δ9.01 (s, 1H), 8.36 (s, 1H), 8.31 (d, 1H, J = 2 Hz), 8.1 (d,, 1H, J = 1 Hz), 7.91-7.50 (m, 5H), 3.78 (m, 2H), 3.55 (m, 2H), 3.27 (m, 2H), 3.14 (m, 2H); $^{13}$C NMR (125 MHz, DMSO-$d_6$) δ183.9, 165.4, 161.3, 153.1, 151.1, 141.2, 133.8, 132.9, 131.3, 129.5, 128.7, 127.2, 125.9, 125.6, 122.7, 121.7, 113.0, 49.2, 48.7, 44.6. HRMS: 504.1370 (calc. 504.1366) |
| A-14 | 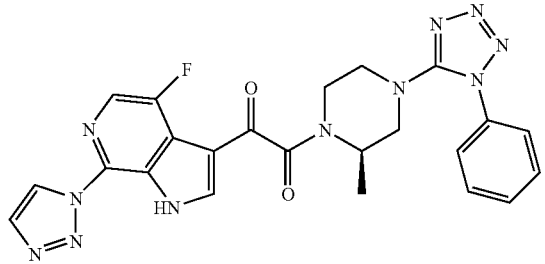 | B | 502.19 | 502.20<br>Rf = 1.80 min (column F, flow rate b)<br>HRMS: 502.1874 (calc. 502.1864) |
| A-15 | 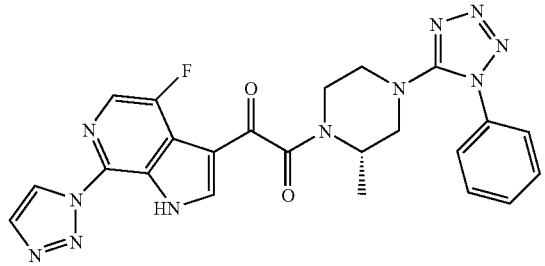 | B | 502.19 | 502.22<br>Rf = 1.88 min (column F, flow rate b)<br>HRMS: 502.1874 (calc. 502.1864) |

TABLE A-2-continued

| Compd # | Structure | Method Used | MS (M + H)+ Calcd. | MS (M + H)+ Observ. And Retention Time and NMR |
|---|---|---|---|---|
| A-16 | 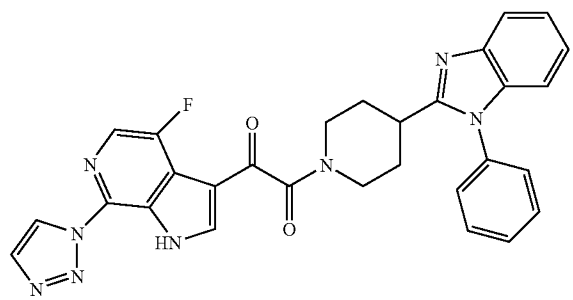 | B | 535.20 | 535.28<br>Rf = 1.57 min (column F, flow rate b)<br>HRMS: 535.1990 (calc. 535.2006) |
| A-17 | 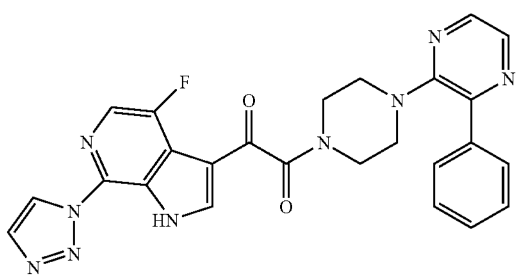 | B | 498.18 | 498.20<br>Rf = 2.02 min (column F, flow rate b)<br>$^1$H NMR (500 MHz, DMSO-$d_6$) δ9.05 (s, 1H), 8.37-7.42 (m, 10H), 3.67 (m, 2H), 3.44 (m, 2H), 3.24 (m, 2H), 3.11 (m, 2H) |
| A-18 | 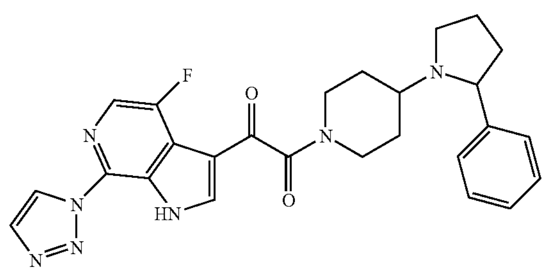 | B | 488.22 | 488.22<br>Rf = 1.54 min (column F, flow rate b) |
| A-19 | 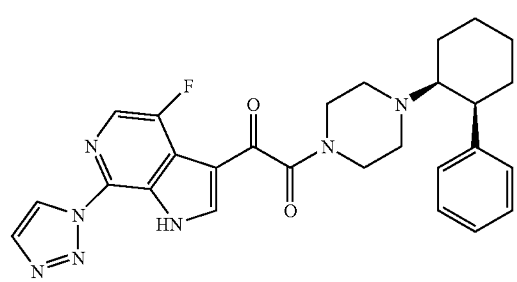 | B | 502.24 | 502.24<br>Rf = 1.68 min (column F, flow rate b) |
| A-20 | 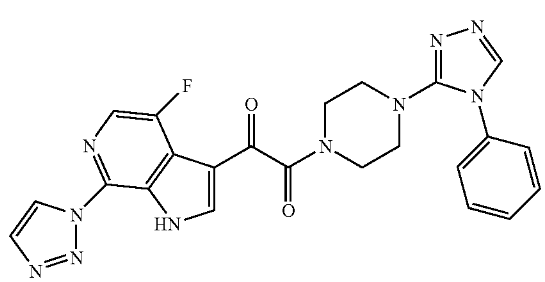 | B | 487.18 | 487.30<br>Rf = 1.60 min (column F, flow rate b) |

TABLE A-2-continued

| Compd # | Structure | Method Used | MS (M + H)+ Calcd. | MS (M + H)+ Observ. And Retention Time and NMR |
|---|---|---|---|---|
| A-21 | 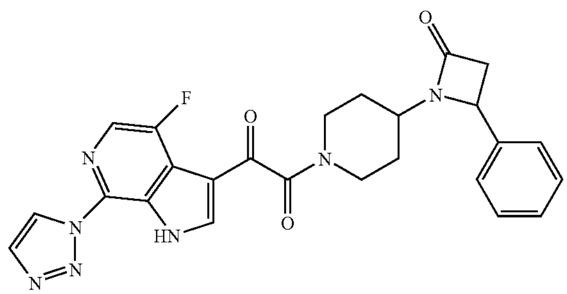 | B | 488.18 | 488.30<br>Rf = 2.08 min (column F, flow rate b) |
| A-22 | 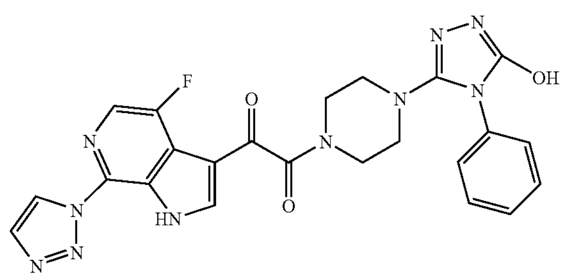 | B | 503.17 | 503.28<br>Rf = 1.75 min (column F, flow rate b) |
| A-23 | 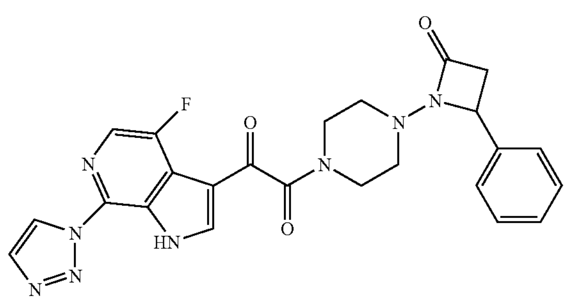 | B | 489.18 | 489.32<br>Rf = 1.98 min (column F, flow rate b) |
| A-24 | 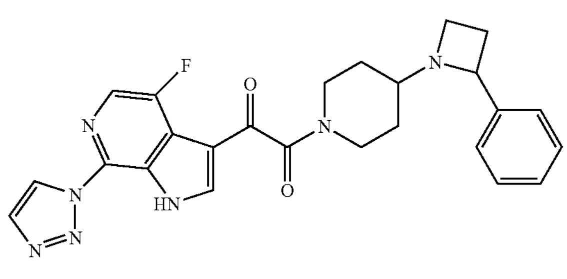 | B | 474.21 | 474.37<br>Rf = 1.72 min (column F, flow rate b) |
| A-25 | 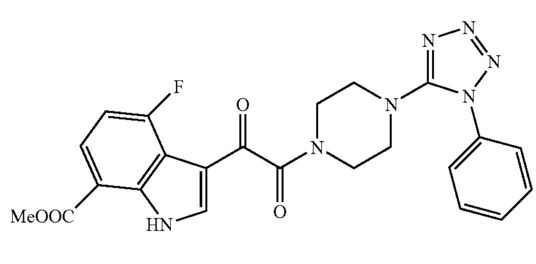 | A | 478.16 | 478.11<br>Rf = 1.82 min (column F, flow rate b) |

TABLE A-2-continued

| Compd # | Structure | Method Used | MS (M + H)+ Calcd. | MS (M + H)+ Observ. And Retention Time and NMR |
|---|---|---|---|---|
| A-26 | 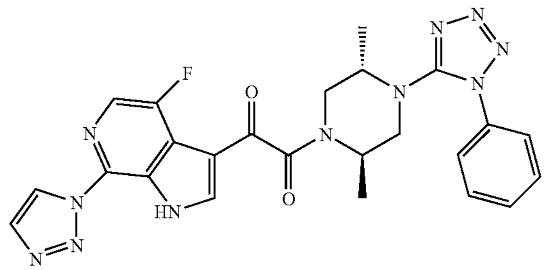 | B | 516.20 | 516.24<br>Rf = 1.84 min (column F, flow rate b) |
| A-27 | 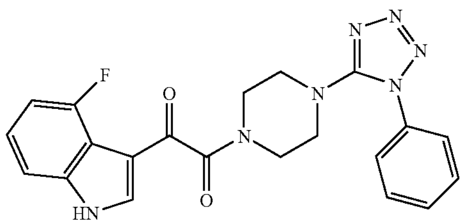 | A | 420.16 | 420.30<br>Rf = 1.62 min (column H, flow rate b) |
| A-28 | 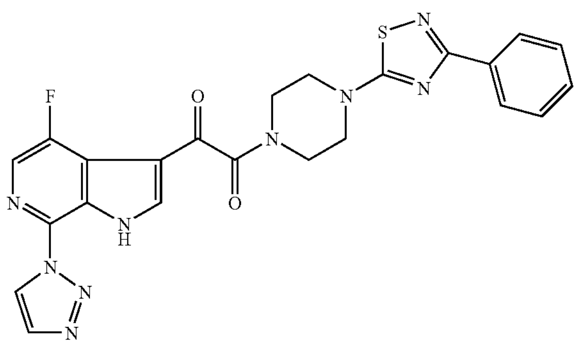 | B | 504.14 | 503.87<br>Rf = 2.19 min (column F, flow rate b) |
| A-29 | 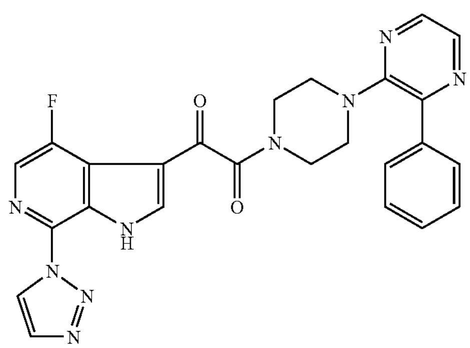 | B | 498.18 | 498.20<br>Rf = 2.02 min (column F, flow rate b) |
| A-30 | 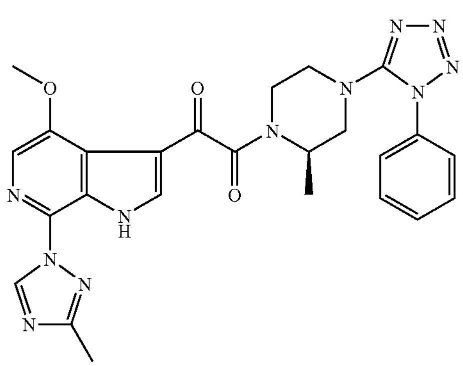 | B | 528.22 | 528.27<br>Rf = 1.73 min (column F, flow rate b) |

TABLE A-2-continued

| Compd # | Structure | Method Used | MS (M + H)+ Calcd. | MS (M + H)+ Observ. And Retention Time and NMR |
|---|---|---|---|---|
| A-31 | 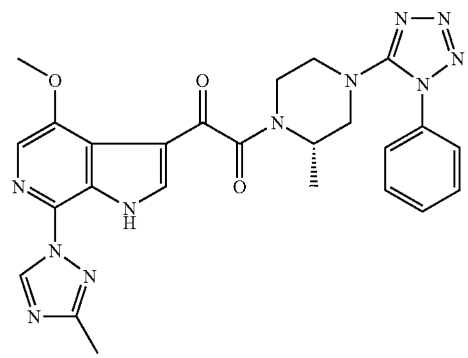 | B | 528.22 | 528.27<br>Rf = 1.71 min (column F, flow rate b) |
| A-32 | 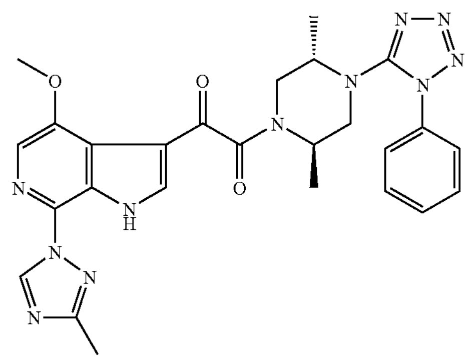 | B | 542.24 | 542.28<br>Rf = 1.77 min (column F, flow rate b) |
| A-33 | 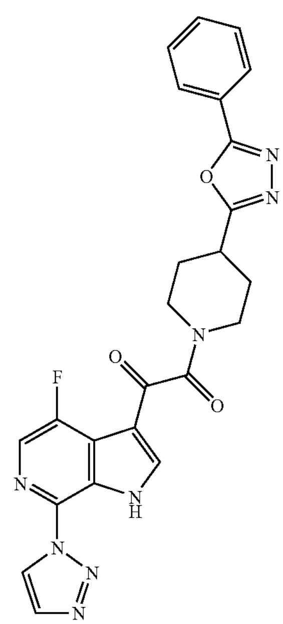 | B | 487.16 | 487.02<br>Rf = 1.46 min (column K, flow rate 3 ml/min, solvent A = water, solvent B = acetonitrile, modifier = 10 mM NH$_4$OAC, start % solvent B = 10%, final % solvent B = 95%) |

TABLE A-2-continued

| Compd # | Structure | Method Used | MS (M + H)+ Calcd. | MS (M + H)+ Observ. And Retention Time and NMR |
|---|---|---|---|---|
| A-34 | 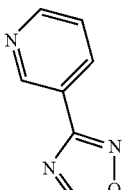 | B | 488.16 | 488.00<br>Rf = 1.37 min (column K, flow rate 3 ml/min, solvent A = water, solvent B = acetonitrile, modifier = 10 mM NH₄OAC, start % solvent B = 10%, final % solvent B = 95%) |
| A-35 | 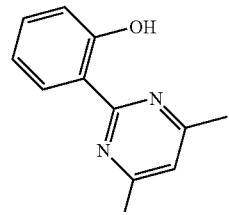 | B | 528.19 | 528.06<br>Rf = 1.87 min (column K, flow rate 3 ml/min, solvent A = water, solvent B = acetonitrile, modifier = 10 mM NH₄OAC, start % solvent B = 10%, final % solvent B = 95%) |

TABLE A-2-continued
| Compd # | Structure | MS Method Used | MS (M + H)+ Calcd. | MS (M + H)+ Observ. And Retention Time and NMR |
|---|---|---|---|---|
| A-36 | 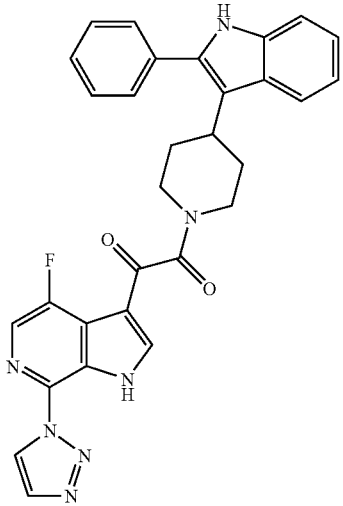 | B | 534.21 | 534.13<br>Rf = 2.00 min (column K, flow rate 3 ml/min, solvent A = water, solvent B = acetonitrile, modifier = 10 mM NH4OAC, start % solvent B = 10%, final % solvent B = 95%) |
| A-37 | 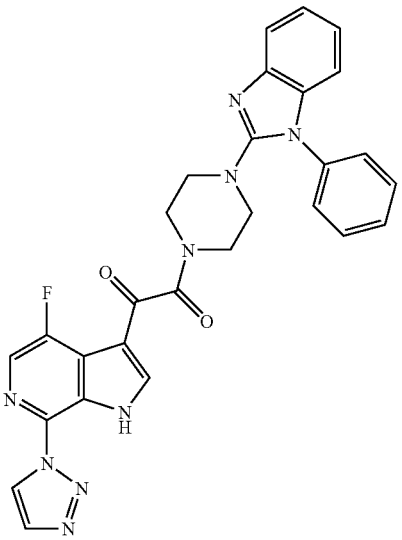 | B | 536.20 | 536.41<br>Rf = 1.66 min (column F, flow rate b) |

TABLE A-2-continued

| Compd # | Structure | Method Used | MS (M + H)+ Calcd. | MS (M + H)+ Observ. And Retention Time and NMR |
|---|---|---|---|---|
| A-38 | 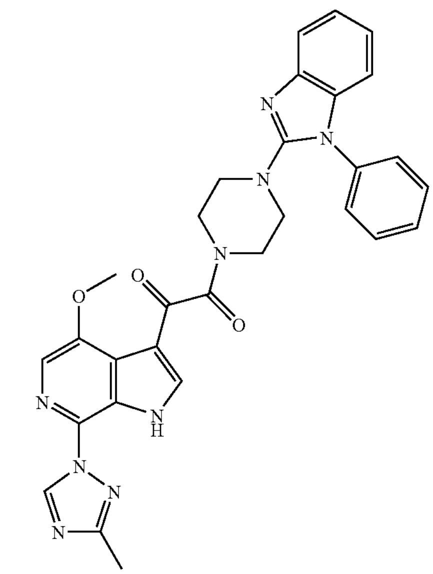 | B | 562.23 | 562.42<br>Rf = 1.62 min (column F, flow rate b) |
| A-39 | 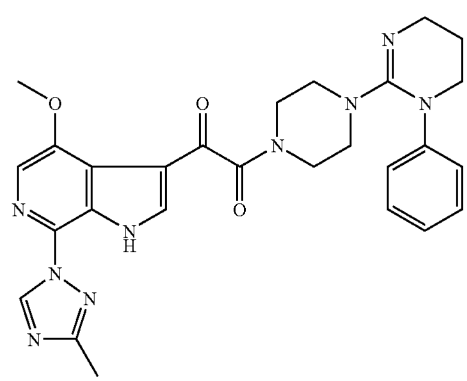 | B | 528.25 | 528.21<br>Rf = 3.00 min (column H, flow rate b, gradient time 4 min, start % solvent B = 20%, final % solvent B = 60%) |
| A-40 | 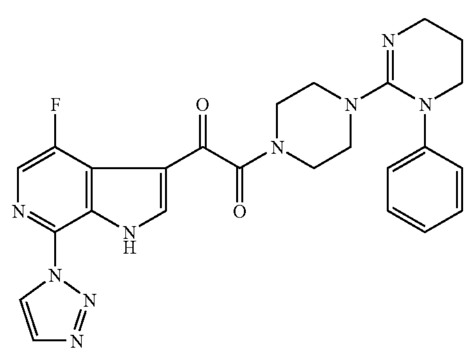 | B | 502.21 | 502.30<br>Rf = 1.57 min (column F, flow rate b) |

TABLE A-2-continued

| Compd # | Structure | Method Used | MS (M + H)+ Calcd. | MS (M + H)+ Observ. And Retention Time and NMR |
|---|---|---|---|---|
| A-41 | 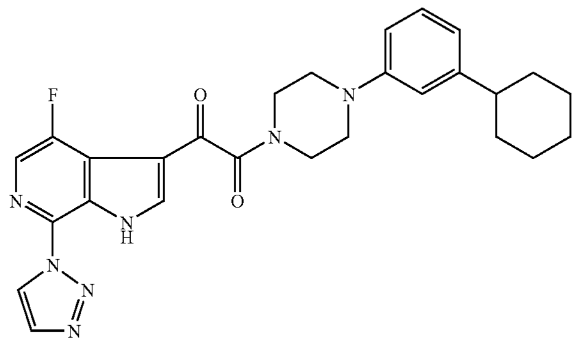 | B | 502.24 | 502.31<br>Rf = 2.46 min (column F, flow rate b) |
| A-42 | 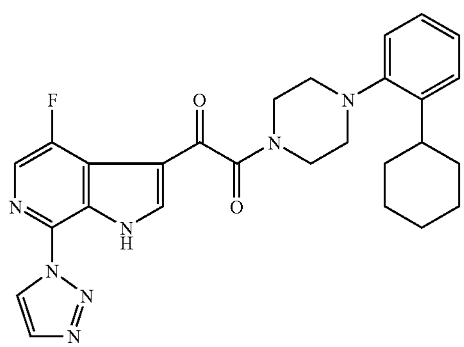 | B | 502.24 | 502.33<br>Rf = 2.57 min (column F, flow rate b) |
| A-43 | 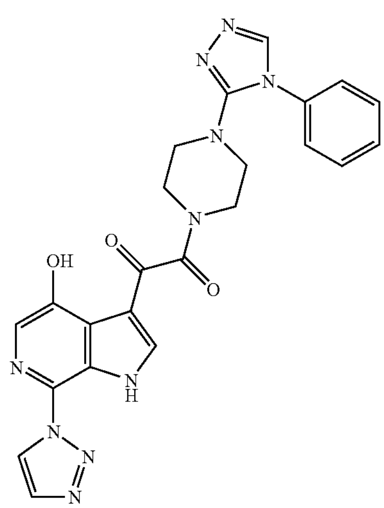 | B | 485.18 | 485.33<br>Rf = 1.47 min (column F, flow rate b) |

TABLE A-2-continued

| Compd # | Structure | Method Used | MS (M + H)+ Calcd. | MS (M + H)+ Observ. And Retention Time and NMR |
|---|---|---|---|---|
| A-44 | 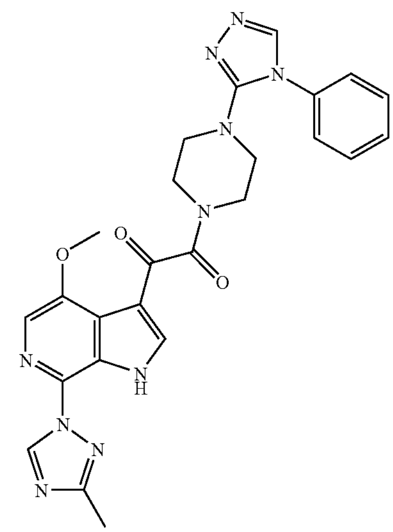 | B | 513.21 | 513.31<br>Rf = 1.53 min (column F, flow rate b)<br>$^1$H, NMR (500 MHz, CDCl$_3$) δ10.94 (s, 1H), 9.25 (s, 1H), 8.30 (d, 1H), 8.20 (d, 1H), 7.76 (s, 1H), 7.61 (m, 3H), 7.50 (d, 2H), 4.03 (s, 3H), 3.79 (m, 2H), 3.56 (m, 2H), 3.38 (m, 2H), 3.31 (m, 2H), 2.60 (s, 3H). |
| A-45 | 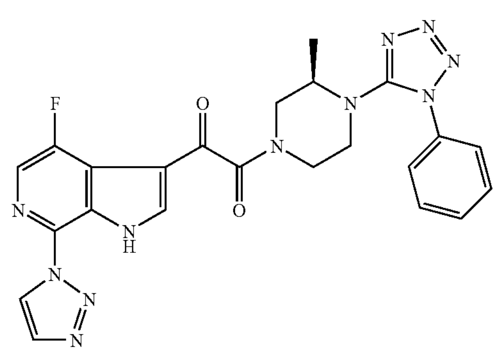 | B | 502.19 | 502.33<br>Rf = 1.88 min (column F, flow rate b) |
| A-46 | 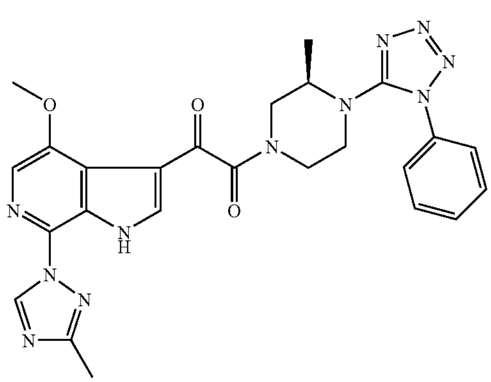 | B | 528.22 | 528.37<br>Rf = 1.88 min (column F, flow rate b) |

TABLE A-2-continued

| Compd # | Structure | MS Method Used | MS (M + H)+ Calcd. | MS (M + H)+ Observ. And Retention Time and NMR |
|---|---|---|---|---|
| A-47 | 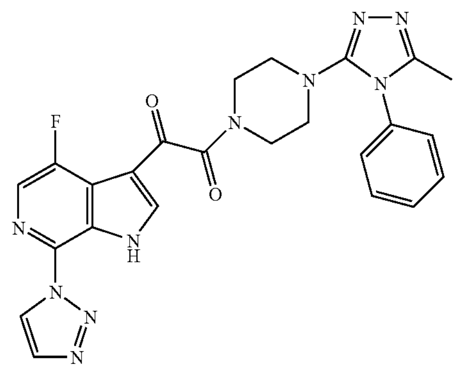 | B | 501.19 | 501.31<br>Rf = 1.53 min (column F, flow rate b) |
| A-48 | 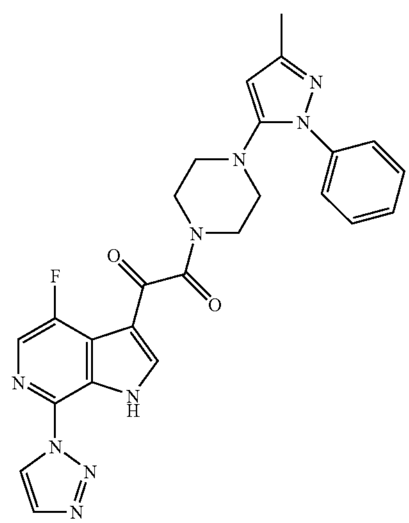 | B | 500.20 | 500.35<br>Rf = 1.97 min (column F, flow rate b) |
| A-49 | 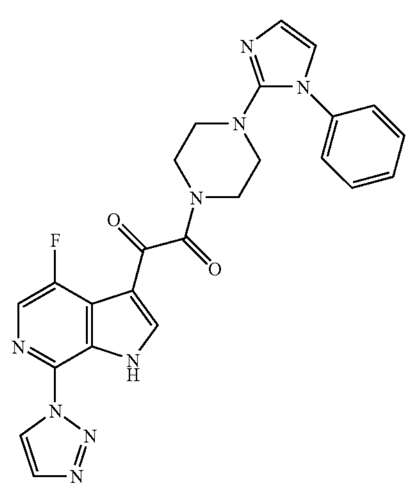 | B | 486.18 | 486.23<br>Rf = 1.52 min (column F, flow rate b) |

TABLE A-2-continued

| Compd # | Structure | Method Used | MS (M + H)+ Calcd. | MS (M + H)+ Observ. And Retention Time and NMR |
|---|---|---|---|---|
| A-50 | 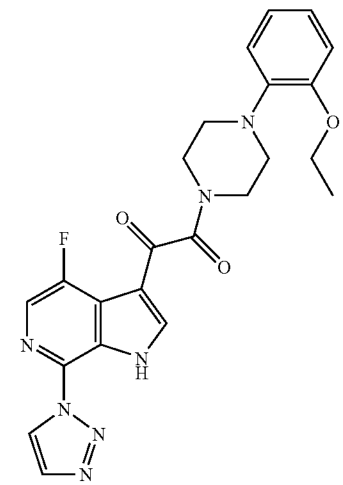 | B | 464.18 | 464.05<br>Rf = 1.68 min (column K, flow rate 3 ml/min, solvent A = water, solvent B = acetonitrile, modifier = 10 mM NH₄OAC, start % solvent B = 10%, final % solvent B = 95%) |
| A-51 | 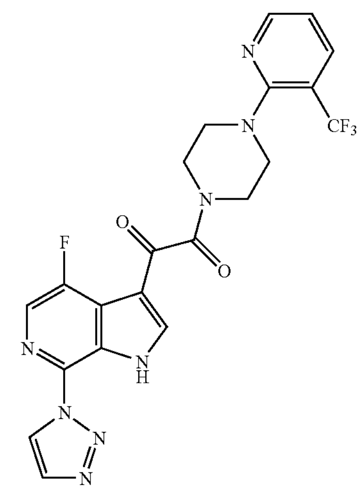 | B | 489.14 | 489.00<br>Rf = 1.77 min (column K, flow rate 3 ml/min, solvent A = water, solvent B = acetonitrile, modifier = 10 mM NH₄OAC, start % solvent B = 10%, final % solvent B = 95%) |
| A-52 | 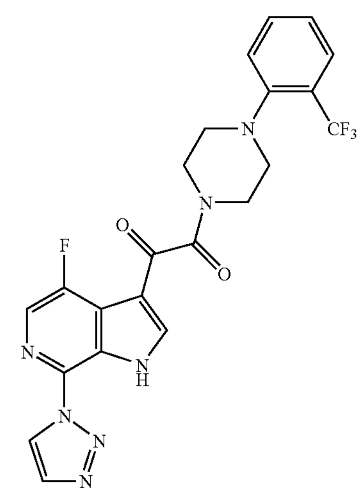 | B | 488.15 | 488.00<br>Rf = 2.02 min (column K, flow rate 3 ml/min, solvent A = water, solvent B = acetonitrile, modifier = 10 mM NH₄OAC, start % solvent B = 10%, final % solvent B = 95%) |

TABLE A-2-continued

| Compd # | Structure | Method Used | MS (M + H)+ Calcd. | MS (M + H)+ Observ. And Retention Time and NMR |
|---|---|---|---|---|
| A-53 | 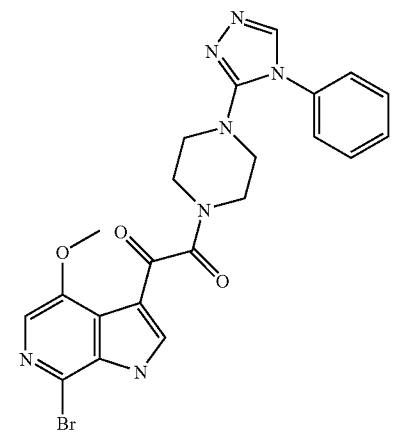 | B | 511.35 | 511.94<br>Rf = 1.53 (Column F, Flow rate b) |
| A-54 | 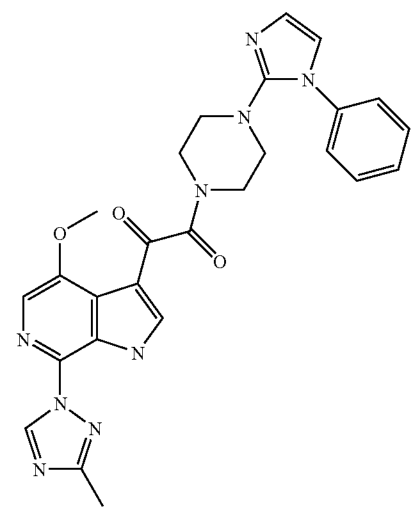 | A | 512.55 | 512.34<br>Rf = 1.41 (Column F, Flow rate b) |
| A-55 | 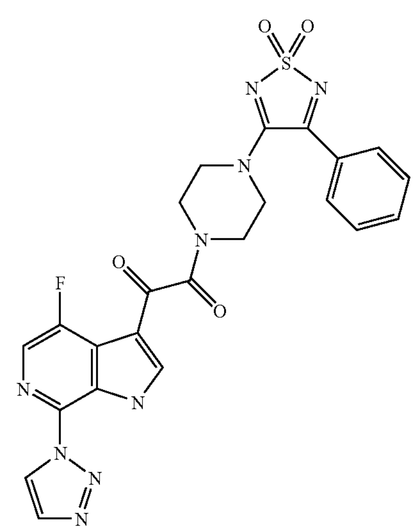 | A | 536.52 | 536.23<br>Rf = 1.77 min (Column F, Flow rate b) |

TABLE A-2-continued

| Compd # | Structure | Method Used | MS (M + H)+ Calcd. | MS (M + H)+ Observ. And Retention Time and NMR |
|---|---|---|---|---|
| A-56 | 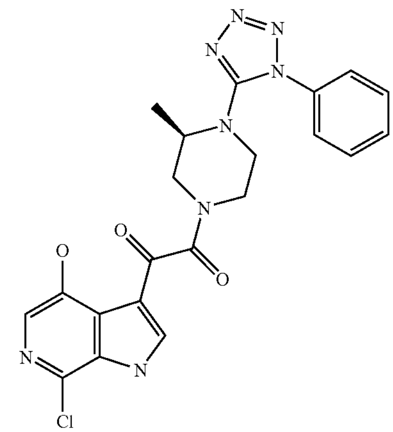 | B | 467.89 | 467.55<br>Rf = 2.63 (Column F, Flow rate a) |
| A-57 | 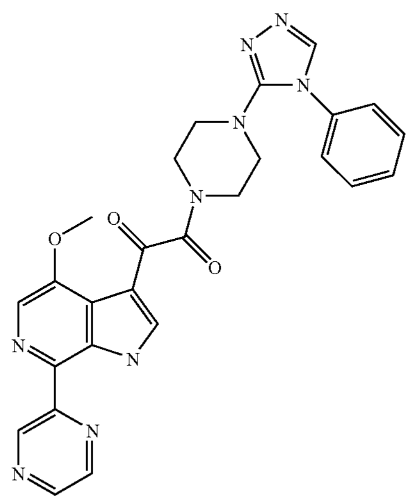 | E | 510.53 | 509.96<br>Rf = 1.51 (Column F, Flow rate b) |
| A-58 | 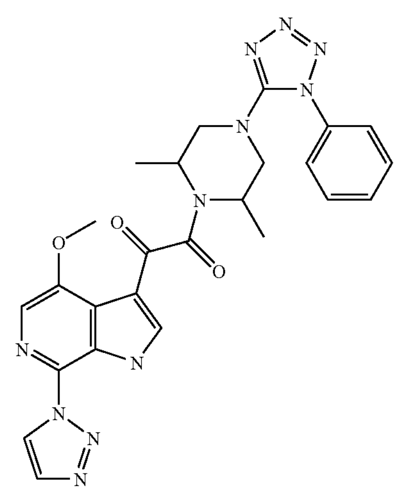 | B | 528.55 | 528.18<br>Rf = 1.75 (Column F, Flow rate b) |

TABLE A-2-continued

| Compd # | Structure | Method Used | MS (M + H)+ Calcd. | MS (M + H)+ Observ. And Retention Time and NMR |
|---|---|---|---|---|
| A-59 | 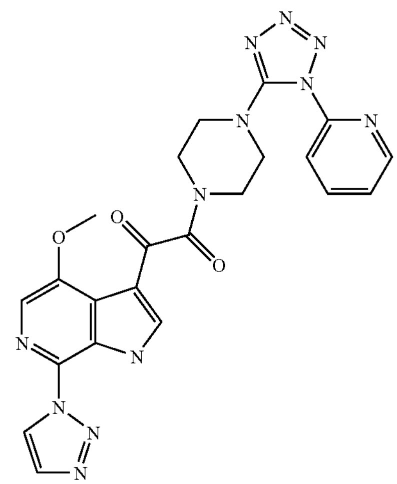 | B | 501.48 | 501.14<br>Rf = 1.47 (Column F, Flow rate b)<br>¹H NMR (500 MHz, CDCl₃) δ11.35 (s, 1H), 8.71 (s, 1H) 8.60 (s, 1H), 8.25 (d, 1H), 7.88 (m, 1H), 7.83 (m, 3H), 7.45 (m, 1H), 4.07 (s, 3H), 3.90 (m, 2H), 3.66 (m, 2H), 3.58 (m, 2H), 3.51 (m, 2H). |
| A-60 | 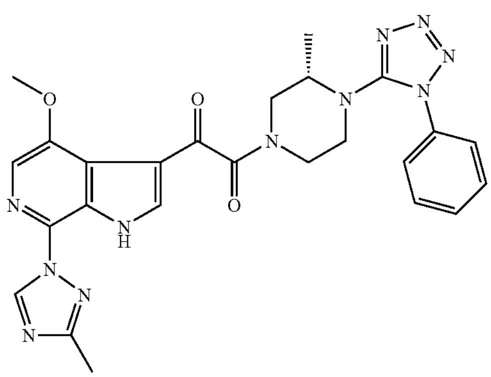 | B | 528.22 | 528.53<br>Rf = 1.84 min (column F, flow rate b)<br>HRMS: 528.2233 (calc. 528.2220)<br>¹H NMR (500 MHz, CDCl₃) δ11.06 (s, 1H), 9.05 (s, 1H), 8.16-8.13 (d & d, 1H, J = 3.05, 3.05 Hz), 7.69 (s, 1H), 7.60-7.50 (m, 5H), 4.34-4.09 (m, 1H), 4.00 (d, 3H, J = 2.14 Hz), 3.88-3.65 (m, 2H), 3.53-3.28 (m, 4H), 2.52 (s, 3H) 1.27-1.18 (d & d, 3H, J = 6.72, 6.72 Hz). |
| A-61 | 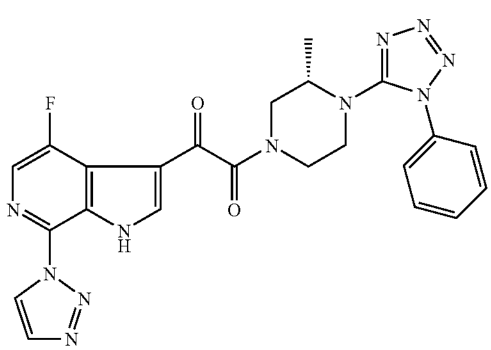 | B | 502.19 | 502.50<br>Rf = 1.88 min (column F, flow rate b)<br>HRMS: 502.1873 (calc. 502.1864)<br>¹H NMR (500 MHz, DMSO-D₆) δ13.03 (s, 1H), 8.99 (d, 1H, J = 4.88 Hz), 8.41-8.23 (m, 2H), 8.01 (s, 1H), 7.69-7.57 (m, 5H), 4.08 (m, 1H), 3.80-3.69 (m, 2H), 3.40-3.20 (m, 4H), 1.15-1.01 (d & d, 3H, J = 6.72, 6.71 Hz) |

TABLE A-2-continued

| Compd # | Structure | Method Used | MS (M + H)+ Calcd. | MS (M + H)+ Observ. And Retention Time and NMR |
|---|---|---|---|---|
| A-62 | 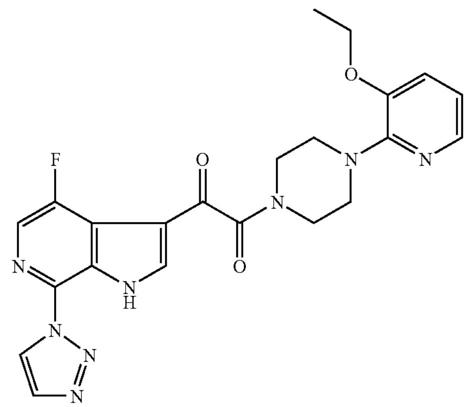 | B | 465.18 | 465.61<br>Rf = 1.66 min (column F, flow rate b)<br>HRMS: 465.1817 (calc. 465.1799) |
| A-63 | 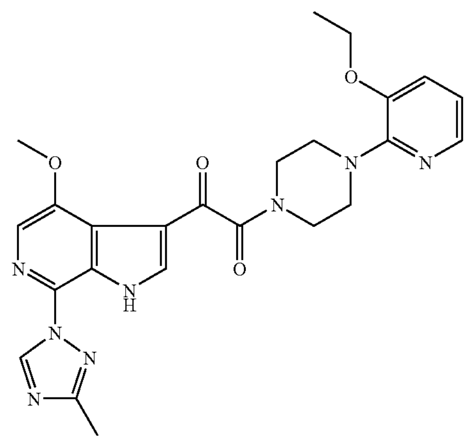 | B | 491.22 | 491.66<br>Rf = 2.01 min (column F, flow rate b)<br>HRMS: 491.2145 (calc. 491.2155) |
| A-64 | 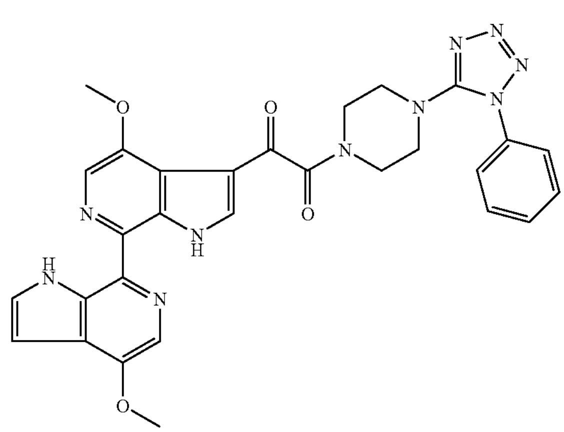 | B | 579.22 | 579.46<br>Rf = 1.84 min (column I, flow rate a) |

TABLE A-2-continued

| Compd # | Structure | Method Used | MS (M + H)+ Calcd. | MS (M + H)+ Observ. And Retention Time and NMR |
|---|---|---|---|---|
| A-66 | 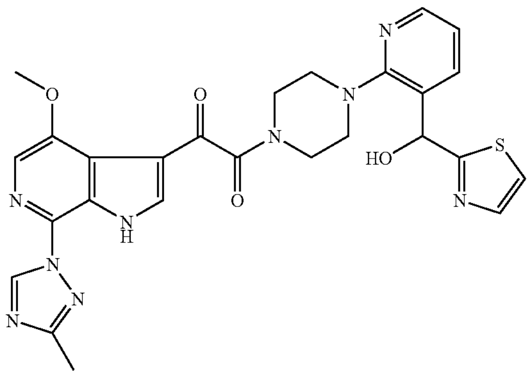 | B | 560.18 | 560.11<br>Rf = 1.40 min (column F, flow rate b) |
| A-67 | 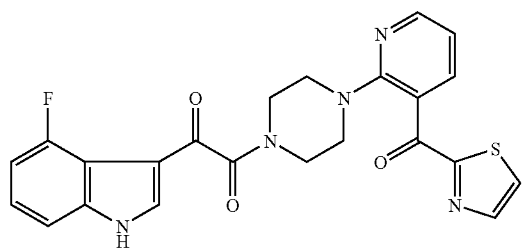 | A | 464.12 | 464.07<br>Rf = 1.60 min (column F, flow rate b) |
| A-68 | 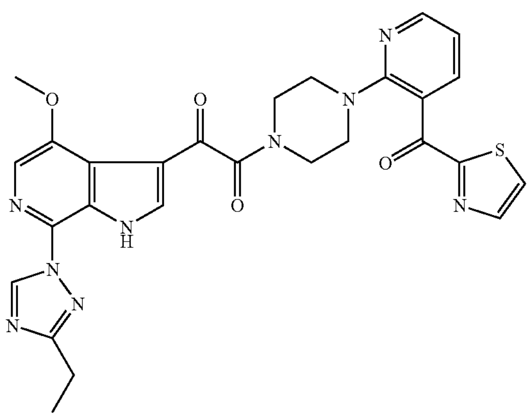 | B | 572.18 | 571.97<br>Rf = 1.74 min (column F, flow rate b)<br>¹H NMR (500 MHz, MeOD) δ9.11 (s, 1H), 8.33 (dd, 1H, J = 4.73, 1.98 Hz), 8.23 (s, 1H), 8.07 (dd, 1H, J = 7.78, 1.98 Hz), 8.04 (d, 1H, J = 3.05 Hz), 7.90 (d, 1H, J = 3.05 Hz), 7.75 (s, 1H), 6.91 (dd, 1H, J = 7.63, 4.85 Hz), 4.01 (s, 3H), 3.74-3.68 (m, 2H), 3.54-3.43 (m, 4H), 3.40-3.36 (m, 2H), 2.88 (q, 2H, J = 7.63 Hz), 1.39 (t, 3H, J = 7.63 Hz). |
| A-69 | 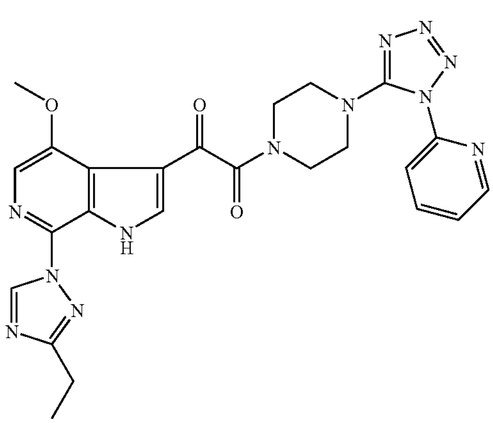 | B | 529.22 | 529.01<br>Rf = 1.53 min (column F, flow rate b)<br>¹H NMR (500 MHz, MeOD) δ9.10 (s, 1H), 8.59-8.58 (m, 1H), 8.25 (s, 1H), 8.05-8.01 (m, 1H), 7.81 (d, 1H, J = 7.93 Hz), 7.76 (s, 1H), 7.52-7.49 (m, 1H), 4.03 (s, 3H), 3.88-3.86 (m, 2H), 3.64-3.59 (m, 2H), 3.55-3.51 (m, 2H), 3.46-3.41 (m, 2H), 2.88 (q, 2H, J = 7.63 Hz), 1.38 (t, 3H, J = 7.63 Hz). |

TABLE A-2-continued

| Compd # | Structure | Method Used | MS (M + H)+ Calcd. | MS (M + H)+ Observ. And Retention Time and NMR |
|---|---|---|---|---|
| A-70 | 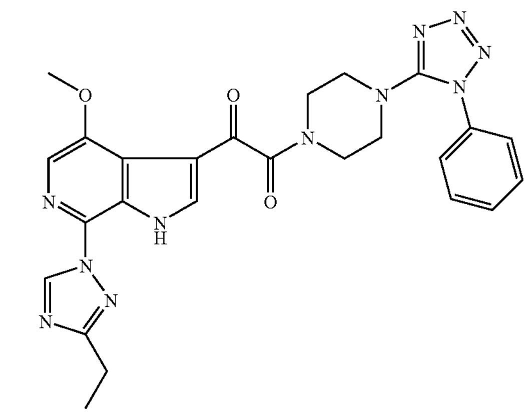 | B | 528.22 | 528.01<br>Rf = 1.57 min (column F, flow rate b)<br>$^1$H NMR (500 MHz, MeOD) δ9.11 (s, 1H), 8.24 (s, 1H), 7.76 (s, 1H), 7.61-7.55 (m, 5H), 4.02 (s, 3H), 3.84-3.77 (m, 2H), 3.57-3.52 (m, 2H), 3.43-3.38 (m, 2H), 3.29-3.25 (m, 2H), 2.88 (q, 2H, J = 7.63 Hz), 1.38 (t, 3H, J = 7.63 Hz). |
| A-71 | 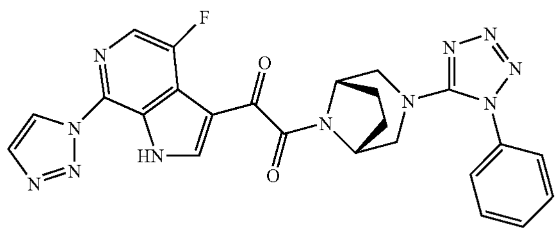 | B | 514.19 | 514.18<br>HRMS: 514.1844 (calc. 514.1864)<br>$^1$H NMR (500 MHz, DMSO-D$_6$) δ13.00 (s, 1H), 9.01 (s, 1H) 8.37 (s, 1H), 8.30 (d, J = 2 Hz, 1H), 8.11 (d, J = 1 Hz, 1H), 7.68-7.61 (m, 5H), 4.67 (s, 1H), 4.23 (s, 1H), 3.33-3.29 (m, 2H), 3.25-3.18 (m, 2H), 1.90-1.83 (m, 4H). |
| A-72 | 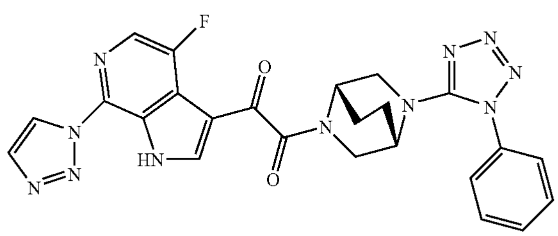 | B | 514.19 | 514.19<br>Rf = 2.30 min (column E, flow rate b, gradient time 4 min)<br>HRMS: 514.1874 (calc. 514.1864)<br>$^1$H NMR (300 MHz, DMSO-D6) δ13.01 (s, 1H), 8.98 (s, 1H), 8.42-8.27 (m, 2H), 8.11 (s, 1H), 7.62-7.50 (m, 5H), 4.53-4.23 (m, 1H), 4.05-3.87 (m, 2H), 3.70-3.59 (m, 1H), 3.42-3.10 (m, 2H), 2.13-2.10 (m, 1H), 1.98-1.72 (m, 3H). |
| A-73 | 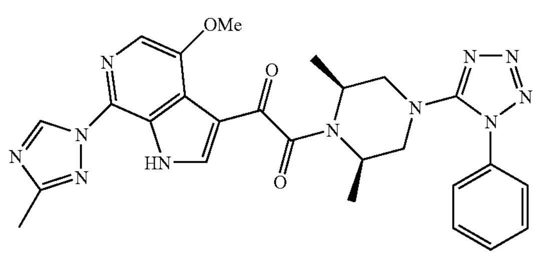 | B | 542.24 | 542.23<br>HRMS: 516.2366 (calc. 516.2377)<br>$^1$H NMR (300 MHz, DMSO-D$_6$) δ12.36 (s, 1H), 9.23 (s, 1H), 8.19 (s, 1H), 7.87 (s, 1H), 7.70-7.62 (m, 5H), 4.59-4.56 (m, 1H), 3.95 (s, 3H), 3.83-3.79 (m, 1H), 3.40-3.28 (m, 2H), 3.17-3.12 (dd, J = 12, 4 Hz, 1H), 2.98-2.93 (dd, J = 12, 4 Hz, 1H), 2.48 (s, 3H), 1.23-1.17 (m, 6H). |

TABLE A-2-continued

| Compd # | Structure | Method Used | MS (M + H)+ Calcd. | MS (M + H)+ Observ. And Retention Time and NMR |
|---|---|---|---|---|
| A-74 | 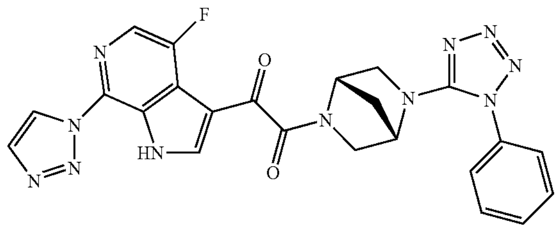 | B | 500.17 | 500.47<br>HRMS: 500.1707 (calc. 500.1683)<br>$^1$H NMR (300 MHz, DMSO-D$_6$) δ ppm 13.00 (s, 1H), 9.00 (s, 1H), 8.51-8.44 (m, 1H), 8.28 (d, J = 2 Hz, 1H), 8.12 (s, 1H), 7.64-7.54 (m, 5H), 4.84-4.49 (m, 2H), 3.85-3.55 (m, 2H), 3.26-3.16 (m, 1H), 3.07-2.98 (m, 1H), 2.01-1.93 (t, J = 12 Hz, 2H) |

Example Chemistry Section B

The following general methods apply to Example Chemistry Section B:

LCMS Data:

Method 1
  Gradient time: 2 min
  Flow rate: 4 mL/min
  Stop time Gradient time+1 minute
  Starting conc: 0% B
  Eluent A: 10% MeOH/90% H$_2$O with 0.1% TFA
  Eluent B: 90% MeOH/10% H$_2$O with 0.1% TFA
  Column: Phenomenex-luna 3.0×50 mm S10

Method 2
  Gradient time: 2 min
  Flow rate: 5 mL/min
  Stop time Gradient time+1 minute
  Starting conc: 0% B
  Eluent A: 10% MeOH/90% H$_2$O with 0.1% TFA
  Eluent B: 90% MeOH/10% H$_2$O with 0.1% TFA
  Column: Phenomenex-luna 10 u C18 3.0×50 mm Method 3
  Gradient time: 2 min
  Flow rate: 5 mL/min
  Stop time Gradient time+1 minute
  Starting conc: 0% B
  Eluent A: 5% ACN/95% H$_2$O with 10 mm Ammonium Acetate
  Eluent B: 95% ACN/5% H$_2$O with 10 mm Ammonium Acetate
  Column: Luna 4.6×50 mm S10

Method 4
  Gradient time: 3 min
  Flow rate: 4 mL/min
  Stop time Gradient time+1 minute
  Starting conc: 0% B
  Eluent A: 10% MeOH/90% H$_2$O with 0.1% TFA
  Eluent B: 90% MeOH/10% H$_2$O with 0.1% TFA
  Column: Phenomenex-luna 10 u C18 3.0×50 mm Method 5
  Gradient time: 4 min
  Flow rate: 4 mL/min
  Stop time Gradient time+1 minute
  Starting conc: 0% B
  Eluent A: 10% MeOH/90% H$_2$O with 0.1% TFA
  Eluent B: 90% MeOH/10% H$_2$O with 0.1% TFA
  Column: Phenomenex-luna 10 u C18 3.0×50 mm Method 6
  Gradient time: 3 min
  Flow rate: 4 mL/min
  Stop time Gradient time+1 minute
  Starting conc: 0% B
  Eluent A: 10% MeOH/90% H$_2$O with 0.1% TFA
  Eluent B: 90% MeOH/10% H$_2$O with 0.1% TFA
  Column: Phenomenex-luna 10 u C18 30×4.6 mm Method 7
  Gradient time: 3 min
  Flow rate: 4 mL/min
  Stop time Gradient time+1 minute
  Starting conc: 0% B
  Eluent A: 10% MeOH/90% H$_2$O with 0.1% TFA
  Eluent B: 90% MeOH/10% H$_2$O with 0.1% TFA
  Column: Phenomenex-luna 10 u C18 3.0×50 mm Method 8
  Gradient time: 3 min
  Flow rate: 4 ml/min
  Stop time Gradient time+1 min
  Starting conc.: 0% B
  Eluent A: 95% water/5% ACN with 10 mm Ammonium Acetate
  Eluent B: 5% water/95% ACN with 10 mm Ammonium Acetate
  Column: Xterra 3.0×50 mm S7

Method 9
  Gradient time: 4 min
  Flow rate: 4 mL/min
  Stop time Gradient time+1 minute
  Starting conc: 0% B
  Eluent A: 5% ACN/95% H$_2$O with 10 mm Ammonium Acetate
  Eluent B: 95% ACN/5% H$_2$O with 10 mm Ammonium Acetate
  Column: Luna 4.6×50 mm Phenomenex Luna Method 10:
  LC-MS instrument: WFD-442A-LCMS2, Wavelength=220
  Gradient time: 2 min
  Flow rate: 4 mL/min
  Stop time Gradient time+1 minute
  Starting conc: 0% B Eluent A: 10% MeOH/90% H$_2$O with 0.1% TFA
Eluent B: 90% MeOH/10% H$_2$O with 0.1% TFA
Column: Phenomenex-luna 4.6×30 mm S10

Preparation of 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (Compound B-1)

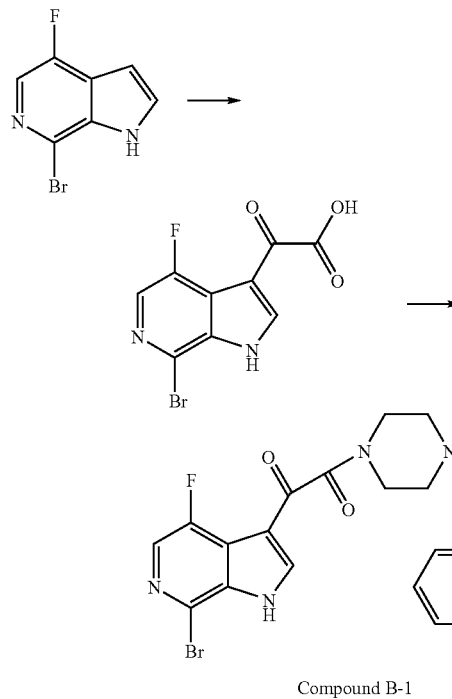

Compound B-1

Preparation of 1-(4-fluoro-7-(3-methyl-1H-pyrazol-1-yl)-1H-pyrrolo[2,3-c]pyridin-3-yl)-2-(4-(1-phenyl-1H-tetrazol-5-yl)piperazin-1-yl)ethane-1,2-dione (Compound B-2) and 1-(4-fluoro-7-(5-methyl-1H-pyrazol-1-yl)-1H-pyrrolo[2,3-c]pyridin-3-yl)-2-(4-(1-phenyl-1H-tetrazol-5-yl)piperazin-1-yl)ethane-1, 2-dione (Compound B-3)

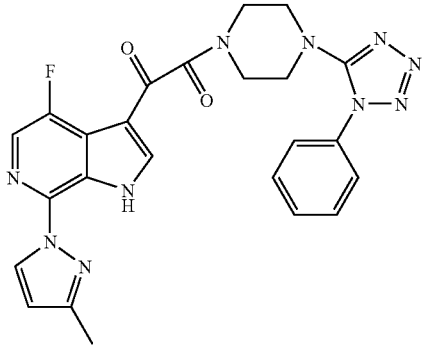

Compound B-2

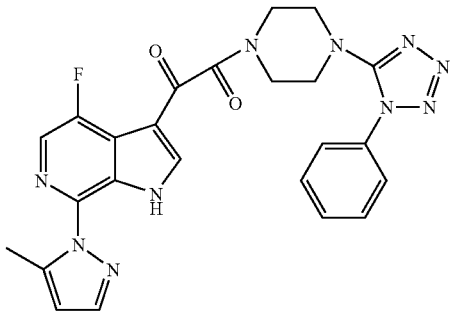

Compound B-3

7-bromo-4-fluoro-1H-pyrrolo[2,3-c]pyridine (2.0 g, 9.3 mmol) was added to a mixture of AlCl$_3$ (7.5 g, 55.8 mmol) and ethylmethylimidazolium chloride (2.7 g, 18.6 mmol). Methyl chlorooxoacetate (2.1 mL, 18.6 mmol) was added slowly to the above solution and the mixture was stirred at room temperature for 3 h. Reaction flask was placed in an ice bath and water was slowly added until a white precipitate formed. The solid was collected by filtration and washed with water to afford 2-(7-bromo-4-fluoro-1H-pyrrolo[2,3-c]pyridin-3-yl)-2-oxoacetic acid (2.4 g, 92%). LCMS: m/e 287 (M+H)$^+$, ret time 0.91 min (method 1).

2-(7-bromo-4-fluoro-1H-pyrrolo[2,3-c]pyridin-3-yl)-2-oxoacetic acid (5.0 g, 17.5 mmol) was dissolved in DMF (100 mL) and treated with 1-(1-phenyl-1H-tetrazol-5-yl)piperazine (4.0 g, 17.5 mmol), Hunig's base (9.2 mL, 52.6 mmol) and TBTU (5.6 g, 17.5 mmol) and the reaction mixture was stirred at rt for 18 h. Solvent was removed in vacuum and water was added. A white solid precipitated out and it was collected by filtration and recrystallized twice with MeOH to afford the title compound (4.58 g) as a white solid. The mother liquid was concentrated and purified using silica gel (CH$_2$Cl$_2$ to 5% MeOH/CH$_2$Cl$_2$) to afford more title compound (1.8 g). $^1$HNMR (500 MHz, DMSO) δ 8.47 (s, 1H), 8.16 (s, 1H), 7.70-7.59 (m, 5H), 3.67 (m, 2H), 3.44 (m, 2H), 3.37 (m, 2H), 3.20 (m, 2H). LCMS: m/e 499 (M+H)$^+$, ret time 1.50 min (method 1).

A mixture of 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (50 mg, 0.1 mmol), potassium carbonate (13 mg, 0.1 mmol), copper (6.0 mg, 0.1 mmol) and 3-methylpyrazole (32 uL, 0.4 mmol) in N-methylpyrrolidinone (0.5 mL) was heated at 160° C. for 6 h. MeOH (3 mL) was added and the solution was filtered through Celite. Solvent was removed in vacuum and residue was dissolved in DMF and purified using reverse phase prep HPLC to afford 1-(4-fluoro-7-(3-methyl-1H-pyrazol-1-yl)-1H-pyrrolo[2,3-c]pyridin-3-yl)-2-(4-(1-phenyl-1H-tetrazol-5-yl)piperazin-1-yl)ethane-1,2-dione (6.9 mg) as a white solid; $^1$HNMR (500 MHz, CDCl$_3$) δ 8.46 (d, J=2 Hz, 1H), 8.19 (s, 1H), 8.93 (d, J=2.0 Hz, 1H), 7.55-7.50 (m, 5H), 6.25 (d, J=2.0 Hz, 1H), 3.78 (m, 2H), 3.56 (m, 2H), 3.35 (m, 2H), 3.25 (m, 2H), 2.36 (s, 3H). LCMS: m/e 501 (M+H)$^+$, ret time 2.34 min (method 2) and 1-(4-fluoro-7-(5-methyl-1H-pyrazol-1-yl)-1H-pyrrolo[2,3-c]pyridin-3-yl)-2-(4-(1-phenyl-1H-tetrazol-5-yl)piperazin-1-yl)ethane-1,2-dione (13.7 mg); $^1$HNMR (500 MHz, CDCl$_3$) δ 8.25 (m, 1H), 8.08 (bs, 1H), 7.65 (m, 1H), 7.60 (m, 5H), 6.27 (m, 1H), 3.87 (m, 2H), 3.66 (m, 2H), 3.46 (m, 2H), 3.36 (m, 2H), 2.83 (s, 3H). LCMS: m/e 501 (M+H)$^+$, ret time 2.34 min (method 2).

Preparation of 1-(7-(3-amino-1H-pyrazol-1-yl)-4-fluoro-1H-pyrrolo[2,3-c]pyridin-3-yl)-2-(4-(1-phenyl-1H-tetrazol-5-yl)piperazin-1-yl)ethane-1,2-dione (Compound B-4) and 1-(7-(5-amino-1H-pyrazol-1-yl)-4-fluoro-1H-pyrrolo[2,3-c]pyridin-3-yl)-2-(4-(1-phenyl-1H-tetrazol-5-yl)piperazin-1-yl)ethane-1,2-dione (Compound B-5).

Compound B-4

Compound B-5

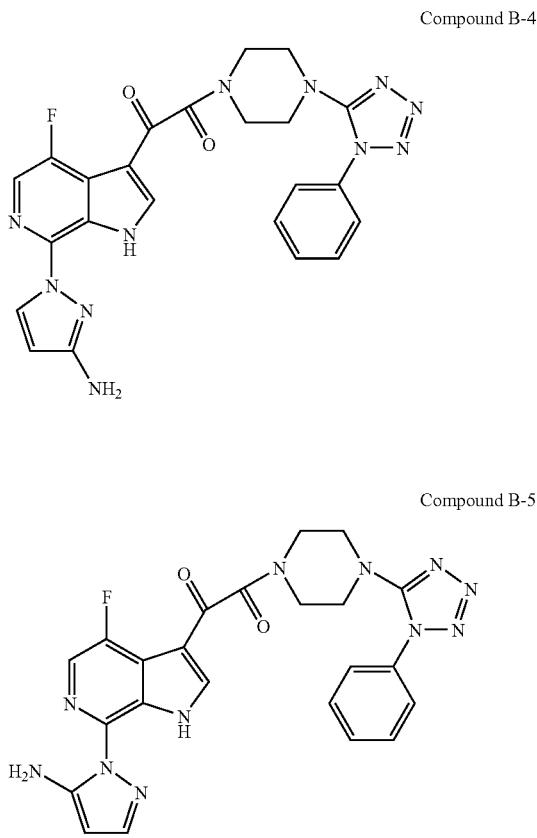

A mixture of 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (100 mg, 0.2 mmol), potassium carbonate (26 mg, 0.2 mmol), copper (13 mg, 0.2 mmol) and 3-aminopyrazole (100 uL, 1 mmol) in N-methylpyrrolidinone (0.5 mL) was heated at 160° C. for 5 h. Solvent was removed in vacuum and residue was dissolved in DMF and purified using reverse phase prep HPLC to afford 1-(7-(3-amino-1H-pyrazol-1-yl)-4-fluoro-1H-pyrrolo[2,3-c]pyridin-3-yl)-2-(4-(1-phenyl-1H-tetrazol-5-yl)piperazin-1-yl)ethane-1,2-dione (15.9 mg) as a pale yellow solid; $^1$HNMR (500 MHz, DMSO) δ 8.34 (d, J=2.0 Hz, 1H), 8.29 (d, J=1.5 Hz, 1H), 8.03 (s, 1H), 7.70-7.58 (m, 5H), 5.92 (d, J=2.5 Hz, 1H), 5.25 (m, 2H), 3.71 (m, 2H), 3.47 (m, 2H), 3.32 (m, 2H), 3.16 (m, 2H). LCMS: m/e 502 (M+H)$^+$, ret time 1.26 min (method 3); and 1-(7-(5-amino-1H-pyrazol-1-yl)-4-fluoro-1H-pyrrolo[2,3-c]pyridin-3-yl)-2-(4-(1-phenyl-1H-tetrazol-5-yl)piperazin-1-yl)ethane-1,2-dione (8.8 mg) as a pale yellow solid; $^1$HNMR (500 MHz, CDCl$_3$) δ 8.21 (m, 1H), 8.11 (bs, 1H), 7.60 (m, 6H), 6.94 (m, 2H), 5.52 (m, 1H), 3.71 (m, 2H), 3.47 (m, 2H), 3.31 (m, 2H), 3.16 (m, 2H); LCMS: m/e 502 (M+H)$^+$, ret time 1.26 min (method 3).

Preparation of 1-(4-fluoro-7-(1H-pyrazol-3-yl)-1H-pyrrolo[2,3-c]pyridin-3-yl)-2-(4-(1-phenyl-1H-tetrazol-5-yl)piperazin-1-yl)ethane-1,2-dione

B-28

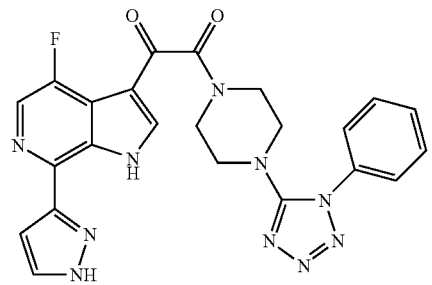

A mixture of 2-(7-bromo-4-fluoro-1H-pyrrolo[2,3-c]pyridin-3-yl)-2-oxoacetic acid (500 mg, 1.0 mmo) (compound B-1), 3-(tributylstannyl)-1H-pyrazole (358 mg, 1 mmol) and tetrakis(triphenylphosphine)palladium(0) (346 mg, 0.3 mmol) in 1,4-dioxane (3 mL) was heated at 110° C. for 6 h. Reaction was cooled to room temperature, diluted with DMF and methanol, filtered through celite and concentrated under reduced pressure. The crude was then redissolved in DMF and purified using reverse phase HPLC to afford the title compound as a white solid (180 mg, 37%). $^1$H NMR (500 MHz, DMSO-D$_6$) δ ppm 3.17 (s, 2H) 3.33 (s, 2H) 3.47 (s, 2H) 3.72 (s, 2H) 6.97 (s, 1H) 7.59 (s, 1H) 7.64 (s, 2H) 7.69 (s, 2H) 7.96 (s, 1H) 8.25 (s, 1H) 8.31 (s, 1H). LCMS: m/e 487 (M+H)$^+$, ret time 1.32 min (method 2).

Preparation of 1-(4-fluoro-7-(1-methyl-1H-pyrazol-3-yl)-1H-pyrrolo[2,3-c]pyridin-3-yl)-2-(4-(1-phenyl-1H-tetrazol-5-yl)piperazin-1-yl)ethane-1,2-dione

B-29

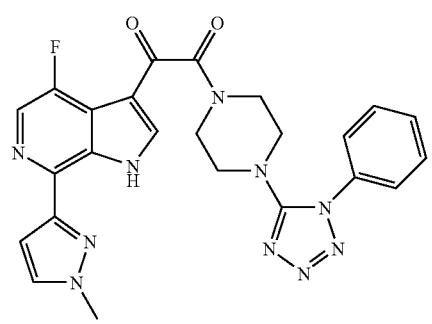

1-(4-fluoro-7-(1H-pyrazol-3-yl)-1H-pyrrolo[2,3-c]pyridin-3-yl)-2-(4-(1-phenyl-1H-tetrazol-5-yl)piperazin-1-yl)ethane-1,2-dione (30 mg, 0.06 mmol) in DMF (1 mL) was treated with sodium hydride (60% in oil, 31.2 mg, 0.78 mmol) and stirred at room temperature for 5 min. Methyl iodide (56 uL, 0.9 mmol) was added and the mixture was stirred at rt for 1 h. Reaction was quenched with H$_2$O and concentrated under reduced pressure. The residue was dissolved in DMF and purified using reverse phase prep HPLC to afford the title compound as a white solid (20 mg, 67%). $^1$H NMR (500 MHz, DMSO-D$_6$) δ ppm 3.15 (s, 2H) 3.32 (s, 2H) 3.47 (s, 2H) 3.71 (s, 2H) 4.05 (s, 3H) 6.92 (s, 1H) 7.58-7.65 (m, 3H) 7.69 (s, 2H) 7.91 (s, 1H) 8.30 (d, J=12.83 Hz, 2H) 12.30 (s, 1H). LCMS: m/e 501 (M+H)$^+$, ret time 1.37 min (method 3).

Preparation 1-(7-(1-(2-(dimethylamino)ethyl)-H-pyrazol-3-yl)-4-fluoro-1H-pyrrolo[2,3-c]pyridin-3-yl)-2-(4-(1-phenyl-1H-tetrazol-5-yl)piperazin-1-yl)ethane-1,2-dione

B-30

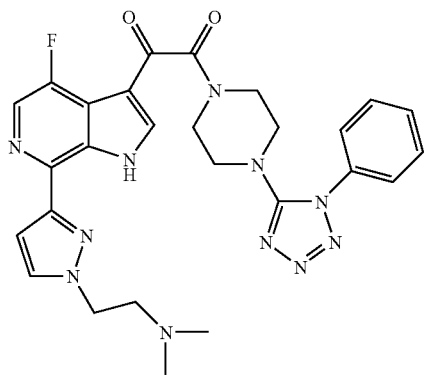

1-(4-fluoro-7-(1H-pyrazol-3-yl)-1H-pyrrolo[2,3-c]pyridin-3-yl)-2-(4-(1-phenyl-1H-tetrazol-5-yl)piperazin-1-yl)ethane-1,2-dione (40 mg, 0.08 mmol) in DMF (1 mL) was treated with sodium hydride (60% in oil, 33.0 mg, 0.8 mmol) and stirred at room temperature for 5 min. 2-chloro-N,N-dimethylethanamine hydrochloride (115.2 mg, 0.8 mmol) was added and the mixture was stirred at rt for 1 h. Reaction was quenched with H$_2$O and concentrated under reduced pressure. The residue was dissolved in DMF and purified using reverse phase prep HPLC to afford the title compound as a white solid (15 mg, 34%). $^1$H NMR (500 MHz, MeOD) δ ppm 2.96 (s, 6H) 3.37 (s, 2H) 3.63 (s, 2H) 3.82 (s, 2H) 3.89 (s, 2H) 4.76 (s, 2H) 7.11 (s, 1H) 7.59 (s, 1H) 7.64 (s, 2H) 7.68 (s, 2H) 7.92 (s, 1H) 8.25 (s, 1H) 8.36 (s, 1H). LCMS: m/e 558 (M+H)$^+$, ret time 1.37 min (method 3).

Preparation 1-(4-fluoro-7-(1-(2-morpholinoethyl)-1H-pyrazol-3-yl)-1H-pyrrolo[2,3-c]pyridin-3-yl)-2-(4-(1-phenyl-1H-tetrazol-5-yl)piperazin-1-yl)ethane-1,2-dione

B-31

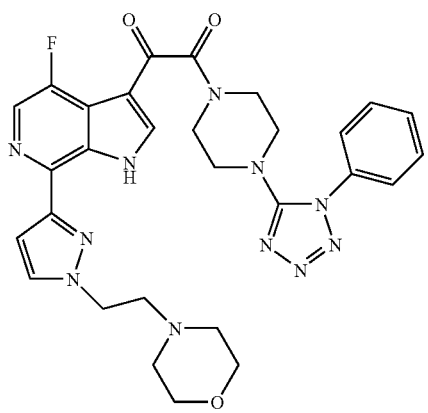

1-(4-fluoro-7-(1H-pyrazol-3-yl)-1H-pyrrolo[2,3-c]pyridin-3-yl)-2-(4-(1-phenyl-1H-tetrazol-5-yl)piperazin-1-yl)ethane-1,2-dione (40 mg, 0.08 mmol) in DMF (1 mL) was treated with sodium hydride (60% in oil, 33 mg, 0.8 mmol) and stirred at room temperature for 5 min. 4-(2-chloroethyl)morpholine (149 mg, 0.8 mmol) was added and the mixture was stirred at rt for 1 h. Reaction was quenched with H$_2$O and concentrated under reduced pressure. The residue was dis-solved in DMF and purified using reverse phase prep HPLC to afford the title compound as a white solid (20 mg, 67%). $^1$H NMR (500 MHz, MeOD) δ ppm 3.43 (s, 1H) 3.77 (s, 5H) 3.81 (s, 5H) 4.08 (s, 2H) 4.28 (s, 3H) 4.37 (s, 4H) 5.27 (s, 6H) 7.56 (s, 1H) 8.06-8.12 (m, 2H) 8.13 (s, 2H) 8.38 (s, 1H) 8.70 (s, 1H) 8.85 (s, 1H). LCMS: m/e 600 (M+H)$^+$, ret time 1.22 min (method 3).

Preparation 4-methoxy-3-(2-oxo-2-(4-(1-phenyl-1H-tetrazol-5-yl)piperazin-1-yl)acetyl)-1H-pyrrolo[2,3-b]pyridine 7-oxide

B-32

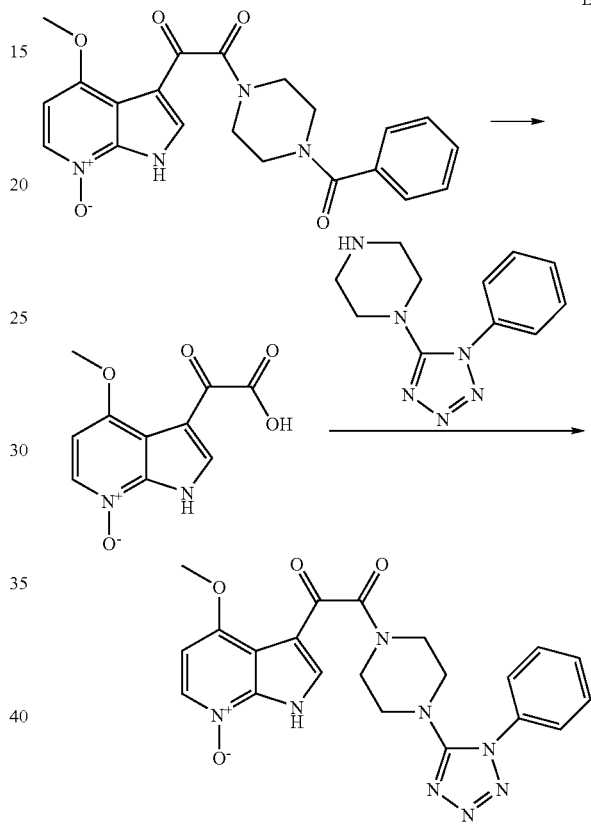

3-(2-(4-benzoylpiperazin-1-yl)-2-oxoacetyl)-4-methoxy-1H-pyrrolo[2,3-b]pyridine 7-oxide (2.0 g, 4.9 mmol) in a 10% aqueous solution of HCl (20 mL) was heated at 100° C. for 18 h. Reaction was concentrated under reduced pressure and the residue was washed with ethyl acetate and chloroform. NaOH (1N) was added until reaching pH=7; Then ethyl acetate was added to wash the solid. Solid containing 3-(carboxycarbonyl)-4-methoxy-1H-pyrrolo[2,3-b]pyridine 7-oxide was taken to next step without further purification.

A mixture of the solid containing 3-(carboxycarbonyl)-4-methoxy-1H-pyrrolo[2,3-b]pyridine 7-oxide from above (200 mg, 0.84 mmol), triethylamine (0.5 mL, sssss), 1-(1-phenyl-1H-tetrazol-5-yl)piperazine (234 mg, 1.01 mmol) and TBTU (404 mg, 1.26 mmol) was stirred at rt in DMF (1 mL) for 24 h. H2O was added and the reaction mixture was concentrated under reduced pressure. The residue was purified using reverse phase prep HPLC to afford the title compound as a white solid (15 mg, 4%). $^1$H NMR (500 MHz, CDCl$_3$) δ ppm 3.32 (s, 2H) 3.37 (s, 2H) 3.56 (s, 2H) 3.79 (s, 2H) 4.13 (s, 3H) 6.83 (d, J=7.32 Hz, 1H) 7.53 (d, J=6.71 Hz, 1H) 7.54-7.60 (m, 3H) 8.16 (s, 1H) 8.34 (d, J=6.71 Hz, 1H). LCMS: m/e 449 (M+H)$^+$, ret time 0.99 min (method 2).

Preparation of 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (Compound B-6)

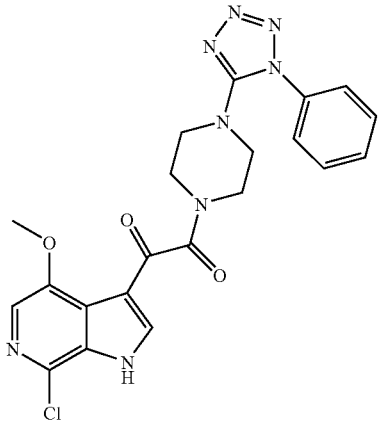

Compound B-6

To a solution of 2-(7-chloro-4-methoxy-1H-pyrrolo[2,3-c]pyridin-3-yl)-2-oxoacetic acid (5.3 g, 20.8 mmol) (prepared as described on US20050090522A1) in DMF (100 mL) was added 1-(1-phenyl-1H-tetrazol-5-yl)piperazine (4.8 g, 20.8 mmol), TBTU (7.4 g, 23.0 mmol), and N,N-diisopropylethylamine (12.0 mL, 68.9 mmol). The mixture was stirred at rt for 16 hr. The solvent was removed under reduced pressure, and the remaining residue was dissolved in hot MeOH. Upon cooling, precipitate formed. The precipitate was collected by filtration, and was washed with H$_2$O (3×75 mL). The mother liquor was concentrated under reduced pressure, then subjected to a second crystallization using the same method. The combined precipitates gave 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione as a light brown solid (7.3 g, 15.6 mmol). $^1$H NMR (500 MHz, CDCl$_3$) δ 9.64 (s, 1H), 8.11 (s, 1H), 7.76 (s, 1H), 7.62-7.50 (m, 5H), 4.00 (s, 3H), 3.83-3.81 (m, 2H), 3.57-3.56 (m, 2H), 3.43-3.41 (m, 2H), 3.33-3.32 (m, 2H). LCMS: m/e 467.3 (M+H)$^+$, ret time 1.99 min (method 2).

Preparation of ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (Compound B-7)

(Compound B-7)

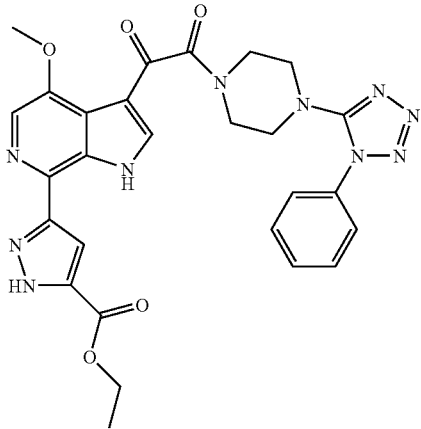

To a suspension of 1-(7-chloro-4-methoxy-1H-pyrrolo[2,3-c]pyridin-3-yl)-2-(4-(1-phenyl-1H-tetrazol-5-yl)piper-azin-1-yl)ethane-1,2-dione (2.50 g, 5.35 mmol) in 1,4-dioxane (60 mL) in a sealable flask was added ethyl 3-(tributylstannyl)-1H-pyrazole-5-carboxylate (2.30 g, 5.36 mmol) followed by tetrakis(triphenylphosphine)palladium (0) (1.86 g, 1.61 mmol). The mixture was flushed with N$_2$, the flask was sealed, and the mixture was heated to 120° C. for 16 hr. The mixture was cooled to rt and diluted with MeOH (50 mL). The remaining solids were removed by filtering the mixture through a pad of celite and were washed with MeOH (25 mL). The remaining solvent was concentrated under reduced pressure. The resulting residue was dissolved in MeOH, and loaded onto a silica gel. After the silica was dry, a column was run using the biotage system with a 0 to 10% MeOH in CH$_2$Cl$_2$ gradient. After concentrating the desired fractions, 1.05 g of ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate was recovered as an orange solid. LCMS: m/e 571.2 (M+H)$^+$, ret time 2.01 min (method 2). 1H NMR (500 MHz, DMSO-D$_6$) δ ppm 12.39-12.72 (m, 1H) 8.37 (s, 1H) 8.11 (s, 1H) 7.52-7.76 (m, 6H) 4.68-4.85 (m, 1H) 4.38 (q, J=7.02 Hz, 2H) 3.98-4.06 (m, 3H) 3.67-3.73 (m, 2H) 3.43-3.49 (m, 2H) 3.28-3.36 (m, 2H) 3.14-3.22 (m, 2H) 1.36 (t, J=7.17 Hz, 3H).

Preparation of N-(2-hydroxyethyl)-3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxamide.TFA (Compound B-8)

(Compound B-8)

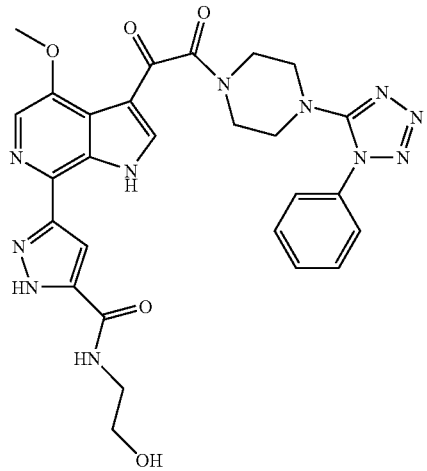

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.100 g, 0.175 mmol) was combine with ethanolamine (0.75 mL) in a sealable tube. The mixture was flushed with N$_2$, and the tube was sealed. The mixture was stirred for 67 hrs at rt. The mixture was diluted with DMF, and loaded onto the reverse phase prep HPLC for purification. After concentrating the fractions containing product, 0.085 g of the N-(2-hydroxyethyl)-3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxamide.TFA were recovered as an off-white solid. LCMS: m/e 586.3 (M+H)$^+$, ret time 1.19 min (method 1). 1H NMR (300 MHz, DMSO-D$_6$) δ ppm 12.51 (s, 1H) 8.64 (s, 1H) 8.36 (s, 1H) 8.10 (s, 1H) 7.56-7.71 (m, 6H) 7.25 (brs, 1H) 4.01 (s, 3H) 3.70 (s, 2H) 3.55 (t, J=6.22 Hz, 2H) 3.27-3.48 (m, 7H) 3.16 (s, 2H).

Preparation of N-(2-(2-hydroxyethoxy)ethyl)-3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxamide.TFA (Compound B-9)

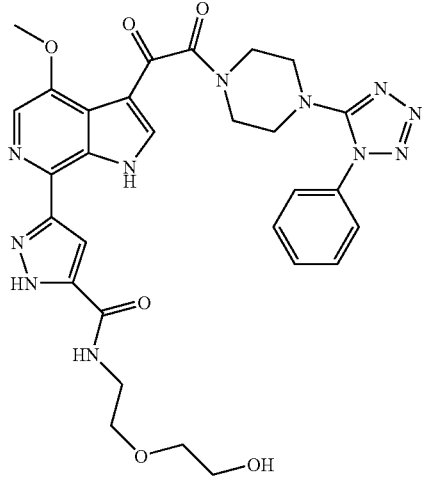

(Compound B-9)

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.100 g, 0.175 mmol) was combine with 2-(2-aminoethoxy)ethanol (0.75 mL) in a sealable tube. The mixture was flushed with $N_2$, and the tube was sealed. The mixture was stirred for 67 hrs at rt. The mixture was diluted with DMF, and loaded onto a reverse phase prep HPLC for purification. After concentrating the fractions containing product, 0.064 g of the N-(2-(2-hydroxyethoxy)ethyl)-3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxamide.TFA were recovered as an off-white solid. LCMS: m/e 630.2 (M+H)$^+$, ret time 1.84 min (method 2). 1H NMR (500 MHz, MeOD) δ ppm 8.55-8.62 (m, 1H) 7.99-8.07 (m, 1H) 7.53-7.75 (m, 6H) 4.07-4.18 (m, 3H) 3.79-3.88 (m, 2H) 3.58-3.76 (m, 8H) 3.29-3.43 (m, 6H).

Preparation of 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(3-(4-methylpiperazin-1-yl)propyl)-1H-pyrazole-5-carboxamide.TFA (Compound B-10)

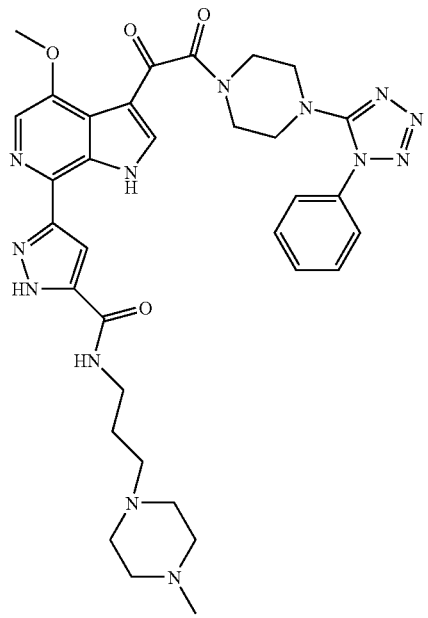

(Compound B-10)

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.100 g, 0.175 mmol) was combine with 1-(3-aminopropyl)-4-methyl piperazine (0.75 mL) in a sealable tube. The mixture was flushed with $N_2$, and the tube was sealed. The mixture was stirred for 67 hrs at rt. The mixture was diluted with DMF, and loaded onto a reverse phase prep HPLC for purification. After concentrating the fractions containing product, 0.093 g of the 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(3-(4-methylpiperazin-1-yl)propyl)-1H-pyrazole-5-carboxamide.TFA were recovered as an off-white solid. LCMS: m/e 682.4 (M+H)$^+$, ret time 1.11 min (method 1). 1H NMR (300 MHz, DMSO-D6) δ ppm 12.48 (s, 1H) 10.82 (s, 1H) 8.82 (s, 1H) 8.35 (s, 1H) 8.11 (s, 1H) 7.53-7.72 (m, 6H) 4.01 (s, 3H) 3.10-3.79 (m, 20H) 2.89 (s, 3H) 1.88-2.03 (m, 2H).

Preparation of 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(2-(pyrrolidin-1-yl)ethyl)-1H-pyrazole-5-carboxamide.TFA (Compound B-11)

(Compound B-11)

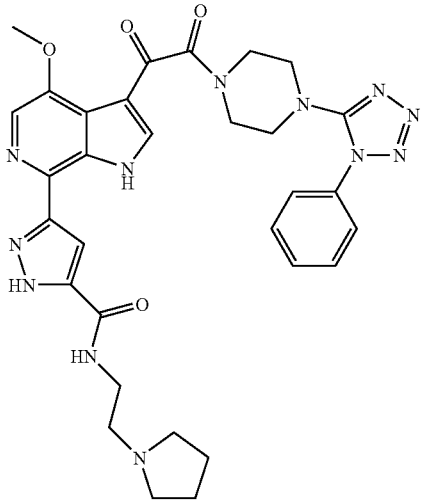

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.100 g, 0.175 mmol) was combine with 1-(2-aminoethyl)-pyrrolidine (0.75 mL) in a sealable tube. The mixture was flushed with $N_2$, and the tube was sealed. The mixture was stirred for 67 hrs at rt. The mixture was diluted with DMF, and loaded onto a reverse phase prep HPLC for purification. After concentrating the fractions containing product, 0.100 g of the 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(2-(pyrrolidin-1-yl)ethyl)-1H-pyrazole-5-carboxamide.TFA were recovered as dark orange solid. LCMS: m/e 639.3 $(M+H)^+$, ret time 1.78 min (method 2). 1H NMR (500 MHz, MeOD) δ ppm 8.56 (s, 1H) 8.06 (s, 1H) 7.55-7.73 (m, 6H) 4.11 (s, 3H) 3.79-3.92 (m, 4H) 3.13-3.67 (m, 12H) 2.03-2.25 (m, 4H).

Preparation of 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(2-(pyridin-4-yl)ethyl)-1H-pyrazole-5-carboxamide.TFA (Compound B-12)

(Compound B-12)

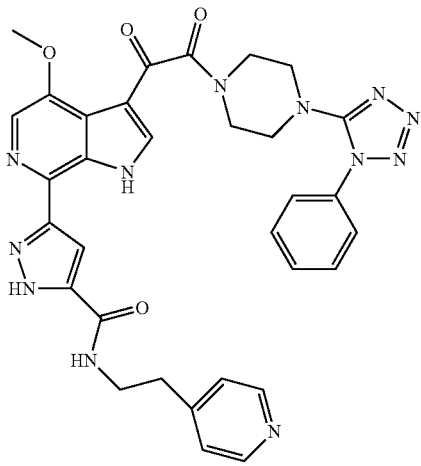

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.100 g, 0.175 mmol) was combine with 4-(2-aminoethyl)-pyridine (0.75 mL) in a sealable tube. The mixture was flushed with $N_2$, and the tube was sealed. The mixture was stirred for 67 hrs at rt. The mixture was diluted with DMF, and loaded onto a reverse phase prep HPLC for purification. After concentrating the fractions containing product, 0.035 g of the 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(2-(pyridin-4-yl)ethyl)-1H-pyrazole-5-carboxamide.TFA were recovered as an off-white solid. LCMS: m/e 647.2 $(M+H)^+$, ret time 1.77 min (method 2). 1H NMR (500 MHz, MeOD) δ ppm 8.74-8.83 (m, 2H) 8.52-8.60 (m, 1H) 8.02-8.12 (m, 3H) 7.56-7.74 (m, 6H) 4.08-4.16 (m, 3H) 3.79-3.90 (m, 4H) 3.59-3.67 (m, 2H) 3.28-3.45 (m, 6H).

Preparation of 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(2-morpholinoethyl)-1H-pyrazole-5-carboxamide.TFA (Compound B-13)

(Compound B-13)

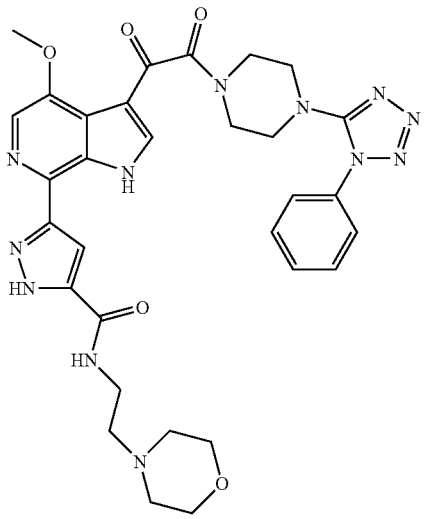

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.075 g, 0.131 mmol) was combine with 4-(2-aminoethyl)morpholine (0.75 mL) in a sealable tube. The mixture was flushed with $N_2$, and the tube was sealed. The mixture was stirred for 67 hrs at rt. The mixture was diluted with DMF, and loaded onto a reverse phase prep HPLC for purification. After concentrating the fractions containing product, 0.073 g of the 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(2-morpholinoethyl)-1H-pyrazole-5-carboxamide.TFA were recovered as an off-white solid. LCMS: m/e 655.3 $(M+H)^+$, ret time 1.74 min (method 2). 1H NMR (300 MHz, MeOD) δ ppm 8.57 (s, 1H) 8.07 (s, 1H) 7.56-7.74 (m, 6H) 3.17-4.17 (m, 23H).

129

Preparation of 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(2-(piperazin-1-yl)ethyl)-1H-pyrazole-5-carboxamide.TFA (Compound B-14)

(Compound B-14)

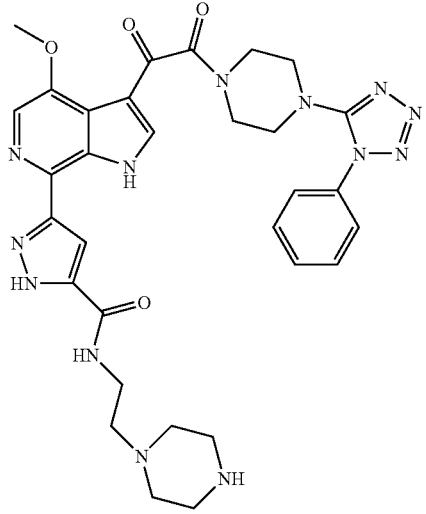

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.100 g, 0.175 mmol) was combine with 1-(2-aminomethyl)piperazine (0.75 mL) in a sealable tube. The mixture was flushed with $N_2$, and the tube was sealed. The mixture was stirred for 67 hrs at rt. The mixture was diluted with DMF, and loaded onto a reverse phase prep HPLC for purification. After concentrating the fractions containing product, 0.089 g of the 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-N-(2-(piperazin-1-yl)ethyl)-1H-pyrazole-5-carboxamide.TFA were recovered as a tan solid. LCMS: m/e 654.3 (M+H)$^+$, ret time 1.73 min (method 2). 1H NMR (500 MHz, MeOD) δ ppm 8.54-8.62 (m, 1H) 8.01-8.10 (m, 1H) 7.54-7.74 (m, 6H) 4.08-4.16 (m, 3H) 3.77-3.89 (m, 4H) 3.60 (s, 10H) 3.22-3.47 (m, 6H).

130

Preparation of N-(3-(dimethylamino)propyl)-3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxamide.TFA (Compound B-15)

(Compound B-15)

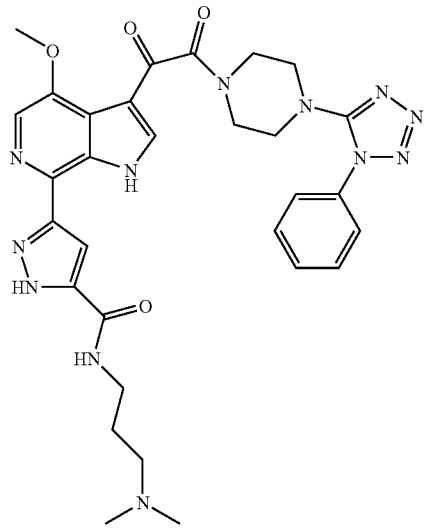

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.125 g, 0.219 mmol) was combine with 3-dimethylaminopropylamine (0.70 mL) in a sealable tube. The mixture was flushed with $N_2$, and the tube was sealed. The mixture was stirred for 36 hrs at rt. The mixture was diluted with DMF, and loaded onto a reverse phase prep HPLC for purification. After concentrating the fractions containing product, 0.010 g of the N-(3-(dimethylamino)propyl)-3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxamide.TFA were recovered as an off-white solid. LCMS: m/e 627.6 (M+H)$^+$, ret time 1.75 min (method 2). 1H NMR (300 MHz, DMSO-$D_6$) δ ppm 8.78-9.19 (m, 2H) 8.23 (s, 1H) 8.09 (s, 1H) 7.55-7.73 (m, 6H) 4.00 (s, 3H) 2.70-2.79 (m, 6H) 2.68-3.93 (m, 12H) 1.96-2.15 (m, 2H).

Preparation of N-(2-(dimethylamino)ethyl)-3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxamide.TFA (Compound B-16)

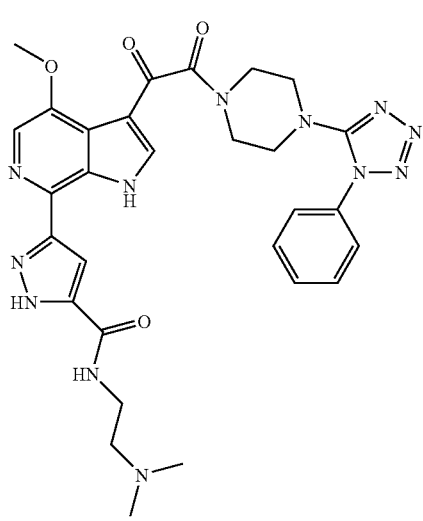

(Compound B-16)

Ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.05 g, 0.088 mmol) was combine with N,N-dimethylethylenediamine (0.70 mL) in a sealable tube. The mixture was flushed with $N_2$, and the tube was sealed. The mixture was stirred for 38 hrs at rt. The mixture was diluted with DMF, and loaded onto a reverse phase prep HPLC for purification. After concentrating the fractions containing product, 0.020 g of the N-(2-(dimethylamino)ethyl)-3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxamide.TFA were recovered as a tan solid. LCMS: m/e 613.2 $(M+H)^+$, ret time 1.75 min (method 2). 1H NMR (500 MHz, MeOD) δ ppm 8.56 (s, 1H) 8.08 (s, 1H) 7.59-7.73 (m, 6H) 4.13 (s, 3H) 3.82-3.86 (m, 4H) 3.62-3.66 (m, 2H) 3.40-3.48 (m, 4H) 3.33-3.37 (m, 2H) 3.03 (s, 6H).

Preparation of 1-(7-amino-4-fluoro-1H-pyrrolo[2,3-c]pyridin-3-yl)-2-(4-(1-phenyl-1H-tetrazol-5-yl)piperazin-1-yl)ethane-1,2-dione (Compound B-17)

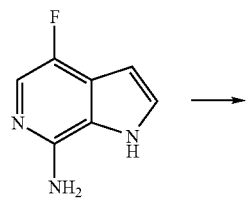

-continued

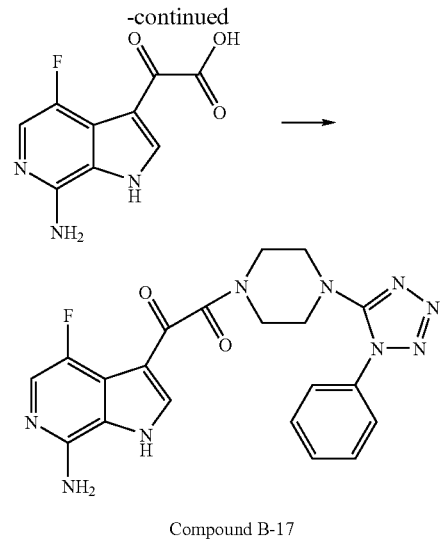

Compound B-17

4-fluoro-1H-pyrrolo[2,3-c]pyridin-7-amine (2.26 g, 15 mmol) was added to a mixture of $AlCl_3$ (12.0 g, 90.0 mmol) and ethylmethylimidazolium chloride (4.38 g, 30.0 mmol). Methyl chlorooxoacetate (3.6 mL, 30.0 mmol) was added slowly to the above solution and the mixture was stirred at rt for 3 h. Reaction flask was placed in an ice bath and water was slowly added until a white precipitate formed. The solid was collected by filtration and suspended in DMF. TEA (7 mL) was added and the mixture was stirred at rt for 1 h. Solvent was removed in vacuum. Chloroform (50 mL) was added and the solid was collected by filtration to afford 2-(7-amino-4-fluoro-1H-pyrrolo[2,3-c]pyridin-3-yl)-2-oxoacetic acid as a bright yellow solid (2.3 g, 90% pure). LCMS: m/e 238 $(M+H)^+$, ret time 0.96 min (method 3).

2-(7-amino-4-fluoro-1H-pyrrolo[2,3-c]pyridin-3-yl)-2-oxoacetic acid (2.3 g, 10.0 mmol) was dissolved in DMF (66 mL) and treated with 1-(1-phenyl-1H-tetrazol-5-yl)piperazine (2.31 g, 10.0 mmol), triethylamine (2.8 mL, 20.0 mmol) and TBTU (3.5 g, 11.0 mmol) and a catalytic amount of DMAP. The reaction mixture was stirred at rt for 18 h. Solvent was removed in vacuum and water was added. A white solid precipitated out and it was collected by filtration and recrystallized with MeOH to afford the title compound (2.4 g) as a yellow solid. $^1$HNMR (500 MHz, DMSO-$D_6$) δ 8.53 (s, 1H), 7.81 (d, J=4.0 Hz; 1H), 7.75-7.54 (m, 5H), 3.69 (m, 2H), 3.44 (m, 2H), 3.33 (m, 2H), 3.17 (m, 2H). LCMS: m/e 436 $(M+H)^+$, ret time 1.73 min (method 2).

Preparation of N-(4-fluoro-3-(2-oxo-2-(4-(1-phenyl-1H-tetrazol-5-yl)piperazin-1-yl)acetyl)-1H-pyrrolo[2,3-c]pyridin-7-yl)acetamide (Compound B-18)

Compound B-18

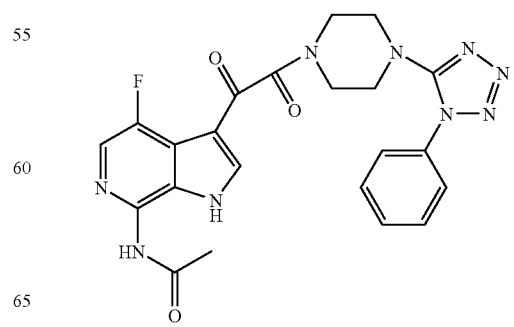

1-(7-amino-4-fluoro-1H-pyrrolo[2,3-c]pyridin-3-yl)-2-(4-(1-phenyl-1H-tetrazol-5-yl)piperazin-1-yl)ethane-1,2-dione (100 mg, 0.23 mmol) was dissolved in pyridine (2 mL) and the mixture was heated at 50° C. Acetyl chloride (65 uL, 0.92 mmol) was added and the mixture was stirred at this temperature for 1 h. Solvent was removed in vacuum and the residue was purified using reverse phase prep HPLC to afford the title compound as a white solid (55 mg). $^1$HNMR (500 MHz, DMSO-$D_6$) δ 8.34 (s, 1H), 8.04 (d, J=1.0 Hz, 1H), 7.70-7.58 (m, 5H), 3.69 (m, 2H), 3.45 (m, 2H), 3.34 (m, 2H), 3.16 (m, 2H), 2.17 (s, 3H). LCMS: m/e 478 (M+H)$^+$, ret time 1.07 min (method 3).

Preparation of 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1,1-dimethylurea (Compound B-19)

Compound B-19

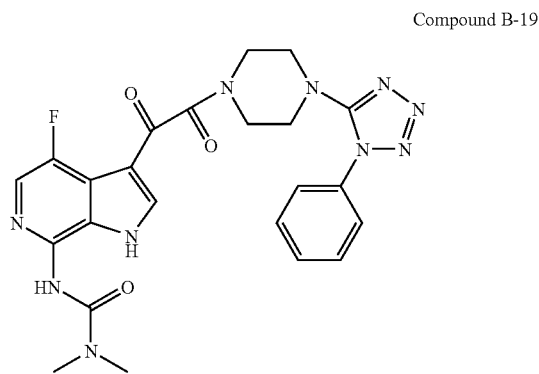

1-(7-amino-4-fluoro-1H-pyrrolo[2,3-c]pyridin-3-yl)-2-(4-(1-phenyl-1H-tetrazol-5-yl)piperazin-1-yl)ethane-1,2-dione (100 mg, 0.23 mmol) was dissolved in pyridine (1 mL). Dimethylcarbamyl chloride (0.21 mL, 2.3 mmol) was added and the mixture was heated at 50° C. for 18 h. Solvent was removed in vacuum and the residue was purified using reverse phase prep HPLC to afford the title compound as a pale tan solid (10 mg). $^1$HNMR (500 MHz, DMSO-$D_6$) δ 8.89 (s, 1H), 8.25 (s, 1H), 7.70-7.59 (m, 5H), 3.67 (m, 2H), 3.44 (m, 2H), 3.37 (m, 2H), 3.20 (m, 2H), 3.11 (s, 3H), 2.88 (s, 3H). LCMS: m/e 507 (M+H)$^+$, ret time 1.04 min (method 3).

Preparation of $N^1$-(4-fluoro-3-(2-oxo-2-(4-(1-phenyl-1H-tetrazol-5-yl)piperazin-1-yl)acetyl)-1H-pyrrolo[2,3-c]pyridin-7-yl)-$N^2$,$N^2$-dimethyloxalamide (Compound B-20)

Compound B-20

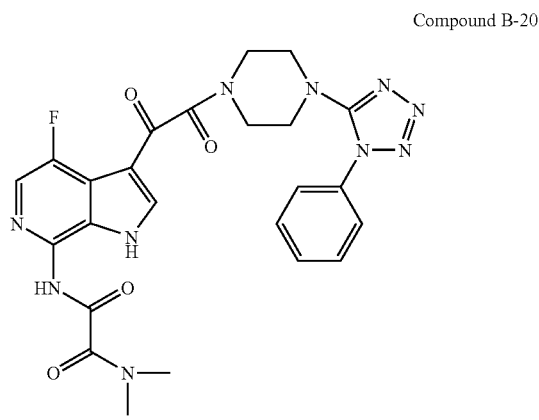

1-(7-amino-4-fluoro-1H-pyrrolo[2,3-c]pyridin-3-yl)-2-(4-(1-phenyl-1H-tetrazol-5-yl)piperazin-1-yl)ethane-1,2-dione (100 mg, 0.23 mmol) was dissolved in DMF (2 mL) and treated with N,N-dimethyloxamic acid (27 mg, 0.23 mmol), Hunig's base (0.14 mL, 0.8 mmol) and TBTU (81 mg, 0.25 mmol). The reaction mixture was stirred at rt for 18 h. Solvent was removed in vacuum and water was added. A solid precipitated out and it was collected by filtration, dissolved in DMF and purified using reverse phase prep HPLC to afford the title compound as a pale yellow solid (11 mg). $^1$HNMR (500 MHz, DMSO-$D_6$) δ 8.47 (s, 1H), 8.16 (s, 1H), 7.70-7.50 (m, 5H), 5.76 (m, 1H), 4.10-3.10 (m, 6H), 3.16 (s, 6H). LCMS: m/e 535 (M+H)$^+$, ret time 1.33 min (method 1).

Preparation of 3-(tributylstannyl)-1H-pyrazole-5-carbaldehyde and (3-(tributylstannyl)-1H-pyrazol-5-yl)methanol

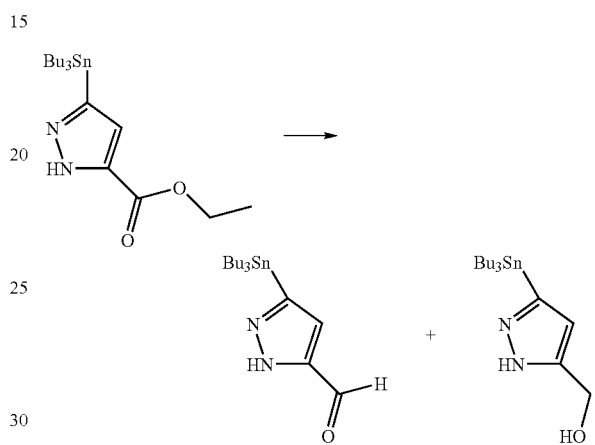

A solution of ethyl 3-(tributylstannyl)-1H-pyrazole-5-carboxylate (3.94 g, 9.18 mmol) in toluene (10 mL) was cooled −78° C. A 1M solution of DIBAL-H in toluene (11.5 mL, 11.5 mmol) was slowly added to the mixture. The mixture was warmed to 0° C. and stirred for 9 h. After the 9 h, the mixture was carefully quenched with $H_2O$ (50 mL) while the mixture was still being cooled. The mixture was partitioned with EtOAc, and the compound was extracted (4×75 mL) with EtOAc. The combined organic layers were washed with saturated NaCl, dried with $Na_2SO_4$, filtered, and concentrated under reduced pressure. The residue was then loaded onto a silica gel column, and purified using the biotage system with a 0 to 40% EtOAc in hexanes gradient to first remove the aldehyde and unreacted starting material. The column was then flushed with a 50% $CH_2Cl_2$ in MeOH solution to remove the remaining alcohol. After concentrating the desired fractions, 3-(tributylstannyl)-1H-pyrazole-5-carbaldehyde (1.125 g) was recovered as a clear, colorless oil, and (3-(tributylstannyl)-1H-pyrazol-5-yl)methanol (0.525 g) was recovered as a white solid. LCMS: m/e 387.2 (M+H)$^+$, ret time 2.01 min (method 3) for 3-(tributylstannyl)-1H-pyrazole-5-carbaldehyde and LCMS: m/e 389.3 (M+H)$^+$, ret time 2.59 min (method 2) for (3-(tributylstannyl)-1H-pyrazol-5-yl)methanol.

The following amino pyrazole intermediates were formed by the standardized reductive amination procedure that follows:

2-((3-(tributylstannyl)-1H-pyrazol-5-yl)methylamino)ethanol (pyrazole 1)
$N^1$,$N^1$-dimethyl-$N^2$-((3-(tributylstannyl)-1H-pyrazol-5-yl)methyl)ethane-1,2-diamine (pyrazole 2)
$N^1$,$N^1$,$N^2$-trimethyl-$N^2$-((3-(tributylstannyl)-1H-pyrazol-5-yl)methyl)ethane-1,2-diamine (pyrazole 3)
2-(pyridin-4-yl)-N-((3-(tributylstannyl)-1H-pyrazol-5-yl)methyl)ethanamine (pyrazole 4)

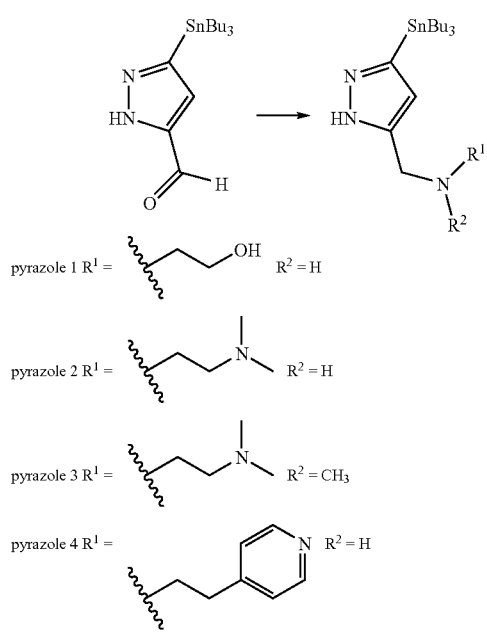

pyrazole 1 R¹ = ~~~CH₂CH₂OH   R² = H pyrazole 2 R¹ = ~~~CH₂CH₂N(CH₃)   R² = H pyrazole 3 R¹ = ~~~CH₂CH₂N(CH₃)   R² = CH₃ pyrazole 4 R¹ = ~~~CH₂CH₂-(4-pyridyl)   R² = H

To a solution of 3-(tributylstannyl)-1H-pyrazole-5-carbaldehyde (1.0 eq, approximately 0.5 mmol scale) in DCE (2-3 mL) was added AcOH (1.0 eq) followed by the amine (1.05-1.1 eq), and finally Sodium triacetoxyborohydride (1.4 eq). The mixture was stirred at room temperature for 1-3 h. The mixture was made basic with 1N NaOH (pH=13) and was extracted three times with CH₂Cl₂. The combined organic layers were dried with Na₂SO₄, the drying agent was removed by filtration, and resulting solution was concentrated under reduced pressure. No further purification was necessary. LCMS: m/e 432.1 (M+H)⁺, ret time 2.52 min (method 2) for 2-((3-(tributylstannyl)-1H-pyrazol-5-yl)methylamino)ethanol. LCMS: m/e 459.2 (M+H)⁺, ret time 3.44 min (method 4) for N1,N1-dimethyl-N2-((3-(tributylstannyl)-1H-pyrazol-5-yl)methyl)ethane-1,2-diamine. LCMS: m/e 473.3.1 (M+H)⁺, ret time 2.65 min (method 2) for N¹,N¹,N²-trimethyl-N²-((3-(tributylstannyl)-1H-pyrazol-5-yl)methyl)ethane-1,2-diamine. LCMS: m/e 493.6 (M+H)⁺, ret time 4.29 min (method 5) for 2-(pyridin-4-yl)-N-((3-(tributylstannyl)-1H-pyrazol-5-yl)methyl)ethanamine.

Preparation of 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylic acid (Compound B-21)

(Compound B-21)

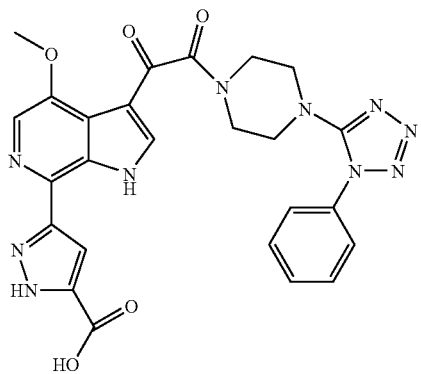

To a suspension of ethyl 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.124 g, 0.217 mmol) in DMF (1.5 mL) and H₂O (1.5 mL) was added LiOH monohydrate (0.027 g, 0.651 mmol). The mixture was heated to 120° C. for 24 h. The reaction was not complete, so an additional 0.05 g of LiOH hydrate along with 2 mL of H₂O were added to the mixture, and it was again heated to 120° C. After 24 h of heating, the reaction was nearly complete by LCMS, so it was cooled to rt, and made acidic (pH=1) with 6N HCl. The mixture was diluted with H₂O, and partitioned with EtOAc. The product precipitated from between the two layers, and was collected by filtration. The solids were washed with cold MeOH and H₂O. The 3-(4-methoxy-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylic acid (0.08 g) was collected as a light yellow solid. LCMS: m/e 542.97 (M+H)⁺, ret time 1.86 min (method 2). 1H NMR (500 MHz, DMSO-D₆) δ ppm 12.10-12.22 (s, 1H) 8.25 (s, 1H) 8.10 (s, 1H) 7.56-7.77 (m, 5H) 7.39 (s, 1H) 3.99 (s, 3H) 3.67-3.72 (m, 2H) 3.40-3.46 (m, 2H) 3.29-3.36 (m, 2H) 3.14-3.20 (m, 2H).

Preparation of 1-(7-(5-(hydroxymethyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione (Compound B-22)

(Compound B-22)

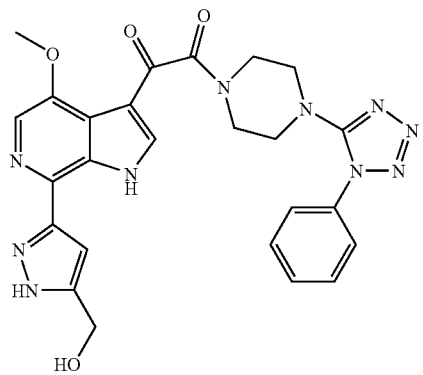

In a sealable, flask a mixture of 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (0.150 g, 0.321 mmol) in 1,4-dioxane (5 mL) was prepared. (3-(tributylstannyl)-1H-pyrazol-5-yl)methanol (0.137 g, 0.353 mmol) was added followed by tetrakis(triphenylphosphine)palladium (0) (0.150 g, 0.130 mmol). The mixture was flushed with N₂, and flask was sealed. The mixture was then heated to 120° C. for 14 h. After cooling to rt, the mixture was diluted with DMF, and filtered through a plug of celite to remove any solids. The liquid was concentrated under reduced pressure, and the residue was dissolved in DMF. The DMF solution was purified by prep HPLC to give 0.037 g of an off-white solid as the 1-(7-(5-(hydroxymethyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione. LCMS: m/e 529.2 (M+H)⁺, ret time 1.78 min (method 2). 1H NMR (500 MHz, MeOD) δ ppm 8.65 (s, 1H) 7.98 (s, 1H) 7.56-7.80 (m, 5H) 7.16 (s, 1H) 4.81 (s, 2H) 4.15 (s, 3H) 3.83-3.87 (m, 2H) 3.63-3.68 (m, 2H) 3.40-3.44 (m, 2H) 3.34-3.39 (m, 2H).

Preparation of N¹,N¹-dimethyl-N²-(1H-pyrazol-3-yl)ethane-1,2-diamine

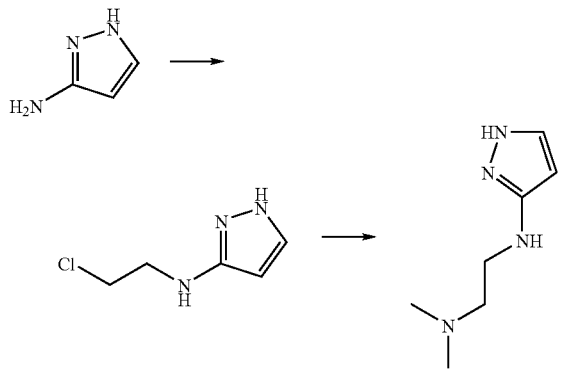

3-aminopyrazole (5.0 g, 60.2 mmol) was dissolved in AcOH (20 mL). A 50% in H₂O solution of chloroacetaldehyde (8.0 mL, 63.2 mmol) was slowly added to the mixture. The mixture was cooled to 0° C., and sodium cyanoborohydride (4.2 g, 66.8 mmol) was added in two portions over ten minutes to the cooled solution. The mixture was warmed to rt and stirred for 5 h. The mixture was carefully made basic with 1N NaOH to pH=10. The mixture was partitioned with CH₂Cl₂, and was extracted five times. The combined organic layers were dried with MgSO₄, filtered, and concentrated under reduced pressure. A column was run to purify the product using a 0 to 5% MeOH in CH₂Cl₂ gradient. The resulting N-(2-chloroethyl)-1H-pyrazol-3-amine was recovered as a clear, colorless oil (2.1 g). LCMS: m/e 146.2 (M+H)⁺, ret time 0.72 min (method 3).

In a sealable flask, the N-(2-chloroethyl)-1H-pyrazol-3-amine (0.214 g, 1.47 mmol) were combined with 1.5 mL of dimethylamine (40% in H₂O). The mixture flask was sealed, and the mixture was heated to 100° C. fir 16 h. The mixture was cooled to rt, and transferred to a rb flask with MeOH. The solvent was removed under reduced pressure to give the N1,N1-dimethyl-N2-(1H-pyrazol-3-yl)ethane-1,2-diamine in quantitative yield. LCMS: m/e 155.3 (M+H)⁺, ret time 0.96 min (method 3).

Preparation of 1-(7-(3-(2-(dimethylamino)ethylamino)-1H-pyrazol-1-yl)-4-fluoro-1H-pyrrolo[2,3-c]pyridin-3-yl)-2-(4-(1-phenyl-1H-tetrazol-5-yl)piperazin-1-yl)ethane-1,2-dione TFA (Compound B-23)

(Compound B-23)

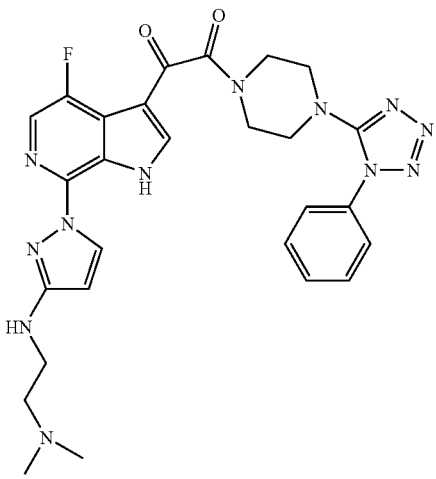

1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (0.100 g, 0.200 mmol) was combined with the N¹,N¹-dimethyl-N²-(1H-pyrazol-3-yl)ethane-1,2-diamine (0.140 g, 0.200 mmol), 1-methyl-2-pyrrolidinone (0.5 mL), K₂CO₃ (0.028 g, 0.200 mmol), and Cu powder (0.013 g, 0.200 mmol). The mixture was heated to 160° C. for 4.5 h. The mixture was cooled to rt, and diluted with DMF. The DMF mixture was filtered through a pad of celite to remove any solids, and the solution was purified by prep HPLC. After purification, the 1-(7-(3-(2-(dimethylamino)ethylamino)-1H-pyrazol-1-yl)-4-fluoro-1H-pyrrolo[2,3-c]pyridin-3-yl)-2-(4-(1-phenyl-1H-tetrazol-5-yl)piperazin-1-yl)ethane-1,2-dione.TFA (0.010 g) was recovered as a brown solid. LCMS: m/e 573.5 (M+H)⁺, ret time 1.88 min (method 2). 1H NMR (500 MHz, MeOD) δ ppm 8.42 (d, J=2.52 Hz, 1H) 8.30 (s, 1H) 7.95 (d, J=2.06 Hz, 1H) 7.56-7.72 (m, 5H) 6.01 (d, J=2.75 Hz, 1H) 3.78-3.86 (m, 4H) 3.59-3.64 (m, 2H) 3.42-3.46 (m, 2H) 3.34-3.39 (m, 4H) 2.95 (s, 6H)

Preparation of 1-(7-(5-((2-hydroxyethylamino)methyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione TFA (Compound B-24)

(Compound B-24)

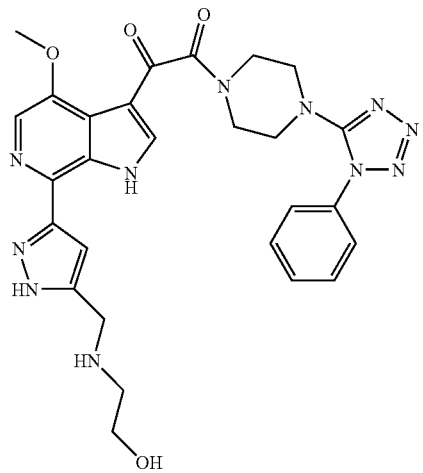

In a sealable flask, a mixture of 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (0.240 g, 0.509 mmol) in 1,4-dioxane (5 mL) was prepared. 2-((3-(tributylstannyl)-1H-pyrazol-5-yl)methylamino)ethanol (0.241 g, 0.560 mmol) was added followed by tetrakis(triphenylphosphine)palladium (0) (0.177 g, 0.153 mmol). The mixture was flushed with N₂, and flask was sealed. The mixture was then heated to 120° C. for 14 h. After cooling to rt, the mixture was diluted with DMF, and filtered through a plug of celite to remove any solids. The liquid was concentrated under reduced pressure, and the residue was dissolved in DMF. The DMF solution was purified by prep HPLC to give 0.050 g of a light yellow solid as the 1-(7-(5-((2-hydroxyethylamino)methyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione.TFA. LCMS: m/e 572.5 (M+H)⁺, ret time 1.68 min (method 2). 1H NMR (500 MHz, MeOD) δ ppm 8.57 (s, 1H) 8.06 (s, 1H) 7.60-7.75 (m, 5H) 7.42 (s, 1H) 4.54 (s, 2H) 4.14 (s, 3H) 3.83-3.91 (m, 4H) 3.62-3.68 (m, 2H) 3.24-3.45 (m, 6H).

Preparation of 1-(7-(5-((2-(dimethylamino)ethylamino)methyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione TFA (Compound B-25)

(Compound B-25)

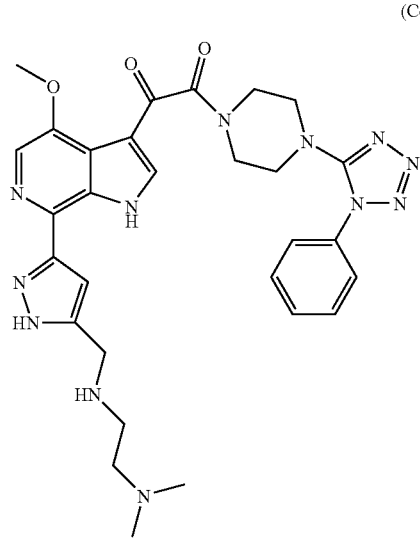

Preparation of 1-(7-(5-(((2-(dimethylamino)ethyl)(methyl)amino)methyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione TFA (Compound B-26)

(Compound B-26)

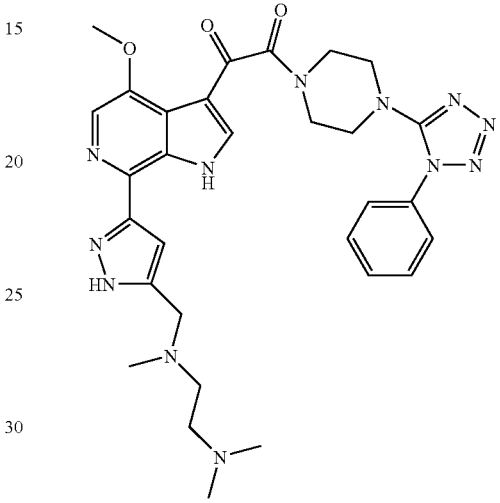

In a sealable flask, a mixture of 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (0.140 g, 0.306 mmol) in 1,4-dioxane (5 mL) was prepared. 2-((3-(tributylstannyl)-1H-pyrazol-5-yl)methylamino)ethanol (0.14 g, 0.306 mmol) was added followed by tetrakis(triphenylphosphine)palladium (0) (0.106 g, 0.092 mmol). The mixture was flushed with $N_2$, and flask was sealed. The mixture was then heated to 120° C. for 15 h. After cooling to rt, the mixture was diluted with DMF, and filtered through a plug of celite to remove any solids. The liquid was concentrated under reduced pressure, and the residue was adsorbed to silica gel. A flash column was run using a 0 to 100% MeOH in $CH_2Cl_2$ gradient. Still the product was on the column, so it was flushed with DMF to remove the product. The DMF was mostly removed under reduced pressure, and was further removed by dissolving the product in $CH_2Cl_2$ and washing the organic layer 5 times with $H_2O$. The organic layer was dried with $Na_2SO_4$, was filtered, and concentrated under reduced pressure. The 1-(7-(5-((2-(dimethylamino)ethylamino)methyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione.TFA (0.053 g) was recovered as a light yellow solid. LCMS: m/e 599.4 $(M+H)^+$, ret time 1.73 min (method 2). 1H NMR (500 MHz, MeOD) δ ppm 8.27 (s, 1H) 7.95 (s, 1H) 7.54-7.68 (m, 5H) 6.92 (s, 1H) 4.02 (s, 3H) 3.93 (s, 2H) 3.77-3.82 (m, 2H) 3.52-3.58 (m, 2H) 3.35-3.40 (m, 2H) 3.24-3.30 (m, 2H) 2.78 (t, J=6.71 Hz, 2H) 2.53 (t, J=6.71 Hz, 2H) 2.28 (s, 6H).

In a sealable flask, a mixture of 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (0.165 g, 0.353 mmol) in 1,4-dioxane (5 mL) was prepared. $N^1,N^1,N^2$-trimethyl-$N^2$-((3-(tributylstannyl)-1H-pyrazol-5-yl)methyl)ethane-1,2-diamine (0.175 g, 0.371 mmol) was added followed by tetrakis(triphenylphosphine)palladium (0) (0.122 g, 0.106 mmol). The mixture was flushed with $N_2$, and flask was sealed. The mixture was then heated to 120° C. for 15 h. After the reaction was incomplete by LCMS, an additional 0.050 g of $N^1,N^1$, $N^2$-trimethyl-$N^2$-((3-(tributylstannyl)-1H-pyrazol-5-yl)methyl)ethane-1,2-diamine was added along with 0.075 g of tetrakis(triphenylphosphine)palladium (0). The mixture was flushed with $N_2$, sealed, and reheated to 120° C. for 6 h. After cooling to rt, the mixture was diluted with DMF, and filtered through a plug of celite to remove any solids. The liquid was concentrated under reduced pressure, and the residue was dissolved in DMF. The DMF solution was purified by prep HPLC to give 0.040 g of a light yellow solid as the 1-(7-(5-(((2-(dimethylamino)ethyl)(methyl)amino)methyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione.TFA. LCMS: m/e 613.4 $(M+H)^+$, ret time 1.80 min (method 2). 1H NMR (500 MHz, MeOD) δ ppm 8.66 (s, 1H) 8.06 (s, 1H) 7.59-7.74 (m, 5H) 7.45 (s, 1H) 4.33 (s, 2H) 4.15 (s, 3H) 3.82-3.87 (m, 2H) 3.62-3.67 (m, 2H) 3.56 (t, J=6.56 Hz, 2H) 3.39-3.44 (m, 2H) 3.32-3.38 (m, 4H) 2.99 (s, 6H) 2.66-2.69 (m, 3H).

Preparation of 1-(4-methoxy-7-(5-((2-(pyridin-4-yl)ethylamino)methyl)-1H-pyrazol-3-yl)-1H-pyrrolo[2,3-c]pyridin-3-yl)-2-(4-(1-phenyl-1H-tetrazol-5-yl)piperazin-1-yl)ethane-1,2-dione TFA (Compound B-27)

(Compound B-27)

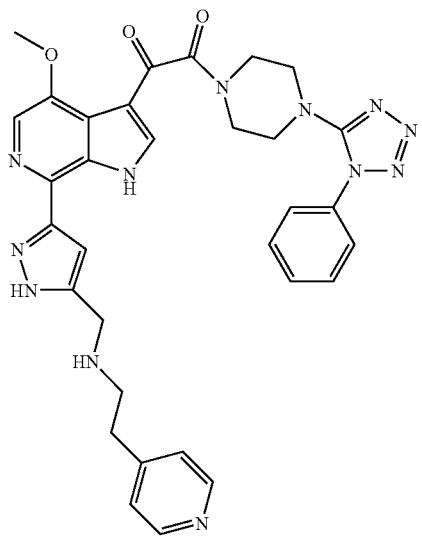

In a sealable flask, a mixture of 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (0.195 g, 0.417 mmol) in 1,4-dioxane (7 mL) was prepared. 2-(pyridin-4-yl)-N-((3-(tributylstannyl)-1H-pyrazol-5-yl)methyl)ethanamine (0.205 g, 0.417 mmol) was added followed by tetrakis(triphenylphosphine)palladium (0) (0.144 g, 0.125 mmol). The mixture was flushed with $N_2$, and flask was sealed. The mixture was then heated to 120° C. for 14 h. After cooling to rt, the mixture was diluted with $CH_2Cl_2$ and MeOH, and filtered through a plug of celite to remove any solids. Solids were washed with MeOH to be sure no product was left behind. The liquid was concentrated under reduced pressure, and the residue was dissolved in DMF. The DMF solution was purified by prep HPLC to give 0.028 g of a light yellow solid as the 1-(7-(5-((2-hydroxyethylamino)methyl)-1H-pyrazol-3-yl)-4-methoxy-1H-pyrrolo[2,3-c]pyridin-3-yl)-2-(4-(1-phenyl-1H-tetrazol-5-yl)piperazin-1-yl)ethane-1,2-dione.TFA. LCMS: m/e 633.4 (M+H)$^+$, ret time 1.70 min (method 2). 1H NMR (500 MHz, MeOD) δ ppm 8.80-8.85 (m, J=6.10 Hz, 2H) 8.60 (s, 1H) 8.05-8.10 (m, 3H) 7.59-7.73 (m, 5H) 7.50 (s, 1H) 4.61 (s, 2H) 4.14 (s, 3H) 3.81-3.87 (m, 2H) 3.60-3.68 (m, 4H) 3.04-3.07 (m, 6H).

Preparation of ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate

B-33

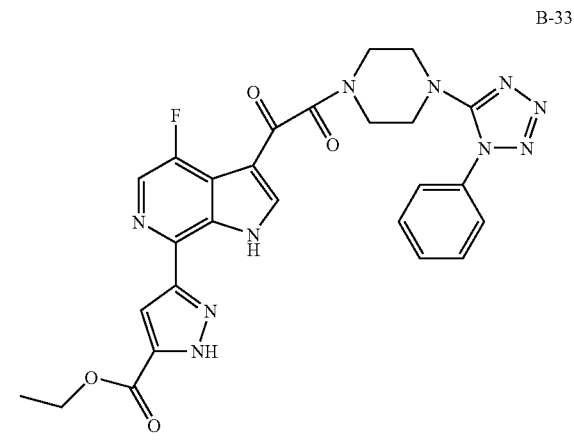

To a sealed tube containing 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (Compound B-1) (1.24 g, 2.48 mmol) in 1,4-dioxane (20 mL) was added ethyl 3-(tributylstannyl)-1H-pyrazole-5-carboxylate (1.12 g, 2.61 mmol) and Pd(PPh$_3$)$_4$ (0.87 g, 0.75 mmol). The mixture was flushed with $N_2$, and was sealed and heated to 100° C. After 14 h of heating, the mixture was cooled to rt, was diluted with MeOH, and was filtered through a pad of celite to remove any solids. The solution was concentrated under reduced pressure, and was re-dissolved in DMF. The DMF solution was loaded on the prep HPLC for purification. After purification, the title product was isolated as an off-white solid (0.901 g). LCMS: m/e 559.6 (M+H)$^+$, ret time 2.283 min (method 2). 1H NMR (500 MHz, DMSO-D$_6$) δ ppm 14.52 (s, 1H) 12.35 (s, 1H) 8.26-8.41 (m, 2H) 7.36-7.76 (m, 6H) 4.29-4.47 (m, J=6.71 Hz, 2H) 3.09-3.80 (m, 8H) 1.36 (s, 3H).

Preparation of 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylic acid

B-34

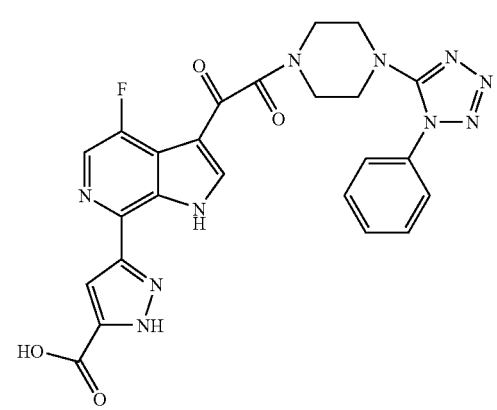

To a rb flask containing ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.058 g, 0.10 mmol) in DMF (5 mL) and water (5 mL) was added lithium hydroxide monohydrate (0.044 g, 1.05 mmol). The mixture was heated to 100° C. for 21.5 h. The mixture was cooled to rt, and HCl was added to PH=1. Solids precipitated out of solution, and were collected by filtration to give the title compound as a yellow solid (0.03 g). LCMS: m/e 531.15 (M+H)+, ret time 2.10 min (method 2). 1H NMR (500 MHz, DMSO-D$_6$) δ ppm 14.37 (s, 1H) 13.58 (s, 1H) 12.23 (s, 1H) 8.21-8.42 (m, 2H) 7.52-7.77 (m, 5H) 7.35 (s, 1H) 3.08-3.76 (m, 8H).

C-7 Pyrazole carboxamides were made using two different methods. A general procedure for each method is provided along with characterizations of those compounds from each method.

Method 1

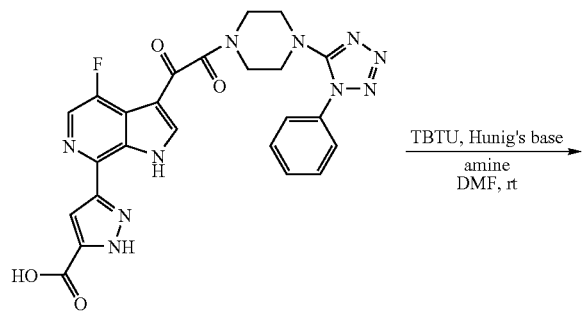

-continued

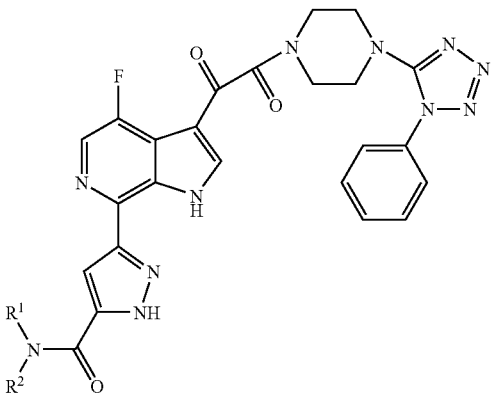

To a flask containing of 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylic acid (0.02-0.07 g, 1 equiv) in DMF (2 mL) was added Hunig's base (0.2 mL) followed by the amine (1.2 equiv) and TBTU (1.1 equiv). The mixture was flushed with N$_2$, and was stirred at rt. After 15-72 h, the mixture was quenched with water and the solution was concentrated under reduced pressure. The resulting residue was dissolved in DMF, and filtered through a pad of celite to remove any remaining solids. The DMF solution was purified by prep HPLC to give the amide products as their TFA salts.

| R$_1$ | R$_2$ | Mass recovered after purification | LC/MS (M + 1) (Method 2) | Retention time (minutes) | Compound Name |
|---|---|---|---|---|---|
| B-35 (dimethylaminoethyl) | CH$_3$ | 7 mg | 615.8 | 1.90 | N-(2-(dimethylamino)ethyl)-3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-methyl-1H-pyrazole-5-carboxamide•TFA |
| B-36 (2-hydroxyethyl) | CH$_3$ | 31 mg | 588.3 | 2.01 | 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-hydroxyethyl)-N-methyl-1H-pyrazole-5-carboxamide•TFA |
| B-37 (2-hydroxyethyl) | H | 14.8 mg | 574.6 | 2.01 | 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-hydroxyethyl)-1H-pyrazole-5-carboxamide•TFA |

-continued

| $R_1$ | $R_2$ | Mass recovered after purification | LC/MS (M + 1) (Method 2) | Retention time (minutes) | Compound Name |
|---|---|---|---|---|---|
| 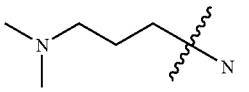 B-38 | CH₃ | 9.4 mg | 629.6 | 1.90 | N-(3-(dimethylamino)propyl)-3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-methyl-1H-pyrazole-5-carboxamide•TFA |
| 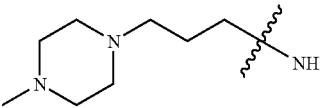 B-39 | H | 13 mg | 670.4 | 1.87 | 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(3-(4-methylpiperazin-1-yl)propyl)-1H-pyrazole-5-carboxamide•TFA |

Compound: N-(2-(dimethylamino)ethyl)-3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-methyl-1H-pyrazole-5-carboxamide.TFA 1H NMR (500 MHz, MeOD) δ ppm 8.37-8.42 (m, 1H) 8.29 (s, 1H) 7.58-7.74 (m, 5H) 7.49 (s, 1H) 3.97-4.04 (m, 2H) 3.82-3.87 (m, 2H) 3.61-3.67 (m, 2H) 3.27-3.55 (m, 9H) 3.06 (s, 6H)

Compound: 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-hydroxyethyl)-N-methyl-1H-pyrazole-5-carboxamide.TFA 1H NMR (500 MHz, MeOD) δ ppm 8.45 (s, 1H) 8.28 (d, J=2.75 Hz, 1H) 7.57-7.71 (m, 5H) 7.42 (d, J=6.71 Hz, 1H) 3.71-3.89 (m, 6H) 3.62-3.66 (m, 2H) 3.16-3.46 (m, 7H)

Compound: 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-hydroxyethyl)-1H-pyrazole-5-carboxamide.TFA 1H NMR (500 MHz, MeOD) δ ppm 8.39 (s, 1H) 8.24 (d, J=2.44 Hz, 1H) 7.57-7.71 (m, 5H) 7.44 (s, 1H) 3.81-3.85 (m, 2H) 3.76 (t, J=5.65 Hz, 2H) 3.61-3.66 (m, 2H) 3.55 (t, J=5.65 Hz, 2H) 3.36-3.41 (m, 2H) 3.29-3.35 (m, 2H)

Compound: N-(3-(dimethylamino)propyl)-3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-methyl-1H-pyrazole-5-carboxamide.TFA 1H NMR (500 MHz, MeOD) δ ppm 8.40 (s, 1H) 8.29 (s, 1H) 7.59-7.73 (m, 5H) 7.47 (s, 1H) 3.81-3.87 (m, 2H) 3.69-3.76 (m, 2H) 3.62-3.66 (m, 2H) 3.16-3.48 (m, 7H) 2.97 (s, 6H) 2.87-2.91 (m, 2H) 2.11-2.25 (m, 2H)

Compound: 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(3-(4-methylpiperazin-1-yl)propyl)-1H-pyrazole-5-carboxamide.TFA 1H NMR (500 MHz, MeOD) δ ppm 8.37 (s, 1H) 8.27 (d, J=2.44 Hz, 1H) 7.58-7.74 (m, 5H) 7.46 (s, 1H) 3.80-3.86 (m, 2H) 3.60-3.66 (m, 2H) 3.27-3.58 (m, 14H) 3.05-3.12 (m, 2H) 2.94 (s, 3H) 1.99-2.07 (m, 2H)

Method 2

To a sealable flask containing ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.05 g, 0.09 mmol) was added the amine (0.5 mL). The mixture was stirred at rt for three days, then was diluted with DMF and passed through a pad of celite to remove any solids. The DMF solution was then purified by prep HPLC to give the desired amide products.

| $R_1$ | $R_2$ | Mass recovered after purification | LC/MS (M + 1) (Method 2) | Retention time (minutes) | Compound Name |
|---|---|---|---|---|---|
| 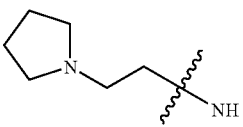 B-40 | H | 39.7 mg | 627.4 | 1.92 | 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-(pyrrolidin-1-yl)ethyl)-1H-pyrazole-5-carboxamide•TFA |

| R₁ | R₂ | Mass recovered after purification | LC/MS (M + 1) (Method 2) | Retention time (minutes) | Compound Name |
|---|---|---|---|---|---|
| B-41 (pyridyl-CH₂CH₂-CH(NH-)) | H | 40.2 mg | 635.3 | 1.94 | 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-(pyridin-4-yl)ethyl)-1H-pyrazole-5-carboxamide•TFA |
| B-42 (morpholino-CH₂CH₂-CH(NH-)) | H | 23.6 mg | 643.5 | 1.91 | 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-morpholinoethyl)-1H-pyrazole-5-carboxamide•TFA |

Compound: 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-(pyrrolidin-1-yl)ethyl)-1H-pyrazole-5-carboxamide.TFA 1H NMR (500 MHz, MeOD) δ ppm 8.38 (s, 1H) 8.25 (d, J=2.44 Hz, 1H) 7.56-7.70 (m, 5H) 7.45 (s, 1H) 3.78-3.89 (m, 6H) 3.61-3.66 (m, 2H) 3.50 (t, J=5.80 Hz, 2H) 3.35-3.41 (m, 2H) 3.29-3.35 (m, 2H) 3.16-3.26 (m, 2H) 2.01-2.26 (m, 4H).

Compound: 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-(pyridin-4-yl)ethyl)-1H-pyrazole-5-carboxamide.TFA 1H NMR (500 MHz, MeOD) δ ppm 8.78 (d, J=6.71 Hz, 2H) 8.37 (s, 1H) 8.23 (d, J=2.44 Hz, 1H) 8.07 (d, J=6.71 Hz, 2H) 7.62-7.69 (m, 5H) 7.38 (s, 1H) 3.80-3.86 (m, 4H) 3.61-3.64 (m, 2H) 3.28-3.41 (m, 6H).

Compound: 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-morpholinoethyl)-1H-pyrazole-5-carboxamide.TFA 1H NMR (500 MHz, MeOD) δ ppm 8.38 (s, 1H) 8.27 (d, J=2.75 Hz, 1H) 7.58-7.71 (m, 5H) 7.47 (s, 1H) 4.11 (s, 2H) 3.68-3.89 (m, 8H) 3.63 (d, J=4.88 Hz, 4H) 3.61-3.65 (m, 2H) 3.48 (t, J=5.95 Hz, 2H) 3.37-3.40 (m, 2H).

Preparation of ethyl 3-(4-fluoro-1-methyl-3-(2-oxo-2-(4-(1-phenyl-1H-tetrazol-5-yl)piperazin-1-yl)acetyl)-1H-pyrrolo[2,3-c]pyridin-7-yl)-1-methyl-1H-pyrazole-5-carboxylate and ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1-methyl-1H-pyrazole-5-carboxylate

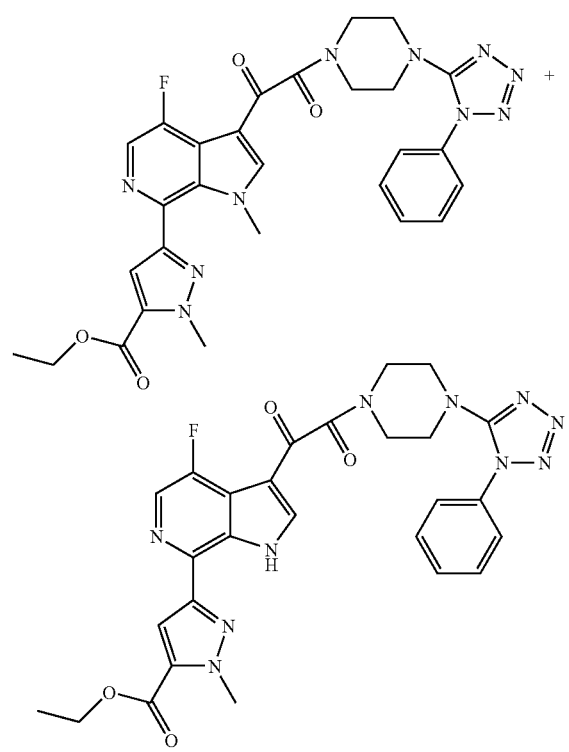

B-43 and B-60

To a solution of ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylate (0.050 g, 0.09 mmol) in DMF (2 mL) was added a 2M in THF solution of NaHMDS (0.11 mL, 0.22 mmol) dropwise followed by MeI (0.05 mL, 0.9 mmol). The mixture was stirred for 60 minutes at rt, and was quenched with 2 mL H₂O. The solvent was removed under reduced pressure, and the residue was re-dissolved in DMF. The DMF solution was passed through a plug of celite to remove any remaining solids, and was purified by prep HPLC to give ethyl 3-(4-fluoro-1-methyl-3-(2-oxo-2-(4-(1-phenyl-1H-tetrazol-5-yl)piperazin-1-yl)acetyl)-1H-pyrrolo[2,3-c]pyridin-7-yl)-1-methyl-1H-pyrazole-5-carboxylate (0.011 g) and ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1-methyl-1H-pyrazole-5-carboxylate (0.011 g) as the products.

Ethyl 3-(4-fluoro-1-methyl-3-(2-oxo-2-(4-(1-phenyl-1H-tetrazol-5-yl)piperazin-1-yl)acetyl)-1H-pyrrolo[2,3-c]pyridin-7-yl)-1-methyl-1H-pyrazole-5-carboxylate: LCMS: m/e 587.7 (M+H)⁺, ret time 2.213 min (method 2). 1H NMR (500 MHz, MeOD) δ ppm 8.42 (s, 1H) 8.31 (s, 1H) 7.51-7.70 (m, 5H) 7.25 (s, 1H) 4.40 (q, J=6.92 Hz, 2H) 4.27 (s, 3H) 3.77-3.83 (m, 2H) 3.73 (s, 3H) 3.57-3.63 (m, 2H) 3.33-3.40 (m, 2H) 3.26-3.33 (m, 2H) 1.39 (t, J=7.02 Hz, 3H).

Ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1-methyl-1H-pyrazole-5-carboxylate: LCMS: m/e 573.5 (M+H)⁺, ret time 1.747 min (method 1). 1H NMR (500 MHz, CHLOROFORM-D) δ ppm 11.55 (s, 1H) 8.43 (s, 1H) 8.29 (s, 1H) 7.73 (s, 1H) 7.48-7.67 (m, 5H) 4.35-4.48 (m, 2H) 4.31 (s, 3H) 3.80-3.89 (m, 2H) 3.62-3.72 (m, 2H) 3.30-3.47 (m, 4H) 1.34-1.49 (m, 3H).

Preparation of 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-N-(2-hydroxyethyl)-1-methyl-1H-pyrazole-5-carboxamide.TFA.

B-44

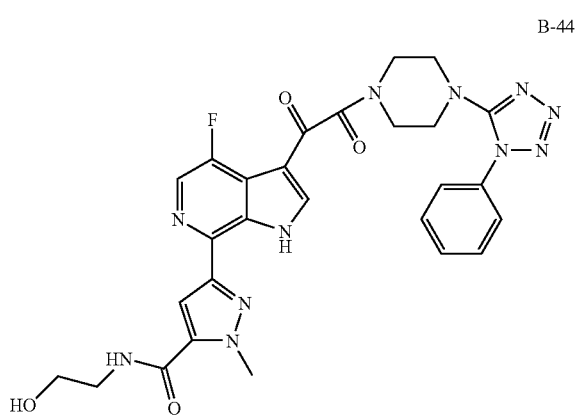

To a sealable flask containing ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1-methyl-1H-pyrazole-5-carboxylate (0.047 g, 0.08 mmol) was added ethanolamine (0.7 mL). The mixture was sealed and heated to 50° C. for 20.5 h. The mixture was cooled to rt, and was diluted with DMF and was passed through a plug of celite to remove any solids. The DMF solution was purified by prep HPLC to give 3-(4-fluoro-3-(2-oxo-2-(4-(1-phenyl-1H-tetrazol-5-yl)piperazin-1-yl) acetyl)-1H-pyrrolo[2,3-c]pyridin-7-yl)-N-(2-hydroxyethyl)-1-methyl-1H-pyrazole-5-carboxamide.TFA (0.014 g) as an off-white solid. LCMS: m/e 588.7 (M+H)⁺, ret time 2.03 min (method 2) 1H NMR (500 MHz, CDCl₃) δ ppm 8.35 (s, 1H) 8.23 (s, 1H) 7.50-7.61 (m, 6H) 4.29 (s, 3H) 3.78-3.85 (m, 4H) 3.54-3.64 (m, 4H) 3.40 (s, 2H) 3.29-3.34 (m, 2H) 2.79 (s, 1H).

Preparation of N-(3-(dimethylamino)propyl)-3-(4-fluoro-3-(2-oxo-2-(4-(1-phenyl-1H-tetrazol-5-yl) piperazin-1-yl)acetyl)-1H-pyrrolo[2,3-c]pyridin-7-yl)-1-methyl-1H-pyrazole-5-carboxamide.TFA

B-45

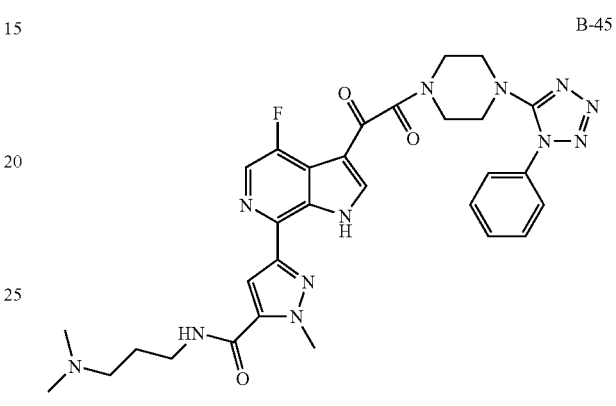

To a sealable flask containing ethyl 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1-methyl-1H-pyrazole-5-carboxylate (0.058 g, 0.10 mmol) was added N1,N1-dimethylpropane-1,3-diamine (0.7 mL). The mixture was sealed and heated to 50° C. for 20.5 h. The mixture was cooled to rt, and was diluted with DMF and was passed through a plug of celite to remove any solids. The DMF solution was purified by prep HPLC to give N-(3-(dimethylamino)propyl)-3-(4-fluoro-3-(2-oxo-2-(4-(1-phenyl-1H-tetrazol-5-yl) piperazin-1-yl)acetyl)-1H-pyrrolo[2,3-c]pyridin-7-yl)-1-methyl-1H-pyrazole-5-carboxamide.TFA. (0.020 g) as an off-white solid. LCMS: m/e 629.5 (M+H)⁺, ret time 1.93 min (method 2). 1H NMR (500 MHz, MeOD) δ ppm 8.75 (s, 1H) 8.61 (s, 1H) 7.97-8.11 (m, 5H) 7.79 (s, 1H) 4.69 (s, 3H) 4.21-4.25 (m, 2H) 4.01-4.04 (m, 2H) 3.91 (t, J=6.26 Hz, 2H) 3.76-3.82 (m, J=3.66 Hz, 2H) 3.65-3.75 (m, 10H) 2.45-2.52 (m, 2H).

Preparation of 4-fluoro-3-(2-oxo-2-(4-(1-phenyl-1H-tetrazol-5-yl)piperazin-1-yl)acetyl)-1H-pyrrolo[2,3-c]pyridine-7-carbonitrile

B-46

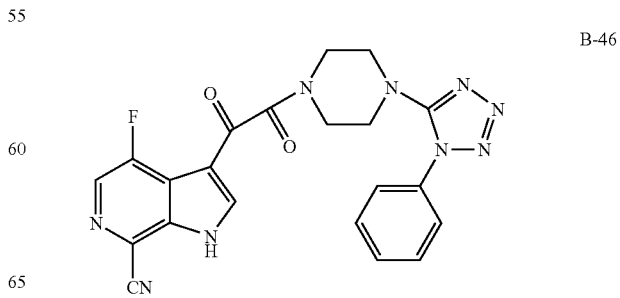

To a sealable flask containing 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (0.10 g, 0.20 mmol) in 1,4-dioxane (5 mL) was added tributyltin cyanide (0.07 g, 0.22 mmol) followed by Pd(PPh$_3$)$_4$ (0.07 g, 0.06 mmol). The mixture was flushed with N$_2$, and the tube was sealed and heated to 100° C. After 16 h of heating, the mixture was cooled to rt, and the solvent was removed in vacuo. The residue was dissolved in DMF and was filtered through a pad of celite to remove any remaining solids. The DMF solution was purified by prep HPLC to give the title compound as an off-white solid (0.028 g). LCMS: m/e 446.2 (M+H)$^+$, ret time 1.81 min (method 2). 1H NMR (500 MHz, DMSO-D$_6$) δ ppm 14.06 (s, 1H) 8.66 (s, 1H) 8.50 (d, J=2.14 Hz, 1H) 7.56-7.70 (m, 5H) 3.67-3.72 (m, 2H) 3.33-3.50 (m, 4H) 3.13-3.17 (m, 2H).

Preparation of 1-(7-acetyl-4-fluoro-1H-pyrrolo[2,3-c]pyridin-3-yl)-2-(4-(1-phenyl-1H-tetrazol-5-yl)piperazin-1-yl)ethane-1,2-dione

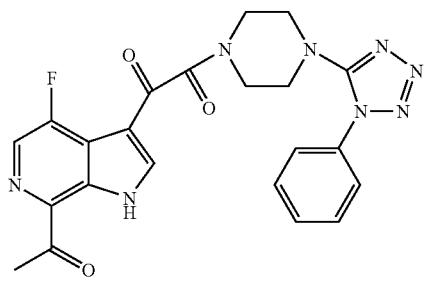

B-47

To a sealable flask containing 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (0.10 g, 0.20 mmol) in 1,4-dioxane (5 mL) was added tributyl(1-ethoxyvinyl)tin (0.079 g, 0.22 mmol) followed by Pd(PPh$_3$)$_4$ (0.07 g, 0.06 mmol). The mixture was flushed with N$_2$, and the tube was sealed and heated to 100° C. After 16 h of heating, the mixture was cooled to rt, and the solvent was removed in vacuo. The residue was dissolved in DMF and was filtered through a pad of celite to remove any remaining solids. The DMF solution was purified by prep HPLC to give the title compound as an off-white solid (0.025 g). LCMS: m/e 463.38 (M+H)$^+$, ret time 1.88 min (method 2). 1H NMR (500 MHz, CDCl$_3$) δ ppm 11.02 (s, 1H) 8.35 (s, 1H) 8.31 (d, J=2.75 Hz, 1H) 7.52-7.62 (m, 5H) 3.81-3.85 (m, 2H) 3.61-3.65 (m, 2H) 3.39-3.43 (m, 2H) 3.31-3.35 (m, 2H) 2.80-2.83 (m, 3H).

Preparation of (E)-1-(4-fluoro-7-(1-(methoxyimino)ethyl)-1H-pyrrolo[2,3-c]pyridin-3-yl)-2-(4-(1-phenyl-1H-tetrazol-5-yl)piperazin-1-yl)ethane-1,2-dione

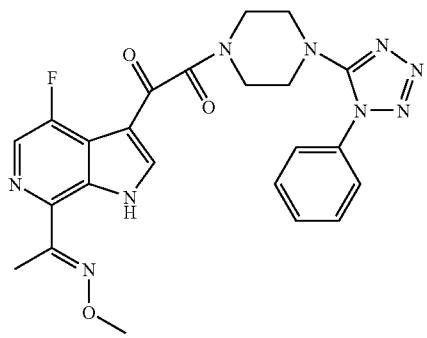

B-48

To a suspension of 1-(7-acetyl-4-fluoro-1H-pyrrolo[2,3-c]pyridin-3-yl)-2-(4-(1-phenyl-1H-tetrazol-5-yl)piperazin-1-yl)ethane-1,2-dione (0.05 g, 0.11 mmol) in EtOH (10 mL) was added methoxylamine hydrochloride (0.05 g, 0.60 mmol). The mixture was heated to reflux for 1 h, and was then cooled to rt, and concentrated in vacuo. The residue was diluted with MeOH, and the solids that formed were collected and washed with water. The title compound was isolated as a light-yellow solid (0.025 g). LCMS: m/e 492.4 (M+H)$^+$, ret time 2.068 min (method 2). 1H NMR (500 MHz, DMSO-D$_6$) δ ppm 12.02 (s, 1H) 8.36 (d, J=2.14 Hz, 1H) 8.27 (d, J=3.36 Hz, 1H) 7.56-7.71 (m, 5H) 4.13-4.16 (m, 3H) 3.68-3.73 (m, 2H) 3.43-3.48 (m, 2H) 3.29-3.36 (m, 2H) 3.13-3.18 (m, 2H) 2.36 (s, 3H).

Preparation of (E)-1-(4-fluoro-7-(1-(hydroxyimino)ethyl)-1H-pyrrolo[2,3-c]pyridin-3-yl)-2-(4-(1-phenyl-1H-tetrazol-5-yl)piperazin-1-yl)ethane-1,2-dione

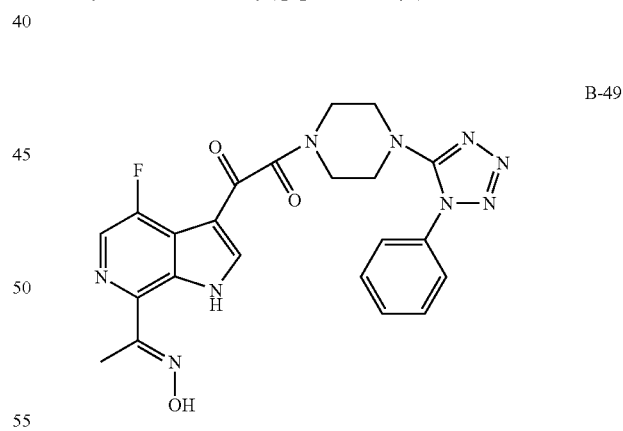

B-49

To a suspension of 1-(7-acetyl-4-fluoro-1H-pyrrolo[2,3-c]pyridin-3-yl)-2-(4-(1-phenyl-1H-tetrazol-5-yl)piperazin-1-yl)ethane-1,2-dione (0.05 g, 0.11 mmol) in EtOH (10 mL) was added hydroxylamine hydrochloride (0.04 g, 0.58 mmol). The mixture was heated to reflux for 1 h, and was then cooled to rt, and concentrated in vacuo. The residue was diluted with MeOH, and the solids that formed were collected and washed with water. The title compound was isolated as an off-white solid (0.027 g). LCMS: m/e 478.5 (M+H)$^+$, ret time 1.53 min (method 1). 1H NMR (500 MHz, DMSO-D$_6$) δ ppm 11.95 (s, 1H) 11.61 (s, 1H) 8.34 (d, J=1.83 Hz, 1H) 8.30 (d, J=3.36 Hz, 1H) 7.56-7.71 (m, 5H) 3.68-3.72 (m, 2H) 3.43-3.48 (m, 2H) 3.30-3.34 (m, 2H) 3.13-3.17 (m, 2H) 2.35 (s, 3H).

Preparation of 4-fluoro-3-(2-oxo-2-(4-(1-phenyl-1H-tetrazol-5-yl)piperazin-1-yl)acetyl)-1H-pyrrolo[2,3-c]pyridine-7-carboxamide

B-50

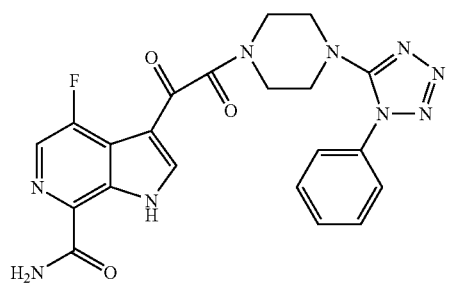

To a sealable flask containing 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (1.0 g, 2.0 mmol) in 1,4-dioxane (20 mL) was added tributyltin cyanide (0.70 g, 2.2 mmol) followed by Pd(PPh$_3$)$_4$ (0.12 g, 0.1 mmol). The mixture was flushed with N$_2$, and the tube was sealed and heated to 100° C. After 20 h of heating, the mixture was cooled to rt, and was diluted with MeOH (50 mL) and was filtered through a pad of celite to remove solids. To the solution was added H$_2$O (20 mL), and the mixture was heated with a heat gun. Solids formed upon cooling, and were collected by filtration. The solids were dissolved in DMF and were purified by prep HPLC to give the title compound as an off-white solid (30 mg). LCMS: m/e 464.11 (M+H)$^+$, ret time 1.095 min (method 3). 1H NMR (500 MHz, DMSO-D$_6$) δ ppm 12.78 (s, 1H) 8.34 (d, J=2.14 Hz, 1H) 8.30 (s, 1H) 8.25 (d, J=3.36 Hz, 1H) 7.88 (s, 1H) 7.56-7.71 (m, 5H) 3.67-3.72 (m, 2H) 3.43-3.47 (m, 2H) 3.30-3.34 (m, 2H) 3.13-3.17 (m, 2H).

Preparation of ethyl 3-(4-fluoro-3-(2-oxo-2-(4-(3-phenyl-1H-pyrazol-4-yl)piperazin-1-yl)acetyl)-1H-pyrrolo[2,3-c]pyridin-7-yl)-1H-pyrazole-5-carboxylate

B-51

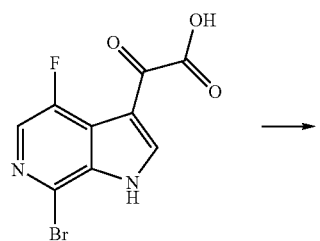

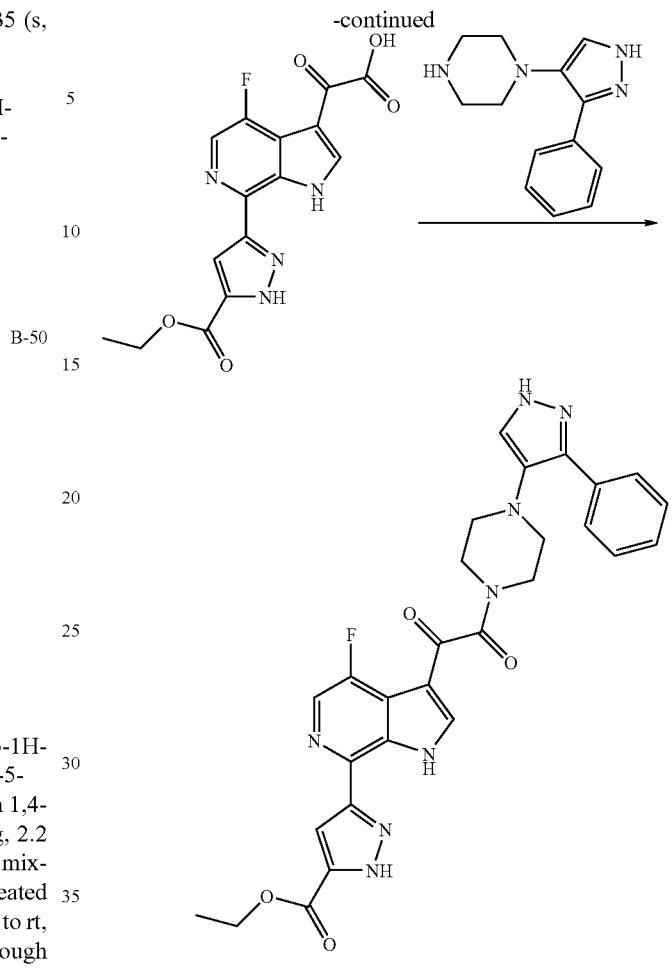

To a sealable flask containing 2-(7-bromo-4-fluoro-1H-pyrrolo[2,3-c]pyridin-3-yl)-2-oxoacetic acid (0.15 g, 0.52 mmol) in 1,4-dioxane (5 mL) was added 2-(7-(5-(ethoxycarbonyl)-1H-pyrazol-3-yl)-4-fluoro-1H-pyrrolo[2,3-c]pyridin-3-yl)-2-oxoacetic acid (0.24 g, 0.55 mmol) followed by Pd(PPh$_3$)$_4$ (0.18 g, 0.16 mmol). The mixture was flushed with N$_2$, and the tube was sealed and heated to 100° C. After 3 h of heating, the mixture was cooled to rt, and was diluted with MeOH. The solution was passed through a pad of celite to remove solids, and the resulting solution was concentrated under reduced pressure. The residue was dissolved in DMF, and was loaded on the prep HPLC for purification. The 2-(7-(5-(ethoxycarbonyl)-1H-pyrazol-3-yl)-4-fluoro-1H-pyrrolo[2,3-c]pyridin-3-yl)-2-oxoacetic acid was isolated as an off-white solid (0.043 g). LCMS: m/e 347.3 (M+H)$^+$, ret time 1.68 min (method 2).

To a solution of 2-(7-(5-(ethoxycarbonyl)-1H-pyrazol-3-yl)-4-fluoro-1H-pyrrolo[2,3-c]pyridin-3-yl)-2-oxoacetic acid (0.017 g, 0.049 mmol) in DMF (1.5 mL) was added TBTU (0.017 g, 0.054 mmol), diisopropylethylamine (0.15 mL), and 1-(3-phenyl-1H-pyrazol-4-yl)piperazine (0.011 g, 0.049 mmol). The mixture was stirred under N$_2$ at rt for 14.5 h and was quenched with 10 mL of H$_2$O. The solvent was removed under reduced pressure, and the residue was dissolved in DMF. The DMF solution was passed though a plug of celite to remove solids, and the DMF solution was purified by prep HPLC to give the title compound as a white solid (13.3 mg). LCMS: m/e 557.4 (M+H)$^+$, ret time 1.79 min (method 1). 1H NMR (500 MHz, MeOD) δ ppm 8.44 (s, 1H) 8.31 (d, J=2.44 Hz, 1H) 7.95 (d, J=7.32 Hz, 2H) 7.63 (s, 1H) 7.56 (s, 1H) 7.46 (t, J=7.63 Hz, 2H) 7.36 (t, J=7.48 Hz, 1H) 4.46 (q, J=7.22 Hz, 2H) 3.88-3.92 (m, 2H) 3.65-3.70 (m, 2H) 3.00-3.04 (m, 2H) 2.91-2.95 (m, 2H) 1.45 (t, J=7.02 Hz, 3H).

Preparation of 3-(4-fluoro-3-(2-oxo-2-(4-(3-phenyl-1H-pyrazol-4-yl)piperazin-1-yl)acetyl)-1H-pyrrolo[2,3-c]pyridin-7-yl)-N-(2-hydroxyethyl)-1H-pyrazole-5-carboxamide.TFA

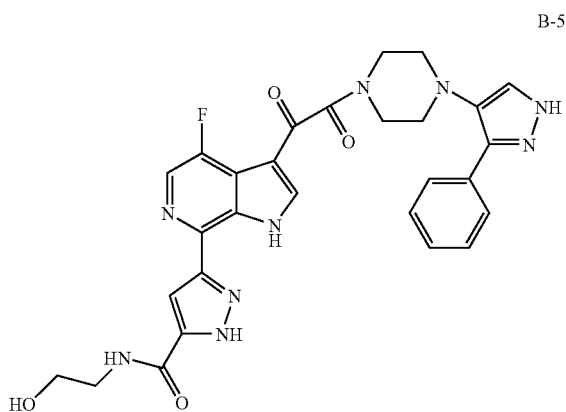

B-52

To a flask containing ethyl 3-(4-fluoro-3-(2-oxo-2-(4-(3-phenyl-1H-pyrazol-4-yl)piperazin-1-yl)acetyl)-1H-pyrrolo[2,3-c]pyridin-7-yl)-1H-pyrazole-5-carboxylate (0.025 g, 0.045 mmol) was added ethanolamine (0.5 mL). The mixture was stirred at rt for 15.5 h, and was diluted with DMF and passed through a pad of celite to remove any solids. The DMF solution was purified by prep HPLC to give the title compound as an off-white solid (0.010 g). LCMS: m/e 572.4 (M+H)$^+$, ret time 1.87 min (method 2). 1H NMR (500 MHz, DMSO-D$_6$) δ ppm 12.23 (s, 1H) 8.67 (s, 1H) 8.36 (s, 1H) 8.28 (s, 1H) 7.95-8.00 (m, 2H) 7.57-7.64 (m, 2H) 7.38-7.44 (m, 6.87 Hz, 2H) 7.28 (t, J=6.56 Hz, 1H) 3.74-3.80 (m, 2H) 3.32-3.62 (m, 7H) 2.84-2.91 (m, 2H) 2.73-2.80 (m, 2H).

Preparation of N-(3-(dimethylamino)propyl)-3-(4-fluoro-3-(2-oxo-2-(4-(3-phenyl-1H-pyrazol-4-yl)piperazin-1-yl)acetyl)-1H-pyrrolo[2,3-c]pyridin-7-yl)-1H-pyrazole-5-carboxamide.TFA

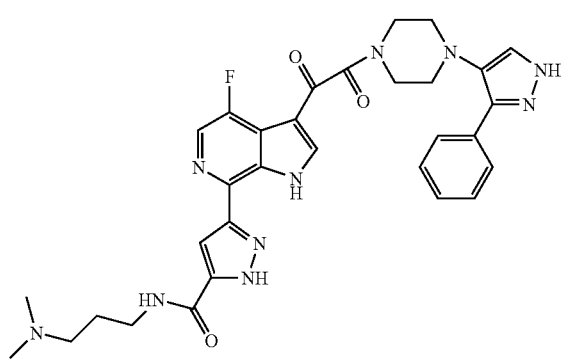

B-53

To a flask containing ethyl 3-(4-fluoro-3-(2-oxo-2-(4-(3-phenyl-1H-pyrazol-4-yl)piperazin-1-yl)acetyl)-1H-pyrrolo[2,3-c]pyridin-7-yl)-1H-pyrazole-5-carboxylate (0.043 g, 0.077 mmol) was added N1,N1-dimethylpropane-1,3-diamine (0.5 mL). The mixture was stirred at rt for 113 h, and was diluted with DMF and passed through a pad of celite to remove any solids. The DMF solution was purified by prep HPLC to give the title compound as an off-white solid (0.03 g). LCMS: m/e 613.3 (M+H)$^+$, ret time 1.91 min (method 6). 1H NMR (500 MHz, MeOD) δ ppm 8.40 (s, 1H) 8.27 (d, J=2.75 Hz, 1H) 7.94 (d, J=7.32 Hz, 2H) 7.64 (s, 1H) 7.43-7.47 (m, 3H) 7.35 (t, J=7.32 Hz, 1H) 3.87-3.91 (m, 2H) 3.64-3.68 (m, 2H) 3.53 (t, J=6.41 Hz, 2H) 3.24-3.29 (m, 2H) 2.99-3.03 (m, 2H) 2.95 (s, 6H) 2.90-2.94 (m, 2H) 2.05-2.13 (m, 2H).

Preparation of 3-(4-fluoro-3-(2-oxo-2-(4-(3-phenyl-1H-pyrazol-4-yl)piperazin-1-yl)acetyl)-1H-pyrrolo[2,3-c]pyridin-7-yl)-N-(2-morpholinoethyl)-1H-pyrazole-5-carboxamide.TFA

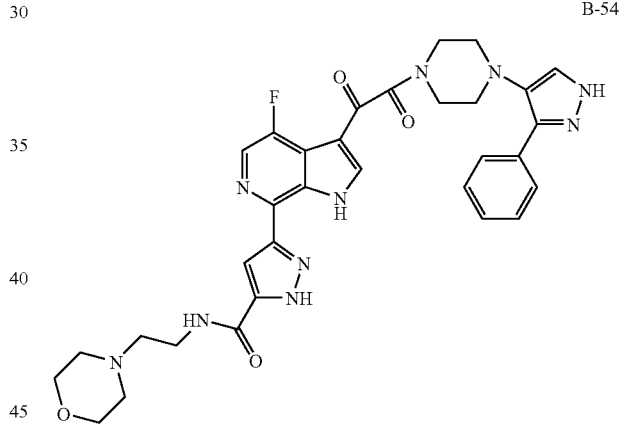

B-54

To a flask containing ethyl 3-(4-fluoro-3-(2-oxo-2-(4-(3-phenyl-1H-pyrazol-4-yl)piperazin-1-yl)acetyl)-1H-pyrrolo[2,3-c]pyridin-7-yl)-1H-pyrazole-5-carboxylate (0.038 g, 0.068 mmol) was added 2-morpholinoethanamine (0.5 mL). The mixture was stirred at rt for 113 h, and was diluted with DMF and passed through a pad of celite to remove any solids. The DMF solution was purified by prep HPLC to give the title compound as an off-white solid (0.041 g). LCMS: m/e 641.6 (M+H)$^+$, ret time 1.73 min (method 2). 1H NMR (500 MHz, MeOD) δ ppm 8.39 (s, 1H) 8.25-8.31 (m, 1H) 7.92-7.97 (m, 2H) 7.63 (s, 1H) 7.42-7.47 (m, 3H) 7.35 (t, J=7.48 Hz, 1H) 4.07-4.16 (m, 2H) 3.79-3.91 (m, 6H) 3.70-3.77 (m, 2H) 3.63-3.69 (m, 2H) 3.46-3.50 (m, 2H) 3.20-3.31 (m, 2H) 2.98-3.03 (m, 2H) 2.89-2.94 (m, 2H).

Preparation of 4-fluoro-N-(2-hydroxyethyl)-3-(2-oxo-2-(4-(1-phenyl-1H-tetrazol-5-yl)piperazin-1-yl)acetyl)-1H-pyrrolo[2,3-c]pyridine-7-carboxamide

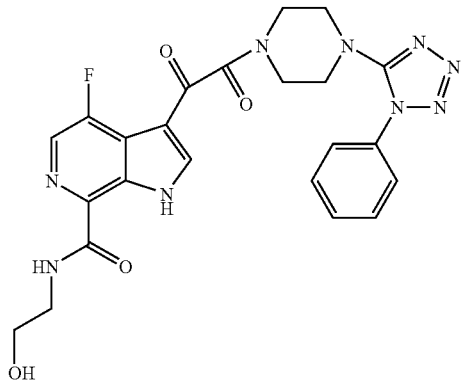

B-55

To a 15 mL rb flask containing 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (0.05 g, 0.10 mmol) was added DMF (2.0 mL), triethylamine (0.4 mL), ethanolamine (0.02 g, 0.33 mmol), and finally Pd(PPh$_3$)$_4$ (0.03 g, 0.03 mmol). The flask was placed in a Parr reaction vessel equipped with a pressure gauge and a gas inlet valve. The vessel was sealed and purged with N$_2$ three times, and was then purged with carbon monoxide three times, leaving the final fill pressure of carbon monoxide at 50 psi. The vessel was heated to 50° C. After 15 h of heating, the mixture was cooled to rt, the carbon monoxide was removed by vacuum, and the vessel was flushed with N$_2$. The mixture was concentrated under reduced pressure, and was diluted with DMF. The DMF solution was passed through a plug of celite to remove solids, and was purified by prep HPLC. The title compound was recovered as an off-white solid (0.014 g). LCMS: m/e 508.3 (M+H)$^+$, ret time 1.35 min (method 1). 1H NMR (500 MHz, DMSO-D$_6$) δ ppm 12.85 (s, 1H) 8.82 (s, 1H) 8.36 (s, 1H) 8.28 (s, 1H) 7.56-7.71 (m, 5H) 3.67-3.72 (m, 2H) 3.55-3.60 (m, 2H) 3.39-3.50 (m, 5H) 3.30-3.35 (m, 2H) 3.13-3.17 (m, 2H).

Preparation of 4-(dimethylamino)-N-(2-hydroxyethyl)-3-(2-oxo-2-(4-(1-phenyl-1H-tetrazol-5-yl)piperazin-1-yl)acetyl)-1H-pyrrolo[2,3-c]pyridine-7-carboxamide.TFA

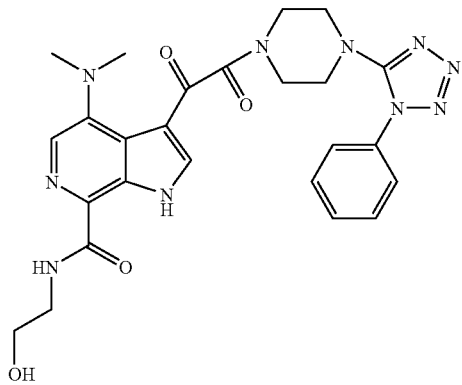

B-56

To a 15 mL rb flask containing 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (0.05 g, 0.10 mmol) was added DMF (2.0 mL), triethylamine (0.4 mL), ethanolamine (0.02 g, 0.33 mmol), and finally Pd(PPh$_3$)$_4$ (0.03 g, 0.03 mmol). The flask was placed in a Parr reaction vessel equipped with a pressure gauge and a gas inlet valve. The vessel was sealed and purged with N$_2$ three times, and was then purged with carbon monoxide three times, leaving the final fill pressure of carbon monoxide at 50 psi. The vessel was heated to 70° C. After 15 h of heating, the mixture was cooled to rt, the carbon monoxide was removed by vacuum, and the vessel was flushed with N$_2$. The mixture was concentrated under reduced pressure, and was diluted with DMF. The DMF solution was passed through a plug of celite to remove solids, and was purified by prep HPLC. The title compound was recovered as a yellow solid (0.020 g). LCMS: m/e 533.5 (M+H)$^+$, ret time 1.35 min (method 2). 1H NMR (500 MHz, MeOD) δ ppm 8.96 (s, 1H) 8.65 (s, 1H) 7.59-7.72 (m, 5H) 3.86-3.89 (m, 2H) 3.79 (t, J=5.65 Hz, 2H) 3.68-3.71 (m, 2H) 3.64 (t, J=5.65 Hz, 2H) 3.58 (s, 6H) 3.40-3.44 (m, 2H) 3.30-3.35 (m, 2H).

Preparation of ethyl 4-fluoro-3-(2-oxo-2-(4-(1-phenyl-1H-tetrazol-5-yl)piperazin-1-yl)acetyl)-1H-pyrrolo[2,3-c]pyridine-7-carboxylate

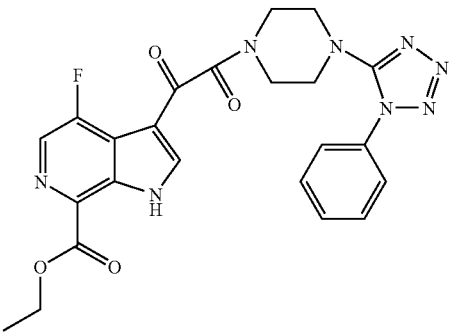

B-57

To a 15 mL rb flask containing 1-(7-bromo-4-fluoro-1H-pyrrolo[2,3-c]pyridin-3-yl)-2-(4-(1-phenyl-1H-tetrazol-5-yl)piperazin-1-yl)ethane-1,2-dione (0.10 g, 0.20 mmol) was added DMF (4.0 mL), triethylamine (0.8 mL), ethanol (0.05 g, 1.00 mmol), and finally Pd(PPh$_3$)$_4$ (0.06 g, 0.06 mmol). The flask was placed in a Parr reaction vessel equipped with a pressure gauge and a gas inlet valve. The vessel was sealed and purged with N$_2$ three times, and was then purged with carbon monoxide three times, leaving the final fill pressure of carbon monoxide at 50 psi. The vessel was heated to 100° C. After 6 h of heating, the mixture was cooled to rt, the carbon monoxide was removed by vacuum, and the vessel was flushed with N$_2$. The mixture was concentrated under reduced pressure, and was diluted with DMF. The DMF solution was passed through a plug of celite to remove solids, and was purified by prep HPLC. The title compound was recovered as an off-white solid (0.020 g). LCMS: m/e 493.4 (M+H)$^+$, ret time 1.82 min (method 2). 1H NMR (500 MHz, DMSO-D$_6$) δ ppm 12.82 (s, 1H) 8.43 (s, 1H) 8.35 (d, J=3.05 Hz, 1H) 7.57-7.70 (m, 5H) 4.46 (q, J=7.12 Hz, 2H) 3.67-3.72 (m, 2H) 3.43-3.47 (m, 2H) 3.31-3.35 (m, 2H) 3.13-3.17 (m, 2H) 1.39 (t, J=7.17 Hz, 3H).

Preparation of 2-(1,3-dioxolan-2-yl)-4-(trimethylstannyl)thiazole

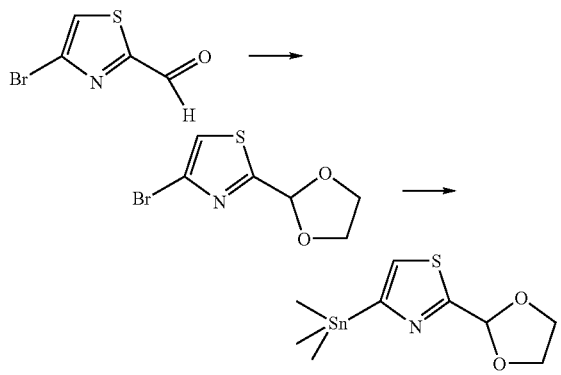

To a rb flask with an attached Dean-Stark trap containing molecular sieves, 4A (0.25 g) was added 4-bromothiazole-2-carbaldehyde (4.4 g, 22.91 mmol). The starting material was dissolved in Benzene (45 ml) and Ethylene glycol (1.406 ml, 25.2 mmol) was added followed by pTsOH (0.218 g, 1.146 mmol). The mixture was heated to reflux for 3 h. The mixture was cooled to rt, and was partitioned with sat. aq. NaHCO$_3$. The mixture was washed 2× with sat. NaHCO$_3$ (40 mL), then once with sat. NaCl (40 mL). The organic layer was dried with Na$_2$SO$_4$. The drying agent was removed by filtration, and the mixture was concentrated under reduced pressure. The residue was purified by biotage flash chromatography using a 40+M column and a 0 to 20% EtOAc in hexanes gradient. The product, 4-bromo-2-(1,3-dioxolan-2-yl)thiazole (5.1 g, 21.60 mmol, 94% yield), was collected as a light-yellow solid.

To a solution of 4-bromo-2-(1,3-dioxolan-2-yl)thiazole (5.09 g, 21.56 mmol) in Toluene (100 ml) was added Hexamethylditin (10 g, 30.5 mmol) followed by Tetrakis (2.491 g, 2.156 mmol). The mixture was attached to a reflux condenser, and was flushed with N$_2$. The mixture was heated to 100° C. for 4 h. The mixture was cooled to rt, and was loaded onto a 40+M biotage cartridge that was pre-saturated with hexanes with 0.1% Et$_3$N. The desired product was purified using a 0-20% EtOAc in hexanes with 0.1% Et$_3$N gradient. After concentrating in vacuo, the product, 2-(1,3-dioxolan-2-yl)-4-(trimethylstannyl)thiazole (4.64 g, 14.50 mmol, 67.3% yield), was isolated as a light-yellow oil. LCMS: m/e 322.0 (M+H)$^+$, ret time 2.23 min (method 7); 1H NMR (500 MHz, CDCl$_3$) δ ppm 7.39 (s, 1H) 6.20 (s, 1H) 4.03-4.20 (m, 4H) 0.27-0.42 (m, 9H).

Preparation of 1-(7-(2-(1,3-dioxolan-2-yl)thiazol-4-yl)-4-methoxy-1H-pyrrolo[2,3-c]pyridin-3-yl)-2-(4-(1-phenyl-1H-tetrazol-5-yl)piperazin-1-yl)ethane-1,2-dione

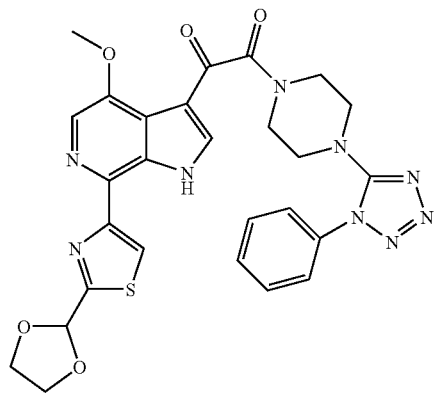

To a sealable 75 mL flask containing 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (0.3 g, 0.643 mmol) was added a solution of 2-(1,3-dioxolan-2-yl)-4-(trimethylstannyl)thiazole (0.210 g, 0.655 mmol) in 1,4-Dioxane (10 ml). The mixture was flushed with N$_2$ and Pd(PPh$_3$)$_4$ (0.149 g, 0.129 mmol) was added. The mixture was again flushed with N2, and the flask was sealed and heated in an oil bath to 100° C. After 20 h of heating, the mixture was cooled to rt. The mixture was transferred to a rb flask using MeOH as the transfer solvent. The solvent was removed under reduced pressure. The residue was re-dissolved in DMF, and was passed through a pad of celite to remove any remaining solids. The DMF solution was purified by prep HPLC. After the prep HPLC, a mostly-pure sample was collected as an off-white solid. A small portion of this material was removed and re-purified by flash chromatography (0-5% MeOH in dichloromethane gradient) [20 mg after the purification]. The remainder of the product was carried forward to the next step with no additional purification (0.305 g). LCMS: m/e 588.1 (M+H)$^+$, ret time 1.30 min (method 3). 1H NMR (500 MHz, DMSO-D$_6$) δ ppm 12.20 (s, 1H) 8.38 (s, 1H) 8.22 (s, 1H) 8.11 (s, 1H) 7.68-7.72 (m, 2H) 7.57-7.66 (m, 3H) 6.29 (s, 1H) 4.16-4.20 (m, 2H) 4.07-4.10 (m, 2H) 3.99 (s, 3H) 3.67-3.71 (m, 2H) 3.41-3.45 (m, 2H) 3.30-3.32 (m, 2H) 3.15-3.19 (m, 2H).

Preparation of 1-(4-methoxy-7-(2-((methylamino)methyl)thiazol-4-yl)-1H-pyrrolo[2,3-c]pyridin-3-yl)-2-(4-(1-phenyl-1H-tetrazol-5-yl)piperazin-1-yl)ethane-1,2-dione TFA

B-59

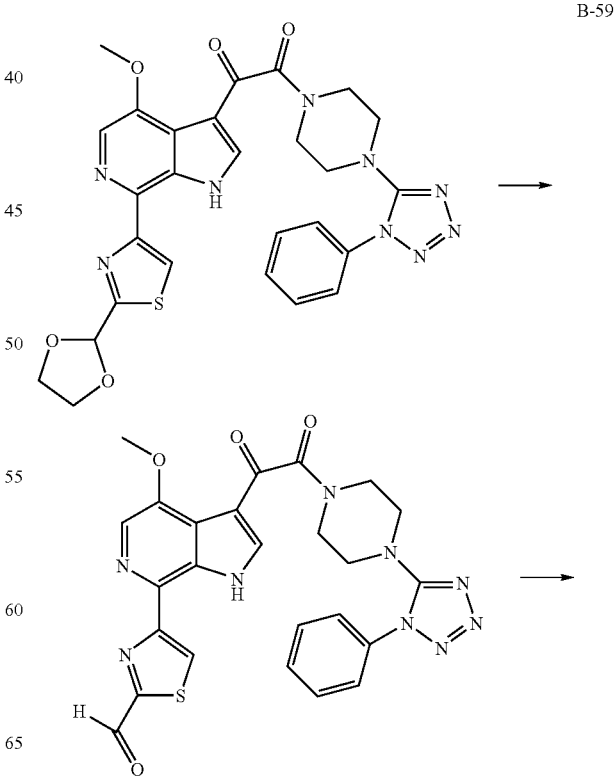

-continued

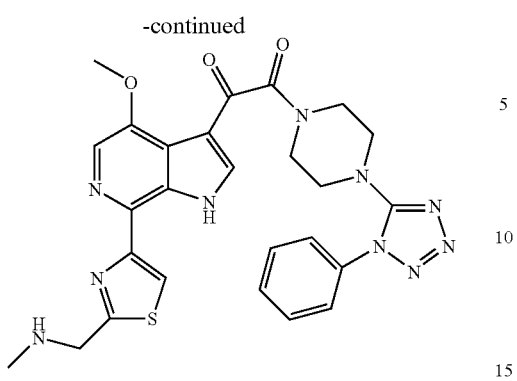

To a suspension of 1-(7-(2-(1,3-dioxolan-2-yl)thiazol-4-yl)-4-methoxy-1H-pyrrolo[2,3-c]pyridin-3-yl)-2-(4-(1-phenyl-1H-tetrazol-5-yl)piperazin-1-yl)ethane-1,2-dione (0.305 g, 0.519 mmol) in H$_2$O (2 mL, 111 mmol) was added TFA (1 mL, 12.98 mmol). The mixture was heated to 70° C. After 18 h of heating, the mixture was cooled to rt, and was stirred at rt for an additional 20 h. The mixture was concentrated under reduced pressure. The residue was dissolved in dichloromethane and was partitioned with sat. NaHCO$_3$. The mixture was extracted with dichloromethane (3×10 mL) and was dried with Na$_2$SO$_4$. The drying agent was removed by filtration. The organic solution was concentrated under reduced pressure, and the resulting mixture was purified by flash chromatography (0 to 5% methanol in dichloromethane gradient). The product, 4-(4-methoxy-3-(2-oxo-2-(4-(1-phenyl-1H-tetrazol-5-yl)piperazin-1-yl)acetyl)-1H-pyrrolo[2,3-c]pyridin-7-yl)thiazole-2-carbaldehyde (0.103 g, 0.189 mmol, 36.5% yield) was collected as a light-yellow solid.

To a solution of 4-(4-methoxy-3-(2-oxo-2-(4-(1-phenyl-1H-tetrazol-5-yl)piperazin-1-yl)acetyl)-1H-pyrrolo[2,3-c]pyridin-7-yl)thiazole-2-carbaldehyde (0.088 g, 0.162 mmol) in DCE (3 ml) was added ACETIC ACID (9.27 µl, 0.162 mmol) and 2M (in THF) methylamine (0.405 ml, 0.809 mmol). The mixture was stirred for 15 minutes at rt, and sodium triacetoxyborohydride was added to the mixture (0.069 g, 0.324 mmol). The mixture was stirred for 4 h at rt. An additional 0.05 g of Na(OAc)$_3$BH was added, and the mixture was stirred overnight at rt. The mixture was neutralized with sat. NaHCO$_3$. The mixture was extracted with dichloromethane (3×10 mL), and was dried with Na$_2$SO$_4$. The drying agent was removed by filtration, and the solution was concentrated under reduced pressure. The resulting residue was dissolved in DMF, and was filtered through a pad of celite to remove any solids. The DMF solution was purified by prep HPLC to give 1-(4-methoxy-7-(2-((methylamino)methyl)thiazol-4-yl)-1H-pyrrolo[2,3-c]pyridin-3-yl)-2-(4-(1-phenyl-1H-tetrazol-5-yl)piperazin-1-yl)ethane-1,2-dione, TFA (32.6 mg, 0.048 mmol, 29.9% yield) as a light-yellow solid. LCMS: m/e 559.1 (M+H)$^+$, ret time 1. 12 min (method 3). 1H NMR (500 MHz, MeOD) δ ppm 8.54-8.59 (m, 2H) 8.08 (s, 1H) 7.57-7.74 (m, 5H) 4.82 (s, 2H) 4.11 (s, 3H) 3.82-3.86 (m, 2H) 3.60-3.63 (m, 2H) 3.39-3.42 (m, 2H) 3.33 (s, 2H) 2.95 (s, 3H).

Preparation of 1-(4-methoxy-7-(pyrimidin-4-ylamino)-1H-pyrrolo[2,3-c]pyridin-3-yl)-2-(4-(1-(pyridin-2-yl)-1H-tetrazol-5-yl)piperazin-1-yl)ethane-1,2-dione Preparation of 1-(4-methoxy-7-(pyrimidin-5-yl)-1H-pyrrolo[2,3-c]pyridin-3-yl)-2-(4-(1-(pyridin-2-yl)-1H-tetrazol-5-yl)piperazin-1-yl)ethane-1,2-dione

B-61

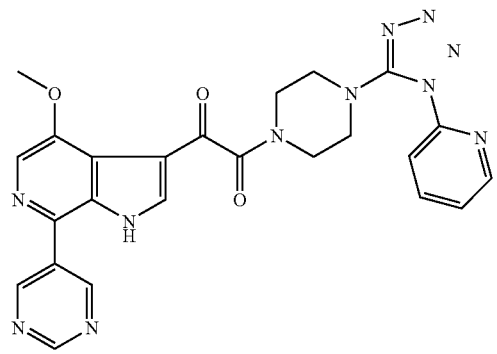

Compounds 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (100 mg, 0.195 mmol), pyrimidin-5-ylboronic acid (72.6 mg, 0.586 mmol), 1,1'-Bis(diphenylphosphino)ferrocene palladium (II) chloride complex with dichloromethane (16.06 mg, 0.020 mmol) and Cesium carbonate (127 mg, 0.390 mmol) were combined in Dioxane (2 mL) and Water (0.5 mL). The mixture was heated at 115° C. for 4 hours. After cooling to rt, the mixture was diluted with 10 ml of MeOH and filtered. The filtration was concentrated and purified by HPLC to give 1-(4-methoxy-7-(pyrimidin-5-yl)-1H-pyrrolo[2,3-c]pyridin-3-yl)-2-(4-(1-(pyridin-2-yl)-1H-tetrazol-5-yl)piperazin-1-yl)ethane-1,2-dione (34 mg, 0.066 mmol, 34.1% yield). LCMS: m/e 512.3 (M+H)$^+$, ret time 1.04 min. $^1$H NMR (500 MHz, MeOD) δ ppm 9.35 (s, 1H) 9.19 (s, 2H) 8.61 (d, J=4.88 Hz, 1H) 8.49 (s, 1H) 8.20 (s, 1H) 8.05-8.11 (m, 1H) 7.83 (d, J=7.93 Hz, 1H) 7.53-7.58 (m, J=7.17, 5.34 Hz, 1H) 4.12 (s, 3H) 3.86-3.90 (m, 2H) 3.63-3.68 (m, 2H) 3.43-3.55 (m, 4H).

Preparation of 1-(7-(3,5-dimethylisoxazol-4-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione

B-62

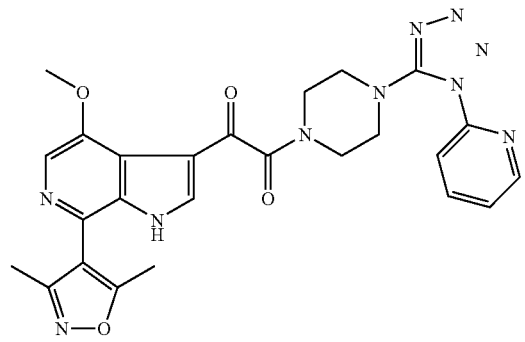

Compounds 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (100 mg, 0.195 mmol), 3,5-dimethyl-4-(4,4,5,5-tetramethyl-1,3,2-dioxaborolan-2-yl)isoxazole, 1,1'-Bis(diphenylphosphino)ferrocene palladium (II) chloride complex with dichloromethane (16.06 mg, 0.020 mmol) and Cesium carbonate (127 mg, 0.390 mmol) were combined in Dioxane (2 mL) and Water (0.5 mL). The mixture was heated at 115° C. for 2 hours. After cooling to rt, the mixture was diluted with 10 ml of MeOH and filtered. The filtration was concentrated and purified by HPLC to give 1-(7-(3,5-dimethylisoxazol-4-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (56 mg, 0.106 mmol, 54.3% yield). LCMS: m/e 529.3 (M+H)$^+$, ret time 1.03 min. $^1$H NMR (500 MHz, MeOD) δ ppm 8.65 (s, 1H) 8.62-8.64 (m, J=4.88 Hz, 1H) 8.23 (s, 1H) 8.08-8.13 (m, 1H) 7.84 (d, J=8.24 Hz, 1H) 7.55-7.60 (m, J=6.71, 4.88 Hz, 1H) 4.15 (s, 3H) 3.87-3.90 (m, 2H) 3.66-3.69 (m, 2H) 3.44-3.54 (m, 4H) 2.41 (s, 3H) 2.22 (s, 3H).

Preparation of 1-(4-methoxy-7-(pyrimidin-5-yl)-1H-pyrrolo[2,3-c]pyridin-3-yl)-2-(4-(1-phenyl-1H-tetrazol-5-yl)piperazin-1-yl)ethane-1,2-dione

B-63

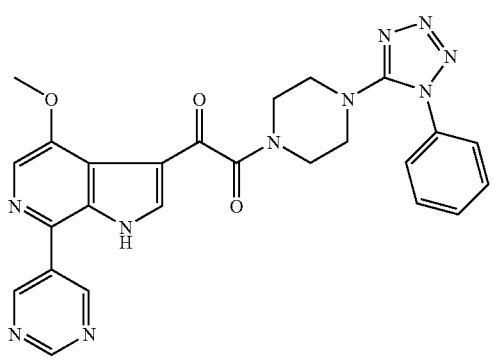

To a suspension of 2-(4-methoxy-7-(pyrimidin-5-yl)-1H-pyrrolo[2,3-c]pyridin-3-yl)-2-oxoacetic acid (50 mg, 0.168 mmol), 1-(1-phenyl-1H-tetrazol-5-yl)piperazine hydrochloride (40.2 mg, 0.151 mmol) and 2-(1H-Benzotriazol-1-yl)-1,1,3,3-tetramethyluronium tetrafluoroborate (59.2 mg, 0.184 mmol) in DMF (1 ml) was added N,N-Diisopropylethylamine (0.146 ml, 0.838 mmol). The mixture was stirred at room temperature for 4 hours. The mixture was diluted with 150 ml of $CH_2Cl_2$ and washed with 5% $NaHCO_3$ (30 ml), brine (30 ml). The organic layer was dried over $Na_2SO_4$ and concentrated to give a residue, which was purified by prep. HPLC to give 1-(4-methoxy-7-(pyrimidin-5-yl)-1H-pyrrolo[2,3-c]pyridin-3-yl)-2-(4-(1-phenyl-1H-tetrazol-5-yl)piperazin-1-yl)ethane-1,2-dione (10 mg, 0.020 mmol, 11.68% yield) (light tan solid). LCMS: m/e 511.4 (M+H)$^+$, ret time 1.25 min. $^1$H NMR (500 MHz, MeOD) δ ppm 9.30 (s, 1H) 9.17 (s, 2H) 8.38 (s, 1H) 8.16 (s, 1H) 7.58-7.65 (m, 5H) 4.09 (s, 3H) 3.80-3.83 (m, 2H) 3.57-3.60 (m, 2H) 3.38-3.42 (m, 2H) 3.31-3.33 (m, 2H).

Preparation of N-(2-hydroxyethyl)-4-methoxy-3-(2-oxo-2-(4-(1-phenyl-1H-tetrazol-5-yl)piperazin-1-yl)acetyl)-1H-pyrrolo[2,3-c]pyridine-7-carboxamide

B-64

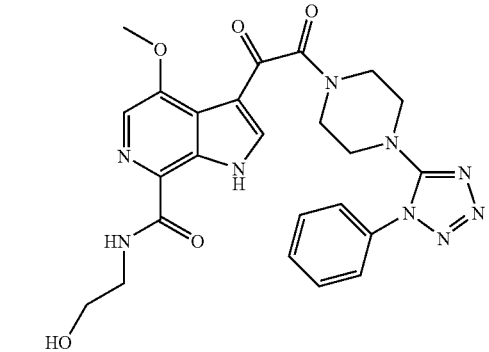

To a stainless steel pressure vessel containing 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (0.16 g, 0.343 mmol) in Dioxane (10 mL) was added triethylamine (0.7 mL, 5.02 mmol), water (0.05 mL), ethanolamine (0.021 mL, 0.343 mmol), and tetrakis (0.079 g, 0.069 mmol). The mixture was flushed with $N_2$. The stainless steel pressure vessel was purged of air, and refilled with $N_2$ three times. After the final fill with $N_2$, the $N_2$ was removed by vacuum. The vessel was filled and purged with 50 psi carbon monoxide three times, then filled the vessel to an initial reaction pressure of 90 psi of carbon monoxide. The vessel was heated in an oil bath at 100° C. After 16 h, the mixture was cooled to 0° C. The excess CO was removed by vacuum, and the mixture was diluted with MeOH and was transferred to a flask. The mixture was concentrated under reduced pressure. The residue was taken up in DMF, and was filtered through a pad of celite to remove any solids. The DMF solution was purified by prep HPLC. After the first purification, the product was purified a second time using a biotage 25+M cartridge and a 0-5% MeOH in dichloromethane as the gradient. The product, N-(2-hydroxyethyl)-4-methoxy-3-(2-oxo-2-(4-(1-phenyl-1H-tetrazol-5-yl)piperazin-1-yl)acetyl)-1H-pyrrolo[2,3-c]pyridine-7-carboxamide (0.074 g, 0.142 mmol, 41.6% yield), was isolated as a white solid. $^1$H NMR (500 MHz, DMSO-D6) δ ppm 12.53 (s, 1H) 8.66 (s, 1H) 8.12 (s, 1H) 8.07 (s, 1H) 7.56-7.72 (m, 5H) 4.83 (t, J=5.49 Hz, 1H) 4.02 (s, 3H) 3.66-3.70 (m, 2H) 3.57 (q, J=5.90 Hz, 2H) 3.39-3.46 (m, 4H) 3.28-3.32 (m, 2H) 3.17 (d, J=3.36 Hz, 2H). LCMS: m/e 520.32 (M+H)$^+$, ret time 2.165 min (method 4).

Preparation of 4-methoxy-N-methyl-3-(2-oxo-2-(4-(1-phenyl-1H-tetrazol-5-yl)piperazin-1-yl)acetyl)-1H-pyrrolo[2,3-c]pyridine-7-carboxamide

B-65

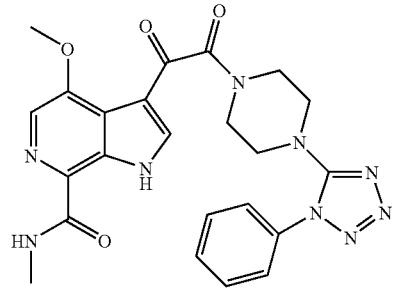

To a stainless steel pressure vessel containing 1-(7-chloro-4-methoxy-1H-pyrrolo[2,3-c]pyridin-3-yl)-2-(4-(1-phenyl-1H-tetrazol-5-yl)piperazin-1-yl)ethane-1,2-dione (0.1 g, 0.21 mmol) in Dioxane (4 mL) was added triethylamine (0.5 mL, 3.59 mmol), water (0.05 mL), methylamine (2M in THF) (0.86 mL, 1.7 mmol), and tetrakis (0.050 g, 0.043 mmol). The mixture was flushed with $N_2$. The stainless steel pressure vessel was purged of air, and refilled with $N_2$ three times. After the final fill with $N_2$, the $N_2$ was removed by vacuum. The vessel was filled and purged with 50 psi carbon monoxide three times, then filled the vessel to an initial reaction pressure of 90 psi of carbon monoxide. The vessel was heated in an oil bath at 100° C. After 14 h, the mixture was cooled to 0° C. The excess CO was removed by vacuum, and the mixture was diluted with MeOH and was transferred to a flask. The mixture was concentrated under reduced pressure, and the resulting residue was taken up in DMF. The DMF mixture was passed through a pad of celite to remove solids. The DMF solution was then purified by prep HPLC. The desired product, 4-methoxy-N-methyl-3-(2-oxo-2-(4-(1-phenyl-1H-tetrazol-5-yl)piperazin-1-yl)acetyl)-1H-pyrrolo[2,3-c]pyridine-7-carboxamide, TFA (0.066 g, 0.109 mmol, 51.1% yield), was isolated as a light-yellow solid. $^1$H NMR (500 MHz, CHLOROFORM-D) δ ppm 11.55 (s, 1H) 8.56-8.60 (m, 1H) 8.34 (s, 1H) 7.99 (s, 1H) 7.52-7.60 (m, 5H) 4.09 (s, 3H) 3.79-3.84 (m, 2H) 3.55-3.59 (m, 2H) 3.38-3.42 (m, 2H) 3.32-3.35 (m, 2H) 3.05 (d, J=4.88 Hz, 3H). LCMS: m/e 490.36 (M+H)$^+$, ret time 2.262 min (method 4).

Preparation of N-cyclopropyl-4-methoxy-3-(2-oxo-2-(4-(1-(pyridin-2-yl)-1H-tetrazol-5-yl)piperazin-1-yl)acetyl)-1H-pyrrolo[2,3-c]pyridine-7-carboxamide

B-66

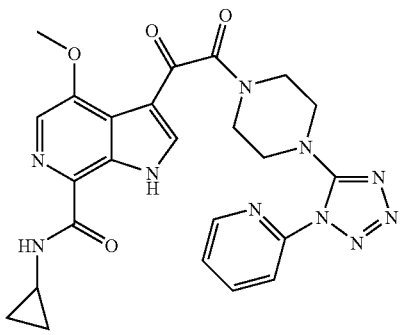

To a stainless steel pressure vessel containing 1-(7-chloro-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (0.076 g, 0.162 mmol) in Dioxane (4 mL) was added triethylamine (0.5 mL, 3.59 mmol), water (0.05 mL), cyclopropylamine (0.034 mL, 0.487 mmol), and tetrakis (0.038 g, 0.032 mmol). The mixture was flushed with $N_2$. The stainless steel pressure vessel was purged of air, and refilled with $N_2$ three times. After the final fill with $N_2$, the $N_2$ was removed by vacuum. The vessel was filled and purged with 50 psi carbon monoxide three times, then filled the vessel to an initial reaction pressure of 90 psi of carbon monoxide. The vessel was heated in an oil bath at 100° C. After 15 h, the mixture was cooled to 0° C. The excess CO was removed by vacuum, and the mixture was diluted with MeOH and was filtered through a pad of celite to remove the solids. The product was purified by prep HPLC to give N-cyclopropyl-4-methoxy-3-(2-oxo-2-(4-(1-(pyridin-2-yl)-1H-tetrazol-5-yl)piperazin-1-yl)acetyl)-1H-pyrrolo[2,3-c]pyridine-7-carboxamide (0.014 g, 0.027 mmol, 16.7% yield) as an off-white solid. $^1$H NMR (500 MHz, DMSO-D6) δ ppm 12.54 (s, 1H) 8.77 (s, 1H) 8.63-8.68 (m, 1H) 8.12-8.19 (m, 2H) 8.02 (s, 1H) 7.84 (d, J=7.93 Hz, 1H) 7.64 (dd, J=7.48, 4.73 Hz, 1H) 4.01 (s, 3H) 3.68-3.73 (m, 2H) 3.38-3.45 (m, 4H) 3.22-3.27 (m, 2H) 2.92-2.99 (m, 1H) 0.69-0.74 (m, 4H). LCMS: m/e 517.18 (M+H)$^+$, ret time 1.378 min (method 3).

The following tertiary alcohol intermediates were formed by the standardized reaction that follows.

Preparation of 2-(3-(tributylstannyl)-1H-pyrazol-5-yl)propan-2-ol, and 3-(3-(tributylstannyl)-1H-pyrazol-5-yl)pentan-3-ol

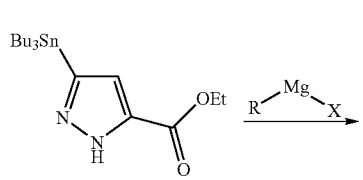

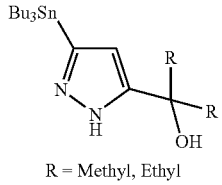

R = Methyl, Ethyl

To a solution of ethyl 3-(tributylstannyl)-1H-pyrazole-5-carboxylate (0.1-0.25 g) in tetrahydrofuran was added the grignard reagent (4 equiv) dropwise. The mixture was stirred at rt for 2.5 h, and was carefully quenched with water. The mixture was extracted with EtOAc (3×30 mL), washed with brine (30 mL), and dried with $MgSO_4$. The drying agent was removed by filtration, and the organic solution was concentrated under reduced pressure. The product was isolated as an oil and was used with no further purification. LCMS: m/e 417.00 (M+H)$^+$, ret time 3.618 min (method 9) for 2-(3-(tributylstannyl)-1H-pyrazol-5-yl)propan-2-ol; LCMS: m/e 445.08 (M+H)$^+$, ret time 4.063 min (method 9) for 3-(3-(tributylstannyl)-1H-pyrazol-5-yl)pentan-3-ol.

The general procedure for coupling of tin reagents to the either the 1-(7-chloro-4-methoxy-1H-pyrrolo[2,3-c]pyridin-3-yl)-2-(4-(1-(pyridin-2-yl)-1H-tetrazol-5-yl)piperazin-1-yl)ethane-1,2-dione core or the 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione core was applied to the following compounds.

General Tin Coupling Procedure 1-(7-chloro-4-methoxy-1H-pyrrolo[2,3-c]pyridin-3-yl)-2-(4-(1-(pyridin-2-yl)-1H-tetrazol-5-yl)piperazin-1-yl) ethane-1,2-dione or 1-(7-bromo-4-methoxy-1H-pyrrolo[2,3-c]pyridin-3-yl)-2-(4-(1-(pyridin-2-yl)-1H-tetrazol-5-yl) piperazin-1-yl)ethane-1,2-dione (0.05-2 g) was weighed into a sealable flask. The tin reagent (1-1.25 equiv) was added, and the mixture was diluted with 1,4-dioxane (0.02-0.2 molar solution). To the mixture was added tetrakis(triphenylphosphine)palladium(0) (0.2 equivalents) and the mixture was flushed with $N_2$, sealed, and heated to 100° C. After heating for 14-24 h, The mixture was cooled to rt, and was transferred to a flask using MeOH and dichloromethane as the wash solvents. The solution was concentrated and the residue was purified using either the prep HPLC or biotage flash chromatography.

Preparation of 1-(7-(5-(hydroxymethyl)-1H-pyrazol-3-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione) using the general tin coupling procedure

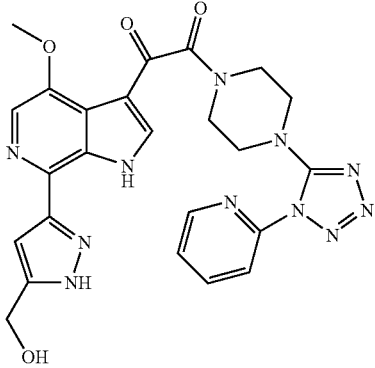

B-67

1-(7-(5-(hydroxymethyl)-1H-pyrazol-3-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (54 mg, 0.102 mmol, 23.86% yield), white solid. $^{1}$H NMR (500 MHz, DMSO-D6) δ ppm 13.09 (s, 1H) 12.02 (s, 1H) 8.65-8.68 (m, 1H) 8.13-8.19 (m, 2H) 8.06 (s, 1H) 7.85 (d, J=8.24 Hz, 1H) 7.63 (dd, J=7.32, 4.88 Hz, 1H) 6.79 (s, 1H) 5.38 (t, J=5.65 Hz, 1H) 4.60 (d, J=5.49 Hz, 2H) 3.96 (s, 3H) 3.69-3.73 (m, 2H) 3.39-3.46 (m, 4H) 3.23-3.27 (m, 2H). LCMS: m/e 530.36 (M+H)$^{+}$, ret time 1.742 min (method 4).

Preparation of 1-(7-(5-(2-hydroxypropan-2-yl)-1H-pyrazol-3-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione using the general tin coupling procedure

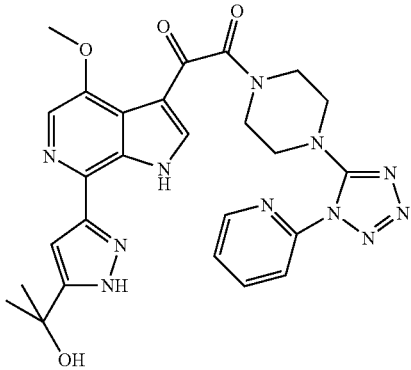

B-68

1-(7-(5-(2-hydroxypropan-2-yl)-1H-pyrazol-3-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione, TFA (48 mg, 0.071 mmol, 20.52% yield), an off-white solid. $^{1}$H NMR (500 MHz, DMSO-D6) δ ppm 12.43 (s, 1H) 8.67 (dd, J=4.88, 1.22 Hz, 1H) 8.39 (s, 1H) 8.14-8.18 (m, 1H) 8.04 (s, 1H) 7.85 (d, J=7.93 Hz, 1H) 7.64 (dd, J=6.87, 5.34 Hz, 1H) 6.93 (s, 1H) 4.01 (s, 3H) 3.70-3.74 (m, 2H) 3.40-3.49 (m, 4H) 3.25-3.29 (m, 2H) 1.55 (s, 6H). LCMS: m/e 558.43 (M+H)$^{+}$, ret time 1.905 min (method 4).

Preparation of 1-(4-methoxy-7-(2-methoxythiazol-4-yl)-1H-pyrrolo[2,3-c]pyridin-3-yl)-2-(4-(1-(pyridin-2-yl)-1H-tetrazol-5-yl)piperazin-1-yl)ethane-1,2-dione Using the General Tin Coupling Procedure

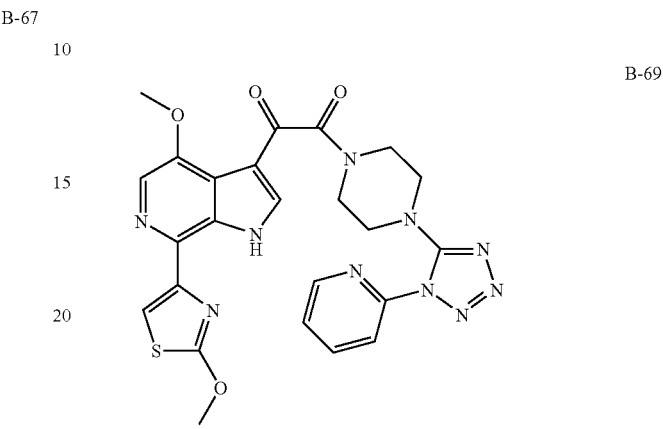

B-69

1-(4-methoxy-7-(2-methoxythiazol-4-yl)-1H-pyrrolo[2,3-c]pyridin-3-yl)-2-(4-(1-(pyridin-2-yl)-1H-tetrazol-5-yl)piperazin-1-yl)ethane-1,2-dione (0.014 g, 0.026 mmol, 15.98% yield) was isolated as a light-yellow solid. $^{1}$H NMR (500 MHz, CHLOROFORM-D) δ ppm 11.31 (s, 1H) 8.57-8.60 (m, 1H) 8.18 (s, 1H) 7.94-7.99 (m, 2H) 7.84 (d, J=8.24 Hz, 1H) 7.69 (s, 1H) 7.43 (dd, J=7.63, 4.88 Hz, 1H) 4.21 (s, 3H) 4.04 (s, 3H) 3.89-3.92 (m, 2H) 3.64-3.68 (m, 2H) 3.56-3.60 (m, 2H) 3.47-3.51 (m, 2H). LCMS: m/e 547.35 (M+H)$^{+}$, ret time 2.053 min (method 4).

Preparation of 1-(4-methoxy-7-(thiazol-4-yl)-1H-pyrrolo[2,3-c]pyridin-3-yl)-2-(4-(1-(pyridin-2-yl)-1H-tetrazol-5-yl)piperazin-1-yl)ethane-1,2-dione Using the General Tin Coupling Procedure

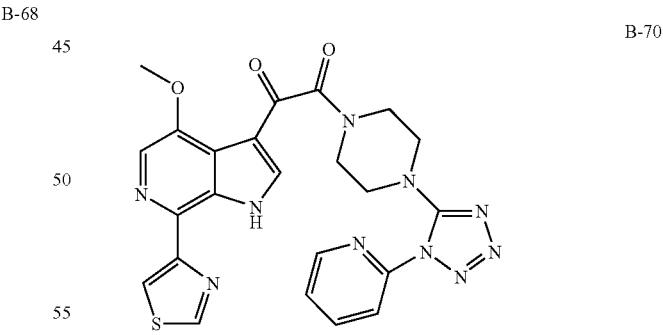

B-70

1-(4-methoxy-7-(thiazol-4-yl)-1H-pyrrolo[2,3-c]pyridin-3-yl)-2-(4-(1-(pyridin-2-yl)-1H-tetrazol-5-yl)piperazin-1-yl)ethane-1,2-dione, TFA (7.6 mg, 0.012 mmol, 7.52% yield), was isolated as an off-white $^{1}$H NMR (500 MHz, CHLOROFORM-D) δ ppm 12.18 (s, 1H) 9.44 (s, 1H) 9.08 (d, J=1.83 Hz, 1H) 8.61 (d, J=4.88 Hz, 1H) 8.54 (s, 1H) 8.30 (s, 1H) 7.97-8.02 (m, 1H) 7.88 (d, J=8.24 Hz, 1H) 7.44-7.49 (m, 1H) 4.15 (s, 3H) 3.90-3.94 (m, 2H) 3.71-3.76 (m, 2H) 3.56-3.62 (m, 4H). LCMS: m/e 517.35 (M+H)$^{+}$, ret time 1.810 min (method 4).

Preparation of 1-(4-methoxy-7-(thiazol-5-yl)-1H-pyrrolo[2,3-c]pyridin-3-yl)-2-(4-(1-(pyridin-2-yl)-1H-tetrazol-5-yl)piperazin-1-yl)ethane-1,2-dione Using the General Tin Coupling Procedure

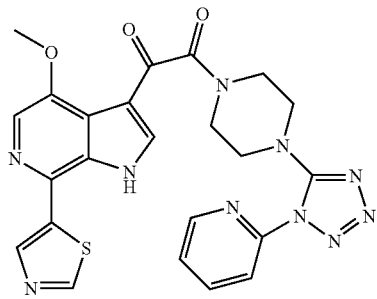

B-71

1-(4-methoxy-7-(thiazol-4-yl)-1H-pyrrolo[2,3-c]pyridin-3-yl)-2-(4-(1-(pyridin-2-yl)-1H-tetrazol-5-yl)piperazin-1-yl)ethane-1,2-dione, TFA (7.6 mg, 0.012 mmol, 7.5% yield), was isolated as an off-white solid. $^1$H NMR (500 MHz, DMSO-D6) δ 12.76 (s, 1H) 9.20 (s, 1H) 8.66-8.69 (m, 1H) 8.63 (s, 1H) 8.34 (d, J=3.05 Hz, 1H) 8.13-8.19 (m, 1H) 8.11 (s, 1H) 7.85 (d, J=7.93 Hz, 1H) 7.64 (dd, J=6.41, 4.88 Hz, 1H) 3.98 (s, 3H) 3.69-3.74 (m, 2H) 3.41-3.62 (m, 4H) 3.25-3.29 (m, 2H). LCMS: m/e 517.40 (M+H)$^+$, ret time 1.858 min (method 4).

Preparation of 1-(4-methoxy-7-(1H-pyrazol-3-yl)-1H-pyrrolo[2,3-c]pyridin-3-yl)-2-(4-(1-(pyridin-2-yl)-1H-tetrazol-5-yl)piperazin-1-yl)ethane-1,2-dione Using the General Tin Coupling Procedure

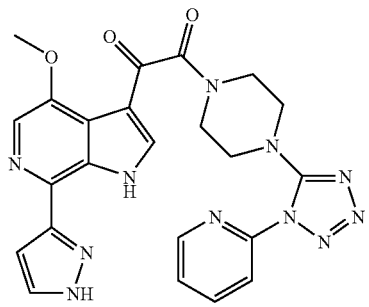

B-72

1-(4-methoxy-7-(1H-pyrazol-3-yl)-1H-pyrrolo[2,3-c]pyridin-3-yl)-2-(4-(1-(pyridin-2-yl)-1H-tetrazol-5-yl)piperazin-1-yl)ethane-1,2-dione, TFA (0.09 g, 0.147 mmol, 24.89% yield) was isolated as a white solid. $^1$H NMR (500 MHz, DMSO-D6) δ ppm 12.49 (s, 1H) 8.67 (dd, J=4.88, 1.22 Hz, 1H) 8.35 (s, 1H) 8.12-8.19 (m, 1H) 8.06 (s, 1H) 8.01 (d, J=2.14 Hz, 1H) 7.85 (d, J=8.24 Hz, 1H) 7.64 (dd, J=7.17, 5.34 Hz, 1H) 7.08 (s, 1H) 4.01 (s, 3H) 3.70-3.75 (m, 2H) 3.40-3.49 (m, 4H) 3.25-3.30 (m, 2H). LCMS: m/e 500.4 (M+H)$^+$, ret time 1.767 min (method 4).

Preparation of 1-(4-methoxy-7-(1-methyl-1H-pyrazol-3-yl)-1H-pyrrolo[2,3-c]pyridin-3-yl)-2-(4-(1-(pyridin-2-yl)-1H-tetrazol-1-yl)piperazin-1-yl)ethane-1,2-dione

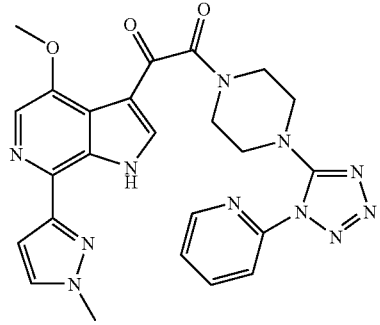

B-73

To a solution of 1-(4-methoxy-7-(1H-pyrazol-3-yl)-1H-pyrrolo[2,3-c]pyridin-3-yl)-2-(4-(1-(pyridin-2-yl)-1H-tetrazol-5-yl)piperazin-1-yl)ethane-1,2-dione (0.069 g, 0.138 mmol) in DMF (3 mL) was added NaH (0.055 g, 1.381 mmol). The mixture was stirred for ten minutes and MeI (0.017 mL, 0.276 mmol) was added. After being stirred for 45 minutes, the mixture was quenched with water. The mixture was concentrated under reduced pressure. The resulting residue was diluted with DMF and was passed through a plug of cotton to remove solids. The DMF solution was purified by prep HPLC to give 1-(4-methoxy-7-(1-methyl-1H-pyrazol-3-yl)-1H-pyrrolo[2,3-c]pyridin-3-yl)-2-(4-(1-(pyridin-2-yl)-1H-tetrazol-5-yl)piperazin-1-yl)ethane-1,2-dione as a light-yellow solid (0.017 g, 0.033 mmol, 33.1% yield). $^1$H NMR (500 MHz, DMSO-D6) δ ppm 12.37 (s, 1H) 8.67 (dd, J=4.88, 1.22 Hz, 1H) 8.33 (s, 1H) 8.13-8.18 (m, 1H) 8.05 (s, 1H) 7.93 (d, J=2.14 Hz, 1H) 7.85 (d, J=7.93 Hz, 1H) 7.64 (dd, J=7.48, 4.73 Hz, 1H) 6.99 (s, 1H) 4.05 (s, 3H) 4.00 (s, 3H) 3.70-3.74 (m, 2H) 3.40-3.48 (m, 4H) 3.24-3.29 (m, 2H). LCMS: m/e 514.38 (M+H)$^+$, ret time 1.820 min (method 1).

Preparation of 2-(7-(1-(carboxymethyl)-1H-pyrazol-3-yl)-4-methoxy-3-(2-oxo-2-(4-(1-(pyridin-2-yl)-1H-tetrazol-5-yl)piperazin-1-yl)acetyl)-1H-pyrrolo[2,3-c]pyridin-1-yl)acetic acid and 2-(3-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-pyrazol-1-yl)acetic acid

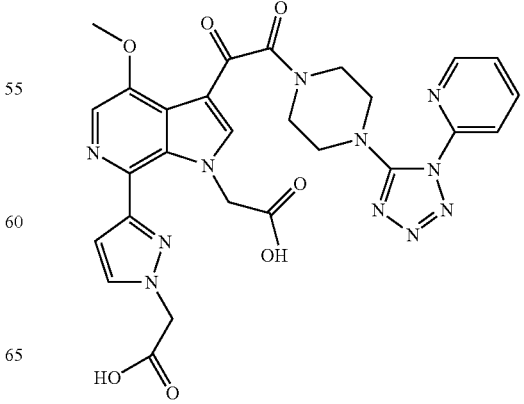

B-74 and B-75

-continued

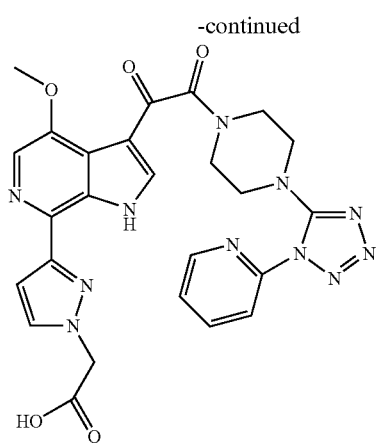

To a solution of 1-(4-methoxy-7-(1H-pyrazol-3-yl)-1H-pyrrolo[2,3-c]pyridin-3-yl)-2-(4-(1-(pyridin-2-yl)-1H-tetrazol-5-yl)piperazin-1-yl)ethane-1,2-dione (0.207 g, 0.414 mmol) in DMF (2 mL) was added NaH (0.083 g, 2.072 mmol). The mixture was stirred for 5 minutes at rt and methyl bromoacetate (0.047 mL, 0.497 mmol) was added. The mixture was stirred at rt for 30 minutes. LC/MS showed starting material still present, so an additional 0.05 mL of methyl bromoacetate was added. The mixture was stirred for 1 h at rt, and was quenched with water. The solvent was removed under reduced pressure, and the residue was partitioned with water and dichloromethane. The aqueous layer was acidified to pH=1 using 0.1N HCl. The solids that formed were collected by filtration, dissolved in DMF, and were purified by prep HPLC. The aqueous layer containing the remainder of the material was concentrated under reduced pressure, and was dissolved in DMF. The DMF solution was filtered through a plug of celite to remove solids, and the DMF solution was purified by prep HPLC. A second prep HPLC run was used to purify the product. 2-(7-(1-(carboxymethyl)-1H-pyrazol-3-yl)-4-methoxy-3-(2-oxo-2-(4-(1-(pyridin-2-yl)-1H-tetrazol-5-yl)piperazin-1-yl)acetyl)-1H-pyrrolo[2,3-c]pyridin-1-yl)acetic acid was isolated as a light-yellow solid (0.032 g, 0.052 mmol, 12.5% yield). $^1$H NMR (500 MHz, DMSO-D6) δ ppm 8.65-8.69 (m, 1H) 8.50 (s, 1H) 8.13-8.19 (m, 2H) 7.92 (s, 1H) 7.85 (d, J=7.93 Hz, 1H) 7.64 (dd, J=7.63, 4.88 Hz, 1H) 6.65 (s, 1H) 5.17 (s, 2H) 5.05 (s, 2H) 4.01 (s, 3H) 3.72 (s, 2H) 3.45 (dd, J=11.60, 3.05 Hz, 4H) 3.29 (d, J=3.36 Hz, 2H). LCMS: m/e 616.34 (M+H)$^+$, ret time 1.565 min (method 4). 2-(3-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-pyrazol-1-yl)acetic acid was isolated as an off-white solid (0.132 g, 0.237 mmol, 52.1% yield). $^1$H NMR (500 MHz, DMSO-D6) δ ppm $^1$H NMR (500 MHz, DMSO-D6) d ppm 12.37 (s, 1H) 8.65-8.68 (m, 1H) 8.32 (s, 1H) 8.13-8.18 (m, 1H) 8.07 (s, 1H) 7.96 (d, J=2.44 Hz, 1H) 7.85 (d, J=7.93 Hz, 1H) 7.64 (dd, J=7.48, 4.73 Hz, 1H) 7.03 (d, J=1.83 Hz, 1H) 5.17-5.20 (m, 2H) 4.01 (s, 3H) 3.70-3.75 (m, 2H) 3.40-3.49 (m, 4H) 3.24-3.29 (m, 2H). LCMS: m/e 558.19 (M+H)$^+$, ret time 0.955 min (method 3).

Preparation of 2-(3-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-pyrazol-1-yl)-N,N-dimethylacetamide

B-76

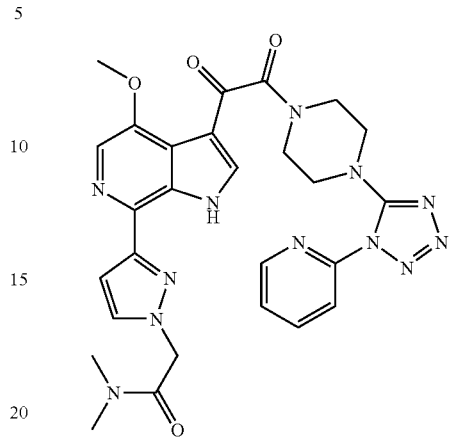

To a sealable vial containing a mixture of 2-(3-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-pyrazol-1-yl)acetic acid (0.05 g, 0.090 mmol) in DMF (4 mL) was added Hunig's Base (0.157 mL, 0.897 mmol), o-Benzotriazol-1-yl-N,N,N',N'-tetramethyluronium tetrafluoroborate (0.043 g, 0.135 mmol), and dimethylamine (0.224 mL, 0.448 mmol). The vial containing the mixture was sealed and stirred at rt for 16 h. The mixture was quenched with water and stripped of solvent under reduced pressure. The resulting residue was taken up in DMF and filtered through a plug of cotton. The DMF solution was purified using the prep HPLC. A second prep HPLC was run for purification. The product, 2-(3-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-pyrazol-1-yl)-N,N-dimethylacetamide, TFA (32 mg, 0.046 mmol, 51.1% yield), was isolated as an off white solid. $^1$H NMR (500 MHz, DMSO-D6) δ ppm 12.45 (s, 1H) 8.67 (d, J=3.66 Hz, 1H) 8.38 (s, 1H) 8.13-8.19 (m, 1H) 8.06 (s, 1H) 7.83-7.91 (m, 2H) 7.64 (dd, J=6.71, 4.88 Hz, 1H) 7.08 (s, 1H) 5.35 (s, 2H) 4.02 (s, 3H) 3.69-3.75 (m, 2H) 3.40-3.50 (m, 4H) 3.24-3.30 (m, 2H) 3.10 (s, 3H) 2.89 (s, 3H). LCMS: m/e 585.39 (M+H)$^+$, ret time 1.760 min (method 4).

Preparation of 2-(3-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-pyrazol-1-yl)-N-methylacetamide

B-77

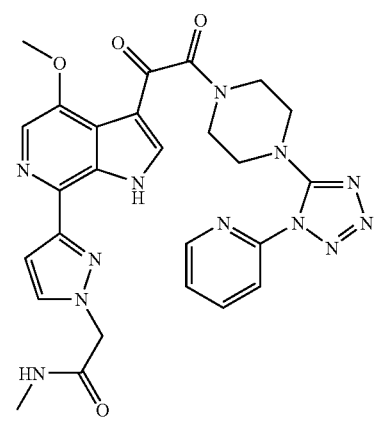

To a sealable vial containing a solution of 2-(3-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-pyrazol-1-yl)acetic acid (60 mg, 0.108 mmol) in DMF (4 mL) was added o-Benzotriazol-1-yl-N,N,N',N'-tetramethyluronium tetrafluoroborate (51.8 mg, 0.161 mmol), Hunig's Base (0.188 mL, 1.076 mmol), and methylamine (0.538 mL, 1.076 mmol). The mixture was sealed in a vial, and was stirred for 14.5 h at rt. The mixture was quenched with water and stripped of solvent under reduced pressure. The resulting residue was taken up in DMF and filtered through a plug of cotton. The DMF solution was purified using prep HPLC. 2-(3-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-pyrazol-1-yl)-N-methylacetamide, TFA (0.032 g, 0.047 mmol, 43.4% yield) was isolated as an off-white solid. $^1$H NMR (500 MHz, DMSO-D6) δ ppm 12.36 (s, 1H) 8.67 (dd, J=4.88, 1.22 Hz, 1H) 8.35 (s, 1H) 8.13-8.19 (m, 1H) 8.01-8.09 (m, 2H) 7.94 (d, J=2.14 Hz, 1H) 7.85 (d, J=7.94 Hz, 1H) 7.64 (dd, J=7.63, 4.88 Hz, 1H) 7.04 (s, 1H) 5.02 (s, 2H) 3.99-4.03 (m, 3H) 3.70-3.75 (m, 2H) 3.40-3.50 (m, 4H) 3.24-3.29 (m, 2H) 2.65 (d, J=4.58 Hz, 3H). LCMS: m/e 571.44 (M+H)$^+$, ret time 1.742 min (method 4).

Preparation of intermediate 2-(7-(5-(3-hydroxypentan-3-yl)-1H-pyrazol-3-yl)-4-methoxy-1H-pyrrolo[2,3-c]pyridin-3-yl)-2-oxoacetic acid

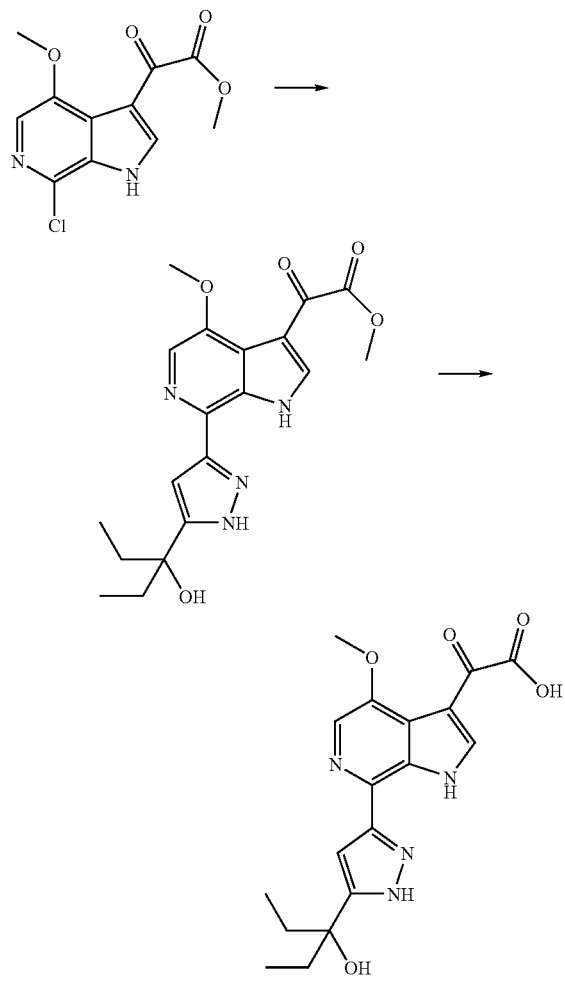

To a sealable flask containing methyl 2-(7-chloro-4-methoxy-1H-pyrrolo[2,3-c]pyridin-3-yl)-2-oxoacetate (0.070 g, 0.262 mmol) and 3-(3-(tributylstannyl)-1H-pyrazol-5-yl)pentan-3-ol (0.116 g, 0.262 mmol) was added tetrakis(triphenylphosphine)palladium(0) (0.060 g, 0.052 mmol). 1,4-Dioxane (5 ml) was added and the mixture was flushed with N$_2$. The tube was sealed, and the mixture was heated to 115° C. After 16 h of heating, the mixture was cooled to rt and the solvent was removed under reduced pressure. The residue was diluted with MeOH and was filtered through a pad of celite to remove any solids. The solution was concentrated again under reduced pressure and the residue was dissolved in DMF and was purified by prep HPLC to give the product, methyl 2-(7-(5-(3-hydroxypentan-3-yl)-1H-pyrazol-3-yl)-4-methoxy-1H-pyrrolo[2,3-c]pyridin-3-yl)-2-oxoacetate (0.073 g, 0.189 mmol, 72.2% yield) as an off-white solid. LCMS: m/e 387.19 (M+H)$^+$, ret time 1.075 min (method 3).

To a flask containing methyl 2-(7-(5-(3-hydroxypentan-3-yl)-1H-pyrazol-3-yl)-4-methoxy-1H-pyrrolo[2,3-c]pyridin-3-yl)-2-oxoacetate (0.066 g, 0.171 mmol) was added MeOH (1 mL) and Water (1 mL). To the mixture was added potassium carbonate (0.118 g, 0.854 mmol). After 1 h, the mixture was made acidic (pH=1) by adding 1N HCl. No precipitate formed, so the solvent was removed under reduced pressure. The crude mixture containing 2-(7-(5-(3-hydroxypentan-3-yl)-1H-pyrazol-3-yl)-4-methoxy-1H-pyrrolo[2,3-c]pyridin-3-yl)-2-oxoacetic acid was carried forward to the next step with no further purification. LCMS: m/e 373.22 (M+H)$^+$, ret time 1.723 min (method 4).

Preparation 1-(7-(5-(3-hydroxypentan-3-yl)-1H-pyrazol-3-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione

B-78

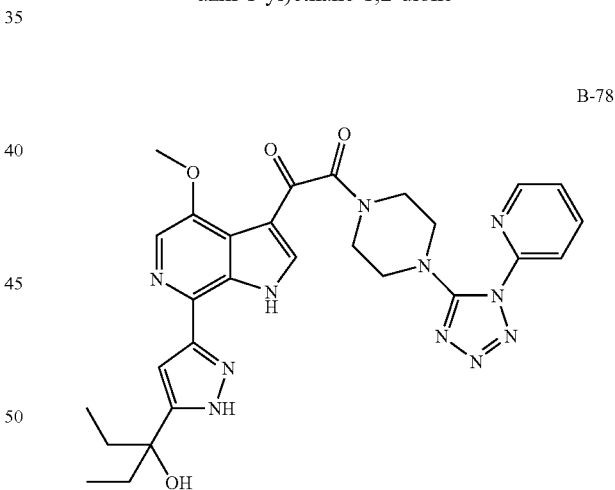

To a flask containing a solution of 2-(7-(5-(3-hydroxypentan-3-yl)-1H-pyrazol-3-yl)-4-methoxy-1H-pyrrolo[2,3-c]pyridin-3-yl)-2-oxoacetic acid (0.06 g, 0.16 mmol) in DMF (5 ml) was added Hunig's Base (1.1 ml, 6.30 mmol), 1-(1-(pyridin-2-yl)-1H-tetrazol-5-yl)piperazine (0.043 g, 0.188 mmol) and TBTU (0.121 g, 0.376 mmol). The flask was flushed with N$_2$, and was stirred at rt. for 24 h. The mixture was quenched with water. The solvent was removed under reduced pressure, and the resulting residue was taken up in DMF. The DMF solution was filtered through a pad of celite to remove any solids, and was purified by prep HPLC to give, 1-(7-(5-(3-hydroxypentan-3-yl)-1H-pyrazol-3-yl)-4-methoxy-1H-pyrrolo[2,3-c]pyridin-3-yl)-2-(4-(1-(pyridin-2-yl)-

1H-tetrazol-5-yl)piperazin-1-yl)ethane-1,2-dione, TFA (0.015 g, 0.021 mmol, 13% yield) as an off-white solid. ¹H NMR (500 MHz, DMSO-D6) δ ppm 13.19 (s, 1H) 12.37 (s, 1H) 8.65-8.68 (m, 1H) 8.38 (s, 1H) 8.13-8.18 (m, 1H) 8.03 (s, 1H) 7.85 (d, J=7.93 Hz, 1H) 7.64 (dd, J=7.02, 5.19 Hz, 1H) 6.87 (s, 1H) 4.01 (s, 3H) 3.70-3.74 (m, 2H) 3.44-3.48 (m, 2H) 3.40-3.44 (m, 2H) 3.25-3.29 (m, 2H) 1.76-1.86 (m, 4H) 0.79 (t, J=7.32 Hz, 6H). LCMS: m/e 586.55 (M+H)⁺, ret time 2.102 min (method 4).

Preparation of intermediate 2-(7-(4-chloro-1H-pyrazol-1-yl)-4-methoxy-1H-pyrrolo[2,3-c]pyridin-3-yl)-2-oxoacetic acid

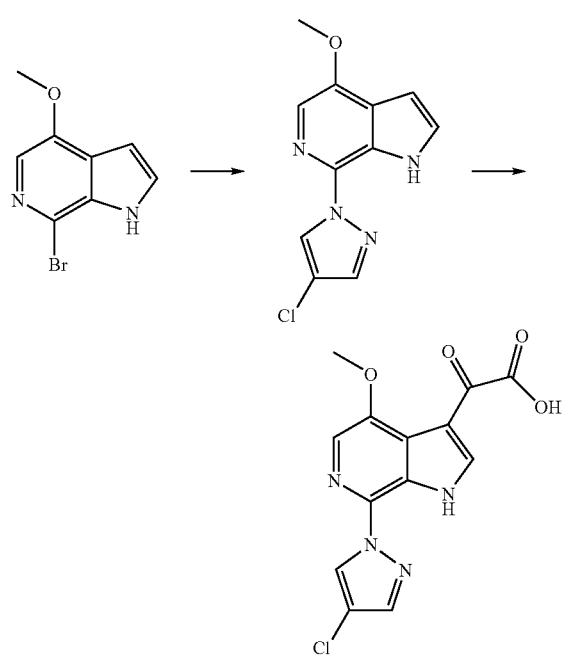

To a sealable flask containing 7-bromo-4-methoxy-1H-pyrrolo[2,3-c]pyridine (1 g, 4.40 mmol) was added 4-chloro-1H-pyrazole (0.903 g, 8.81 mmol), potassium carbonate (2.435 g, 17.62 mmol), copper(I) iodide (0.419 g, 2.202 mmol), and trans-1,2-bis(methylamino)cyclohexane (0.626 g, 4.40 mmol). The mixture was diluted with 1,4-Dioxane (15 mL) and was sealed and heated to 100° C. for 3 h. The mixture was cooled to rt and was filtered through a pad of celite to remove any solids. The organic solution as concentrated under reduced pressure, and the residue was purified by flash chromatography to give 7-(4-chloro-1H-pyrazol-1-yl)-4-methoxy-1H-pyrrolo[2,3-c]pyridine (0.79 g, 3.18 mmol, 72.1% yield) as an off-white solid. LCMS: m/e 249.12 (M+H)⁺, ret time 2.851 min (method 4).

To sealable flask containing 7-(4-chloro-1H-pyrazol-1-yl)-4-methoxy-1H-pyrrolo[2,3-c]pyridine (0.785 g, 3.16 mmol) in dichloromethane (35 mL) was added nitromethane (3.5 mL, 64.9 mmol) and aluminum chloride (2.53 g, 18.94 mmol). The mixture was stirred for 5 minutes and methyl oxalyl chloride (0.872 mL, 9.47 mmol) was added.

The mixture was sealed and heated to 50° C. for 6 h. The mixture was cooled to rt and stirred overnight. The mixture was quenched carefully with water and the solids that formed were collected by filtration and were washed with water. 2-(7-(4-chloro-1H-pyrazol-1-yl)-4-methoxy-1H-pyrrolo[2,3-c]pyridin-3-yl)-2-oxoacetic acid (0.45 g, 1.403 mmol, 44.5% yield), was isolated as an orange solid. LCMS: m/e 321.14 (M+H)⁺, ret time 2.523 min (method 4).

Preparation 1-(7-(4-chloro-1H-pyrazol-1-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione

B-79

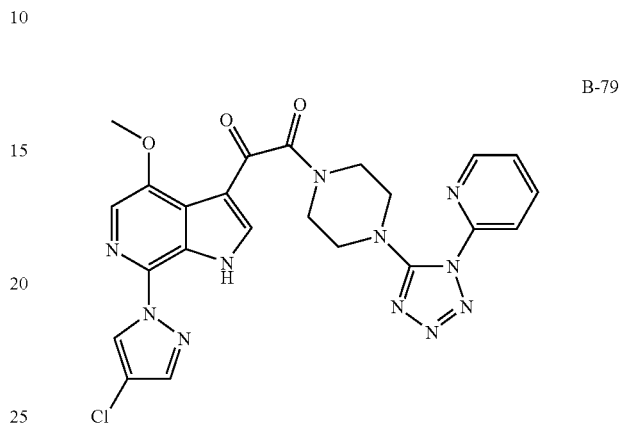

A solution of 2-(7-(4-chloro-1H-pyrazol-1-yl)-4-methoxy-1H-pyrrolo[2,3-c]pyridin-3-yl)-2-oxoacetic acid (0.449 g, 1.4 mmol) in DMF (15 mL) was added to a flask containing 1-(1-(pyridin-2-yl)-1H-tetrazol-5-yl)piperazine, HCl (0.402 g, 1.5 mmol). To the mixture was added Hunig's Base (2.445 mL, 14.00 mmol) followed by o-benzotriazol-1-yl-N,N,N',N'-tetramethyluronium tetrafluoroborate (0.562 g, 1.750 mmol). The mixture was stirred at rt for 78 h and was quenched with water. The solids that formed were collected by filtration and were washed with water. The solids had some impurities, so they were purified further by prep HPLC. The mother liquor was concentrated under reduced pressure and was purified by flash chromatography. The combined purified fractions gave 1-(7-(4-chloro-1H-pyrazol-1-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (0.42 g, 0.787 mmol, 56.2% yield) as an off-white solid. ¹H NMR (500 MHz, DMSO-D6) δ 12.48 (s, 1H) 8.85 (s, 1H) 8.67 (d, J=3.05 Hz, 1H) 8.13-8.21 (m, 2H) 8.09 (s, 1H) 7.82-7.89 (m, 2H) 7.64 (dd, J=7.63, 4.88 Hz, 1H) 3.97 (s, 3H) 3.69-3.74 (m, 2H) 3.38-3.49 (m, 4H) 3.23-3.28 (m, 2H). LCMS: m/e 534.30 (M+H)⁺, ret time 2.696 min (method 4).

Preparation of N-(1-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-1,2,4-triazol-3-yl)pivalamide

B-80

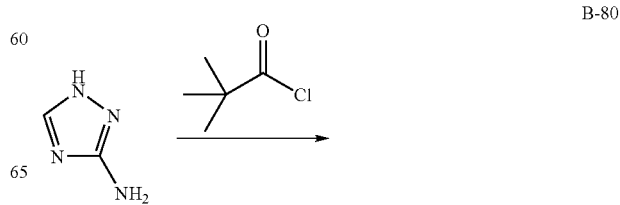

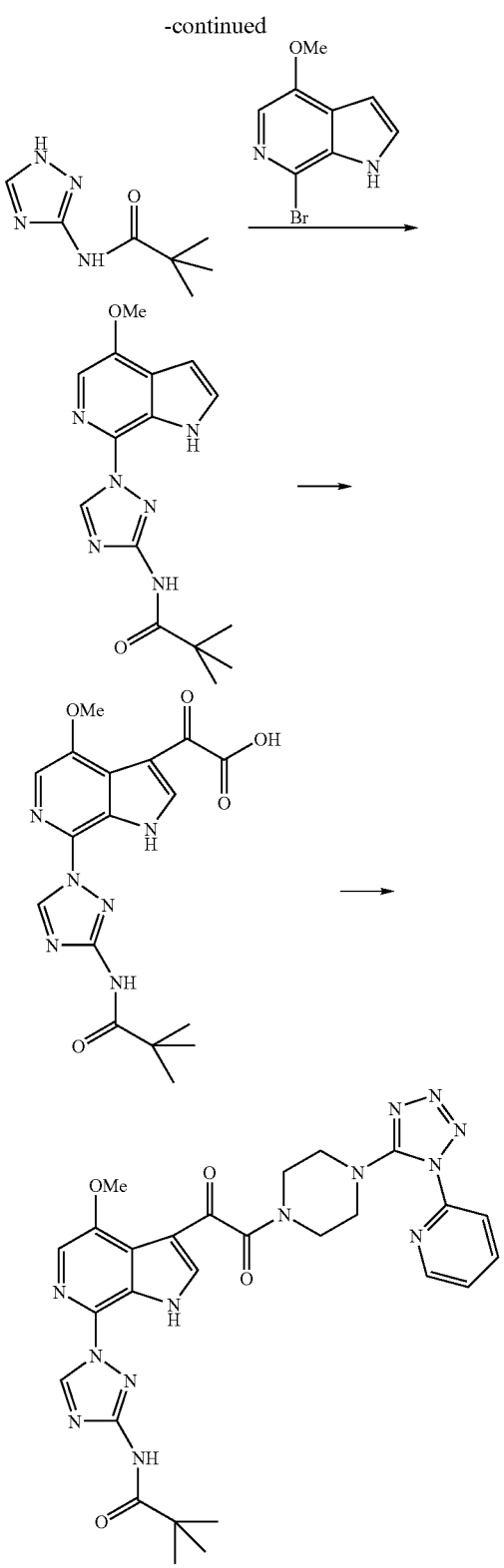

Step-1

To a mixture of 1H-1,2,4-triazol-3-amine (500 mg, 5.95 mmol) and TEA (0.829 mL, 5.95 mmol) in toluene (25 mL) was added pivaloyl chloride (0.732 mL, 5.95 mmol). The mixture was heated up at 110° C. for 13 h. The reaction mixture was quenched with water, filtered and the extracted with ethyl acetate (3×10 ml). The organic layer was washed with brine, dried over MgSO$_4$, filtered and concentrated under reduced pressure to afford N-(1H-1,2,4-triazol-3-yl)pivalamide (250 mg, 25%) as white solid. 1H NMR (500 MHz, MeOD) δ ppm 1.48 (s, 9H) 7.48 (s, 1H).

Step-2

A mixture of 7-bromo-4-methoxy-1H-pyrrolo[2,3-c]pyridine (250 mg, 1.101 mmol), potassium carbonate (457 mg, 3.30 mmol), copper(I) iodide (105 mg, 0.551 mmol), N-(1H-1,2,4-triazol-3-yl)pivalamide and (1R,2R)—N1,N2-dimethylcyclohexane-1,2-diamine (78 mg, 0.551 mmol) in 1,4-dioxane (2 mL) were heated up at 110° C. for 13 h. The reaction mixture was filtered through a silica gel pad and concentrated under reduced pressure. The resulting crude was purified by prep HPLC to give N-(1-(4-methoxy-1H-pyrrolo[2,3-c]pyridin-7-yl)-1H-1,2,4-triazol-3-yl)pivalamide (90 mg, 26%) as pale yellow oil. LCMS: m/e 315.05 (M+H)$^+$, ret time 1.55 min (method 8).

Step-3

To an oven-dried flask in ice bath was added AlCl$_3$ (382 mg, 2.86 mmol), then CH$_2$Cl$_2$ (4 mL) was introduced at 0° C. Nitromethane (10.84 μL, 0.201 mmol) was added at that temperature. Ice bath was removed and the mixture was stirred at room temperature for 30 min. N-(1-(4-methoxy-1H-pyrrolo[2,3-c]pyridin-7-yl)-1H-1,2,4-triazol-3-yl)pivalamide (90 mg, 0.286 mmol) and methyl 2-chloro-2-oxoacetate (0.079 mL, 0.859 mmol) were added at 0° C. The reaction mixture was stirred for three hours at room temperature. The reaction mixture was quenched with ammonium acetate (8 mL) and extracted with ethyl acetate (3×10 mL). The organic layer was washed with brine, dried over MgSO$_4$, filtered and concentrated under reduced pressure to afford methyl 2-(4-methoxy-7-(3-pivalamido-1H-1,2,4-triazol-1-yl)-1H-pyrrolo[2,3-c]pyridin-3-yl)-2-oxoacetate (40 mg, 45%) as white solid.

To a mixture of methyl 2-(4-methoxy-7-(3-pivalamido-1H-1,2,4-triazol-1-yl)-1H-pyrrolo[2,3-c]pyridin-3-yl)-2-oxoacetate (40 mg, 0.100 mmol) in water (1 mL) and MeOH (1 mL) was added K$_2$CO$_3$ (83 mg, 0.599 mmol) at room temperature. The reaction mixture was stirred overnight at room temperature. MeOH was removed under reduced pressure. The water layer was acidified to PH=5-6 using 1N HCl and concentrated under reduced pressure. The resulting residue was washed with water, filtered and dried to give 2-(4-methoxy-7-(3-pivalamido-1H-1,2,4-triazol-1-yl)-1H-pyrrolo[2,3-c]pyridin-3-yl)-2-oxoacetic acid (30 mg, 78%) as white solid. LCMS: m/e 387.18 (M+H)$^+$, ret time 2.46 min (method 4).

Step-4

A mixture of 2-(4-methoxy-7-(3-pivalamido-1H-1,2,4-triazol-1-yl)-1H-pyrrolo[2,3-c]pyridin-3-yl)-2-oxoacetic acid (15 mg, 0.039 mmol), 4-(1-(pyridin-2-yl)-1H-tetrazol-5-yl)piperazin-1-ium chloride (11.43 mg, 0.043 mmol), 2-(1H-Benzotriazol-1-yl)-1,1,3,3-tetramethyluronium tetrafluoroborate (13.71 mg, 0.043 mmol) and N,N-diisopropyl ethylamine (0.022 ml, 0.124 mmol) in DMF (1 ml) was stirred overnight at room temperature. The reaction mixture was filtered through a silica gel pad and concentrated under reduced pressure. The resulting crude was purified by prep HPLC to give N-(1-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)-1H-1,2,4-triazol-3-yl)pivalamide (10 mg, 43%) as white solid. LCMS: m/e 600.47 (M+H)$^+$, ret time 2.67 min (method 4). $^1$H NMR (500 MHz, DMSO-D6) δ ppm 1.22 (s, 9H) 3.23-3.29 (m, 2H) 3.39-3.49 (m, 4H) 3.68-3.74 (m, 2H) 3.99 (s, 3H) 7.64 (dd, J=7.63, 4.88 Hz, 1H) 7.85 (d, J=8.24 Hz, 1H) 7.88 (s, 1H) 8.13-8.18 (m, 1H) 8.21 (s, 1H) 8.23 (d, J=3.66 Hz, 1H) 8.64-8.69 (m, 1H) 11.36 (s, 1H) 12.59 (d, J=3.36 Hz, 1H)

Preparation of 4-(4-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxylate, 1-(4-methoxy-7-(4-(piperazin-1-yl)phenyl)-1H-pyrrolo[2,3-c]pyridin-3-yl)-2-(4-(1-(pyridin-2-yl)-1H-tetrazol-5-yl)piperazin-1-yl)ethane-1,2-dione and isopropyl 4-(4-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxylate

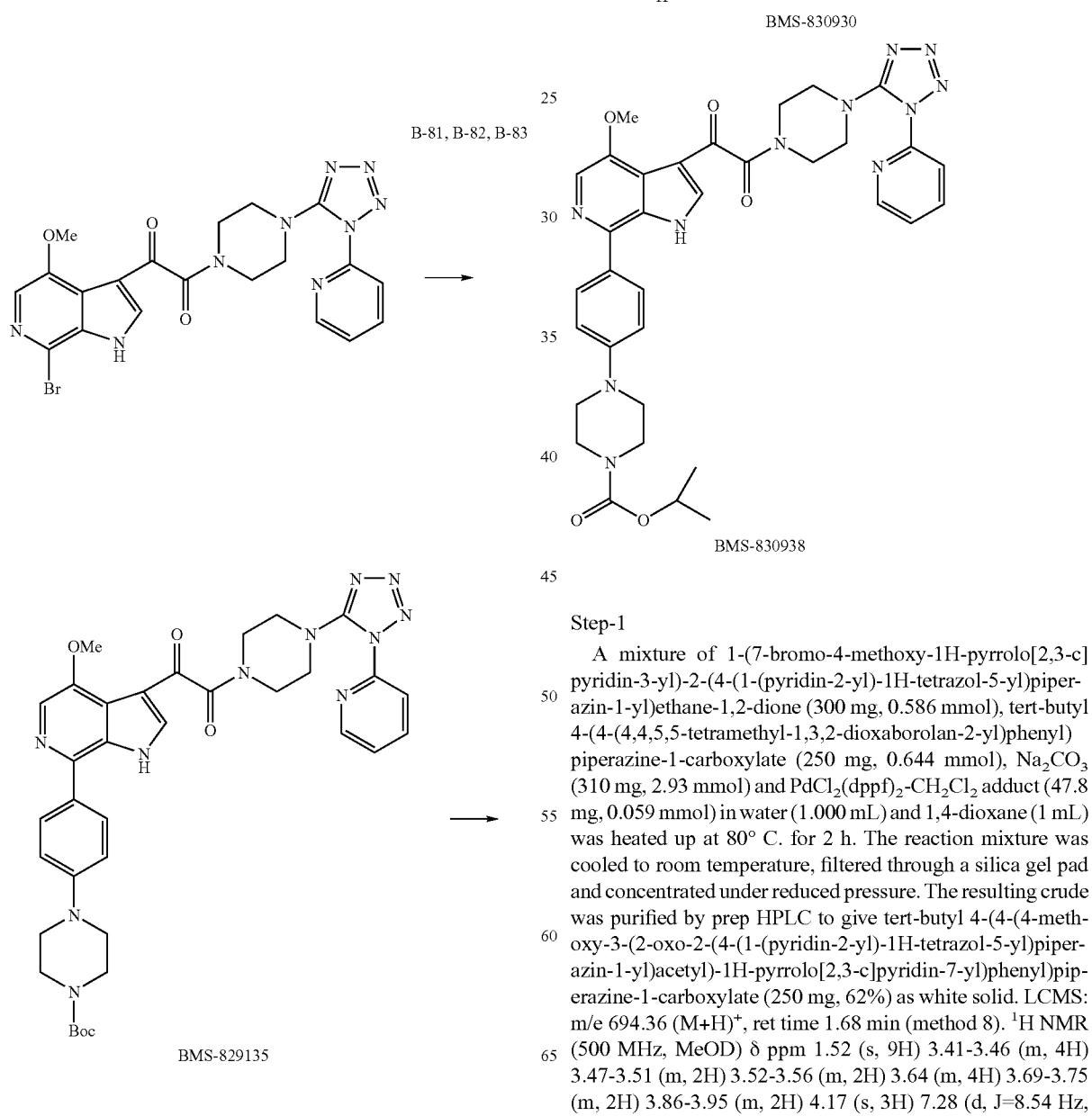

Step-1

A mixture of 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (300 mg, 0.586 mmol), tert-butyl 4-(4-(4,4,5,5-tetramethyl-1,3,2-dioxaborolan-2-yl)phenyl)piperazine-1-carboxylate (250 mg, 0.644 mmol), Na$_2$CO$_3$ (310 mg, 2.93 mmol) and PdCl$_2$(dppf)$_2$·CH$_2$Cl$_2$ adduct (47.8 mg, 0.059 mmol) in water (1.000 mL) and 1,4-dioxane (1 mL) was heated up at 80° C. for 2 h. The reaction mixture was cooled to room temperature, filtered through a silica gel pad and concentrated under reduced pressure. The resulting crude was purified by prep HPLC to give tert-butyl 4-(4-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxylate (250 mg, 62%) as white solid. LCMS: m/e 694.36 (M+H)$^+$, ret time 1.68 min (method 8). $^1$H NMR (500 MHz, MeOD) δ ppm 1.52 (s, 9H) 3.41-3.46 (m, 4H) 3.47-3.51 (m, 2H) 3.52-3.56 (m, 2H) 3.64 (m, 4H) 3.69-3.75 (m, 2H) 3.86-3.95 (m, 2H) 4.17 (s, 3H) 7.28 (d, J=8.54 Hz, 2H) 7.63 (dd, J=7.63, 4.88 Hz, 1H) 7.77 (d, J=8.55 Hz, 2H) 7.90 (d, J=8.24 Hz, 1H) 8.00 (s, 1H) 8.17 (t, J=7.78 Hz, 1H) 8.68 (s, 2H)

Step-2

To a solution of tert-butyl 4-(4-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxylate (250 mg, 0.360 mmol) in 1,4-dioxane (2 mL) was added 4N HCl in 1,4-dioxane (0.450 mL, 1.802 mmol) at room temperature, the mixture was stirred for 2 hours at room temperature. The reaction mixture was concentrated under reduced pressure. The resulting crude was purified by prep HPLC to give 1-(4-methoxy-7-(4-(piperazin-1-yl)phenyl)-1H-pyrrolo[2,3-c]pyridin-3-yl)-2-(4-(1-(pyridin-2-yl)-1H-tetrazol-5-yl)piperazin-1-yl)ethane-1,2-dione (200 mg, 93%) as white solid. LCMS: m/e 594.55 (M+H)+, ret time 1.76 min (method 4). $^1$H NMR (500 MHz, MeOD) δ ppm 3.42-3.48 (m, 4H) 3.50 (m, 2H) 3.54 (m, 2H) 3.64-3.70 (m, 4H) 3.71 (m, 2H) 3.90 (m, 2H) 4.16 (s, 3H) 7.36 (d, J=8.54 Hz, 2H) 7.63 (dd, J=7.17, 5.04 Hz, 1H) 7.82 (d, J=8.85 Hz, 2H) 7.90 (d, J=8.24 Hz, 1H) 8.04 (s, 1H) 8.17 (t, J=7.63 Hz, 1H) 8.63-8.75 (m, 2H).

Step-3

To a solution of 1-(4-methoxy-7-(4-(piperazin-1-yl)phenyl)-1H-pyrrolo[2,3-c]pyridin-3-yl)-2-(4-(1-(pyridin-2-yl)-1H-tetrazol-5-yl)piperazin-1-yl)ethane-1,2-dione (50 mg, 0.084 mmol) in THF (1 mL) and DMF (1 mL) were added TEA (0.023 mL, 0.168 mmol) and isopropyl carbonochloridate (13.42 mg, 0.109 mmol) at room temperature. The reaction mixture was stirred for 3 hours. The reaction mixture was concentrated under reduced pressure. The resulting crude was purified by prep HPLC to give isopropyl 4-(4-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxylate (20 mg, 35%) as white solid. LCMS: m/e 680.58 (M+H)+, ret time 2.49 min (method 4). $^1$H NMR (500 MHz, MeOD) δ ppm 1.30 (d, J=6.10 Hz, 6H) 3.41-3.50 (m, 6H) 3.50-3.58 (m, 2H) 3.65-3.75 (m, 6H) 3.86-3.93 (m, 2H) 4.14 (s, 3H) 4.95-4.99 (m, 1H) 7.28 (d, J=8.85 Hz, 2H) 7.63 (dd, J=7.32, 4.88 Hz, 1H) 7.77 (d, J=8.55 Hz, 2H) 7.89 (d, J=7.93 Hz, 1H) 8.01 (s, 1H) 8.12-8.20 (m, 1H) 8.67 (s, 2H).

The following compounds were prepared in the same manner from 1-(4-methoxy-7-(4-(piperazin-1-yl)phenyl)-1H-pyrrolo[2,3-c]pyridin-3-yl)-2-(4-(1-(pyridin-2-yl)-1H-tetrazol-5-yl)piperazin-1-yl)ethane-1,2-dione and the corresponding acylating agent.

| Structure | Name | LC/MS (M + H)+ RT (min) | NMR |
|---|---|---|---|
| B-84 | isobutyl 4-(4-(4-methoxy-3-2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxylate | 694.66 2.64 (Method 4) | $^1$H NMR (500 MHz, MeOD) δ ppm 0.95-1.08 (m, 6H) 1.91-2.08 (m, 1H) 3.42-3.50 (m, 6H) 3.50-3.57 (m, 2H) 3.70 (s, 6H) 3.86-3.91 (m, 2H) 3.93 (d, J = 6.41 Hz, 2H) 4.14 (s, 3H) 7.27 (d, J = 8.85 Hz, 2H) 7.62 (dd, J = 6.71, 4.88 Hz, 1H) 7.76 (d, J = 8.85 Hz, 2H) 7.89 (d, J = 7.93 Hz, 1H) 8.01 (s, 1H) 8.11-8.21 (m, 1H) 8.64-8.72 (m, 2H) |

-continued

| Structure | Name | LC/MS (M + H)+ RT (min) | NMR |
|---|---|---|---|
| 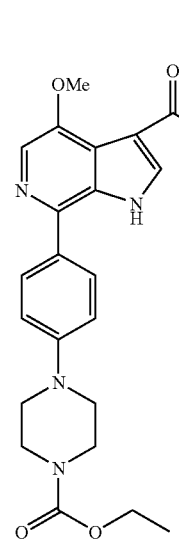<br>B-85 | ethyl 4-(4-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxylate | 666.62<br>2.38<br>(Method 4) | $^1$H NMR (500 MHz, MeOD) δ ppm 1.32 (t, J = 7.17 Hz, 3H) 3.42-3.51 (m, 6H) 3.51-3.57 (m, 2H) 3.64-3.75 (m, 6H) 3.86-3.94 (m, 2H) 4.15 (s, 3H) 4.20 (q, J = 7.02 Hz, 2H) 7.28 (d, J = 9.16 Hz, 2H) 7.63 (dd, J = 7.63, 4.88 Hz, 1H) 7.77 (d, J = 8.85 Hz, 2H) 7.89 (d, J = 8.24 Hz, 1H) 8.01 (s, 1H) 8.13-8.21 (m, 1H) 8.64-8.72 (m, 2H) |
| 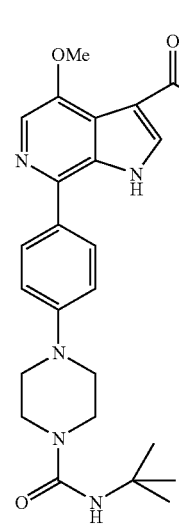<br>B-86 | N-tert-butyl-4-(4-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxamide | 693.73<br>2.36<br>(Method 4) | $^1$H NMR (500 MHz, MeOD) δ ppm 1.38 (s, 9H) 3.43-3.47 (m, 4H) 3.48-3.51 (m, 2H) 3.52-3.56 (m, 2H) 3.56-3.61 (m, 4H) 3.67-3.75 (m, 2H) 3.86-3.96 (m, 2H) 4.15 (s, 3H) 7.27 (d, J = 8.85 Hz, 2H) 7.64 (d, 1H) 7.77 (d, J = 8.85 Hz, 2H) 7.90 (d, J = 7.93 Hz, 1H) 8.00 (s, 1H) 8.13-8.20 (m, 1H) 8.68 (s, 2H) |

| Structure | Name | LC/MS (M + H)+ RT (min) | NMR |
|---|---|---|---|
| (B-87) | N-isopropyl-4-(4-(4-methoxy-3-(2-oxo-2-(4-(1-(pyridin-2-yl)-1H-tetrazol-5-yl)piperazin-1-yl)acetyl)-1H-pyrrolo[2,3-c]pyridin-7-yl)phenyl)piperazine-1-carboxamide | 679.74 2.24 (Method 4) | 1H NMR (500 MHz, MeOD) δ ppm 1.19 (d, J = 6.71 Hz, 6H) 3.43-3.51 (m, 6H) 3.52-3.57 (m, 2H) 3.59-3.66 (m, 4H) 3.68-3.75 (m, 2H) 3.87-3.99 (m, 3H) 4.15 (s, 3H) 7.27 (d, J = 8.85 Hz, 2H) 7.63 (dd, J = 7.32, 4.88 Hz, 1H) 7.77 (d, J = 8.85 Hz, 2H) 7.90 (d, J = 7.93 Hz, 1H) 8.00 (s, 1H) 8.12-8.21 (m, 1H) 8.68 (s, 2H) |

Preparation of 1-(4-methoxy-7-(2-methoxythiazol-5-yl)-1H-pyrrolo[2,3-c]pyridin-3-yl)-2-(4-(1-(pyridin-2-yl)-1H-tetrazol-5-yl)piperazin-1-yl)ethane-1,2-dione

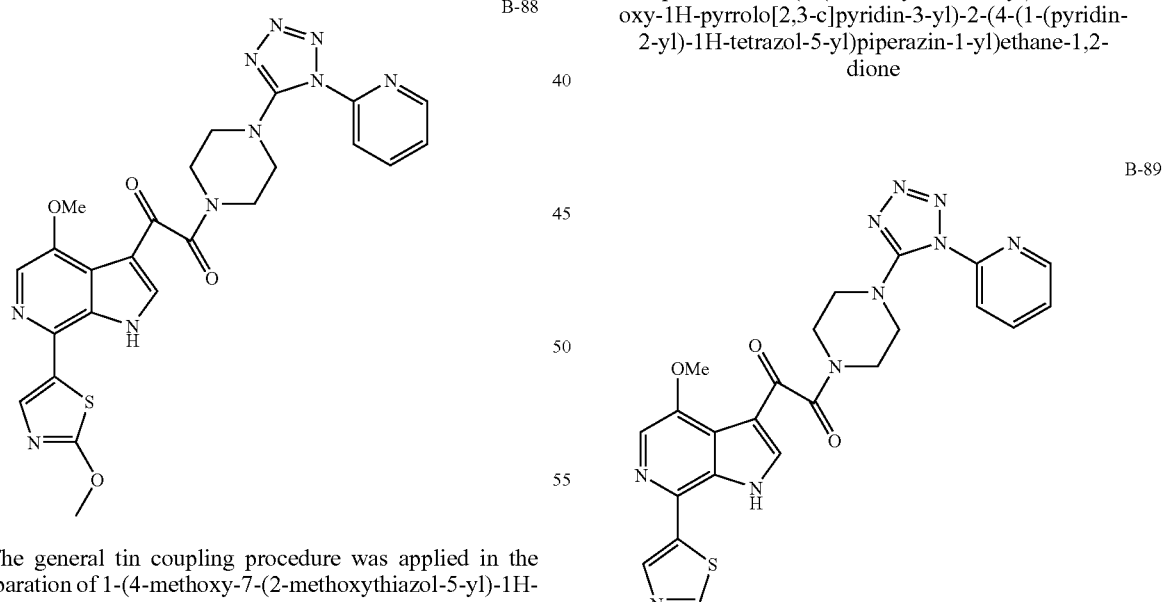

B-88

The general tin coupling procedure was applied in the preparation of 1-(4-methoxy-7-(2-methoxythiazol-5-yl)-1H-pyrrolo[2,3-c]pyridin-3-yl)-2-(4-(1-(pyridin-2-yl)-1H-tetrazol-5-yl)piperazin-1-yl)ethane-1,2-dione (16 mg, 15%) from 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione using 2-methoxy-5-(tributylstannyl)thiazole as a tin reagent. LCMS: m/e 547.19 (M+H)+, ret time 1.28 min (method 8). 1H NMR (500 MHz, DMSO-D6) δ ppm 3.22-3.31 (m, 2H) 3.44 (d, J=10.38 Hz, 4H) 3.67-3.76 (m, 2H) 3.92-3.99 (m, 3H) 4.08 (s, 3H) 7.64 (dd, J=7.63, 4.88 Hz, 1H) 7.85 (d, J=8.24 Hz, 1H) 7.97-8.05 (m, 2H) 8.11-8.19 (m, 1H) 8.33 (d, J=3.36 Hz, 1H) 8.64-8.70 (m, 1H) 12.66 (d, J=2.75 Hz, 1H).

Preparation of 1-(7-(2-ethoxythiazol-5-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione

B-89

The general tin coupling procedure was applied in the preparation of 1-(7-(2-ethoxythiazol-5-yl)-4-methoxy-1H- pyrrolo[2,3-c]pyridin-3-yl)-2-(4-(1-(pyridin-2-yl)-1H-tetrazol-5-yl)piperazin-1-yl)ethane-1,2-dione (30 mg, 27%) from 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione using 2-ethoxy-5-(tributylstannyl)thiazole as a tin reagent. LCMS: m/e 561.2 (M+H)$^+$, ret time 1.39 min (method 8). $^1$H NMR (500 MHz, MeOD) δ ppm 1.52 (t, J=7.02 Hz, 3H) 3.46 (d, J=4.58 Hz, 2H) 3.52 (s, 2H) 3.69 (s, 2H) 3.89 (d, J=5.19 Hz, 2H) 4.15 (s, 3H) 4.58-4.66 (m, 2H) 7.67 (dd, J=6.71, 4.88 Hz, 1H) 7.82-7.94 (m, 2H) 8.07 (s, 1H) 8.15-8.24 (m, 1H) 8.64-8.73 (m, 2H).

Preparation of 1-(4-methoxy-7-(2-methylthiazol-5-yl)-1H-pyrrolo[2,3-c]pyridin-3-yl)-2-(4-(1-(pyridin-2-yl)-1H-tetrazol-5-yl)piperazin-1-yl)ethane-1,2-dione

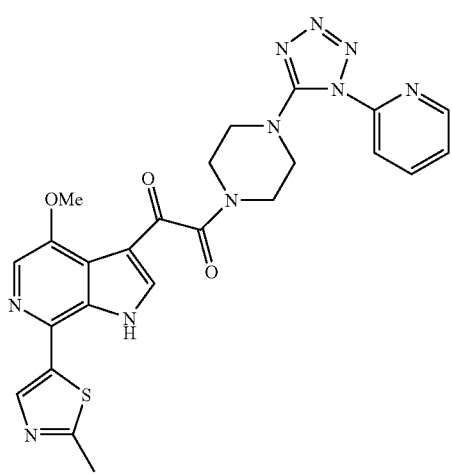

B-90

The general tin coupling procedure was applied in the preparation of 1-(4-methoxy-7-(2-methylthiazol-5-yl)-1H-pyrrolo[2,3-c]pyridin-3-yl)-2-(4-(1-(pyridin-2-yl)-1H-tetrazol-5-yl)piperazin-1-yl)ethane-1,2-dione (22 mg, 21%) from 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione using 2-methyl-5-(tributylstannyl)thiazole as a tin reagent. LCMS: m/e 531.19 (M+H)$^+$, ret time 1.12 min (method 8). $^1$H NMR (500 MHz, MeOD) δ ppm 2.86 (s, 3H) 3.43-3.49 (m, 2H) 3.51-3.58 (m, 2H) 3.65-3.73 (m, 2H) 3.87-3.94 (m, 2H) 4.13 (s, 3H) 7.62 (dd, J=7.48, 5.04 Hz, 1H) 7.89 (d, J=7.94 Hz, 1H) 8.10 (s, 1H) 8.12-8.19 (m, 1H) 8.25 (s, 1H) 8.52 (s, 1H) 8.65-8.70 (m, 1H).

Preparation of 1-(7-(2-ethylthiazol-5-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione

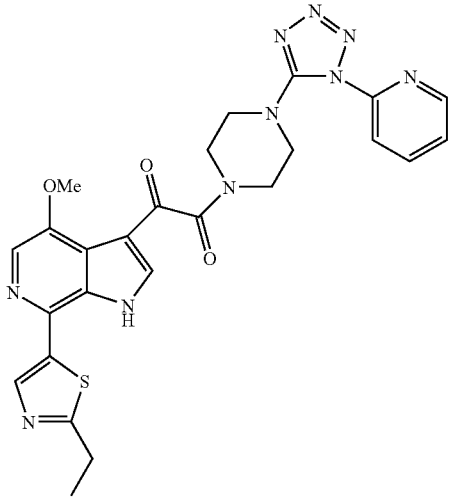

B-91

The general tin coupling procedure was applied in the preparation of 1-(7-(2-ethylthiazol-5-yl)-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (25 mg, 24%) from 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione using 2-ethyl-5-(tributylstannyl)thiazole as a tin reagent. LCMS: m/e 543.23 (M+H)$^+$, ret time 1.43 min (method 8). $^1$H NMR (500 MHz, MeOD) δ ppm 1.51 (t, J=7.48 Hz, 3H) 3.22 (q, J=7.63 Hz, 2H) 3.44-3.50 (m, 2H) 3.51-3.57 (m, 2H) 3.66-3.73 (m, 2H) 3.87-3.93 (m, 2H) 4.15 (s, 3H) 7.62 (dd, J=7.63, 4.88 Hz, 1H) 7.90 (d, J=8.24 Hz, 1H) 8.12 (s, 1H) 8.14-8.19 (m, 1H) 8.30 (s, 1H) 8.59 (s, 1H) 8.68 (d, J=4.88 Hz, 1H).

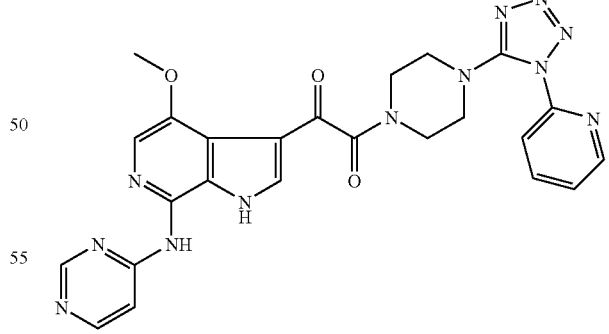

B-92

A suspension of 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (100 mg, 0.195 mmol), pyrimidin-4-amine (55.7 mg, 0.586 mmol), Tris(dibenzylideneacetone)dipalladium(0) (8.94 mg, 9.76 μmol), 4,5-Bis(diphenylphosphino)-9,9-dimethylxanthene (11.29 mg, 0.020 mmol) and Cesium carbonate (127 mg, 0.390 mmol) in Dioxane (2 mL) was heated at 115° C. for 4 hours.

After cooling to rt, the mixture was diluted with MeOH and filtered. The filtrate was concentrated and purified by prep. HPLC to give 1-(4-methoxy-7-(pyrimidin-4-ylamino)-1H-pyrrolo[2,3-c]pyridin-3-yl)-2-(4-(1-(pyridin-2-yl)-1H-tetrazol-5-yl)piperazin-1-yl)ethane-1,2-dione (4.1 mg, 7.79 μmol, 3.99% yield). LCMS: m/e 527.3 (M+H)$^+$, ret time 1.02 min. 1H NMR (500 MHz, MeOD) δ ppm 8.87 (s, 1H) 8.61 (d, J=3.66 Hz, 1H) 8.49 (d, J=6.10 Hz, 1H) 8.42 (s, 1H) 8.03-8.10 (m, 1H) 7.83 (d, J=7.94 Hz, 1H) 7.67 (s, 1H) 7.51-7.56 (m, 2H) 4.02 (s, 3H) 3.83-3.90 (m, 2H) 3.62-3.67 (m, 2H) 3.43-3.56 (m, 4H).

Example Chemistry Section C

The following general methods apply to Example Chemistry Section C:

HPLC Methods

1 Dynamex C18, 4.6×250 mm, 8 micrometer, Sol. A 0.05% TFA in water/ACN (90:10), Sol. B 0.05% TFA in water/ACN (10:90), grad. 0% B to 100% B;

2 Phenomenex Gemini C18, 4.6×150 mm, 5 micrometer, Sol. A 10 mM ammonium bicarb (pH 7.8) in water/ACN (95:5), Sol. B 10 mM ammonium bicarb (pH 7.8) in water/ACN (10:90), grad. 10% B to 50% B;

3 Waters Xterra C18, 4.6×150 mm, 3.5 micrometer, Sol. A 10 nM ammonium acetate (pH 6.8) in water/ACN (95:5). Sol. B 10 nM ammonium acetate (pH 6.8) in water/ACN (10:90), grad. 5% B to 100% B (13.15 min retention).

Preparation of 1-((2R,6S)-2,6-dimethyl-4-(1-phenyl-1H-tetrazol-5-yl)piperazin-1-yl)-2-(4-fluoro-7-(1H-1,2,3-triazol-1-yl)-1H-pyrrolo[2,3-c]pyridin-3-yl)ethane-1,2-dione (Compound C-1)

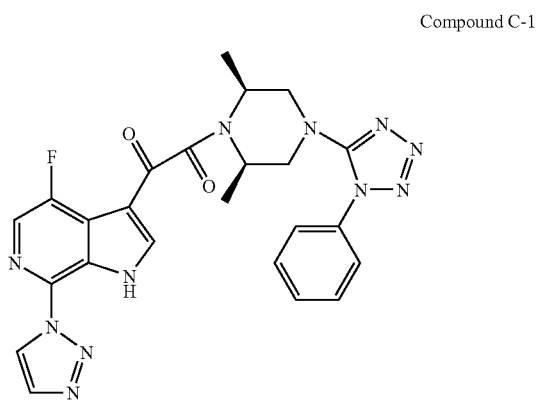

Compound C-1

(3R,5S)-3,5-dimethyl-1-(1-phenyl-1H-tetrazol-5-yl)piperazine was prepared via method A in chemistry section 1 using (2R,6S)-2,6-dimethylpiperazine and 5-chloro-1-phenyl-1H-tetrazole. (3R,5S)-3,5-dimethyl-1-(1-phenyl-1H-tetrazol-5-yl)piperazine was coupled with 2-(4-fluoro-7-(1H-1,2,3-triazol-1-yl)-1H-pyrrolo[2,3-c]pyridin-3-yl)-2-oxoacetic acid using method B for the preparation of compound 3 in chemistry section A to provide the desired product 1-((2R,6S)-2,6-dimethyl-4-(1-phenyl-1H-tetrazol-5-yl)piperazin-1-yl)-2-(4-fluoro-7-(1H-1,2,3-triazol-1-yl)-1H-pyrrolo[2,3-c]pyridin-3-yl)ethane-1,2-dione with the following characteristics:

Purity and Retention Times Obtained Via Each HPLC Method:

Method 1) 98.6% purity, 15.8 min. retention time

Method 2) 98.8% purity, 12.85 min. retention time

Method 3) 99.1% purity, 13.15 min retention time

MS 516 (M+H)+, 514 (M−H)−

HRMS cal. 516.2020 found 516.2007 mp. 254-256 deg. C.

H1 NMR DMSO-d6: 1.19-1.24 (t, 6H, J=6.6 Hz), 2.99-3.05 (dd, 1H, J=3.9, 12.6 Hz), 3.15-3.21 (dd, 1H, J=4.5, 12.6 Hz), 3.24-3.42 (m, 2H), 3.87-3.90 (m, 1H), 4.58-4.61 (m, 1H), 7.62-7.71 (m, 5H), 8.11-8.12 (d, 1H, J=0.9 Hz), 8.30-8.31 (m, 2H), 9.00-9.01 (d, 1H, J=1.2 Hz), 13.04 (s, 1H).

Example Chemistry Section D

The following general methods apply to Example Chemistry Section D:

LC-MS Analytical Method:

Method 1
  Gradient time: 4 min
  Flow rate: 3 mL/min
  Stop time Gradient time+1 minute
  Starting conc: 10% B
  Eluent A: H$_2$O with 10 mM NH$_4$OAc
  Eluent B: ACN
  Column: Phenomenex, Onyx Monolithic C18 50×4.6 mm Method 2
  Gradient time: 3 min
  Flow rate: 1 mL/min
  Stop time Gradient time+1 minute
  Starting conc: 0% B
  Eluent A: 5:95 ACN:Water with 10 mM NH$_4$OAc
  Eluent B: 95:5 ACN:Water with 10 mM NH$_4$OAc
  Column: Waters Xbridge 2.1×50 mm 5 um C18

Method 3
  Gradient time: 7.5 min
  Flow rate: 1.2 mL/min
  Stop time Gradient time+1 minute
  Starting conc: 10% B
  Eluent A: Water with 10 mM NH$_4$OAc
  Eluent B: ACN
  Column: Agilent Zorbax SB-CN 4.6×75 mm 3.5 micron Preparation of compound D

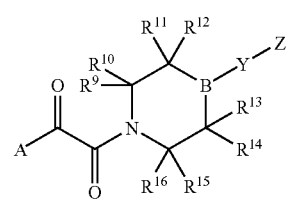

Method A

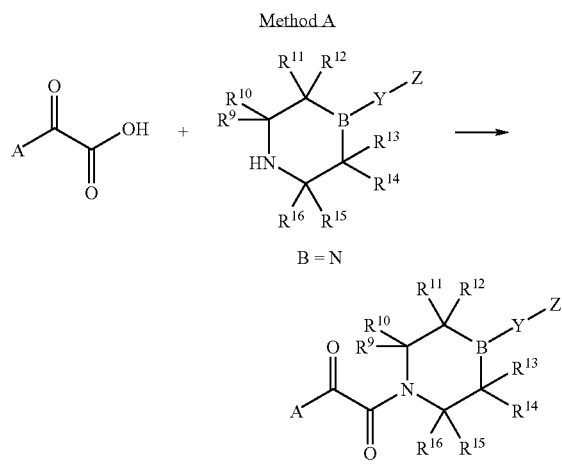

2-Keto acid (1 eq.), piperazine (1-5 eq.), O-(1H-benzotriazol-1-yl)-N,N,N',N'-tetramethyluronium tetrafluoroborate (TBTU) (1-5 eq.) and Hunig's Base (1-5 eq.) were combined in DMF. The mixture was stirred at room temperature for 17 hours. The product was purified by Waters or Dinox automated preparative HPLC System.

Method B

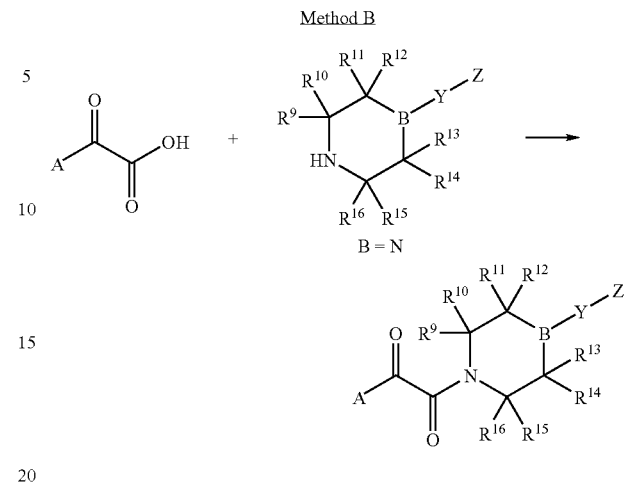

2-Keto acid (1 eq.), piperazine (1-5 eq.), (2-(7-Aza-1H-benzotriazole-1-yl)-1,1,3,3-tetramethyluronium hexafluorophosphate) (HATU) (1-5 eq.) and Hunig's Base (1-5 eq.) were combined in DMF. The mixture was stirred at room temperature for 17 hours. The product was purified by Waters or Dinox automated preparative HPLC System.

TABLE D-1

| Compd # | Structure | Method Used | MS (M + H)+ Calcd. | MS (M + H)+ Observ. And Retention Time and NMR |
|---|---|---|---|---|
| D-1 | 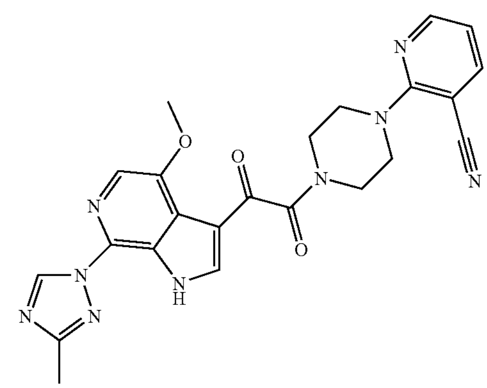 | B | 472.19 | 472.16<br>Rf = 1.64 min.<br>LCMS Method 2 |
| D-2 | 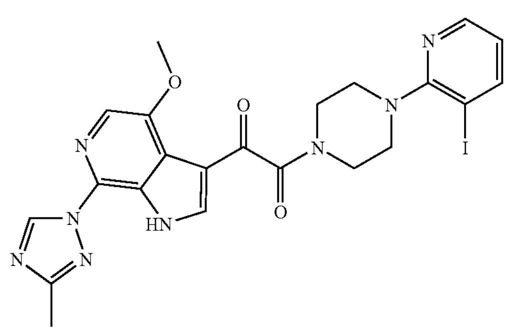 | B | 573.09 | 573.09<br>Rf = 1.73 min.<br>LCMS Method 2 |

TABLE D-1-continued

| Compd # | Structure | Method Used | MS (M + H)+ Calcd. | MS (M + H)+ Observ. And Retention Time and NMR |
|---|---|---|---|---|
| D-3 | 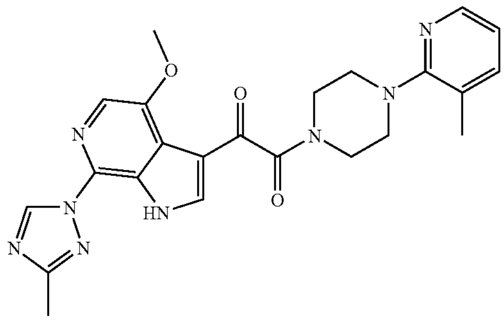 | B | 461.21 | 461.22<br>Rf = 1.63 min.<br>LCMS Method 2<br>1H NMR<br>(600 MHz, DMSO-$d6$)<br>δ ppm 12.36 (s, 1 H), 9.22 (s, 1 H), 8.23 (s, 1 H), 8.11 (s, 1 H), 7.89 (s, 1 H), 7.52 (d, J = 6.44 Hz, 1 H), 6.95 (s, 1 H), 4.00 (s, 3 H), 3.65-3.85 (m, 2 H), 3.41-3.57 (m, 2 H), 3.19-3.30 (m, 3 H), 3.12-3.21 (m, 2 H), 2.96-3.10 (m, 2 H), 2.26 (s, 3 H) |
| D-4 | 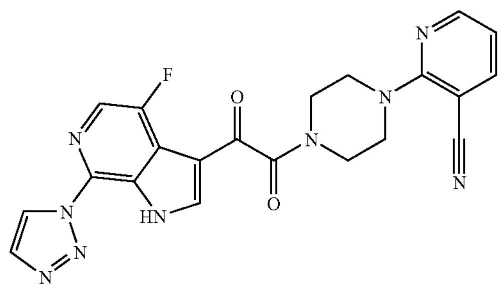 | B | 446.15 | 446.11<br>Rf = 1.59 min.<br>LCMS Method 2 |
| D-5 | 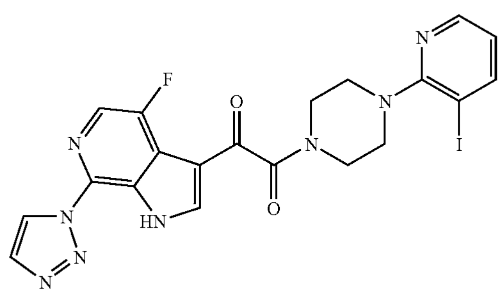 | B | 547.05 | 547.09<br>Rf = 1.70 min.<br>LCMS Method 2 |
| D-6 | 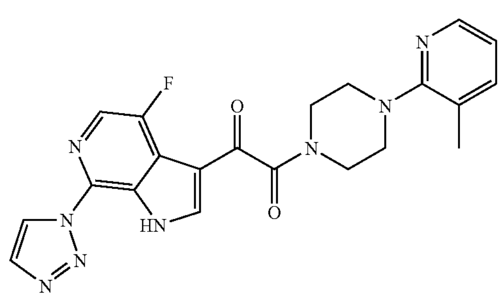 | B | 435.17 | 435.180<br>Rf = 1.60 min.<br>LCMS Method 2 |

TABLE D-1-continued

| Compd # | Structure | Method Used | MS (M + H)+ Calcd. | MS (M + H)+ Observ. And Retention Time and NMR |
|---|---|---|---|---|
| D-7 | 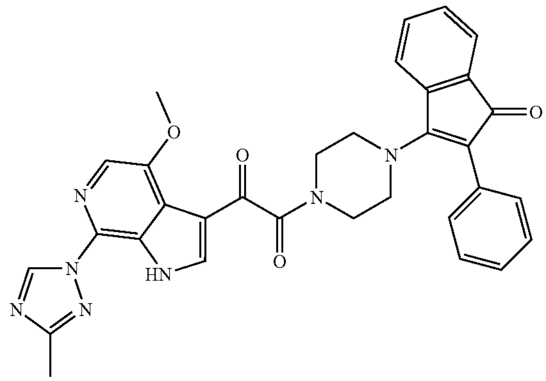 | B | 574.22 | 574.32<br>Rf = 1.71 min.<br>LCMS Method 2 |
| D-8 | 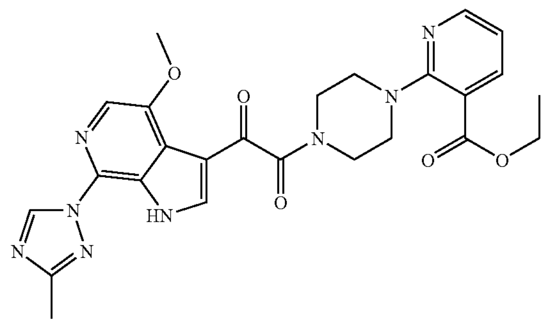 | B | 519.21 | 519.21<br>Rf = 1.63 min.<br>LCMS Method 2 |
| D-9 | 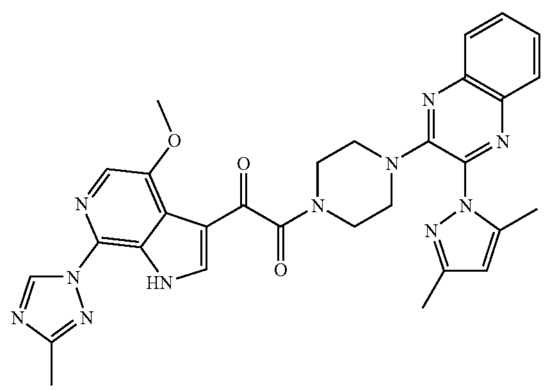 | B | 592.26 | 592.27<br>Rf = 1.74 min.<br>LCMS Method 2 |
| D-10 | Chiral | B | 608.22 | 608.25<br>Rf = 1.86 min.<br>LCMS Method 2 |

TABLE D-1-continued
| Compd # | Structure | Method Used | MS (M + H)+ Calcd. | MS (M + H)+ Observ. And Retention Time and NMR |
|---|---|---|---|---|
| D-11 | 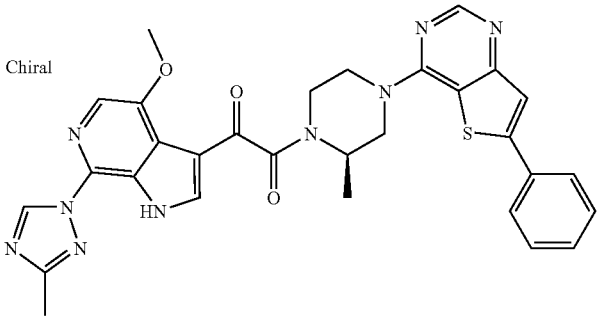 | B | 594.21 | 594.287<br>Rf = 1.71 min.<br>LCMS Method 2 |
| D-12 | 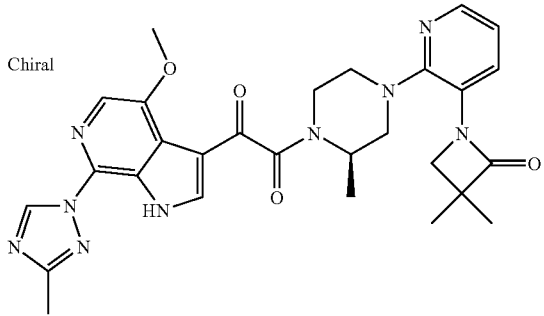 | B | 558.26 | 558.24<br>Rf = 1.61 min.<br>LCMS Method 2 |
| D-13 | 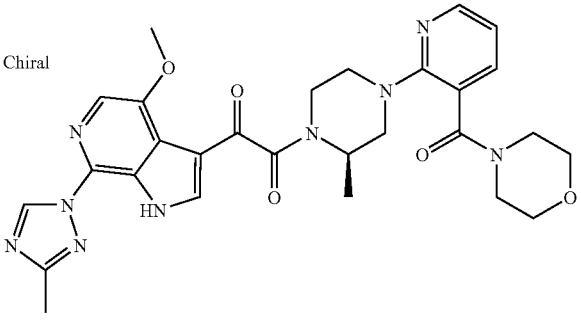 | B | 574.25 | 574.25<br>Rf = 1.41 min.<br>LCMS Method 2 |
| D-14 | 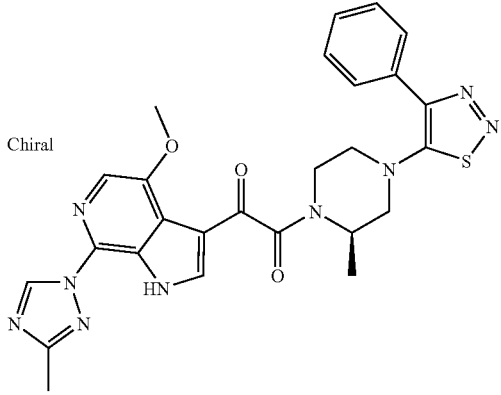 | B | 544.19 | 544.21<br>Rf = 1.41 min.<br>LCMS Method 2 |

TABLE D-1-continued

| Compd # | Structure | Method Used | MS (M + H)+ Calcd. | MS (M + H)+ Observ. And Retention Time and NMR |
| --- | --- | --- | --- | --- |
| D-15 | 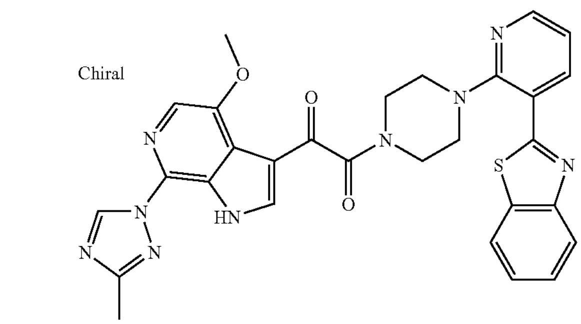 | B | 580.19 | 580.23 Rf = 1.79 min. LCMS Method 2 |
| D-16 | 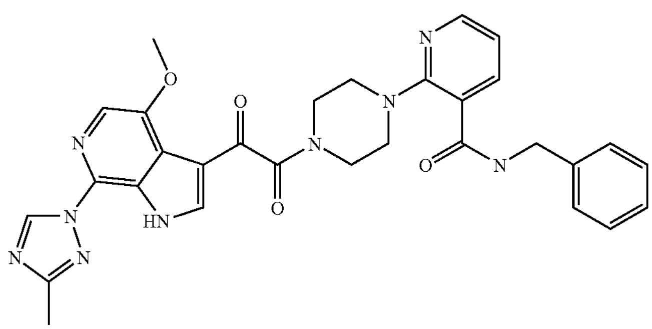 | B | 580.24 | 580.24 Rf = 1.55 min. LCMS Method 2 |
| D-17 | 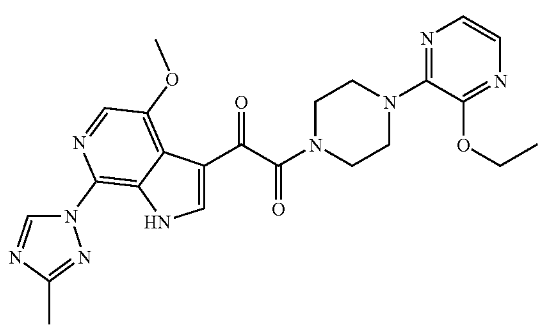 | B | 492.21 | 492.22 Rf = 1.62 min. LCMS Method 2 |
| D-18 | 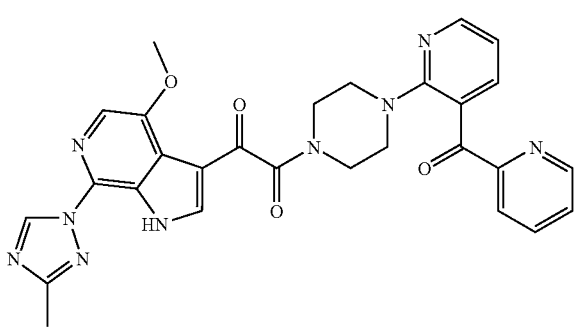 | B | 552.2 | 552.22 Rf = 1.51 min. LCMS Method 2 |

TABLE D-1-continued
| Compd # | Structure | Method Used | MS (M + H)+ Calcd. | MS (M + H)+ Observ. And Retention Time and NMR |
|---|---|---|---|---|
| D-19 | 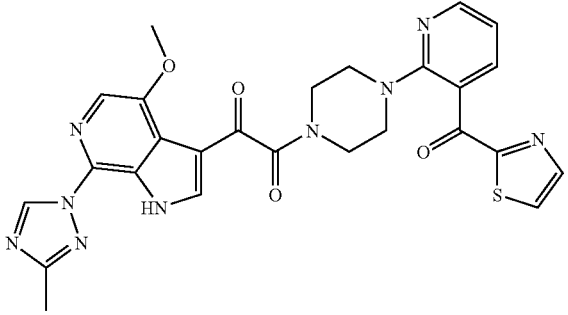 | B | 558.18 | 558.24<br>Rf = 1.56 min.<br>LCMS Method 2 |
| D-20 | 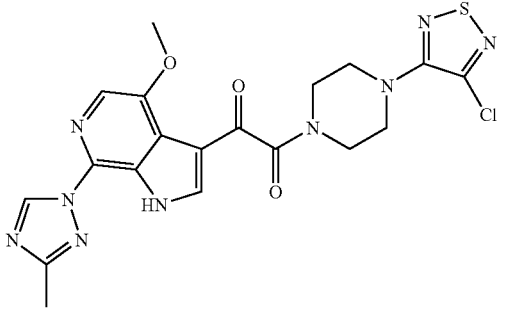 | B | 488.09 | 488.09<br>Rf = 1.68 min.<br>LCMS Method 2<br>1H NMR (600 MHz, DMSO-$d_6$)<br>δ ppm 12.38 (s, 1 H), 9.23 (s, 1 H), 8.29 (d, J = 11.13 Hz, 1 H), 7.97 (s, 1 H), 4.04 (s, 3 H), 3.74-3.94 (m, 2 H), 3.53-3.68 (m, 4 H), 3.43-3.52 (m, 2 H), 3.22-3.41 (m, 3 H) |
| D-21 | 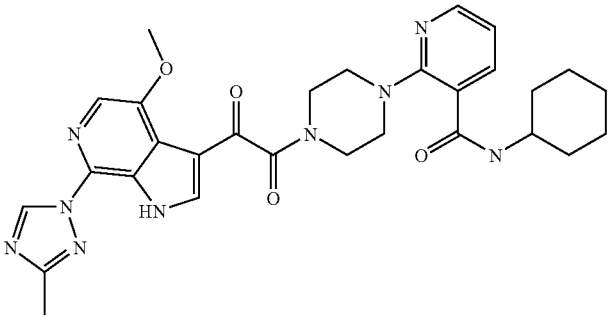 | B | 572.28 | 572.28<br>Rf = 1.62 min.<br>LCMS Method 2 |
| D-22 | 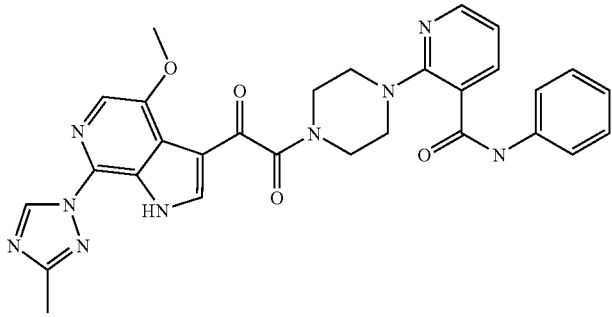 | B | 566.23 | 566.29<br>Rf = 1.62 min.<br>LCMS Method 2 |

TABLE D-1-continued

| Compd # | Structure | Method Used | MS (M + H)+ Calcd. | MS (M + H)+ Observ. And Retention Time and NMR |
|---|---|---|---|---|
| D-23 | 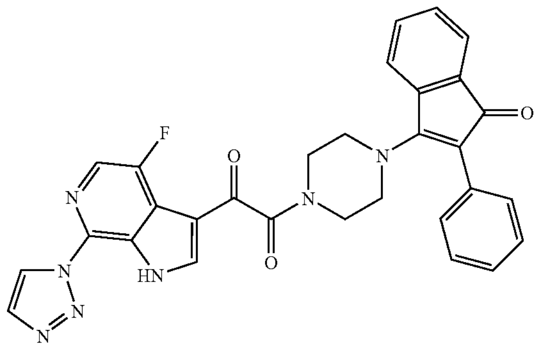 | B | 548.19 | 548.28<br>Rf = 1.80 min.<br>LCMS Method 2 |
| D-24 | 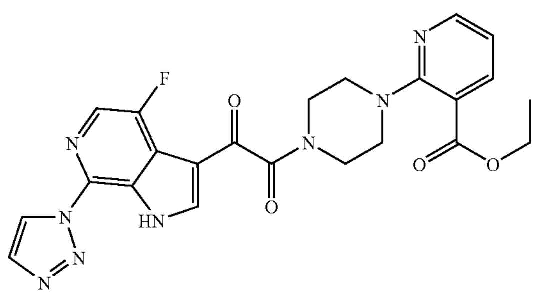 | B | 493.18 | 493.18<br>Rf = 1.71 min.<br>LCMS Method 2 |
| D-25 | 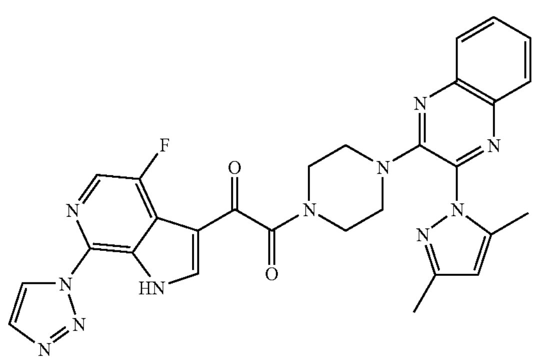 | B | 566.22 | 566.24<br>Rf = 1.83 min.<br>LCMS Method 2 |
| D-26 | Chiral | B | 582.19 | 582.20<br>Rf = 1.95 min.<br>LCMS Method 2 |

TABLE D-1-continued

| Compd # | Structure | Method Used | MS (M + H)+ Calcd. | MS (M + H)+ Observ. And Retention Time and NMR |
|---|---|---|---|---|
| D-27 | Chiral | B | 568.17 | 568.24<br>Rf = 1.83 min.<br>LCMS Method 2 |
| D-28 | Chiral | B | 532.22 | 532.21<br>Rf = 1.70 min.<br>LCMS Method 2 |
| D-29 | Chiral | B | 548.22 | 548.23<br>Rf = 1.50 min.<br>LCMS Method 2 |
| D-30 | Chiral | B | 518.15 | 518.19<br>Rf = 1.82 min.<br>LCMS Method 2 |
| D-31 | 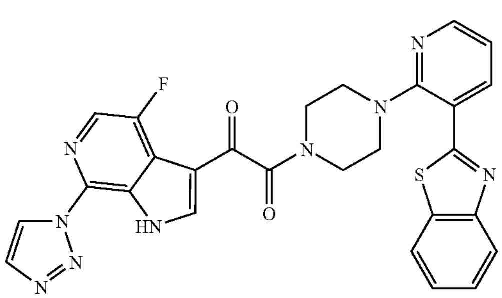 | B | 554.15 | 554.23<br>Rf = 1.89 min.<br>LCMS Method 2 |

TABLE D-1-continued

| Compd # | Structure | Method Used | MS (M + H)+ Calcd. | MS (M + H)+ Observ. And Retention Time and NMR |
|---|---|---|---|---|
| D-32 | 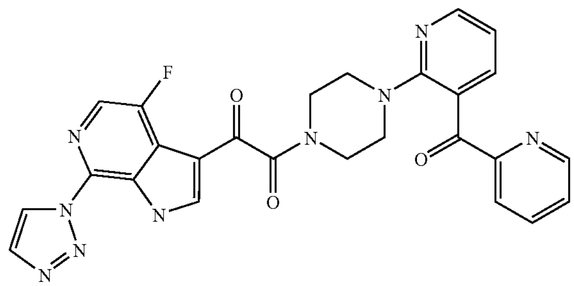 | B | 526.18 | 526.20<br>Rf = 1.60 min.<br>LCMS Method 2 |
| D-33 | 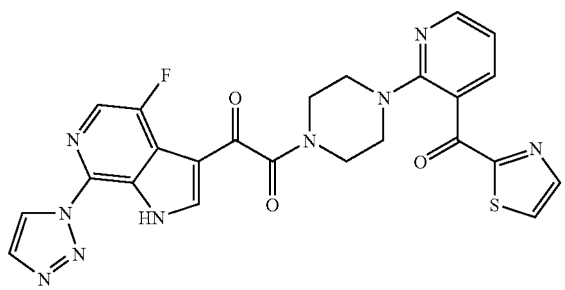 | B | 532.13 | 532.21<br>Rf = 1.64 min.<br>LCMS Method 2 |
| D-34 | 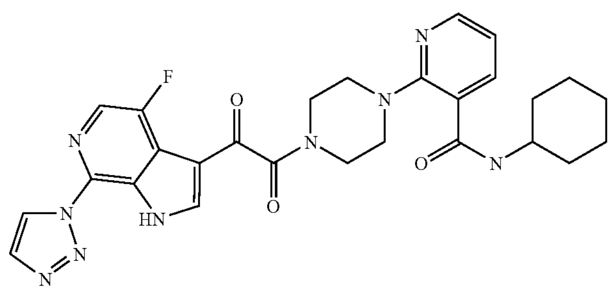 | B | 546.24 | 546.26<br>Rf = 1.70 min.<br>LCMS Method 2 |
| D-35 | 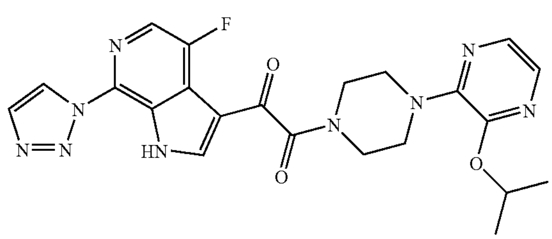 | B | 480.19 | 480.33<br>Rf = 1.82 min.<br>LCMS Method 2 |
| D-36 | Chiral | B | 542.21 | 542.27<br>Rf = 1.69 min.<br>LCMS Method 2 |

TABLE D-1-continued
| Compd # | Structure | Method Used | MS (M + H)+ Calcd. | MS (M + H)+ Observ. And Retention Time and NMR |
|---|---|---|---|---|
| D-37 | 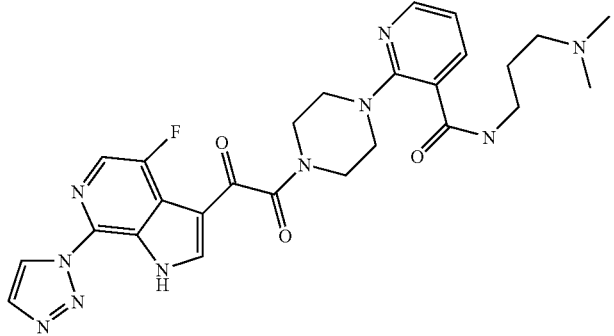 | B | 549.25 | 549.29<br>Rf = 1.36 min.<br>LCMS Method 2 |
| D-38 | 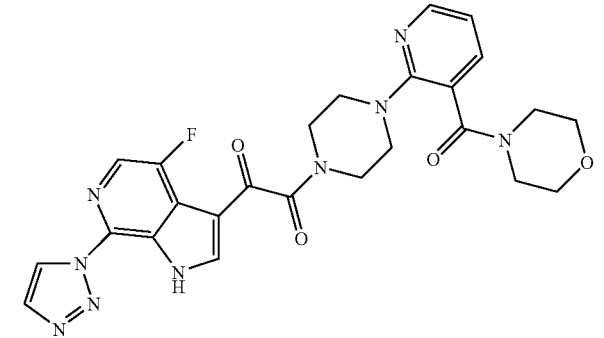 | B | 534.20 | 534.33<br>Rf = 1.49 min.<br>LCMS Method 2 |
| D-39 | 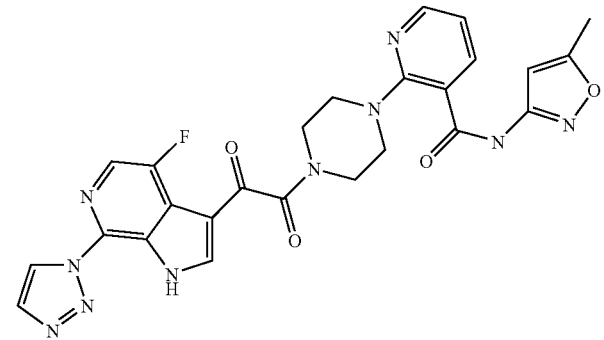 | B | 545.18 | 545.26<br>Rf = 1.66 min.<br>LCMS Method 2 |
| D-40 | 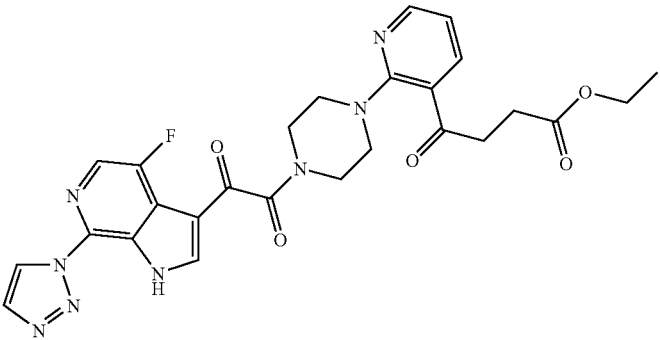 | B | 549.20 | 549.33<br>Rf = 1.71 min.<br>LCMS Method 2 |

TABLE D-1-continued

| Compd # | Structure | Method Used | MS (M + H)+ Calcd. | MS (M + H)+ Observ. And Retention Time and NMR |
|---|---|---|---|---|
| D-41 | 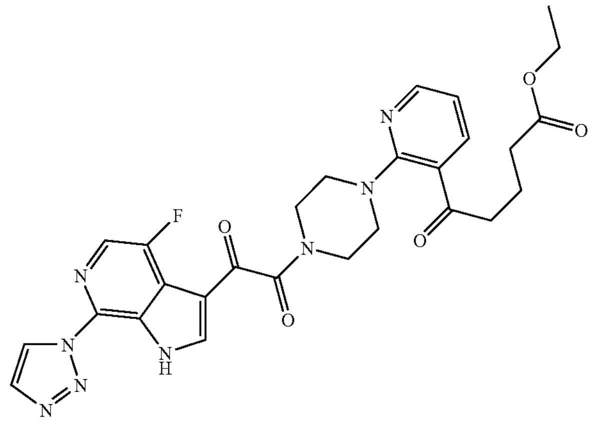 | B | 563.22 | 563.28<br>Rf = 1.75 min.<br>LCMS Method 2 |
| D-42 | 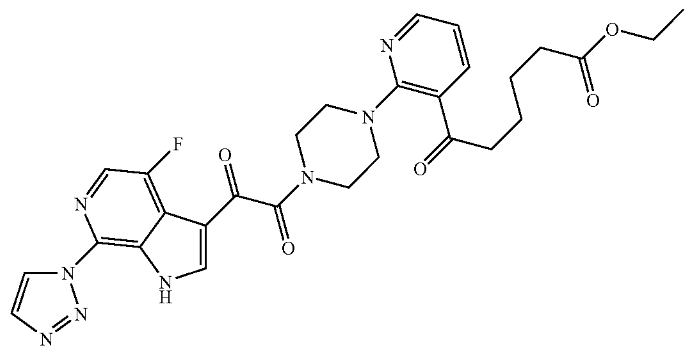 | B | 577.23 | 577.31<br>Rf = 1.79 min.<br>LCMS Method 2 |
| D-43 | 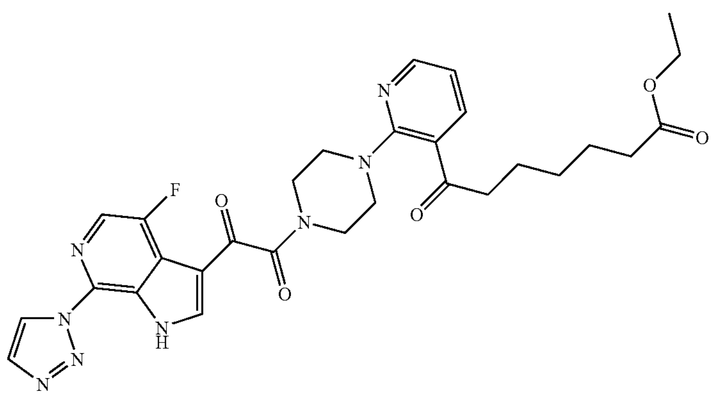 | B | 591.25 | 591.32<br>Rf = 1.86 min.<br>LCMS Method 2 |
| D-44 | 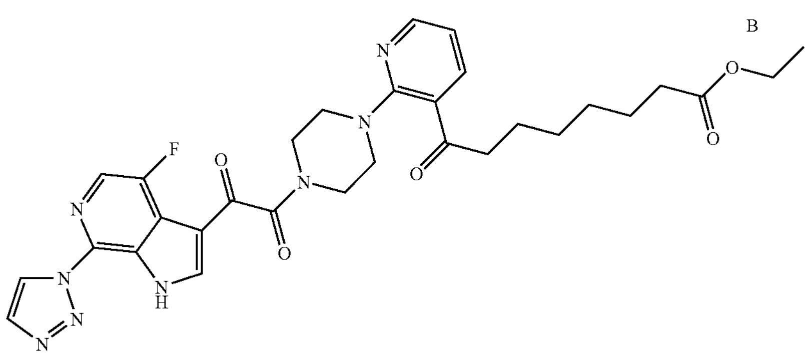 | B | 605.27 | 605.40<br>Rf = 1.90 min.<br>LCMS Method 2 |

TABLE D-1-continued

| Compd # | Structure | Method Used | MS (M + H)+ Calcd. | MS (M + H)+ Observ. And Retention Time and NMR |
| --- | --- | --- | --- | --- |
| D-45 | 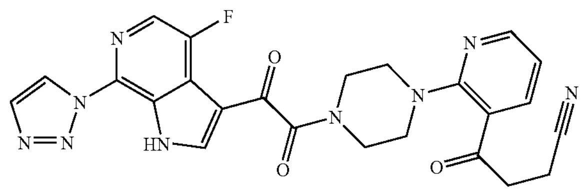 | B | 502.18 | 502.24<br>Rf = 1.60 min.<br>LCMS Method 2 |
| D-46 | 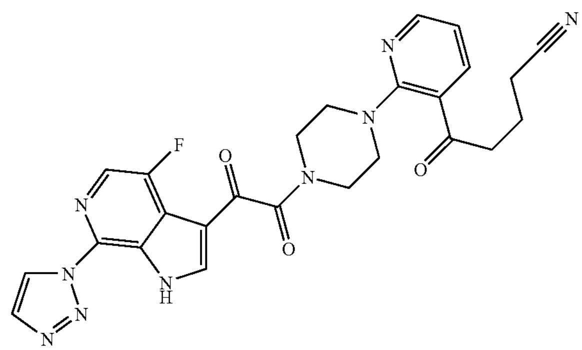 | B | 516.19 | 516.27<br>Rf = 1.64 min.<br>LCMS Method 2 |
| D-47 | 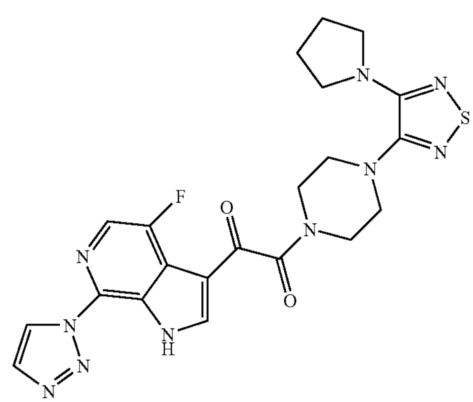 | B | 497.17 | 497.24<br>Rf = 1.89 min.<br>LCMS Method 2 |
| D-48 | 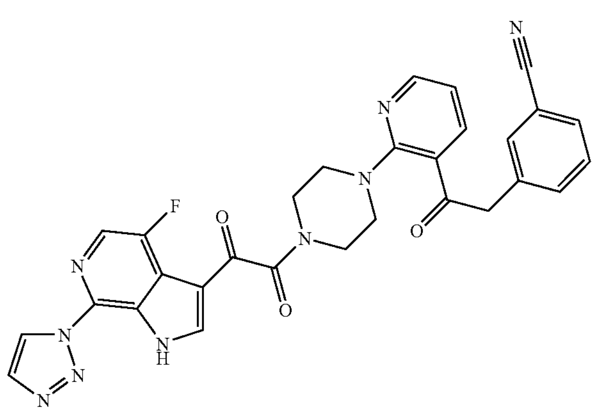 | B | 564.19 | 564.34<br>Rf = 1.76 min.<br>LCMS Method 2 |

TABLE D-1-continued

| Compd # | Structure | Method Used | MS (M + H)+ Calcd. | MS (M + H)+ Observ. And Retention Time and NMR |
|---|---|---|---|---|
| D-49 | 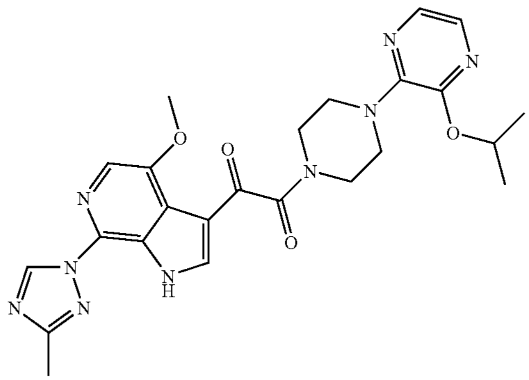 | B | 506.23 | 506.18<br>Rf = 4.04 min.<br>LCMS Method 2 |
| D-50 | Chiral | B | 568.24 | 568.23<br>Rf = 4.00 min.<br>LCMS Method 3 |
| D-51 | 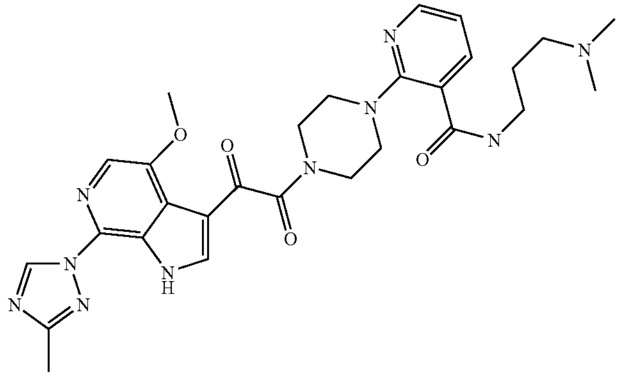 | B | 575.29 | 575.25<br>Rf = 4.06 min.<br>LCMS Method 3 |

TABLE D-1-continued

| Compd # | Structure | Method Used | MS (M + H)+ Calcd. | MS (M + H)+ Observ. And Retention Time and NMR |
|---|---|---|---|---|
| D-52 | 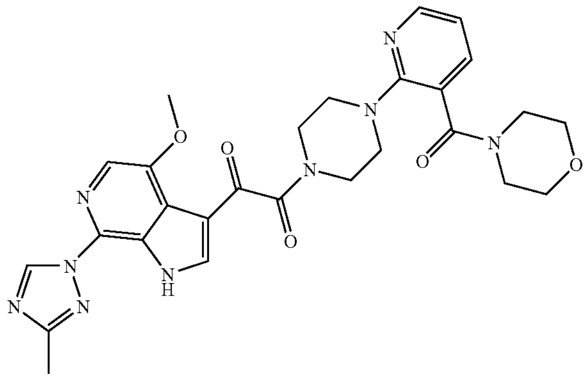 | B | 560.24 | 560.20<br>Rf = 3.06 min.<br>LCMS Method 3 |
| D-53 | 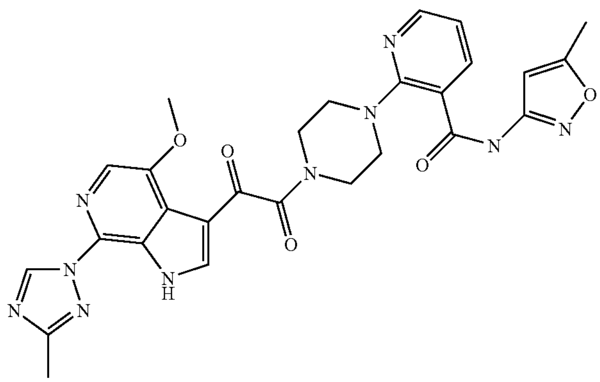 | B | 571.22 | 571.18<br>Rf = 3.79 min.<br>LCMS Method 3 |

Example Chemistry Section E

Preparation of 1-(4-fluoro-7-(1H-1,2,3-triazol-1-yl)-1H-pyrrolo[2,3-c]pyridinyl-3-yl)-2-(4-(1-(pyridin-2-yl)-1H-tetrazol-5-yl)piperazin-1-yl)ethane-1,2-dione

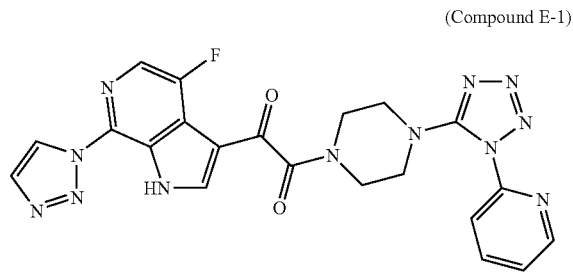

(Compound E-1)

Part A: To a solution of 2-aminopyridine (9.41 g, 100 mmol) in methylene chloride (200 mL) at 25° C. was added thiocarbonyl diimidazole (18.75 g, 100 mmol), and the resulting mixture was stirred at 25° C. for 20 h. To the reaction mixture then was added tert-butyl piperazine-1-carboxylate (18.60 g, 100 mmol), and the resulting mixture was stirred at 25° C. for another 24 h. The mixture was diluted with diethyl ether, washed with water (×3) and brine, dried over anhyd. sodium sulfate, filtered, and concentrated. Column chromatography on silica gel (elution: 0-20% diethyl ether/methylene chloride) to afford tert-butyl 4-(pyridin-2-ylcarbamothioyl)piperazine-1-carboxylate (13.60 g) as a colorless solid, following crystallization from a mixture of 1-chlorobutane/hexane; $^1$H NMR (300 MHz, CDCl$_3$) δ 7.97 (m, 1H), 7.64 (m, 2H), 6.88 (m, 1H), 4.00 (m, 4H), 3.51 (m, 4H), 1.44 (s, 9H).

When commercially available the isothiocyanates were allowed to react directly with tert-butyl piperazine-1-carboxylate in methylene chloride at 25° C. The desired thiourea then was isolated as described above.

Part B: A mixture of tert-butyl 4-(pyridin-2-ylcarbamothioyl)piperazine-1-carboxylate (15.30 g, 47.5 mmol), potassium carbonate (13.10 g, 95.0 mmol), iodomethane (3.00 mL, 47.5 mmol), and DMSO (200 mL) was stirred at 25° C. for 24 h. The reaction mixture was diluted with ethyl acetate, washed with water (×4) and brine, dried over anhyd. sodium sulfate, filtered, and concentrated to provide tert-butyl 4-(methylthio(pyridin-2-ylimino)methyl)piperazine-1-carboxylate (12.00 g) as a waxy solid; $^1$H NMR (300 MHz, CDCl$_3$) δ 8.25 (m, 1H), 7.63 (m, 1H), 6.88 (m, 2H), 3.70 (m, 4H), 3.52 (m, 4H), 2.04 (s, 3H), 1.44 (s, 9H).

Part C: To a solution of tert-butyl 4-(methylthio(pyridin-2-ylimino)methyl)piperazine-1-carboxylate (12.00 g, 36.0 mmol) in DMF (200 mL) at 25° C. was added sodium azide (11.60 g, 178 mmol), followed by mercury(II)chloride (10.90 g, 40.0 mmol), and the resulting mixture was stirred at 25° C. for 19 d. The mixture then was filtered, and the solids were washed with DMF. The combined filtrate was concentrated under vacuum, and the residue was diluted with ethyl acetate.

The resulting mixture was filtered again. The filtrate was washed with water (×3) and brine, dried over anhyd. sodium sulfate, filtered, and concentrated. Column chromatography on silica gel (elution: 0-20% diethyl ether/methylene chloride) to afford tert-butyl 4-(1-(pyridin-2-yl)-1H-tetrazol-5-yl)piperazine-1-carboxylate (10.10 g) as an off-white solid, following crystallization from a mixture of 1-chlorobutane/hexane; Mass Spec.: m/e: 332.11 (M+H)$^+$ [calc'd: 332.17]; $^1$HNMR (300 MHz, CDCl$_3$) δ 8.57 (m, 1H), 7.94 (m, 1H), 7.79 (d, 1H, J=8 Hz), 7.40 (m, 1H), 3.52 (m, 4H), 3.34 (m, 4H), 1.43 (s, 9H).

Part C': When the procedures described above were employed utilizing 2-amino-6-fluoropyridine as the commercial starting material the isolated crude product of part C was 3.90 g of a mixture of tert-butyl 4-(1-(6-fluoropyridin-2-yl)-1H-tetrazol-5-yl)piperazine-1-carboxylate and tert-butyl 4-(1-(6-azidopyridin-2-yl)-1H-tetrazol-5-yl)piperazine-1-carboxylate. This crude product was dissolved in a mixture of 120 mL of methanol and 20 mL of water. To this solution at 25° C. was added in portions 1.60 g of sodium borohydride, and the mixture was stirred at 25° C. for 4 h. The reaction mixture then was concentrated under vacuum, and the residue was diluted with water and ethyl acetate. The phases were separated, and the organic phase was washed with water (×2) and brine, dried over anhydrous sodium sulfate, filtered, and concentrated. Column chromatography on silica gel (elution: 0-100% diethyl ether/methylene chloride) afforded tert-butyl 4-(1-(6-fluoropyridin-2-yl)-1H-tetrazol-5-yl)piperazine-1-carboxylate (3.26 g) [Mass Spec.: m/e: 350.32 (M+H)$^+$ [calc'd: 350.17]; $^1$H NMR (300 MHz, CDCl$_3$) δ 8.05 (m, 1H), 7.78 (m, 1H), 7.05 (m, 1H), 3.60 (m, 4H), 3.40 (m, 4H), 1.46 (s, 9H)] and tert-butyl 4-(1-(6-aminopyridin-2-yl)-1H-tetrazol-5-yl)piperazine-1-carboxylate (0.28 g) [Mass Spec.: m/e: 347.37 (M+H)$^+$ [calc'd: 347.19]; $^1$H NMR (300 MHz, DMSO-D$_6$) δ 7.64 (t, 1H, J=8 Hz), 6.79 (d, 1H, J=8 Hz), 6.60 (d, 1H, J=8 Hz), 6.55 (br s, 2H), 3.40 (m, 4H), 3.24 (m, 4H), 1.41 (s, 9H)].

Part C'': To a solution of tert-butyl 4-(1-(6-fluoropyridin-2-yl)-1H-tetrazol-5-yl)piperazine-1-carboxylate (0.349 g, 1.00 mmol) in 20 mL of tetrahydrofuran at 25° C. was added a solution of lithium hydroxide monohydrate (0.084 g, 2.00 mmol) in 5 mL of water, and the resulting mixture was stirred at 25° C. for 11 days. The reaction mixture was diluted with water, the pH of the solution was adjusted to ~pH 6 employing aqueous sodium bisulfate solution, and the mixture was extracted with ethyl acetate. The combined extracts were washed with brine, dried over anhydrous sodium sulfate, filtered, and concentrated. Column chromatography on silica gel (elution: 0-50% diethyl ether/methylene chloride) to afford tert-butyl 4-(1-(6-hydroxypyridin-2-yl)-1H-tetrazol-5-yl)piperazine-1-carboxylate (0.090 g); Mass Spec.: m/e: 348.24 (M+H)$^+$ [calc'd: 348.18]; $^1$H NMR (300 MHz, CDCl$_3$) δ 7.84 (m, 1H), 7.21 (m, 1H), 6.89 (m, 1H), 3.52 (m, 4H), 3.32 (m, 4H), 1.45 (s, 9H).

The following tetrazole intermediates were prepared from the indicated commercial starting materials employing the procedures described above.

| Structure | Commercial Starting material | MS (M + H)$^+$ Observ. (Calc'd) and NMR |
|---|---|---|
| BocN-piperazine-tetrazole-pyridin-3-yl | NCS (3-pyridyl) | 332.17 (calc'd: 332.17) $^1$H NMR (300 MHz, CDCl$_3$) δ 8.92 (d, 1 H, J = 2.2 Hz), 8.75 (d, 1 H, J = 4.7 Hz), 7.96 (m, 1 H), 7.52 (d of d, 1 H, J = 8.0, 4.7 Hz), 3.49 (m, 4 H), 3.20 (m, 4 H), 1.42 (s, 9 H). |
| BocN-piperazine-tetrazole-thiazol-2-yl | NH2-thiazole | 338.05 (calc'd: 338.13) $^1$H NMR (300 MHz, CDCl$_3$) δ 7.71 (d, 1 H, J = 3.5 Hz), 7.38 (d, 1 H, J = 3.5 Hz), 3.57 (m, 4 H), 3.48 (m, 4 H), 1.44 (s, 9 H). |
| BocN-piperazine-tetrazole-oxazol-2-yl | NH2-oxazole | 322.17 (calc'd: 322.15) $^1$H NMR (300 MHz, CDCl$_3$) δ 7.77 (m, 1 H), 7.38 (m, 1 H), 3.52 (m, 4 H), 3.40 (m, 4 H), 1.43 (s, 9 H). |

-continued

| Structure | Commercial Starting material | MS (M + H)+ Observ. (Calc'd) and NMR |
|---|---|---|
| 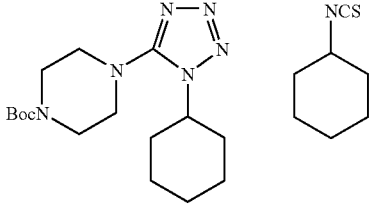 | 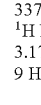 NCS | 337.23 (calc'd: 337.22)<br>¹H NMR (300 MHz, CDCl₃) δ3.99 (m, 1 H), 3.59 (m, 4 H), 3.17 (m, 4 H), 2.01-1.93 (m, 6 H), 1.75 (m, 1 H), 1.46 (s, 9 H), 1.42-1.31 (m, 3 H). |
| 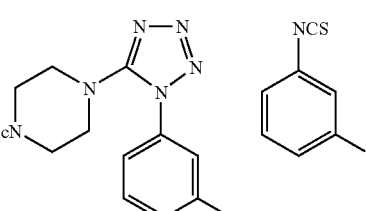 | 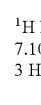 NCS | ¹H NMR (300 MHz, CDCl₃) δ7.41 (t, 1 H, J = 8.0 Hz), 7.16-7.10 (m, 2 H), 7.00 (d of d, 1 H, J = 8.0, 2.2 Hz), 3.83 (s, 3 H), 3.46 (m, 4 H), 3.19 (m, 4 H), 1.42 (s, 9 H). |
| 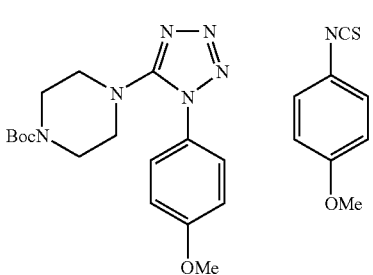 | 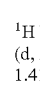 NCS | ¹H NMR (300 MHz, CDCl₃) δ7.45 (d, 2 H, J = 9.2 Hz), 7.01 (d, 2 H, J = 9.2 Hz), 3.85 (s, 3 H), 3.43 (m, 4 H), 3.17 (m, 4 H), 1.41 (s, 9 H). |
| 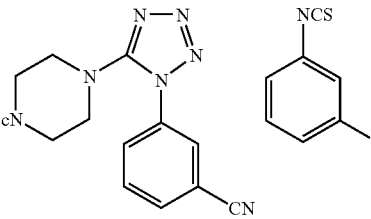 | 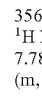 NCS | 356.17 (calc'd: 356.17)<br>¹H NMR (300 MHz, CDCl₃) δ7.97 (m, 1 H), 7.92 (m, 1 H), 7.78 (m, 1 H), 7.69 (t, 1 H, J = 7.8 Hz), 3.50 (m, 4 H), 3.20 (m, 4 H), 1.43 (s, 9 H). |
| 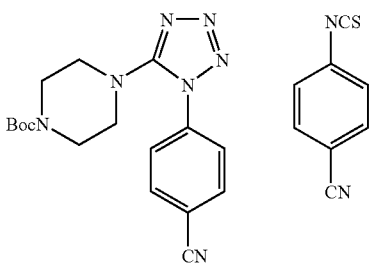 | 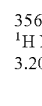 NCS | 356.19 (calc'd: 356.17)<br>¹H NMR (300 MHz, CDCl₃) δ7.83 (m, 4 H), 3.50 (m, 4 H), 3.20 (m, 4 H), 1.42 (s, 9 H). |
| 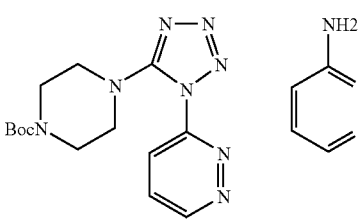 | 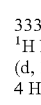 NH2 | 333.18 (calc'd: 333.18)<br>¹H NMR (300 MHz, CDCl₃) δ9.28 (d, 1 H, J = 5 Hz), 8.11 (d, 1 H, J = 9 Hz), 7.76 (d of d, 1 H, J = 9, 5 Hz), 3.61 (m, 4 H), 3.47 (m, 4 H), 1.46 (s, 9 H). |

Part D: To a solution of tert-butyl 4-(1-(pyridin-2-yl)-1H-tetrazol-5-yl)piperazine-1-carboxylate (0.166 g, 0.50 mmol) in 1,4-dioxane (10 mL) at 25° C. was added 4.00 N HCl in 1,4-dioxane (10 mL), and the mixture was stirred at 25° C. for 16 h. The mixture then was concentrated under vacuum. The resulting solids were dissolved in DMF (10 mL). To this solution was added sequentially 2-(4-fluoro-7-(1H-1,2,3-triazol-1-yl)-1H-pyrrolo[2,3-c]pyridin-3-yl)-2-oxoacetic acid (0.137 g, 0.50 mmol), N-methylmorpholine (0.165 mL, 1.50 mmol), and TBTU (0.176 g, 0.55 mmol), and the mixture was stirred at 25° C. for 24 h. The reaction mixture was filtered, and the filtrate was concentrated under vacuum. The residue was dissolved in hot methanol, and the solution then was allowed to cool slowly to room temperature. The precipitate was recovered by filtration, washed with methanol, and dried under vacuum to provide 1-(4-fluoro-7-(1H-1,2,3-triazol-1-yl)-1H-pyrrolo[2,3-c]pyridinyl-3-yl)-2-(4-(1-(pyridin-2-yl)-1H-tetrazol-5-yl)piperazin-1-yl)ethane-1,2-dione (0.076 g) as an off-white solid; HRMS: 489.1662 (M+H)+ [calc'd: 489.1660]; $^1$H NMR (500 MHz, DMSO-D$_6$) δ 13.08 (br s, 1H), 9.02 (s, 1H), 8.67 (m, 1H), 8.39 (s, 1H), 8.16 (t, 1H, J=7.8 Hz), 8.13 (s, 1H), 7.85 (d, 1H, J=7.8 Hz), 7.64 (m, 1H), 3.74 (m 2H), 3.50 (m, 2H), 3.44 (m, 2H), 3.26 (m, 2H).

The following compounds were prepared employing the procedures described above.

| Compd # | Structure | MS (M + H)+ Observ. (Calc'd) and NMR |
|---|---|---|
| E-2 | 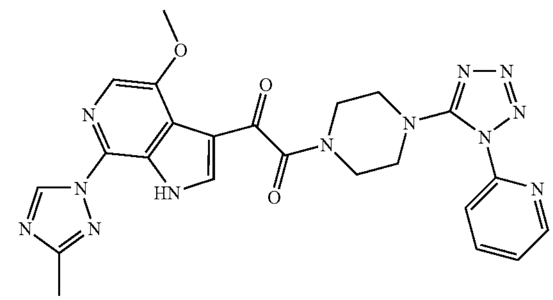 | HRMS: 515.2036 (calc'd. 515.2016) $^1$H NMR (500 MHz, DMSO-D$_6$) δ12.41 (br s, 1 H), 9.24 (s, 1 H), 8.68 (m, 1 H), 8.25 (s, 1 H), 8.16 (d of d, 1 H, J = 7.8, 1.8 Hz), 7.89 (s, 1 H), 7.86 (d, 1 H, J = 7.8 Hz), 7.65 (d of d, 1 H, J = 7.8, 5.0 Hz), 3.99 (s, 3 H), 3.72 (m, 2 H), 3.46 (m, 2 H), 3.43 (m, 2 H), 3.27 (m, 2 H), 2.49 (s, 3 H). |
| E-3 | 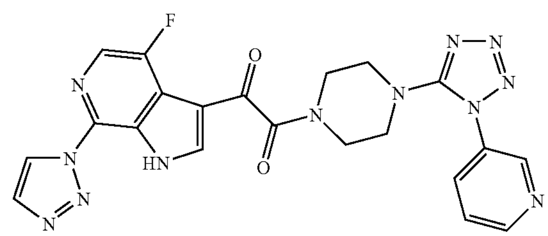 | HRMS: 489.1662 (calc'd. 489.1660) $^1$H NMR (500 MHz, DMSO-D$_6$) δ13.07 (br s, 1 H), 9.01 (s, 1 H), 8.92 (d, 1 H, J = 2.4 Hz), 8.78 (d of d, 1 H, J = 4.8, 1.8 Hz), 8.37 (s, 1 H), 8.31 (d, 1 H, J = 1.8 Hz), 8.19 (m, 1 H), 8.12 (d, 1 H, J = 1.8 Hz), 7.69 (d of d, 1 H, J = 8.0, 4.8 Hz), 3.72 (m, 2 H), 3.48 (m, 2 H), 3.35 (m, 2 H), 3.18 (m, 2 H). |
| E-4 | 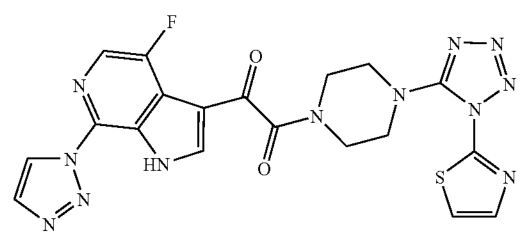 | HRMS: 495.1214 (calc'd. 495.1224) $^1$H NMR (500 MHz, DMSO-D$_6$) δ13.06 (br s, 1 H), 9.02 (s, 1 H), 8.40 (s, 1 H), 8.31 (s, 1 H), 8.12 (s, 1 H), 7.97 (d, 1 H, J = 3.4 Hz), 7.90 (d, 1 H, J = 3.4 Hz), 3.79 (m, 2 H), 3.59 (m, 2 H), 3.56 (m, 2 H), 3.42 (m, 2 H). |
| E-5 | 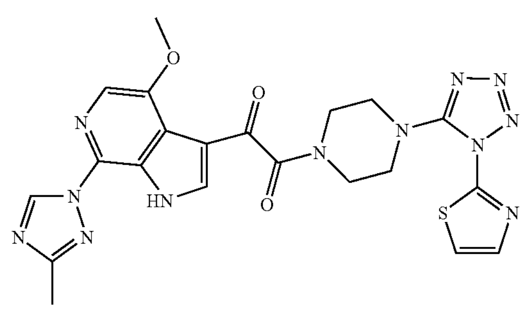 | HRMS: 521.1579 (calc'd. 521.1580) $^1$H NMR (500 MHz, DMSO-D$_6$) δ12.39 (br s, 1 H), 9.24 (s, 1 H), 8.27 (s, 1 H), 7.97 (d, 1 H, J = 3.4 Hz), 7.90 (m, 2 H), 4.00 (s, 3 H), 3.77 (m, 2 H), 3.58 (m, 2 H), 3.52 (m, 2 H), 3.43 (m, 2 H), 2.50 (s, 3 H). |

|Compd #|Structure|MS (M + H)+ Observ. (Calc'd) and NMR|
|---|---|---|
|E-6| 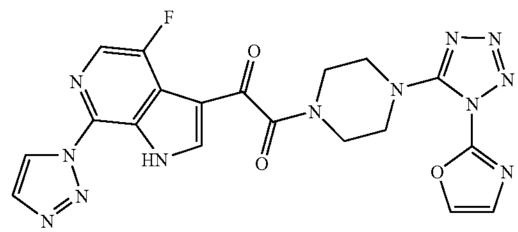 |HRMS: 479.1431 (calc'd. 479.1453) ¹H NMR (500 MHz, DMSO-D₆) δ13.08 (br s, 1 H), 9.02 (s, 1 H), 8.44 (s, 1 H), 8.41 (s, 1 H), 8.33 (s, 1 H), 8.13 (s, 1 H), 7.60 (s, 1 H), 3.78 (m, 2 H), 3.55 (m, 4 H), 3.36 (m, 2 H).|
|E-7| 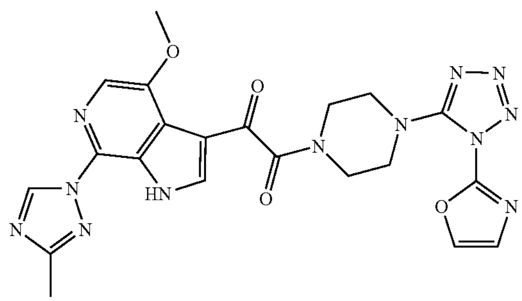 |HRMS: 505.1795 (calc'd. 505.1809) ¹H NMR (500 MHz, DMSO-D₆) δ12.41 (br s, 1 H), 9.24 (s, 1 H), 8.45 (s, 1 H), 8.27 (s, 1 H), 7.89 (s, 1 H), 7.61 (s, 1 H), 3.99 (s, 3 H), 3.76 (m, 2 H), 3.52 (m, 4 H), 3.37 (m, 2 H), 2.50 (s, 3 H).|
|E-8| 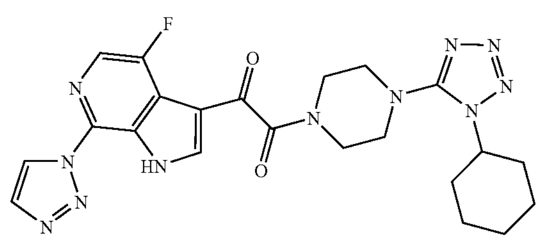 |HRMS: 494.2160 (calc'd. 494.2177) ¹H NMR (500 MHz, DMSO-D₆) δ13.10 (br s, 1 H), 9.02 (s, 1 H), 8.41 (s, 1 H), 8.33 (d, 1 H), J = 2.2 Hz), 8.12 (s, 1 H), 4.22 (m, 1 H), 3.83 (m, 2 H), 3.59 (m, 2 H), 3.35 (m, 2 H), 3.20 (m, 2 H), 2.00 (m, 2 H), 1.79 (m, 4 H), 1.67 (m, 1 H), 1.45 (m, 2 H), 1.26 (m, 1 H),|
|E-9| 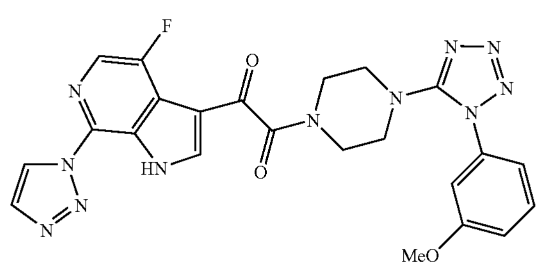 |HRMS: 518.1797 (calc'd. 518.1813) ¹H NMR (500 MHz, DMSO-D₆) δ13.06 (br s, 1 H), 9.01 (s, 1 H), 8.36 (s, 1 H), 8.31 (d, 1 H), J = 2.2 Hz), 8.12 (s, 1 H), 7.52 (t, 1 H), J = 8.0 Hz), 7.24 (m, 2 H), 7.15 (m, 1 H), 3.82 (s, 3 H), 3.71 (m, 2 H), 3.48 (m, 2 H), 3.35 (m, 2 H), 3.18 (m, 2H).|
|E-10| 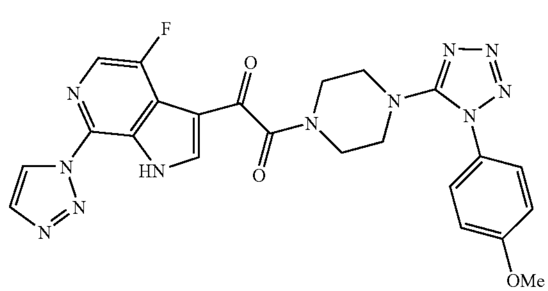 |HRMS: 518.1808 (calc'd. 518.1813) ¹H NMR (500 MHZ, DMSO-D₆) δ13.06 (br s, 1 H), 9.01 (d, 1 H, J = 1.2 Hz), 8.35 (s, 1 H), 8.31 (d, 1 H), J = 2.2 Hz), 8.12 (d, 1 H, J = 1.2 Hz), 7.58 (d, 2 H), J = 8.8 Hz), 7.14 (d, 2 H, J = 8.8 Hz), 3.82 (s, 3 H), 3.70 (m, 2 H), 3.46 (m, 2 H), 3.34 (m, 2 H), 3.15 (m, 2 H).|

-continued

| Compd # | Structure | MS (M + H)+ Observ. (Calc'd) and NMR |
|---|---|---|
| E-11 | 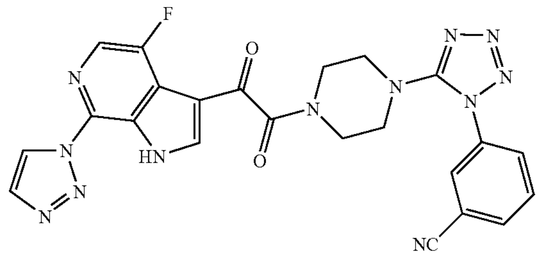 | HRMS: 511.1495 (M − H)− (calc'd. 511.1503) <br>1H NMR (500 MHz, DMSO-D6) δ13.07 (br s, 1 H), 9.01 (s, 1 H), 8.38 (s, 1 H), 8.31 (d, 1 H, J = 2.2 Hz), 8.25 (s, 1 H), 8.12 (s, 1 H), 8.06 (m, 2 H), 7.83 (t, 1 H, J = 8.0 Hz), 3.72 (m, 2 H), 3.48 (m, 2 H), 3.35 (m, 2 H), 3.17 (m, 2 H). |
| E-12 | 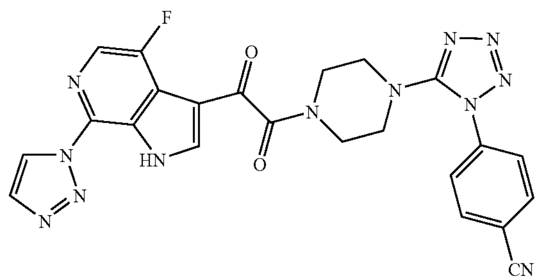 | HRMS: 511.14883 (M − H)− (calc'd. 511.1503) <br>1H NMR (500 MHz, DMSO-D6) δ13.07 (br s, 1 H), 9.01 (s, 1 H), 8.37 (s, 1 H), 8.31 (d, 1 H. J = 2.2 Hz), 8.12 (m, 3 H), 7.94 (d, 2 H, J = 8.9 Hz), 3.74 (m, 2 H), 3.50 (m, 2 H), 3.35 (m, 2 H), 3.16 (m, 2 H). |
| E-12a | 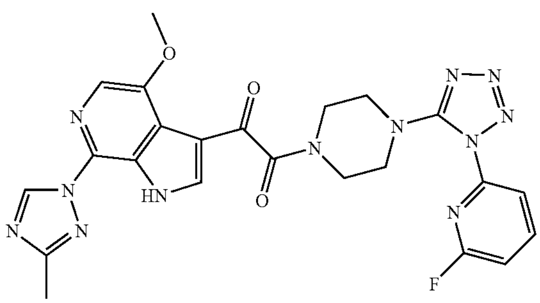 | HRMS: 533.1923 (calc'd. 533.1922) <br>1H NMR (500 MHz, DMSO-D6) δ12.40 (br s, 1 H), 9.24 (s 1 H), 8.34 (m, 1 H), 8.26 (s, 1 H), 7.89 (s, 1 H), 7.83 (d, 1 H, J = 8 Hz), 7.46 (d, 1 H, J = 8 Hz), 3.99 (s, 3 H), 3.74 (m, 2 H), 3.47 (m, 4 H), 3.29 (m, 2 H), 2.49 (s, 3 H). |
| E-12b | 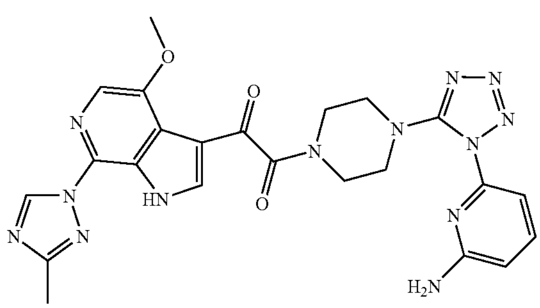 | HRMS: 530.2122 (calc'd. 530.2125) <br>1H NMR (500 MHz, DMSO-D6) δ12.39 (br s, 1 H), 9.24 (s, 1 H), 8.24 (s, 1 H), 7.89 (s, 1 H), 7.63 (t, 1 H, J = 8 Hz), 6.80 (d, 1 H, J = 8 Hz), 6.58 (d, 1 H, J = 8 Hz), 6.55 (br s, 2 H), 3.98 (s, 3 H), 3.73 (m, 2 H), 3.47 (m, 2 H), 3.43 (m, 2 H), 3.30 (m, 2 H), 2.49 (s, 3 H). |
| E-12c | 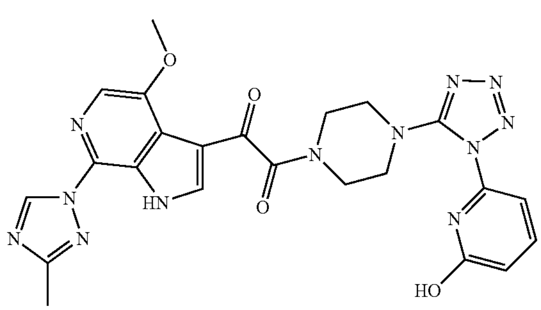 | HRMS: 531.1969 (calc'd. 531.1965) <br>1H NMR (500 MHz, DMSO-D6) δ12.40 (br s, 1 H), 11.58 (br s, 1 H), 9.24 (s, 1 H), 8.25 (s, 1 H), 7.94 (t, 1 H, J = 8 Hz), 7.90 (s, 1 H), 7.25 (d, 1 H, J = 8 Hz), 6.86 (d, 1 H, J = 8 Hz), 3.99 (s, 3 H), 3.73 (m, 2 H), 3.47 (m, 2 H), 3.43 (m, 2 H), 3.28 (m, 2 H), 2.50 (s, 3 H). |

| Compd # | Structure | MS (M + H)+ Observ. (Calc'd) and NMR |
|---|---|---|
| E-12d | 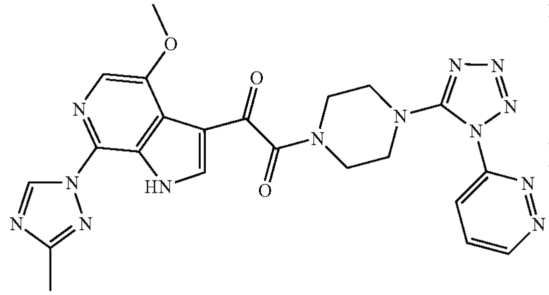 | HRMS: 516.1964 (calc'd. 516.1969) $^1$H NMR (500 MHz, DMSO-D$_6$) δ12.40 (br s, 1 H), 9.45 (d, 1 H, J = 4.9 Hz), 9.24 (s, 1 H), 8.26 (s, 1 H), 8.23 (d, 1 H, J = 8.5 Hz), 8.09 (d of d, 1 H, J = 8.5, 4.9 Hz), 7.90 (s, 1 H), 3.99 (s, 3 H), 3.74 (m, 2 H), 3.47 (m, 4 H), 3.30 (m, 2 H), 2.51 (s, 3 H). |

Preparation of 1-(4-fluoro-7-(1H-1,2,3-triazol-1-yl)-1H-pyrrolo[2,3-c]pyridin-3-yl)-2-(4-(1-phenyl-1H-tetrazol-5-yl)piperidin-1-yl)ethane-1,2-dione (Compound E-13)

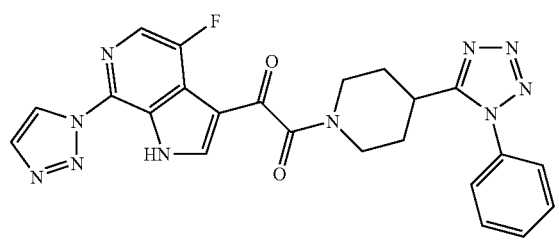

Part A: To a solution of N-Boc-isonipecotic acid (4.85 g, 21.2 mmol) in tetrahydrofuran (80 mL) at 25° C. was added carbonyl diimidazole (3.80 g, 23.3 mmol), and the reaction mixture was stirred for 1.00 h at 25° C. To the resulting mixture was added aniline (2.10 mL, 23.3 mmol) and 1,8-diazabicyclo[5.4.0]undec-7-ene(DBU) (3.20 mL, 21.2 mmol), and the solution was stirred at 25° C. for another 90 h. The reaction mixture was diluted with water, 1.00 N hydrochloric acid (80 mL), and ethyl acetate. The phases were separated, and the organic phase was washed with water (×2) and brine, dried over anhyd. sodium sulfate, filtered, and concentrated. Column chromatography on silica gel (elution: 0-20% diethyl ether/methylene chloride) furnished tert-butyl 4-(phenylcarbamoyl)-piperidine-1-carboxylate (4.25 g) as a white solid; $^1$H NMR (300 MHz, CDCl$_3$) δ 7.48 (d, 2H, J=8.0 Hz), 7.29 (t, 2H, J=8.0 Hz), 7.20 (br s, 1H), 7.08 (t, 1H, J=8.0 Hz), 4.16 (m, 2H), 2.75 (m, 2H), 2.35 (m, 1H), 1.89-1.61 (m, 4H), 1.43 (s, 9H).

Part B: To a solution of tert-butyl 4-(phenylcarbamoyl)piperidine-1-carboxylate (4.24 g, 13.9 mmol) and diisopropylazodicarboxylate (5.40 mL, 27.9 mmol) in tetrahydrofuran (100 mL) at 25° C. was added triphenylphosphine (7.31 g, 27.9 mmol). The resulting reaction mixture showed a slight exotherm, and the solution then was stirred at ambient temperature for ~0.25 h until the reaction mixture had returned to 25° C. To the resulting mixture was added azidotrimethylsilane (3.65 mL, 27.9 mmol). A precipitate formed within minutes, and the mixture then was stirred at 25° C. for 7 days. The reaction mixture was concentrated under vacuum to afford the crude product. Column chromatography on silica gel (elution: 10-50% ethyl acetate/hexane) afforded tert-butyl 4-(1-phenyl-1H-tetrazol-5-yl)piperidine-1-carboxylate (2.58 g) as a white solid, following crystallization from a mixture of 1-chlorobutane/hexane; $^1$H NMR (300 MHz, CDCl$_3$) δ 7.58 (m, 3H), 7.38 (m, 2H), 4.12 (m, 2H), 2.98 (m, 1H), 2.76 (m, 2H), 1.96-1.74 (m, 4H), 1.42 (s, 9H).

Part C: To a solution of tert-butyl 4-(1-phenyl-1H-tetrazol-5-yl)piperidine-1-carboxylate (0.165 g, 0.50 mmol) in 1,4-dioxane (10 mL) at 25° C. was added 4.00 N HCl in 1,4-dioxane (10 mL), and the mixture was stirred at 25° C. for 16 h. The mixture then was concentrated under vacuum. The resulting solids were dissolved in DMF (10 mL). To this solution was added sequentially 2-(4-fluoro-7-(1H-1,2,3-triazol-1-yl)-1H-pyrrolo[2,3-c]pyridin-3-yl)-2-oxoacetic acid (0.137 g, 0.50 mmol), N-methylmorpholine (0.165 mL, 1.50 mmol), and TBTU (0.176 g, 0.55 mmol), and the mixture was stirred at 25° C. for 24 h. The reaction mixture was filtered, and the filtrate was concentrated under vacuum. The residue was dissolved in hot methanol, and the solution then was allowed to cool slowly to room temperature. The precipitate was recovered by filtration, washed with methanol, and dried under vacuum to provide 1-(4-fluoro-7-(1H-1,2,3-triazol-1-yl)-1H-pyrrolo[2,3-c]pyridin-3-yl)-2-(4-(1-phenyl-1H-tetrazol-5-yl)piperidin-1-yl)ethane-1,2-dione (0.142 g) as an off-white solid; mp: 257-258° C.; HRMS: 487.1740 (M+H)+ [calc'd: 487.1755]; $^1$H NMR (500 MHz, DMSO-D$_6$) δ 13.06 (br s, 1H), 9.02 (s, 1H), 8.32 (d, 1H, J=1.8 Hz), 8.30 (s, 1H), 8.12 (s, 1H), 7.58 (s, 5H), 4.37 (m, 1H), 3.67 (m, 1H), 3.32 (m, 1H), 3.25 (m, 1H), 3.03 (m, 1H), 2.01 (m, 1H), 1.88 (m, 1H), 1.83-1.70 (m, 2H).

Preparation of 1-(4-fluoro-7-(1H-1,2,3-triazol-1-yl)-1H-pyrrolo[2,3-c]pyridinyl-3-yl)-2-(4-(1-(pyridin-2-yl)-1H-pyrazol-5-yl)piperazin-1-yl)ethane-1,2-dione (Compound E-14) and 1-(4-methoxy-7-(3-methyl-1H-1,2,4-triazol-1-yl)-1H-pyrrolo[2,3-c]pyridinyl-3-yl)-2-(4-(1-(pyridin-2-yl)-1H-pyrazol-5-yl)piperazin-1-yl)ethane-1,2-dione (Compound E-15)

Compound E-14

Compound E-15

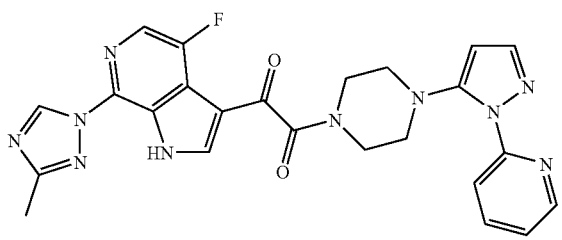

Part A: To a solution of ethyl 3,3-diethoxypropionate (90% tech.) (5.28 g, 25 mmol) in 50 mL of THF was added 1.00 N sodium hydroxide in water (25.00 mL, 25 mmol), and the resulting mixture was stirred at 25° C. for 18 h. The mixture then was concentrated under vacuum to afford a residual white solid. This solid was dissolved in 50 mL of DMF. To the solution was added EDCI (5.75 g, 30.0 mmol), 1-hydroxy-benzotriazole (4.56 g, 33.8 mmol), and benzyl piperazine-1-carboxylate (5.51 g, 25.0 mmol), and the resulting mixture was stirred at 25° C. for 24 h. The reaction mixture was concentrated under vacuum, and the residue was diluted with water. The aqueous mixture was extracted with ethyl acetate, and the combined extracts were washed aqueous sodium bicarbonate solution and brine, dried over anhydrous sodium sulfate, filtered, and concentrated. Column chromatography on silica gel (elution: 10-40% ethyl acetate/chloroform) furnished 8.00 g (88%) of benzyl 4-(3,3-diethoxypropanoyl)piperazine-1-carboxylate as an oil; $^1$H NMR (500 MHz, CDCl$_3$) δ 57.34 (m, 5H), 5.14 (s, 2H), 4.90 (t, 1H, J=5.5 Hz), 3.73-3.46 (m, 12H), 2.68 (d 2H, J=5.5 Hz), 1.19 (t, 6H, J=7.0 Hz).

Part B: To a solution of benzyl 4-(3,3-diethoxypropanoyl)piperazine-1-carboxylate (3.39 g, 9.30 mmol) in 30 mL of chloroform at 0° C. was added a solution of 10.0 mL of water and 10.0 mL of trifluoroacetic acid, and the resulting biphasic mixture was stirred at 25° C. for 20 h. The mixture then was diluted with additional chloroform, washed with water and brine, dried over anhydrous sodium sulfate, filtered, and concentrated. The residue then was dissolved in 50 mL of ethanol. To this solution was added 2-hydrazinopyridine (1.015 g, 9.30 mmol) and methanesulfonic acid (0.060 mL, 0.930 mmol), and the resulting mixture was stirred at 25° C. for 18 h. Pyridine (1.00 mL) was added, and then the reaction mixture was concentrated under vacuum. The residue was dissolved in 50 mL of pyridine. To this solution was added phosphorous oxychloride (1.73 mL, 18.6 mmol), and the mixture was stirred at 25° C. for 20 h. The mixture was concentrated under vacuum. The residue was diluted with water and ethyl acetate, and the phases were separated. The organic phase was washed with water and brine, dried over anhydrous sodium sulfate, filtered, and concentrated. Column chromatography on silica gel (elution: 10-50% ethyl acetate/methylene chloride) afforded 0.38 g (11.2%) of benzyl 4-(1-(pyridin-2-yl)-1H-pyrazol-5-yl)piperazine-1-carboxylate as an oil; Mass Spec.: m/e: 364.20 (M+H)$^+$ [calc'd: 364.18]; $^1$H NMR (500 MHz, DMSO-D$_6$) δ 8.53 (d, 1H, J=5.0 Hz), 7.97 (t, 1H, J=8.0 Hz), 7.73 (d, 1H, J=8.0 Hz), 7.58 (s, 1H), 7.40-7.30 (m, 6H), 6.04 (s, 1H), 5.10 (s, 2H), 3.49 (m, 4H), 2.94 (m, 4H).

Part C: A mixture of benzyl 4-(1-(pyridin-2-yl)-1H-pyrazol-5-yl)piperazine-1-carboxylate (0.34 g, 0.936 mmol) and 10% palladium/carbon (0.34 g) in 20.0 mL of methanol was stirred at 25° C. under hydrogen gas (1.00 atm) for 5 h. The resulting mixture was filtered, and the solids were washed with additional methanol. The combined filtrate was concentrated under vacuum. The residue was dissolved in 20 mL of 1,4-dioxane. To this solution was added hydrogen chloride (4.00 N in 1,4-dioxane) (0.468 mL, 1.871 mmol), and the resulting suspension was concentrated under vacuum to afford a white powder. This hydrochloride salt of the piperazine then was employed in procedures analogous to Part C in the preparation of compound E-13 to provide 1-(4-fluoro-7-(1H-1,2,3-triazol-1-yl)-1H-pyrrolo[2,3-c]pyridinyl-3-yl)-2-(4-(1-(pyridin-2-yl)-1H-pyrazol-5-yl)piperazin-1-yl)ethane-1,2-dione (Compound E-14) and 1-(4-methoxy-7-(3-methyl-1H-1,2,4-triazol-1-yl)-1H-pyrrolo[2,3-c]pyridinyl-3-yl)-2-(4-(1-(pyridin-2-yl)-1H-pyrazol-5-yl)piperazin-1-yl)ethane-1,2-dione (Compound E-15).

Compound E-14: HRMS: m/e: 487.1749 (M+H)$^+$ [calc'd: 487.1755]; $^1$H NMR (500 MHz, DMSO-D$_6$) δ 13.02 (br s, 1H), 9.02 (s, 1H), 8.54 (m, 1H), 8.37 (s, 1H), 8.33 (s, 1H), 8.13 (s, 1H), 7.97 (m, 1H), 7.74 (m, 1H), 7.59 (s, 1H), 7.38 (m, 1H), 6.08 (s, 1H), 3.74 (m, 2H), 3.50 (m, 2H), 3.11 (m, 2H), 2.99 (m, 2H).

Compound E-15: HRMS: m/e: 513.2102 (M+H)$^+$ [calc'd: 513.2111]; $^1$HNMR (500 MHz, DMSO-D$_6$) δ 12.40 (br s, 1H), 9.25 (s, 1H), 8.54 (m, 1H), 8.24 (s, 1H), 7.98 (t, 1H, J=7.8 Hz), 7.90 (s, 1H), 7.75 (d, 1H, J=7.8 Hz), 7.60 (s, 1H), 7.39 (m, 1H), 6.10 (s, 1H), 4.01 (s, 3H), 3.71 (m, 2H), 3.45 (m, 2H), 3.10 (m, 2H), 2.99 (m, 2H), 2.50 (s, 3H).

Preparation of 1-(4-fluoro-7-(1H-1,2,3-triazol-1-yl)-1H-pyrrolo[2,3-c]pyridinyl-3-yl)-2-(4-(3-(pyridin-2-yl)-1H-pyrazol-4-yl)piperazin-1-yl)ethane-1,2-dione (Compound E-16) and 1-(4-methoxy-7-(3-methyl-1H-1,2,4-triazol-1-yl)-1H-pyrrolo[2,3-c]pyridinyl-3-yl)-2-(4-(3-(pyridin-2-yl)-1H-pyrazol-4-yl)piperazin-1-yl)ethane-1,2-dione (Compound E-17)

Compound E-16

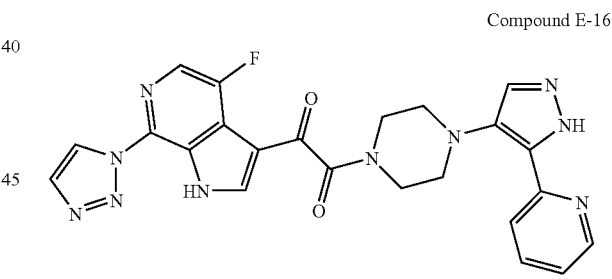

Compound E-17

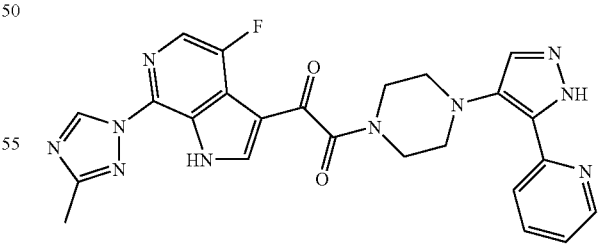

Part A: To a mixture of tert-butyl piperazine-1-carboxylate (1.863 g, 10.00 mmol) and cesium carbonate (6.52 g, 20.00 mmol) in 50 mL of DMF at 25° C. was added 2-(bromoacetyl)pyridine hydrobromide (2.81 g, 10.00 mmol) in portions over five minutes. The reaction mixture then was stirred at 25° C. for 3 h. The resulting mixture was diluted with water and ethyl acetate. The phases were separated, and the organic phase was washed with water (×3) and brine, dried over anhydrous sodium sulfate, filtered, and concentrated. Column chromatography on silica gel (elution: 10-50% ethyl acetate/chloroform) provided 1.61 g (53%) of tert-butyl 4-(2-oxo-2-(pyridin-2-yl)ethyl)piperazine-1-carboxylate as a crystalline solid; $^1$H NMR (500 MHz, CDCl$_3$) δ 8.63 (d, 1H, J=4.5 Hz), 8.05 (m, 1H), 7.85 (t, 1H, J=9 Hz), 7.49 (m, 1H), 4.30 (s, 2H), 3.62 (m, 4H), 2.75 (m, 4H), 1.46 (s, 9H).

Part B: A solution of tert-butyl 4-(2-oxo-2-(pyridin-2-yl)ethyl)piperazine-1-carboxylate (1.46 g, 4.78 mmol) and N,N-dimethylformamide dimethyl acetal (10.00 mL, 75 mmol) was heated at reflux for 5 h. After cooling to room temperature the mixture was concentrated under vacuum. The residue was dissolved in 20 mL of ethanol. To this solution was added anhydrous hydrazine (1.50 mL, 47.8 mmol), and the mixture was heated at reflux for 2 h. After cooling to room temperature the reaction mixture was concentrated under vacuum, and the residue was dissolved in ethyl acetate. The solution then was washed with aqueous sodium bicarbonate solution and brine, dried over anhydrous sodium sulfate, filtered, and concentrated. Column chromatography on silica gel (elution: 1-5% isopropanol/chloroform w/0.5% conc. ammonia) provided 0.600 g (38%) of tert-butyl 4-(3-(pyridin-2-yl)-1H-pyrazol-4-yl)piperazine-1-carboxylate as an oil; Mass Spec.: m/e: 330.30 (M+H)$^+$ [calc'd: 330.19]; $^1$H NMR (300 MHz, DMSO-D$_6$) δ 13.19 (br s, 1H), 8.60 (m, 1H), 8.09 (m, 1H), 7.90 (m, 1H), 7.53 (m, 1H), 7.31 (m, 1H), 3.50 (m, 4H), 2.82 (m, 4H), 1.43 (s, 9H).

Part C: The tert-butyl 4-(3-(pyridin-2-yl)-1H-pyrazol-4-yl)piperazine-1-carboxylate then was employed in procedures analogous to Part C in the preparation of compound E-13 to provide 1-(4-fluoro-7-(1H-1,2,3-triazol-1-yl)-1H-pyrrolo[2,3-c]pyridinyl-3-yl)-2-(4-(3-(pyridin-2-yl)-1H-pyrazol-4-yl)piperazin-1-yl)ethane-1,2-dione (Compound E-16) and 1-(4-methoxy-7-(3-methyl-1H-1,2,4-triazol-1-yl)-1H-pyrrolo[2,3-c]pyridinyl-3-yl)-2-(4-(3-(pyridin-2-yl)-1H-pyrazol-4-yl)piperazin-1-yl)ethane-1,2-dione (Compound E-17).

Compound E-16: HRMS: m/e: 487.1747 (M+H)$^+$ [calc'd: 487.1755]; $^1$H NMR (500 MHz, DMSO-D$_6$) δ 13.07 (br s, 1H), 9.03 (s, 1H), 8.61 (m, 1H), 8.37 (m, 1H), 8.33 (m, 1H), 8.13 (m, 2H), 7.96 (m, 1H), 7.56 (m, 1H), 7.32 (m, 1H), 3.84 (m, 2H), 3.59 (m, 2H), 3.00 (m, 2H), 2.89 (m, 2H).

Compound E-17: HRMS: m/e: 513.2104 (M+H)$^+$ [calc'd: 513.2111]; $^1$HNMR (500 MHz, DMSO-D$_6$) δ 12.40 (br s, 1H), 9.25 (s, 1H), 8.61 (m, 1H), 8.25 (m, 1H), 7.91 (m, 3H), 7.57 (m, 1H), 7.31 (m, 1H), 4.04 (s, 3H), 3.81 (m, 2H), 3.54 (m, 2H), 3.00 (m, 2H), 2.88 (m, 2H), 2.50 (s, 3H).

Example Chemistry Section F

Preparation of the Library of Amido Pyrazoles

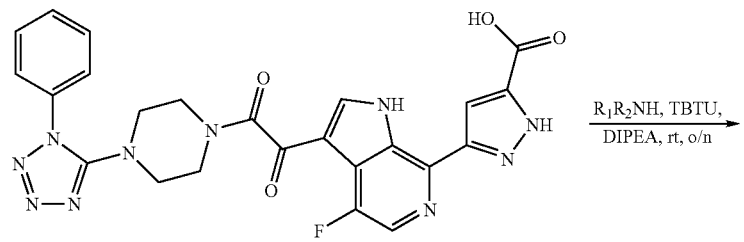

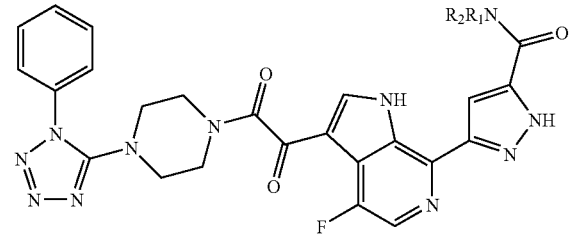

A mixture of 3-(4-fluoro-3-(2-oxo-2-(4-(1-phenyl-1H-tetrazol-5-yl)piperazin-1-yl)acetyl)-1H-pyrrolo[2,3-c]pyridin-7-yl)-1H-pyrazole-5-carboxylic acid (42 mg, 0.8 mmol), an amine (3.36 mmol), TBTU (0.88 mmol) and DIPEA (38.4 mmol) was agitated at room temperature overnight. The crude reaction mixtures were purified using reverse phase prep HPLC.

LC Conditions Used to Analyze Final Compounds:

Column: Waters Xbridge 4.6×50 mm 5 um C18

Method: 10% B/90% A+modifier to 95% B/5% A+modifier

A=Water

B=ACN

Modifier=10 mM NH4OAc

Flow=2.5 mL/min

Gradient time: 4 min

Stop time: 5 min

| Comp. # | Structure | LC/MS data | Amine |
|---|---|---|---|
| F-1 | 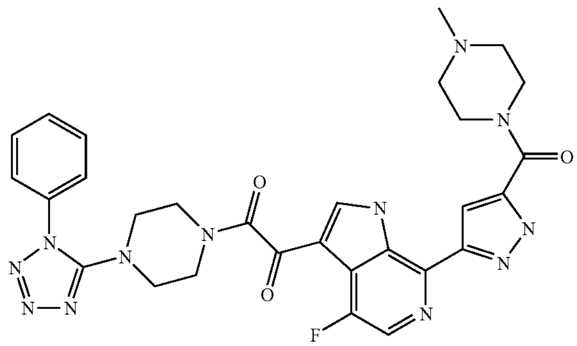 | Rt: 2.13 min. Reported Mass: 613.360 | |
| F-2 | 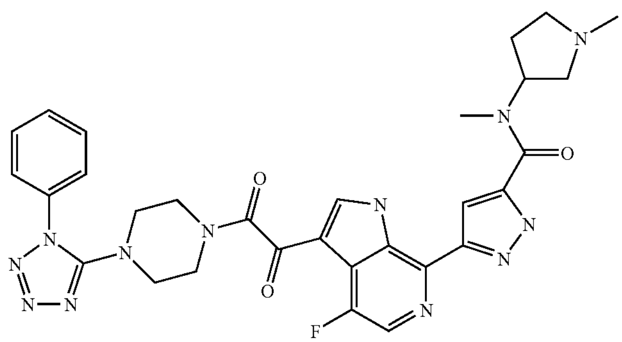 | Rt: 2.05 min. Reported Mass: 627.410 | |
| F-3 | Chiral | Rt: 2.10 min. Reported Mass: 600.330 | |
| F-4 | 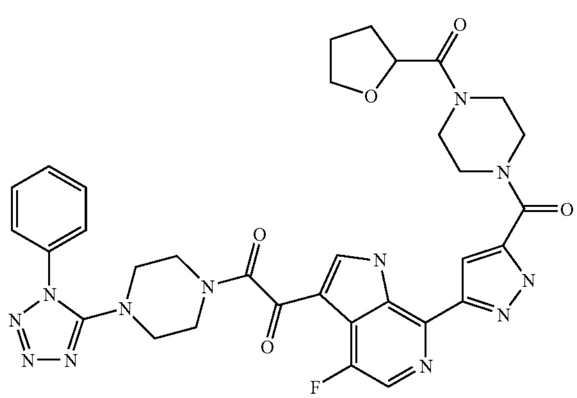 | Rt: 2.20 min. Reported Mass: 697.450 | |

-continued
| Comp. # | Structure | LC/MS data | Amine |
|---|---|---|---|
| F-5 | 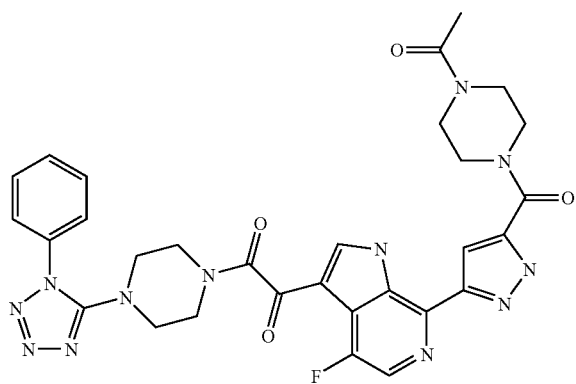 | Rt: 2.12 min. Reported Mass: 641.390 | 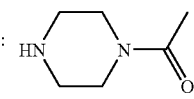 |
| F-6 Chiral | 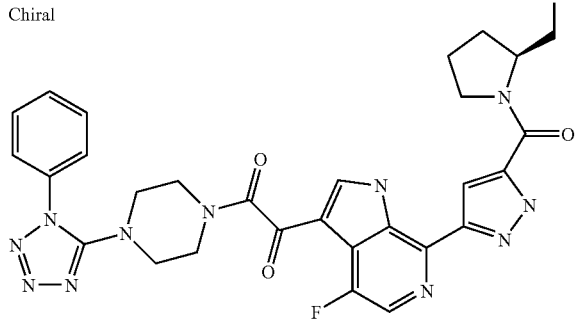 | Rt: 2.25 min. Reported Mass: 614.360 | 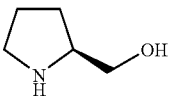 |
| F-7 | 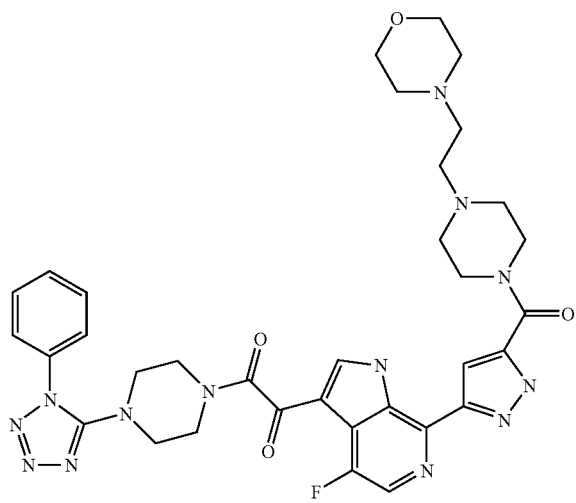 | Rt: 2.08 min. Reported Mass: 712.490 | 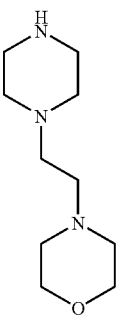 |

-continued
| Comp. # | Structure | LC/MS data | Amine |
|---|---|---|---|
| F-8 | 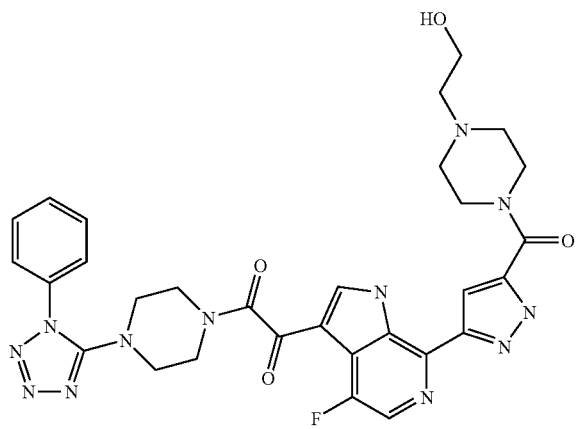 | Rt: 2.03 min. Reported Mass: 643.400 | 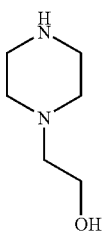 |
| F-9 | 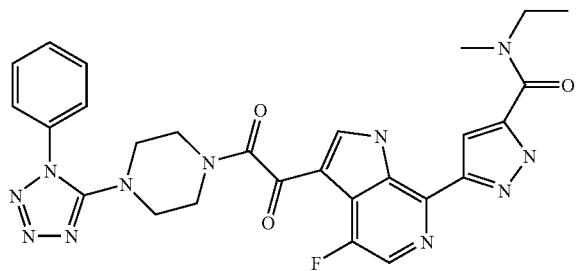 | Rt: 2.40 min. Reported Mass: 572.320 |  |
| F-10 | 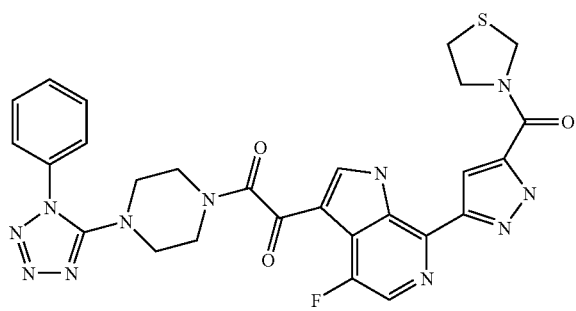 | Rt: 2.49 min. Reported Mass: 602.270 | 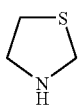 |
| F-11 | 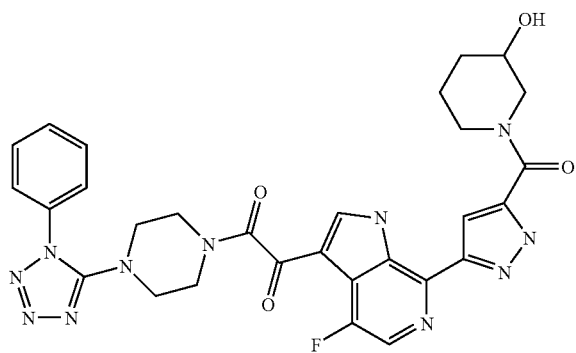 | Rt: 2.18 min. Reported Mass: 614.360 | 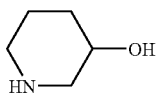 |

-continued

| Comp. # | Structure | LC/MS data | Amine |
|---|---|---|---|
| F-12 | 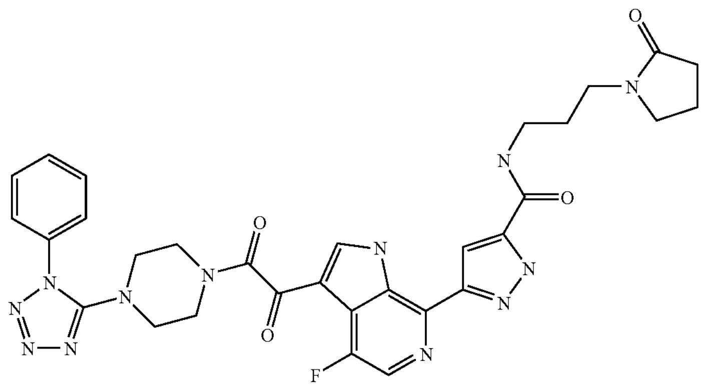 | Rt: 2.19 min. Reported Mass: 655.420 | |
| F-13 | 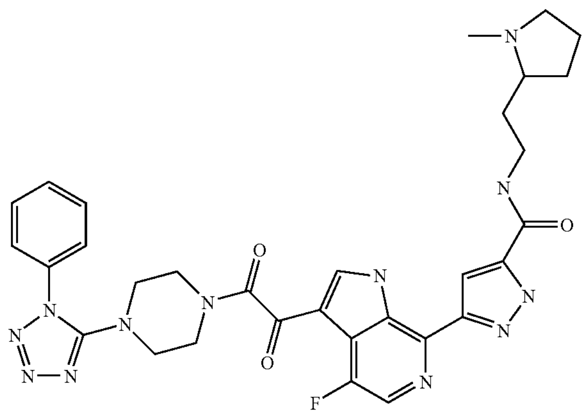 | Rt: 2.02 min. Reported Mass: 641.440 | |
| F-14 | 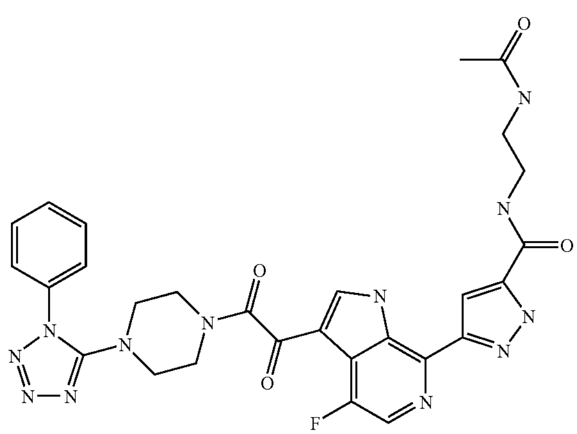 | Rt: 2.07 min. Reported Mass: 615.350 | |

-continued

| Comp. # | Structure | LC/MS data | Amine |
|---|---|---|---|
| F-15 | 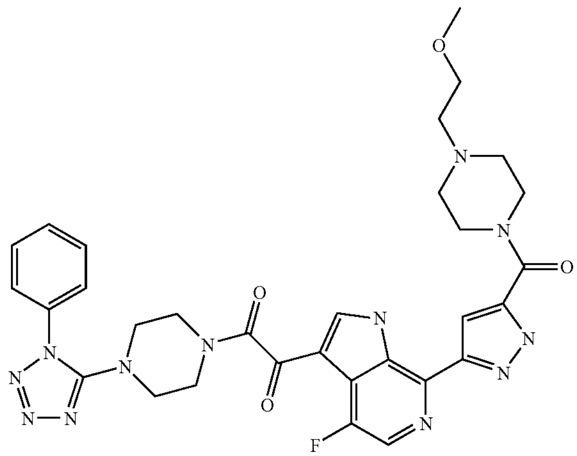 | Rt: 2.21 min. Reported Mass: 657.430 | |
| F-16 | 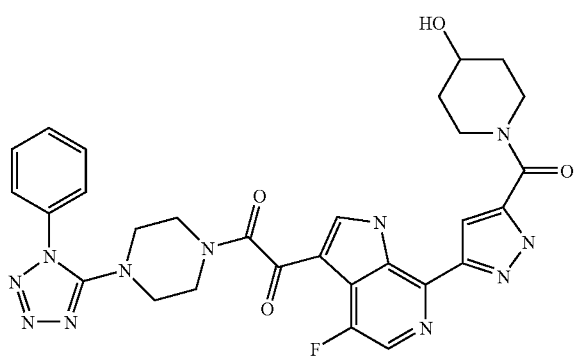 | Rt: 2.10 min. Reported Mass: 614.360 | |

Example Chemistry Section G

Preparation of Compound G-1a and G-2b

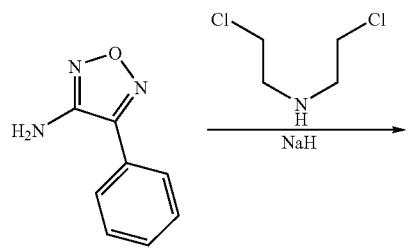

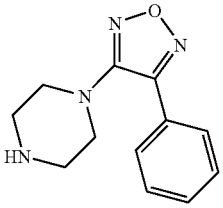

G-1-In

Step-1

Sodium hydride (0.12 g) was taken in dry DMF (5 ml) and a solution of 3-amino-4-phenyl isoxazole (0.2 g in 2 ml of DMF) was added slowly at 0° C. The reaction mixture was stirred for 30 min at 0° C. and a solution of bis-(2-chloroethylamine) hydrochloride (0.22 g) in DMF (1 mL) was added very slowly. The reaction mixture was allowed to stir over night at room temperature. The reaction mixture was quenched with cold water (5 ml) and extracted with ethyl acetate (3×40 ml). Evaporation of solvent under reduced pressure gave crude product, which, was purified by column chromatography using MeOH/CHCl₃ (2:8) as eluent to afford G-1-In as pure solid product.

¹H NMR (400 MHz, CDCl₃): δ 3.02 (d, 4H), 3.50 (d, 4H), 7.27-7.80 (m, 5H).

LCMS: 230.9 (M⁺+1).

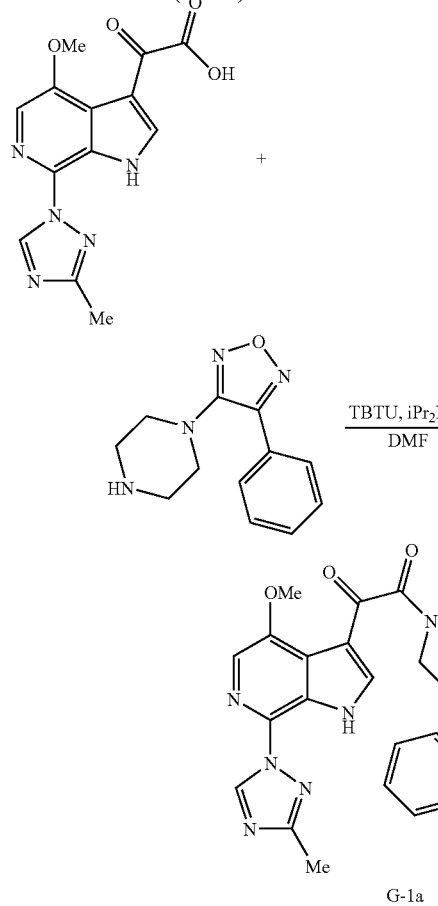

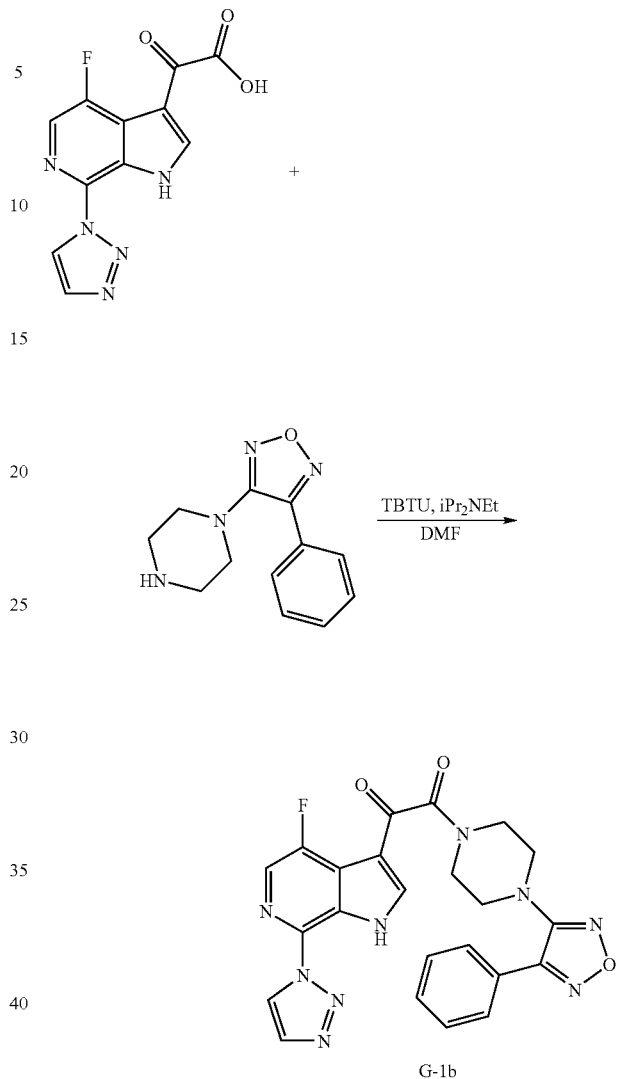

Step-2

2-(4-Methoxy-7-(3-methyl-1H-1,2,4-triazol-1-yl)-1H-pyrrolo[2,3-c]pyridin-3-yl)-2-oxoacetic acid (0.18 g), G-1-In (0.1 g), TBTU (0.15 g) and Hunig's base (0.15 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO₃ and brine. The organic layer was dried over anhydrous Na₂SO₄ and concentrated under reduced pressure. The resulting crude was purified by column chromatography using MeOH/CHCl₃ (1:9) as eluent to afford G-1a as yellow solid.

¹H NMR (400 MHz, CDCl₃): δ 2.58 (s, 3H), 3.26 (bs, 2H), 3.36 (bs, 2H), 3.63 (bs, 2H), 3.89 (bs, 2H), 4.06 (s, 3H), 7.53 (s, 3H), 7.77 (d, 3H, J=8 Hz), 8.21 (s, 1H), 9.13 (s, 1H), 11.04 (s, 1H).

¹³C NMR (400 MHz, CDCl₃): δ 14.04, 40.48, 45.1, 48.91, 49.26, 57.02, 115.77, 121.39, 123.2, 124.14, 126.25, 127.79, 129.21, 129.55, 130.7, 136.52, 141.13, 147.66, 149.71, 158.53, 166.37, 185.23.

LCMS: 514.1 (M⁺+1), 512.6 (M⁺−1).

HPLC: 97.6% (NH₄OAc/ACN; Column: C18 XDB, 250× 4.6 mm).

2-(4-Fluoro-7-(1H-1,2,3-triazol-1-yl)-1H-pyrrolo[2,3-c]pyridin-3-yl)-2-oxoacetic acid (0.18 g), G-1-In (0.1 g), TBTU (0.15 g) and Hunig's base (0.15 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO₃ and brine. The organic layer was dried over anhydrous Na₂SO₄ and concentrated under reduced pressure. The resulting crude was purified by column chromatography using MeOH/CHCl₃ (1:9) as eluent to afford G-1b as yellow solid.

¹H NMR (400 MHz, CDCl₃): δ 3.27 (t, 2H, J=6 Hz), 3.35 (t, 2H, J=6 Hz), 3.71 (t, 2H, J=6 Hz), 3.90 (t, 2H, J=6 Hz), 7.52 (t, 3H, J=4 Hz), 7.78 (d, 2H, J=8 Hz), 7.94 (s, 1H), 8.16 (s, 1H), 8.39 (s, 1H), 8.77 (s, 1H), 11.29 (s, 1H).

LCMS: 488.1 (M⁺+1).

HPLC: 96.6% (NH₄OAc/ACN; Column: C18 XDB, 250× 4.6 mm).

Preparation of Compound G-2a, G-2b and G-2c

Preparation of Intermediate G-2-In

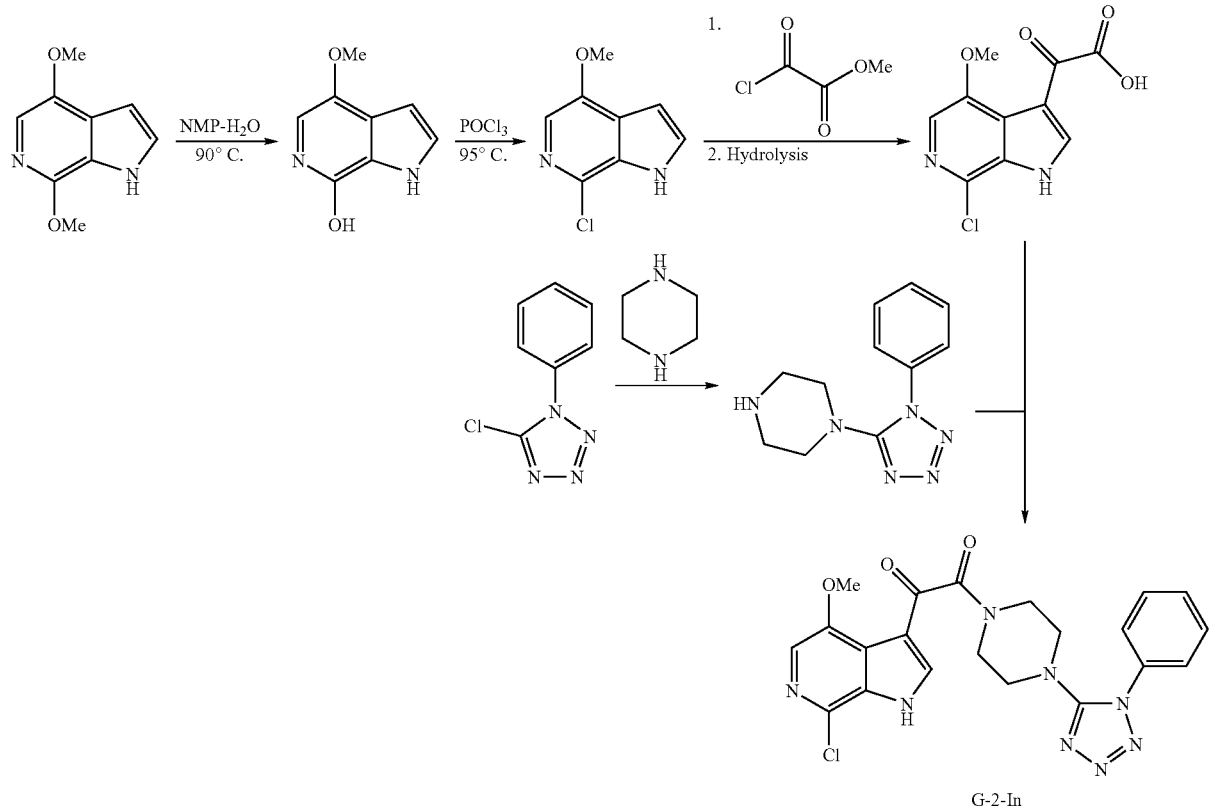

Step-1

To 4,7-dimethoxy-1H-pyrrolo[2,3-c]pyridine hydrochloride (50 g) taken in 2 L 3-necked round bottom flask, 250 ml N-methyl-2-pyrrolidinone was added followed by 8 ml of water, and was heated to 90° C. for about 4 hrs. The reaction mixture was cooled to room temperature, diluted with water (1 L) and the whole mixture was kept in cold room for about one hour. The resulting solid was collected by filtration, washed with cold water and dried in vacuum oven at 50° C. for 4 hrs to afford 7-hydroxyl-4-methoxy-6-azaindole as white solid.

$^1$H NMR (400 MHz, DMSO-$d_6$): δ 3.70 (s, 3H), 6.32-6.33 (dd, 1H), 6.38 (s, 1H), 7.25-7.26 (d, 1H, J=4 Hz), 10.5 (bs, 1H), 12.1 (bs, 1H).

Step-2

To the above compound 7-hydroxyl-4-methoxy-6-azaindole (33 g) taken in single necked round bottom flask, phosphorusoxychloride (400 ml) was added and the mixture was heated to 100° C. for 18 hrs. Reaction mixture was cooled to room temperature and concentrated to remove excess phosphorus oxychloride. Residue was slowly poured into ice and neutralized with solid sodium bicarbonate. The mixture was extracted with Ethyl acetate (3×100 ml). The combined organic layer was dried over anhydrous sodium sulphate and concentrated to afford 7-chloro-1-4-methoxy-6-azaindole as white solid.

$^1$H NMR (400 MHz, CDCl$_3$): δ 4.03 (s, 3H), 6.73-6.74 (dd, 1H), 7.36-7.37 (t, 1H), 7.63 (s, 1H) 8.9 (bs, 1H).

LCMS: 182.7 (M$^+$+1).

Step-3

A solution of 7-chloro-4-methoxy-6-azaindole (3 g) and aluminium chloride (2.3 g) in 100 ml dichloromethane was added to a mixture of methylchlorooxalate (6 g) and aluminium chloride (3.7 g) in 50 ml of dichloromethane. The whole mixture was stirred at room temperature for 18 hrs under nitrogen atmosphere. Reaction mixture was quenched with 100 ml of saturated aqueous ammonium acetate solution and extracted with ethyl acetate (2×100 ml). The combined organic layers was washed with brine solution, dried over anhydrous sodiumsulphate, filtered and concentrated under reduced pressure. The resulting crude product was treated with methanol and filtered to give pure ester as white solid.

$^1$H NMR (400 MHz, DMSO-$d_6$): δ 3.85-3.88 (s, 3H), 3.94 (s, 3H), 7.83 (s, 1H), 8.45 (s, 1H), 13.3 (bs, 1H).

Step-4

Above ester (1 g) and K$_2$CO$_3$ (0.95 g) were combined in 6 ml of methanol/water (1:1) mixture and stirred at room temperature for over night. The mixture was extracted with ethyl acetate to remove the non-polar impurities. And the aqueous layer was neutralized with 1.5 N HCl to pH5. The reaction mixture was concentrated under reduced pressure to afford desired acid, 2-(7-chloro-4-methoxy-1H-pyrrolo[2,3-c]pyridin-3-yl)-2-oxoacetic acid which was used for the next step without further purification.

$^1$H NMR (400 MHz, DMSO-$d_6$): δ 3.91 (s, 3H), 7.79 (s, 1H), 8.35 (s, 1H), 13.30 (bs, 1H)

LCMS: 254.9 (M$^+$+1).

Step-5

To sodium hydride (2.1 g) taken in dry DMF (10 ml), 5-chloro-1H-tetrazole (5 g) dissolved in dry DMF (20 ml) was added drop wise at 0° C. under nitrogen. Reaction mixture was allowed to stir at 0° C. for about 30 min and piperazine (2.8 g) in DMF (10 ml) was added drop wise at 0° C. for about 10 min. The whole mixture was heated to 80° C. for 18 hrs then cooled to room temperature and slowly poured into ice. The resulting solid was filtered, washed with water and dried to afford 1-(1-phenyl-1H-tetrazol-5-yl)piperazine as a solid product.

$^1$H NMR (400 MHz, CDCl$_3$): δ 2.91-2.93 (m, 4H), 3.22-3.33 (m, 4H), 7.49-7.63 (m, 5H).

Step-6

To 2-(7-chloro-4-methoxy-1H-pyrrolo[2,3-c]pyridin-3-yl)-2-oxoacetic acid (0.15 g) taken in dry DMF (3 ml), 1-(1-phenyl-1H-tetrazol-5-yl) pauperizing (0.1 g), TBTU (0.219 g) and Hunig's base (0.2 ml) were added. The reaction mixture was stirred at room temperature for over night. The reaction was quenched with methanol (10 ml) and the volatiles were removed under reduced pressure. The resulting oil was diluted with ethyl acetate (50 ml), washed with 10% NaHCO$_3$ (2×20 ml) and brine (20 ml). The organic layer was dried over anhydrous Na$_2$SO$_4$ and after concentration under reduced pressure the crude was purified by column chromatography using MeOH/CHCl$_3$ (1:9) as eluent to afford G-2-In as yellow solid.

$^1$H NMR (400 MHz, DMSO-d$_6$): δ 3.31-3.34 (s, 3H), 3.39 (bs, 2H), 3.47 (bs, 2H), 3.87-3.91 (s, 2H), 4.09 (s, 3H), 7.570-7.7 (s, 1H), 8.31-8.34 (d, 1H), 13.3 (bs, 1H).

LCMS: 465.3 (M$^+$+1).

Preparation of G-2a

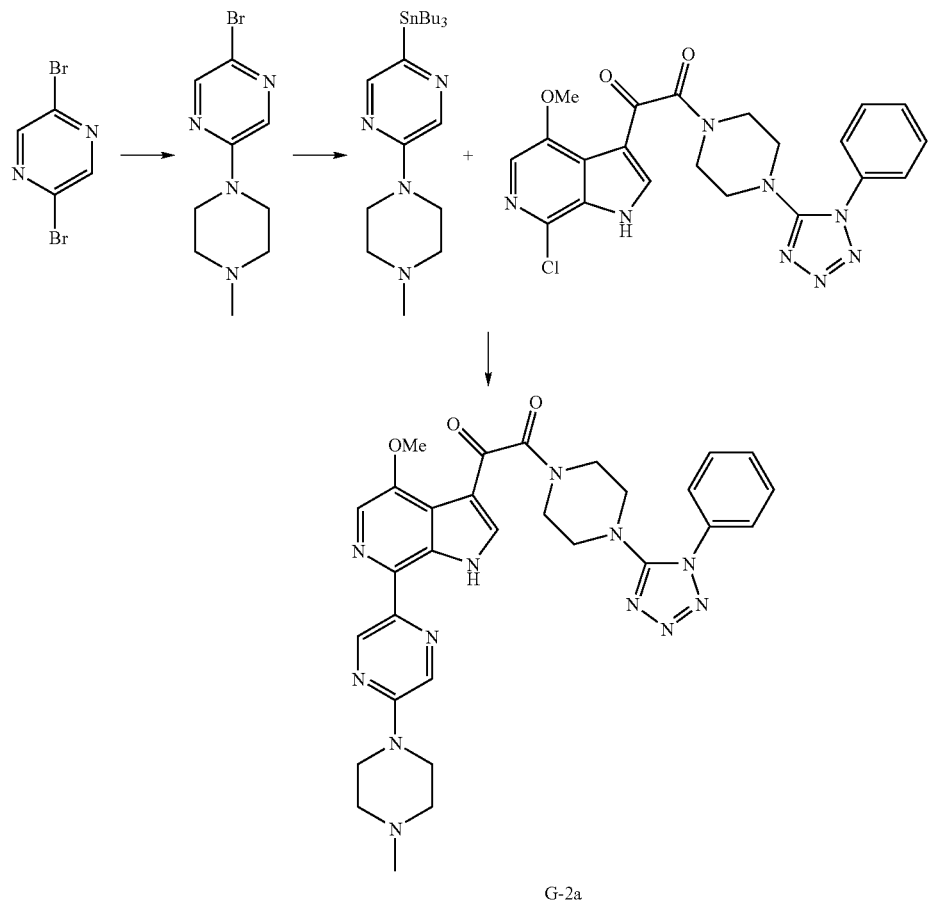

G-2a

Step-1

To sodium hydride (0.20 g) taken in dry THF (15 ml), N-methyl piperazine (0.93 ml) was added under nitrogen at 0° C. 2,3-Dibromopyrazine (2 g) taken in 15 ml dry THF was added to the above mixture at 0° C. The reaction mixture was allowed to reflux for overnight and quenched with water (5 ml). The organic layer was removed under vacuum. The resulting crude mass was purified by column chromatography to afford 2-bromo-5-(4-methylpiperazin-1-yl)pyrazine as pure product.

$^1$H NMR (400 MHz, CDCl$_3$): δ 2.39 (s, 3H), 2.57 (t, 4H, J=6 Hz), 3.62 (t, 4H, J=6 Hz), 7.88 (s, 1H), 8.14 (s, 1H).

Step-2

To the compound 2-bromo-5-(4-methylpiperazin-1-yl)pyrazine (0.25 g) dissolved in dry DMF (5 ml), hexa-n-butyl di-tin (0.615 ml) was added. The reaction mixture was degasified under argon atmosphere for 3-5 times. Tetrakis (triphenyl phosphine) palladium (0.128 g) was added to the above mixture and further degasified under argon atmosphere for 3-5 times. The reaction mixture was refluxed overnight, then cooled to room temperature, diluted with ethyl acetate and filtered through celite bed. The filtrate was concentrated and purified by column chromatography to afford compound 2-(4-methylpiperazin-1-yl)-5-(tributylstannyl)pyrazine as pale yellow color liquid.

$^1$H NMR (400 MHz, CDCl$_3$): δ 1.36 (s, 10H), 1.58 (s, 6H), 1.63 (s, 6H), 1.69 (s, 6H), 2.39 (s, 3H), 3.95 (s, 4H), 4.07 (s, 4H), 8.18 (s, 1H), 9.30 (s, 1H).

Step-3

To a stirred solution of intermediate 2-(4-methylpiperazin-1-yl)-5-(tributylstannyl)pyrazine (0.25 g) and G-In-2 (0.38 g) taken in dry xylene (15 ml) under nitrogen atmosphere, copper (I) iodide (10 mg) was added. The reaction mixture was degasified using nitrogen and to that mixture Pd(Ph)$_4$ (0.065 g) was added. The reaction mixture was refluxed for 24 hours at 130° C. The reaction mixture was cooled to room temperature and concentrated under vacuum to remove the solvent. The resulting crude was purified by column chromatography using MeOH/CHCl$_3$ (1:9) as eluent to afford G-2a as white solid product.

$^1$H NMR (400 MHz, DMSO-d$_6$): δ 2.26 (s, 3H), 3.16 (s, 2H) 3.32 and 3.42 (m, 7H), 3.67 (s, 7H), 3.97 (s, 3H), 7.57-7.64 (m, 3H), 7.69 (d, 2H, J=8 Hz), 8.10 (s, 1H), 8.18 (d, 1H, J=4 Hz), 8.33 (s, 1H), 9.07 (s, 1H), 12.45 (s, 1H).

LCMS: 609.2 (M$^+$+1).

HPLC: 95.3% (NH$_4$OAc+0.1% TFA/ACN; Column: C18 XDB, 250×4.6 mm).

Preparation of G-2b

Step-1

To sodium hydride (0.20 g) taken in THF (15 ml), morpholine (0.735 ml) was added under nitrogen, at 0° C. The reaction mixture stirred for about 15 minutes, then 2,3-dibromopyrazine (2 g) dissolved in dry THF (15 ml) was added. The reaction mixture was allowed to stir at reflux conditions for overnight. The reaction mixture was quenched with water (5 ml), and volatiles were removed under vacuum. The resulting crude mass was purified by column chromatography to afford pure 4-(5-bromopyrazin-2-yl)morpholine.

$^1$H NMR (400 MHz, CDCl$_3$): δ 3.53 (t, 4H, J=6 Hz), 3.84 (t, 4H, J=6 Hz), 7.88 (s, 1H), 8.16 (s, 1H).

Step-2

To compound 4-(5-bromopyrazin-2-yl)morpholine (0.25 g) taken in dry THF (5 ml) and cooled to −78° C., n-butyl lithium (0.4 ml, 1M solution in Hexane) was added stirred for 2 hrs at −78° C. To the above reaction mixture tri-n-butyl tin chloride (1.1 mmol) was added drop wise at −78° C. Reaction mixture was stirred at −78° C. for one hour, quenched with saturated ammonium chloride solution and extracted with ethyl acetate (3×15 ml). The organic layer was washed with water (20 ml) followed by brine, dried over anhydrous sodiumsulphate and concentrated using rotary evaporator. The resulting crude was purified by column chromatography to afford 4-(5-(tributylstannyl)pyrazin-2-yl)morpholine as pale yellow color liquid.

$^1$H NMR (400 MHz, CDCl$_3$): δ 1.36 (s, 10H), 1.58 (s, 6H), 1.63 (s, 6H), 1.67 (s, 6H), 3.57 (s, 4H), 3.85 (s, 4H), 8.13 (s, 1H), 8.36 (s, 1H).

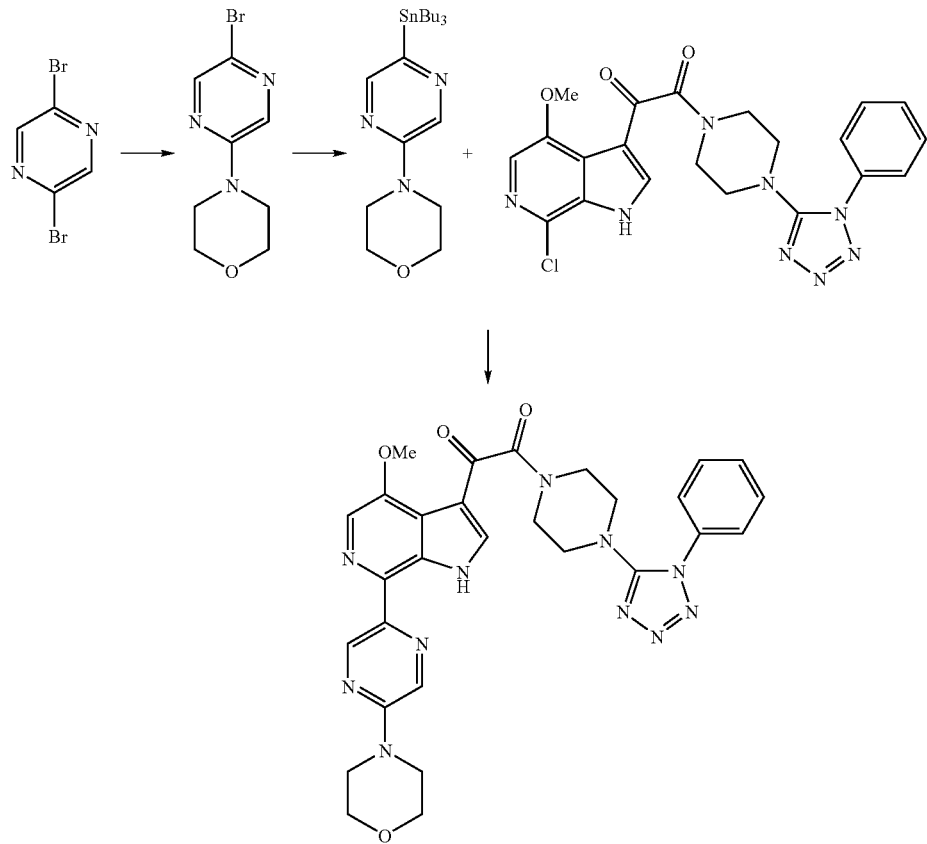

G-2b

Step-3

To a stirred solution of intermediate 4-(5-(tributylstannyl) pyrazin-2-yl)morpholine (0.25 g) and G-2-In (0.38 g) taken in dry xylene under nitrogen atmosphere, copper (I) iodide (10 mg) was added. The reaction mixture was degasified using nitrogen and Pd(PPh$_3$)$_4$ (0.065 g) was added. The reaction mixture was refluxed for 24 hours concentrated under vacuum to remove the solvent. The crude was purified by column chromatography using MeOH/CHCl$_3$ (1:9) as eluent to afford G-2b as white solid product.

$^1$H NMR (400 MHz, DMSO-d$_6$): δ 3.16 (s, 2H), 3.42 (s, 3H), 3.63, 3.68, 3.75 (3s, 11H), 4.04 (s, 3H), 7.57-7.7 (m, 6H), 8.1, 8.19, 8.32 (3s, 3H), 9.09 (s, 1H).

LCMS: 596.1 (M$^+$+1).

HPLC: 92% (0.1% TFA/ACN; Column: C18 BDS, 4.6× 250 mm).

Preparation of G-2c

Step-2

To compound 2-bromo-5-(1H-imidazol-1-yl)pyrazine (0.25 g) taken in dry xylene, hexa-n-butyl di tin (0.615 ml) was added. The reaction mixture was degasified under argon atmosphere for 3-5 times. To that tetrakis (triphenyl phosphine) palladium (0.128 g) was added and further degasified under argon atmosphere for 3-5 times. The reaction mixture was stirred under reflux conditions for overnight. The reaction mixture was cooled room temperature, diluted with ethyl acetate and filtered through celite bed. The filtrate was concentrated and purified by column chromatography to afford 2-(1H-imidazol-1-yl)-5-(tributylstannyl)pyrazine as pale yellow color liquid.

$^1$H NMR (400 MHz, CDCl$_3$): δ 1.36 (s, 10H), 1.58 (s, 6H), 1.63 (s, 6H), 1.67 (s, 6H), 3.57 (d, 1H), 4.45 (d, 1H), 4.65 (s, 1H), 8.13 (s, 1H), 8.36 (s, 1H).

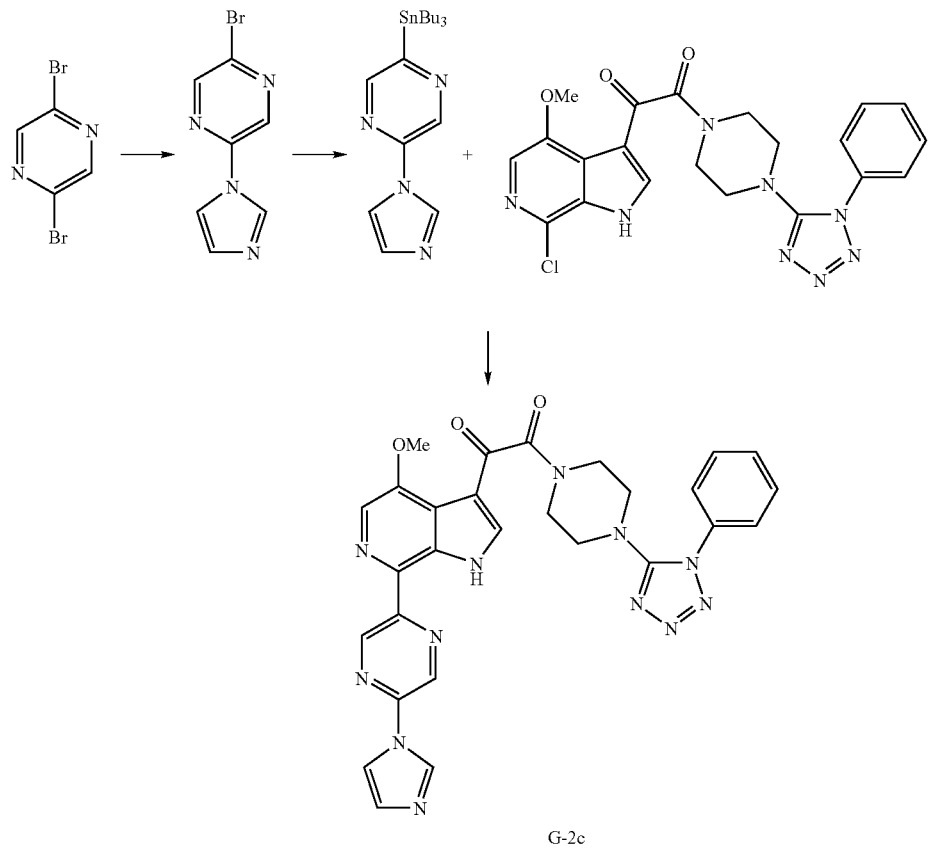

G-2c

Step-1

To sodium hydride (0.20 g) in THF (15 ml), imidazole (0.57 g) was added and cooled to 0° C. To the above mixture 2,3-dibromopyrazine (2 g) was added and entire reaction mixture was allowed to reflux for overnight. The reaction mixture was quenched with water 5 ml volatiles were removed under vacuum. The resulting crude mass was purified by column chromatography to afford 2-bromo-5-(1H-imidazol-1-yl)pyrazine as pure product.

$^1$H NMR (400 MHz, CDCl$_3$): δ 7.30 (s, 1H), 7.65 (s, 1H), 8.44 (s, 1H), 8.58 (s, 1H), 8.60 (s, 1H).

Step-3

To a stirred solution of intermediate 2-(1H-imidazol-1-yl)-5-(tributylstannyl)pyrazine (0.25 g) and G-2-In (0.38 g) taken in dry xylene under nitrogen atmosphere, copper (I) iodide (10 mg) was added. The reaction mixture was degasified using nitrogen and Pd(PPh$_3$)$_4$ (0.065 g) was added. The reaction mixture was refluxed for 24 hours concentrated under vacuum to remove the solvent. The crude was purified by column chromatography using MeOH/CHCl$_3$ (1:9) as eluent to afford G-2c as white solid product.

¹H NMR (400 MHz, DMSO-d₆): δ 3.17 (t, 2H, J=8 Hz), 3.44 (t, 2H, J=4 Hz), 3.69 (t, 2H, J=6 Hz), 4.04 (s, 3H), 7.24 (bs, 1H), 7.56-7.71 (m, 5H), 8.12 (d, 1H, J=8 Hz), 8.26 (s, 2H), 8.73 (bs, 1H), 9.18 (s, 1H), 9.48 (s, 1H), 12.65 (s, 1H).

LCMS: 575.2 (M⁺−1).

HPLC: 90.6% (0.1% TFA/ACN; Column: Hypersil BDS C18, 4.6×50 mm).

Preparation of Compound G-3a and G-3b

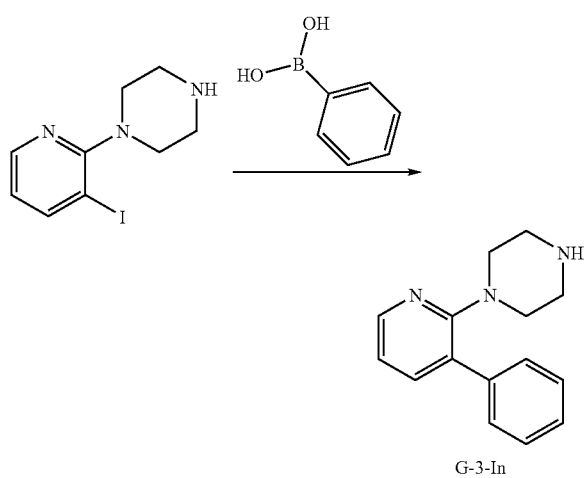

G-3-In

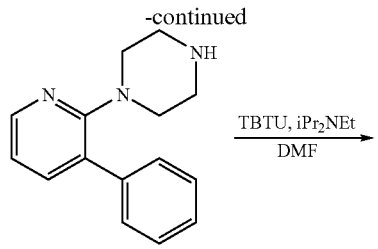

Step-1

To 1-(3-iodopyridin-2-yl)piperazine (0.5 g) taken in dry toluene (10 ml), added phenyl boronic acid (0.25 g) under nitrogen atmosphere. To reaction mixture was added Pd(PPh₃)₄ (10 mg) and a solution of sodium carbonate (0.3 g) in water (2 ml). Reaction mixture was bubbled with Nitrogen gas for about 10 min and refluxed for over-night. Reaction mixture was cooled to r.t and diluted with EtOAC, washed with 10% NaHCO₃ and brine. The organic layer was dried over anhydrous Na₂SO₄ and concentrated under reduced pressure. The resulting crude was purified by column chromatography using EtOAc/Hexane (2:8) as eluent to afford G-3-In as brown viscous liquid.

¹H NMR (400 MHz, CDCl₃): δ 3.06 (d, 4H), 3.14 (d, 4H), 6.94 (s, 1H), 7.31 (s, 1H), 7.38-7.68 (m, 5H), 8.25 (s, 1H).

LCMS: 239.9 (M⁺+1).

Step-2

2-(4-Methoxy-7-(3-methyl-1H-1,2,4-triazol-1-yl)-1H-pyrrolo[2,3-c]pyridin-3-yl)-2-oxoacetic acid (0.18 g), G-3-In (0.1 g), TBTU (0.15 g) and Hunig's base (0.15 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO₃ and brine. The organic layer was dried over anhydrous Na₂SO₄ and concentrated under reduced pressure. The resulting crude was purified by column chromatography using MeOH/CHCl₃ (1:9) as eluent to afford G-3a as yellow solid.

¹H NMR (400 MHz, CDCl₃): δ 2.56 (s, 3H), 3.15 (s, 2H), 3.28 (s, 2H), 3.44 (s, 2H), 3.71 (s, 2H), 4.04 (s, 3H), 7.0 (t, 1H, J=6 Hz), 7.34 (t, 1H, J=6 Hz), 7.44 (t, 2H, J=6 Hz), 7.53 and 7.57 (2×d, 3H, J=8 Hz and 4 Hz), 7.72 (s, 1H), 8.17 (d, 1H, J=2 Hz), 8.25 (d, 1H, J=2 Hz), 9.09 (s, 1H), 11.03 (s, 1H).

¹³C NMR (400 MHz, CDCl₃): δ 14.16, 41.12, 45.72, 48.49, 49.09, 56.93, 115.86, 117.62, 121.29, 123.11, 124.14, 127.51, 127.74, 127.89, 128.92, 136.44, 141.32, 149.66, 162.2, 166.47, 185.64.

LCMS: 523.1 (M⁺+1).

HPLC: 97.7% (NH₄OAc/ACN; Column: C18 XDB, 250×4.6 mm).

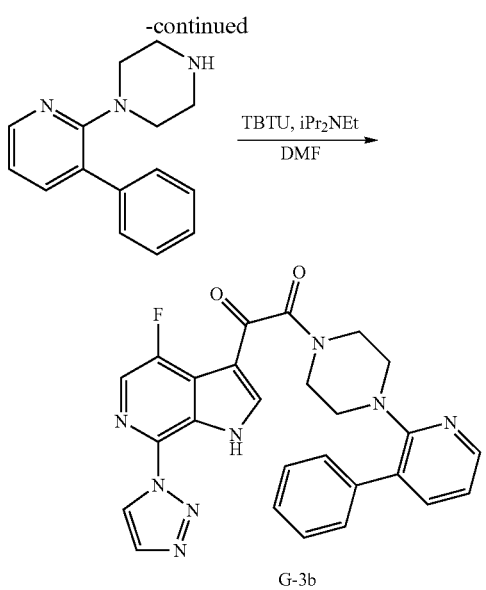

2-(4-Fluoro-7-(1H-1,2,3-triazol-1-yl)-1H-pyrrolo[2,3-c]pyridin-3-yl)-2-oxoacetic acid (0.18 g), G-In-3 (0.1 g), TBTU (0.15 g) and Hunig's base (0.15 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using MeOH/CHCl$_3$ (1:9) as eluent to afford G-3b as yellow solid.

$^1$H NMR (400 MHz, CDCl$_3$): δ 3.15 (t, 2H, J=4 Hz), 3.29 (t, 2H, J=6 Hz), 3.49 (d, 2H, J=8 Hz), 3.73 (t, 2H, J=4 Hz), 7.01 (d, 1H, J=8 Hz), 7.36 (d, 1H, J=8 Hz), 7.45 (t, 2H, J=8 Hz), 7.54 and 7.57 (dd, 3H, J=8 Hz and 4 Hz), 7.93 (s, 1H), 8.14 (s, 1H), 8.25 (d, 1H, J=4 Hz), 8.33 (d, 1H, J=4 Hz), 8.76 (s, 1H), 11.22 (s, 1H).

LCMS: 497.1 (M$^+$+1).

HPLC: 95.7% (NH$_4$OAc/ACN; Column: C18 XDB, 250×4.6 mm).

Preparation of Compound G-4a, G-4b, G-4c and G-4d

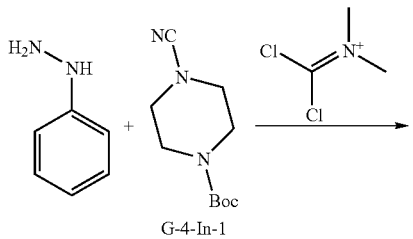

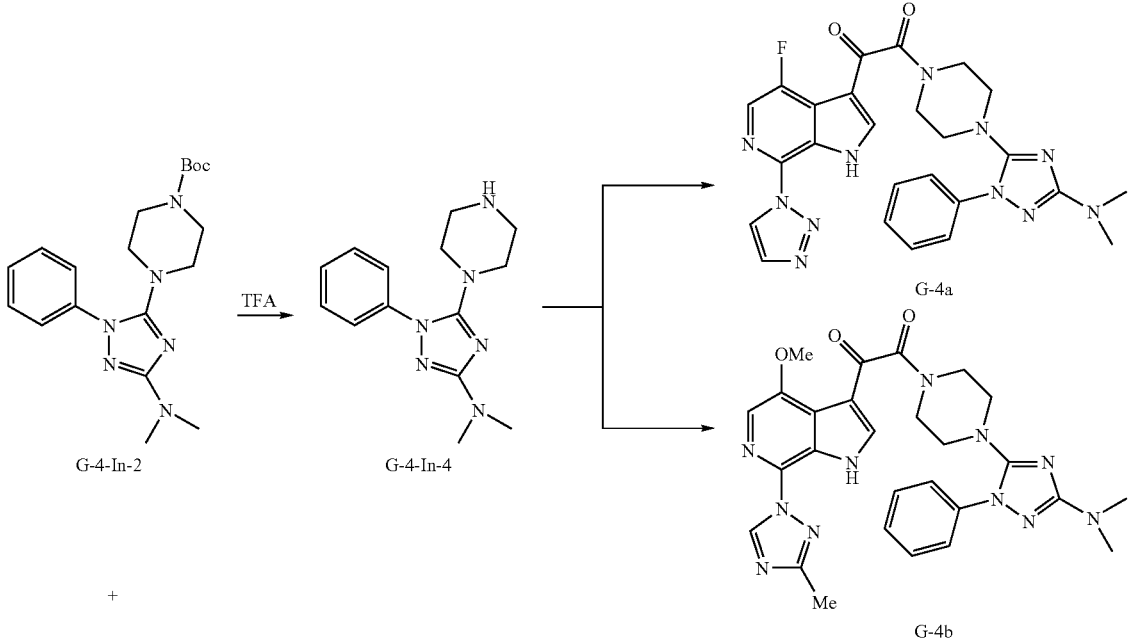

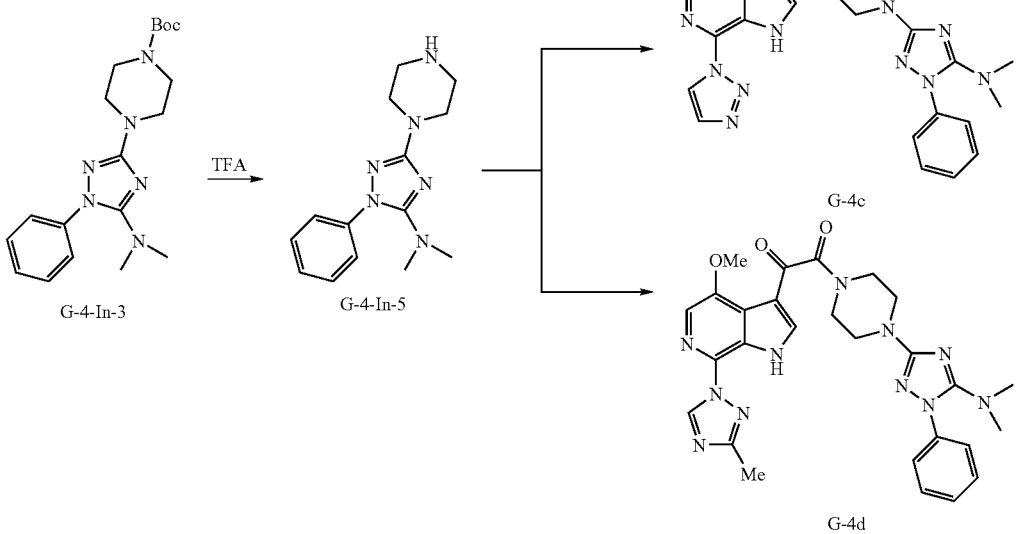

Step-1

To a stirred solution of cyano intermediate G-4-In-1 (300 mg) taken in dry dichloromethane (10 ml) under nitrogen added N-dichloromethylene N,N-dimethyl ammonium chloride (0.39 g) at rt under nitrogen. The reaction mixture is allowed to stir at r.t. for 15 minutes. The reaction mixture was allowed to reflux at 50° C. for one hour. The reaction mixture was cooled to room temperature and added phenyl hydrazine (0.168 g), triethyl amine (0.6 ml) in dichloromethane (5 ml) drop wise for one hour. The reaction mixture was allowed to stir at room temperature for 2 hours, and then allowed to reflux at 55° C. for one hour. The reaction mixture was allowed to cool to −10° C. and added water (10 ml) and concentrated KOH (2 g in 5 ml) and allowed to stir for 15 minutes at −10° C. The reaction mixture was extracted with dichloromethane (5×20 ml). The combined organic layer was dried over anhydrous sodium sulphate and concentrated under vacuum. The resulting crude mixture of G-4-In-2 and G-4-In-3 was purified by flash column chromatography using hexane/ethyl acetate (2:8) as eluent to afford pure G-4-In-2 and G-4-In-3 as pale yellow liquids.

$^1$H NMR (400 MHz, CD$_3$OD): δ 1.45 (s, 9H), 2.95 (s, 6H), 3.09 (t, 4H, J=4 Hz), 3.44 (bs, 4H), 7.38 (t, 1H, J=8 Hz), 7.51 (t, 2H, J=8 Hz), 7.62 (d, 2H, J=8 Hz).

LCMS: 373 (M$^+$+1).

HPLC: 97.6% (0.1% HCOOH/ACN; Column: Genesis C18, 4.6×50 mm).

Step-2

BOC protected amine G-4-In-2 (500 mg) dissolved in dry dichloromethane (10 ml) and TFA (5 ml) was added to it at 0° C. The reaction mixture was allow reach at r.t. and stirred for over-night. The volatiles were completely removed under reduced pressure and the resulting crude was diluted with dichloromethane (10 ml). The organic layer was washed with saturated NaHCO$_3$ (2×10 ml) and brine (20 ml) and dried over Na$_2$SO$_4$. Evaporation of solvent gave the desired amine In-4-In-4, which was used for the next reaction without any purification.

$^1$H NMR (400 MHz, DMSO-d$_6$): δ 2.68 (s, 6H), 2.73 (m, 4H), 3.17 (t, 4H, J=4 Hz), 7.31 (m, 1H), 7.48 (m, 4H).

$^{13}$C NMR (DMSO-d6): δ 40.21 (2C), 41.29 (2C), 45.37, 47.06, 123.57 (2C), 127.09, 129.57 (2C), 139.3, 158.16, 162.97.

LCMS: 273 (M$^+$+1).

HPLC: 97.5% (0.1% TFA/ACN; Column: C18 BDS, 4.6×50 mm).

Step-3

To a stirred solution of 2-(4-fluoro-7-(1H-1,2,3-triazol-1-yl)-1H-pyrrolo[2,3-c]pyridin-3-yl)-2-oxoacetic acid (100 mg) in dry DMF (5 ml) added amine G-4-In-4 (0.099 g), TBTU (0.178 g) and DIPEA (0.15 ml) were combined in. The reaction mixture was stirred at r.t. for over night. The mixture was quenched with methanol (10 ml) and volatiles were removed under reduced pressure. Resulting oil was diluted with ethyl acetate (50 ml) and washed with 10% NaHCO$_3$ and brine. The organic layer was dried over anhydrous Na$_2$SO$_4$ and concentrated under rotary evaporator. The resulting semi solid was purified by column chromatography using MeOH/CHCl$_3$ (0.5:9.5) as eluent to afford G-4a as yellow solid.

$^1$H NMR (400 MHz, DMSO-d$_6$): δ 2.85 (s, 6H), 3.06 (bs, 2H), 3.17 (bs, 2H), 3.49 (bs, 2H), 3.71 (bs, 2H), 7.30 (t, 1H, J=8 Hz), 7.47 (t, 2H, J=8 Hz), 7.65 (d, 2H, J=8 Hz), 8.10 (s, 1H), 8.35 (s, 1H), 9.01 (s, 1H), 13.05 (s, 1H).

LCMS: 530.1 (M$^+$+1).

HPLC: 95.9% (0.1% TFA/ACN; Column: Hypersil BDS C18, 4.6×50 mm).

Step-4

To a stirred solution of 2-(4-methoxy-7-(3-methyl-1H-1,2,4-triazol-1-yl)-1H-pyrrolo[2,3-c]pyridin-3-yl)-2-oxoacetic acid (100 mg) in dry DMF (5 ml) added amine G-4-In-4 (0.090 g), TBTU (0.117 g) and DIPEA (0.15 ml) were combined in. The reaction mixture was stirred at r.t. for over night. The mixture was quenched with methanol (10 ml) and volatiles were removed under reduced pressure. The resulting oil was diluted with ethyl acetate (50 ml) and washed with 10%

NaHCO₃ and brine. The organic layer was dried over anhydrous Na₂SO₄ and concentrated under reduced pressure. The resulting crude was purified by column chromatography using MeOH/CHCl₃ (0.5:9.5) as eluent to afford G-4-b as yellow solid.

¹H NMR (400 MHz, DMSO-d₆): δ 2.5 (s, 3H), 2.87 (s, 6H), 3.07 (bs, 2H), 3.16 (bs, 2H), 3.43 (bs, 2H), 3.69 (bs, 2H), 3.99 (s, 3H), 7.30 (t, 1H, J=8 Hz), 7.48 (t, 2H, J=8 Hz), 7.66 (d, 2H, J=8 Hz), 7.89 (s, 1H), 8.22 (s, 1H), 9.24 (s, 1H), 12.39 (s, 1H).

LCMS: 556.1 (M⁺+1), 554.4 (M⁺−1).

HPLC: 98.5% (0.1% TFA/ACN; Column: Hypersil BDS C18, 4.6×50 mm).

Step-5

To BOC protected amine G-4-In-3 (500 mg) dissolved in dry dichloromethane (10 ml), TFA (5 ml) was added to it at 0° C. The reaction mixture was allowed reach at r.t. and stirred for over-night. The volatiles were completely removed under reduced pressure and the residue was diluted with dichloromethane (10 ml). The organic layer was washed with saturated NaHCO₃ (2×10 ml) and brine (20 ml). The organic layer was dried over Na₂SO₄ and concentrated to dryness to afford amine G-4-In-5, which was used in the next step without any purification.

¹H NMR (400 MHz, DMSO-d₆): δ 2.68 (s, 6H), 2.75 (bs, 4H), 3.18 (bs, 4H), 7.31 (m, 1H), 7.49 (m, 4H).

¹³C NMR (DMSO-d₆): δ 40.21 (2C), 41.29 (2C), 45.37, 47.06, 123.57 (2C), 127.09, 129.57 (2C), 139.3, 158.16, 162.97.

LCMS: 272.9 (M⁺+1).

HPLC: 97.5% (0.1% TFA/ACN; Column: C18 BDS, 4.6×50 mm).

Step-6

To a stirred solution of 2-(4-fluoro-7-(1H-1,2,3-triazol-1-yl)-1H-pyrrolo[2,3-c]pyridin-3-yl)-2-oxoacetic acid (100 mg) in dry DMF (5 ml), amine G-4-In-5 (0.099 g), TBTU (0.127 g) and DIPEA (0.15 ml) were added. The reaction mixture was stirred at r.t. for over night. The mixture was quenched with methanol (10 ml) and volatiles were removed under reduced pressure. The oil was diluted with ethyl acetate (50 ml), washed with 10% NaHCO₃ and brine. The organic layer was dried over anhydrous Na₂SO₄ and concentrated using rotary evaporator. The resulting crude was purified by column chromatography using MeOH/CHCl₃ (0.5:9.5) as eluent to afford G-4-c as a yellow solid.

¹H NMR (400 MHz, DMSO-d₆): δ 2.69 (s, 6H), 3.28 (s, 3H), 3.41 (d, 2H, J=4 Hz), 3.47 (d, 2H, J=4 Hz), 3.73 (t, 2H, J=6 Hz), 7.32 (m, 1H), 7.44-7.50 (m, 4H), 8.12 (s, 1H), 8.32 (d, 1H, J=4 Hz), 8.36 (s, 1H), 9.01 (d, 1H, J=4 Hz).

LCMS: 530.2 (M⁺+1).

HPLC: 96.3% (0.1% TFA/ACN; Hypersil BDS C18, 4.6×50).

Step-7

To a stirred solution of 2-(4-methoxy-7-(3-methyl-1H-1,2,4-triazol-1-yl)-1H-pyrrolo[2,3-c]pyridin-3-yl)-2-oxoacetic acid (100 mg) in dry DMF (5 ml), amine G-4-in-5 (0.090 g), TBTU (0.117 g) and DIPEA (0.15 ml) were added. The reaction mixture was stirred at r.t. for over night. The mixture was quenched with methanol (10 ml) and solvents were removed under reduced pressure. The resulting oil was diluted with ethyl acetate (50 ml) and washed with 10% NaHCO₃ and brine. The organic layer was dried over anhydrous Na₂SO₄ and concentrated under reduced pressure. The crude was purified by column chromatography using MeOH/CHCl₃ (0.5:9.5) as eluent to afford G-4d as solid product.

¹H NMR (400 MHz, DMSO-d₆): δ 2.49 (s, 3H), 2.70 (s, 6H), 3.28 (bs, 2H), 3.42 (bs, 4H), 3.70 (bs, 2H), 3.99 (s, 3H), 7.32 (m, 1H), 7.49 (m, 4H), 7.89 (s, 1H), 8.24 (s, 1H), 9.24 (s, 1H), 12.39 (s, 1H).

LCMS: 556.1 (M⁺+1), 554.4 (M⁺−1).

HPLC: 99.5% (0.1% TFA/ACN; Column: Hypersil BDS C18, 4.6×50 mm).

Preparation of Compound 5a and 5b

Preparation of Intermediate G-5-In

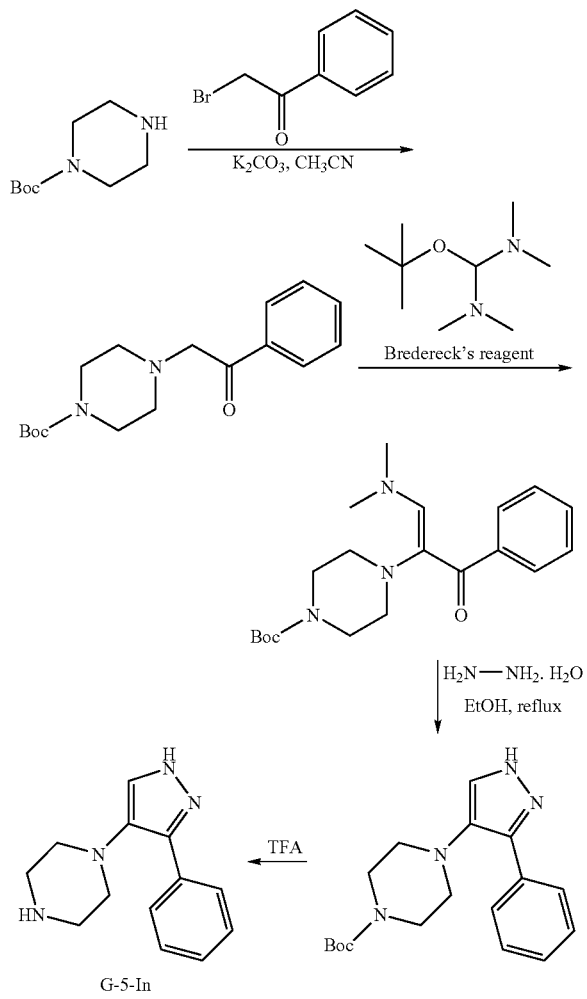

G-5-In

Step-1

A one liter three necked round bottom flask was charged with Boc-piperazine (20 g), dry potassium carbonate (44.5 g) and dry DMF (150 ml) under nitrogen atmosphere. The reaction mixture was cooled to 0° C. and bromoacetophenone (23.5 g) was added into the reaction mixture very slowly. The reaction mixture was stirred at room temperature for overnight. The progress of reaction was monitored by TLC. After consumption of starting material, ice-cold water (200 ml) was added to reaction mixture. The precipitated white solid was filtered, washed with water (4×50 ml) and dried to afford tert-butyl 4-(2-oxo-2-phenylethyl)piperazine-1-carboxylate as pure product.

¹H NMR (400 MHz, CDCl₃): δ 1.48 (s, 9H), 2.59 (s, 4H), 3.52-3.54 (s, 4H), 3.87 (s, 2H), 7.27-7.29 (m, 1H).

Step-2

To the compound tert-butyl 4-(2-oxo-2-phenylethyl)piperazine-1-carboxylate (18 g) taken in round bottom flask, Bredereck's reagent (11.33 g) was added very slowly under nitrogen atmosphere. The reaction mixture was stirred at 55° C. for over-night. The progress of reaction was monitored by TLC. After consumption of starting material, diethyl ether was added to the reaction mixture. The resulting solid was filtered and dried under reduced pressure to afford tert-butyl 4-(1-(dimethylamino)-3-oxo-3-phenylprop-1-en-2-yl)piperazine-1-carboxylate as pure product.

¹H NMR (400 MHz, DMSO-d₆): δ 1.36-1.41 (s, 9H), 2.87 (s, 4H), 3.01 (s, 6H), 3.33 (s, 4H), 6.53 (s, 1H), 7.32-7.42 (m, 5H).

Step-3

To the compound tert-butyl 4-(1-(dimethylamino)-3-oxo-3-phenylprop-1-en-2-yl)piperazine-1-carboxylate (4 g) dissolved in ethanol (40 ml), and hydrazine hydrate (1.17 g) was added and the reaction mixture was refluxed for 6 hrs with vigorous stirring. The progress of reaction was monitored by TLC. After consumption of starting material, the reaction mixture was cooled to room temperature and concentrated under reduced pressure to afford tert-butyl 4-(3-phenyl-1H-pyrazol-4-yl)piperazine-1-carboxylate.

¹H NMR (400 MHz, CDCl₃): δ 1.48 (s, 9H), 2.81 (s, 4H), 3.48-3.55 (m, 4H), 7.27-7.43 (m, 5H), 7.94 (s, 1H), 8.3 (bs, 1H).

Step-4

To BOC protected amine tert-butyl 4-(3-phenyl-1H-pyrazol-4-yl)piperazine-1-carboxylate (1 g) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated NaHCO₃ (2×10 ml), brine, dried over Na₂SO₄. Evaporation of solvent gave desire amine G-5-In, which was used for the next reaction without further purification.

¹H NMR (400 MHz, CDCl₃): δ 2.81 (s, 4H), 3.48-3.55 (m, 4H), 7.27-7.43 (m, 5H), 7.94 (s, 1H), 8.3 (bs, 1H).

LCMS: 228.29 (M⁺+1).

HPLC: 99.64% (TFA/ACN; Column: C18 BDS, 4.6×50 mm).

Preparation of G-5a

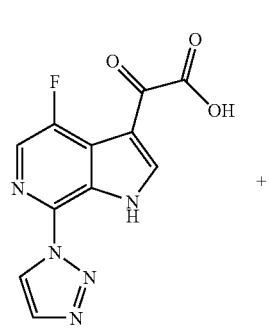

+

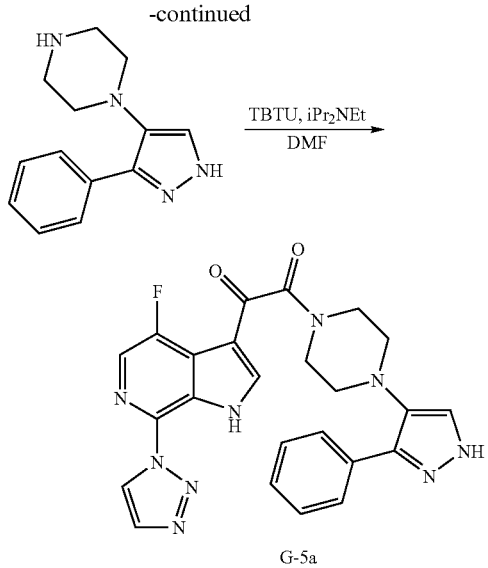

To a stirred solution of 2-(4-fluoro-7-(1H-1,2,3-triazol-1-yl)-1H-pyrrolo[2,3-c]pyridin-3-yl)-2-oxoacetic acid (90 mg) in dry DMF (5 ml), G-5-In (75 mg), TBTU (0.117 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO₃ and brine. The organic layer was dried over anhydrous Na₂SO₄ and concentrated using rotary evaporator. The resulting crude was purified by column chromatography using MeOH/CHCl₃ (2:8) as eluent to afford G-5a as yellow color solid.

¹H NMR (400 MHz, DMSO-d₆): δ 2.78 (d, 2H), 2.87 (d, 2H), 3.53 (d, 2H), 3.77 (d, 2H), 7.27-7.63 (m, 5H), 8.0 (s, 1H), 8.12 (s, 1H), 8.34 (d, 2H), 9.01 (s, 1H), 12.62 (bs, 1H), 13.06 (bs, 1H).

¹³C NMR (DMSO-d₆): δ 54.14, 51.83, 52.13, 112.53, 122.59, 121.18, 121.39, 122.37, 125.31, 125.58, 126.36, 127.84, 128.24, 130.96, 133.24, 133.58, 140.85, 150.42, 153.0, 164.92, 183.79.

LCMS: 486.1 (M⁺+1).

HPLC: 98.28% (H₂O/ACN; Column: C18 XDB, 4.6×250 mm).

Preparation of G-5b

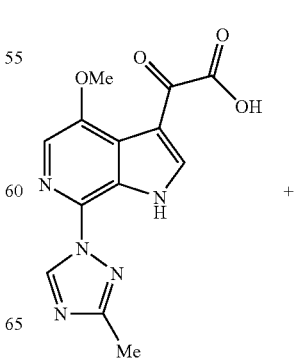

+

-continued

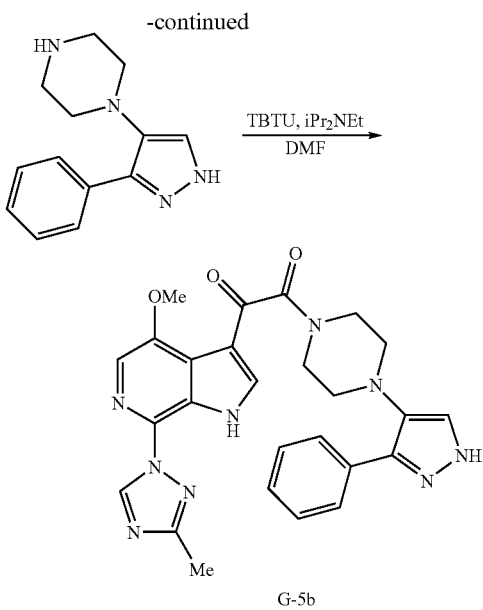

G-5b

To a stirred solution of 2-(4-methoxy-7-(3-methyl-1H-1,2,4-triazol-1-yl)-1H-pyrrolo[2,3-c]pyridin-3-yl)-2-oxoacetic acid (100 mg) in dry DMF (5 ml), G-5-In (75 mg), TBTU (0.117 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% $NaHCO_3$ and brine. The organic layer was dried over anhydrous $Na_2SO_4$ and concentrated using rotary evaporator. The resulting crude was purified by column chromatography using $MeOH/CHCl_3$ (2:8) as eluent to afford G-5b as yellow color solid $^1$H NMR (400 MHz, DMSO-$d_6$): δ 2.48 (s, 3H), 2.78 (m, 2H), 2.87 (m, 2H), 3.35 (m, 2H), 3.49 (m, 2H), 4.01 (s, 3H), 7.27 (m, 5H), 7.40-8.23 (m, 3H), 9.24 (s, 1H), 12.39 (bs, 1H), 12.63 (bs, 1H).

$^{13}$C NMR (DMSO-$d_6$): δ 14.44, 46.02, 52.82, 52.95, 57.34, 114.71, 121.57, 123.27, 124.24, 126.20, 127.35, 128.85, 130.11, 139.18, 142.67, 149.77, 161.85, 166.67, 186.09.

LCMS: 512.0 (M$^+$+1).

HPLC: 97.27% ($H_2O$/ACN; Column: C18 XDB, 4.6×250 mm).

Preparation of Compound G-6a and G-6b

Preparation of Intermediate G-In-6

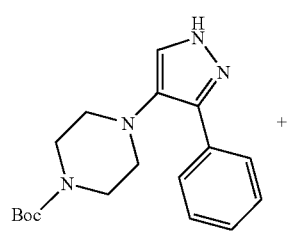

+

-continued

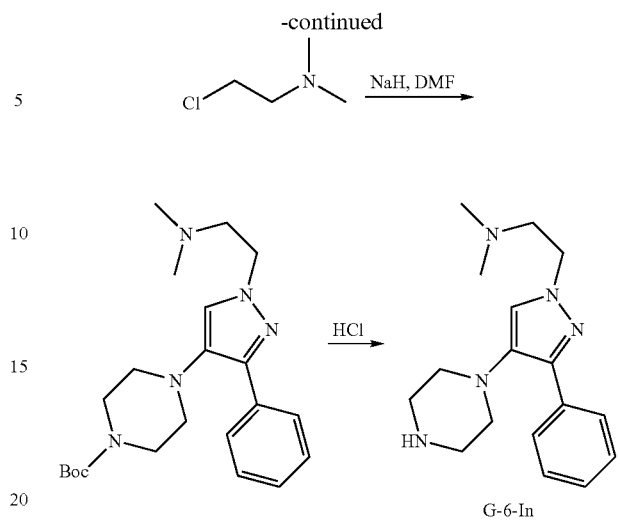

G-6-In

Step-1

To sodium hydride (0.1 g) taken in a dry 100 ml 3-necked round bottom flask cooled to 0° C., dry dimethylformamide (2 ml) was added. To the above mixture, compound tert-butyl 4-(3-phenyl-1H-pyrazol-4-yl)piperazine-1-carboxylate (0.5 g) in DMF (2 ml) was slowly added at 0° C. After 30 min, 2-chloro-N,N-dimethylethylamine (200 mg) in DMF (1 ml) was added to the above mixture. Reaction mixture was allowed to stir at room temperature for overnight, quenched with ice and extracted with ethyl acetate. The organic layer was washed with water (10 ml), brine and dried over sodiumsulphate. The organic layer was filtered and concentrated under reduced pressure. The resulting crude product was purified by column chromatography using 6% Ethyl acetate in hexane as eluant afford tert-butyl 4-(1-(2-(dimethylamino)ethyl)-3-phenyl-1H-pyrazol-4-yl)piperazine-1-carboxylate as half white solid.

$^1$H NMR (400 MHz, $CDCl_3$): δ 1.49 (s, 9H), 2.33 (s, 6H), 2.83-2.85 (t, 4H), 2.87 (t, 2H), 3.53 (t, 4H), 4.25 (t, 2H), 7.27-7.29 (m, 1H), 8.01 (s, 1H).

Step-2

BOC protected amine tert-butyl 4-(1-(2-(dimethylamino)ethyl)-3-phenyl-1H-pyrazol-4-yl)piperazine-1-carboxylate (300 mg) dissolved in dry dichloromethane (5 ml) and ethereal solution of HCl (10 ml) was added to it at 0° C. The reaction mixture was allowed reach at r.t. and stirred for an hour. The reaction mixture was neutralized with saturated sodium bicarbonate solution and extracted with dichloromethane (3×10 ml). The combined organic layer was dried over sodiumsulphate, filtered and concentrated under reduced pressure. The resulting crude product G-6-In was taken for next step without further purification.

¹H NMR (400 MHz, CDCl₃): δ 2.33 (s, 6H), 2.83-2.85 (t, 4H), 2.87 (t, 2H), 3.53 (t, 4H), 4.25 (t, 2H), 7.27-7.29 (m, 1H), 8.01 (s, 1H).

Preparation of G-6a

Preparation of G-6b

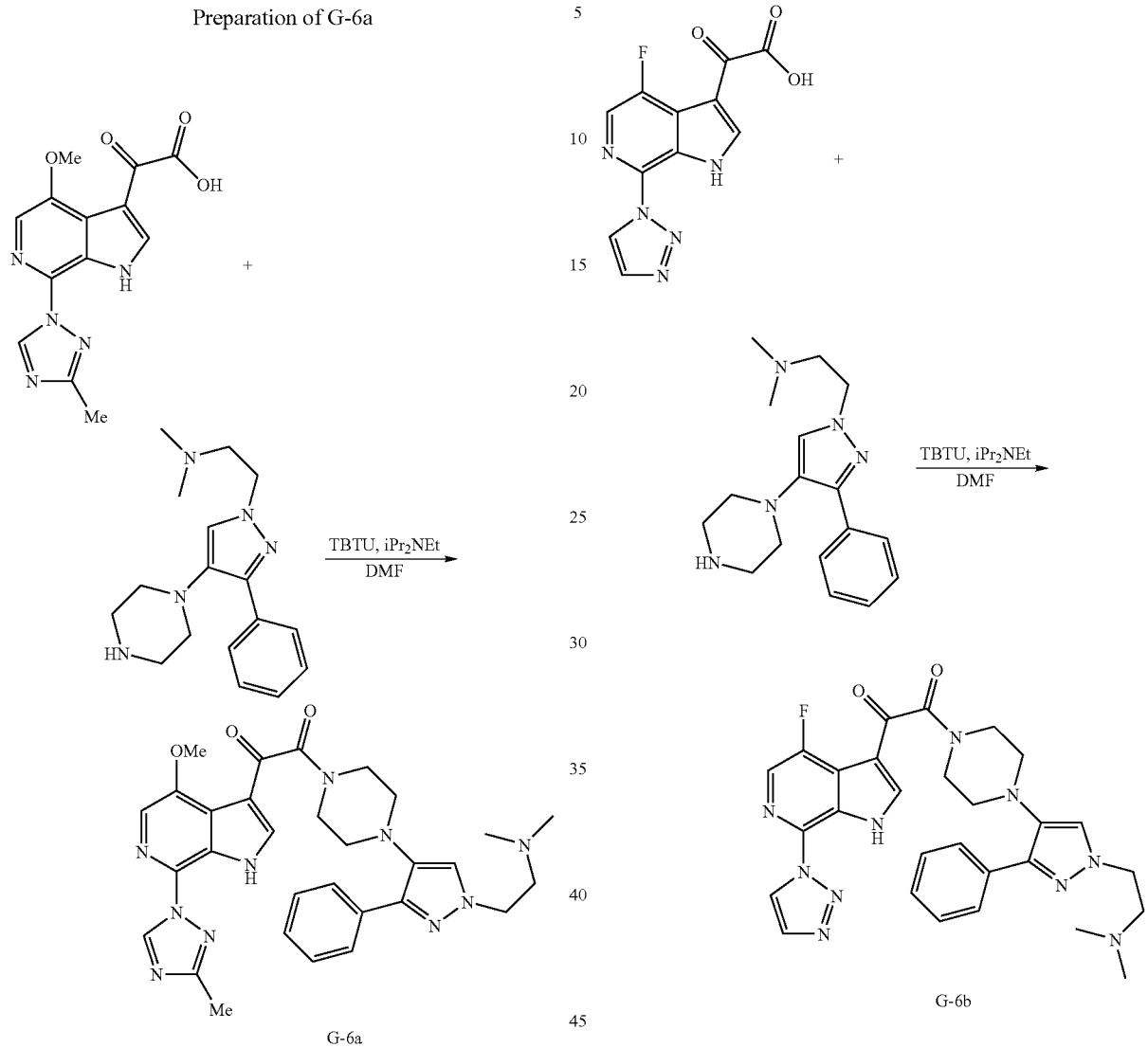

G-6a

G-6b

To 2-(4-methoxy-7-(3-methyl-1H-1,2,4-triazol-1-yl)-1H-pyrrolo[2,3-c]pyridin-3-yl)-2-oxoacetic acid (0.15 g) taken in dry DMF (3 ml), amine G-6-In (0.1 g), TBTU (0.219 g, 0.67 m mol) and Hunig's base (0.2 ml) were added. The reaction mixture was stirred at r.t. for over night. The mixture was quenched with methanol (10 ml) and the volatiles were removed under reduced pressure. The resulting oil was diluted with ethyl acetate (50 ml) and washed with 10% NaHCO₃ (2×20 ml) and brine (20 ml). The organic layer was dried over anhydrous Na₂SO₄ and concentrated under reduced pressure. The resulting crude was purified by Column chromatography using MeOH/CHCl₃ (1:9) as eluent to afford G-6a as solid product.

¹H NMR (CDCl₃): δ 2.58 (s, 8H), 2.8-3.0 (m, 5H), 3.35 (bs, 2H), 3.61 (s, 2H), 3.86 (s, 2H), 4.1 (s, 2H), 4.55 (s, 2H), 7.32 (m, 1H), 7.41 (m, 3H), 7.97 (d, 2H), 8.24 (s, 1H), 9.12 (s, 1H).

LCMS: 583.3 (M⁺+1)

HPLC: 94.1% (Water/ACN; Column: C 18, XDB, 4.6×250 mm)..

To 2-(4-fluoro-7-(1H-1,2,3-triazol-1-yl)-1H-pyrrolo[2,3-c]pyridin-3-yl)-2-oxoacetic acid (0.15 g) taken in dry DMF (3 ml), amine G-6-In (0.1 g), TBTU (0.219 g) and Hunig's base (0.2 ml) were added. The reaction mixture was stirred at r.t. for over night. The mixture was quenched with methanol (10 ml) and the volatiles were removed under reduced pressure. The resulting oil was diluted with ethyl acetate (50 ml) and washed with 10% NaHCO₃ (2×20 ml) and brine (20 ml). The organic layer was dried over anhydrous Na₂SO₄ and concentrated under reduced pressure. The resulting crude was purified by Column chromatography using MeOH/CHCl₃ (1:9) as eluent to afford G-6b as solid product.

¹H NMR (DMSO-d₆): δ 2.31 (s, 6H), 2.80 (m, 6H), 3.53 (s, 2H), 3.76 (s, 2H), 4.18 (t, 2H, J=6 Hz), 7.24 (t, 1H, J=6 Hz), 7.38 (t, 2H, 8 Hz), 7.67 (s, 1H), 7.96 (d, 2H, J=8 Hz), 8.09 (s, 1H), 8.25 (s, 1H), 8.31 (s, 1H), 9.02 (s, 1H).

LCMS: 557.1 (M⁺+1).

HPLC: 99% (0.1% HCOOH/ACN; Column: Genesis C18, 50×4.6 mm, 3µ).

Preparation of Compound G-7a and G-7b

Preparation of Intermediate G-7-In

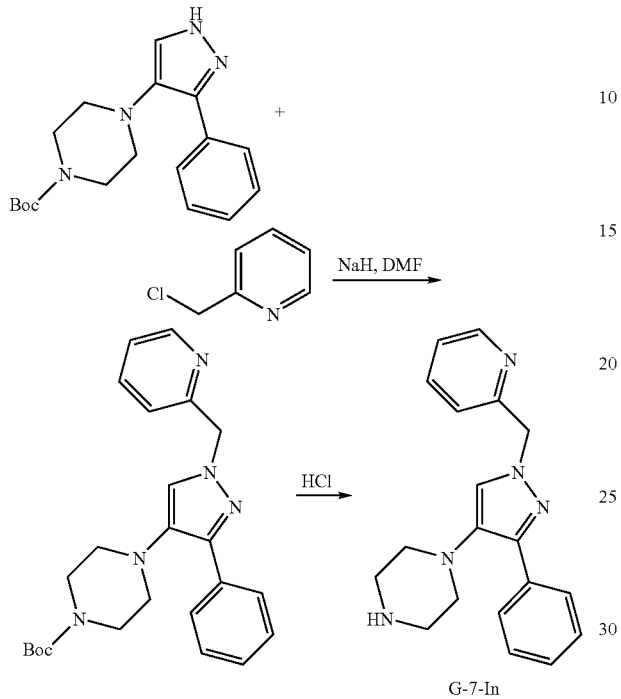

G-7-In

Step-1

To sodium hydride (0.1 g) taken in a dry 100 ml 3-necked round bottom flask cooled to 0° C. dry DMF (2 ml) was added under nitrogen. To the above mixture compound tert-butyl 4-(3-phenyl-1H-pyrazol-4-yl)piperazine-1-carboxylate (0.5 g) in DMF (2 ml) was slowly added and allowed to stir at 0° C. for 30 minutes. 2-Chloromethyl pyridine (300 mg) in DMF (1 ml) was slowly added to the above mixture at 0° C. The reaction mixture was allowed to stir at room temperature for overnight and quenched with ice. The product was extracted with ethyl acetate (3×10 ml). The combined organic layer was washed with water, brine, dried over sodiumsulphate and concentrated under reduced pressure. The resulting crude product was purified by column chromatography using 6% ethyl acetate in hexane, to afford tert-butyl 4-(3-phenyl-1-(pyridin-2-ylmethyl)-1H-pyrazol-4-yl)piperazine-1-carboxylate as half white solid.

$^1$H NMR (400 MHz, CDCl$_3$): δ 1.48 (s, 9H), 2.80 (s, 4H), 3.53 (s, 4H), 5.57 (s, 2H), 7.27-7.33 (m, 5H), 7.85-8.02 (m, 4H), 8.61 (s, 1H).

Step-2

To tert-butyl 4-(3-phenyl-1-(pyridin-2-ylmethyl)-1H-pyrazol-4-yl)piperazine-1-carboxylate (300 mg) dissolved in dry dichloromethane (5 ml), ethereal solution of HCl (10 ml) was added at 0° C. The reaction mixture was allowed to reach room temperature and stirred for an hour. The reaction mixture was neutralized with saturated sodium bicarbonate solution and extracted with dichloromethane (3×10 ml). The combined organic layer was dried over sodiumsulphate, filtered and concentrated under reduced pressure. The resulting crude product G-7-In was taken for the next step with out further purification.

$^1$H NMR (400 MHz, CDCl$_3$): δ 2.80 (s, 4H), 3.53 (s, 4H), 5.57 (s, 2H), 7.27-7.33 (m, 5H), 7.85-8.02 (m, 4H), 8.61 (s, 1H).

Preparation of G-7a

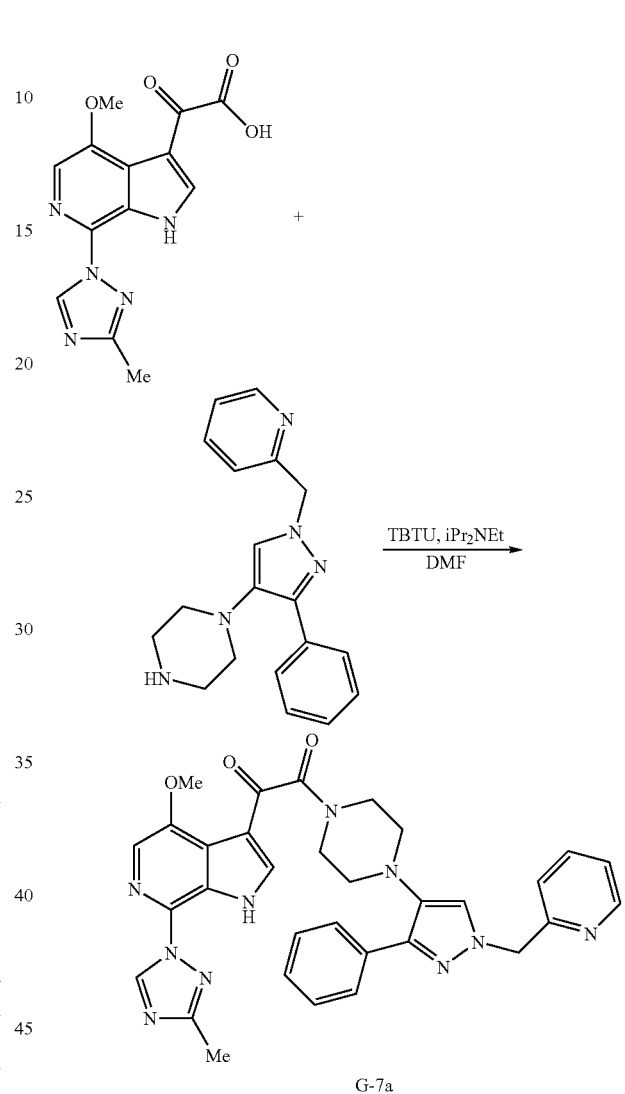

G-7a

To 2-(4-methoxy-7-(3-methyl-1H-1,2,4-triazol-1-yl)-1H-pyrrolo[2,3-c]pyridin-3-yl)-2-oxoacetic acid (0.15 g) taken in dry DMF (3 ml), amine G-7-In (0.1 g), TBTU (0.219 g) and Hunig's base (0.2 ml) were added. The reaction mixture was stirred at r.t. for over night. The mixture was quenched with methanol (10 ml) and the volatiles were removed under reduced pressure. The resulting oil was diluted with ethyl acetate (50 ml) and washed with 10% NaHCO$_3$ (2×20 ml) and brine (20 ml). The organic layer was dried over anhydrous Na$_2$SO$_4$ and concentrated using rotary evaporator. The resulting crude was purified by Column chromatography using MeOH/CHCl$_3$ (1:9) as eluent to afford G-7a as solid product.

$^1$H NMR (DMSO-d$_6$): δ 2.77 (s, 2H), 2.87 (s, 2H), 3.49 (s, 3H), 3.74 (s, 2H), 4.01 (s, 3H), 5.38 (s, 2H), 7.08 (d, 1H, J=8 Hz), 7.35 (m, 4H), 7.79 (m, 2H), 7.89 (s, 1H), 7.96 (d, 2H, J=4 Hz), 8.23 (s, 1H), 8.53 (s, 1H), 9.25 (s, 1H), 12.38 (bs, 1H).

LCMS: 603.2 (M$^+$+1)

HPLC: 96% (0.1% TFA/ACN; Column: Hypersil BDS C18, 4.6×50 mm, 5μ). .

Preparation of G-7b

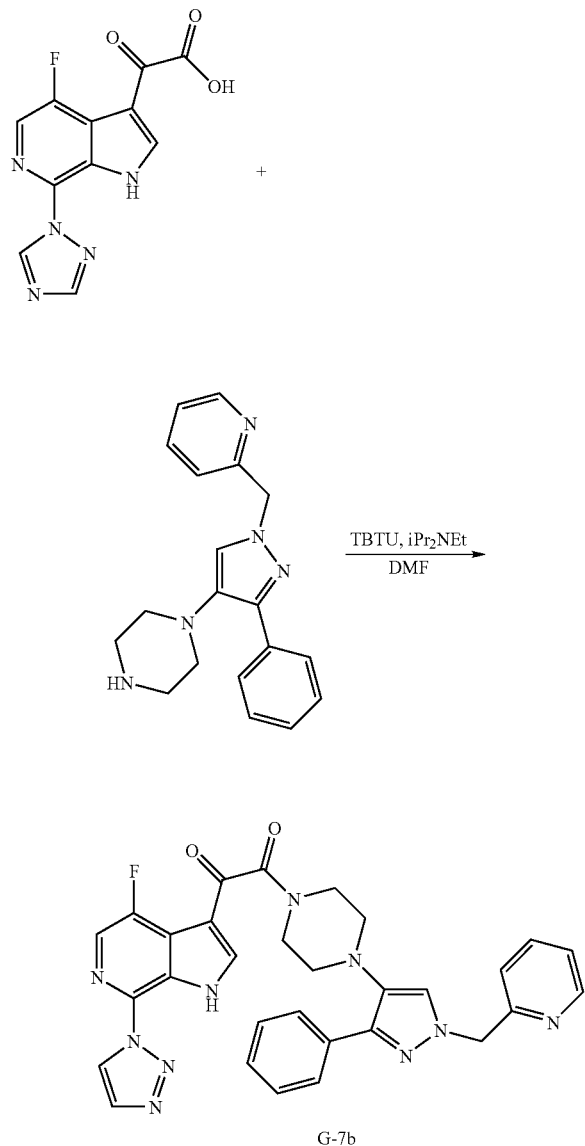

G-7b

To 2-(4-fluoro-7-(1H-1,2,3-triazol-1-yl)-1H-pyrrolo[2,3-c]pyridin-3-yl)-2-oxoacetic acid (0.15 g) taken in dry DMF (3 ml), amine G-7-In (0.1 g), TBTU (0.219 g) and Hunig's base (0.2 ml) were added. The reaction mixture was stirred at r.t. for over night. The mixture was quenched with methanol (10 mL) and the volatiles were removed under reduced pressure. The resulting oil was diluted with ethyl acetate (50 ml) and washed with 10% NaHCO₃ (2×20 ml) and brine (20 ml). The organic layer was dried over anhydrous Na₂SO₄ and concentrated using rotary evaporator. The resulting crude was purified by Column chromatography using MeOH/CHCl₃ (1:9) as eluent to afford G-7b as solid product.

¹H NMR (DMSO-d₆): δ 2.77 (s, 2H), 2.87 (s, 2H), 3.54 (s, 2H), 3.77 (s, 2H), 5.37 (s, 2H), 7.08 (d, 1H, J=8 Hz), 7.32 (m, 4H), 7.76 (s, 2H), 7.96 (d, 2H, J=8 Hz), 8.12 (s, 1H), 8.34 (d, 2H, J=12 Hz), 8.53 (s, 1H), 9.02 (s, 1H).

HPLC: 98% (0.1% TFA/ACN; Column: Hypersil BDS C18, 5µ, 4.6×50 mm).

Preparation of Compound G-8a and G-8b

Preparation of Intermediate G-8-In

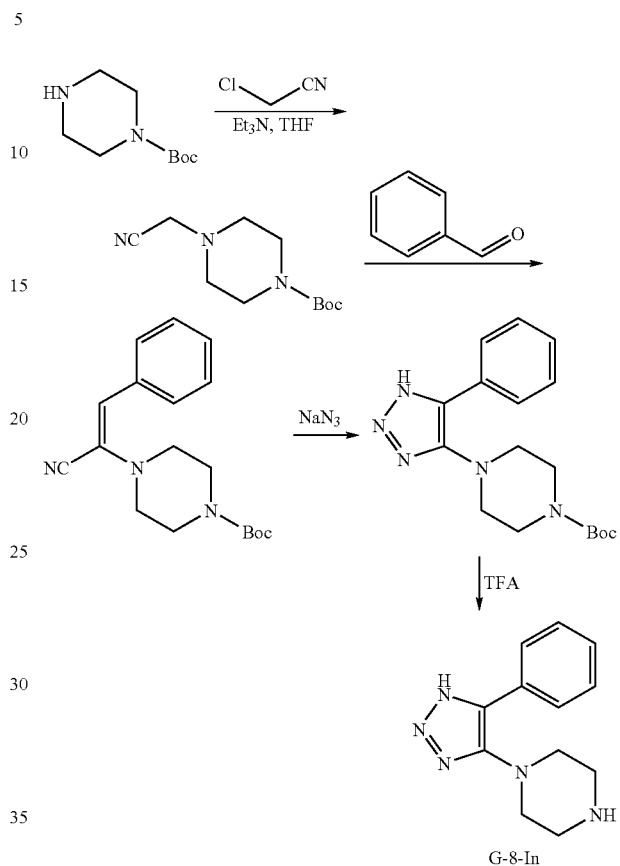

G-8-In

Step-1

To a stirred solution of N-Boc piperazine (1 g) in dry THF (20 ml), triethylamine (3 ml), followed by chloroacetonitrile (5.02 ml) were added dropwise. The reaction mixture was allowed to stir at room temperature for overnight. The solvent was removed under vacuum and residue was diluted ethyl acetate (20 ml). The organic layer was concentrated to dryness under reduced pressure to afford tert-butyl 4-(cyanomethyl)piperazine-1-carboxylate, which was used for the next reaction without further purification.

¹H NMR (400 MHz, CDCl₃): δ 1.47 (s, 9H), 2.55 (t, 4H, J=6 Hz), 3.49 (t, 4H, J=4 Hz), 3.55 (s, 2H).

GC MS: 225

Step-2

To sodium hydride (0.1 g) taken in dry DMF (5 ml), under nitrogen, compound tert-butyl 4-(cyanomethyl)piperazine-1-carboxylate (0.5 g) was added and allowed to stir at room temperature for half an hour. Benzaldehyde (280 mg) was added to the above reaction mixture and allowed to stir for 3 hours at room temperature. The reaction mixture was quenched with ice water (50 ml) and extracted with ethyl acetate (3×10 ml). The combined organic layer was washed with brine (10 ml), dried over sodium sulfate and concentrated under reduced pressure. The resulting residue was purified by column chromatography using MeOH: CH₂Cl₂ (0.5:

9.5) as an eluent to afford tert-butyl 4-(1-cyano-2-phenylvinyl)piperazine-1-carboxylate as pure product.

$^1$H NMR (400 MHz, CDCl$_3$): δ 1.48 (s, 9H), 3.09 (t, 4H, J=6 Hz), 3.56 (t, 4H, J=4 Hz), 6.22 (s, 1H), 7.30 (d, 1H, J=12 Hz), 7.38 (d, 2H, J=8 Hz), 7.55 (d, 2H, J=8 Hz).

Step-3

To a stirred solution of tert-butyl 4-(1-cyano-2-phenylvinyl)piperazine-1-carboxylate (100 mg) taken in dry DMSO (2 ml) added sodium azide (0.2 g) and heated to 110° C. overnight. The reaction mixture was carefully quenched with water (10 ml) and the reaction mixture was extracted with dichloromethane (3×10 ml). The combined organic layer was washed with brine (10 ml), dried over sodium sulfate and concentrated under reduced pressure. The resulting residue was purified by column chromatography using MeOH: CH$_2$Cl$_2$ (1:9) as an eluent to afford tert-butyl 4-(5-phenyl-1H-1,2,3-triazol-4-yl)piperazine-1-carboxylate as white solid.

$^1$H NMR (400 MHz, DMSO-d$_6$): δ 1.4 (s, 9H), 2.92 (d, 4H, J=4 Hz), 3.43 (m, 4H), 7.33 (m, 1H, J=12 Hz and 16 Hz), 7.45 (t, 2H, 8 Hz), 7.85 (d, 2H, J=8 Hz), 14.32 (s, 1H).

Step-4

To tert-butyl 4-(5-phenyl-1H-1,2,3-triazol-4-yl)piperazine-1-carboxylate (500 mg) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated NaHCO$_3$ (2×10 ml), brine, dried over Na$_2$SO$_4$. Evaporation of solvent gave desire amine G-8-In, which was used for the next reaction without further purification.

$^1$H NMR (400 MHz, DMSO-d$_6$): δ 2.84 (2s, 8H), 7.32 (t, 1H, J=8 Hz), 7.45 (t, 2H, J=6 Hz), 7.83 (d, 2H, J=8 Hz).

LCMS: 230.1 (M$^+$+1).

Preparation of G-8a

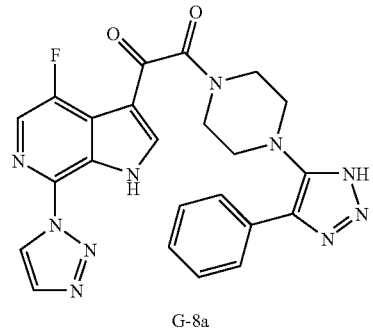

G-8a

Step-5

To a stirred solution of 2-(4-fluoro-7-(1H-1,2,3-triazol-1-yl)-1H-pyrrolo[2,3-c]pyridin-3-yl)-2-oxoacetic acid (100 mg) in dry DMF (5 ml), G-8-In (0.083 g), TBTU (0.128 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using MeOH/CHCl$_3$ (2:8) as eluent to afford G-8a as yellow color solid.

$^1$H NMR (400 MHz, DMSO-d$_6$): δ 2.99 (s, 2H), 3.09 (s, 2H), 3.57 (s, 2H), 3.8 (s, 2H), 7.35 (d, 1H, J=8 Hz), 7.45 (t, 2H, J=6 Hz), 7.87 (d, 2H, J=8 Hz), 8.12 (s, 1H), 8.34 (d, 2H, J=16 Hz), 9.02 (s, 1H), 13.08 (s, 1H), 14.4 (s, 1H).

LCMS: 487.1 (M$^+$+1).

HPLC: 95.2% (0.1% TFA/ACN; Column: Hypersil BDS C18, 4.6×50 mm).

Preparation of G-8b

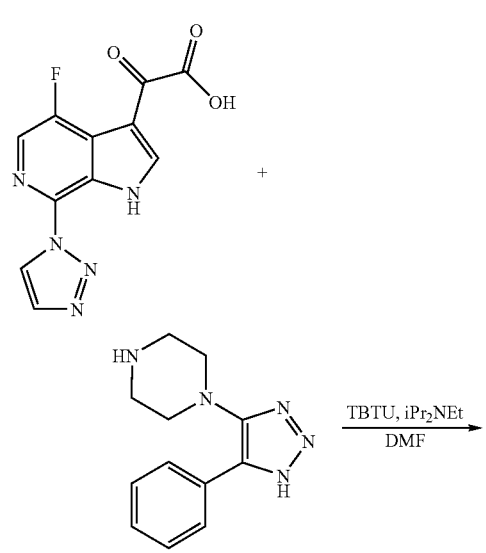

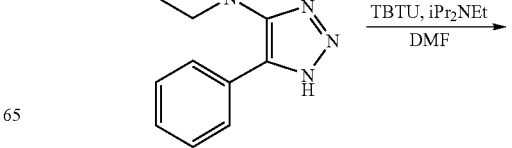

-continued

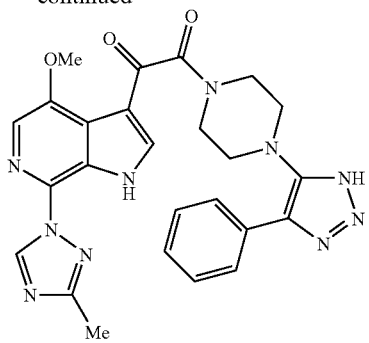

G-8b

To a stirred solution of 2-(4-methoxy-7-(3-methyl-1H-1,2,4-triazol-1-yl)-1H-pyrrolo[2,3-c]pyridin-3-yl)-2-oxoacetic acid (100 mg) in dry DMF (5 ml), G-8-In (0.076 g), TBTU (0.117 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using MeOH/CHCl$_3$ (2:8) as eluent to afford G-8b as an amorphous solid.

$^1$H NMR (400 MHz, DMSO-d$_6$): δ 2.50 (s, 3H), 2.99 (t, 2H, J=4 Hz), 3.1 (t, 2H, J=6 Hz), 3.52 (t, 2H, J=4 Hz), 3.77 (t, 2H, J=6 Hz), 4.0 (s, 3H), 7.34 (t, 1H, J=8 Hz), 7.46 (t, 2H, J=8 Hz), 7.88 (t, 3H, J=4 Hz), 8.23 (s, 1H), 9.25 (s, 1H), 12.4 (bs, 1H), 14.5 (bs, 1H).

LCMS: 513.1 (M$^+$+1).

HPLC: 90.39% (0.1% TFA/ACN; Column: Hypersil BDS C18, 4.6×50 mm).

Preparation of Compound G-9a and G-9b

Step-1

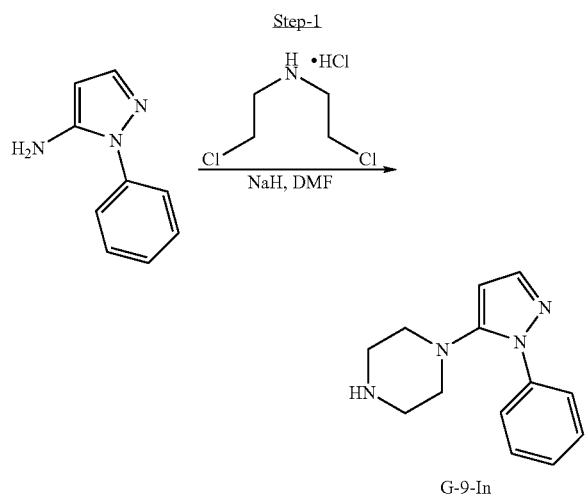

G-9-In

Sodium hydride (0.3 g) was taken in dry DMF (2 ml) and a solution of 5-amino-1-phenyl-pyrazole (0.5 g) was added slowly at 0° C. The reaction mixture was stirred for 1 hour at room temperature. Again the reaction mixture was cooled at 0° C. and a solution of bis(2-chloroethylamine) hydrochloric (0.61 g) in DMF (2 ml) was added very slowly. The reaction mixture was allowed to stir over night at room temperature. The reaction mixture was quenched with cold water (5 ml) and extracted with ethyl acetate (3×40 ml). Evaporation of solvent under reduced pressure gave crude product, which, was purified by column chromatography using MeOH/CHCl$_3$ (2:8) as eluent to afford G-9-In as pure solid product.

$^1$H NMR (400 MHz, DMSO-d$_6$): δ 2.36-3.06 (m, 8H), 5.95 (s, 1H), 7.29 (m, 1H), 7.30-8.32 (m, 5H).

$^{13}$C NMR (DMSO-d$_6$): δ 45.45, 52.50, 94.80, 122.58, 126.91, 129.47, 140.16, 140.53, 152.63.

Step-2

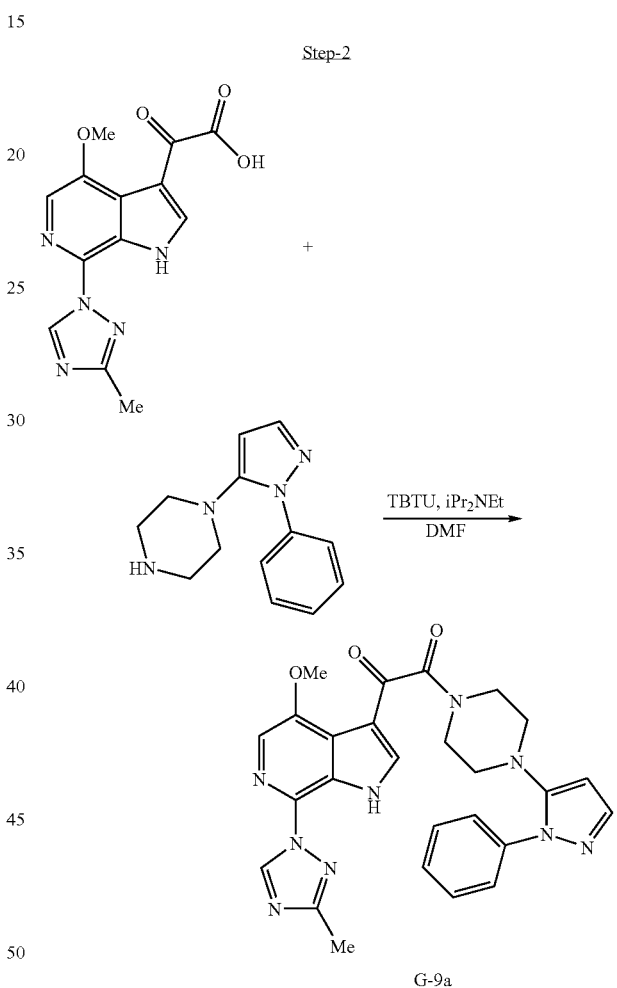

G-9a 2-(4-Methoxy-7-(3-methyl-1H-1,2,4-triazol-1-yl)-1H-pyrrolo[2,3-c]pyridin-3-yl)-2-oxoacetic acid (0.098 g), G-9-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using MeOH/CHCl$_3$ (1:9) as eluent to afford G-9a as yellow solid.

$^1$H NMR (400 MHz, CDCl$_3$): δ 2.57 (s, 3H), 2.93-2.94 (t, 2H), 3.02-3.04 (t, 2H), 3.55-3.57 (t, 2H), 3.80-3.82 (t, 2H), 4.06 (s, 3H), 5.93 (s, 1H), 7.27 (s, 1H), 7.31-7.46 (m, 5H), 7.80 (bs, 1H), 8.20 (s, 1H), 9.12 (s, 1H), 11.06 (bs, 1H).

$^{13}$C NMR (CDCl$_3$): δ 14.13, 41.03, 45.63, 50.77, 51.15, 56.97, 94.80, 115.74, 121.38, 123.13, 124.15, 127.22, 129.11, 129.70, 136.51, 139.74, 139.90, 141.28, 149.63, 150.74, 162.12, 166.39, 185.36.

LCMS: 512.1 (M$^+$+1).

HPLC: 96.12% (H$_2$O/ACN; Column: C18 XDB, 4.6×250 mm).

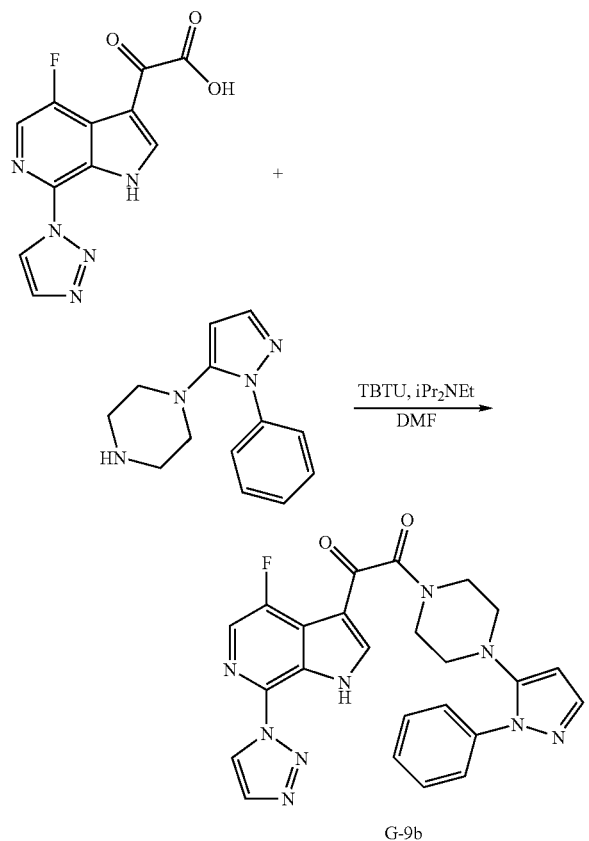

G-9b 2-(4-Fluoro-7-(1H-1,2,3-triazol-1-yl)-1H-pyrrolo[2,3-c]pyridin-3-yl)-2-oxoacetic acid (0.098 g), G-9-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using MeOH/CHCl$_3$ (1:9) as eluent to afford G-9b as yellow solid.

$^1$H NMR (400 MHz, CD$_3$OD): δ 2.93-2.95 (t, 2H), 3.01-3.04 (t, 2H), 3.57-3.59 (t, 1H), 3.79-3.81 (t, 1H), 6.10 (s, 1H), 7.41 (m, 1H), 7.51-7.75 (m, 5H), 8.01 (s, 1H), 8.21 (s, 1H), 8.39 (s, 1H), 8.93 (s, 1H).

$^{13}$C NMR (DMSO-d$_6$): δ 31.13, 45.47, 51.06, 51.42, 95.85, 113.44, 113.50, 122.34, 122.55, 122.72, 123.58, 126.27, 127.16, 129.61, 132.22, 134.42, 140.16, 140.22, 142.83, 151.26, 151.47, 154.05, 166.08, 184.49.

LCMS: 486.1 (M$^+$+1)

HPLC: 99.08% (HCOOH/ACN; Column: C18 XDB, 4.6× 50 mm)..

Preparation of G-10a and G-10b

Preparation of Intermediate G-10-In

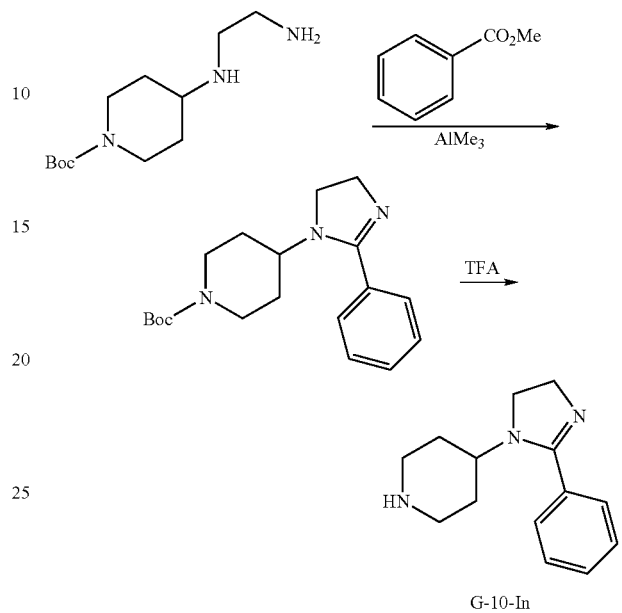

G-10-In

Step-1

To tert-butyl 4-[(2-aminoethyl)amino]piperidine-1-carboxylate (6 g) taken in dry toluene (50 ml) cooled to −10° C., trimethylaluminium was added slowly in dry toluene under nitrogen atmosphere. Reaction mixture was allowed to warm to r.t. and a second lot of solution of tert-butyl 4-[(2-aminoethyl)amino]piperidine-1-carboxylate (6 g in 50 ml of toluene) was added very slowly to it. The combined mixture was heated up to 55° C. for 30 minutes. A solution of ethyl benzoate (7.4 g in 50 ml of dry toluene) was added very-very slowly to the reaction mixture at 55° C. over a period of 40 minutes. After the completion of addition, the reaction mixture was refluxed for over night. Reaction mixture was cooled to 0° C. and water (3×50 ml) was added. The combined mixture was filtered through celite pad. The filtrate was concentrated under reduced pressure and the resulting oil was purified by column chromatography to afford tert-butyl 4-(2-phenyl-4,5-dihydro-1H-imidazol-1-yl)piperidine-1-carboxylate as a pure product.

$^1$H NMR (400 MHz, CD$_3$OD): δ 1.45 (s, 9H), 1.71-1.75 (m, 4H), 2.62 (m, 2H), 3.85 (m, 1H), 3.95 (m, 4H), 4.91 (m, 2H), 7.56-7.63 (m, 5H).

LCMS: 330.1 (M$^+$+1).

Step-2

To tert-butyl 4-(2-phenyl-4,5-dihydro-1H-imidazol-1-yl)piperidine-1-carboxylate (2.2 g) dissolved in dry dichloromethane (100 ml), TFA (50 ml) was added at 0° C. The reaction mixture was allowed to reach room temperature and stirred for over-night. The volatiles were removed and the residue was diluted with dichloromethane. The organic layer was washed with saturated NaHCO$_3$ (2×50 ml), brine (40 ml)

dried over Na$_2$SO$_4$. Evaporation of solvent afforded desired amine G-10-In which was used for the next step without further purification.

$^1$H NMR (400 MHz, DMSO-d$_6$): δ 1.88-1.91 (m, 2H), 2.15-2.21 (m, 2H), 2.85-2.90 (m, 2H), 3.22-3.25 (m, 2H), 3.88-4.05 (m, 5H), 7.46-7.74 (m, 5H), 10.98 (bs, 1H).

$^{13}$C NMR (DMSO-d$_6$): δ 26.05, 42.12, 43.31, 45.48, 51.19, 123.20, 129.07, 129.83, 133.54, 166.19.

LCMS: 229.9 (M$^+$+1).

Preparation of G-10a

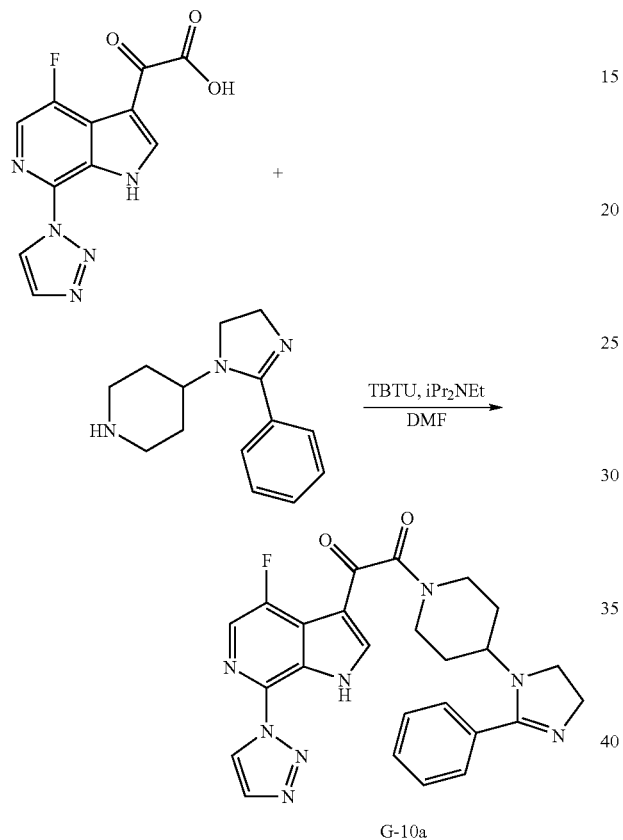

G-10a

To 2-(4-fluoro-7-(1H-1,2,3-triazol-1-yl)-1H-pyrrolo[2,3-c]pyridin-3-yl)-2-oxoacetic acid (0.09 g) in dry DMF (5 mL), amine G-10-In (0.08 g), TBTU (0.12 g) and Hunig's base (0.2 ml) were added. The reaction mixture was stirred at r.t. for over night. The mixture was quenched with methanol (10 ml) and solvents were removed under reduced pressure. The resulting oil was diluted with ethyl acetate (50 ml) and washed with 10% NaHCO$_3$ and brine. The organic layer was dried over anhydrous Na$_2$SO$_4$ and concentrated under reduced pressure. The resulting semi-solid was purified by column chromatography using MeOH/CHCl$_3$ (1:9) as eluent to afford G-10a as solid.

$^1$H NMR (400 MHz, CD$_3$OD): δ 2.22 (m, 4H), 3.77 (m, 4H), 4.2 (m, 2H), 4.6 (m, 2H), 7.70 (m, 5H), 8.01 (s, 1H), 8.43 (s, 1H), 8.5 (s, 1H), 8.93 (s, 1H).

$^{13}$C NMR (CD$_3$OD): δ 30.14, 30.89, 41.25, 45.92, 46.23, 48.36, 79.47, 114.44, 124.50, 124.69, 124.96, 126.02, 126.30, 128.26, 129.21, 129.56, 130.32, 132.84, 134.46, 147.54, 153.38, 155.95, 168.48, 185.58.

LCMS: 487.1 (M$^+$+1).

HPLC: 98.14% (NH$_4$OAc/ACN; Column: C18 XDB, 4.6× 250 mm).

Preparation of G-10b

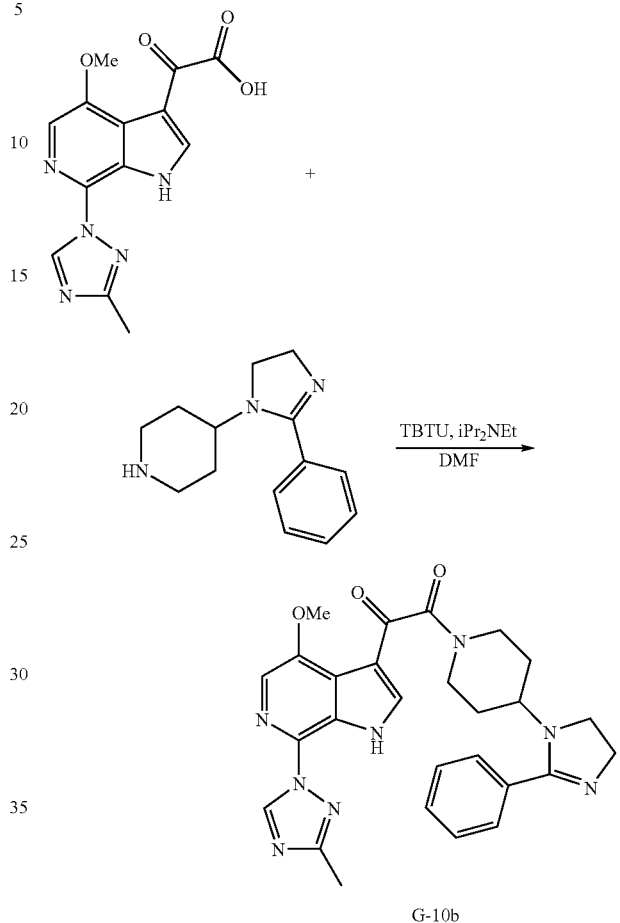

G-10b

To 2-(4-methoxy-7-(3-methyl-1H-1,2,4-triazol-1-yl)-1H-pyrrolo[2,3-c]pyridin-3-yl)-2-oxoacetic acid (0.1 g) taken in dry DMF (5 ml), G-10-In (0.076 g), TBTU (0.117 g) and Hunig's base (0.2 ml) were added. The reaction mixture was stirred at r.t. for over night. The mixture was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The crude was purified by column chromatography using MeOH/CHCl$_3$ (1:9) as eluent to afford G-10b as solid product.

$^1$H NMR (400 MHz, CD$_3$OD): δ 2.55 (s, 3H), 2.76-2.81 (bs, 1H), 3.03-3.09 (t, 1H), 3.78-3.97 (m, 6H), 4.65 (s, 3H), 4.90 (d, 1H), 7.57-7.58 (d, 5H), 7.83 (s, 1H), 8.29 (s, 1H), 9.22 (s, 1H).

$^{13}$C NMR (CD$_3$OD): δ 13.73, 30.31, 30.77, 41.48, 45.62, 46.36, 48.36, 48.58, 54.70, 57.35, 115.64, 122.02, 124.98, 127.28, 129.17, 130.08, 130.54, 131.53, 132.05, 141.34, 143.24, 151.20, 162.78, 168.53, 168.59, 187.35.

LCMS: 513.1 (M$^+$+1)

HPLC: 95.26% (NH$_4$OAc/ACN; Column: C18 XDB, 4.6× 250 mm). .

Preparation of G-11a and G-11b

Preparation of Intermediate G-11-In

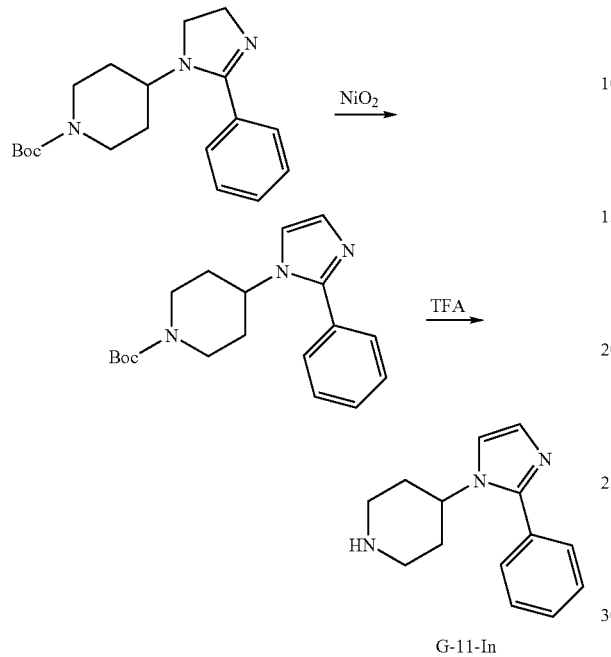

G-11-In

Step-1

Tert-butyl-4-(2-phenyl-4,5-dihydro-1H-imidazol-1-yl)piperidine-1-carboxylate (0.1 g) and nickel peroxide was dissolved in dry benzene (20 ml) and refluxed at 100° C. for over-night. Reaction mixture was allowed to come to room temperature, filtered through a celite pad and washed with CHCl$_3$ (2×20 ml). The organic solvent removed under reduced pressure gave an oil, which was purified by column chromatography using ethyl acetate. Evaporation of solvent gave pure product, tert-butyl 4-(2-phenyl-1H-imidazol-1-yl)piperidine-1-carboxylate.

$^1$H NMR (400 MHz, CD$_3$OD): δ 1.47 (s, 9H), 1.89-1.96 (m, 4H), 3.0 (m, 2H), 4.23 (m, 2H), 4.32 (d, 1H), 7.08 (d, 1H), 7.38 (s, 1H), 7.52-7.55 (m, 5H).

LCMS: 328.1 (M$^+$+1).

Step-2 tert-Butyl 4-(2-phenyl-1H-imidazol-1-yl)piperidine-1-carboxylate (600 mg) dissolved in dry dichloromethane (10 ml) and TFA (5 ml) was added to it at 0° C. The reaction mixture was allowed stir at room temperature and stirred for over-night. The volatiles were completely removed and the residue was diluted with dichloromethane. The organic layer was washed with saturated NaHCO$_3$ (2×10 ml) and brine (20 ml), dried over Na$_2$SO$_4$. Evaporation of solvent afforded desired amine G-11-In which was used for the next step without further purification.

$^1$H NMR (400 MHz, CD$_3$OD): δ 1.88-2.02 (m, 4H), 2.64 (m, 2H), 3.31 (m, 2H), 4.91 (m, 1H), 7.09 (d, 1H), 7.37 (d, 1H), 7.47-7.56 (m, 5H).

$^{13}$C NMR (CD$_3$OD): δ 34.83, 43.73, 46.16, 55.27, 62.18, 118.47, 128.36, 128.47, 128.64, 129.52, 129.61, 130.33, 130.46, 148.59.

Preparation of G-11a

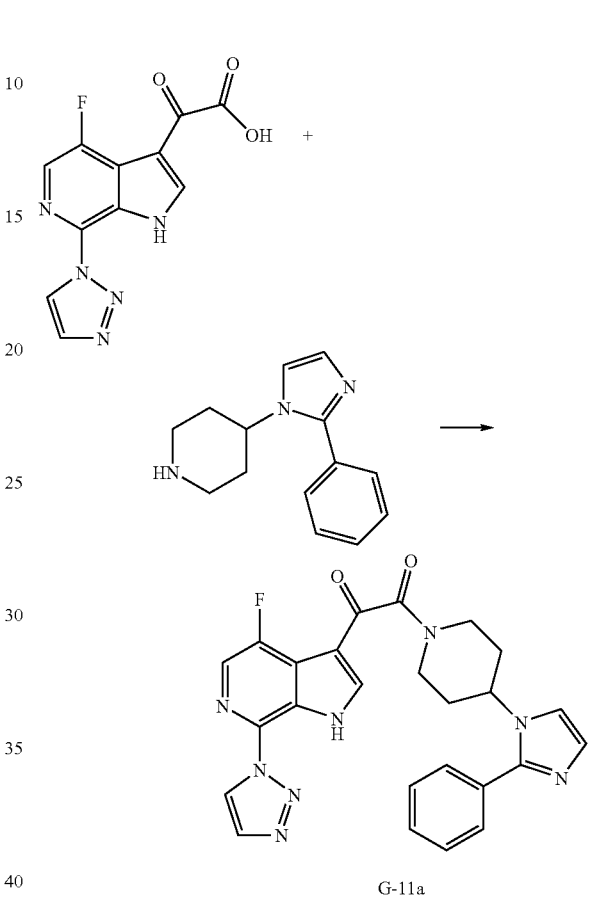

G-11a

To 2-(4-fluoro-7-(1H-1,2,3-triazol-1-yl)-1H-pyrrolo[2,3-c]pyridin-3-yl)-2-oxoacetic acid (0.1 g dissolved in dry DMF (5 m), amine G-11-In (0.074 g), TBTU (0.12 g) and Hunig's base (0.2 ml) were added and allowed to stir at r.t. for over night. The mixture was quenched with methanol (10 ml) and the volatiles were removed under reduced pressure. The resulting oil was diluted with ethyl acetate (50 ml) and washed with 10% NaHCO$_3$ (2×20 ml) and brine (20 ml). The organic layer was dried over anhydrous Na$_2$SO$_4$ and concentrated under reduced pressure. The resulting crude was purified by Column chromatography using MeOH/CHCl$_3$ (1:9) as eluent to afford G-11a as solid product.

$^1$H NMR (400 MHz, CD$_3$OD): δ 2.05-2.17 (m, 4H), 2.94 (bs, 1H), 3.27-3.32 (bs, 1H), 3.95 (d, 1H), 4.73 (bs, 1H), 4.90 (d, 1H), 7.11 (s, 1H), 7.44-7.92 (m, 5H), 8.01 (s, 1H), 8.21 (s, 1H), 8.41 (s, 1H), 8.92 (s, 1H).

$^{13}$C NMR (CD$_3$OD): δ 33.69, 34.54, 41.73, 46.44, 55.03, 114.80, 114.85, 118.64, 123.64, 127.23, 127.51, 128.92, 130.02, 130.40, 130.60, 131.52, 134.80, 141.91, 148.70, 167.63, 185.78.

LCMS: 485.1 (M$^+$+1)

HPLC: 95.38% (0.1% TFA/ACN; Column: C18 BDS, 4.6× 250 mm). .

Preparation of G-11b

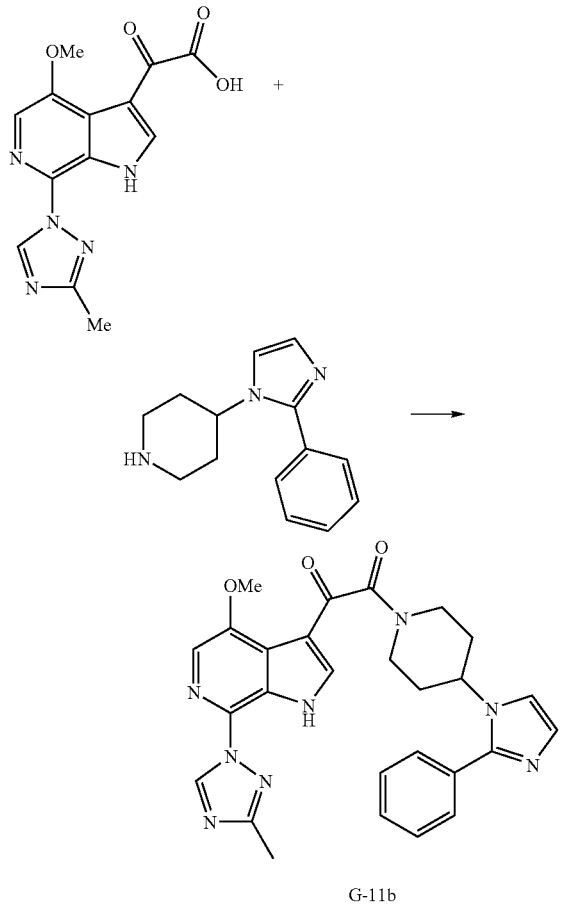

G-11b

Preparation of Compound G-12a and G-12b

Preparation of Intermediate G-12-In

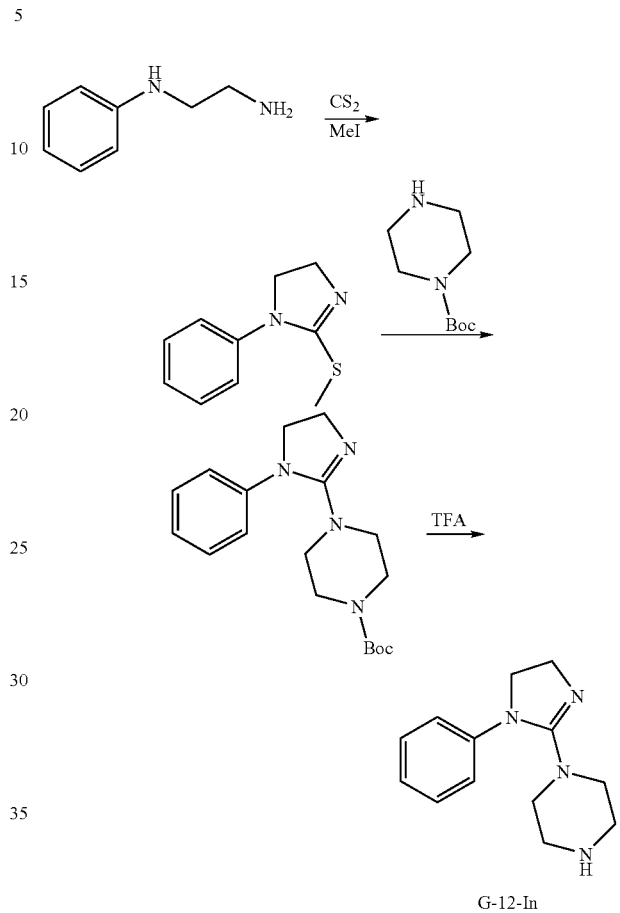

G-12-In

To 2-(4-methoxy-7-(3-methyl-1H-1,2,4-triazol-1-yl)-1H-pyrrolo[2,3-c]pyridin-3-yl)-2-oxoacetic acid (0.1 g) dissolved in dry DMF (5 ml), amine G-11-In (0.079 g), TBTU (0.11 g) and Hunig's base (0.1 ml) were added and the reaction mixture was stirred at r.t. for over night. The mixture was quenched with methanol (10 ml) and the volatiles were removed under reduced pressure. The resulting oil was diluted with ethyl acetate (50 ml) and washed with 10% NaHCO$_3$ (2×20 ml) and brine (20 ml). The organic layer was dried over anhydrous Na$_2$SO$_4$ and concentrated under reduced pressure. The resulting crude was purified by Column chromatography using MeOH/CHCl$_3$ (1:9) as eluent to afford G-11b as solid product.

$^1$H NMR (400 MHz, CD$_3$OD): δ 2.05-2.20 (m, 4H), 2.55 (s, 3H), 2.94-3.20 (t, 1H), 3.23-3.27 (bs, 1H), 3.87 (d, 1H), 4.06 (s, 3H), 4.51 (bs, 1H), 4.91 (d, 1H), 7.11 (s, 1H), 7.43 (s, 1H), 7.53-7.55 (m, 5H), 7.81 (s, 1H), 8.28 (s, 1H), 9.20 (s, 1H).

$^{13}$C NMR (CD$_3$OD): δ 13.77, 33.80, 34.32, 41.68, 46.43, 55.09, 57.38, 115.74, 118.62, 122.15, 124.64, 125.30, 128.96, 130.01, 130.40, 130.56, 131.03, 131.56, 139.49, 142.80, 148.70, 151.08, 162.93, 168.46, 187.54.

LCMS: 511.2 (M$^+$+1).

HPLC: 95.35% (NH$_4$OAc/ACN; Column: C18 XDB, 250×4.6 mm).

Step-1

To a stirred solution of N-phenyl ethylenediamine (2 g) in absolute alcohol (30 ml), carbon disulphide (2.23 g) was added under nitrogen. The reaction mixture was refluxed for three hours and was brought to room temperature. The resulting white solid (thioamide intermediate) was filtered, dried and taken for the next step without further purification.

To a stirred solution of thioamide intermediate (2 g) in dry methanol (20 ml), methyl iodide (3.1 g) was added. The reaction mixture was refluxed for three hours. The volatiles were removed under vacuum and the resulting white color solid, 2-(methylthio)-1-phenyl-4,5-dihydro-1H-imidazole, was taken for the next step without further purification.

$^1$H NMR (400 MHz, DMSO-d6): δ 2.65 (s, 3H), 4.06 (t, 2H), 4.38 (t, 2H), 7.46-7.57 (m, 5H).

LCMS: 192.9 (M$^+$+1).

Step-2

To a stirred solution of 2-(methylthio)-1-phenyl-4,5-dihydro-1H-imidazole (100 mg) in toluene (5 ml), N-Boc piperazine (0.48 g) was added and whole reaction mixture was refluxed for overnight. The solvent was removed completely and ethyl acetate was added to the residue. The resulting white solid, tert-butyl 4-(1-phenyl-4,5-dihydro-1H-imidazol-2-yl)piperazine-1-carboxylate, was filtered, dried and used for the next reaction without further purification.

$^1$H NMR (400 MHz, CD$_3$OD): δ 1.49 (s, 9H), 3.17 (m, 4H), 3.32 (m, 4H), 3.89 (t, 2H), 4.25 (t, 2H), 7.40-7.56 (m, 5H).

LCMS: 331.1 (M$^+$+1).

Step-3

To tert-butyl 4-(1-phenyl-4,5-dihydro-1H-imidazol-2-yl) piperazine-1-carboxylate (500 mg) taken in dry dichloromethane (10 ml), TFA (5 ml) was added at 0° C. The reaction mixture was allowed reach at room temperature and stirred for over-night. The volatiles were removed using reduced pressure and the residue was diluted with dichloromethane (10 ml). The organic layer was washed with saturated NaHCO$_3$ (2×10 ml), brine (20 ml) and was dried over Na$_2$SO$_4$. Evaporation of solvent gave desire amine G-12-In which was taken for the next reaction without further purification.

$^1$H NMR (400 MHz, DMSO-d$_6$): δ 2.52 (m, 4H), 3.06 (m, 4H), 3.66 (t, 2H), 4.04 (t, 2H), 7.18-7.44 (m, 5H).

LCMS: 230.9 (M$^+$+1).

Preparation of G-12a

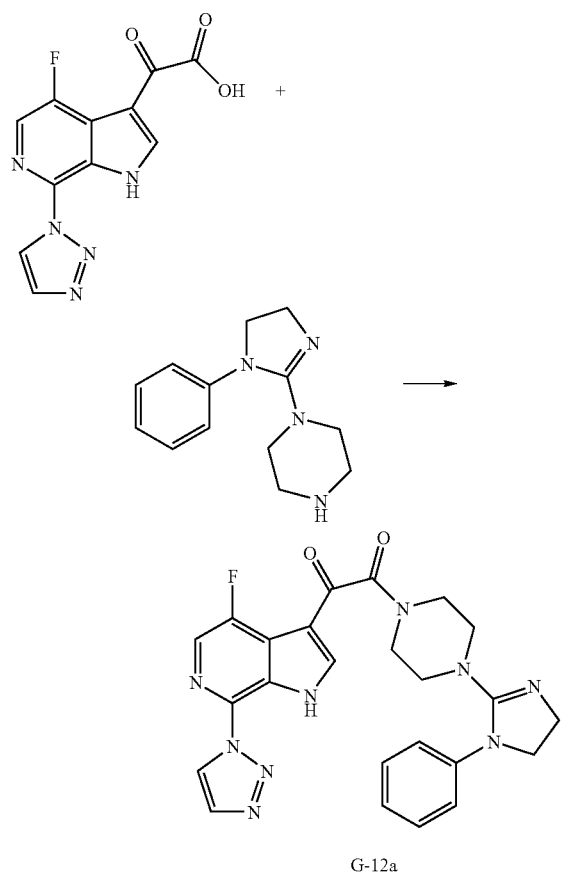

G-12a

To a stirred solution of 2-(4-fluoro-7-(1H-1,2,3-triazol-1-yl)-1H-pyrrolo[2,3-c]pyridin-3-yl)-2-oxoacetic acid (50 mg) in dry DMF (5 ml), amine G-12-In (41 mg), TBTU (64 mg) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using MeOH/CHCl$_3$ (1:9) as eluent to afford G-12a as yellow color solid.

$^1$H NMR (DMSO-d$_6$): δ 3.21 (d, 2H), 3.34 (m, 4H), 3.66 (d, 2H), 3.73-3.77 (t, 2H), 4.14-4.18 (t, 2H), 7.30-7.50 (m, 5H), 8.11 (s, 1H), 8.28 (s, 1H), 8.35 (s, 1H), 9.0 (s, 1H).

LCMS: 488.1 (M$^+$+1).

HPLC: 99.66% (0.1% TFA/ACN; Column: C18 BDS, 4.6× 50 mm).

Preparation of G-12b

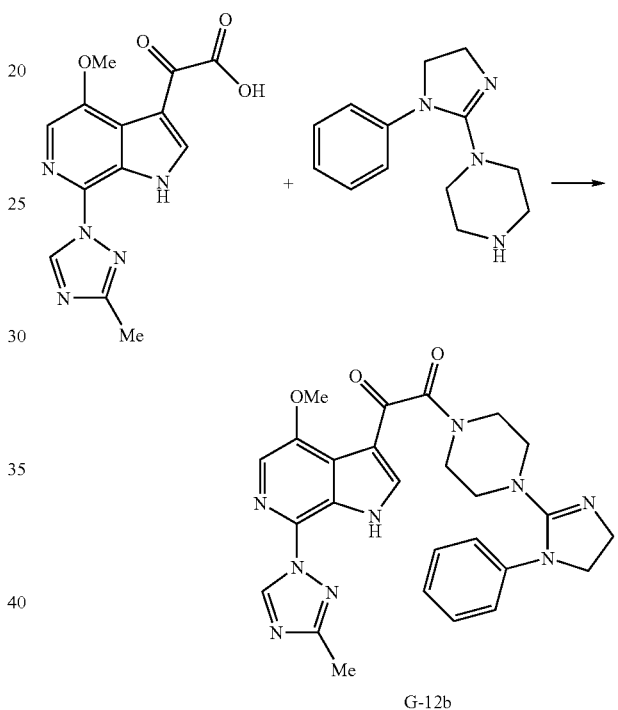

G-12b

To a stirred solution of 2-(4-methoxy-7-(3-methyl-1H-1,2,4-triazol-1-yl)-1H-pyrrolo[2,3-c]pyridin-3-yl)-2-oxoacetic acid (50 mg) in dry DMF (5 ml), amine G-12-In (38 mg), TBTU (0.117 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using MeOH/CHCl$_3$ (1:9) as eluent to afford G-12b as yellow color solid.

$^1$H NMR (DMSO-d$_6$): δ 2.72 (s, 3H), 3.06 (d, 2H), 3.18 (d, 2H), 3.31 (t, 2H), 3.33-3.62 (m, 4H), 3.90 (t, 2H), 3.95 (s, 3H), 7.02-7.26 (m, 5H), 7.82 (s, 1H), 8.18 (s, 1H), 9.28 (s, 1H), 11.89 (bs, 1H).

LCMS: 514.2 (M$^+$+1).

HPLC: 99.25% (NH$_4$OAc/ACN; Column: C18 XDB, 250×4.6 mm).

Preparation of G-13a and G-13b
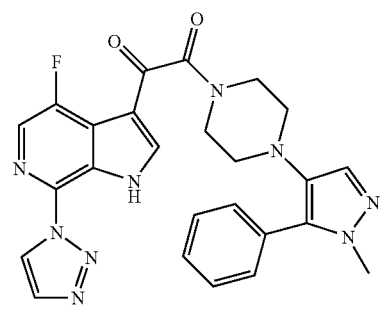
G-13a
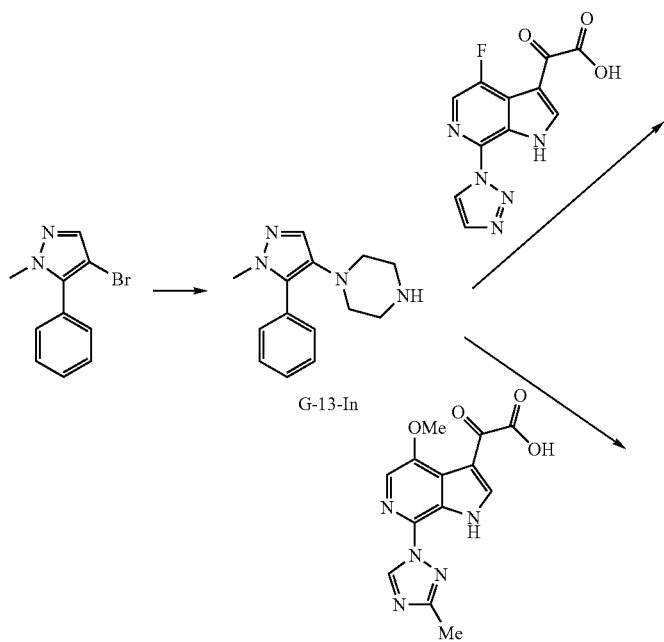
G-13-In
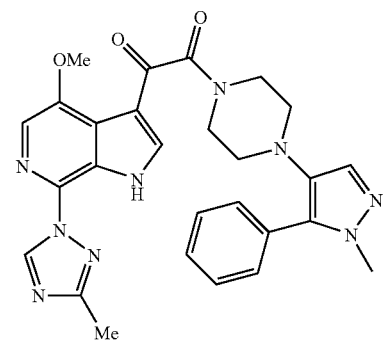
G-13b

Step-1

To a solution of 4-bromo-1-methyl-5-phenyl-1H-pyrazole (0.2 g) in dry toluene (5 ml), piperizene (0.36 g) and sodium tert-butoxide (0.12 g) were added and reaction mixture was degassed for 5 minute. Then, BINAP (0.05 g), Pd(dba)$_2$ and DMF (0.1 ml) were added to the above reaction mixture and again degassed with nitrogen for 5 minute. Reaction mixture was allowed to reflux for over-night. The reaction mixture was filtered through a celite pad and washed with ethyl acetate (2×20 ml). The volatiles ware removed under reduced pressure. The resulting crude product was purified by column chromatography using MeOH/CHCl$_3$ (2:8) as eluent to afford G-13-In as light yellow oil.

$^1$H NMR (400 MHz, DMSO-d$_6$): δ 2.50 (m, 4H), 2.64 (m, 4H), 3.67 (s, 3H), 7.30 (s, 1H), 7.36-7.53 (m, 5H).

$^{13}$C NMR (CD$_3$OD): δ 30.77, 41.09, 46.34, 48.37, 52.90, 53.78, 54.09, 129.88, 130.65, 131.21, 134.72, 135.53, 136.39, 163.08.

LCMS: 242.9 (M$^+$+1).

Step-2

To a stirred solution of 2-(4-fluoro-7-(1H-1,2,3-triazol-1-yl)-1H-pyrrolo[2,3-c]pyridin-3-yl)-2-oxoacetic acid (150 mg) in dry DMF (5 ml), G-13-In (96 mg), TBTU (175 mg) and DIPEA (0.2 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using MeOH/CHCl$_3$ (1:9) as eluent to afford G-13a as yellow color solid.

$^1$H NMR (400 MHz, DMSO-d$_6$): δ 2.50 (t, 2H), 2.70 (t, 2H), 3.38 (bs, 2H), 3.61 (t, 2H), 3.69 (s, 3H), 7.39 (s, 1H), 7.42-7.55 (m, 5H), 8.12 (s, 1H), 8.31 (bs, 1H), 9.01 (s, 1H), 13.05 (bs, 1H).

LCMS: 500.2 (M$^+$+1).

HPLC: 97.37% (0.1% TFA/ACN; Column: C18 BDS 4.6× 50 mm).

To a stirred solution of 2-(4-methoxy-7-(3-methyl-1H-1,2,4-triazol-1-yl)-1H-pyrrolo[2,3-c]pyridin-3-yl)-2-oxoacetic acid (150 mg) in dry DMF (5 ml), G-13-In (96 mg), TBTU (0.117 g) and DIPEA (0.2 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using MeOH/CHCl$_3$ (1:9) as eluent to afford G-13b as yellow color solid.

$^1$H NMR (400 MHz, CDCl$_3$): δ 2.56 (s, 3H), 2.84 (s, 1H), 2.93 (bs, 1H), 3.50 (bs, 2H), 3.77 (bs, 4H), 4.09 (s, 3H), 7.27 (s, 1H), 7.37-7.48 (m, 5H), 8.18 (s, 1H), 9.10 (s, 1H), 11.03 (s, 1H).

LCMS: 526.2 (M$^+$+1).

HPLC: 94.59% (NH$_4$OAc/ACN; Column: C18 XDB, 4.6× 250 mm).

Preparation of Compound G-14a and G-14b

Preparation of Intermediate G-14-In

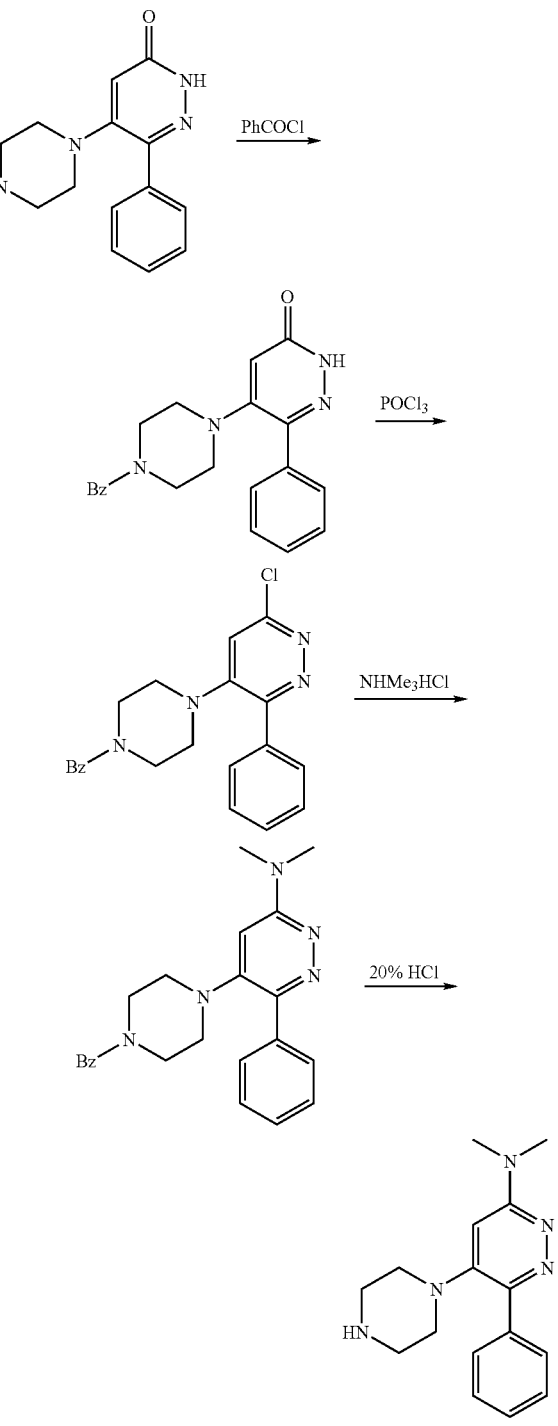

G-14-In

Step-1

A 100 ml three necked round bottom flask was charged with 6-phenyl-5-(piperazin-1-yl)pyridazin-3(2H)-one (2.0 g), dry potassium carbonate (2.1 g) and dry DMF (150 ml) under nitrogen atmosphere. The reaction mixture was stirred at room temperature and benzoylchloride (1.5 g) was added into the reaction mixture very slowly. The reaction mixture was heated 120° C. for 4 hrs. The progress of reaction was monitored by TLC. After consumption of starting material reaction mixture was cooled to 0° C., ice-cold water (20.0 ml) was added to reaction mixture and the organic compound was extracted into ethylacetate (4×20 ml). Combined organic layers were dried ($Na_2SO_4$) and concentrated. The crude material was purified by column chromatography using MeOH/$CHCl_3$ (1:9) as eluent to afford 5-(4-benzoylpiperazin-1-yl)-6-phenylpyridazin-3 (2H)-one.

$^1$H NMR (400 MHz, $CDCl_3$): δ 2.94-3.41 (bs, 4H), 3.49-3.73 (bs, 4H), 6.33 (s, 1H), 7.27-7.68 (m, 10H), 11.5 (bs, 1H).

LCMS: 361.0 ($M^+$+1).

Step-2

To 5-(4-benzoylpiperazin-1-yl)-6-phenylpyridazin-3 (2H)-one (1.3 g) taken in single necked round bottom flask, phosphorusoxychloride (10 ml) was added and the mixture was heated to 80° C. for 4 hrs. Reaction mixture was cooled to room temperature and concentrated to remove excess phosphorus oxychloride. Residue was slowly poured into ice and neutralized with solid sodium bicarbonate. The mixture was extracted with Ethyl acetate (3×100 ml). The combined organic layer was dried over anhydrous sodium sulphate and concentrated to afford (4-(6-chloro-3-phenylpyridazin-4-yl) piperazin-1-yl)(phenyl)methanone as white solid.

$^1$H NMR (400 MHz, $CDCl_3$): δ 2.96-3.09 (bs, 4H), 3.43-3.51 (bs, 2H), 3.80 (bs, 2H), 6.94 (s, 1H), 7.26-7.84 (m, 10H).

LCMS: 378.8 ($M^+$−1).

Step-3

To (4-(6-chloro-3-phenylpyridazin-4-yl)piperazin-1-yl) (phenyl)methanone (1 g) dissolved in methanol (40 ml), and dimethyl amine in THF (10 ml) was added under nitrogen atmosphere and the reaction mixture was heated to 60° C. for 18 hrs. The progress of reaction was monitored by TLC. After consumption of starting material, reaction mixture was cooled to room temperature and neutralized with solid sodium bicarbonate. The mixture was extracted with dichloromethane (3×10 ml). The combined organic layer was dried over anhydrous sodium sulphate and concentrated to afford (4-(6-(dimethylamino)-3-phenylpyridazin-4-yl)piperazin-1-yl)(phenyl)methanone as yellow liquid.

LCMS: 387.9 ($M^+$+1).

Step-4

To (4-(6-(dimethylamino)-3-phenylpyridazin-4-yl)piperazin-1-yl)(phenyl)methanone (18 g) taken in round bottom flask, concentrated hydrochloric acid (10 ml) was added. The reaction mixture was stirred at 85° C. for 6 hrs. The progress of reaction was monitored by TLC. After consumption of starting material, reaction mixture was cooled to room temperature. Residue was slowly poured into ice and neutralized with solid sodium bicarbonate. The mixture was extracted with dichloromethane (3×10 ml). The combined organic layer was dried over anhydrous sodium sulphate and concentrated to afford G-14-In as yellow liquid.

$^1$H NMR (400 MHz, $CDCl_3$): δ 2.46 (s, 6H), 2.96-3.13 (d, 4H), 3.14-3.49 (d, 4H), 6.14 (s, 1H), 7.27-7.43 (m, 5H), 7.87 (s, 1H).

LCMS: 283.9 ($M^+$+1).

Preparation of G-14a

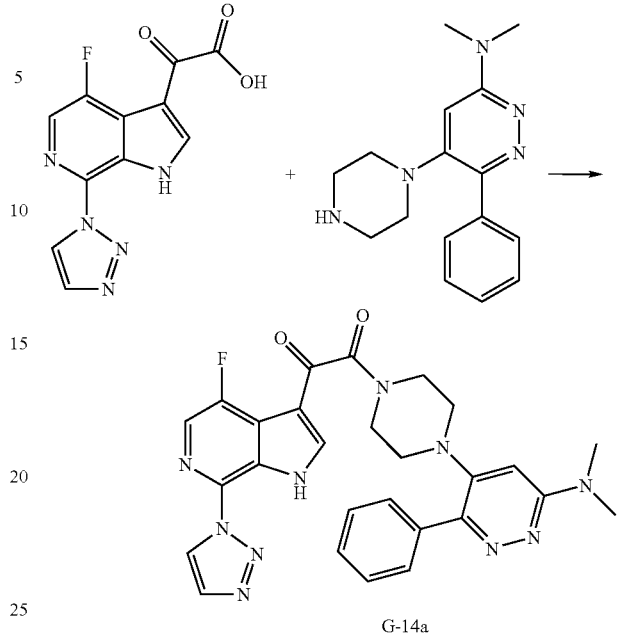

G-14a 2-(4-Fluoro-7-(1H-1,2,3-triazol-1-yl)-1H-pyrrolo[2,3-c] pyridin-3-yl)-2-oxoacetic acid (0.098 g), G-14-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% $NaHCO_3$ and brine. The organic layer was dried over anhydrous $Na_2SO_4$ and concentrated under reduced pressure. The resulting crude was purified by column chromatography using MeOH/$CHCl_3$ (1:9) as eluent to afford G-14a as yellow solid.

$^1$H NMR (400 MHz, DMSO-$d_6$): δ 2.90 (t, 2H), 3.0 (t, 2H), 3.11 (s, 6H), 3.31 (m, 2H), 3.31 (t, 2H), 6.38 (s, 1H), 7.36-7.47 (m, 5H), 8.12 (s, 1H), 8.31 (t, 2H), 9.01 (s, 1H), 13.01 (bs, 1H).

LCMS: 541.1 ($M^+$+1).

HPLC: 99.64% (0.1% TFA/ACN; Column: BDS C18, 4.6×50 mm).

Preparation of G-14b

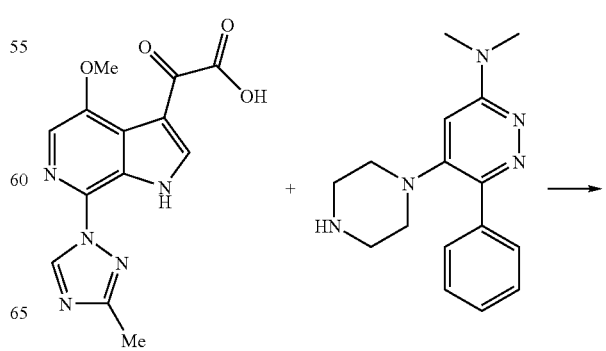

-continued

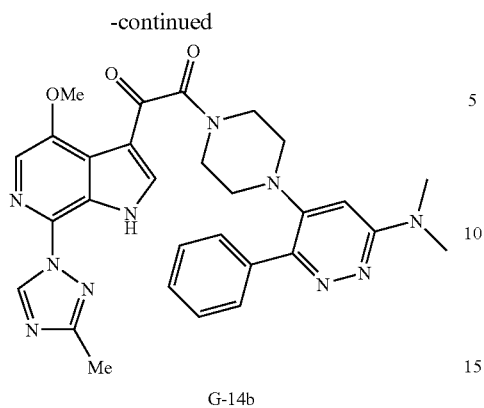

G-14b 2-(4-Methoxy-7-(3-methyl-1H-1,2,4-triazol-1-yl)-1H-pyrrolo[2,3-c]pyridin-3-yl)-2-oxoacetic acid (0.098 g), G-14-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using MeOH/CHCl$_3$ (1:9) as eluent to afford G-14b as yellow solid.

$^1$H NMR (400 MHz, DMSO-d$_6$): δ 2.50 (s, 3H), 2.91 (t, 2H), 2.99 (t, 2H), 3.12 (s, 6H), 3.35 (m, 2H), 3.58 (t, 2H), 3.99 (s, 3H), 6.40 (s, 1H), 7.35-7.47 (m, 5H), 7.89 (s, 1H), 8.20 (s, 1H), 9.22 (s, 1H), 12.35 (bs, 1H).

LCMS: 567.2 (M$^+$+1).

HPLC: 99.82% (0.1% TFA/ACN; Column: BDS C18, 4.6× 50 mm).

Preparation of G-15a and G-15b

Preparation of Intermediate G-15-In

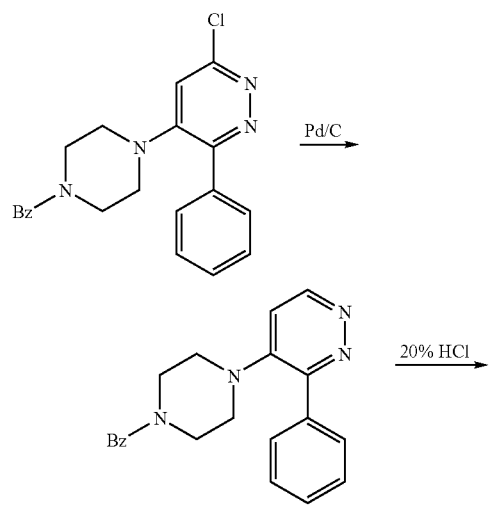

-continued

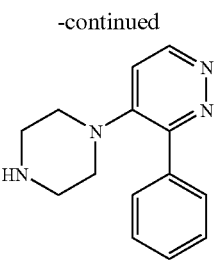

Step-1

To (4-(6-chloro-3-phenylpyridazin-4-yl)piperazin-1-yl) (phenyl)methanone (1 g) dissolved in methanol (40 ml), and palladium carbon (10 mol %) was added very slowly under nitrogen atmosphere and the reaction mixture was stirred under hydrogen atmosphere (1 kg pressure) for 3 hrs. The progress of reaction was monitored by TLC. After consumption of starting material, the reaction mixture was filtered through celite, washed with methanol and the filtrate was concentrated under reduced pressure to get phenyl(4-(3-phenylpyridazin-4-yl)piperazin-1-yl)methanone as white solid.

$^1$H NMR (400 MHz, DMSO-d$_6$): δ 2.45-4.04 (bs, 8H), 7.40 (s, 1H), 7.42-7.95 (m, 10H), 9.0 (s, 1H).

Step-2

To phenyl(4-(3-phenylpyridazin-4-yl)piperazin-1-yl) methanone (18 g) taken in round bottom flask, concentrated hydrochloric acid (10 ml) was added. The reaction mixture was stirred at 85° C. for 6 hrs. The progress of reaction was monitored by TLC. After consumption of starting material, reaction mixture was cooled to room temperature. Residue was slowly poured into ice and neutralized with solid sodium bicarbonate. The mixture was extracted with dichloromethane (3×10 ml). The combined organic layer was dried over anhydrous sodium sulphate and concentrated to afford G-15-In as yellow liquid.

$^1$H NMR (400 MHz, DMSO-d$_6$): δ 2.64 (d, 4H), 2.80 (d, 4H), 4.09 (s, 1H), 7.11 (s, 1H), 7.42-7.83 (m, 5H), 8.82 (s, 1H).

Preparation of G-15a

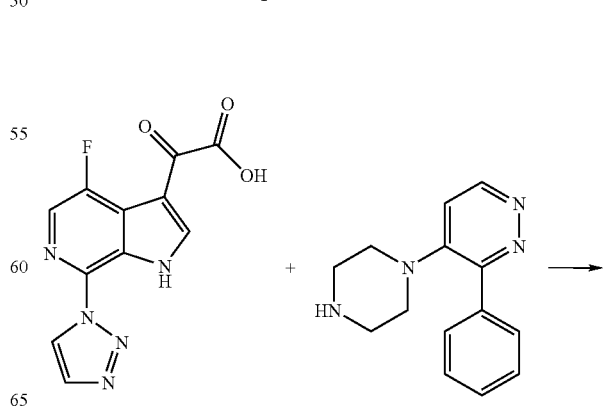

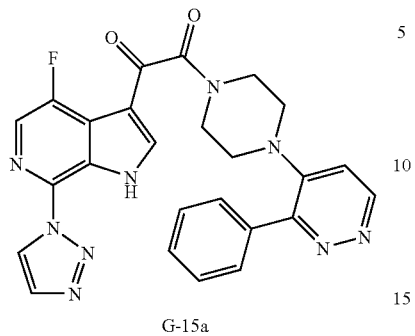

G-15a 2-(4-Fluoro-7-(1H-1,2,3-triazol-1-yl)-1H-pyrrolo[2,3-c]pyridin-3-yl)-2-oxoacetic acid (0.098 g), G-15-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using MeOH/CHCl$_3$ (1:9) as eluent to afford G-15a as yellow solid.

$^1$H NMR (400 MHz, DMSO-d$_6$): δ 2.94 (t, 2H), 3.07 (t, 2H), 3.39 (m, 2H), 3.62 (t, 2H), 7.20 (s, 1H), 7.46-7.54 (m, 5H), 8.12 (s, 1H), 8.31 (d, 2H), 8.88 (d, 1H), 9.01 (s, 1H), 13.01 (bs, 1H).

LCMS: 498.1 (M$^+$+1).

HPLC: 99.41% (0.1% HCOOH/ACN; Column: Genesis C18, 4.6×50 mm).

Preparation of G-15b

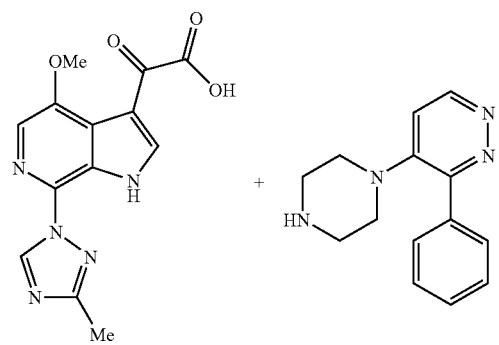

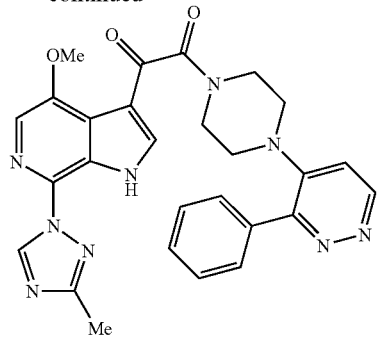

G-15b 2-(4-Methoxy-7-(3-methyl-1H-1,2,4-triazol-1-yl)-1H-pyrrolo[2,3-c]pyridin-3-yl)-2-oxoacetic acid (0.098 g), G-15-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using MeOH/CHCl$_3$ (1:9) as eluent to afford G-15b as yellow solid.

$^1$H NMR (400 MHz, DMSO-d$_6$): δ 2.50 (s, 3H), 2.94 (t, 2H), 3.06 (t, 2H), 3.33 (m, 2H), 3.58 (t, 2H), 3.98 (s, 3H), 7.23 (d, 1H), 7.46-7.54 (m, 5H), 8.21 (s, 1H), 8.89 (d, 1H), 9.24 (s, 1H), 12.39 (bs, 1H).

LCMS: 524.1 (M$^+$+1).

HPLC: 96.79% (0.1% HCOOH/ACN; Column: Genesis C18, 4.6×50 mm).

Preparation of Compound G-16

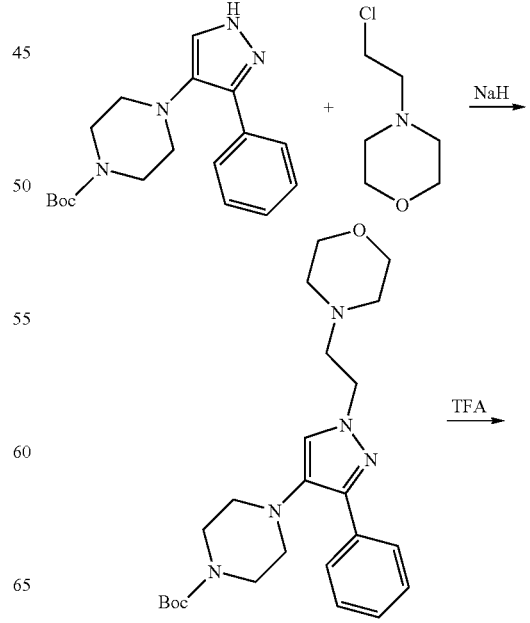

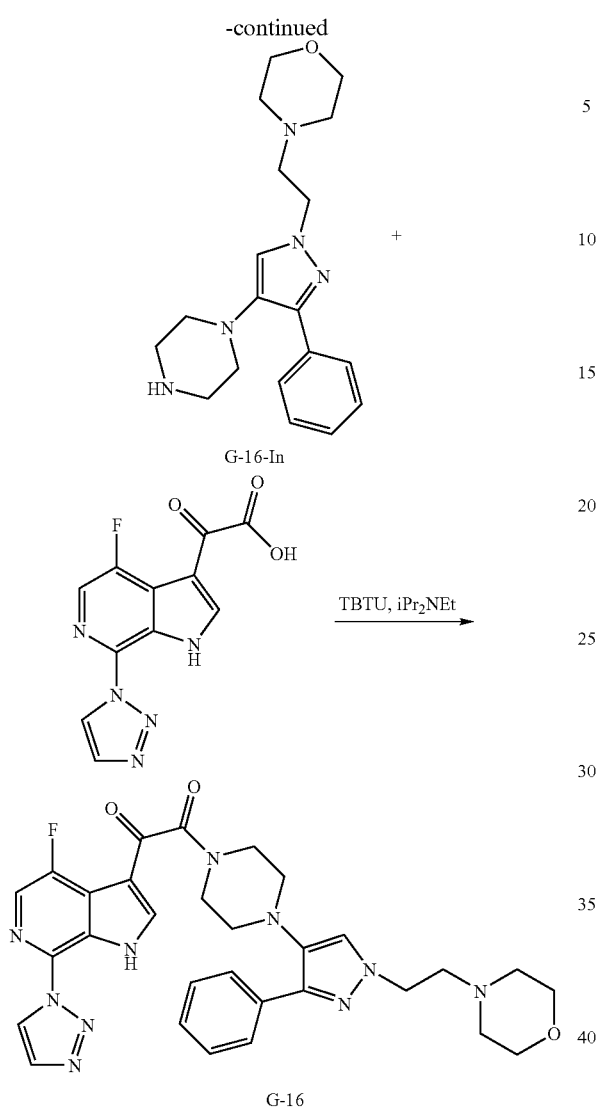

G-16-In

G-16

Step-1

Sodium hydride (0.1 g) was taken in dry DMF (2 ml) and a solution of tert-butyl 4-(3-phenyl-1H-pyrazol-4-yl)piperazine-1-carboxylate (0.5 g in 2 ml of DMF) was added slowly at 0° C. The reaction mixture was stirred for 30 min at 0° C. and a solution of 2-chloroethylmorpholine hydrochloride (0.3 g) in DMF (1 ml) was added very slowly. The reaction mixture was allowed to stir over night at room temperature. The reaction mixture was quenched with cold water (5 ml) and extracted with ethyl acetate (3×40 ml). Evaporation of solvent under reduced pressure gave crude product, which, was purified by column chromatography using ethyl acetate/hexane (2:8) as eluent to afford compound tert-butyl 4-(1-(2-morpholinoethyl)-3-phenyl-1H-pyrazol-4-yl)piperazine-1-carboxylate as pure solid product.

$^1$H NMR (400 MHz, CDCl$_3$): δ 1.48 (s, 9H), 2.65-2.70 (m, 4H), 2.84 (t, 2H), 3.3-3.54 (m, 4H) 3.63 (m, 6H), 3.76 (m, 4H), 7.27-7.43 (m, 5H), 7.54 (s, 1H).

LC-MS: 441 (M$^+$+1)

Step-2

To tert-butyl 4-(1-(2-morpholinoethyl)-3-phenyl-1H-pyrazol-4-yl)piperazine-1-carboxylate (1 g) dissolved in dry dichloromethane (10 ml), TFA (5 ml) was added at 0° C. The reaction mixture was allowed to reach at room temperature and stirred for over-night. The volatiles were completely removed and resulting residue was diluted with dichloromethane (20 ml). The organic layer was washed with saturated NaHCO$_3$ (2×10 ml), brine, dried over Na$_2$SO$_4$. Evaporation of solvent gave desire amine G-16-In, which was used for the next reaction without further purification.

$^1$H NMR (400 MHz, CDCl$_3$): δ 2.65-2.70 (m, 4H), 2.84 (t, 2H), 3.3-3.54 (m, 4H) 3.53 (m, 6H), 3.66 (m, 4H), 7.27-7.43 (m, 5H), 7.54 (s, 1H).

LC-MS: 340 (M$^+$+1)

Step-3

2-(4-fluoro-7-(1H-1,2,3-triazol-1-yl)-1H-pyrrolo[2,3-c]pyridin-3-yl)-2-oxoacetic acid (0.098 g), G-16-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using methanol/chloroform (1:9) as eluent to afford G-16 as yellow solid.

$^1$H NMR (400 MHz, DMSO-d$_6$): δ 2.41 (m, 4H), 2.69-2.75 (m, 4H), 2.84 (s, 2H), 3.53 (d, 6H, 4 Hz), 3.76 (s, 2H), 4.16 (t, 2H, J=8 Hz), 7.25 (t, 1H, J=6 Hz), 7.38 (t, 2H, J=8 Hz), 7.66 (s, 1H), 7.96 (d, 2H, J=8 Hz), 8.11 (s, 1H), 8.30 and 8.34 (2s, 2H), 9.02 (s, 1H), 13.12 (s, 1H).

LCMS: 599.2 (M$^+$+1).

HPLC: 95.4% (0.1% TFA/ACN; Column: Hypersil BDS C18, 4.6×50 mm).

Preparation of Compound G-17a and G-17b

Preparation of Intermediate G-17-In

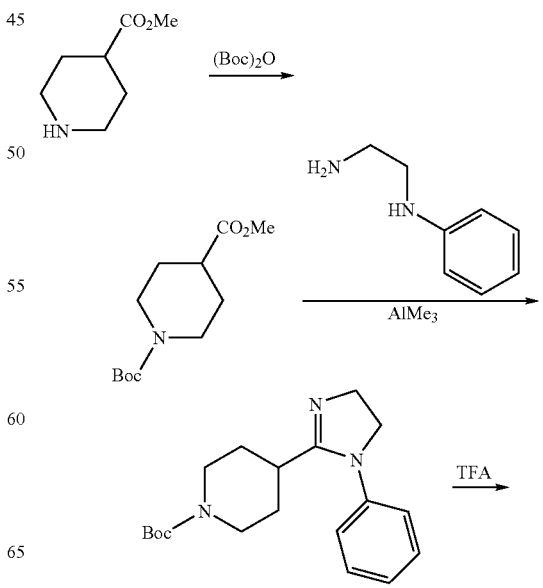

Preparation of G-17a

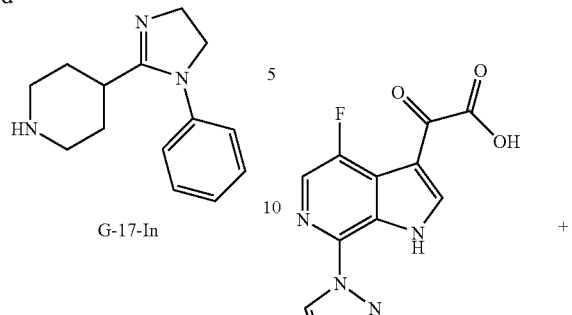

G-17-In

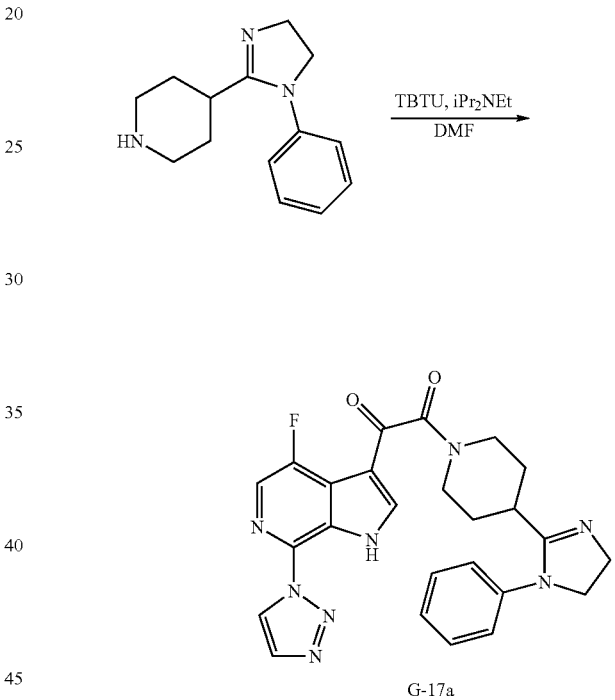

G-17a

Step-1

To a stirred solution of methyl piperidine 4-carboxylate HCl salt (5 g) in dichloromethane, triethylamine was added until the solution is basic. To this basified reaction mixture, Boc-anhydride (7.2 g) was added and allowed to stir at room temperature for overnight. The reaction mixture was quenched with water (20 ml) and extracted with dichloromethane (3×10 ml). The combined organic layers was dried over $Na_2SO_4$ and concentrated to dryness to afford 1-tert-butyl 4-methyl piperidine-1,4-dicarboxylate as a white color solid, which taken for the next reaction without further purification.

$^1$H NMR (400 MHz, $CDCl_3$): δ 1.45 (s, 9H), 1.62-1.64 (m, 2H), 1.89 (m, 2H), 2.83 (m, 2H), 3.69 (s, 3H), 4.1 (m, 2H).

LC-MS: 244 ($M^+$+1)

Step-2

To a stirred solution of phenyl ethylene diamine (3 g) taken in dry toluene (50 ml), cooled to −10° C., trimethylaluminium (36 ml, 2M solution in hexane) was added drop wise for 30 minutes. The reaction mixture was brought to room temperature and was heated to 50° C. 1-tert-Butyl 4-methyl piperidine-1,4-dicarboxylate (8 g) taken in dry toluene (50 ml) added to the above mixture in a drop wise fashion. The combined mixture was stirred at 110° C. for 5 hours, then allowed stir over night at room temperature. To the reaction mixture water (50 ml) was added followed by methanol (50 ml) and allowed to stir for 15 minutes at 0° C. The whole mixture was then filtered through celite bed and washed with chloroform. The combined filtrate was concentrated under reduced pressure. The resulting crude was purified by column chromatography using methanol/chloroform (2:8) as eluent to afford tert-butyl 4-(1-phenyl-4,5-dihydro-1H-imidazol-2-yl)piperidine-1-carboxylate as solid product.

$^1$H NMR (400 MHz, $CD_3OD$): δ 1.47 (s, 9H), 1.57-1.60 (m, 2H), 1.72-1.76 (m, 2H), 2.56-2.57 (m, 3H), 3.84 (m, 2H), 3.92 (m, 2H), 4.08 (m, 2H), 7.27-7.48 (m, 5H).

LCMS: 230.1 ($M^+$+1).

Step-3

To tert-butyl 4-(1-phenyl-4,5-dihydro-1H-imidazol-2-yl)piperidine-1-carboxylate (500 mg) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated $NaHCO_3$ (2×10 ml), brine, dried over $Na_2SO_4$. Evaporation of solvent gave desire amine G-17-In, which was used for the next reaction without further purification.

$^1$H NMR (400 MHz, $CD_3OD$): δ 1.93 (m, 2H), 2.01 (m, 2H), 2.94 (m, 2H), 3.33 (m, 2H), 3.42 (m, 2H), 4.11 (m, 2H), 4.36 (m, 1H), 7.51-7.62 (m, 5H).

$^{13}$C NMR ($CD_3OD$): δ 31.28, 35.85, 46.45, 49.45, 52.11, 54.67, 79.48, 126.54, 127.54, 130.76, 142.57, 170.43.

LCMS: 231.0 ($M^+$+1).

To a stirred solution of 2-(4-fluoro-7-(1H-1,2,3-triazol-1-yl)-1H-pyrrolo[2,3-c]pyridin-3-yl)-2-oxoacetic acid (100 mg) in dry DMF (5 ml), G-17-In (0.083 g), TBTU (0.128 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% $NaHCO_3$ and brine. The organic layer was dried over anhydrous $Na_2SO_4$ and concentrated using rotary evaporator. The resulting crude was purified by column chromatography using methanol/chloroform (2:8) as eluent to afford G-17a as yellow color solid.

$^1$H NMR (DMSO-$d_6$): δ 1.5-1.9 (m, 4H), 2.73 (t, 2H), 3.01 (t, 1H), 3.58 (d, 1H), 3.77 (t, 2H), 3.94 (t, 2H), 4.36 (d, 1H), 7.3 (m, 3H), 7.45 (m, 2H), 8.0 (s, 1H), 8.06 (s, 1H), 9.03 (s, 1H).

LCMS: 487.1 ($M^+$+1).

HPLC: 94.7% (0.1% HCOOH/ACN; Column: Genesis C18 50×4.6 mm, 3µ)

301
Preparation of G-17b

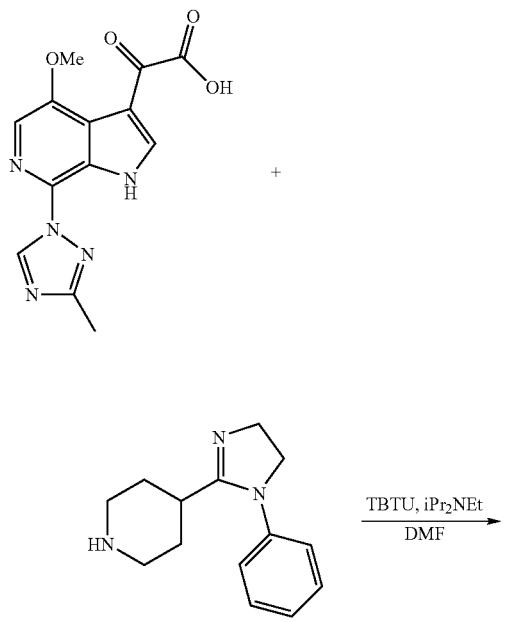

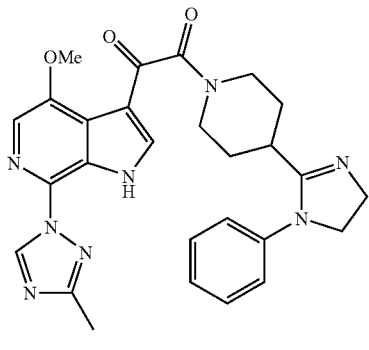

G-17b

To a stirred solution of 2-(4-methoxy-7-(3-methyl-1H-1,2,4-triazol-1-yl)-1H-pyrrolo[2,3-c]pyridin-3-yl)-2-oxoacetic acid (100 mg) in dry DMF (5 ml), G-17-In (0.076 g), TBTU (0.117 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using methanol/chloroform (2:8) as eluent to afford G-17b (30 mg, 17%) as yellow color solid.

$^1$H NMR (DMSO-d$_6$): δ 1.65 (m, 4H), 2.49 (s, 3H), 2.80 (m, 2H), 3.01 (t, 1H), 3.55 (t, 1H), 3.72 (m, 4H), 3.95 (s, 3H), 4.29 (d, 1H), 7.20 (m, 3H), 7.40 (t, 2H), 7.83 (s, 1H), 8.15 (s, 1H), 9.24 (s, 1H).

LCMS: 513.2 (M$^+$+1).

HPLC: 90.3% (0.1% TFA/CAN; Column: C18 BDS, 4.6×250 mm).

302
Preparation of Compound G-18

Preparation of Intermediate G-18-In

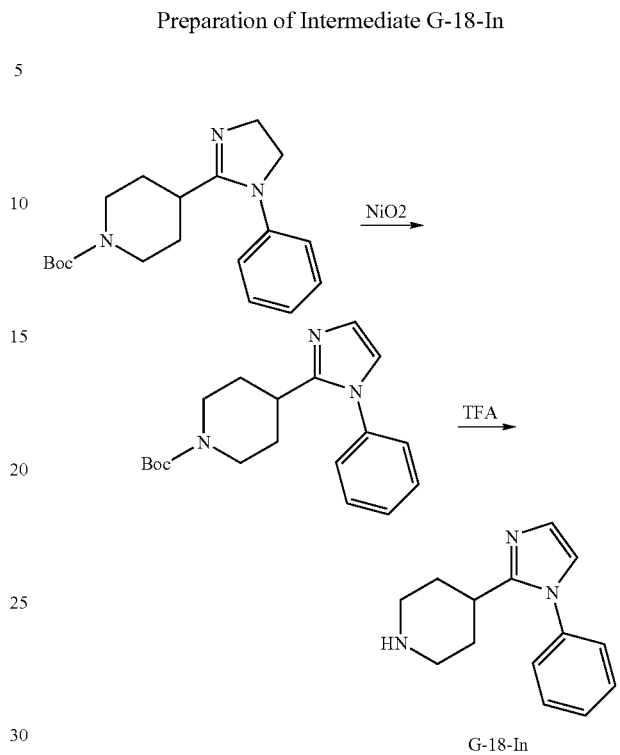

G-18-In

Step-1

To a stirred solution of tert-butyl 4-(1-phenyl-4,5-dihydro-1H-imidazol-2-yl)piperidine-1-carboxylate (100 mg) in dry benzene (5 ml), nickel peroxide (350 mg) dissolved in dry benzene (20 ml) was added. The reaction mixture was refluxed for over-night and filtered through a celite pad using CHCl$_3$ as eluent. The combined organic layer was removed under reduced pressure. The resulting oil was purified by column chromatography using ethyl acetate\hexane (3:7) to afford tert-butyl 4-(1-phenyl-1H-imidazol-2-yl)piperidine-1-carboxylate as pure product $^1$H NMR (400 MHz, CD$_3$OD): δ 1.47 (s, 9H), 1.67-1.70 (m, 2H), 1.72-1.76 (m, 2H), 2.56-2.57 (m, 1H), 3.3 (m, 2H), 3.5 (m, 2H), 7.0-7.2 (S, 2H), 7.27-7.48 (m, 5H).

LC-MS: 328.1 (M$^+$+1).

Step-2

To tert-butyl 4-(1-phenyl-1H-imidazol-2-yl)piperidine-1-carboxylate (500 mg) taken in dry dichloromethane (10 ml), TFA (5 ml) was added at 0° C. The reaction mixture was allowed reach at room temperature and stirred for over-night. The volatiles were removed using reduced pressure and the residue was diluted with dichloromethane (10 ml). The organic layer was washed with saturated NaHCO$_3$ (2×10 ml), brine (20 ml) and was dried over Na$_2$SO$_4$. Evaporation of solvent gave desire amine G-18-In, which was taken for the next reaction without further purification.

$^1$H NMR (400 MHz, CD$_3$OD): δ 1.76-1.82 (m, 2H), 2.56 (m, 2H), 2.76-2.80 (m, 1H), 3.05 (m, 2H), 3.5 (m, 2H), 7.0-7.15 (S, 2H), 7.37-7.48 (m, 5H).

LCMS: 228.1 (M$^+$+1).

Preparation of G-18a

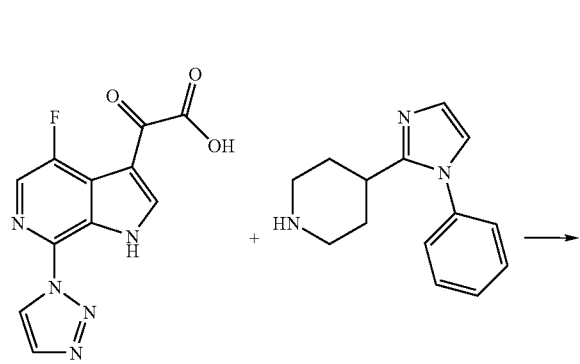

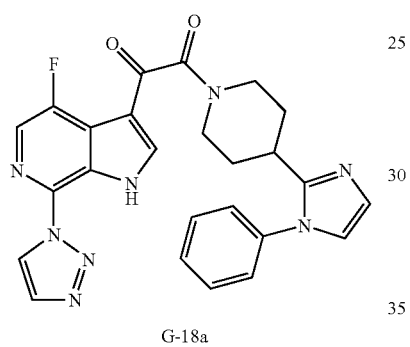

G-18a

To a stirred solution of 2-(4-fluoro-7-(1H-1,2,3-triazol-1-yl)-1H-pyrrolo[2,3-c]pyridin-3-yl)-2-oxoacetic acid (100 mg) in dry DMF (5 ml), G-18-In (0.076 g), TBTU (0.117 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using methanol/chloroform (1:9) as eluent to afford G-18a as yellow color solid.

$^1$H NMR (DMSO-d$_6$): δ 1.8 (m, 4H), 3.0 (m, 3H), 3.62 (d, 1H), 4.36 (d, 1H), 6.97 (s, 1H), 7.24 (s, 1H), 7.43 (d, 2H), 7.55 (m, 3H), 8.12 (s, 1H), 8.25 (s, 1H), 8.31 (s, 1H), 9.02 (s, 1H), 13.06 (bs, 1H).

LCMS: 485.1 (M$^+$+1).

HPLC: 97.3% (0.1% TFA/ACN; Column: C18 BDS, 4.6× 50 mm).

Preparation of G-18b

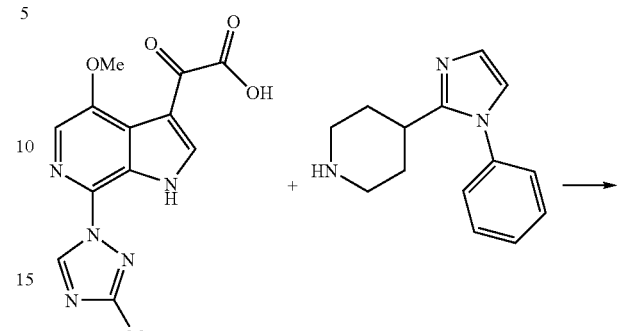

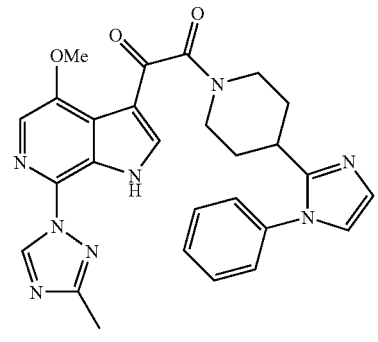

G-18b

To a stirred solution of 2-(4-methoxy-7-(3-methyl-1H-1,2,4-triazol-1-yl)-1H-pyrrolo[2,3-c]pyridin-3-yl)-2-oxoacetic acid (100 mg) in dry DMF (5 ml), G-18-In (0.076 g), TBTU (0.117 g) and DIPEA (0.1 ml) were added. The reaction mixture was stirred at r.t. for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using methanol/chloroform (1:9) as eluent to afford G-18b as yellow color solid.

$^1$H NMR (CD$_3$OD): δ 1.9 (m, 4H), 2.56 (s, 3H), 2.85 (m, 1H), 3.12 (m, 2H), 3.8 (d, 1H), 4.04 (s, 3H), 4.59 (d, 1H), 7.05 (s, 1H), 7.16 (s, 1H), 7.43 (s, 2H), 7.56 (m, 3H), 7.84 (s, 1H), 8.27 (s, 1H), 9.23 (s, 1H).

$^{13}$C NMR (CD$_3$OD): δ 13.76, 31.63, 32.18, 34.95, 42.24, 47.52, 57.55, 115.88, 122.15, 122.71, 124.57, 125.39, 127.52 (2C), 127.94, 130.25, 130.98 (2C), 131.65, 138.62, 139.54, 142.83, 151.21, 151.64, 162.93, 168.43, 187.37.

LCMS: 511.2 (M$^+$+1).

HPLC: 97.3% (0.1% TFA/ACN; Column C18, BDS 4.6× 50 mm).

Preparation of G-19a and G-19b

Preparation of Intermediate G-19-In

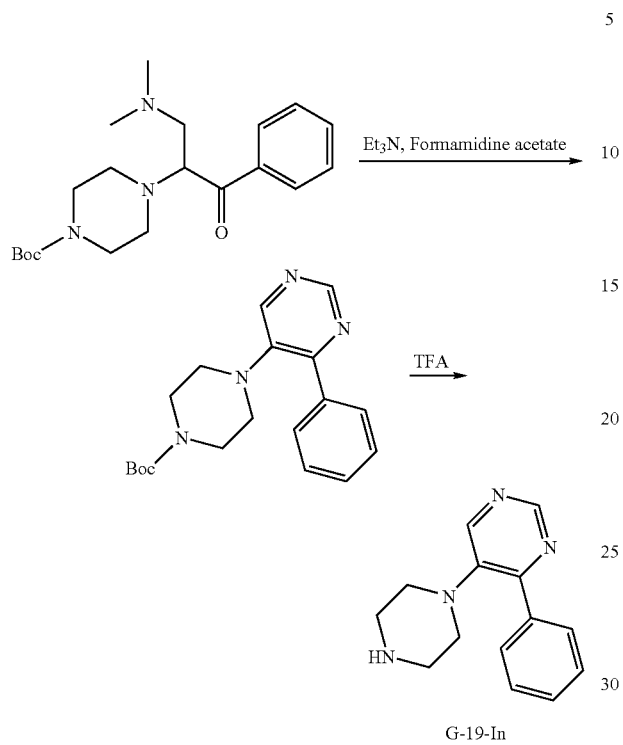

G-19-In

Step-1

To a stirred solution of formamidine acetate (2.8 g) in triethylamine (6 ml) in a sealed tube, was added tert-butyl 4-(1-(dimethylamino)-3-oxo-3-phenylprop-1-en-2-yl)piperazine-1-carboxylate (1.0 g) and the reaction mixture was heated at 140° C. for 6 h. The reaction mixture was brought to room temperature and triethylamine was removed under reduced pressure. Water (10 ml) was added to the residue and the organic compound was extracted into ethylacetate (4×20 ml). Combined organic layers were dried ($Na_2SO_4$) and concentrated. The crude material was purified by column chromatography using methanol/chloroform (1:9) to give tert-butyl 4-(4-phenylpyrimidin-5-yl)piperazine-1-carboxylate.

$^1$H NMR (400 MHz, $CDCl_3$): δ 1.48 (s, 9H), 2.59 (s, 4H), 3.52-3.54 (s, 4H), 7.27-7.50 (m, 5H), 8.41 (s, 1H), 8.97 (s, 1H).

LC-MS: 341 ($M^+$+1)

Step-2

To tert-butyl 4-(4-phenylpyrimidin-5-yl)piperazine-1-carboxylate (1 g) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated $NaHCO_3$ (2×10 ml), brine, dried over $Na_2SO_4$. Evaporation of solvent gave desire amine G-19-In (0.5 g), which was used for the next reaction without further purification.

$^1$H NMR (400 MHz, $CDCl_3$): δ 2.59 (s, 4H), 3.52-3.54 (s, 4H), 7.27-7.50 (m, 5H), 8.41 (s, 1H), 8.97 (s, 1H).

LC-MS: 240 ($M^+$+1)

Preparation of G-19a

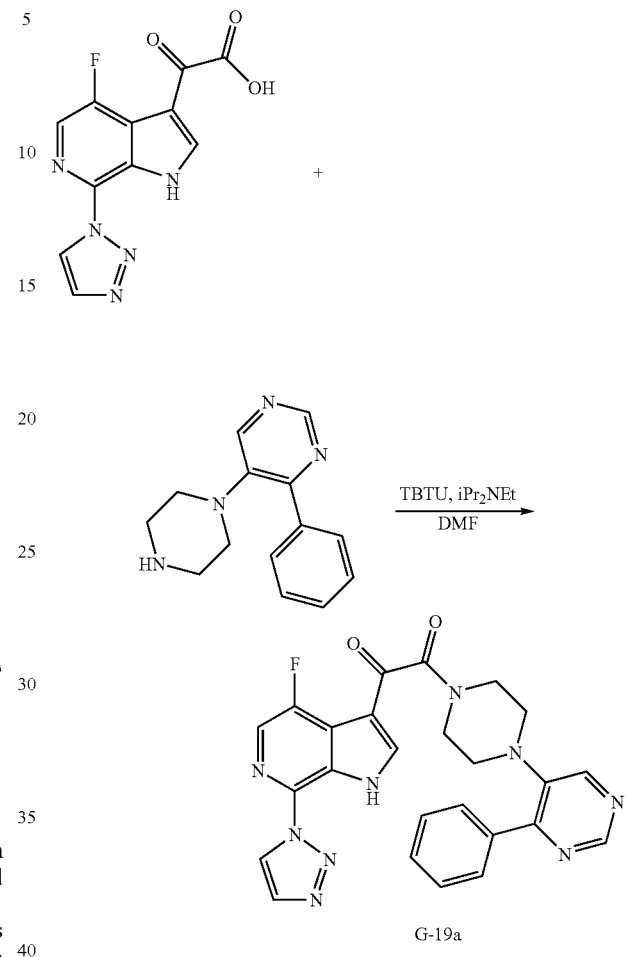

G-19a 2-(4-fluoro-7-(1H-1,2,3-triazol-1-yl)-1H-pyrrolo[2,3-c]pyridin-3-yl)-2-oxoacetic acid (0.098 g), G-19-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% $NaHCO_3$ and brine. The organic layer was dried over anhydrous $Na_2SO_4$ and concentrated under reduced pressure. The resulting crude was purified by column chromatography using methanol/chloroform (1:9) as eluent to afford G-19a as yellow solid.

$^1$H NMR (400 MHz, DMSO-$d_6$): δ 2.92 (bs, 2H), 3.02 (bs, 2H), 3.45 (bs, 2H), 3.67 (bs, 2H), 7.47-7.53 (m, 3H), 8.09-8.12 (m, 3H), 8.33 (m, 2H), 8.56 (s, 1H), 8.89 (s, 1H), 9.01 (s, 1H), 13.06 (bs, 1H).

$^{13}$C NMR (400 MHz, DMSO-$d_6$): δ 14.13, 41.03, 45.63, 50.77, 51.15, 56.97, 94.80, 115.74, 121.38, 123.13, 124.15, 127.22, 129.11, 129.70, 136.51, 139.74, 139.90, 141.28, 149.63, 150.74, 162.12, 166.39, 185.36.

LCMS: 498.1 ($M^+$+1).

HPLC: 96.67% (0.1% TFA/ACN; Column: Hypersil, BDS C18, 4.6×50 mm).

307
Preparation of G-19b

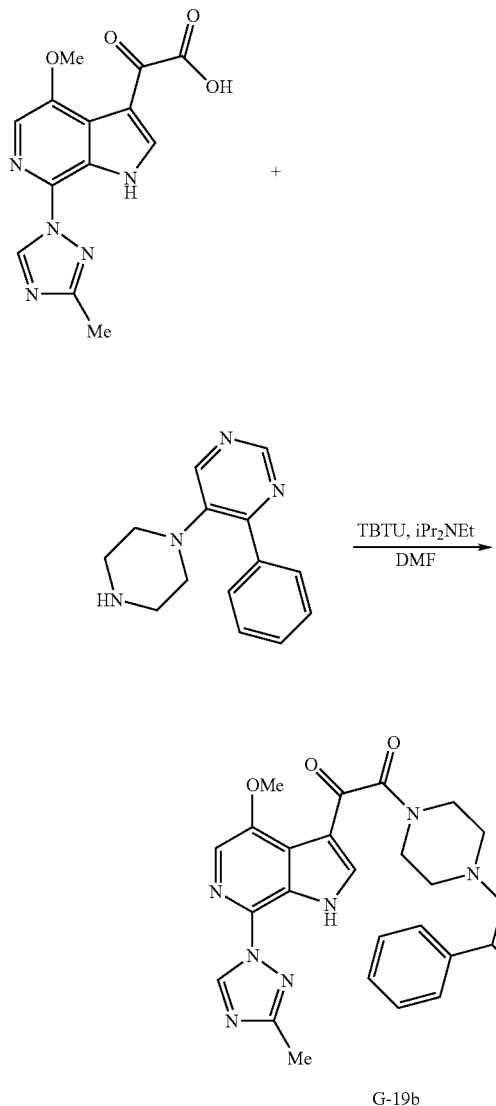

2-(4-Methoxy-7-(3-methyl-1H-1,2,4-triazol-1-yl)-1H-pyrrolo[2,3-c]pyridin-3-yl)-2-oxoacetic acid (0.098 g), G-19-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% $NaHCO_3$ and brine. The organic layer was dried over anhydrous $Na_2SO_4$ and concentrated under reduced pressure. The resulting crude was purified by column chromatography using methanol/chloroform (1:9) as eluent to afford G-19b as yellow solid.

$^1$H NMR (400 MHz, DMSO-$d_6$): δ 2.57 (s, 3H), 3.03 (t, 2H), 3.12 (t, 2H), 3.57 (t, 2H), 3.82 (t, 2H), 4.08 (s, 3H), 7.27-7.51 (m, 5H), 7.78 (s, 1H), 8.22 (s, 1H), 8.45 (s, 1H), 9.00 (s, 1H), 9.12 (s, 1H), 11.05 (bs, 1H).

LCMS: 524.1 ($M^+$+1).

HPLC: 98.38% (0.1% TFA in $H_2O$/ACN; Column: Hypersil BDS C18, 4.6×50 mm).

308
Preparation of Compound 20

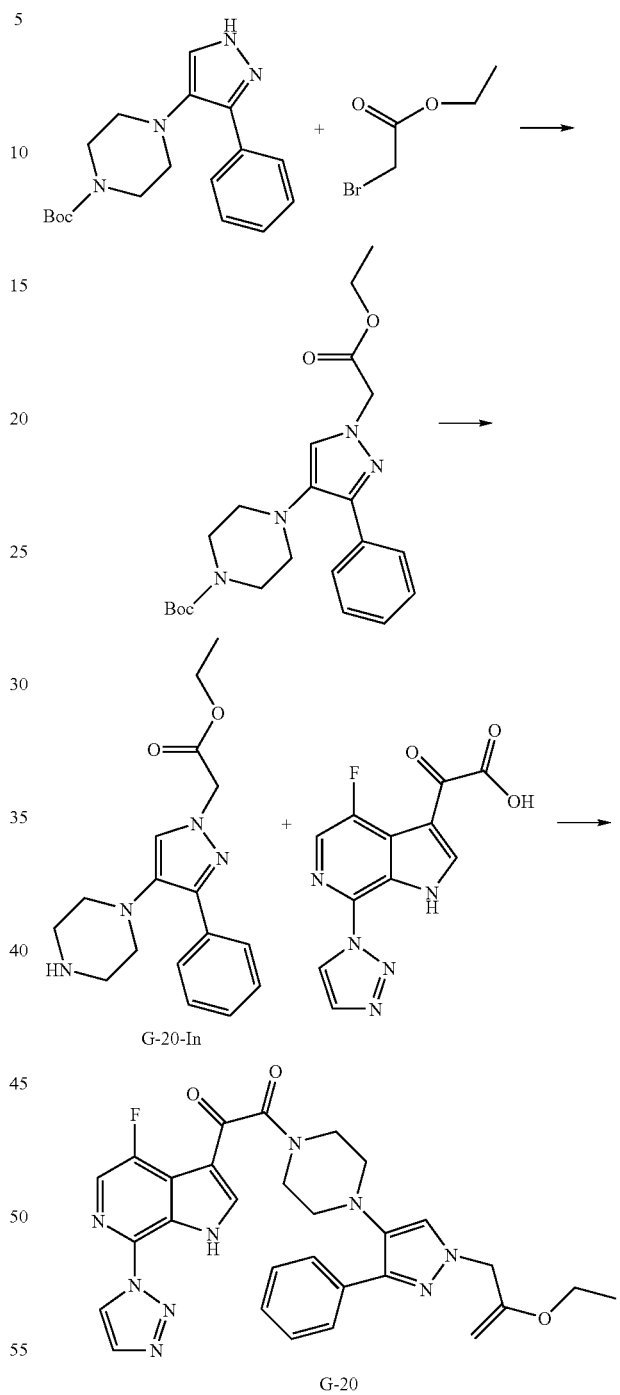

Step-1

Sodium hydride (0.1 g) was taken in dry DMF (2 ml) and a solution of tert-butyl 4-(3-phenyl-1H-pyrazol-4-yl)piperazine-1-carboxylate (0.5 g in 2 ml of DMF) was added slowly at 0° C. The reaction mixture was stirred for 30 min at 0° C. and a solution of ethylbromoacetate (1 g) in DMF (1 ml) was added very slowly. The reaction mixture was allowed to stir over night at room temperature. The reaction mixture was quenched with cold water (5 ml) and extracted with ethyl acetate (3×40 ml). Evaporation of solvent under reduced pressure gave crude product, which, was purified by column chromatography using ethyl acetate/hexane (2:8) as eluent to afford tert-butyl 4-(1-(2-ethoxy-2-oxoethyl)-3-phenyl-1H-pyrazol-4-yl)piperazine-1-carboxylateb as pure solid product.

$^1$H NMR (400 MHz, CDCl$_3$): δ 1.2 (t, 3H), 1.48 (s, 9H), 2.86 (m, 4H), 3.54 (m, 4H), 4.08 (t, 2H), 5.0 (s, 2H), 7.28-7.43 (m, 5H), 7.8 (s, 1H).

LC-MS: 415 (M$^+$+1)

Step-2

To tert-butyl 4-(1-(2-ethoxy-2-oxoethyl)-3-phenyl-1H-pyrazol-4-yl)piperazine-1-carboxylate (1 g) dissolved in dry dichloromethane (10 ml), TFA (5 ml) was added at 0° C. The reaction mixture was allowed to reach at room temperature and stirred for over-night. The volatiles were completely removed and resulting residue was diluted with dichloromethane (20 ml). The organic layer was washed with saturated NaHCO$_3$ (2×10 ml), brine, dried over Na$_2$SO$_4$. Evaporation of solvent gave desire amine G-20-In, which was used for the next reaction without further purification.

Step-3

2-(4-Fluoro-7-(1H-1,2,3-triazol-1-yl)-1H-pyrrolo[2,3-c]pyridin-3-yl)-2-oxoacetic acid (0.1 g), amine G-20-In (0.08 g), TBTU (0.12 g) and Hunig's base (0.15 ml) were combined in dry DMF (5 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using 5% methanol/chloroform (1:9) as eluent to afford G-20.

$^1$H NMR (400 MHz, CDCl$_3$): δ 1.2 (t, 3H), 2.75 (t, 2H), 2.86 (t, 2H), 3.54 (t, 2H), 3.77 (t, 2H), 4.18 (t, 2H), 5.0 (s, 2H), 7.28 (m, 1H), 7.3 (m, 2H), 7.6 (S, 1H), 7.95 (d, 2H), 8.1 (s, 1H), 8.35 (d, 2H), 9.0 (s, 1H), 13 (s, 1H).

LC-MS: 572 (M$^+$+1).

HPLC: 95.166% (0.1% TFA/ACN; Column: Hypersil-BDSC18 5 u (4.6×50) mm).

Preparation of Compound G-21

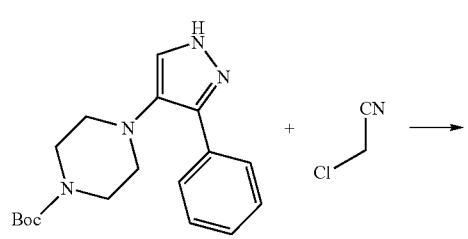

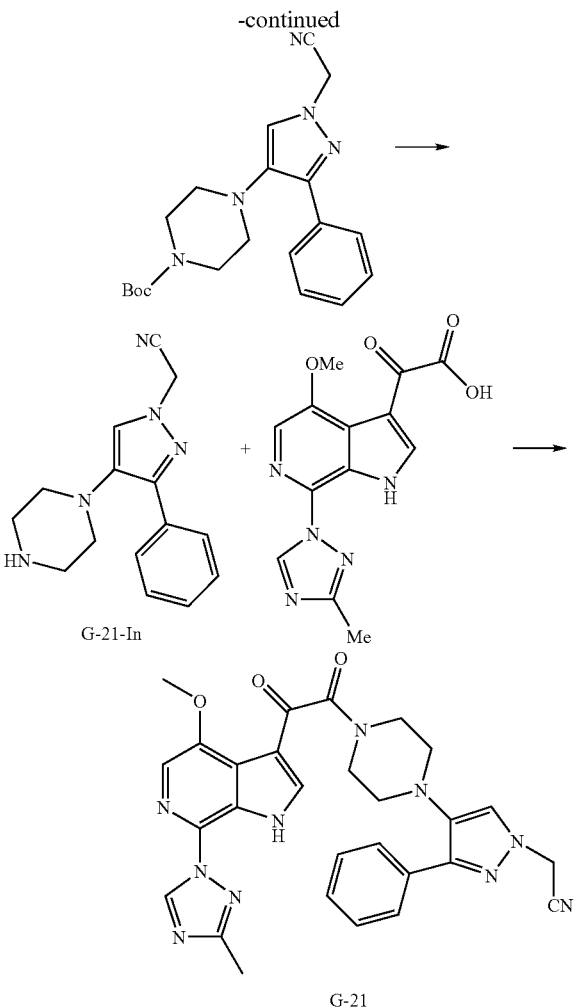

Step-1

Sodium hydride (0.1 g) was taken in dry DMF (2 ml) and a solution of tert-butyl 4-(3-phenyl-1H-pyrazol-4-yl)piperazine-1-carboxylate (0.5 g in 2 ml of DMF) was added slowly at 0° C. The reaction mixture was stirred for 30 min at 0° C. and a solution of chloroacetonitrile (0.138 g) in DMF (1 ml) was added very slowly. The reaction mixture was allowed to stir over night at room temperature. The reaction mixture was quenched with cold water (5 ml) and extracted with ethyl acetate (3×40 ml). Evaporation of solvent under reduced pressure gave crude product, which, was purified by column chromatography using ethyl acetate\hexane (2:8) as eluent to afford tert-butyl 4-(1-(cyanomethyl)-3-phenyl-1H-pyrazol-4-yl)piperazine-1-carboxylate as pure solid product.

$^1$H NMR (400 MHz, CDCl$_3$): δ 1.48 (s, 9H), 2.90 (s, 4H), 3.53-3.55 (s, 4H), 5.05 (s, 2H), 7.26-7.44 (m, 5H), 7.99 (s, 1H).

LC-MS: 367 (M$^+$+1).

Step-2

To tert-butyl 4-(1-(cyanomethyl)-3-phenyl-1H-pyrazol-4-yl)piperazine-1-carboxylate (1 g) dissolved in dry dichloromethane (10 ml), TFA (5 ml) was added at 0° C. The reaction mixture was allowed to reach at room temperature and stirred for over-night. The volatiles were completely removed and resulting residue was diluted with dichloromethane (20 ml). The organic layer was washed with saturated NaHCO₃ (2×10 ml), brine, dried over Na₂SO₄. Evaporation of solvent gave desire amine G-21-In, which was used for the next reaction without further purification.

¹H NMR (400 MHz, CDCl₃): δ 2.90 (s, 4H), 3.53-3.55 (s, 4H), 5.05 (s, 2H), 7.26-7.44 (m, 5H), 7.99 (s, 1H).

LC-MS: 367 (M⁺+1).

Step-3

2-(4-Methoxy-7-(3-methyl-1H-1,2,4-triazol-1-yl)-1H-pyrrolo[2,3-c]pyridin-3-yl)-2-oxoacetic acid (0.098 g), compound G-21-In (0.076 g), TBTU (0.116 g) and Hunig's base (0.1 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO₃ and brine. The organic layer was dried over anhydrous Na₂SO₄ and concentrated under reduced pressure. The resulting crude was purified by column chromatography using methanol/chloroform (1:9) as eluent to afford G-21 as off white solid.

¹H NMR (400 MHz, CDCl₃): δ 2.6 (s, 3H), 2.9-3.2 (d, 4H), 3.63 (s, 2H), 3.9 (s, 2H), 4.1 (s, 3H), 5.06 (s, 2H), 7.31-7.45 (m, 4H), 7.79 (s, 1H), 7.95 (d, 2H), 8.23 (s, 1H), 9.15 (s, 1H), 11.02 (s, 1H).

LCMS: 551.1 (M⁺+1).

HPLC: 95.7% (0.1% TFA/ACN; Column: Hypersil BDS C18, 4.6×50 mm).

Preparation of Compound G-22a and G-22b

Preparation of Intermediate G-22-In

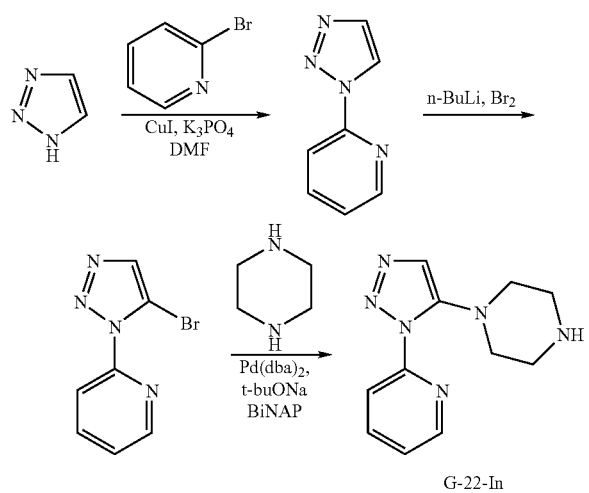

G-22-In

Step-1

1,2,3-Triazole (5 g), 2-bromo pyridine (8.5 ml) and copper iodide (0.68 g) was taken in dry DMF under Nitrogen atmosphere. 1,2-(N,N-dimethyl)cyclohexyl diamine (1.02 g) and potassium phosphate (30.73 g) was added into above mixture. The reaction mixture was reflux at 110° C. for over night. TLC was checked no starting material and the reaction mixture was filtered through celite. The filtrate was diluted with water and product was extracted with dichloromethane. The organic layer was evaporated and the crude product was purified by column chromatography using 60-120 silica gel and pet ether\ethyl acetate as eluent to give compound 2-(1H-1,2,3-triazol-1-yl)pyridine as white solid.

¹H NMR (400 MHz, CDCl₃): δ 7.47 (m, 1H), 8.0 (s, 1H), 8.13 (d, 2H), 8.6 (d, 2H), 8.84 (s, 1H).

LC-MS: 147 (M⁺+1)

Step-2

In a 100 ml 3 necked round bottom flask, 2-(1H-1,2,3-triazol-1-yl)pyridine (2 g) was taken in dry THF (2 ml) under nitrogen. n-Butyl lithium (2.3 ml) was added at −78° C. and stirred for 5 minutes, then bromine (1.86 ml was added dropwise to the above reaction mixture. Reaction mixture was stirred at −78° C. for 1 hour. TLC was checked no starting material and the reaction mixture was quenched with saturated ammonium chloride (50 ml) and ethyl acetate was added. The organic layer was washed with sodium bisulphate, brine, dried and concentrated. The crude product was purified by column chromatography using pet ether & ethyl acetate as eluent to give compound 2-(5-bromo-1H-1,2,3-triazol-1-yl)pyridine as yellow solid.

¹H NMR (400 MHz, CDCl₃): δ 7.68 (m, 1H), 7.86 (m, 1H), 8.1 (s, 1H), 8.15 (m, 1H), 8.7 (m, 1H).

LC-MS: 226 (M⁺+1).

Step-3

In a 100 ml single neck round bottom flask, 2-(5-bromo-1H-1,2,3-triazol-1-yl)pyridine (1.5 g), piperazine (2.8 g) and sodium tert-butoxide (0.56 g) was taken in dry toluene (20 ml) and degasified for 20 min. Then Pd(dba)₂ (0.3 g), BiNAP (0.41 g) was added and again degasified for 10 min. The reaction mixture was reflux at 107° C. for over night. TLC was checked no starting material. Reaction mixture was diluted with 25 ml of water and extracted with dichloromethane. The organic layer was separated and concentrated. The crude product was purified by column chromatography using 60-120 silica gel and 6% methanol\chloroform as eluent to give compound G-22-In as white solid.

¹H NMR (400 MHz, CDCl₃): δ 2.6-2.87 (d, 8H), 7.41 (s, 1H), 7.5-7.6 (m, 1H), 7.73 (d, 1H), 8.0 (m, 1H), 8.64 (d, 1H).

LC-MS: 231 (M⁺+1).

Preparation of G-22a

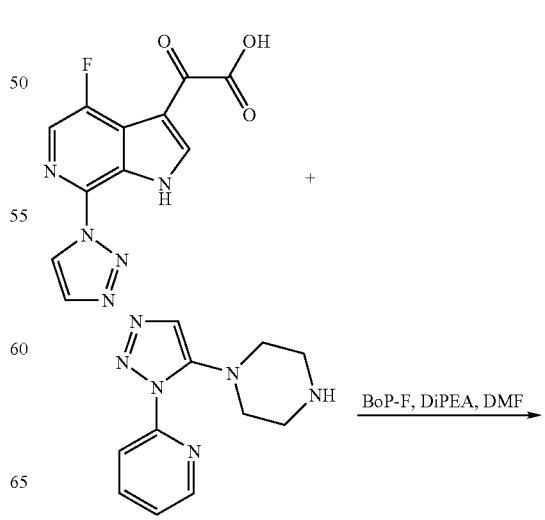

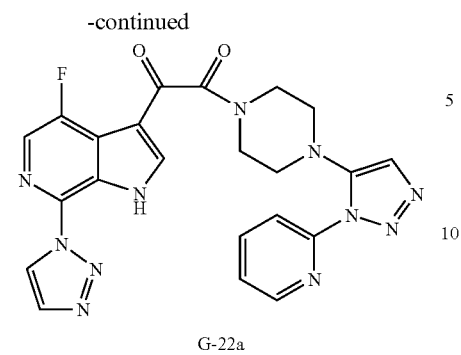

G-22a 2-(4-Fluoro-7-(1H-1,2,3-triazol-1-yl)-1H-pyrrolo[2,3-c]pyridin-3-yl)-2-oxoacetic acid (0.119 g), compound G-22-In (0.1 g), BOP reagent (0.19 g) and Hunig's base (0.22 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% $NaHCO_3$ and brine. The organic layer was dried over anhydrous $Na_2SO_4$ and concentrated under reduced pressure. The resulting crude was purified by column chromatography using methanol\chloroform (1:9) as eluent to afford G-22a as white solid.

$^1$H NMR (400 MHz, DMSO-$d_6$): δ 2.96-2.98 (t, 2H), 3.11 (t, 2H), 3.37-3.46 (t, 2H), 3.68-3.71 (t, 2H), 7.52 (s, 1H), 7.58 (d, 1H), 7.8 (d, 1H), 8.1 (t, 2H), 8.31-8.36 (d, 2H), 8.65 (t, 1H), 9.0 (s, 1H), 13 (s, 1H).

LC-MS: 487 ($M^+$+1).

HPLC: 84.9% (0.1% $H_3PO_4$/ACN; Column: YMC-PACK ODS-AQ (4.6×250) mm).

Preparation of G-22b

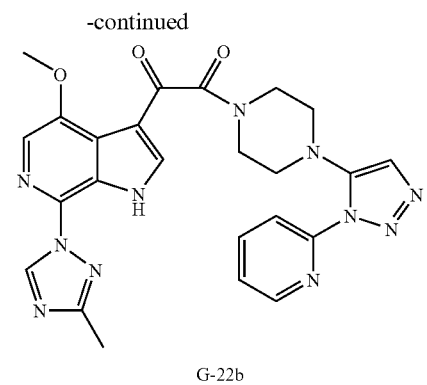

G-22b 2-(4-Methoxy-7-(3-methyl-1H-1,2,4-triazol-1-yl)-1H-pyrrolo[2,3-c]pyridin-3-yl)-2-oxoacetic acid (0.12 g), compound G-22-In (0.1 g), BOP reagent (0.19 g) and Hunig's base (0.22 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% $NaHCO_3$ and brine. The organic layer was dried over anhydrous $Na_2SO_4$ and concentrated under reduced pressure. The resulting crude was purified by column chromatography using methanol\chloroform (1:9) as eluent to afford G-22b as white solid.

$^1$H NMR (400 MHz, DMSO-$d_6$): δ 2.5 (s, 3H), 2.96-2.98 (t, 2H), 3.11 (t, 2H), 3.37-3.46 (t, 2H), 3.68-3.71 (t, 2H), 4.0 (s, 1H), 7.52 (s, 1H), 7.58 (m, 1H), 7.8 (d, 1H), 7.88 (s, 1H) 8.1 (t, 1H), 8.31-8.36 (d, 1H), 8.65 (d, 1H), 9.23 (s, 1H).

LC-MS: 513 ($M^+$+1).

HPLC: 96.9% (0.1% $H_3PO_4$/ACN; Column: YMC-PACK ODS-AQ (4.6×250) mm).

Preparation of Compound G-23

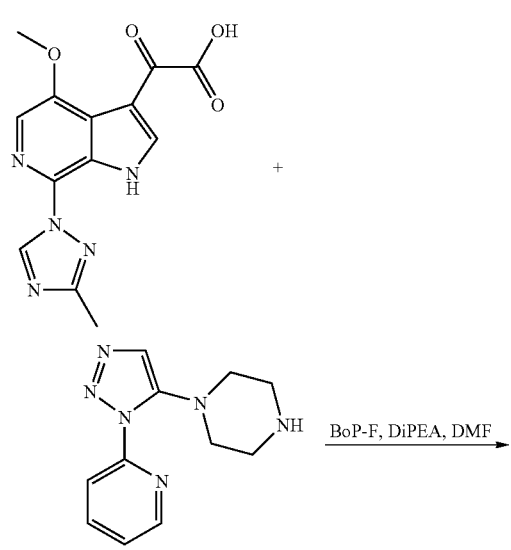

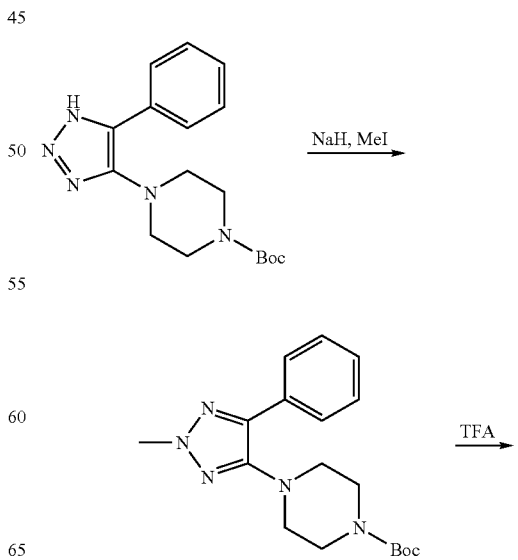

-continued

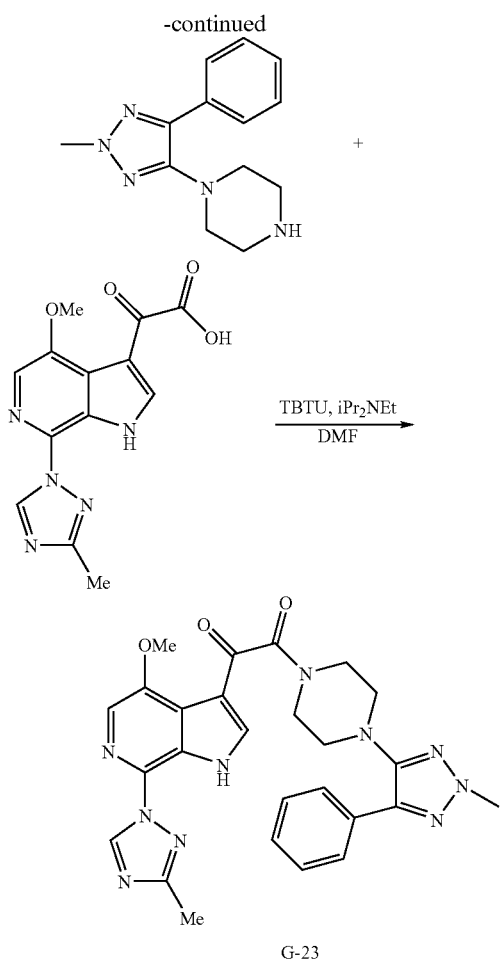

G-23

Step-1

Sodium hydride (0.02 g) was taken in dry DMF (5 ml) and a solution of tert-butyl 4-(5-phenyl-1H-1,2,3-triazol-4-yl)piperazine-1-carboxylate (0.015 g in 5 ml of DMF) was added slowly at 0° C. The reaction mixture was stirred for 30 min at 0° C. and methyl iodide (0.13 g) was added very slowly. The reaction mixture was allowed to stir over night at room temperature. The reaction mixture was quenched with cold water (5 ml) and extracted with ethyl acetate (3×40 ml). Evaporation of solvent under reduced pressure gave crude product, which, was purified by column chromatography using 60-120 silica gel methanol\dichloromethane (1:9) as eluent to afford tert-butyl 4-(2-methyl-5-phenyl-1H-1,2,3-triazol-4-yl)piperazine-1-carboxylate.

$^1$H NMR (400 MHz, DMSO-d$_6$): δ 1.4 (s, 9H), 2.92 (d, 4H), 3.43 (m, 5H), 4.05 (m, 2H), 7.33 (m, 1H), 7.45 (t, 2H), 7.85 (d, 2H).

LCMS: 345.1 (M$^+$+1).

Step-2

To tert-butyl 4-(2-methyl-5-phenyl-1H-1,2,3-triazol-4-yl)piperazine-1-carboxylate. (500 mg) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated NaHCO$_3$ (2×10 ml), brine, dried over Na$_2$SO$_4$. Evaporation of solvent gave desire amine G-23-In, which was used for the next reaction without further purification.

$^1$H NMR (400 MHz, DMSO-d$_6$): δ 2.92 (d, 4H), 3.23 (m, 5H), 4.05 (m, 2H), 7.33 (m, 1H), 7.45 (t, 2H), 7.85 (d, 2H).

LCMS: 245.1 (M$^+$+1).

Step-3

To a stirred solution of 2-(4-methoxy-7-(3-methyl-1H-1,2,4-triazol-1-yl)-1H-pyrrolo[2,3-c]pyridin-3-yl)-2-oxoacetic acid (100 mg\) in dry DMF (5 ml), G-23-In (0.076 g), TBTU (0.117 g) and DIPEA (0.1 ml) were added. The reaction mixture was stirred at room temperature for over night. The reaction was quenched with methanol (10 ml) and the volatiles were removed under reduced pressure. The resulting oil was diluted with ethyl acetate (50 ml) and washed with 10% NaHCO$_3$ and brine. The organic layer was dried over anhydrous Na$_2$SO$_4$ and concentrated using rotary evaporator. The resulting crude was purified by column chromatography using methanol\dichloromethane (2:8) as eluent to afford G-23 as an amorphous solid.

$^1$H NMR (400 MHz, DMSO-d$_6$): δ 2.5 (s, 3H), 2.98-3.0 (t, 2H), 3.0-3.10 (t, 2H), 3.5-3.53 (t, 2H), 3.73-3.79 (t, 2H), 4.01 (s, 3H), 4.07 (s, 3H), 7.33 (m, 1H), 7.45 (t, 2H), 7.85 (d, 2H), 7.9 (s, 1H), 8.23 (s, 1H), 9.25 (s, 1H), 12.42 (s, 1H).

LCMS: 527 (M$^+$+1).

HPLC: 95% (0.1% H$_3$PO$_4$/ACN; Column: YMC-PACK ODS-AQ (4.6×250) mm).

Preparation of Compound G-24a and G-24b

Preparation of Intermediate G-24-In

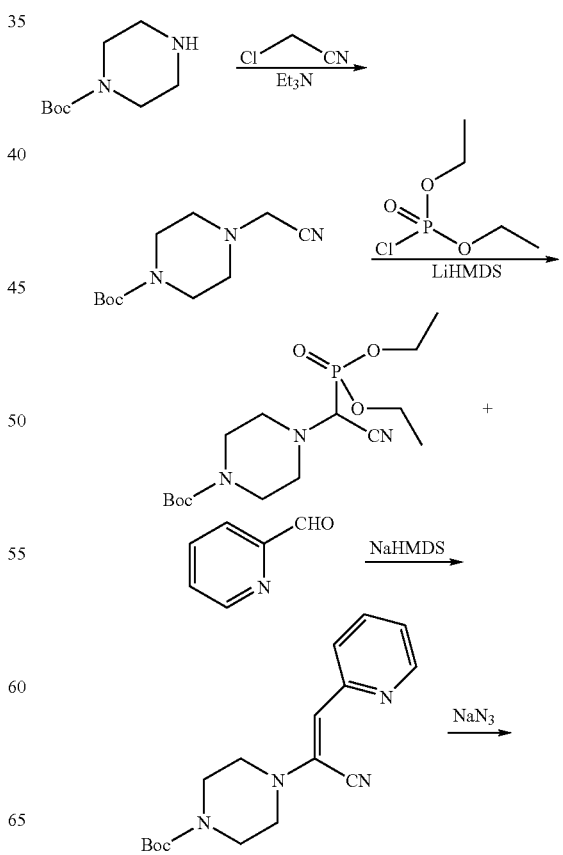

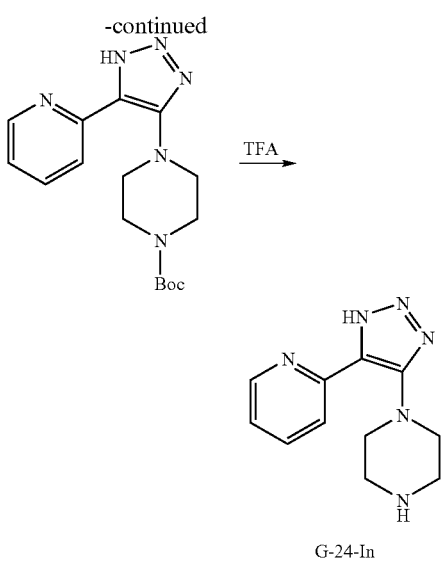

G-24-In

Step-1

To a stirred solution of N-Boc piperazine (5 g) in dry dichloromethane (100 ml), triethyl amine (10 ml) followed by chloro acetonitrile (25.02 ml) were added dropwise. The reaction mixture was allowed to stir at room temperature for overnight. The solvent was removed under vacuum and residue was diluted with dichloromethane (200 ml). The organic layer was washed with water, brine and concentrated to dryness under reduced pressure to afford tert-butyl 4-(cyanomethyl)piperazine-1-carboxylate, which was used for the next reaction without further purification.

$^1$H NMR (400 MHz, CDCl$_3$): δ 1.47 (s, 9H), 2.55 (t, 4H), 3.49 (t, 4H), 3.55 (s, 2H).

GC MS: 225

Step-2

In a 100 ml 3 necked round bottom flask, intermediate tert-butyl 4-(cyanomethyl)piperazine-1-carboxylate (7 g) was taken in dry THF (125 ml) under nitrogen. lithium bis trimethylsilyl amide (10.8 g) was added dropwise at −78° C. and stirred for 1 hr, then diethyl chloro phosphate (5.84 g) in 5 ml dry THF was added drop wise to the above reaction mixture. Reaction mixture was stirred at −78° C. for 1 hour. TLC was checked no starting material and the reaction mixture was quenched with saturated ammonium chloride (250 ml) and ethyl acetate was added. The organic layer was washed with brine, dried and concentrated. The crude product was purified by column chromatography using 230-400 silica gel 2.5% methanol\chloroform as eluent to give compound tert-butyl 4-(cyano(diethoxyphosphoryl)methyl)piperazine-1-carboxylate as yellow liquid.

$^1$H NMR (400 MHz, CDCl$_3$): δ 1.37 (t, 6H), 1.47 (s, 9H), 2.55 (t, 2H), 3.0 (t, 2H), 3.55 (m, 4H), 3.87-3.93 (d, 1H), 4.3 (q, 4H).

LCMS: 262 (M$^+$−101).

Step-3

In a 100 ml 3 necked round bottom flask, intermediate tert-butyl 4-(cyano(diethoxyphosphoryl)methyl)piperazine-1-carboxylate (5.5 g) was taken in dry THF (25 ml) under nitrogen. Sodium bis trimethylsilyl amide (3.3 g) was added dropwise at 0° C. and stirred for 30 min, then pyridine-2-carboxaldehyde (1.67 g) in 15 ml dry THF was added dropwise to the above reaction mixture at 0° C. Reaction mixture was stirred at room temperature for overnight. TLC was checked no starting material and the reaction mixture was quenched with saturated ammonium chloride (50 ml) and ethyl acetate was added. The organic layer was washed with brine, dried and concentrated to get crude product compound tert-butyl 4-(1-cyano-2-(pyridin-2-yl)vinyl)piperazine-1-carboxylate as yellow liquid.

$^1$H NMR (400 MHz, CDCl$_3$): δ 1.47 (s, 9H), 3.10-3.2 (t, 4H), 3.55 (t, 4H), 6.24 (s, 1H), 7.14 (m, 1H), 7.55-7.67 (m, 2H), 8.58-8.6 (d, 1H).

LCMS: 315 (M$^+$+1).

Step-4

To a stirred solution of tert-butyl 4-(1-cyano-2-(pyridin-2-yl)vinyl)piperazine-1-carboxylate (2.5 g), sodium azide (0.4 g) were taken in dry DMSO (4 ml) and heated to 110° C. overnight. The reaction mixture was carefully quenched with water (10 ml) and the reaction mixture was extracted with dichloromethane (3×10 ml). The combined organic layer was washed with brine (10 ml), dried over sodium sulfate and concentrated under reduced pressure. The resulting residue was purified by column chromatography using methanol:chloroform (1:9) as an eluent to afford tert-butyl 4-(5-(pyridin-2-yl)-1H-1,2,3-triazol-4-yl)piperazine-1-carboxylate as white solid.

$^1$H NMR (400 MHz, CDCl$_3$): δ 1.49 (s, 9H), 3.17-3.2 (t, 4H), 3.65 (t, 4H), 7.44 (m, 1H), 8.0 (m, 1H), 8.1 (d, 1H), 8.88 (d, 1H).

LCMS: 331 (M$^+$+1).

Step-5

To tert-butyl 4-(5-(pyridin-2-yl)-1H-1,2,3-triazol-4-yl) piperazine-1-carboxylate (500 mg) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated NaHCO$_3$ (2×10 ml), brine, dried over Na$_2$SO$_4$. Evaporation of solvent gave desire amine G-24-In, which was used for the next reaction without further purification.

$^1$H NMR (400 MHz, DMSO-d$_6$): δ 3.17-3.2 (t, 4H), 3.45 (t, 4H), 7.44 (m, 1H), 8.0 (d, 2H), 8.65 (d, 1H), 8.88 (bs, 1H).

LCMS: 231 (M$^+$+1).

Preparation of G-24a

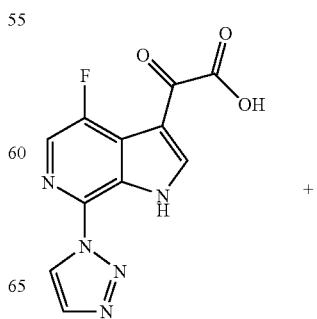

+

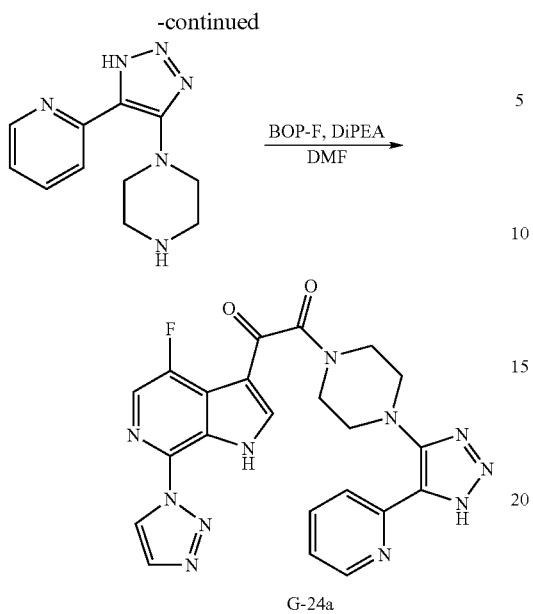

2-(4-Fluoro-7-(1H-1,2,3-triazol-1-yl)-1H-pyrrolo[2,3-c]pyridin-3-yl)-2-oxoacetic acid (95 mg), compound G-24-In (100 mg), BOP reagent (0.16 mg) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using dichloromethane\methanol (1:9) as eluent to afford G-24a as white solid.

$^1$H NMR (400 MHz, DMSO-d$_6$): δ 3.17-3.2 (t, 4H), 3.55 (t, 2H), 3.8 (t, 2H), 7.44 (m, 1H), 7.9-8.0 (m, 2H), 8.15 (s, 1H), 8.33-8.36 (d, 2H), 8.5 (m, 1H), 9 (s, 1H), 13 (bs, 1H), 14.48 (s, 1H).

LCMS: 488.8 (M$^+$+1).

HPLC: 90.4% (0.1% H$_3$PO$_4$/ACN; Column: YMC-PACK ODS-AQ (4.6×250) mm).

Preparation of G-24b 2-(4-Methoxy-7-(3-methyl-1H-1,2,4-triazol-1-yl)-1H-pyrrolo[2,3-c]pyridin-3-yl)-2-oxoacetic acid (95 mg), compound G-24-In (100 mg), BOP reagent (0.16 mg) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using dichloromethane\methanol (1:9) as eluent to afford G-24b as white solid.

$^1$H NMR (400 MHz, DMSO-d$_6$): δ 2.55 (s, 3H), 3.17-3.2 (t, 4H), 3.55 (t, 2H), 3.8 (t, 2H), 4 (s, 3H), 7.31 (m, 1H), 7.9-8.0 (m, 3H), 8.25 (s, 1H), 8.63 (d, 1H), 9.24 (s, 1H), 12.4 (bs, 1H), 14.48 (s, 1H).

LCMS: 512.8 (M$^+$+1).

HPLC: 98.0% (0.1% H$_3$PO$_4$/ACN; Column: YMC-PACK ODS-AQ (4.6×250) mm).

Preparation of Compound G-25a and G-25b

Preparation of Intermediate G-25-In

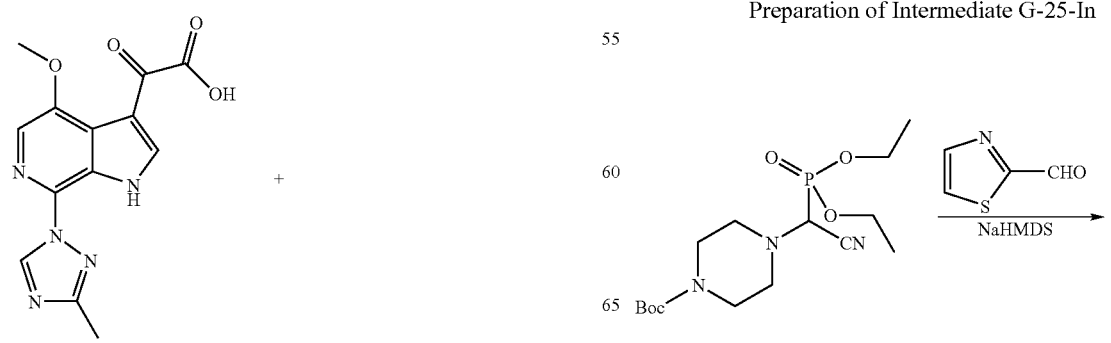

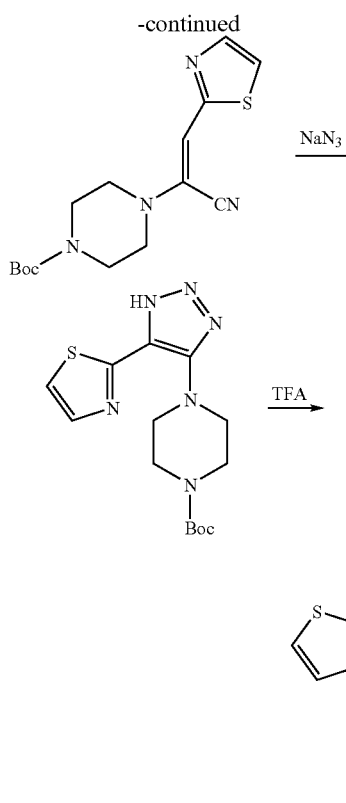

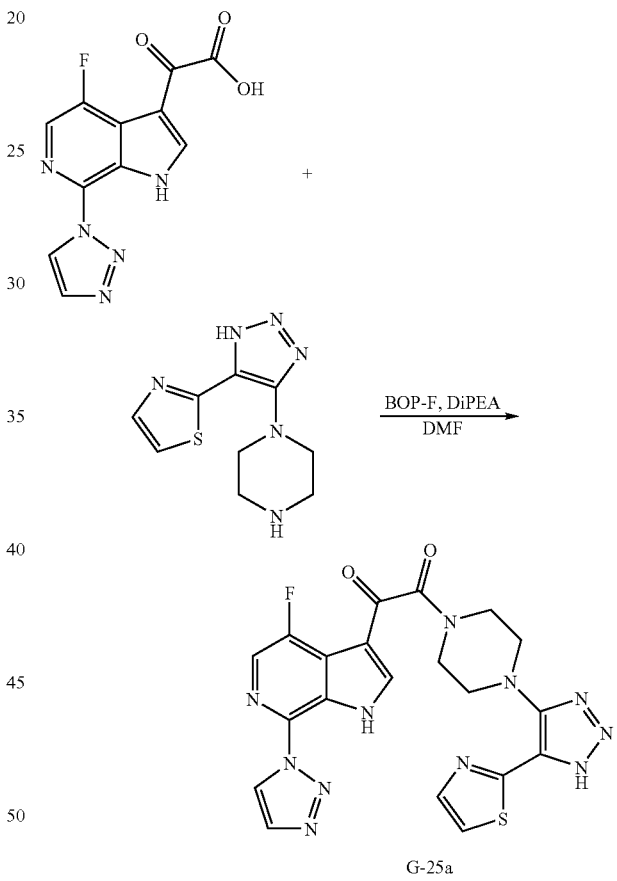

G-25-In

G-25a

Step-1

In a 100 ml 3 necked round bottle flask, tert-butyl 4-(cyano (diethoxyphosphoryl)methyl)piperazine-1-carboxylate (5.0 g) was taken in dry THF (25 ml) under nitrogen. Sodium bis trimethylsilyl amide (3.0 g) was added drop wise at 0° C. and stirred for 30 min, then thiazole-2-carboxaldehyde (1.60 g) in 15 ml dry THF was added drop wise to the above reaction mixture at 0° C. Reaction mixture was stirred at room temperature for overnight. TLC was checked no starting material and the reaction mixture was quenched with saturated ammonium chloride (50 ml) and ethyl acetate was added. The organic layer was washed with brine, dried and concentrated to get crude product tert-butyl 4-(1-cyano-2-(thiazol-2-yl)vinyl)piperazine-1-carboxylate as yellow liquid.

$^1$H NMR (400 MHz, CDCl$_3$): δ 1.49 (s, 9H), 3.33 (t, 4H), 3.55 (m, 4H), 6.8 (s, 1H), 7.31 (s, 1H), 7.82 (s, 1H).

LCMS: 321 (M$^+$+1).

Step-2

To a stirred solution of tert-butyl 4-(1-cyano-2-(thiazol-2-yl)vinyl)piperazine-1-carboxylate (2.25 g), sodium azide (0.4 g) were taken in dry DMSO (4 ml) and heated to 110° C. overnight. The reaction mixture was carefully quenched with water (10 ml) and the reaction mixture was extracted with dichloromethane (3×10 ml). The combined organic layer was washed with brine (10 ml), dried over sodium sulfate and concentrated under reduced pressure. The resulting residue was purified by column chromatography using methanol: chloroform (1:9) as an eluent to afford tert-butyl 4-(5-(thiazol-2-yl)-1H-1,2,3-triazol-4-yl)piperazine-1-carboxylate as white solid.

$^1$H NMR (400 MHz, CDCl$_3$): δ 1.55 (s, 9H), 3.33 (t, 4H), 3.68 (m, 4H), 7.45 (s, 1H), 7.98 (s, 1H).

LCMS: 335.7 (M$^+$+1).

Step-5

To tert-butyl 4-(5-(thiazol-2-yl)-1H-1,2,3-triazol-4-yl)piperazine-1-carboxylate (500 mg) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated NaHCO$_3$ (2×10 ml), brine, dried over Na$_2$SO$_4$. Evaporation of solvent gave desire amine G-25-In, which was used for the next reaction without further purification.

$^1$H NMR (400 MHz, CDCl$_3$): δ 3.33 (t, 4H), 3.68 (m, 4H), 7.45 (s, 1H), 7.98 (s, 1H). LCMS: 237 (M$^+$+1).

Preparation of G-25a 2-(4-Fluoro-7-(1H-1,2,3-triazol-1-yl)-1H-pyrrolo[2,3-c]pyridin-3-yl)-2-oxoacetic acid (95 mg), compound G-25-In (100 mg), BOP reagent (0.16 mg) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using dichloromethane\methanol (1:9) as eluent to afford G-25a as white solid.

¹H NMR (400 MHz, DMSO-d₆): δ 3.47-3.56 (dd, 6H), 3.8 (t, 2H), 7.7-7.9 (s, 2H), 8.15 (s, 1H), 8.33-8.36 (d, 2H), 9 (s, 1H), 13 (bs, 1H), 14.7 (s, 1H).

LCMS: 492 (M⁺−1).

HPLC: 86.6% (0.1% H₃PO₄/ACN; Column: YMC-PACK ODS-AQ (4.6×250) mm).

Preparation of G-25b

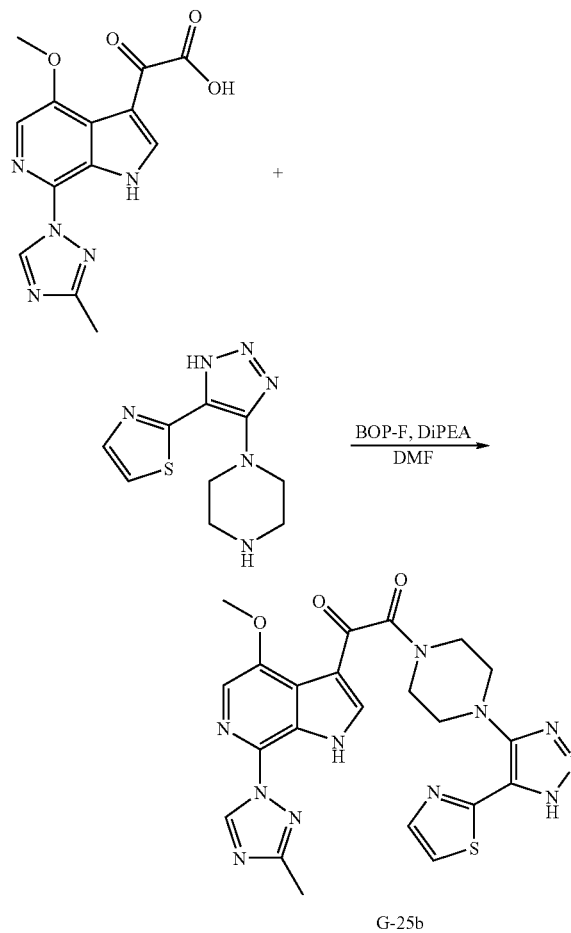

G-25b 2-(4-Methoxy-7-(3-methyl-1H-1,2,4-triazol-1-yl)-1H-pyrrolo[2,3-c]pyridin-3-yl)-2-oxoacetic acid (95 mg), compound G-25-In (100 mg), BOP reagent (0.16 mg) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO₃ and brine. The organic layer was dried over anhydrous Na₂SO₄ and concentrated under reduced pressure. The resulting crude was purified by column chromatography using dichloromethane\methanol (1:9) as eluent to afford G-25b as white solid.

¹H NMR (400 MHz, DMSO-d₆): δ 2.5 (s, 3H), 3.37-3.46 (m, 2H), 3.5 (m, 4H), 3.8 (t, 2H), 3.99 (s, 3H), 7.7 (s, 1H), 7.9 (s, 2H), 8.25 (s, 1H), 9.24 (s, 1H), 12.4 (bs, 1H), 14.7 (s, 1H).

LCMS: 518.6 (M⁺−1).

HPLC: 91.2% (0.1% H₃PO₄/ACN; Column: YMC-PACK ODS-AQ (4.6×250) mm).

Preparation of Compound G-26a and G-26b

Preparation of Intermediate G-26-In

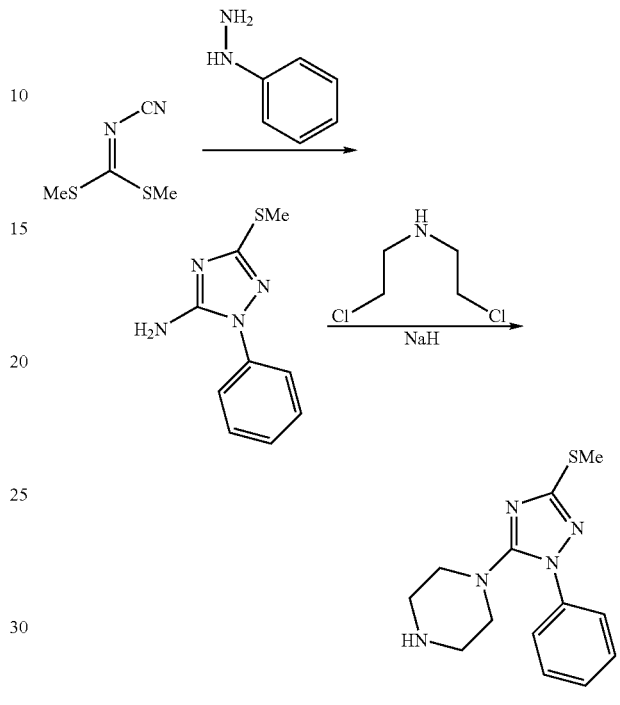

G-26-In

Step-1

To a stirred solution of phenyl hydrazine (3 g) in absolute alcohol (30 ml) added dimethyl-N-cyanodithiocarbonate (4 g) slowly under nitrogen atmosphere. The reaction mixture was stirred at 80° C. for two hours. The progress of reaction was monitored by TLC. After consumption of starting material, the volatiles were removed under reduced pressure from the reaction mixture. The resulting residue was recrystallized from pet ether to afford 3-(methylthio)-1-phenyl-1H-1,2,4-triazol-5-amine as yellow solid. The solid obtained was taken to next step without further purification.

¹H NMR (400 MHz, DMSO-d₆): δ 2.50 (s, 3H), 6.54 (s, 2H), 7.33-7.53 (m, 5H).

LCMS: 206.7 (M⁺+1).

Step-2

Sodium hydride (4.7 g) was taken in dry DMF (100 ml) and a solution of compound 3-(methylthio)-1-phenyl-1H-1,2,4-triazol-5-amine (4 g in 10 ml of DMF) was added slowly at 0° C. The reaction mixture was stirred for 30 min at 0° C. and a solution of bis(2-chloroethyl)amine hydrochloride (4.15 g) in dry DMF (20 ml) was added very slowly. The reaction mixture was allowed to stir over night at room temperature. The reaction mixture was quenched with cold water (5 ml) and extracted with ethyl acetate (3×40 ml). Evaporation of solvent under reduced pressure gave crude product, which, was purified by column chromatography using methanol\dichloromethane (1:9) as eluent to afford 1-(3-(methylthio)-1-phenyl-1H-1,2,4-triazol-5-yl)piperazine, G-26-In, as brown oil.

$^1$H NMR (400 MHz, DMSO-d$_6$): δ 2.50 (s, 3H), 2.54-2.72 (m, 4H), 2.82-3.37 (m, 4H), 7.38-7.60 (m, 5H).

LCMS: 275.9 (M$^+$+1).

Preparation of G-26a

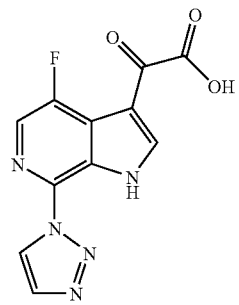

Preparation of G-26b

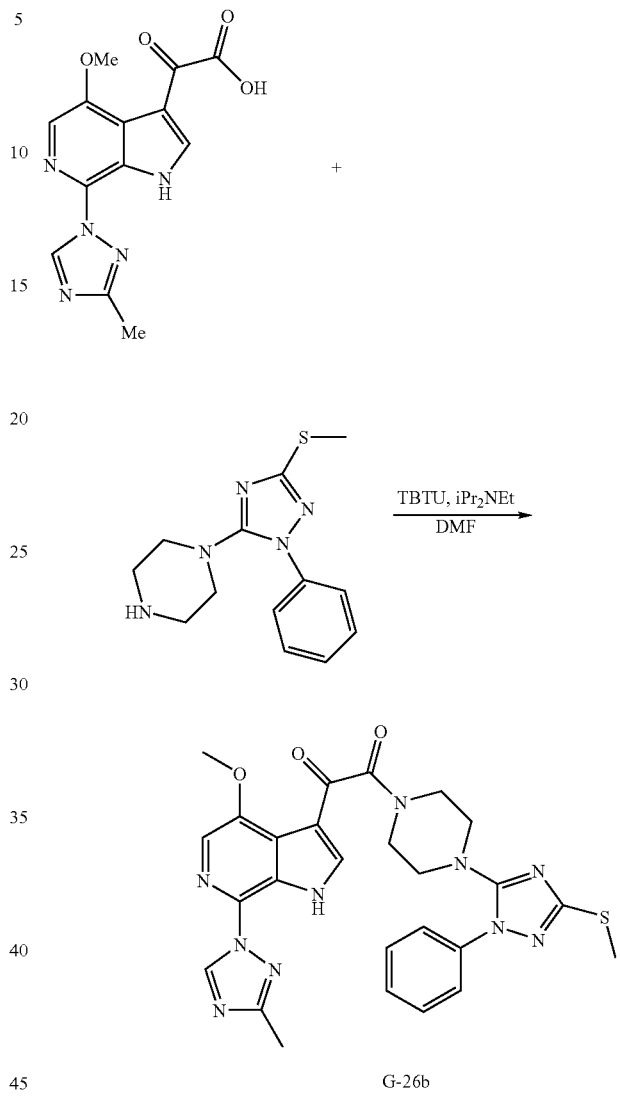

2-(4-Fluoro-7-(1H-1,2,3-triazol-1-yl)-1H-pyrrolo[2,3-c] pyridin-3-yl)-2-oxoacetic acid (0.1 g), amine G-26-In (0.09 g), TBTU (0.128 g) and Hunig's base (0.15 ml) were combined in dry DMF (5 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using methanol\dichloromethane (1:9) as eluent to afford G-26a.

$^1$H NMR (400 MHz, DMSO-d$_6$): δ 2.54 (s, 3H), 3.0 (m, 2H), 3.08 (m, 2H), 3.38 (m, 2H), 3.69 (m, 2H), 7.38-7.66 (m, 5H), 8.12 (s, 1H), 8.31 (d, 2H), 9.01 (s, 1H).

LCMS: 532.9 (M$^+$+1).

HPLC: 97.66% (0.1% TFA/ACN; Column: C18 BDS, 250×4.6 mm).

2-(4-Methoxy-7-(3-methyl-1H-1,2,4-triazol-1-yl)-1H-pyrrolo[2,3-c]pyridin-3-yl)-2-oxoacetic acid (0.1 g), amine G-26-In (0.09 g), TBTU (0.11 g) and Hunig's base (0.15 ml) were combined in dry DMF (5 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using methanol\dichloromethane (1:9) as eluent to afford G-26b.

$^1$H NMR (400 MHz, DMSO-d$_6$): δ 2.48 (s, 3H), 2.50 (s, 3H), 3.08 (m, 2H), 3.20 (m, 2H), 3.42 (m, 2H), 3.67 (m, 2H), 3.98 (s, 3H), 7.39-7.67 (m, 5H), 7.88 (s, 1H), 8.22 (s, 1H), 9.23 (s, 1H).

LCMS: 559.0 (M$^+$+1).

HPLC: 99.71% (0.1% TFA/ACN; Column: C18 BDS, 50×4.6 mm).

Preparation of Compound G-27a and G-27b

Preparation of Intermediate G-27-In

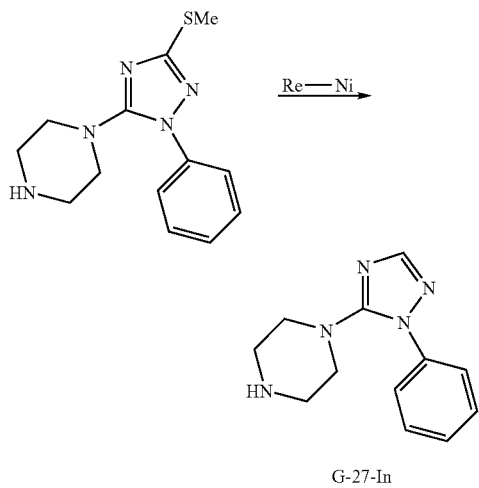

G-27-In

To a stirred solution of Raney nickel (2 g) in dry THF (10 ml) added compound 1-(3-(methylthio)-1-phenyl-1H-1,2,4-triazol-5-yl)piperazine (1 g) in dry THF (10 ml) slowly under nitrogen atmosphere. The reaction mixture was refluxed at 70° C. for three hours. The progress of reaction was monitored by TLC. After consumption of starting material, the catalysts were removed by filtration with the help of methanol (10×2 ml). The filterate was concentrated to remove the volatiles. The resulting crude product was purified by column chromatography methanol\dichloromethane (1:9) as eluent to afford G-27-In as colorless liquid.

$^1$H NMR (400 MHz, CD$_3$OD): δ 2.84-2.87 (t, 4H), 3.11-3.13 (t, 4H), 7.45-7.79 (m, 5H), 7.92 (s, 1H).

LCMS: 229.9 (M$^+$+1).

Preparation of G-27a

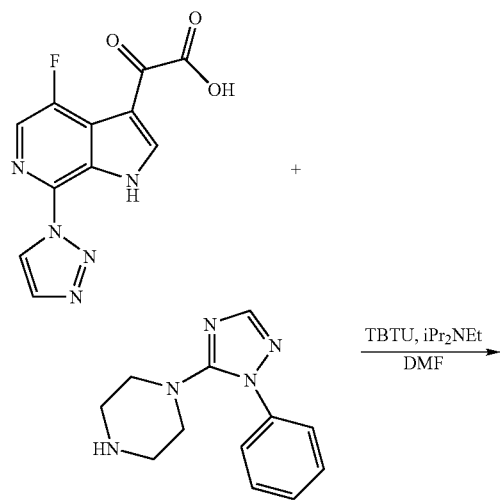

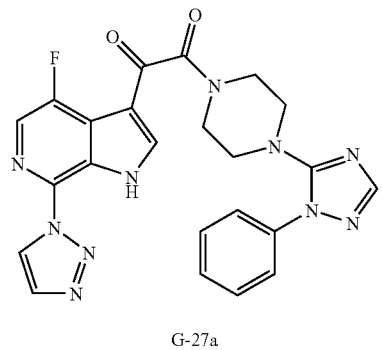

G-27a 2-(4-Fluoro-7-(1H-1,2,3-triazol-1-yl)-1H-pyrrolo[2,3-c]pyridin-3-yl)-2-oxoacetic acid (0.1 g), amine G-27-In (0.08 g), TBTU (0.12 g) and Hunig's base (0.15 ml) were combined in dry DMF (5 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using methanol\dichloromethane (1:9) as eluent to afford G-27a.

$^1$H NMR (400 MHz, DMSO-d$_6$): δ 3.07 (m, 2H), 3.20 (m, 2H), 3.48 (m, 2H), 3.71 (m, 2H), 7.40-7.83 (m, 5H), 8.12 (s, 1H), 8.31 (s, 2H), 8.35 (s, 1H), 9.01 (s, 1H), 13.01 (bs, 1H).

LCMS: 487.1 (M$^+$+1).

HPLC: 94.16% (0.1% TFA/ACN; Column: C18 BDS, 250×4.6 mm).

Preparation of G-27b

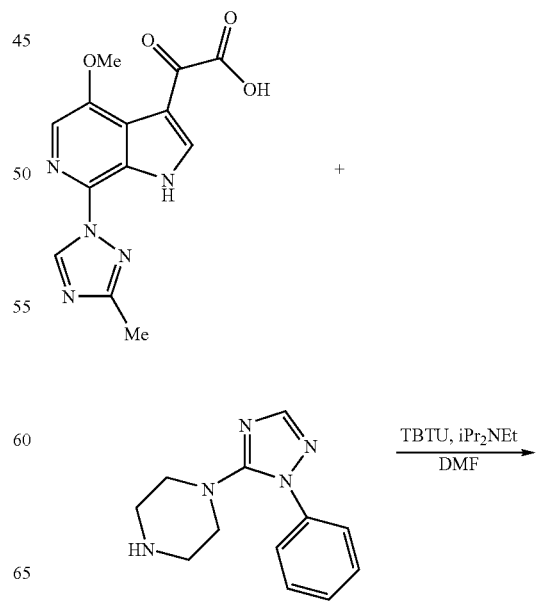

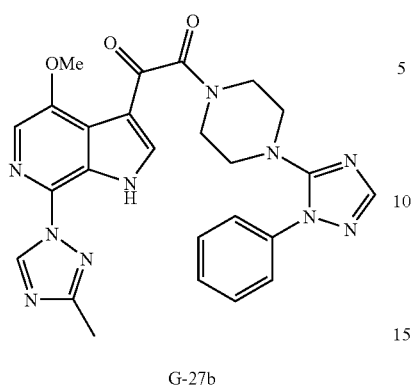

G-27b 2-(4-Methoxy-7-(3-methyl-1H-1,2,4-triazol-1-yl)-1H-pyrrolo[2,3-c]pyridin-3-yl)-2-oxoacetic acid (0.1 g), amine G-27-In (0.076 g), TBTU (0.11 g) and Hunig's base (0.15 ml) were combined in dry DMF (5 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using methanol\dichloromethane (1:9) as eluent to afford G-27b.

$^1$H NMR (400 MHz, DMSO-d$_6$): δ 2.50 (s, 3H), 3.09 (m, 2H), 3.20 (m, 2H), 3.43 (m, 2H), 3.67 (m, 2H), 3.98 (s, 3H), 7.40-7.57 (m, 5H), 7.84 (s, 1H), 7.88 (s, 1H), 8.22 (s, 1H), 9.24 (s, 1H), 12.39 (bs, 1H).

LCMS: 513.1 (M$^+$+1).

HPLC: 99.01% (0.1% TFA/ACN; Column: C18 BDS, 250×4.6 mm).

Preparation of Compound G-28a and G-28b

Preparation of Intermediate G-28-In

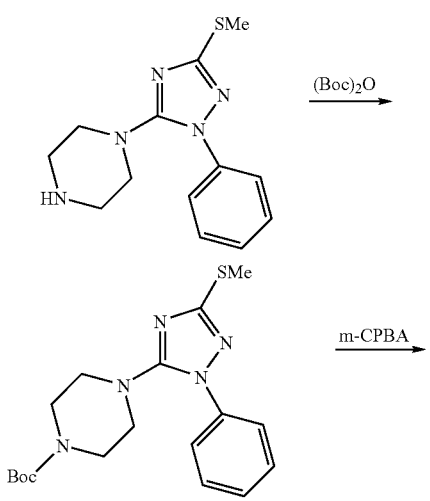

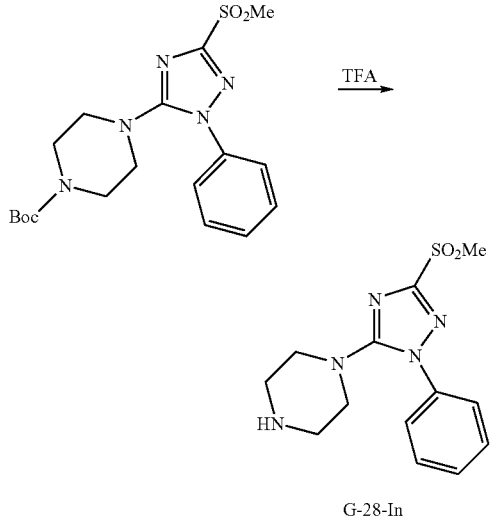

G-28-In

Step-1

To a stirred solution of G-26-In (5 g) in dichloromethane (10 ml), triethylamine (7.6 ml) was added until the solution is basic. To this basified reaction mixture, Boc-anhydride (4.8 g) was added and allowed to stir at room temperature for overnight. The reaction mixture was quenched with water (20 ml) and extracted with dichloromethane (3×10 ml). The combined organic layers was dried over Na$_2$SO$_4$ and concentrated to dryness to afford tert-butyl 4-(3-(methylthio)-1-phenyl-1H-1,2,4-triazol-5-yl)piperazine-1-carboxylate (6 g) as a white color solid, which taken for the next reaction without further purification.

$^1$H NMR (400 MHz, DMSO-d$_6$): δ 1.49 (s, 9H), 2.50 (s, 3H), 2.54-2.72 (m, 4H), 2.82-3.37 (m, 4H), 7.38-7.60 (m, 5H).

LC-MS: 378 (M$^+$+1).

Step-2

To a stirred solution of tert-butyl 4-(3-(methylthio)-1-phenyl-1H-1,2,4-triazol-5-yl)piperazine-1-carboxylate (3 g) in dichloromethane (25 ml), m-chloro per benzoic acid (5.5 g) was added and allowed to stir at room temperature for overnight. The reaction mixture was filtered through celite and celite pad was washed with chloroform (3×10 ml). The combined organic layers were washed with saturated sodium bicarbonate solution, brine and concentrated to dryness to get crude tert-butyl 4-(3-(methylsulfonyl)-1-phenyl-1H-1,2,4-triazol-5-yl)piperazine-1-carboxylate. This was taken for column chromatography using 60-120 silica gel and 1.0% methanol\chloroform as eluent to get pure compound tert-butyl 4-(3-(methylsulfonyl)-1-phenyl-1H-1,2,4-triazol-5-yl)piperazine-1-carboxylate as white solid.

$^1$H NMR (400 MHz, DMSO-d$_6$): δ 1.49 (s, 9H), 3.1 (t, 4H), 3.31-3.36 (m, 7H), 7.38-7.60 (m, 5H).

LC-MS: 411 (M$^+$+1).

Step-3

To tert-butyl 4-(3-(methylsulfonyl)-1-phenyl-1H-1,2,4-triazol-5-yl)piperazine-1-carboxylate (500 mg) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated NaHCO₃ (2×10 ml), brine, dried over Na₂SO₄. Evaporation of solvent gave desire amine G-28-In, which was used for the next reaction without further purification.

¹H NMR (400 MHz, DMSO-d₆): δ 3.1 (t, 4H), 3.31-3.36 (m, 4H), 3.4-3.5 (s, 3H), 7.38-7.60 (m, 5H).

LC-MS: 310 (M⁺+1).

Preparation of G-28a

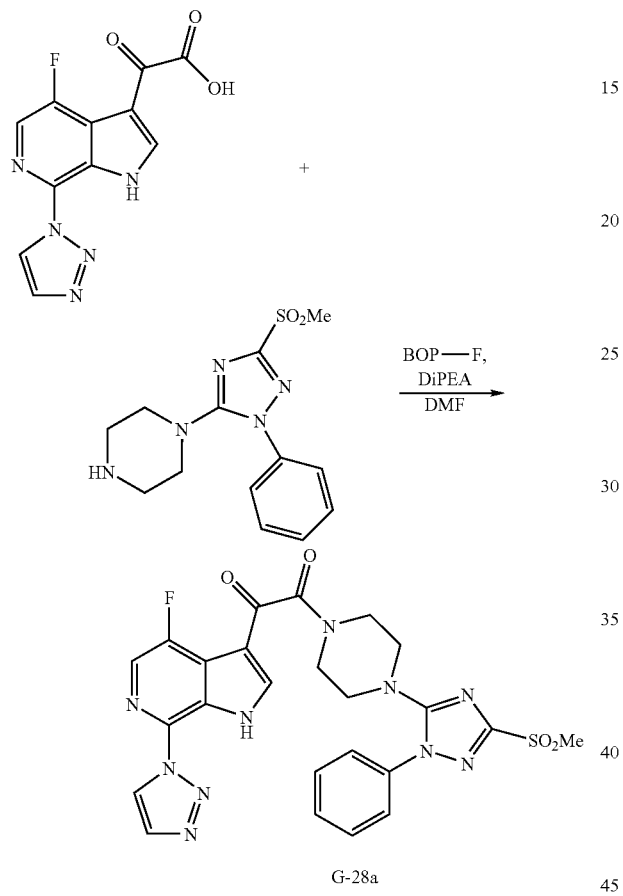

G-28a 2-(4-Fluoro-7-(1H-1,2,3-triazol-1-yl)-1H-pyrrolo[2,3-c]pyridin-3-yl)-2-oxoacetic acid (60 mg), compound G-28-In (80 mg), BOP reagent (0.1 g) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO₃ and brine. The organic layer was dried over anhydrous Na₂SO₄ and concentrated under reduced pressure. The resulting crude was purified by column chromatography using dichloromethane\methanol (1:9) as eluent to afford G-28a as white solid.

¹H NMR (400 MHz, DMSO-d₆): δ 3.15 (t, 2H), 3.28 (t, 2H), 3.3 (s, 3H), 3.48 (t, 2H), 3.69 (t, 2H), 7.5 (m, 1H), 7.53 (m, 2H), 7.71 (d, 2H), 8.12 (s, 1H), 8.31 (s, 1H), 8.36 (s, 1H), 9.01 (s, 1H), 13.07 (s, 1H).

LC-MS: 565 (M⁺+1)

HPLC: 95.2% (0.1% H₃PO₄/ACN; Column: YMC-PACK ODS-AQ (4.6×250) mm)..

Preparation of G-28b

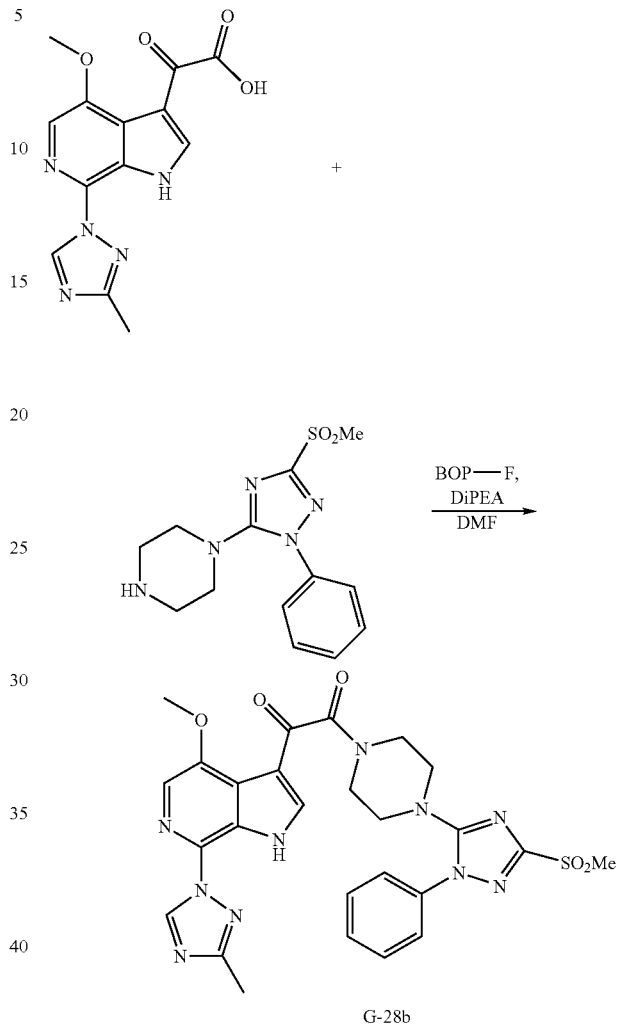

G-28b 2-(4-Methoxy-7-(3-methyl-1H-1,2,4-triazol-1-yl)-1H-pyrrolo[2,3-c]pyridin-3-yl)-2-oxoacetic acid (75 mg), compound G-28-In (80 mg), BOP reagent (0.1 g) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO₃ and brine. The organic layer was dried over anhydrous Na₂SO₄ and concentrated under reduced pressure. The resulting crude was purified by column chromatography using dichloromethane\methanol (1:9) as eluent to afford G-28b as white solid.

¹H NMR (400 MHz, DMSO-d₆): δ 2.5 (s, 3H), 3.15 (t, 2H), 3.28 (t, 2H), 3.3 (s, 3H), 3.48 (t, 2H), 3.69 (t, 2H), 3.97 (s, 3H), 7.5 (m, 1H), 7.53 (m, 2H), 7.61 (d, 2H), 7.88 (s, 1H), 8.23 (s, 1H), 9.21 (s, 1H), 12.4 (s, 1H).

LC-MS: 591 (M⁺+1).

HPLC: 96.0% (0.1% H₃PO₄/ACN; Column: YMC-PACK ODS-AQ (4.6×250) mm).

Preparation of Compound G-29a and G-29b

Preparation of Intermediate G-29-In

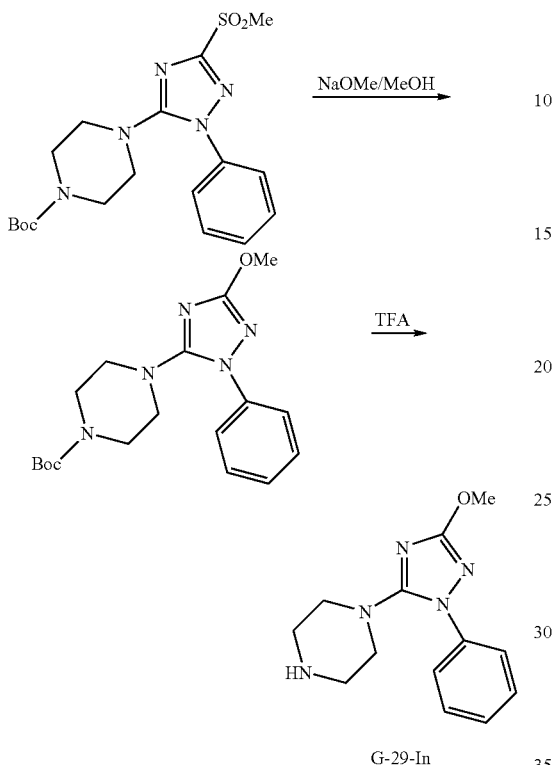

Step-1

Dry methanol (10 ml) was charged to a clean and dry 3 necked round bottom flask fitted with reflux condenser, stirring bar and a nitrogen bubbler. Sodium metal (564 mg) was added portion wise to the above reaction mixture at room temperature. After complete dissolution of sodium metal, tert-butyl 4-(3-(methylsulfonyl)-1-phenyl-1H-1,2,4-triazol-5-yl)piperazine-1-carboxylate (1.0 g) in 5 ml methanol was added and reaction mass was heated to 60° C. Reaction mixture was allowed to stir at 60° C. for over night. Reaction mixture was cooled to room temperature and slowly quenched with ice. Product was extracted with ethyl acetate and organic layer was washed with water, brine, dried and concentrated to get pure tert-butyl 4-(3-methoxy-1-phenyl-1H-1,2,4-triazol-5-yl)piperazine-1-carboxylate as off white solid.

$^1$H NMR (400 MHz, DMSO-$d_6$): δ 1.49 (s, 9H), 3.0 (t, 4H), 3.3 (m, 4H), 4.0 (s, 3H), 7.38-7.60 (m, 5H).

LC-MS: 360 (M$^+$+1).

Step-2

To tert-butyl 4-(3-methoxy-1-phenyl-1H-1,2,4-triazol-5-yl)piperazine-1-carboxylate (500 mg) dissolved in dry dichloromethane (10 ml), TFA (5 ml) was added at 0° C. The reaction mixture was allowed to reach at room temperature and stirred for over-night. The volatiles were completely removed and resulting residue was diluted with dichloromethane (20 ml). The organic layer was washed with saturated NaHCO$_3$ (2×10 ml), brine, dried over Na$_2$SO$_4$. Evaporation of solvent gave desire amine compound G-29-In, which was used for the next reaction without further purification.

$^1$H NMR (400 MHz, DMSO-$d_6$): δ 3.0 (t, 4H), 3.3 (m, 4H), 4.0 (s, 3H), 7.38-7.60 (m, 5H).

LC-MS: 259 (M$^+$+1).

Preparation of G-29a

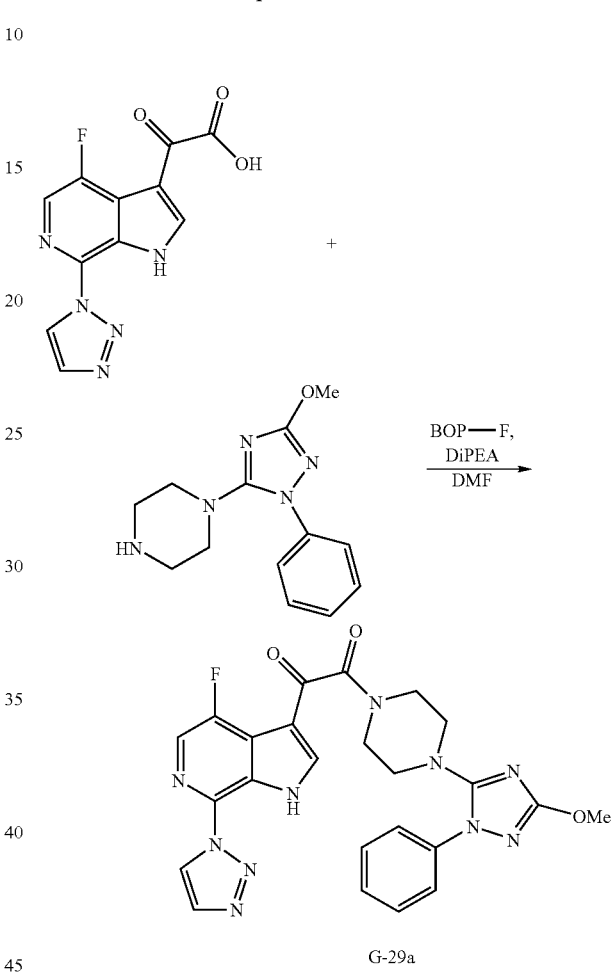

2-(4-Fluoro-7-(1H-1,2,3-triazol-1-yl)-1H-pyrrolo[2,3-c]pyridin-3-yl)-2-oxoacetic acid (95 mg), compound G-29-In (100 mg), BOP reagent (0.16 mg) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using dichloromethane\methanol (1:9) as eluent to afford G-29a as white solid.

$^1$H NMR (400 MHz, DMSO-$d_6$): δ 3.08 (t, 2H), 3.2 (t, 2H), 3.46 (t, 2H), 3.68 (t, 2H), 3.83 (s, 3H), 7.36 (m, 1H), 7.48 (m, 2H), 7.65 (m, 2H), 8.11 (s, 1H), 8.3 (s, 1H), 8.35 (s, 1H), 9.01 (s, 1H), 13.06 (s, 1H).

LC-MS: 517 (M$^+$+1).

HPLC: 97.4% (0.1% H$_3$PO$_4$/ACN; Column: YMC-PACK ODS-AQ (4.6×250) mm).

335
Preparation of G-29b

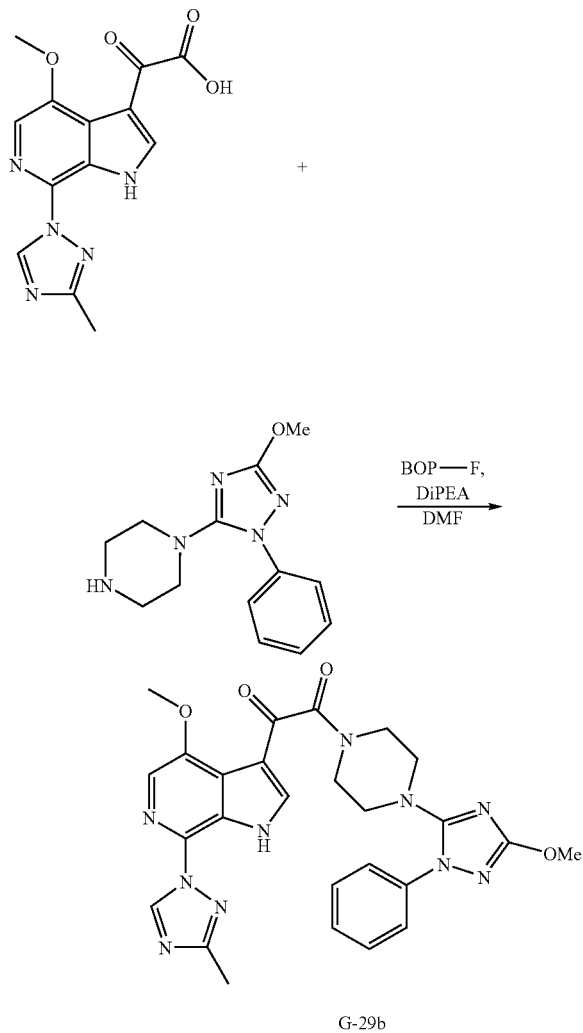

G-29b 2-(4-Methoxy-7-(3-methyl-1H-1,2,4-triazol-1-yl)-1H-pyrrolo[2,3-c]pyridin-3-yl)-2-oxoacetic acid (116 mg), compound G-29-In (100 mg), BOP reagent (0.176 mg) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using dichloromethane\methanol (1:9) as eluent to afford G-29b as white solid.

$^1$H NMR (400 MHz, DMSO-d$_6$): δ 2.48 (s, 3H), 3.08 (t, 2H), 3.2 (t, 2H), 3.46 (t, 2H), 3.68 (t, 2H), 3.83 (s, 3H), 3.98 (s, 3H), 7.36 (m, 1H), 7.48 (m, 2H), 7.65 (m, 2H), 7.88 (s, 1H), 8.22 (s, 1H), 9.23 (s, 1H).

LC-MS: 543 (M$^+$+1).

HPLC: 97.1% (0.1% H$_3$PO$_4$/ACN; Column: YMC-PACK ODS-AQ (4.6×250) mm).

336
Preparation of Compound G-30a and G-30b

Preparation of Intermediate G-30-In

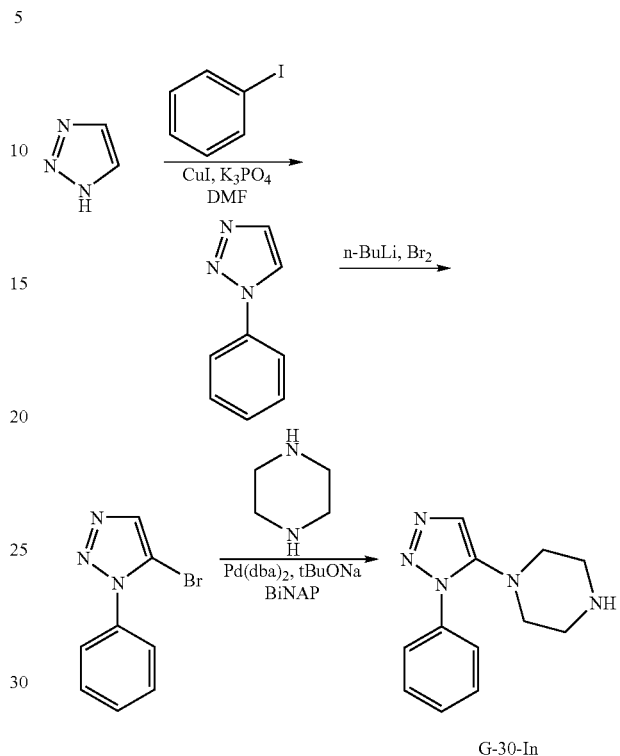

G-30-In

Step-1

1,2,3-Triazole (5 g), iodobenzene (9.72 ml) and copper iodide (0.68 g) was taken in dry DMF under Nitrogen atmosphere. 1,2-(N,N-dimethyl)cyclohexyl diamine (1.02 g) and potassium phosphate (30.73 g) was added into above mixture. The reaction mixture was reflux at 110° C. for over night. TLC was checked no starting material and the reaction mixture was filtered through celite. The filtrate was diluted with water and product was extracted with dichloromethane. The organic layer was evaporated and the crude product was purified by column chromatography using 60-120 silica gel and pet ether\ethyl acetate as eluent to give 1-phenyl-1H-1,2,3-triazole as white solid.

$^1$H NMR (400 MHz, CDCl$_3$): δ 7.47 (m, 1H), 7.5-7.6 (m, 2H), 7.9 (d, 2H), 7.98 (s, 1H), 8.84 (s, 1H).

LC-MS: 145.6 (M$^+$+1).

Step-2

In a 100 ml 3 necked round bottom flask, 1-phenyl-1H-1,2,3-triazole (1.2 g) was taken in dry THF (25 ml) under nitrogen. n-Butyl lithium (3.36 ml) was added at −78° C. and stirred for 5 minutes, then bromine (3.76 ml) was added dropwise to the above reaction mixture. Reaction mixture was stirred at −78° C. for 1 hour. TLC was checked no starting material and the reaction mixture was quenched with saturated ammonium chloride (50 ml) and ethyl acetate was added. The organic layer was washed with sodium bisulphate, brine, dried and concentrated. The crude product was purified by column chromatography using pet ether & ethyl acetate as eluent to give 5-bromo-1-phenyl-1H-1,2,3-triazole as yellow solid.

$^1$H NMR (400 MHz, CDCl$_3$): δ 7.47 (m, 1H), 7.5-7.6 (m, 2H), 7.9 (d, 2H), 8.05 (s, 1H).

LC-MS: 225 (M$^+$+1).

Step-3

In a 100 ml single neck round bottom flask, 5-bromo-1-phenyl-1H-1,2,3-triazole (0.6 g), piperazine (1.11 g) and sodium tert-butoxide (0.38 g) was taken in dry toluene (20 ml) and degasified for 20 min. Then Pd(dba)$_2$ (0.11 g), BiNAP (0.16 g) was added and again degasified for 10 min. The reaction mixture was reflux at 107° C. for over night. TLC was checked no starting material. Reaction mixture was diluted with 25 ml of water and extracted with dichloromethane. The organic layer was separated and concentrated. The crude product was purified by column chromatography using 60-120 silica gel and 6% methanol\chloroform as eluent to give compound G-30-In as white solid.

$^1$H NMR (400 MHz, CDCl$_3$): δ 2.5-2.72 (d, 8H), 7.41 (s, 1H), 7.5-7.6 (m, 3H), 7.73 (d, 2H).

LC-MS: 230 (M$^+$+1).

Preparation of G-30a

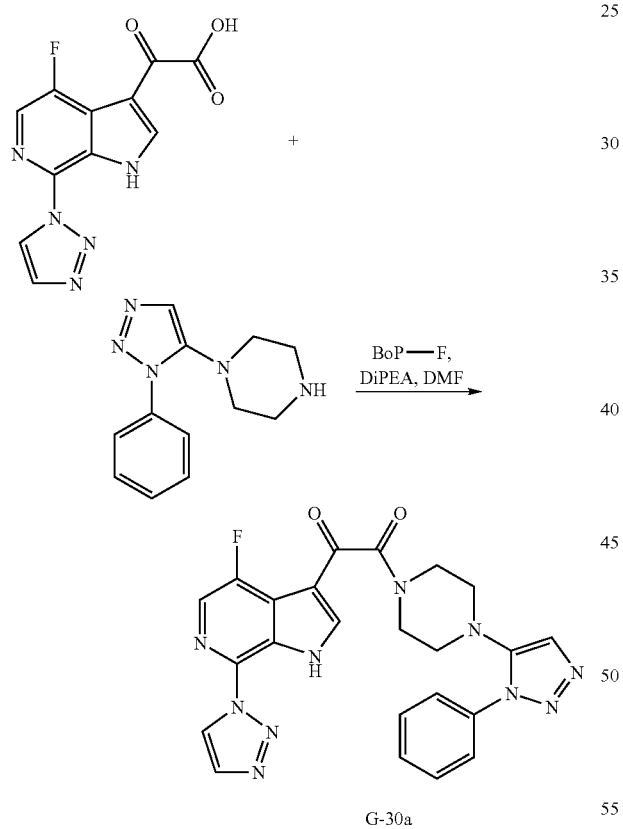

G-30a 2-(4-Fluoro-7-(1H-1,2,3-triazol-1-yl)-1H-pyrrolo[2,3-c]pyridin-3-yl)-2-oxoacetic acid (60 mg), compound G-30-In (50 mg), BOP reagent (0.094 g) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using MeOH/CHCl$_3$ (1:9) as eluent to afford G-30a as white solid.

$^1$H NMR (400 MHz, DMSO-d$_6$): δ 2.86-2.88 (t, 3H), 2.97-2.99 (t, 3H), 3.45-3.38 (t, 3H), 3.67-3.7 (t, 3H), 7.52 (s, 2H), 7.6 (m, 2H), 7.78 (m, 2H), 8.12 (s, 1H), 8.3-8.35 (d, 2H), 9.0 (s, 1H), 13.0 (s, 1H).

LC-MS: 487 (M$^+$+1).

HPLC: 96.4% (0.1% H$_3$PO$_4$/ACN; Column: YMC-PACK ODS-AQ (4.6×250) mm).

Preparation of G-30b

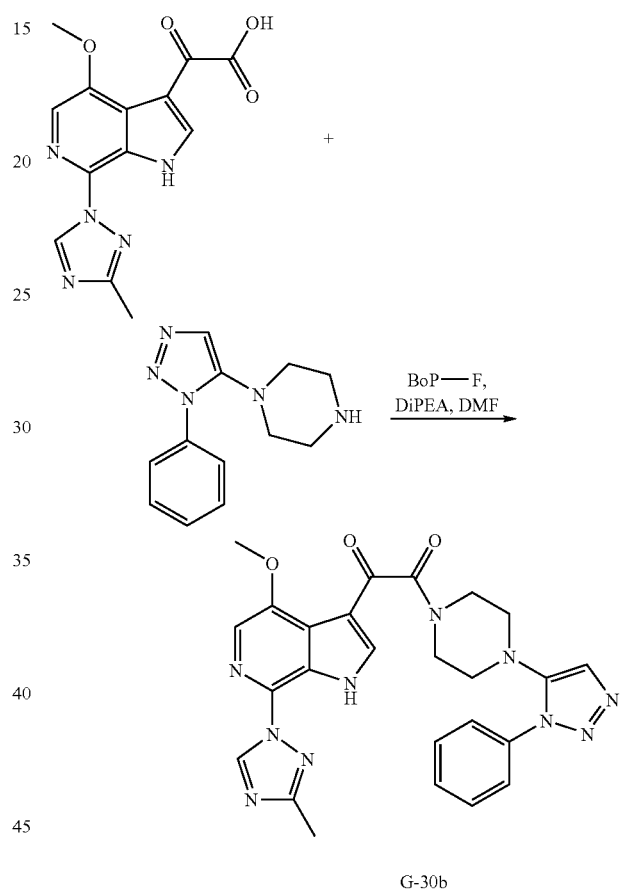

G-30b 2-(4-Methoxy-7-(3-methyl-1H-1,2,4-triazol-1-yl)-1H-pyrrolo[2,3-c]pyridin-3-yl)-2-oxoacetic acid (60 mg), compound G-30-In (50 mg), BOP reagent (0.094 g) and Hunig's base (0.2 ml) were combined in dry DMF (4 ml). The reaction mixture was stirred at room temperature for over night. The mixture was quenched with methanol (10 ml) and volatiles were removed under reduced pressure. The resulting oil was diluted with ethyl acetate (50 ml), washed with 10% NaHCO$_3$ and brine. The organic layer was dried over anhydrous Na$_2$SO$_4$ and concentrated under reduced pressure. The resulting crude was purified by column chromatography using MeOH/CHCl$_3$ (1:9) as eluent to afford G-30b as white solid.

$^1$H NMR (400 MHz, DMSO-d$_6$): δ 2.5 (s, 3H), 2.86-2.88 (t, 2H), 2.95-2.98 (t, 2H), 3.4-3.42 (t, 2H), 3.65-3.67 (t, 2H), 3.97 (s, 3H), 7.52 (s, 2H), 7.6 (m, 2H), 7.76-7.78 (d, 2H), 7.89 (s, 1H), 8.22 (s, 1H), 9.24 (s, 1H), 12.4 (s, 1H).

LC-MS: 513 (M$^+$+1).

HPLC: 97.7% (0.1% H$_3$PO$_4$/ACN; Column: YMC-PACK ODS-AQ (4.6×250) mm).

Preparation of Compound G-31

Preparation of Intermediate G-31-In

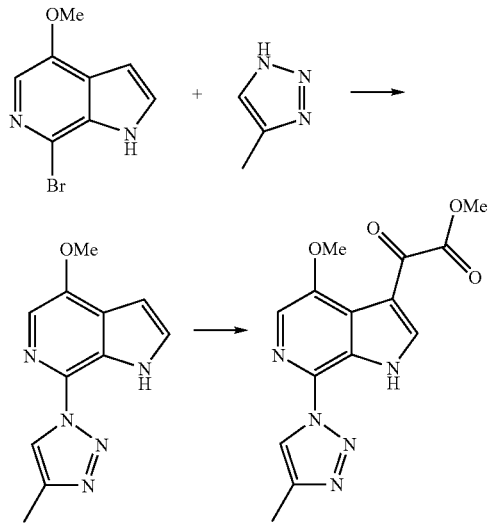

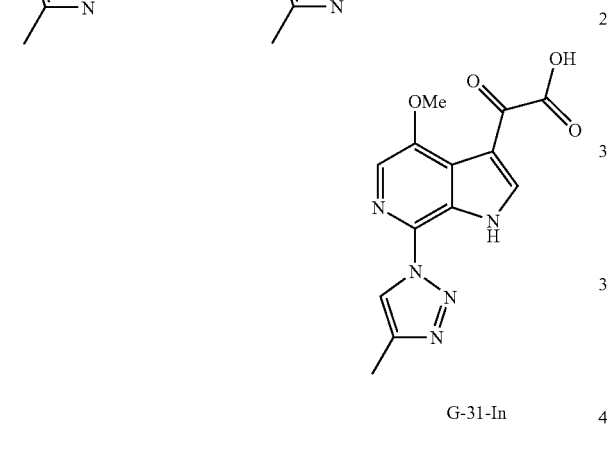

G-31-In

Step-1

4-Methoxy-7-bromo-6-azaindole (120 mg) was added in portions to a melted of 4-methyl-1,2,3-triazole (219 mg) under argon at 110-120° C. The mixture was heated to 130° C. and was stirred at 130° C. for 17 hours. The reaction mixture was cooled to room temperature and the resulting residue was purified by column chromatography using EtOAc/Hexane (6:4) mixture as eluent which afforded 4-methoxy-7-(4-methyl-1H-1,2,3-triazol-1-yl)-1H-pyrrolo[2,3-c]pyridine as a tan solid. $^1$H NMR (400 MHz, DMSO-D6): δ 2.38 (s, 3H), 4.01 (s, 3H), 6.66 (dd, 1H, J=2.9, 2.6), 7.53 (dd, 1H, J=2.9, 2.8), 7.70 (s, 1H), 8.62 (s, 1H), 11.78 (bs, 1H). MS: 230.3 (M$^+$+1).

Step-2

To 4-methoxy-7-(4-methyl-1H-1,2,3-triazol-1-yl)-1H-pyrrolo[2,3-c]pyridine (0.3 g) taken in methyl THF (20 ml) and cooled to −10° C., ethyl magnesium bromide (1.5 ml, 1M solution in THF) was added drop wise by maintaining internal temperature <−5° C. for about 15 min. The reaction mixture was stirred for another 1 hr at same temperature and pyridine (51 mg, 0.645 mmol) was added in one portion. The reaction mixture was further cooled to −40° C., added methoxyoxalyl chloride (0.64 g) drop wise for about 15 min and stirred at the same temperature for 1 hr. The reaction was quenched with isopropyl alcohol (2 ml) followed by saturated ammonium chloride solution. Two layers were separated and aqueous layer was extracted with ethyl acetate (3×20 ml). The combined organic layers were washed with brine, dried over Na$_2$SO$_4$, filtered and concentrated under reduced pressure to afford off-white solid, methyl 2-(4-methoxy-7-(4-methyl-1H-1,2,3-triazol-1-yl)-1H-pyrrolo[2,3-c]pyridin-3-yl)-2-oxoacetate. $^1$H NMR (400 MHz, CDCl$_3$): δ1.38 (s, 3H), 2.5 (s, 3H), 3.9 (s 3H), 7.82 (s, 1H), 8.39 (dd, 1H), 8.43 (s, 1H). MS: 316.3 (M$^+$+1).

Step-3

To methyl 2-(4-methoxy-7-(4-methyl-1H-1,2,3-triazol-1-yl)-1H-pyrrolo[2,3-c]pyridin-3-yl)-2-oxoacetate (0.3 g) dissolved in 20 ml of THF/H2O mixture (1:1), lithium hydroxide (0.1 g) was added. After the reaction was stirred for 16 hours at room temperature, volatiles were removed under reduced pressure and the residue was acidified using dilute HCl to pH ~6. The resulting solid, 2-(4-methoxy-7-(4-methyl-1H-1,2,3-triazol-1-yl)-1H-pyrrolo[2,3-c]pyridin-3-yl)-2-oxoacetic acid, was filtered, dried and used for the next step without further purification. $^1$H NMR (400 MHz, DMSO-D$_6$): δ 2.38 (s, 3H), 4.01 (s, 3H), 7.53 (dd, 1H, J=2.9, 2.8), 7.70 (s, 1H), 8.62 (s, 1H), 11.78 (bs, 1H). MS: 302.3 (M$^+$+1).

Preparation of Compound G-31

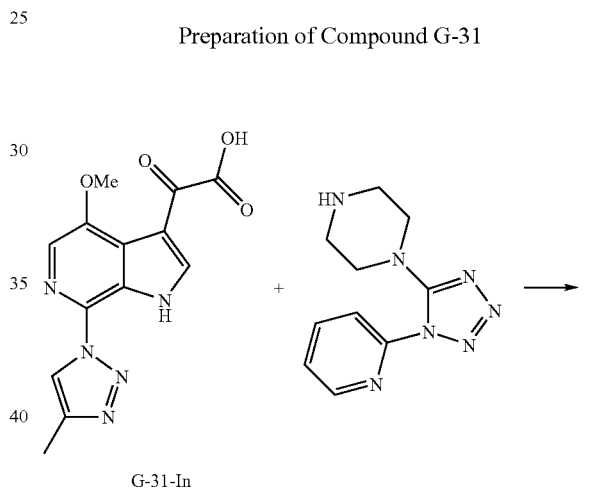

G-31-In

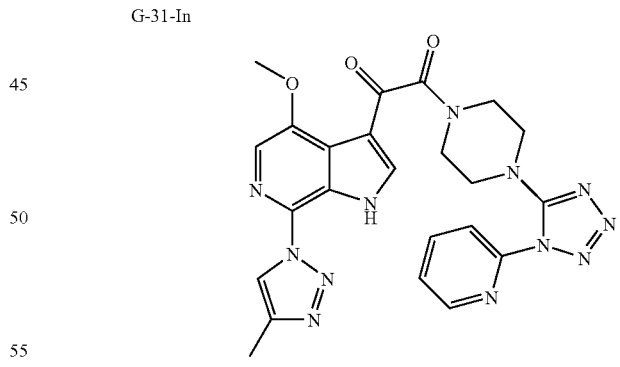

G-31

To a stirred solution of 2-(4-methoxy-7-(4-methyl-1H-1,2,3-triazol-1-yl)-1H-pyrrolo[2,3-c]pyridin-3-yl)-2-oxoacetic acid (75 mg) in dry DMF (5 ml), 1-(1-(pyridin-2-yl)-1H-tetrazol-5-yl)piperazine (86 mg), BOP reagent (110 mg) and DIPEA (0.1 ml) were added. The reaction mixture was stirred at room temperature for 16 hours. The solvent was removed under reduced pressure. The resulting oil was diluted with ethyl acetate (50 ml) and washed with 10% NaHCO$_3$ (10 ml) and brine (10 ml). The organic layer was dried over anhydrous Na₂SO₄ and concentrated using rotary evaporator. The resulting crude was purified by column chromatography using MeOH/CHCl₃ (2:8) as eluent to afford G-31 as off white solid. $^1$H NMR (400 MHz, DMSO-D₆): 2.38 (s, 3H), 3.12-3.15 (m, 2H), 3.3-3.32 (m, 4H), 3.65-3.68 (m, 2H), 4.01 (s, 3H), 7.59-7.62 (m, 2H), 7.77 (s, 1H), 7.80-7.82 (d, 1H), 8.10-8.14 (t, 1H), 8.63-8.64 (d, 2H), 12.01 (bs, 1H). MS: 513.3 (M⁺−1).

Preparation of Compound G-31

Preparation of Intermediate G-31-In

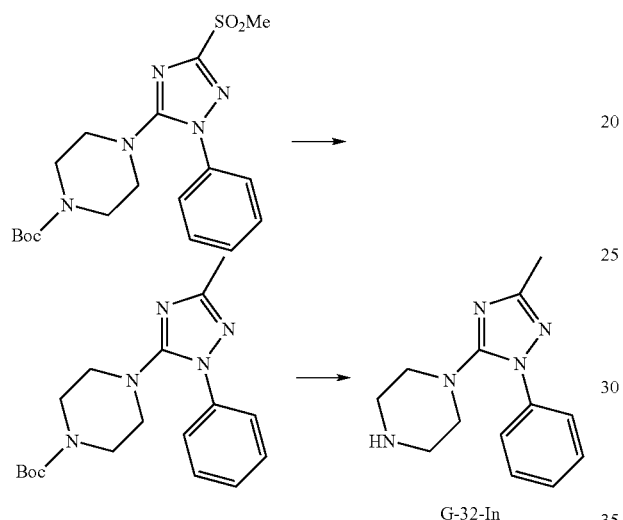

Step-1

To tert-butyl 4-(3-(methylsulfonyl)-1-phenyl-1H-1,2,4-triazol-5-yl)piperazine-1-carboxylate (500 mg) taken in dry THF (50 ml) cooled to 0° C., methyl magnesium bromide (0.9 ml, 3.0M solution in THF) was added drop wise. The reaction mixture was slowly heated to 50° C. and continued for about 18 hrs. The reaction mixture was cooled to 10° C. and quenched with saturated ammonium chloride. The reaction mixture was extracted with ethyl acetate (3×20 ml) and combined organic layer was washed with water, brine and dried over anhydrous sodium sulphate. The volatiles were removed under reduced pressure. The resulting crude product was purified by column chromatography using 230-400 silica gel and 5% methanol\chloroform as eluant to afford desire tert-butyl 4-(3-methyl-1-phenyl-1H-1,2,4-triazol-5-yl)piperazine-1-carboxylate. $^1$H NMR (400 MHz, DMSO-d₆): δ 1.49 (s, 9H), 2.36 (s, 3H), 3.1 (t, 4H), 3.31-3.36 (t, 4H), 7.38-7.60 (m, 5H). MS: 344 (M⁺+1).

Step-6

To tert-butyl 4-(3-methyl-1-phenyl-1H-1,2,4-triazol-5-yl)piperazine-1-carboxylate (500 mg) dissolved in dry dichloromethane (10 ml), TFA (5 ml) was added at 0° C. The reaction mixture was allowed to reach room temperature and stirred for over-night. The volatiles were completely removed and resulting residue was diluted with dichloromethane (20 ml). The organic layer was washed with saturated NaHCO₃ (2×10 ml), brine, dried over Na₂SO₄. Evaporation of solvent gave desire amine G-32-In, which was used for the next reaction without further purification. $^1$H NMR (400 MHz, DMSO-d₆): δ 2.39 (s, 3H), 3.28 (t, 4H), 3.31-3.36 (t, 4H), 7.38-7.60 (m, 5H). MS: 244 (M⁺+1).

Preparation of Compound G-32

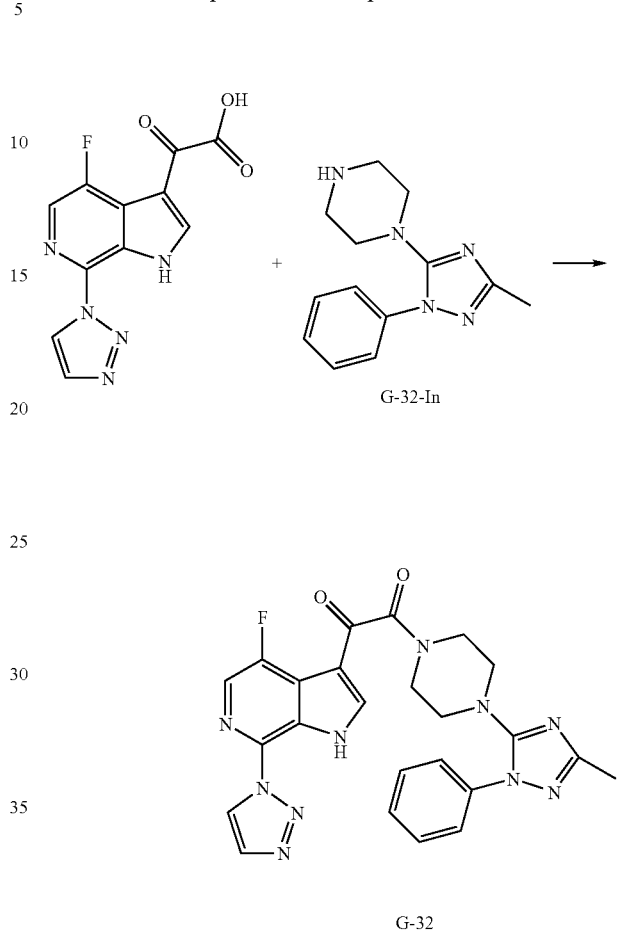

To a stirred solution of 2-(4-fluoro-7-(1H-1,2,3-triazol-1-yl)-1H-pyrrolo[2,3-c]pyridin-3-yl)-2-oxoacetic acid (80 mg) in dry DMF (5 ml), G-32-In (75 mg), BOP reagent and DIPEA (0.1 ml) were added. The reaction was stirred at room temperature for 16 hours. The solvent was removed under reduced pressure. The resulting oil was diluted with dichloromethane (20 ml) and washed with 10% NaHCO₃ and brine. The organic layer was dried over anhydrous Na₂SO₄ and concentrated using rotary evaporator. The resulting crude was purified by column chromatography using MeOH/CHCl₃ (2:8) as eluent to afford G-32 as yellow color solid.

$^1$H NMR (400 MHz, DMSO-d₆): δ 2.43 (s, 3H), 3.24-3.26 (t, 2H), 3.34-3.36 (t, 2H), 3.62-3.65 (t, 2H), 3.82-3.85 (t, 2H), 7.37-7.41 (t, 2H), 7.47-7.51 (t, 2H), 7.61-7.63 (s, 1H), 7.94 (s, 1H), 8.15-8.16 (d, 1H), 8.36-8.37 (d, 1H), 8.76 (s, 1H).

LC-MS: 500.7 (M⁺+1), 500, 1.4 min

Example Chemistry Section H

Compounds in this section were prepared and analyzed using one of the following general procedures and LC-MS condition.

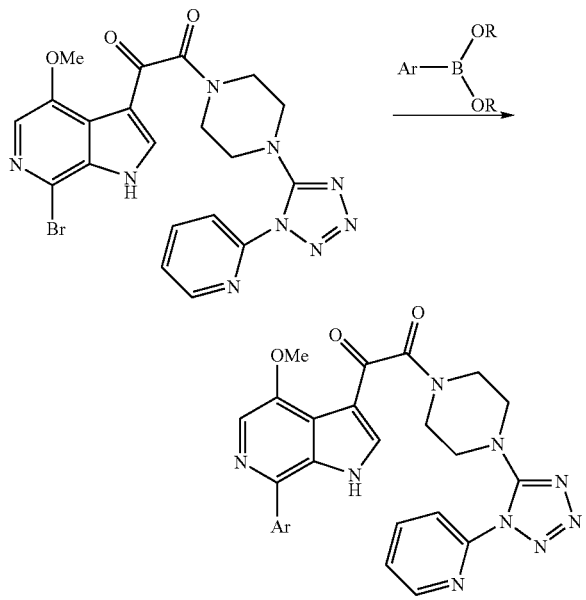

General Procedure for Suzuki Coupling of Bromo Scaffold with Boronic Acids:

The mixture of 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (1 eq), boronic acid (3 eq) and cesium carbonate (3 eq), dissolved in dioxane and water (volume ratio 20:1), was degassed for 30 minutes. To the reaction mixture Pd(dppf)Cl$_2$ (0.2 eq) was added and the reaction mixture was again degassed with nitrogen for 20 minutes. After the reaction mixture was heated to 80° C. in microwave for 3 hours, it was filtered through a celite pad and washed with ethyl acetate. Evaporation of solvent under reduced pressure afforded the crude product, which was purified by column chromatography using MeOH/CHCl$_3$ (2:8) as eluent.

General Procedure for Suzuki Coupling of Bromo Scaffold with Boronic Esters:

A. The mixture of Bromo compound 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (eq), boronic ester (3 eq) and potassium carbonate (3 eq), dissolved in 1,2-dimethoxy ethane and water (volume ratio 20:1), was degassed for 30 minutes. To the reaction mixture Pd(PPh$_3$)$_4$ (0.2 eq) was added and again degassed with nitrogen for 20 minutes and heated to 80° C. in microwave for 3 hours. The reaction mixture was filtered through a celite pad and washed with dichloromethane. Evaporation of solvent under reduced pressure afforded crude product, which was purified by column chromatography using MeOH/CHCl$_3$ (2:8) as eluent.

B. The mixture of 1-(7-bromo-4-methoxy-1H-pyrrolo[2,3-c]pyridin-3-yl)-2-(4-(1-(pyridin-2-yl)-1H-tetrazol-5-yl)piperazin-1-yl)ethane-1,2-dione (1 eq), boronic ester (3 eq) and cesium carbonate (3 eq), dissolved in dioxane, dimethylformamide and water (volume ratio 2:18:1), was degassed for 30 minutes. To the reaction mixture Pd(dppf)Cl$_2$ (0.2 eq) was added and again degassed with nitrogen for 20 minutes. After the reaction mixture was heated to 90° C. in microwave for 3 hours, it was filtered through a celite pad and washed with ethyl acetate. Evaporation of solvent under reduced pressure gave crude product, which was purified by column chromatography using MeOH/CH$_2$Cl$_2$ (2:8) as eluent.

Analytical LC-MS Method:

LC-MS instrument: Agilent 6320 ion Trap

Method info: A-0.1% HCOOH B-CAN FLOW-0.8 ml/min

Column: ATLANTIS C18 75×4.6 mm 5 μm

| Time | % B | % A |
| --- | --- | --- |
| 0 | 70 | 30 |
| 1.0 | 70 | 30 |
| 1.5 | 95 | 05 |
| 2.5 | 95 | 05 |
| 3.0 | 70 | 30 |
| 6.0 | 70 | 30 |

| Compd # | Structure | MS (M + H)$^+$ Observ. (Calc'd), Rf and NMR |
| --- | --- | --- |
| H-1 | (structure) | MS: 529.1 (calc'd. 529.2) Rf = 1.1 min $^1$H NMR (400 MHz, DMSO-d$_6$): δ3.25-3.27(t, 2 H), 3.40-3.42 (t, 4 H), 3.69-3.70 (t, 2 H), 4.0 (s, 3 H), 7.61-7.63 (d, 1 H), 7.83-7.85 (d, 1 H), 8.0-8.2 (m, 1 H), 8.2 (s, 1 H), 8.32-8.33 (d, 2 H), 8.65-8.68 (m, 2 H), 8.86 (s, 1 H), 12.9 (bs, 1 H). |

-continued

| Compd # | Structure | MS (M + H)+ Observ. (Calc'd), Rf and NMR |
|---|---|---|
| H-2 | 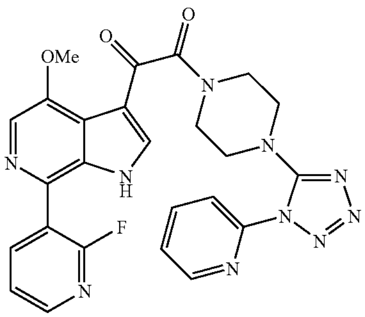 | MS: 529.1 (calc'd. 529.2)<br>Rf = 1.1 min<br>¹H NMR (400 MHz, DMSO-d₆): δ3.26-3.27(t, 2 H), 3.32-3.42 (t, 4 H), 3.69-3.70 (t, 2 H), 3.99 (s, 3 H), 7.35-7.37 (m, 1 H), 7.61-7.64 (m, 1 H), 7.83-7.85 (m, 1 H), 8.13-8.16 (m, 2 H), 8.32-8.38 (m, 2 H), 8.63-8.66 (m, 2 H), 12.85 (bs, 1 H). |
| H-3 | 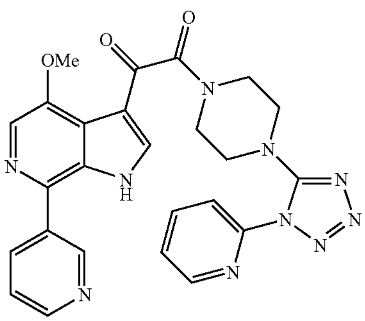 | MS: 511.2 (calc'd. 511.2)<br>Rf = 0.94 min<br>¹H NMR (400 MHz, DMSO-d₆): δ3.27-3.37(t, 4 H), 3.42-3.44 (t, 4 H), 4.0 (s, 3 H), 7.61-7.63 (m, 1 H), 7.63-7.78 (m, 1 H), 7.83-7.85 (d, 1 H), 8.13-8.16 (m, 2 H), 8.32-8.38 (m, 2 H), 8.63-8.66 (d, 1 H), 8.78-8.79 (d, 1 H), 9.0 (s, 1 H), 13.15 (bs, 1 H). |
| H-4 | 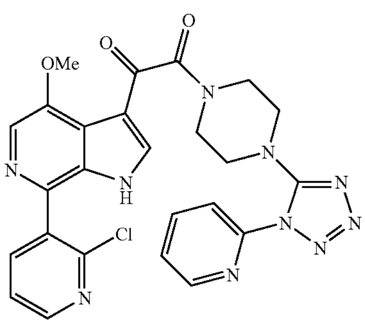 | MS: 545.1 (calc'd. 545.2)<br>Rf = 1.1 min<br>¹H NMR (400 MHz, DMSO-d₆): δ3.26-3.27(t, 2 H), 3.32-3.42 (t, 4 H), 3.69-3.70 (t, 2 H), 3.99 (s, 3 H), 7.55-7.57 (s, 1 H), 7.61-7.64 (m, 1 H), 7.83-7.85 (d, 2 H), 8.13-8.18 (m, 2 H), 8.31-8.33 (d, 2 H), 8.63-8.8 (s, 1 H), 12.69 (bs, 1 H). |
| H-5 | 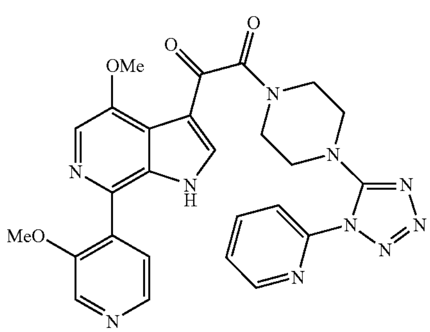 | MS: 541.1 (calc'd. 541.2)<br>Rf = 1.1 min<br>¹H NMR (400 MHz, DMSO-d₆): δ3.26-3.27(t, 2 H), 3.32-3.42 (t, 4 H), 3.69-3.70 (t, 2 H), 3.90 (s, 3 H), 4.01 (s, 3 H), 7.62-7.68 (m, 3 H), 7.83-7.85 (d, 1 H), 8.13-8.17 (t, 1 H), 8.19 (s, 1 H), 8.31-8.33 (s, 1 H), 8.41-8.48 (d, 1 H), 8.65-8.67 (s, 1 H), 12.69 (bs, 1 H). |

-continued

| Compd # | Structure | MS (M + H)+ Observ. (Calc'd), Rf and NMR |
|---|---|---|
| H-6 | 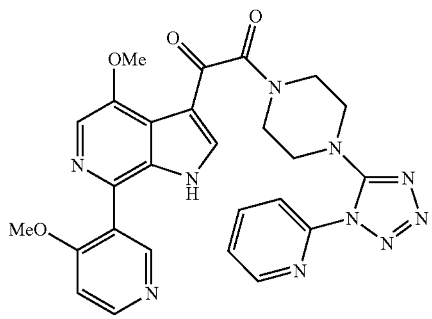 | MS: 541.1 (calc'd. 541.2)<br>Rf = 0.8 min<br>¹H NMR (400 MHz, DMSO-d₆): δ3.26-3.27(t, 2 H), 3.32-3.42 (t, 4 H), 3.69-3.70 (t, 2 H), 3.92 (s, 3 H), 3.98 (s, 3 H), 7.50-7.52 (d, 2 H), 7.61-7.65 (d, 2 H), 7.83-7.85 (d, 1 H), 8.13-8.15 (m, 1 H), 8.17-8.175 (d, 1 H), 8.65-8.66 (d, 1 H), 8.72-8.74 (d, 1 H), 12.69 (bs, 1 H). |
| H-7 | 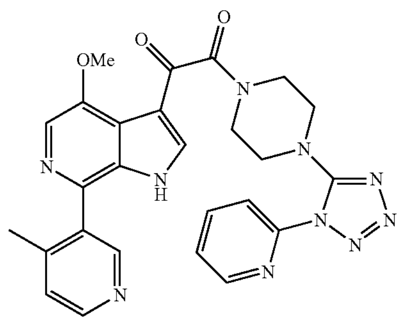 | MS: 525.2 (calc'd. 525.2)<br>Rf = 0.8 min<br>¹H NMR (400 MHz, DMSO-d₆): δ2.26 (s, 3 H), 3.28-3.42 (t, 4 H), 3.49-3.70 (t, 4 H), 4.01 (s, 3 H), 7.62-7.64 (t, 1 H), 7.65-7.653 (d, 1 H), 7.73-7.85 (d, 1 H), 8.13-8.15 (t, 1 H), 8.19 (s, 1 H), 8.65-8.66 (d, 2 H), 8.72-8.74 (d, 2 H), 12.97 (bs, 1 H). |
| H-8 | 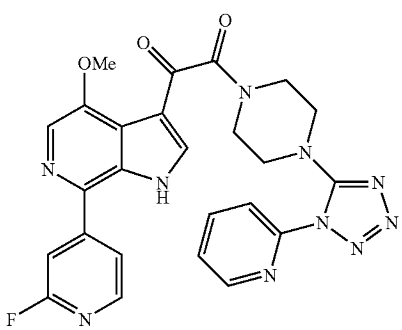 | MS (M − H)+: 527.2 (calc'd. 527.2)<br>Rf = 1.2 min<br>¹H NMR (400 MHz, DMSO-d₆): δ3.26-3.28 (t, 2 H), 3.38-3.42 (t, 4 H), 3.69-3.71 (t, 2 H), 4.01 (s, 3 H), 7.56 (s, 1 H), 7.62-7.64 (d, 1 H), 7.65-7.653 (d, 1 H), 7.73-7.85 (d, 1 H), 8.13-8.15 (t, 1 H), 8.19 (s, 1 H), 8.34-8.39 (d, 2 H), 8.65-8.66 (d, 1 H), 12.85 (bs, 1 H). |
| H-9 | 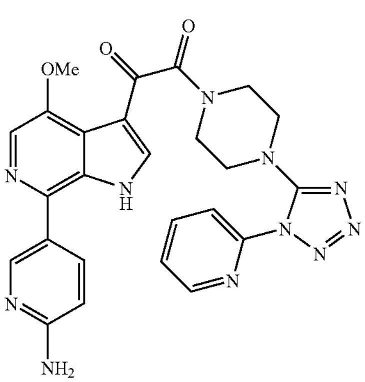 | MS (M − H)+: 524.3 (calc'd. 524.2)<br>Rf = 0.78 min<br>¹H NMR (400 MHz, DMSO-d₆): δ3.23-3.27 (t, 2 H), 3.39-3.41 (t, 4 H), 3.68-3.70 (t, 2 H), 3.93 (s, 3 H), 6.47 (bs, 2 H), 6.63-6.65 (d, 1 H), 7.62-7.64 (m, 2 H), 7.82-7.87 (t, 2 H), 8.0 (s, 1 H), 8.13-8.16 (m, 1 H), 8.20 (s, 1 H), 8.34-8.35 (d, 1 H), 8.65-8.66 (d, 1 H), 12.85 (bs, 1 H). |

-continued

| Compd # | Structure | MS (M + H)+ Observ. (Calc'd), Rf and NMR |
|---|---|---|
| H-10 | 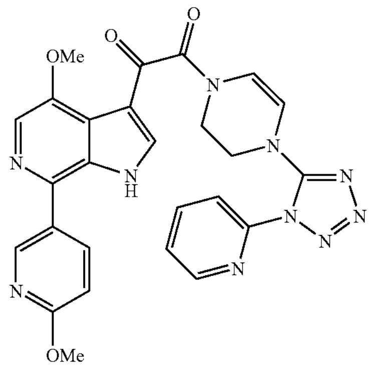 | MS: 541.2 (calc'd. 541.2)<br>Rf = 0.78 min<br>$^1$H NMR (400 MHz, DMSO-d$_6$): δ3.23-3.27 (t, 2 H), 3.39-3.41 (t, 4 H), 3.68-3.70 (t, 2 H), 3.94 (s, 3 H), 3.96 (s, 3 H), 6.98-7.0 (d, 1 H), 7.61-7.64 (t, 1 H), 7.83-7.85 (d, 1 H), 8.10-8.16 (m, 3 H), 8.26 (s, 1 H), 8.58 (s, 1 H), 8.65-8.66 (d, 1 H), 12.82 (bs, 1 H). |
| H-11 | 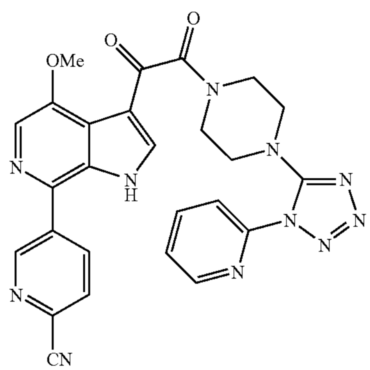 | MS: 536.2 (calc'd. 536.2)<br>Rf = 1.14 min<br>1H NMR (400 MHz, DMSO-d6): δ3.25-3.27(t, 2 H), 3.39-3.41 (t, 4 H), 3.69-3.71 (t, 2 H), 4.0 (s, 3 H), 7.61-7.64 (t, 1 H), 7.83-7.85 (d, 1 H), 8.12-8.14 (t, 1 H), 8.15-8.20 (m, 2 H), 8.35 (s, 1 H), 8.43-8.45 (d, 1 H), 8.65-8.66 (d, 1 H), 9.17 (s, 1 H), 12.95 (bs, 1 H). |
| H-12 | 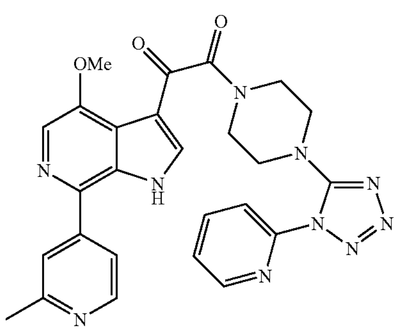 | MS: 525.2 (calc'd. 525.2)<br>Rf = 0.98 min<br>$^1$H NMR (400 MHz, DMSO-d$_6$): δ2.57 (s, 3 H), 3.25-3.27 (t, 2 H), 3.39-3.41 (t, 4 H), 3.69-3.71 (t, 2 H), 3.99 (s, 3 H), 7.60-7.64 (m, 2 H), 7.67 (s, 1 H), 7.83-7.85 (d, 1 H), 8.12-8.17 (m, 1 H), 8.18 (s, 1 H), 8.29-8.30 (d, 1 H), 8.58-8.65 (d, 1 H), 8.66 (d, 1 H), 12.77 (bs, 1 H). |
| H-13 | 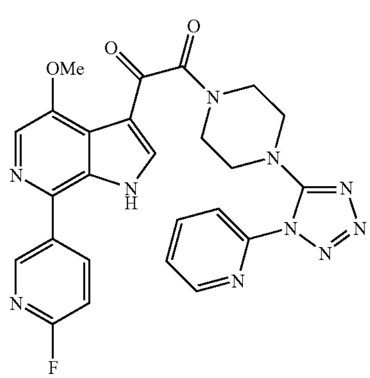 | MS (M − H)+: 529.2 (calc'd. 529.2)<br>Rf = 0.98 min<br>$^1$H NMR (400 MHz, DMSO-d$_6$): δ3.24-3.27 (t, 2 H), 3.39-3.41 (t, 4 H), 3.69-3.71 (t, 2 H), 3.97 (s, 3 H), 7.34-7.37 (dd, 1 H), 7.61-7.64 (dd, 1 H), 7.82-7.84 (d, 1 H), 8.12-8.16 (m, 2 H), 8.30 (s, 1 H), 8.33-8.38 (m, 1 H), 8.62-8.65 (m, 2 H), 12.85 (bs, 1 H). |

Biology

"µM" means micromolar;
"mL" means milliliter;
"µl" means microliter;
"mg" means milligram;

The materials and experimental procedures used to obtain the results reported in Tables 3-4 are described below.

Cells:
Virus production—Human embryonic Kidney cell line, 293T, was propagated in Dulbecco's Modified Eagle Medium (Invitrogen, Carlsbad, Calif.) containing 10% fetal Bovine serum (FBS, Sigma, St. Louis, Mo.).

Virus infection—Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL Geneticin (Invitrogen, Carlsbad, Calif.).

Virus-Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Invitrogen, Carlsbad, Calif.).

Experiment
1. HeLa CD4 cells were plated in 96 well plates at a cell density of $1 \times 10^4$ cells per well in 100 µl Dulbecco's Modified Eagle Medium containing 10% fetal Bovine serum and incubated overnight.
2. Compound was added in a 2 µl dimethylsulfoxide solution, so that the final assay concentration would be $\leq 10$ µM.
3. 100 µl of single-round infectious reporter virus in Dulbecco's Modified Eagle Medium was then added to the plated cells and compound at an approximate multiplicity of infection (MOI) of 0.01, resulting in a final volume of 200 µl per well.
4. Virally-infected cells were incubated at 37 degrees Celsius, in a $CO_2$ incubator, and harvested 72 h after infection.
5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 µl of lysis buffer was added per well. After 15 minutes, 50 µl of freshly-reconstituted luciferase assay reagent was added per well. Luciferase activity was then quantified by measuring luminescence using a Wallac microbeta scintillation counter.
6. The percent inhibition for each compound was calculated by quantifying the level of luciferase expression in cells infected in the presence of each compound as a percentage of that observed for cells infected in the absence of compound and subtracting such a determined value from 100.
7. An $EC_{50}$ provides a method for comparing the antiviral potency of the compounds of this disclosure. The effective concentration for fifty percent inhibition ($EC_{50}$) was calculated with the Microsoft Excel Xlfit curve fitting software. For each compound, curves were generated from percent inhibition calculated at 10 different concentrations by using a four parameter logistic model (model 205). The $EC_{50}$ data for the compounds is shown in Table 4. Table 3 is the key for the data in Table 4.

Results

TABLE 3

| Biological Data Key for $EC_{50}$s | |
|---|---|
| Compounds with $EC_{50} <= 0.5$ µM | Compounds with $EC_{50}$s $> 0.5$ µM |
| Group A | Group B |

TABLE 4

| Compd # | Structure | $EC_{50}$ Group from Table 3 |
|---|---|---|
| A-1 | 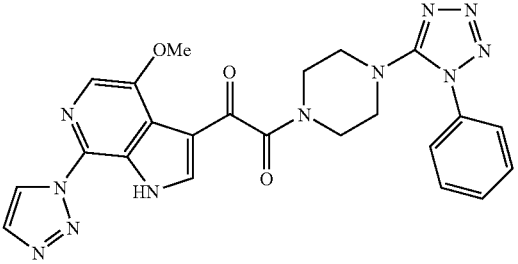 | A |

TABLE 4-continued

| Compd # | Structure | EC$_{50}$ Group from Table 3 |
|---|---|---|
| A-2 | 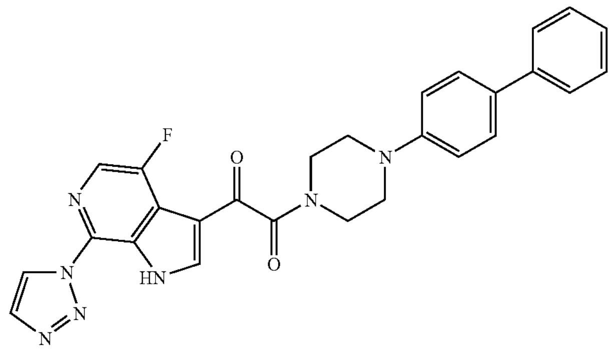 | B |
| A-3 | 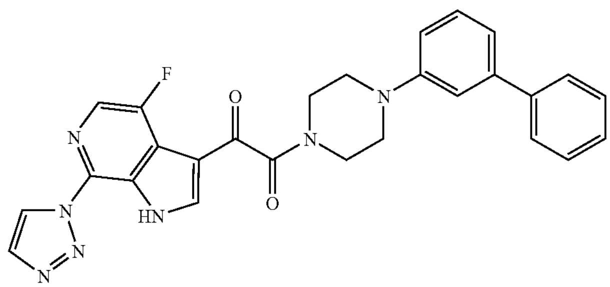 | A |
| A-4 | 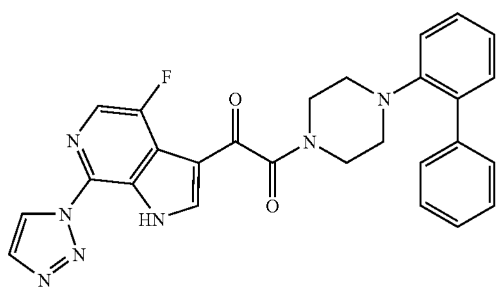 | A |
| A-5 | 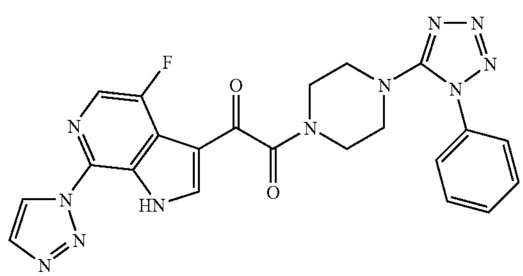 | A |
| A-6 | 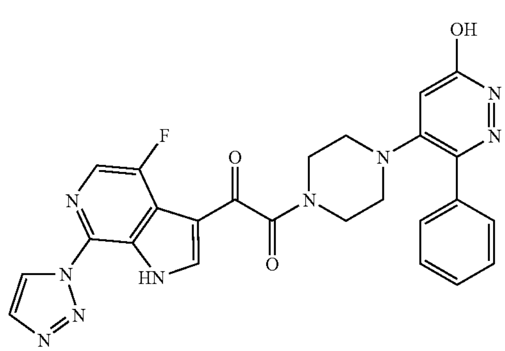 | A |

TABLE 4-continued

| Compd # | Structure | EC$_{50}$ Group from Table 3 |
|---|---|---|
| A-7 | 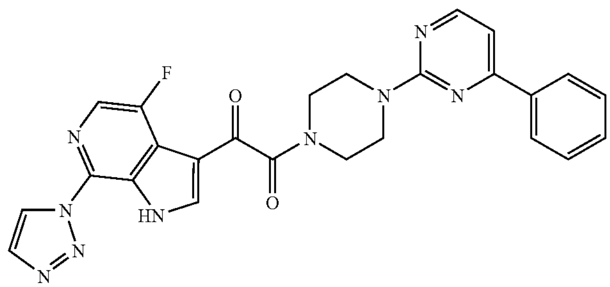 | A |
| A-8 | 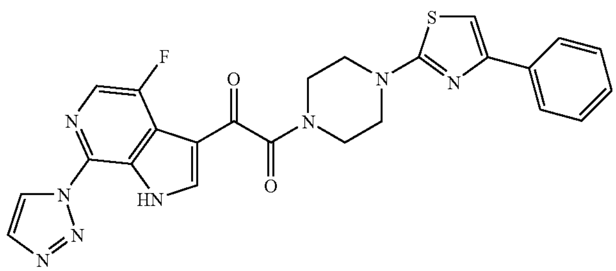 | A |
| A-9 | 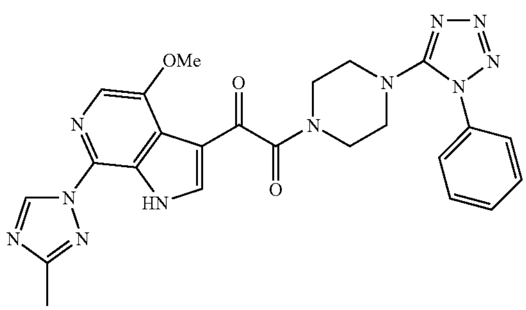 | A |
| A-10 | 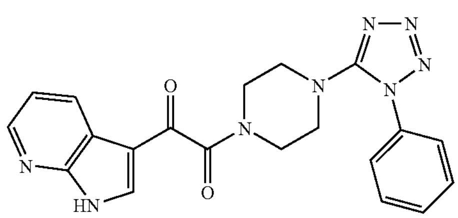 | A |
| A-11 | 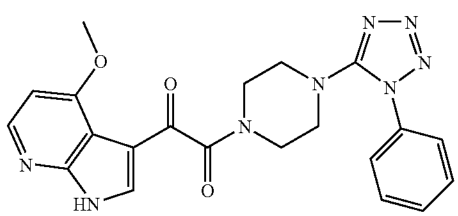 | A |

TABLE 4-continued

| Compd # | Structure | EC$_{50}$ Group from Table 3 |
|---|---|---|
| A-12 | 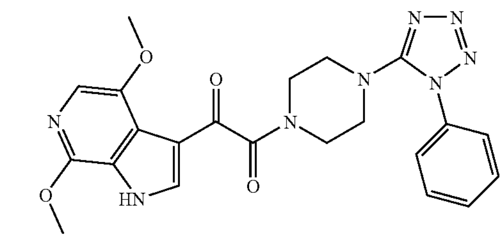 | A |
| A-13 | 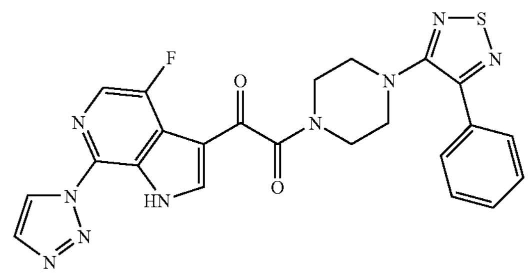 | A |
| A-14 | 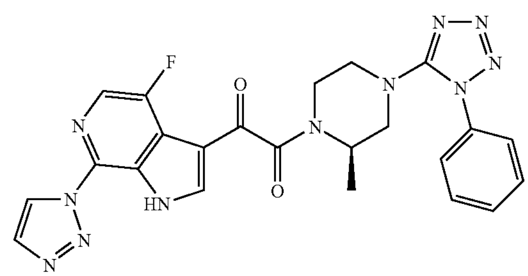 | A |
| A-15 | 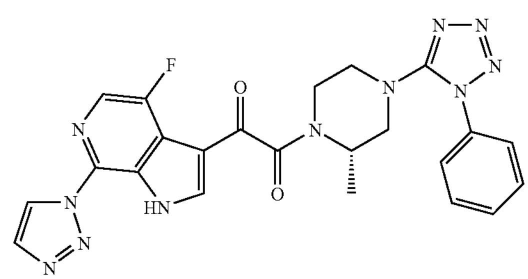 | A |
| A-16 | 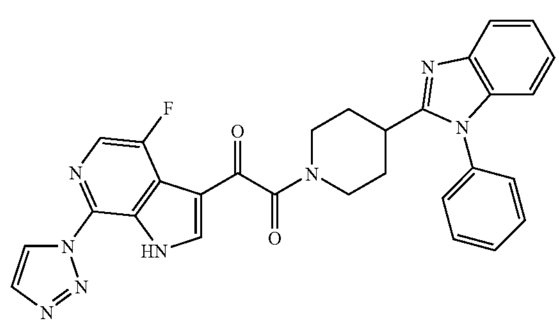 | A |

TABLE 4-continued

| Compd # | Structure | EC$_{50}$ Group from Table 3 |
|---|---|---|
| A-17 | 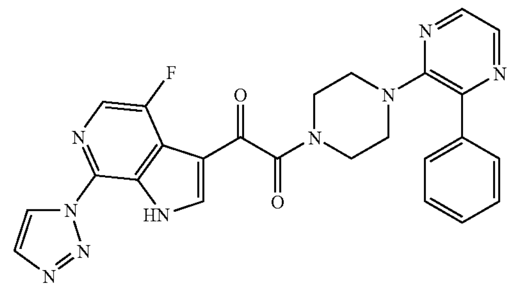 | A |
| A-18 | 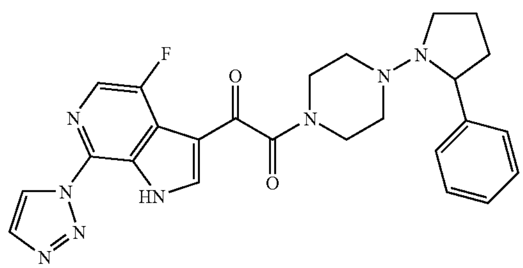 | A |
| A-19 | 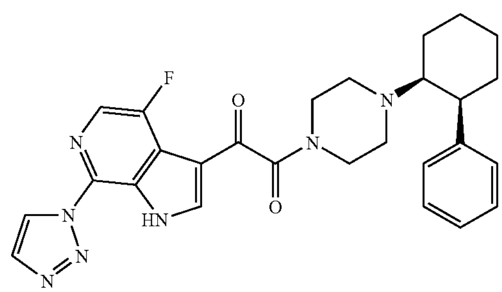 | A |
| A-20 | 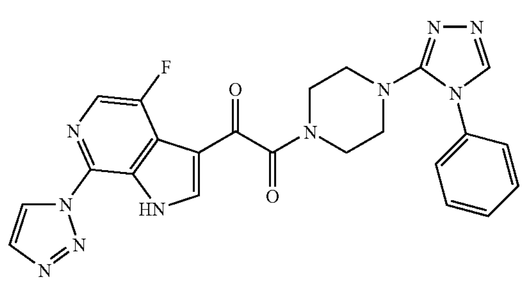 | A |
| A-21 | 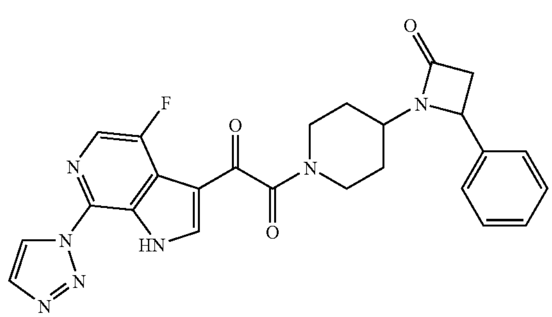 | A |

TABLE 4-continued

| Compd # | Structure | EC$_{50}$ Group from Table 3 |
| --- | --- | --- |
| A-22 | 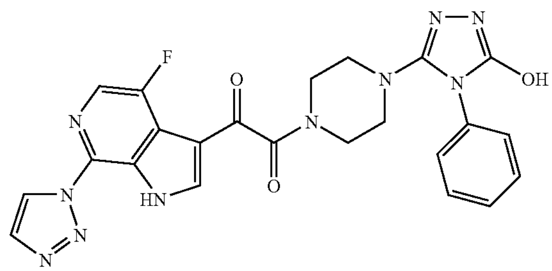 | A |
| A-23 | 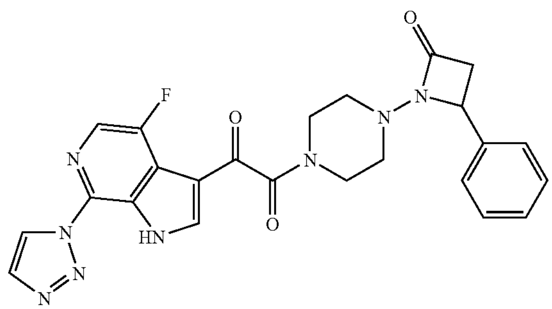 | B |
| A-24 | 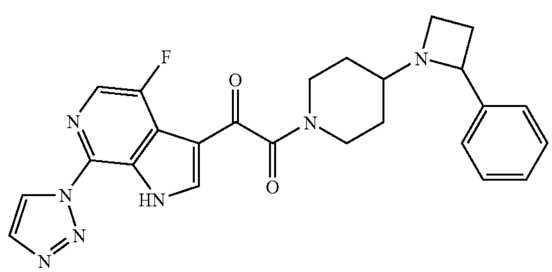 | B |
| A-25 | 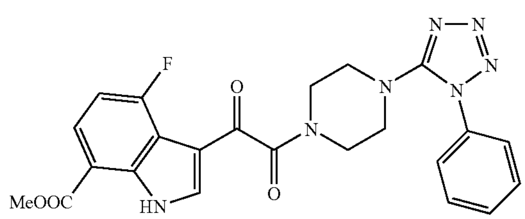 | A |
| A-26 | 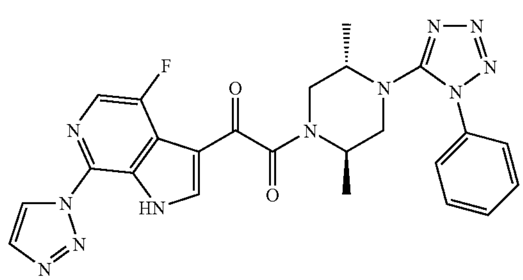 | A |

TABLE 4-continued

| Compd # | Structure | EC$_{50}$ Group from Table 3 |
|---|---|---|
| A-28 | 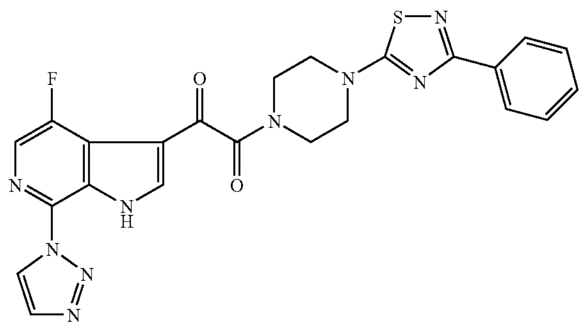 | A |
| A-29 | 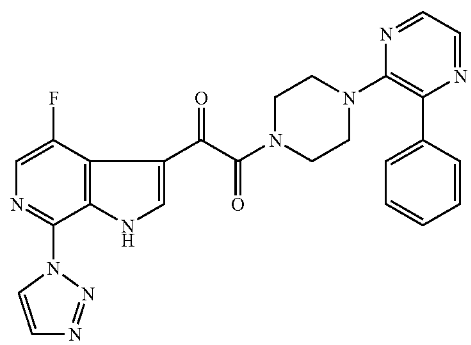 | A |
| A-30 | 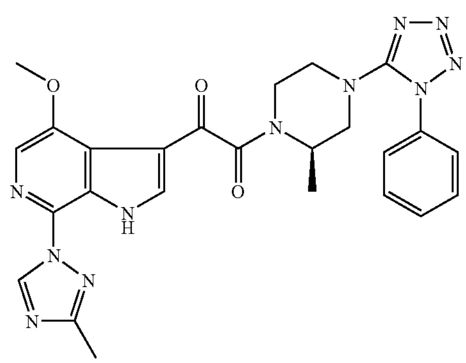 | A |
| A-31 | 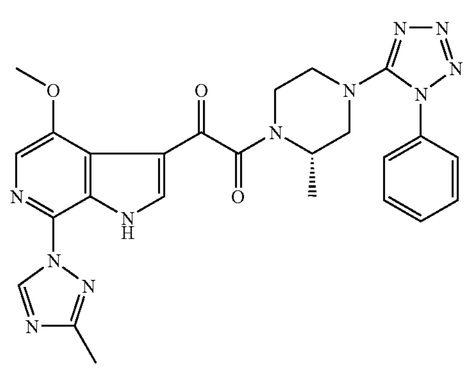 | A |

TABLE 4-continued

| Compd # | Structure | EC$_{50}$ Group from Table 3 |
|---|---|---|
| A-32 | 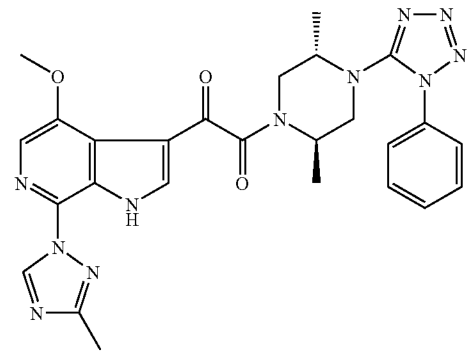 | A |
| A-27 | 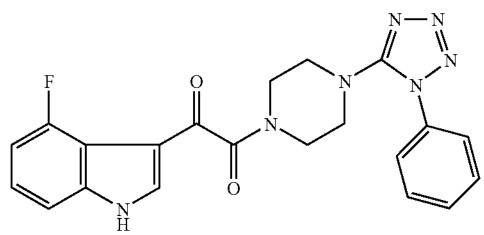 | A |
| A-33 | 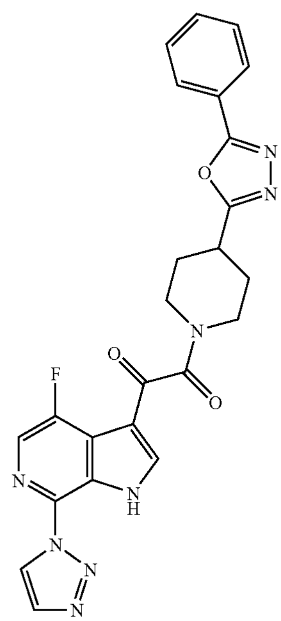 | B |

TABLE 4-continued
| Compd # | Structure | EC$_{50}$ Group from Table 3 |
|---|---|---|
| A-34 | 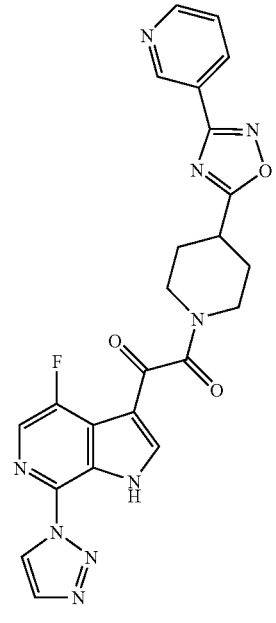 | B |
| A-35 | 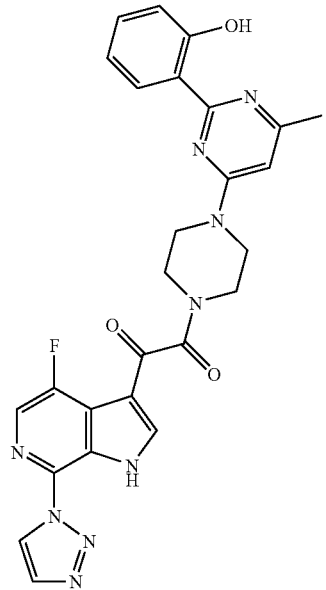 | A |

TABLE 4-continued

| Compd # | Structure | EC$_{50}$ Group from Table 3 |
|---|---|---|
| A-36 | 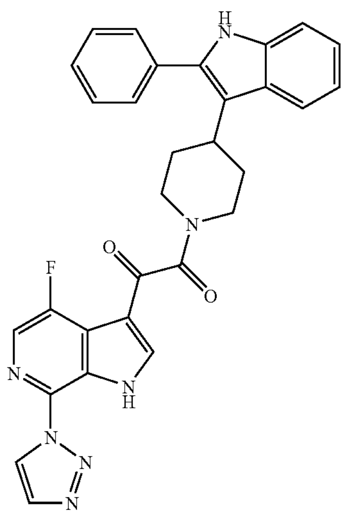 | B |
| A-37 | 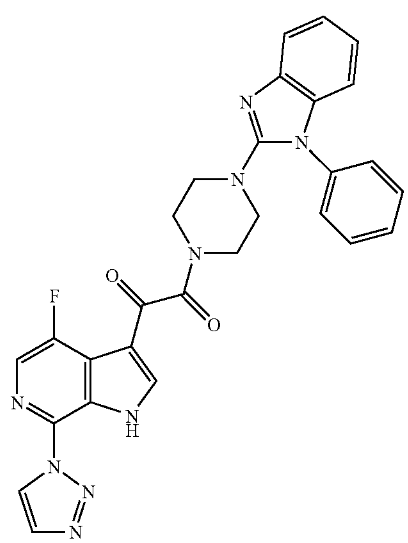 | A |

TABLE 4-continued
| Compd # | Structure | EC$_{50}$ Group from Table 3 |
|---|---|---|
| A-38 | 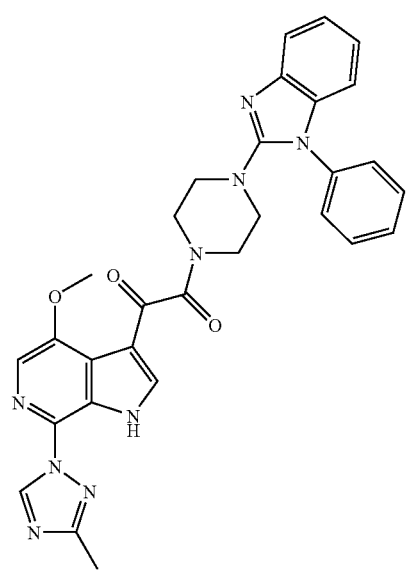 | A |
| A-39 | 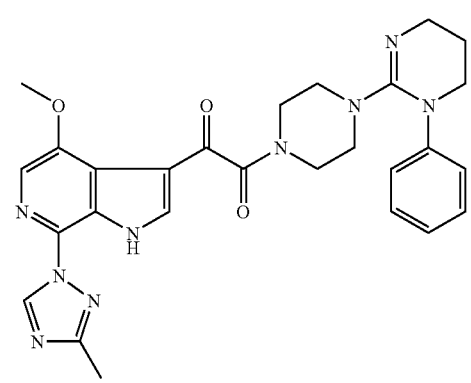 | B |
| B-2 | 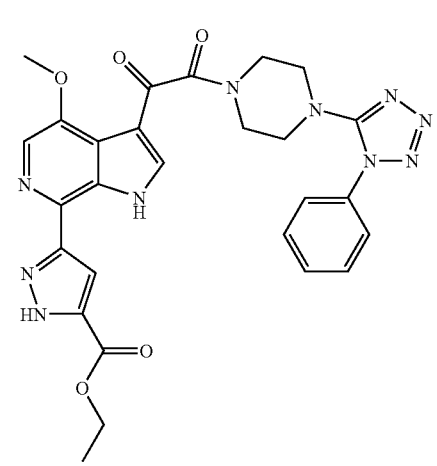 | A |

TABLE 4-continued

| Compd # | Structure | EC$_{50}$ Group from Table 3 |
|---|---|---|
| B-17 | 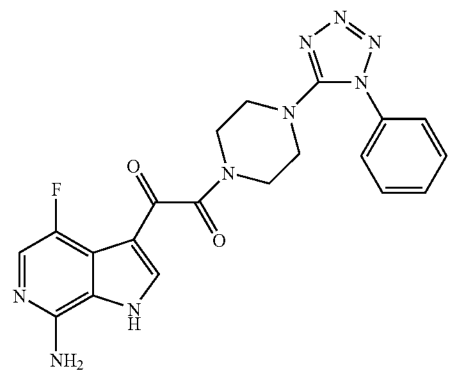 | A |
| A-40 | 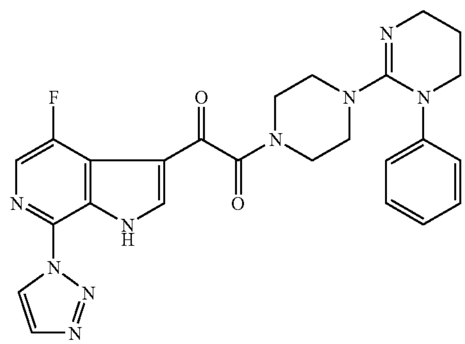 | B |
| A-41 | 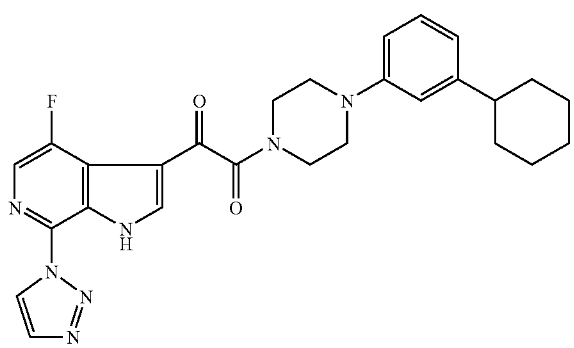 | B |
| A-42 | 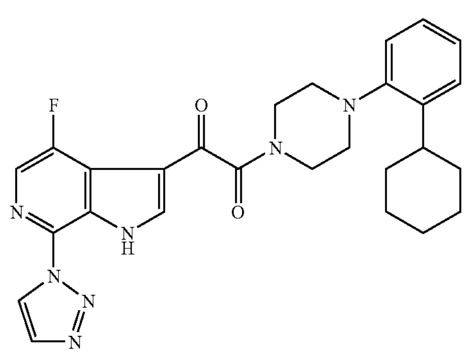 | B |

TABLE 4-continued

| Compd # | Structure | EC$_{50}$ Group from Table 3 |
|---|---|---|
| B-2 | 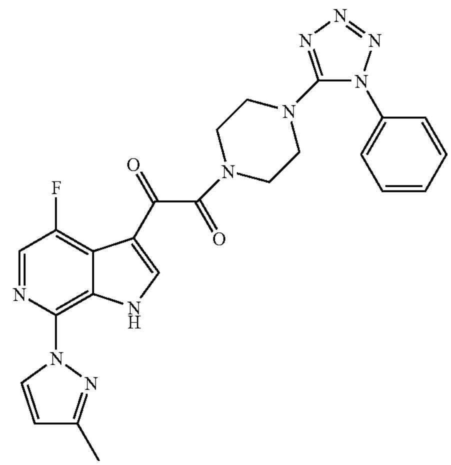 | A |
| B-3 | 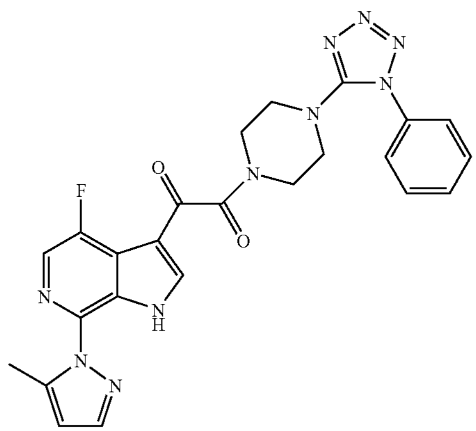 | A |
| B-4 | 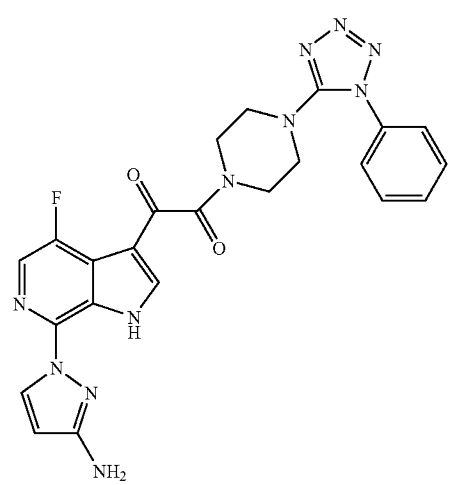 | A |

TABLE 4-continued

| Compd # | Structure | EC$_{50}$ Group from Table 3 |
|---|---|---|
| B-5 | 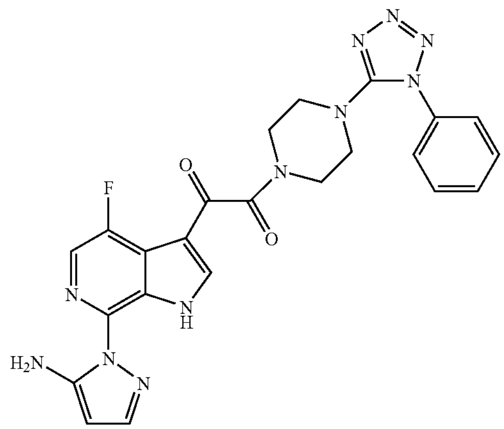 | A |
| A-43 | 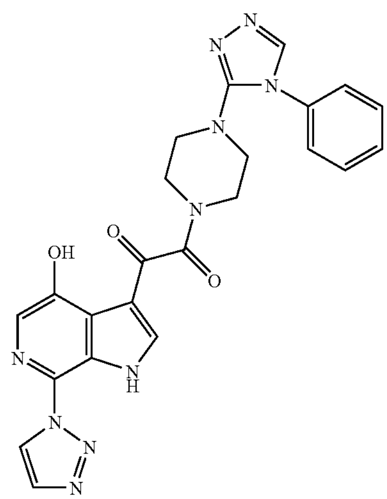 | A |
| B-8 | 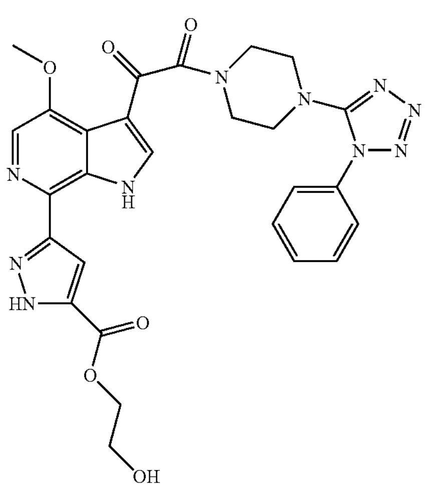 | A |

TABLE 4-continued

| Compd # | Structure | EC$_{50}$ Group from Table 3 |
|---|---|---|
| B-9 | 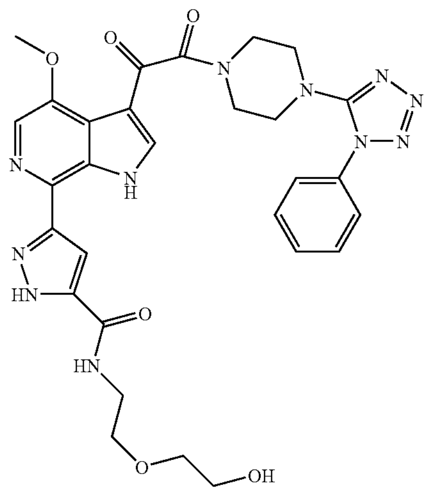 | A |
| B-10 | 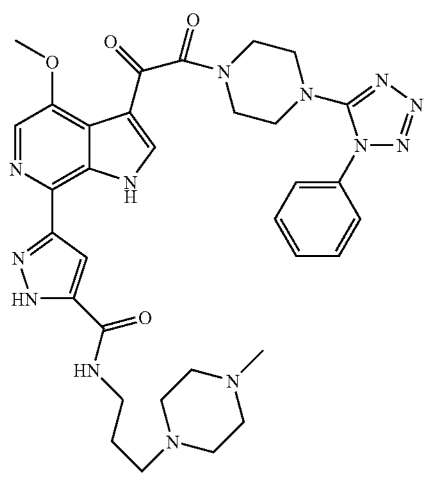 | A |
| B-11 | 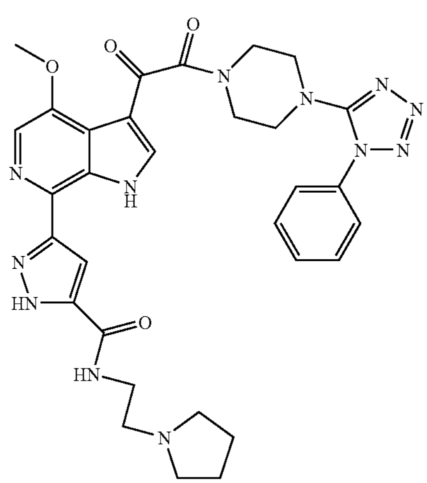 | A |

TABLE 4-continued
| Compd # | Structure | EC$_{50}$ Group from Table 3 |
|---|---|---|
| B-12 | 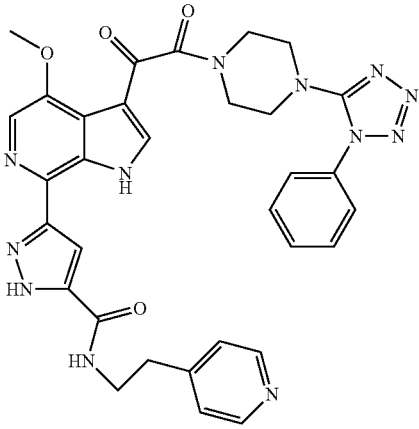 | A |
| B-13 | 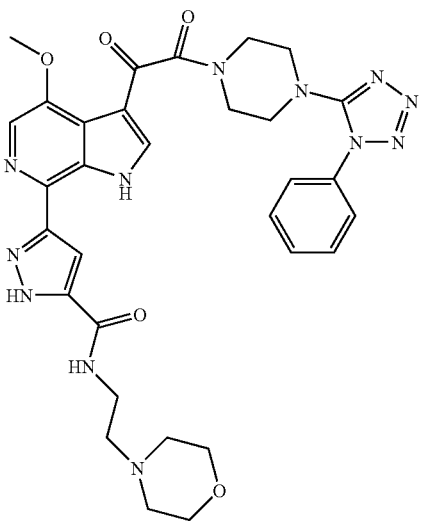 | A |
| C-1 | 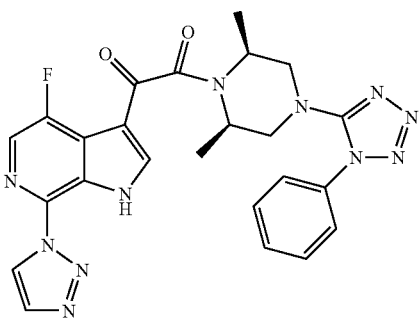 | A |

TABLE 4-continued
| Compd # | Structure | EC$_{50}$ Group from Table 3 |
|---|---|---|
| A-44 | 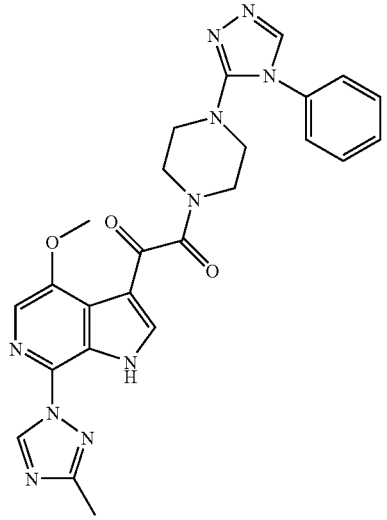 | A |
| A-45 | 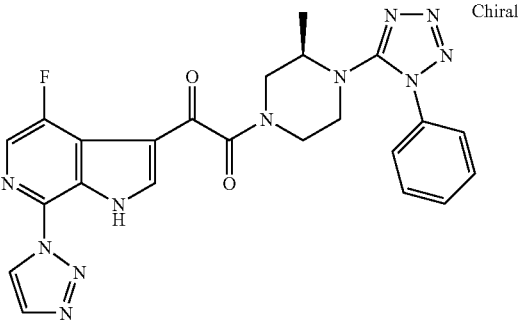 Chiral | A |
| B-18 | 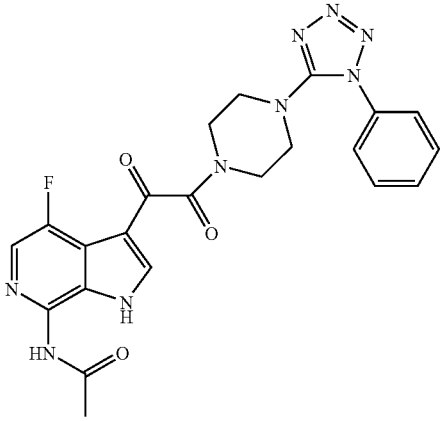 | B |

TABLE 4-continued

| Compd # | Structure | EC$_{50}$ Group from Table 3 |
|---|---|---|
| B-19 | 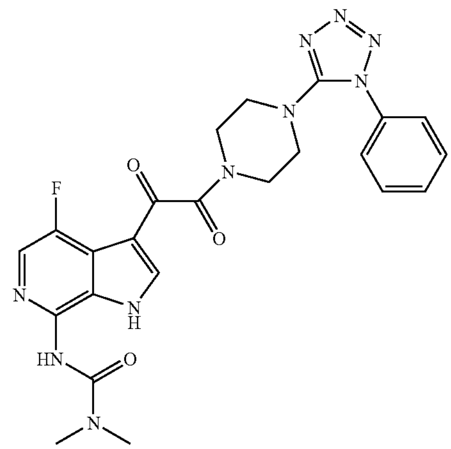 | A |
| B-15 | 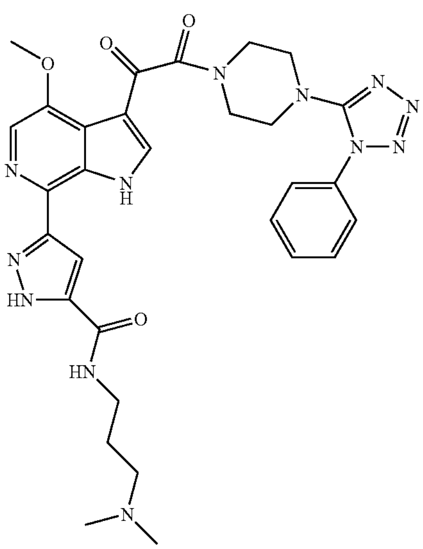 | A |
| A-46 | Chiral | A |

TABLE 4-continued
| Compd # | Structure | EC$_{50}$ Group from Table 3 |
|---|---|---|
| B-24 | 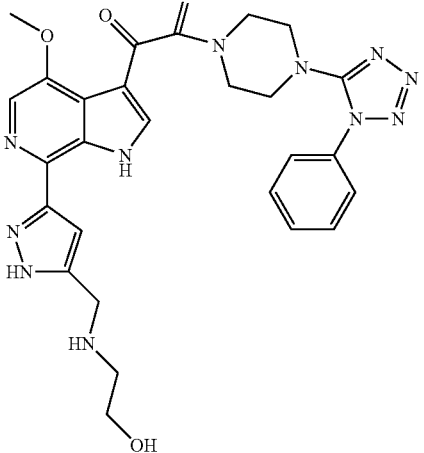 | A |
| A-47 | 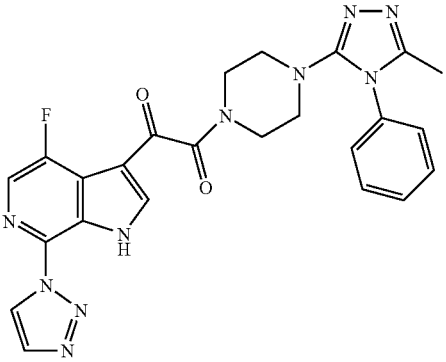 | A |
| B-14 | 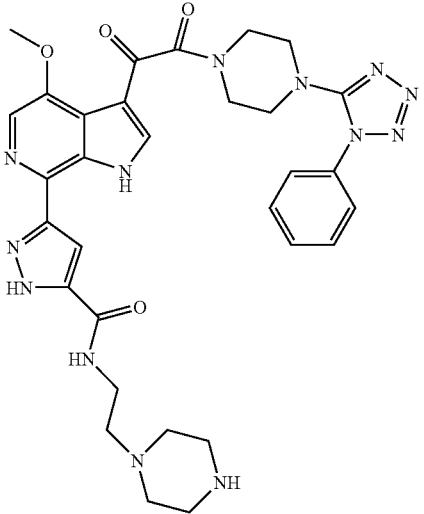 | A |

TABLE 4-continued
| Compd # | Structure | EC$_{50}$ Group from Table 3 |
|---|---|---|
| B-21 | 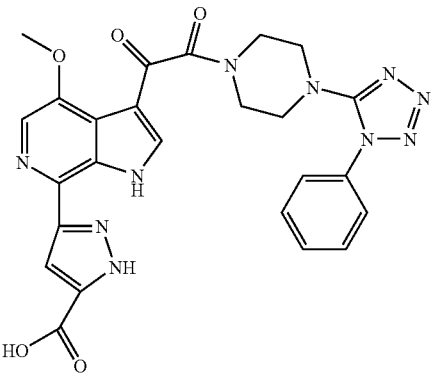 | A |
| B-16 | 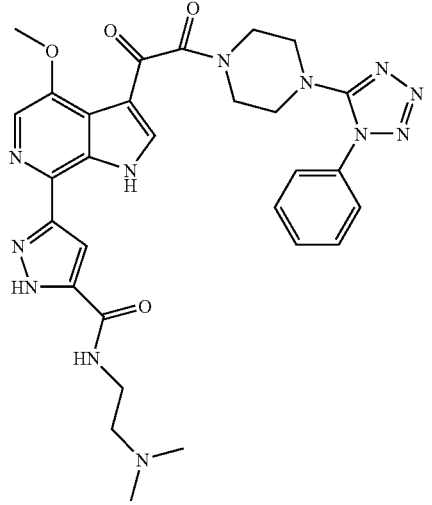 | A |
| B-22 | 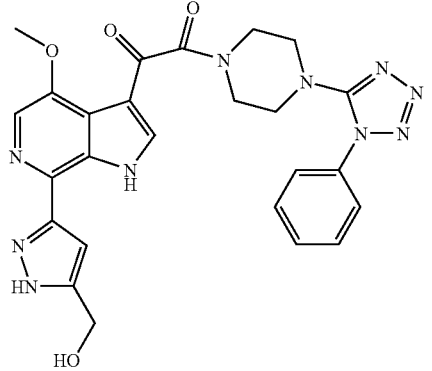 | A |

TABLE 4-continued
| Compd # | Structure | EC$_{50}$ Group from Table 3 |
|---|---|---|
| B-20 | 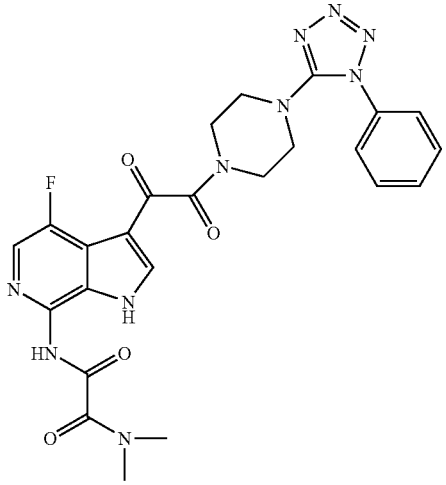 | A |
| B-25 | 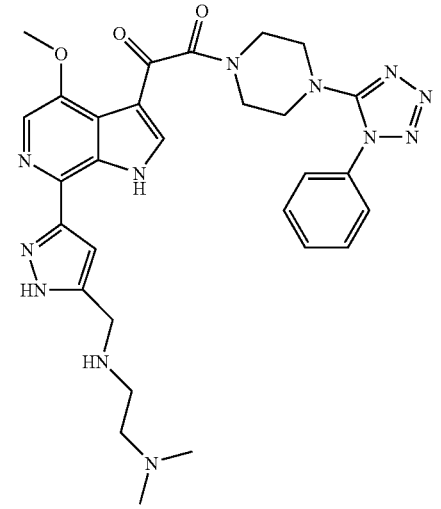 | A |
| B-26 | 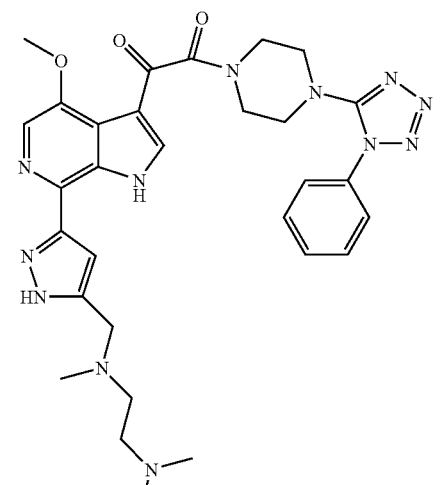 | A |

TABLE 4-continued

| Compd # | Structure | EC$_{50}$ Group from Table 3 |
|---|---|---|
| B-23 | 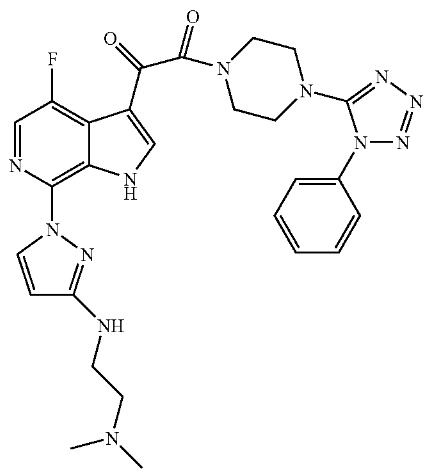 | A |
| A-48 | 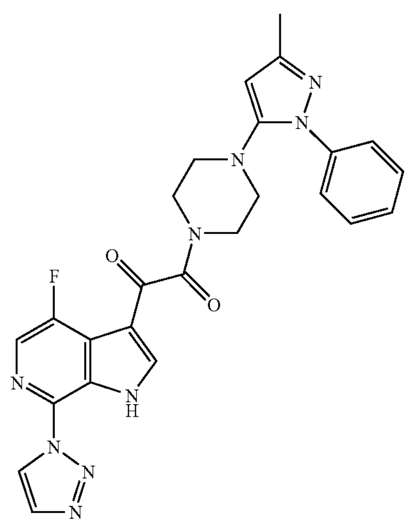 | A |
| A-49 | 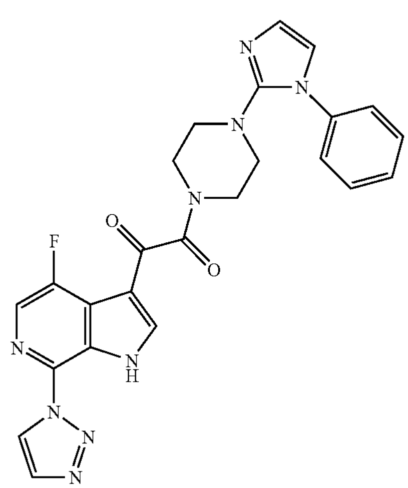 | A |

TABLE 4-continued

| Compd # | Structure | EC$_{50}$ Group from Table 3 |
|---|---|---|
| B-27 | 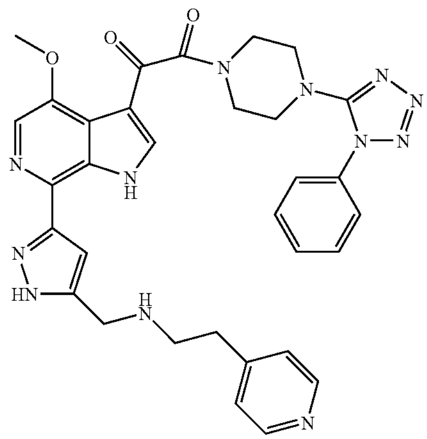 | A |
| A-50 | 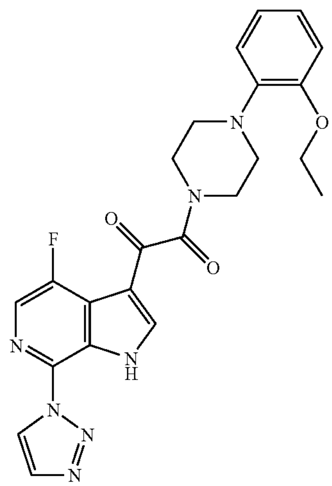 | A |
| A-51 | 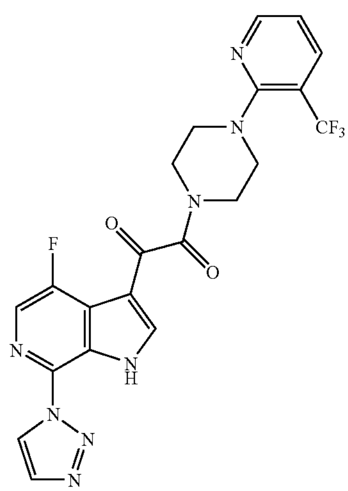 | A |

TABLE 4-continued

| Compd # | Structure | EC$_{50}$ Group from Table 3 |
|---|---|---|
| A-52 | 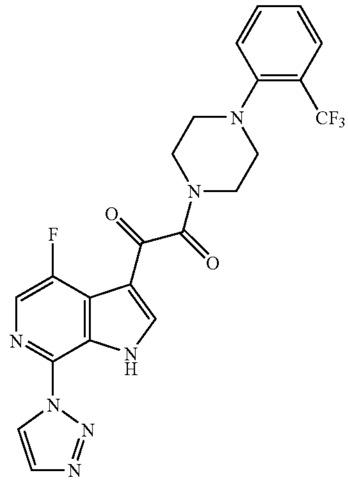 | B |
| D-1 | 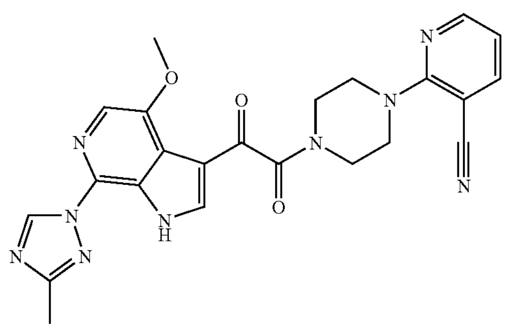 | A |
| D-2 | 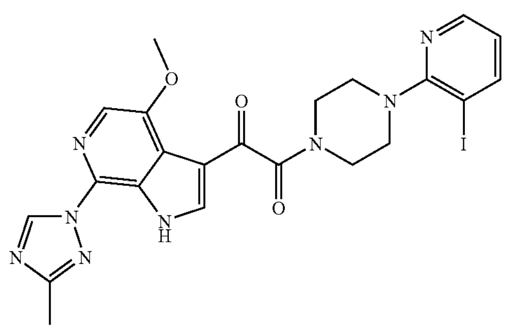 | A |
| D-3 | 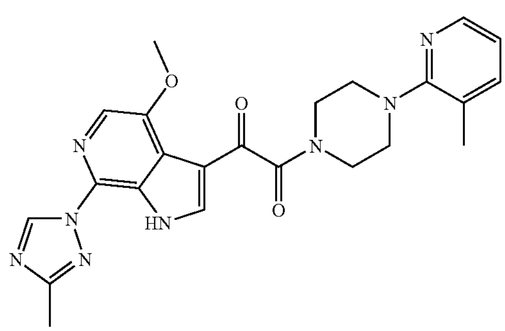 | A |

TABLE 4-continued

| Compd # | Structure | EC$_{50}$ Group from Table 3 |
|---|---|---|
| D-4 | 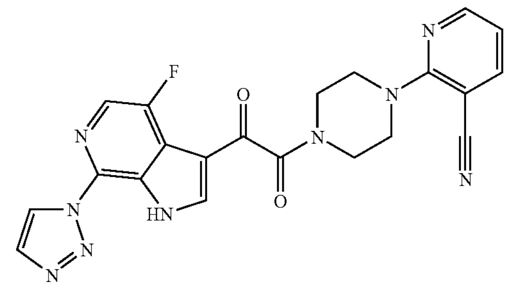 | A |
| D-5 | 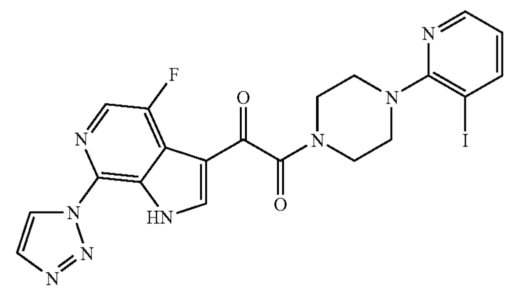 | A |
| D-6 | 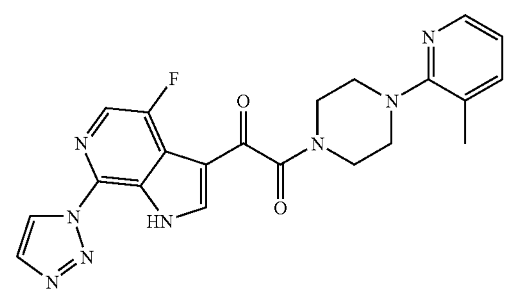 | A |
| D-7 | 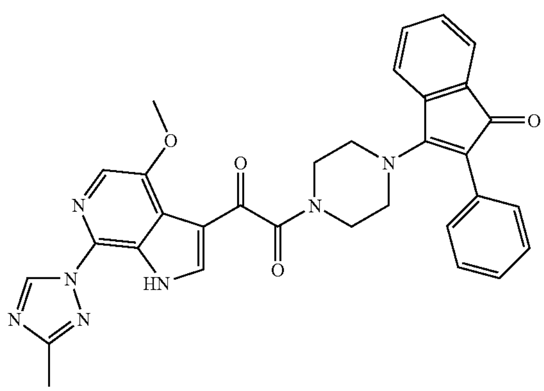 | A |

TABLE 4-continued
| Compd # | Structure | EC$_{50}$ Group from Table 3 |
|---|---|---|
| D-8 | 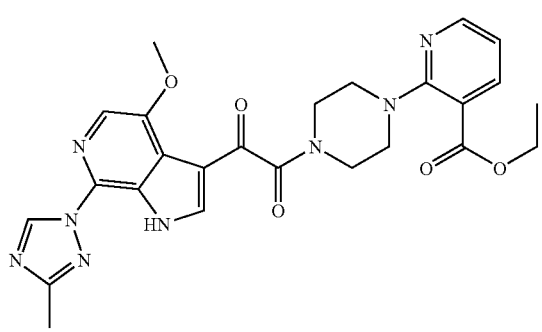 | A |
| D-9 | 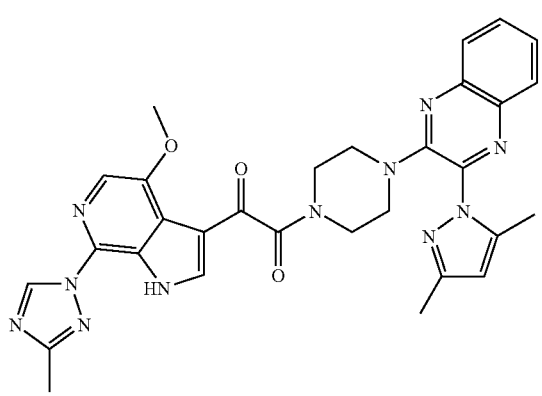 | B |
| D-10 Chiral | 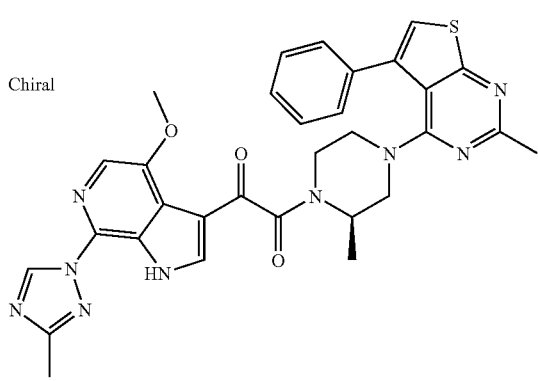 | A |
| D-11 Chiral | 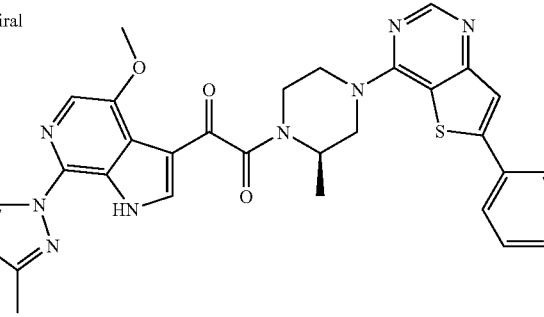 | B |

TABLE 4-continued

| Compd # | Structure | EC$_{50}$ Group from Table 3 |
|---|---|---|
| D-12 | 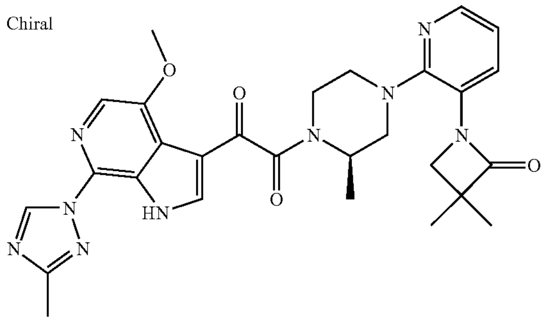 | B |
| D-13 | 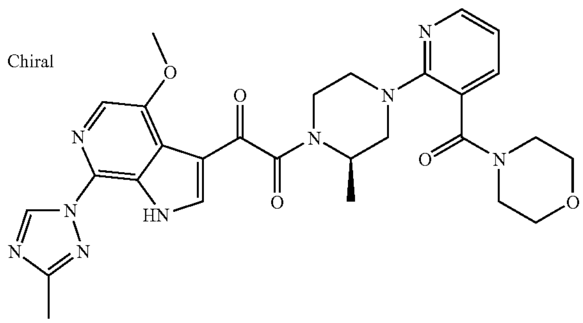 | B |
| D-14 | 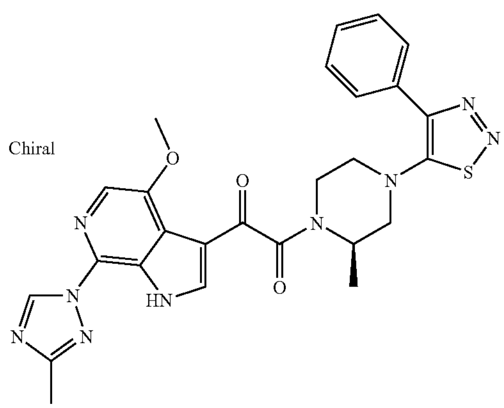 | A |
| D-15 | 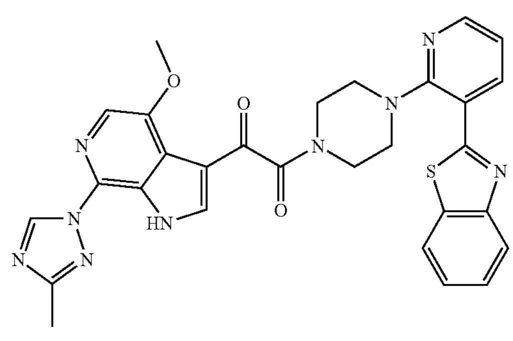 | A |

TABLE 4-continued

| Compd # | Structure | EC$_{50}$ Group from Table 3 |
|---|---|---|
| D-16 | 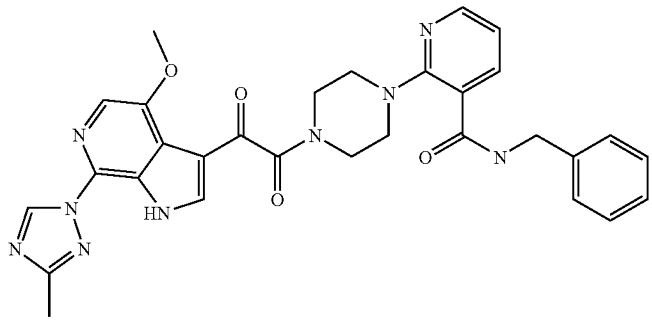 | B |
| D-17 | 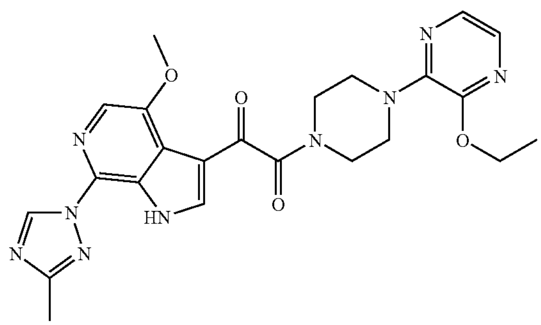 | A |
| D-18 | 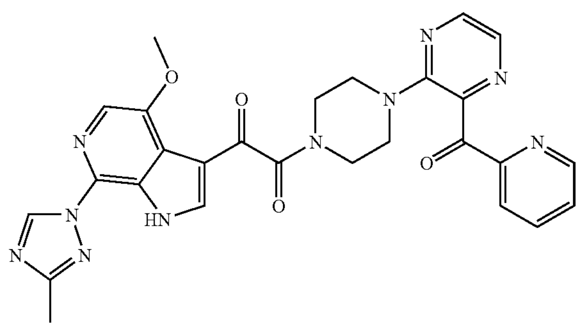 | A |
| D-19 | 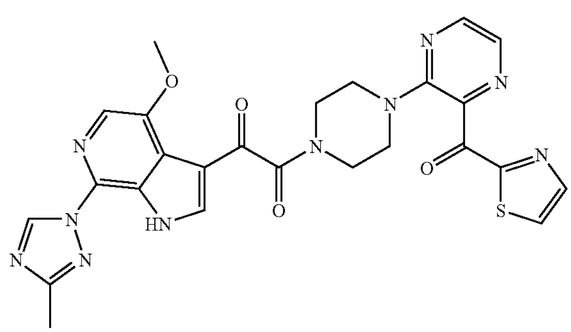 | A |

TABLE 4-continued
| Compd # | Structure | EC$_{50}$ Group from Table 3 |
|---|---|---|
| D-20 | 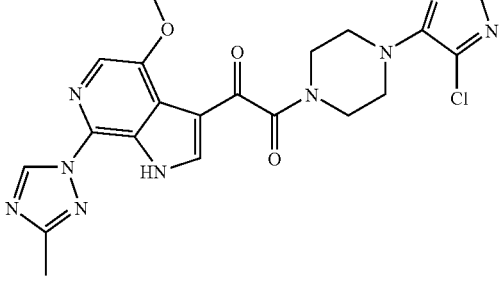 | A |
| D-21 | 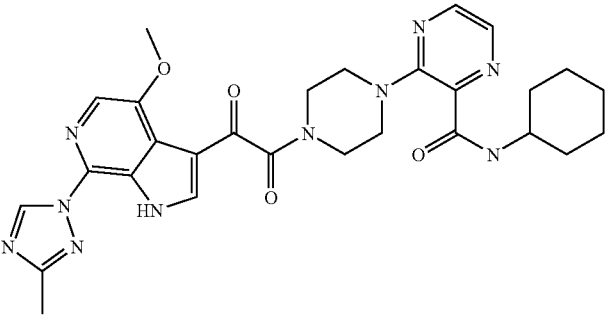 | B |
| D-22 | 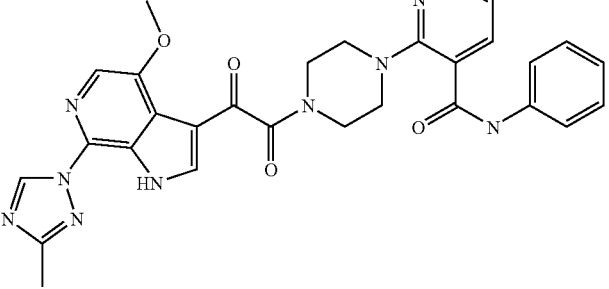 | B |
| D-23 | 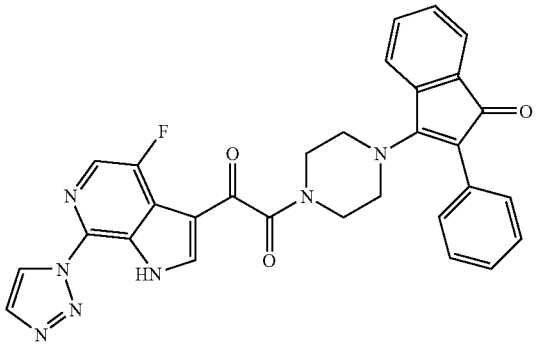 | A |

TABLE 4-continued

| Compd # | Structure | EC$_{50}$ Group from Table 3 |
|---|---|---|
| D-24 | 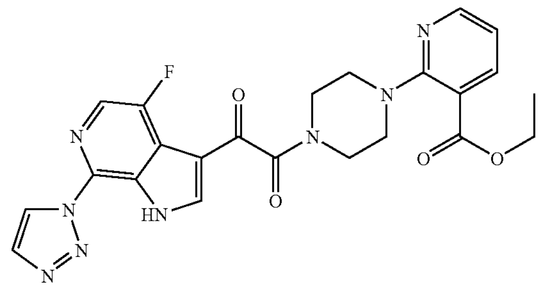 | A |
| D-26 | Chiral | B |
| D-27 | Chiral | A |
| D-28 | Chiral | B |
| D-29 | Chiral | B |

TABLE 4-continued
| Compd # | Structure | EC$_{50}$ Group from Table 3 |
|---|---|---|
| D-30 | 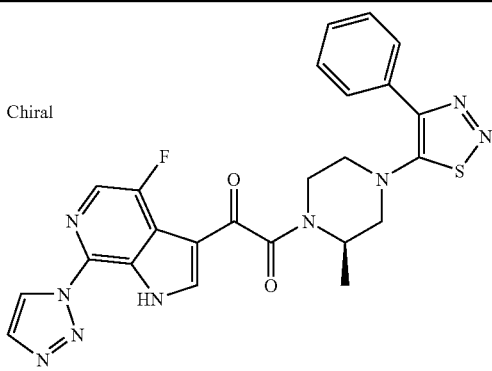 | A |
| D-31 | 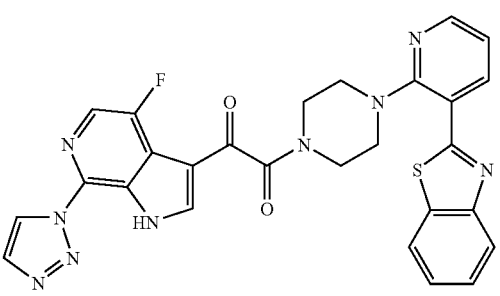 | B |
| D-32 | 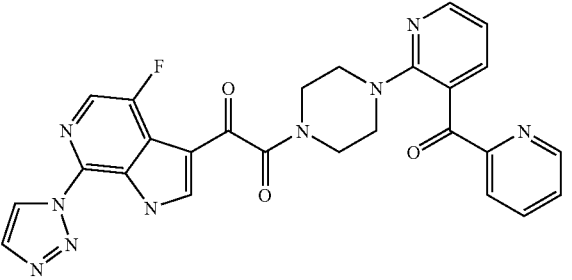 | A |
| D-33 | 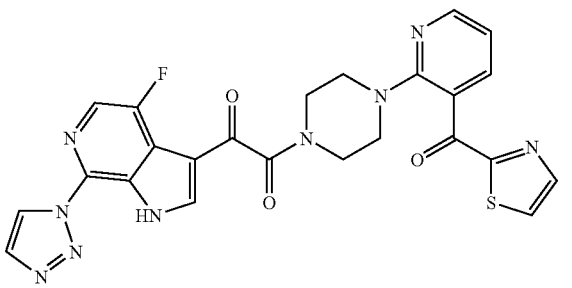 | A |
| D-34 | 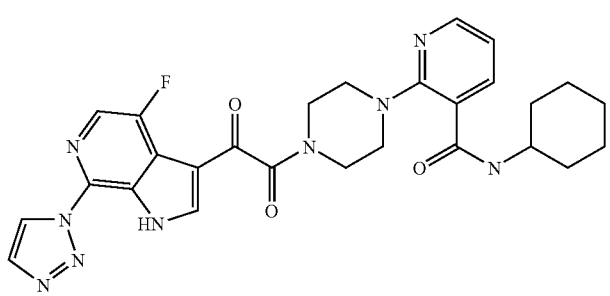 | A |

TABLE 4-continued

| Compd # | Structure | EC$_{50}$ Group from Table 3 |
|---|---|---|
| D-35 | 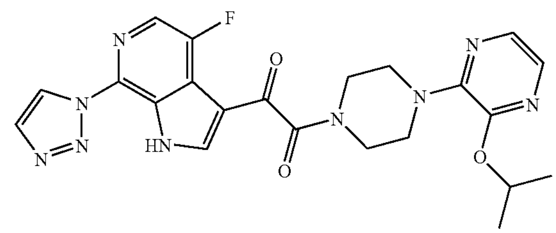 | A |
| D-36 | Chiral | B |
| D-37 | 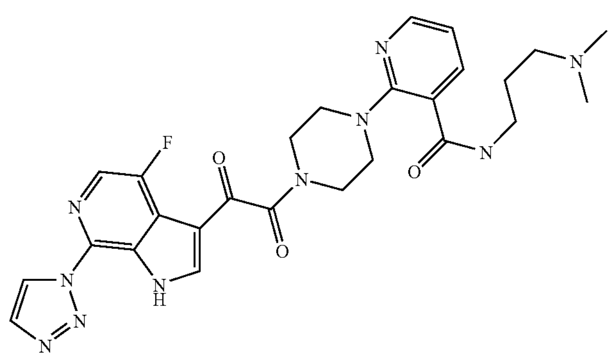 | B |
| D-38 | 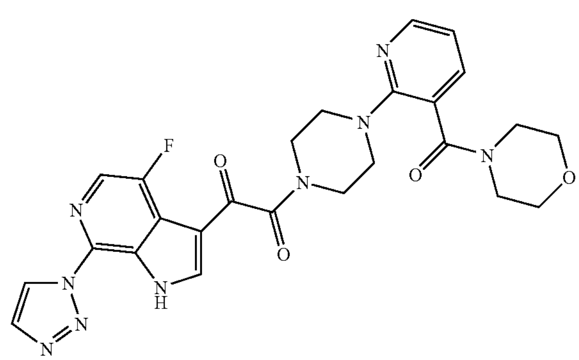 | B |

TABLE 4-continued

| Compd # | Structure | EC$_{50}$ Group from Table 3 |
|---|---|---|
| D-39 | 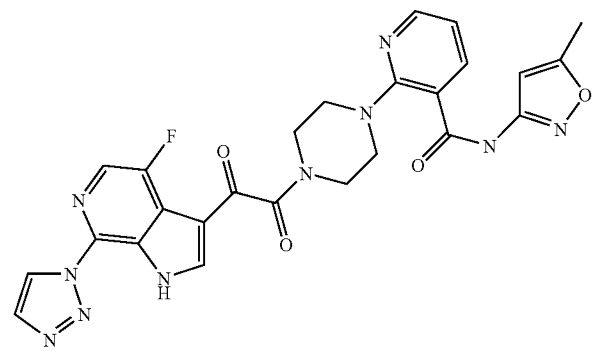 | B |
| D-40 | 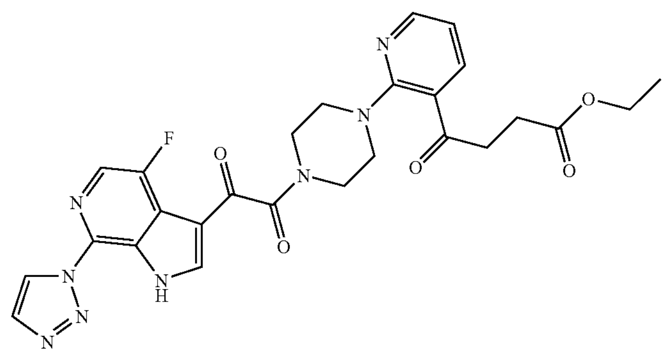 | B |
| D-41 | 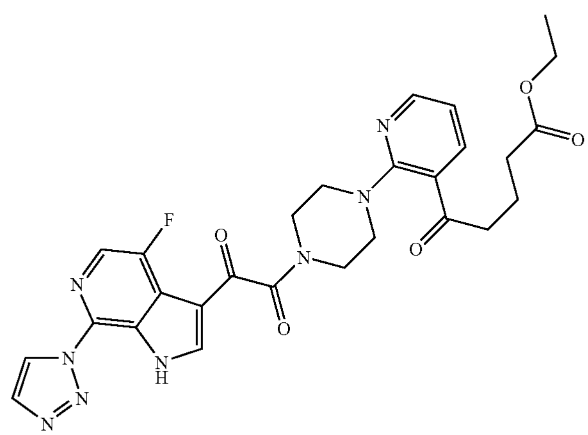 | B |
| D-42 | 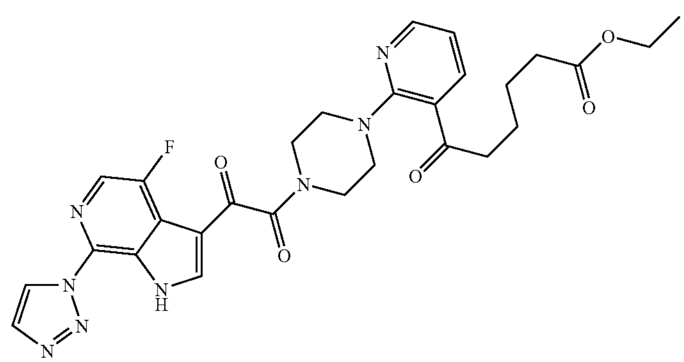 | B |

TABLE 4-continued
| Compd # | Structure | EC$_{50}$ Group from Table 3 |
|---|---|---|
| D-43 | 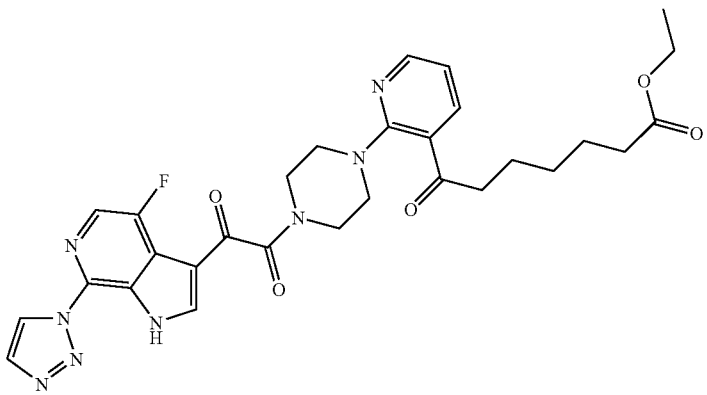 | B |
| D-44 | 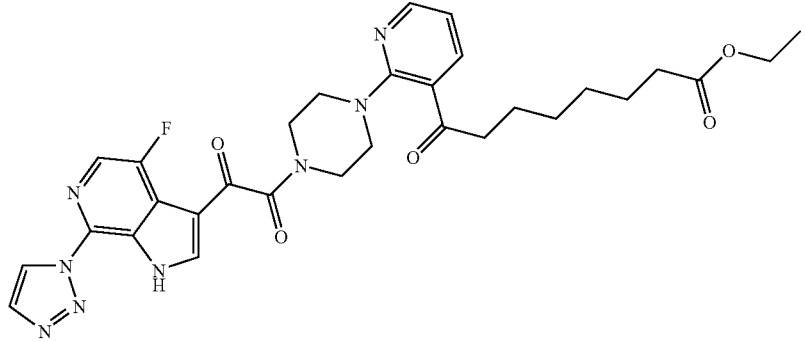 | B |
| D-45 | 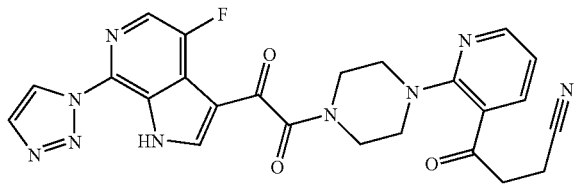 | B |
| D-46 | 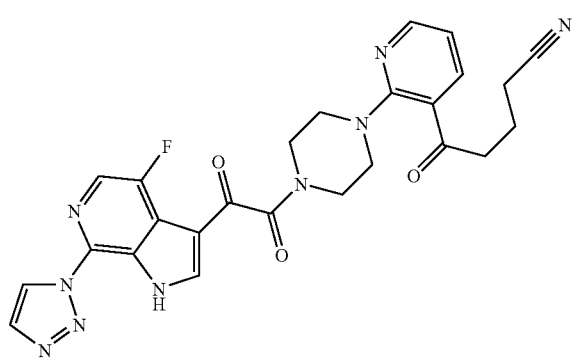 | B |

TABLE 4-continued

| Compd # | Structure | EC$_{50}$ Group from Table 3 |
|---|---|---|
| D-47 | 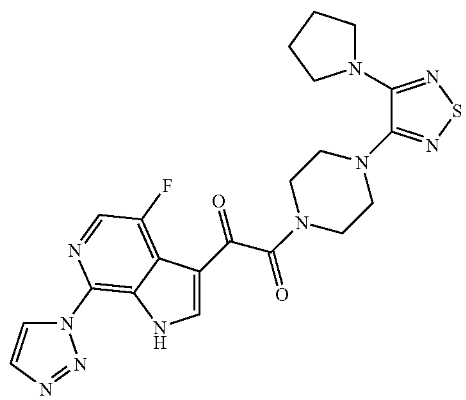 | A |
| D-48 | 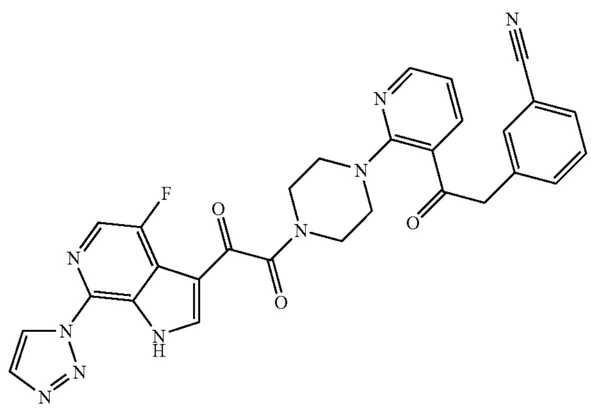 | A |
| D-49 | 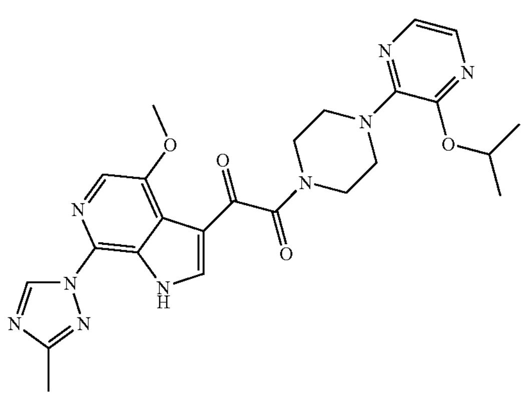 | A |

TABLE 4-continued
| Compd # | Structure | EC₅₀ Group from Table 3 |
|---|---|---|
| D-50 | 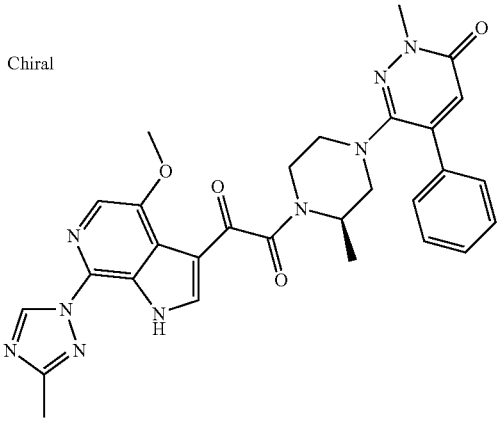 | B |
| D-51 | 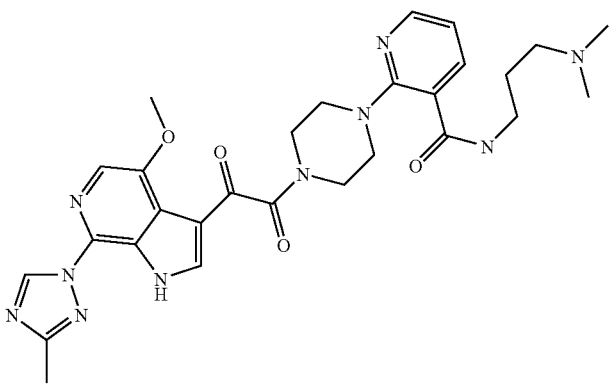 | B |
| A-53 | 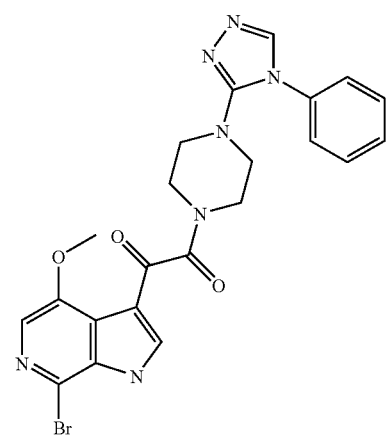 | A |

TABLE 4-continued
| Compd # | Structure | EC$_{50}$ Group from Table 3 |
|---|---|---|
| A-54 | 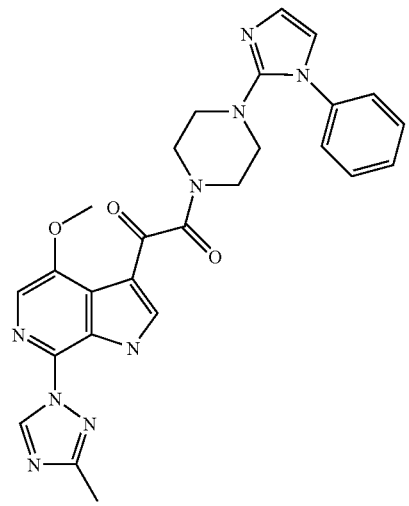 | A |
| A-55 | 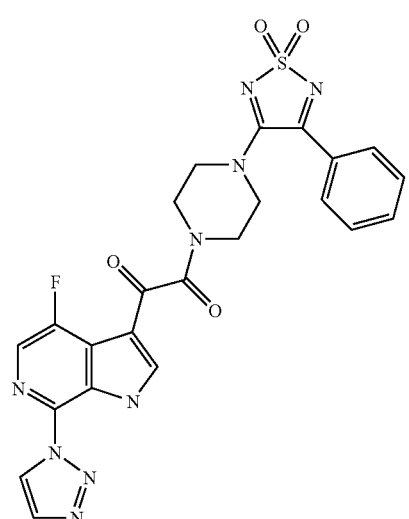 | A |
| A-56 | 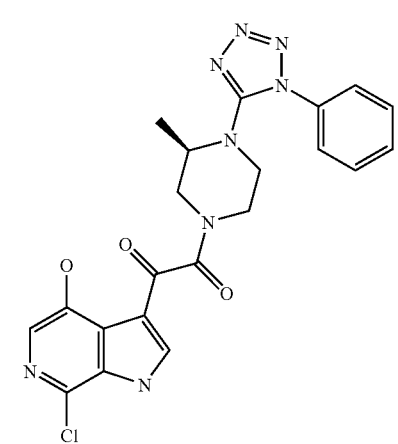 | B |

TABLE 4-continued
| Compd # | Structure | EC$_{50}$ Group from Table 3 |
|---|---|---|
| A-57 | 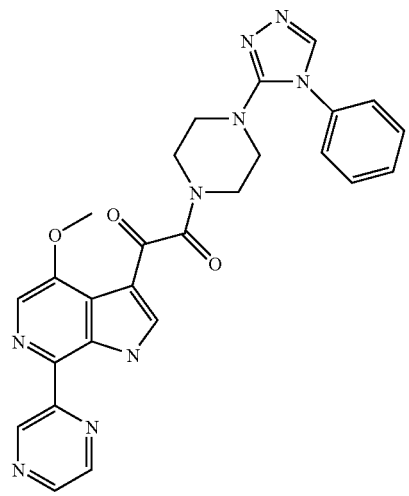 | A |
| A-58 | 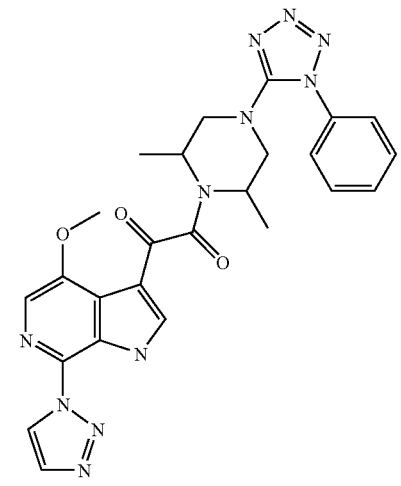 | A |
| A-59 | 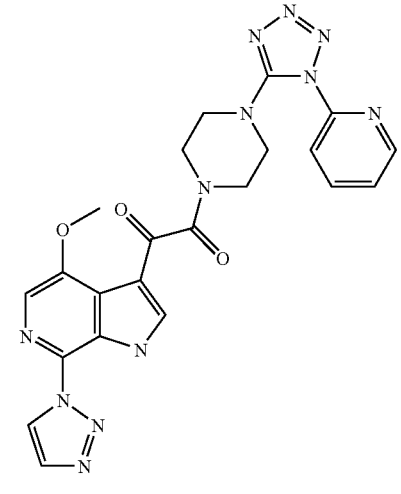 | A |

TABLE 4-continued

| Compd # | Structure | EC$_{50}$ Group from Table 3 |
|---|---|---|
| A-60 | 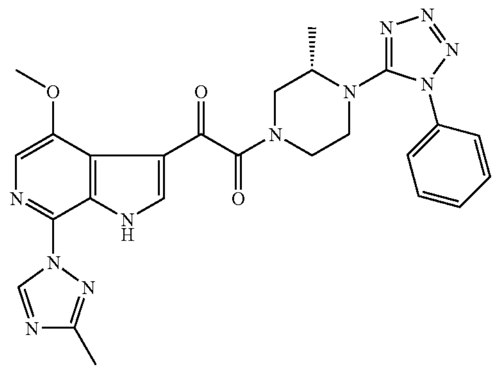 | A |
| A-61 | 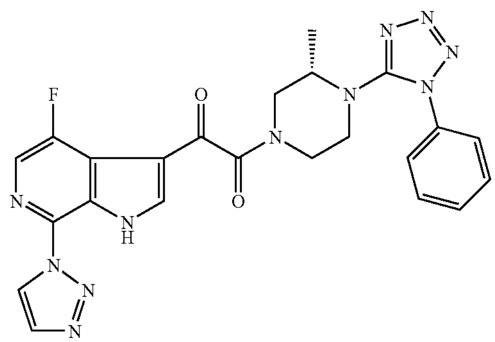 | A |
| A-62 | 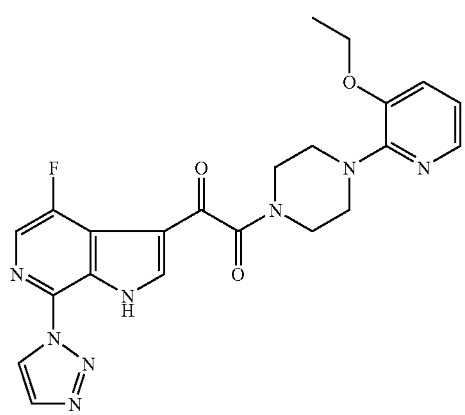 | A |
| A-63 | 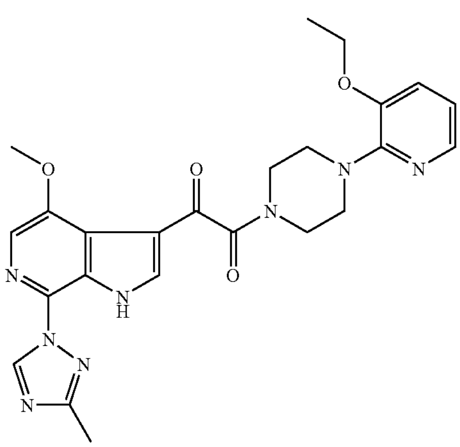 | A |

TABLE 4-continued

| Compd # | Structure | EC$_{50}$ Group from Table 3 |
|---|---|---|
| A-64 | 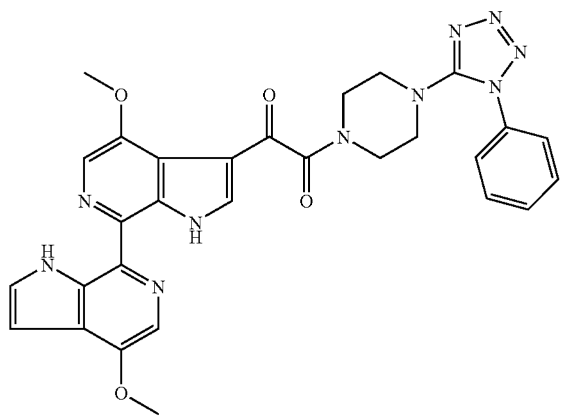 | A |
| A-66 | 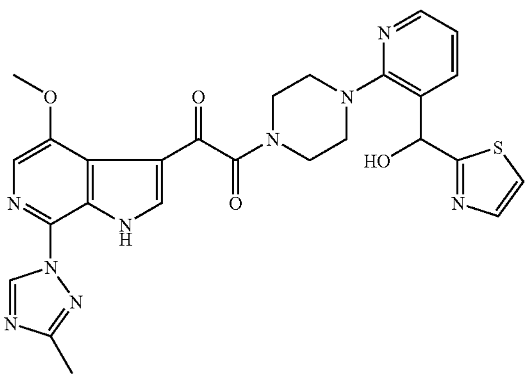 | A |
| A-67 | 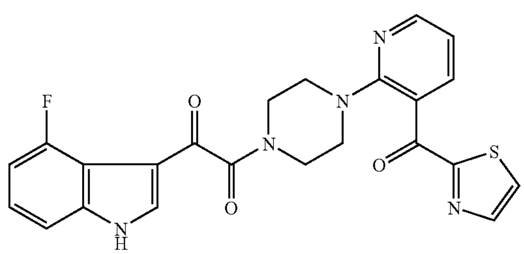 | B |
| A-68 | 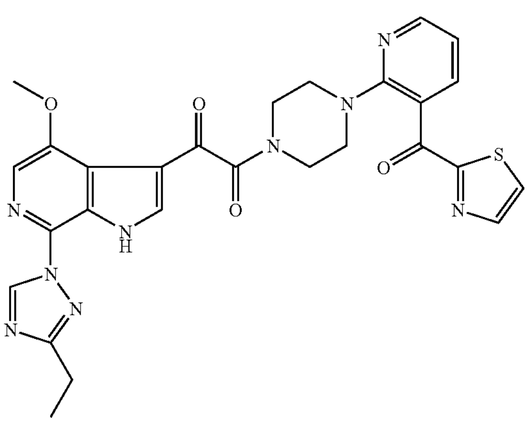 | A |

TABLE 4-continued

| Compd # | Structure | EC$_{50}$ Group from Table 3 |
|---|---|---|
| A-69 | 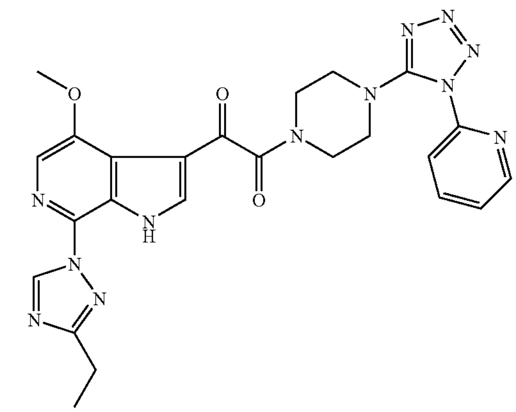 | A |
| A-70 | 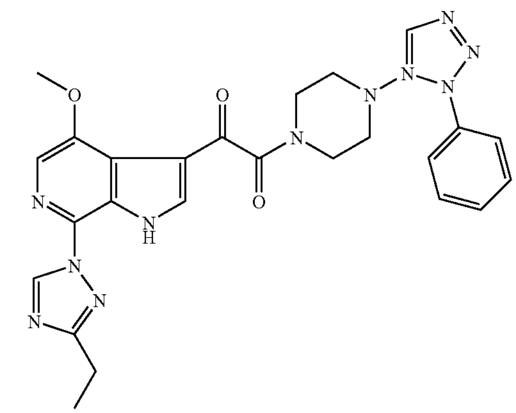 | A |
| A-71 | 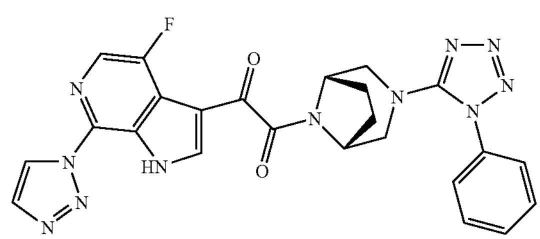 | A |
| A-72 | 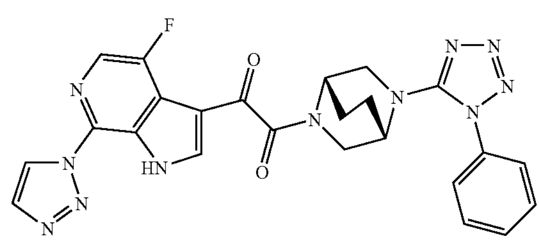 | A |
| A-73 | 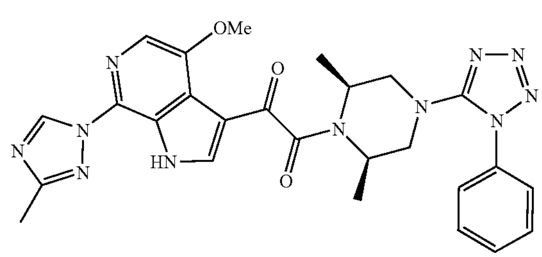 | A |

TABLE 4-continued

| Compd # | Structure | EC$_{50}$ Group from Table 3 |
|---|---|---|
| A-74 | 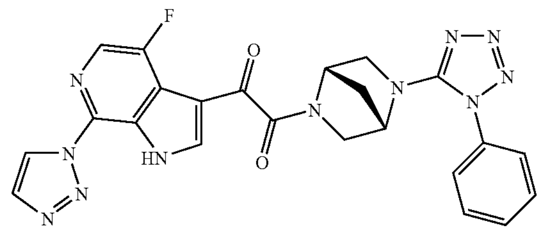 | B |
| E-1 | 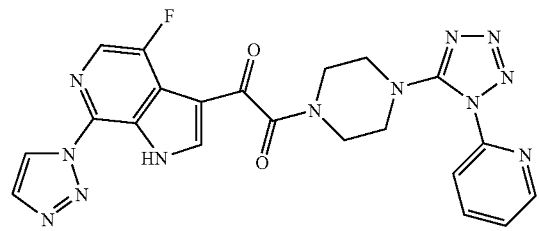 | A |
| E-2 | 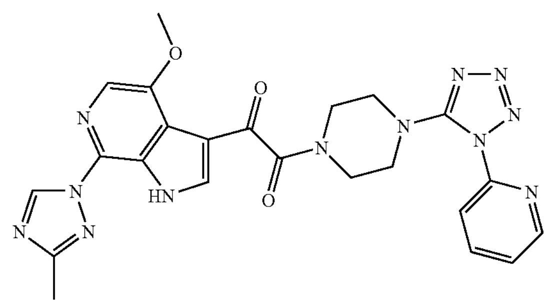 | A |
| E-3 | 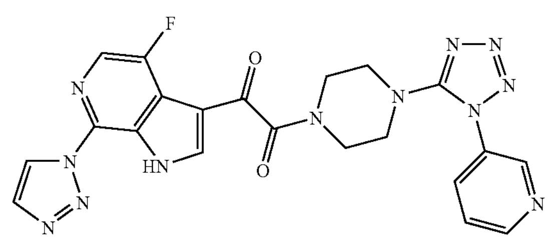 | A |
| E-4 | 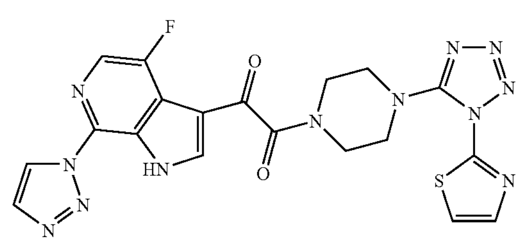 | A |

TABLE 4-continued
| Compd # | Structure | EC$_{50}$ Group from Table 3 |
|---|---|---|
| E-5 | 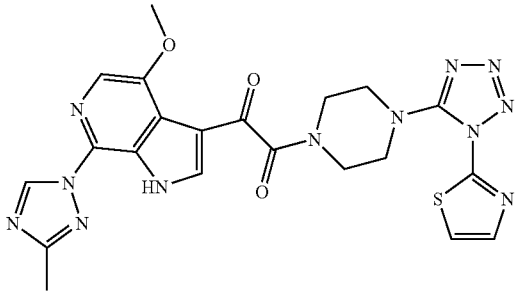 | A |
| E-6 | 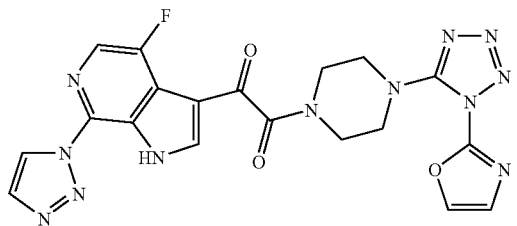 | A |
| E-7 | 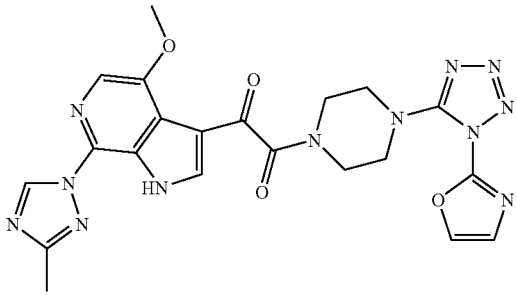 | A |
| E-8 | 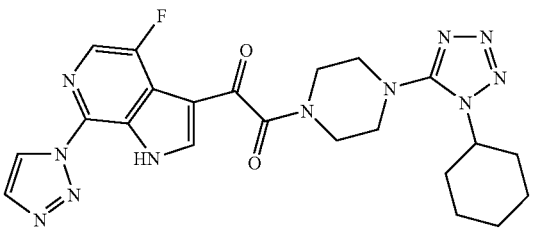 | A |
| E-9 | 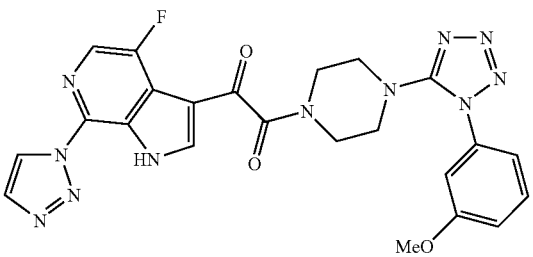 | A |

TABLE 4-continued

| Compd # | Structure | EC$_{50}$ Group from Table 3 |
|---|---|---|
| E-10 | 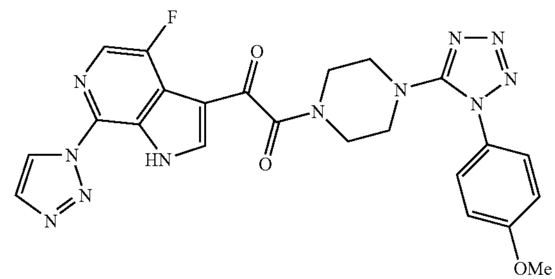 | B |
| E-11 | 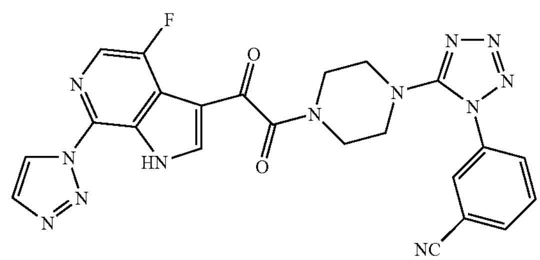 | B |
| E-12 | 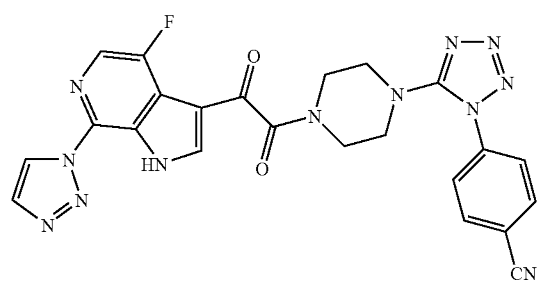 | B |
| E-12a | 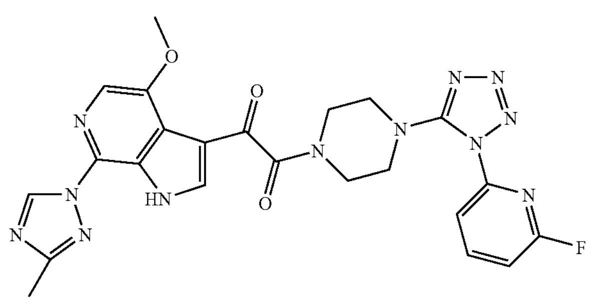 | A |
| E-12b | 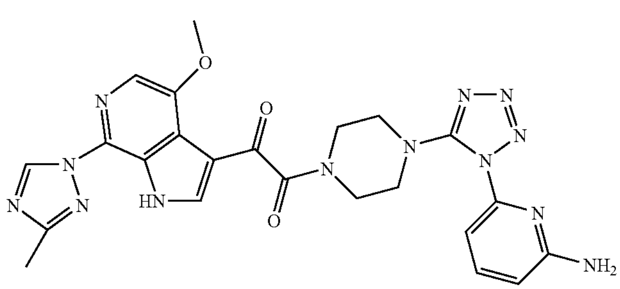 | A |

TABLE 4-continued

| Compd # | Structure | EC$_{50}$ Group from Table 3 |
|---|---|---|
| E-12c | 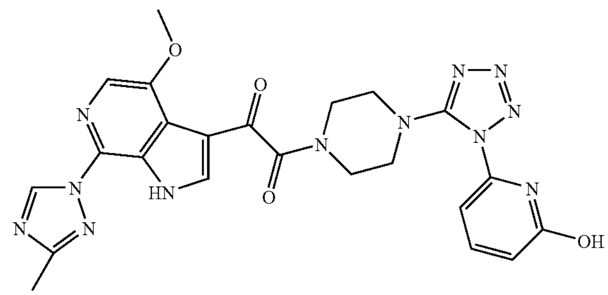 | A |
| E-12d | 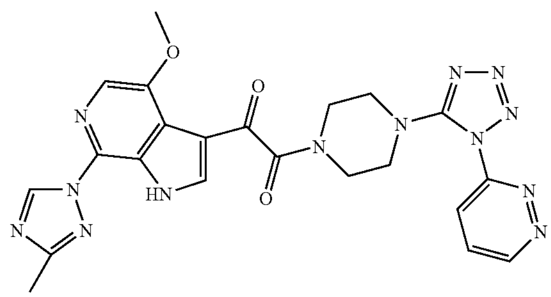 | A |
| E-13 | 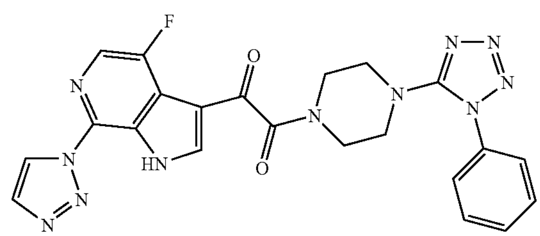 | A |
| E-14 | 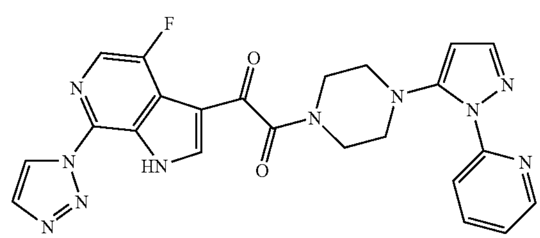 | A |
| E-15 | 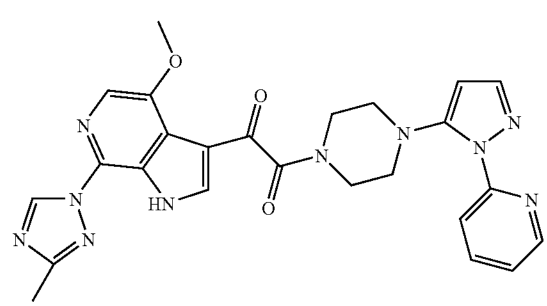 | A |

TABLE 4-continued

| Compd # | Structure | EC$_{50}$ Group from Table 3 |
|---|---|---|
| E-16 | 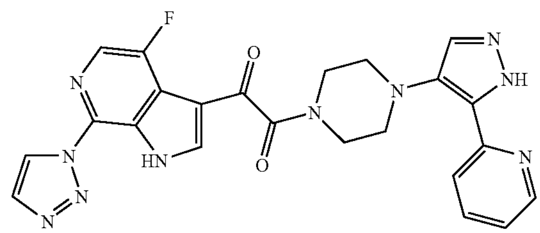 | A |
| E-17 | 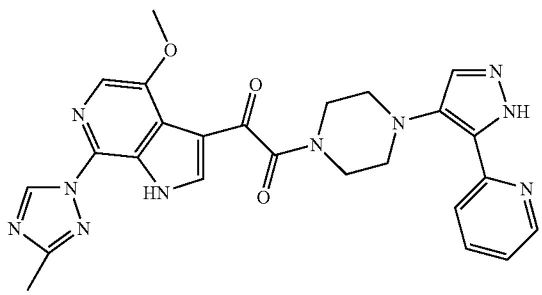 | A |
| F-1 | 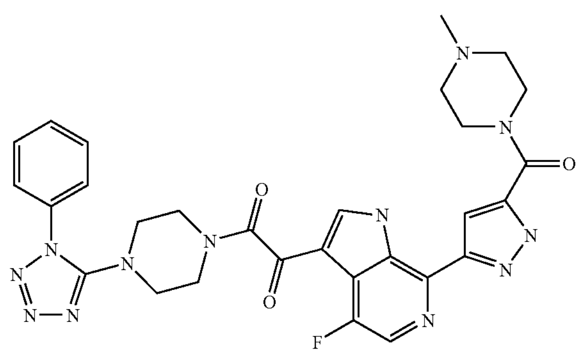 | A |
| F-2 | 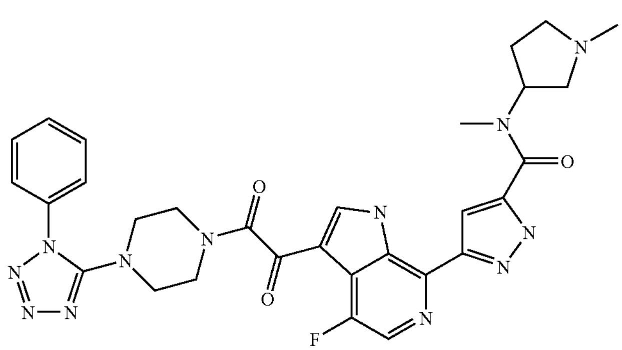 | A |

TABLE 4-continued

| Compd # | Structure | EC$_{50}$ Group from Table 3 |
|---|---|---|
| F-3 | Chiral | A |
| F-4 | 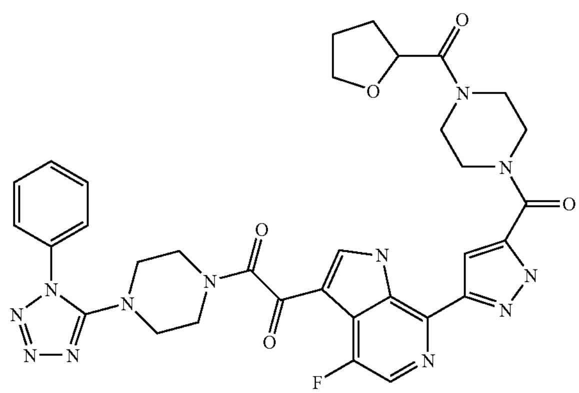 | A |
| F-5 | 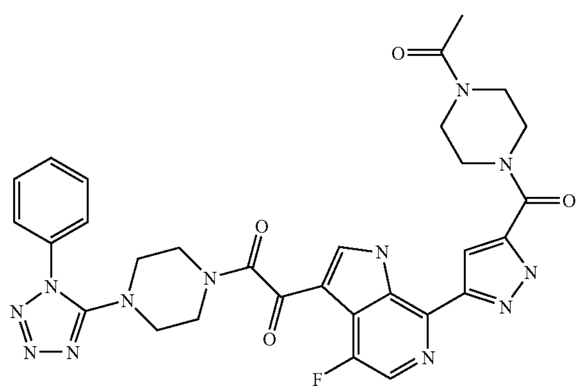 | A |
| F-6 | Chiral | A |

TABLE 4-continued
| Compd # | Structure | EC$_{50}$ Group from Table 3 |
|---|---|---|
| F-7 | 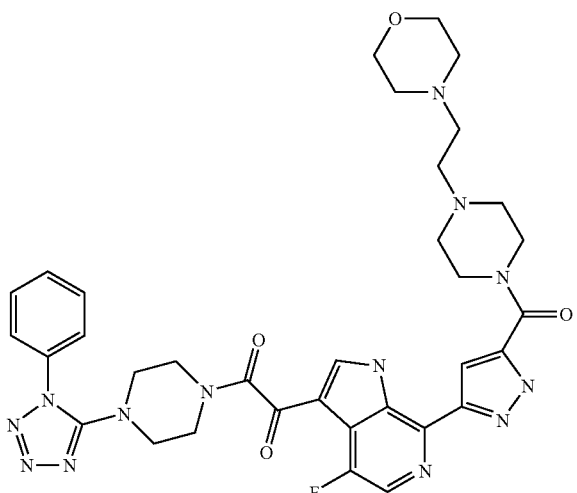 | A |
| F-8 | 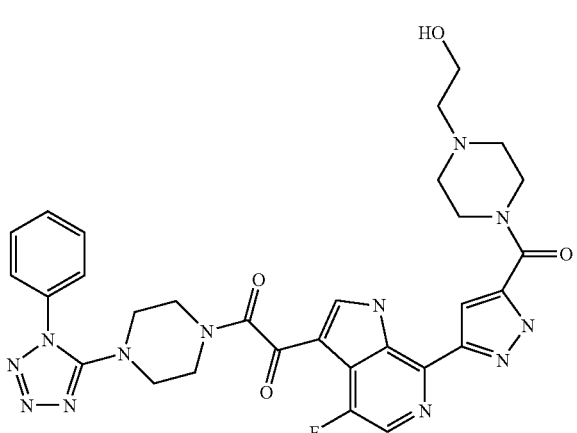 | A |
| F-9 | 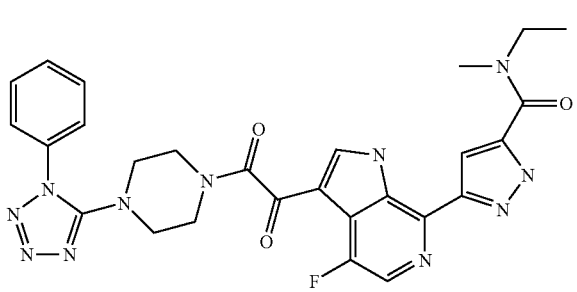 | A |
| F-10 | 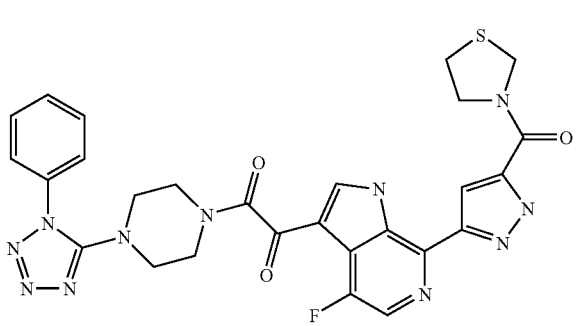 | A |

TABLE 4-continued

| Compd # | Structure | EC$_{50}$ Group from Table 3 |
|---|---|---|
| F-11 | 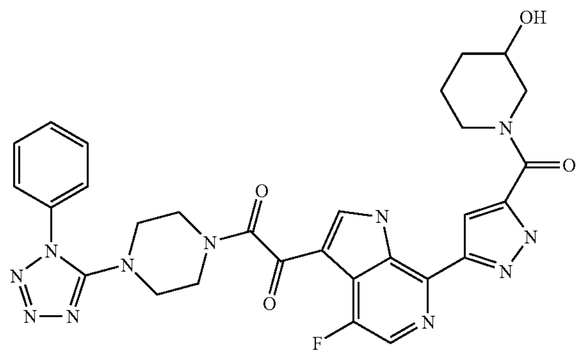 | A |
| F-12 | 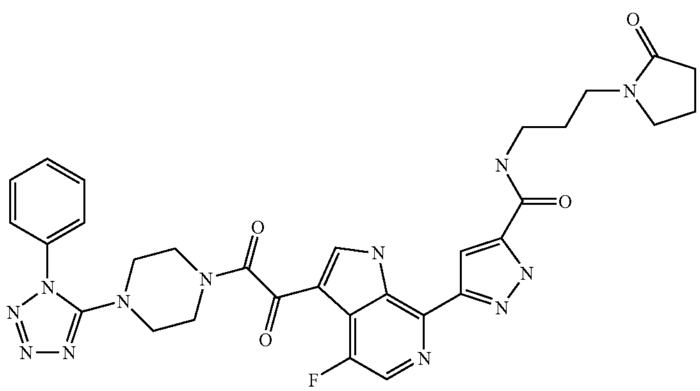 | A |
| F-13 | 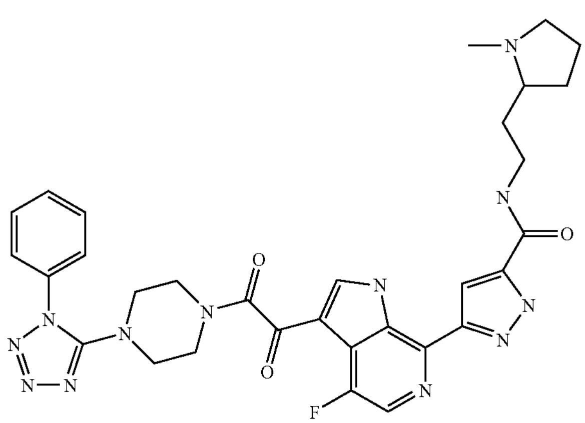 | A |

TABLE 4-continued

| Compd # | Structure | EC$_{50}$ Group from Table 3 |
|---|---|---|
| F-14 | 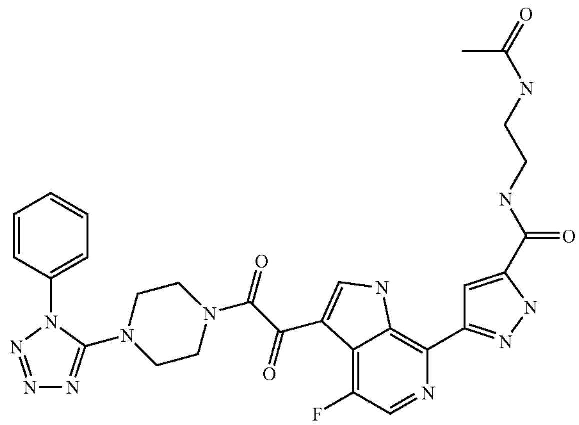 | A |
| F-15 | 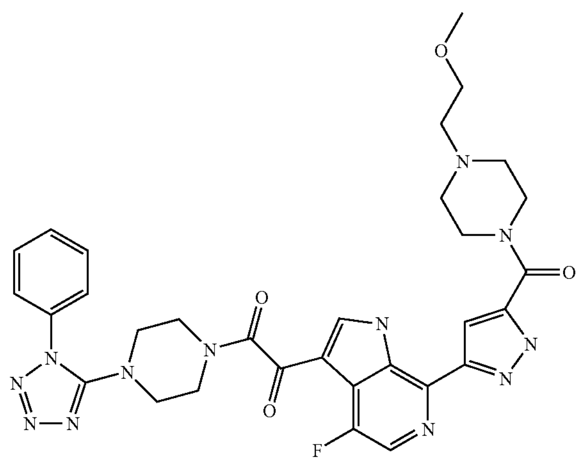 | A |
| F-16 | 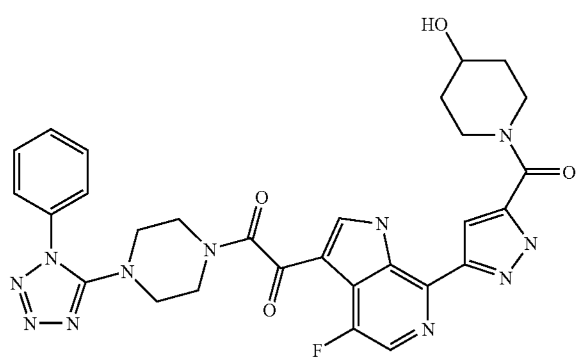 | A |
| B-28 | 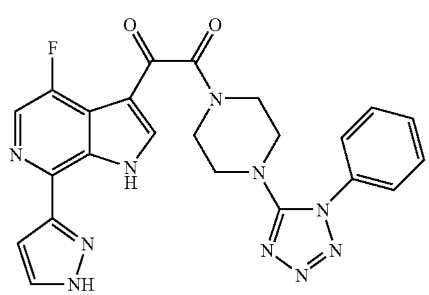 | A |

TABLE 4-continued

| Compd # | Structure | EC$_{50}$ Group from Table 3 |
|---|---|---|
| B-29 | 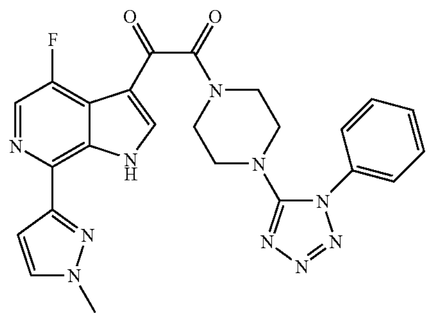 | A |
| B-30 | 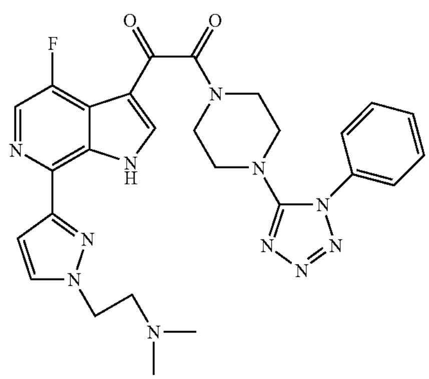 | A |
| B-31 | 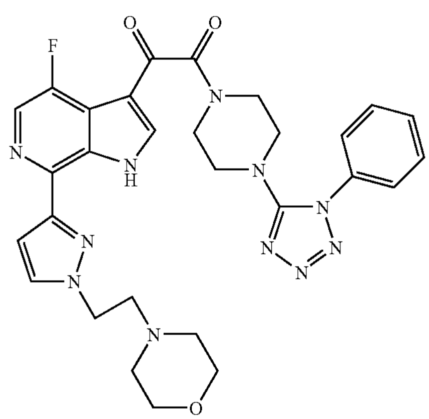 | A |
| B-32 | 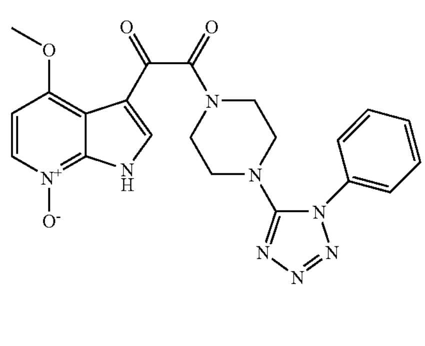 | B |

TABLE 4-continued
| Compd # | Structure | EC$_{50}$ Group from Table 3 |
|---|---|---|
| B-33 | 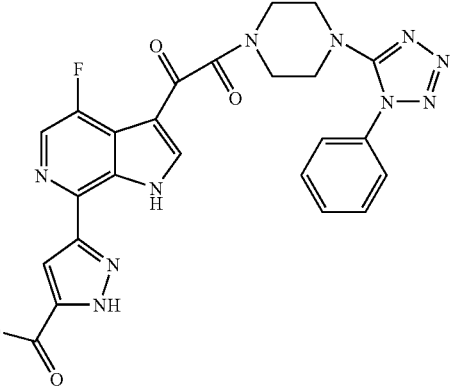 | A |
| B-34 | 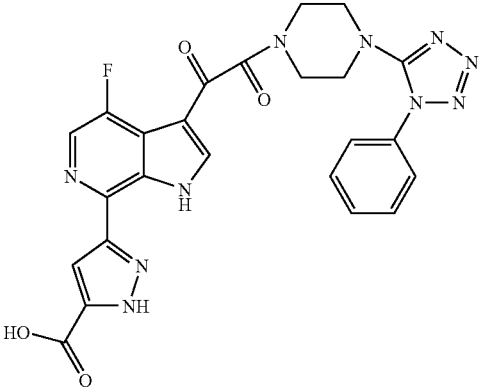 | A |
| B-35 | 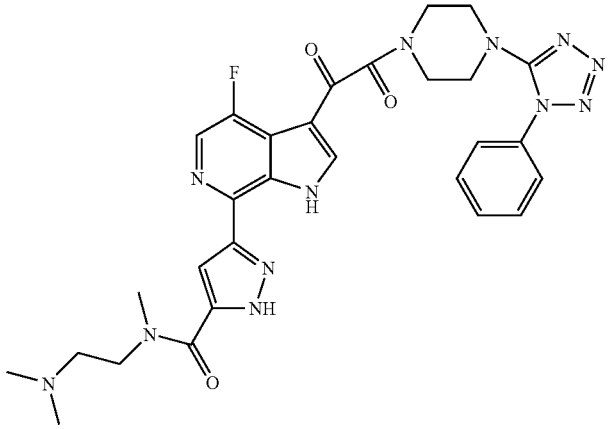 | A |

TABLE 4-continued
| Compd # | Structure | EC$_{50}$ Group from Table 3 |
|---|---|---|
| B-36 | 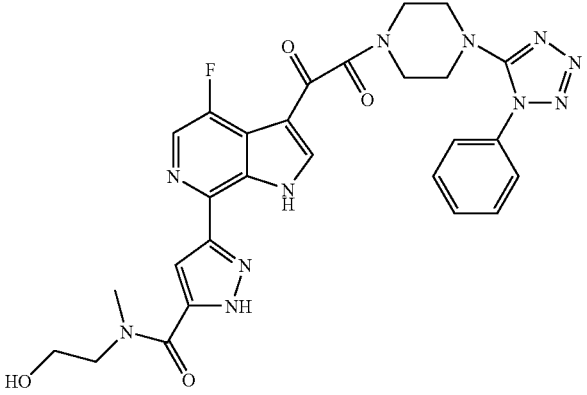 | A |
| B-37 | 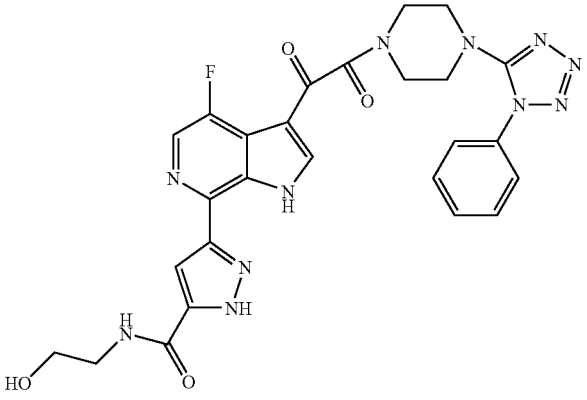 | A |
| B-38 | 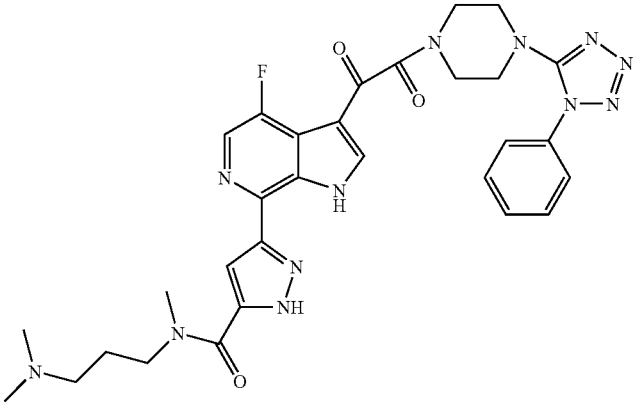 | A |

TABLE 4-continued
| Compd # | Structure | EC$_{50}$ Group from Table 3 |
|---|---|---|
| B-39 | 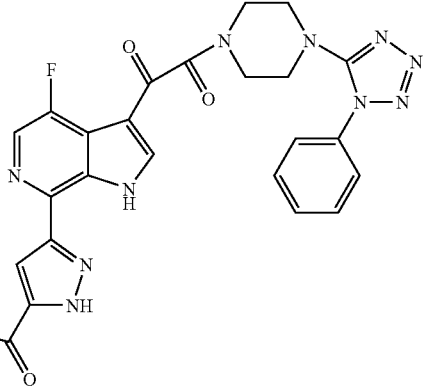 | A |
| B-40 | 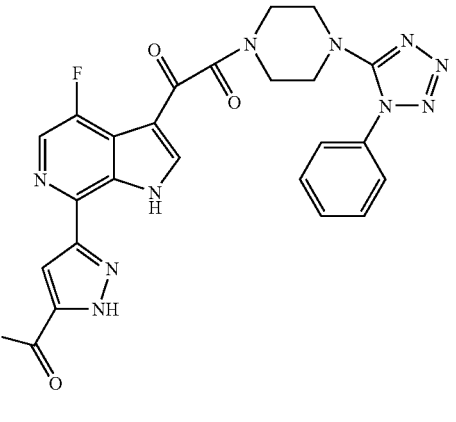 | A |
| B-41 | 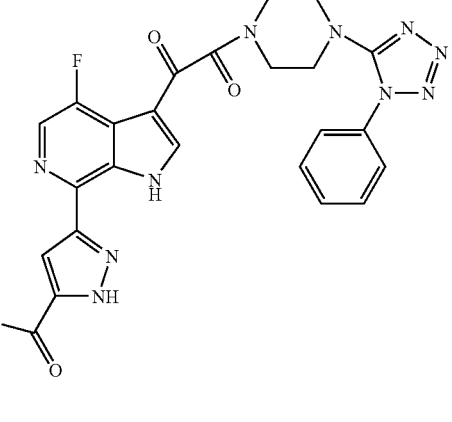 | A |

TABLE 4-continued

| Compd # | Structure | EC$_{50}$ Group from Table 3 |
|---|---|---|
| B-42 | 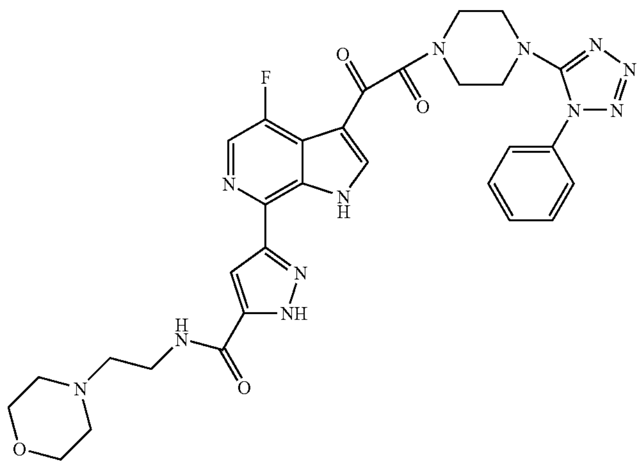 | A |
| B-43 | 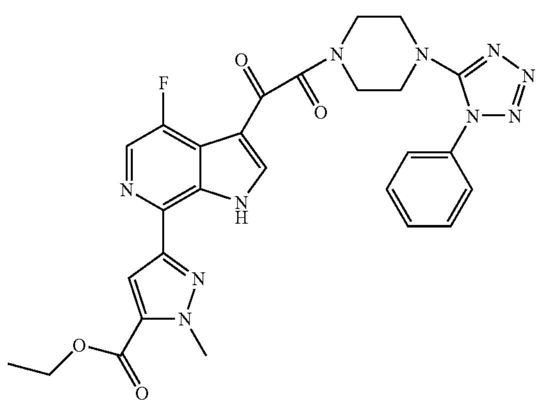 | A |
| B-44 | 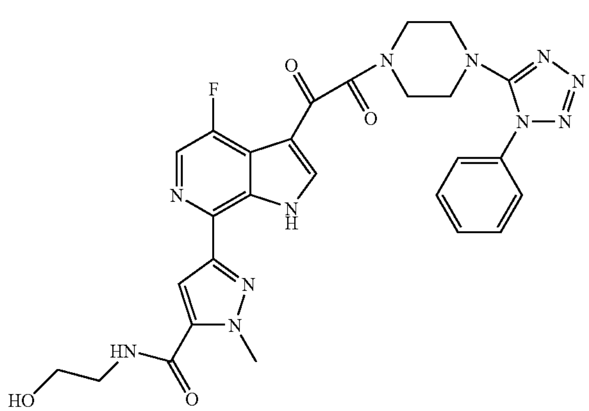 | A |

TABLE 4-continued

| Compd # | Structure | EC$_{50}$ Group from Table 3 |
|---|---|---|
| B-45 | 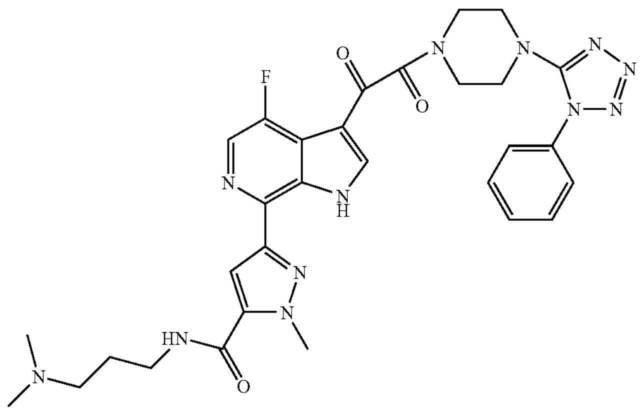 | A |
| B-46 | 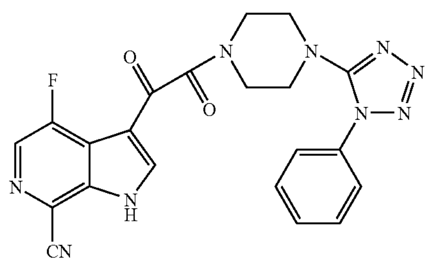 | B |
| B-47 | 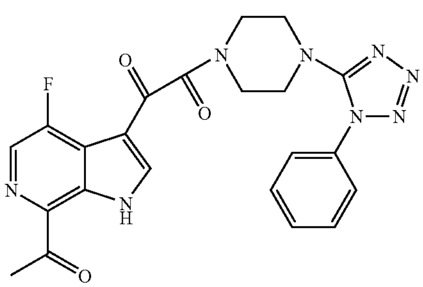 | A |
| B-48 | 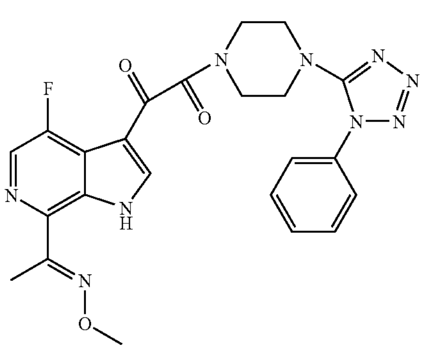 | A |

TABLE 4-continued

| Compd # | Structure | EC$_{50}$ Group from Table 3 |
|---|---|---|
| B-49 | 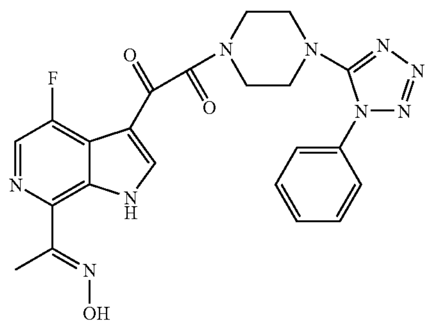 | A |
| B-50 | 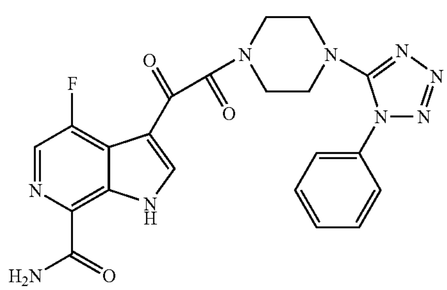 | A |
| B-51 | 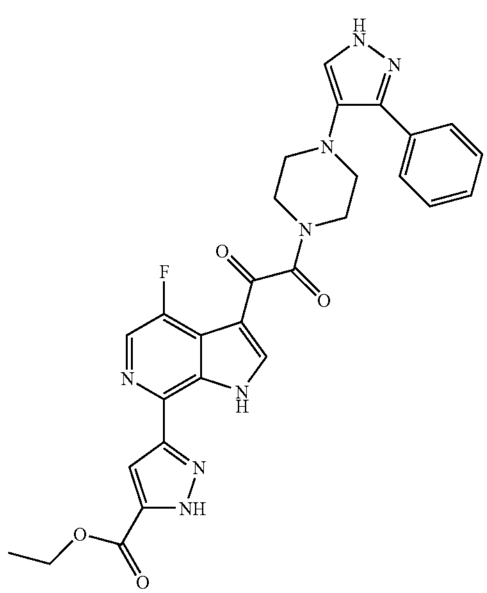 | A |

TABLE 4-continued
| Compd # | Structure | EC$_{50}$ Group from Table 3 |
|---|---|---|
| B-52 | 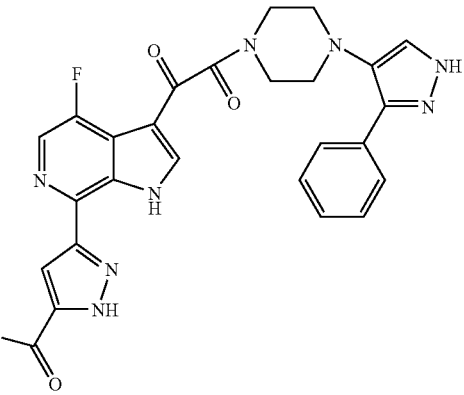 | A |
| B-53 | 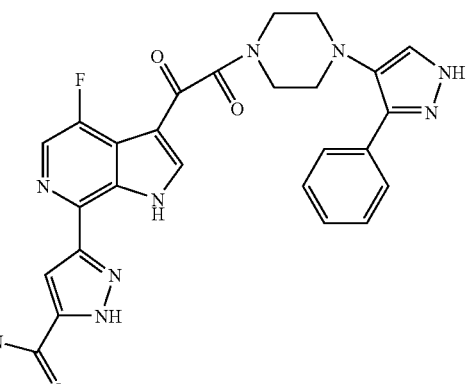 | A |
| B-54 | 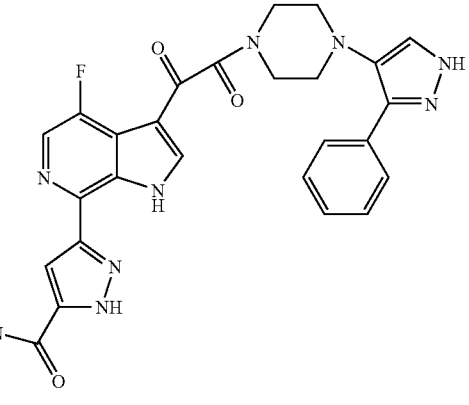 | A |

TABLE 4-continued

| Compd # | Structure | EC$_{50}$ Group from Table 3 |
|---|---|---|
| B-55 | 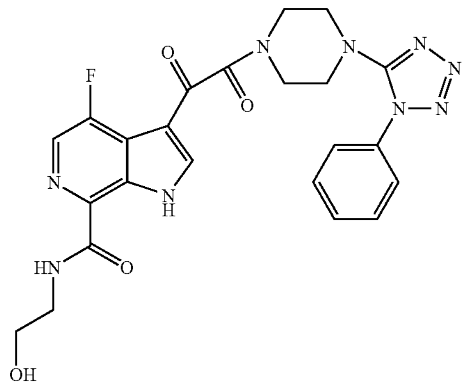 | A |
| B-56 | 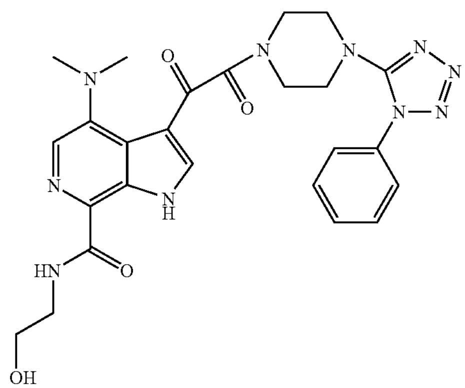 | A |
| B-57 | 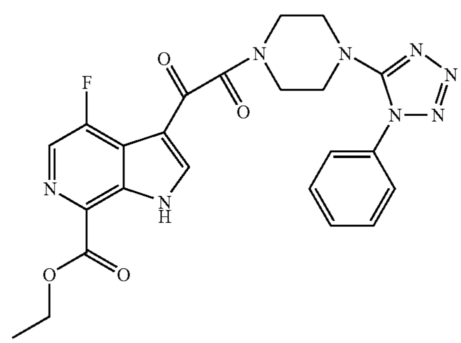 | A |
| B-58 | 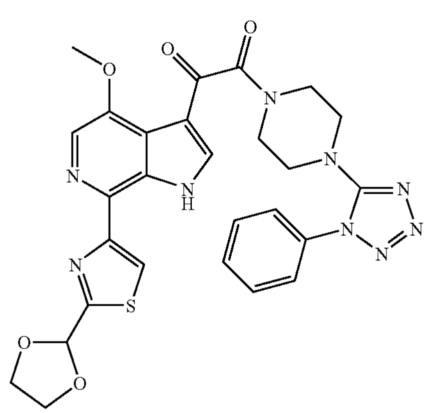 | A |

TABLE 4-continued

| Compd # | Structure | EC$_{50}$ Group from Table 3 |
|---|---|---|
| B-59 | 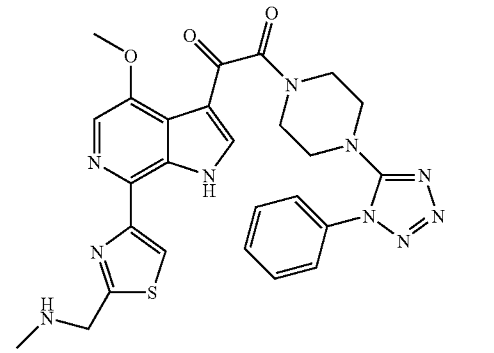 | A |
| B-60 | 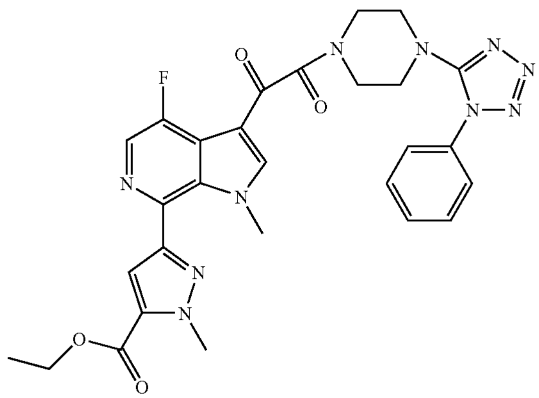 | A |
| B-61 | 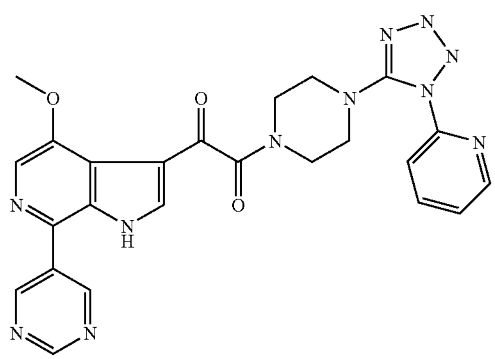 | A |
| B-62 | 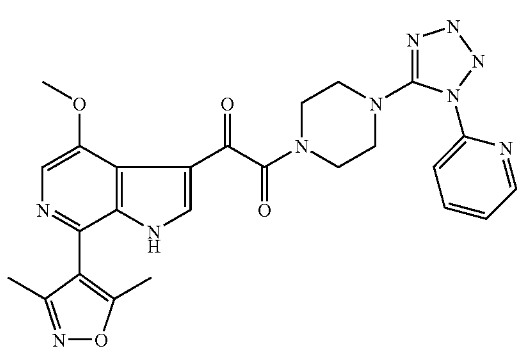 | A |

TABLE 4-continued
| Compd # | Structure | EC$_{50}$ Group from Table 3 |
|---|---|---|
| B-63 | 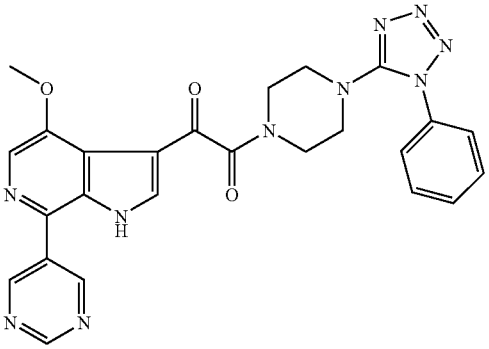 | A |
| B-64 | 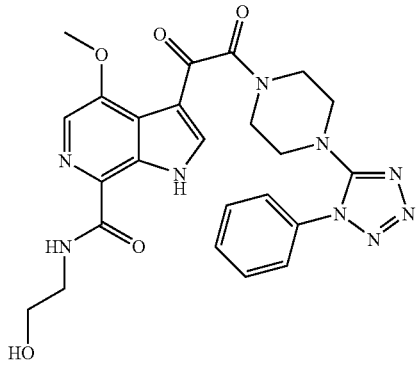 | A |
| B-65 | 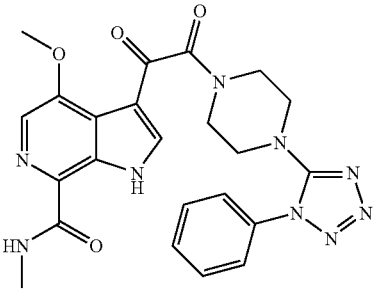 | A |
| B-66 | 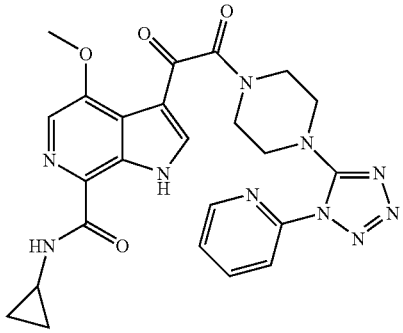 | A |

TABLE 4-continued

| Compd # | Structure | EC$_{50}$ Group from Table 3 |
|---|---|---|
| B-67 | 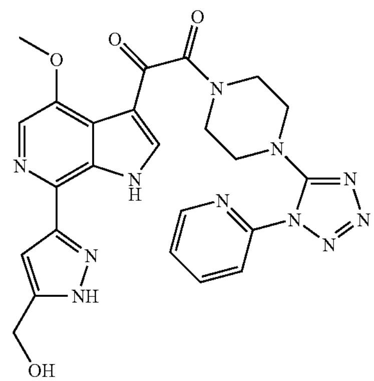 | A |
| B-68 | 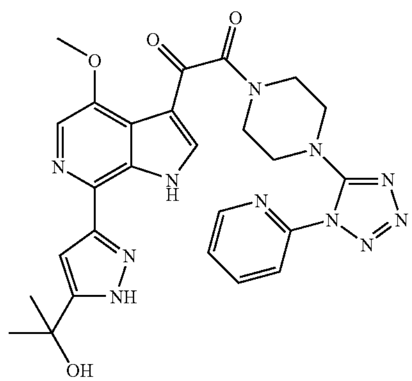 | A |
| B-69 | 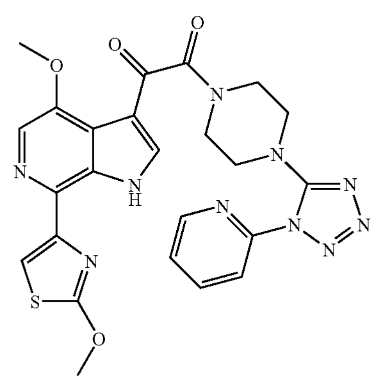 | A |
| B-70 | 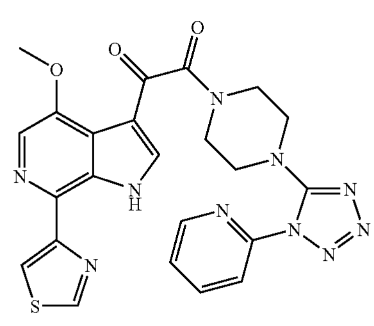 | A |

TABLE 4-continued

| Compd # | Structure | EC$_{50}$ Group from Table 3 |
|---|---|---|
| B-71 | 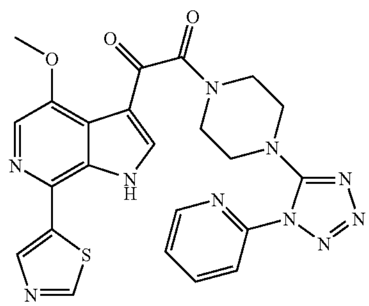 | A |
| B-72 | 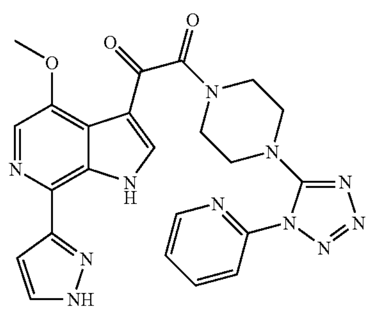 | A |
| B-73 | 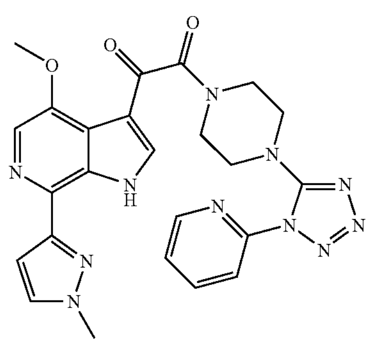 | A |
| B-74 | 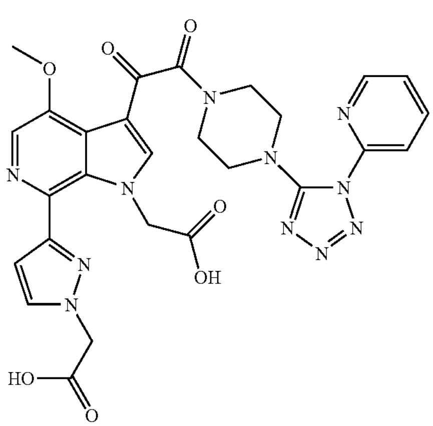 | B |

TABLE 4-continued
| Compd # | Structure | EC$_{50}$ Group from Table 3 |
|---|---|---|
| B-75 | 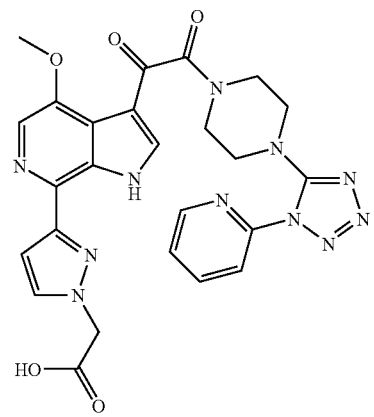 | A |
| B-76 | 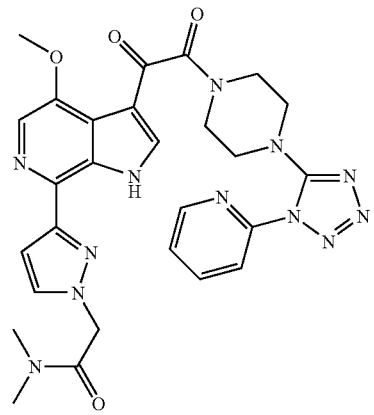 | B |
| B-77 | 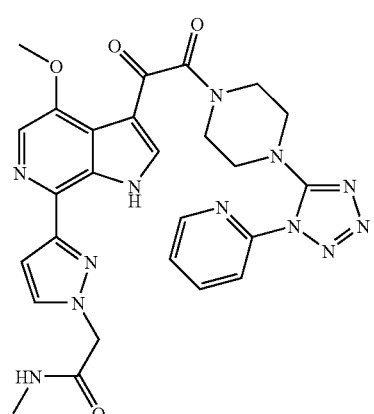 | A |

TABLE 4-continued

| Compd # | Structure | EC$_{50}$ Group from Table 3 |
|---|---|---|
| B-78 | 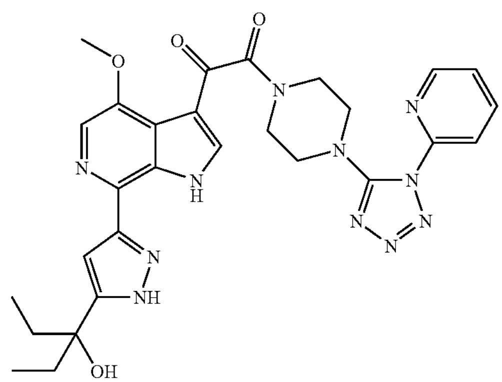 | A |
| B-79 | 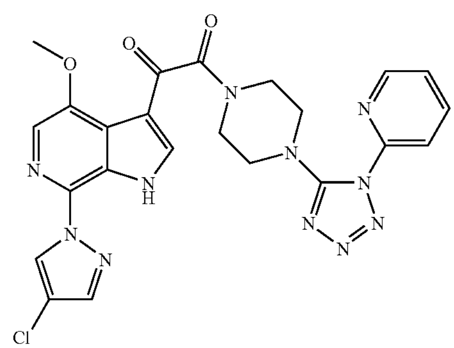 | A |
| B-80 | 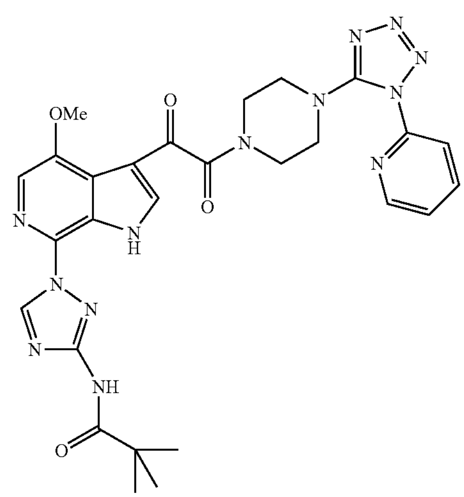 | A |

TABLE 4-continued
| Compd # | Structure | EC$_{50}$ Group from Table 3 |
|---|---|---|
| B-81 | 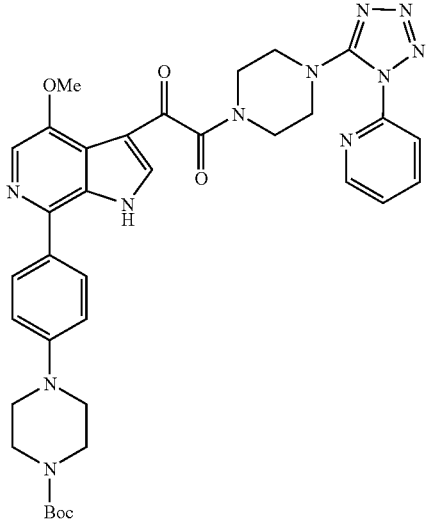 | A |
| B-82 | 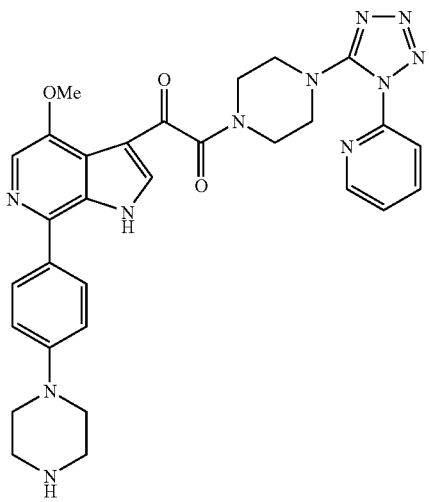 | A |

TABLE 4-continued

| Compd # | Structure | EC$_{50}$ Group from Table 3 |
|---|---|---|
| B-83 | 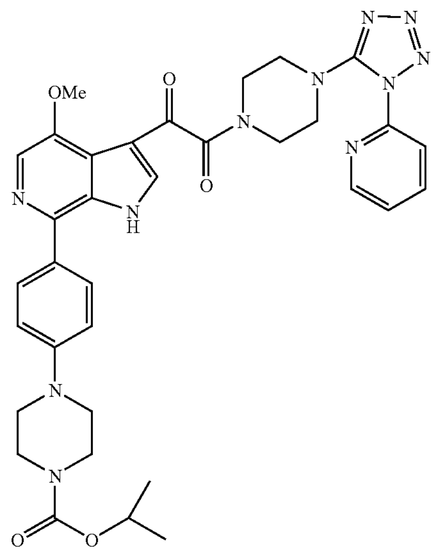 | A |
| B-84 | 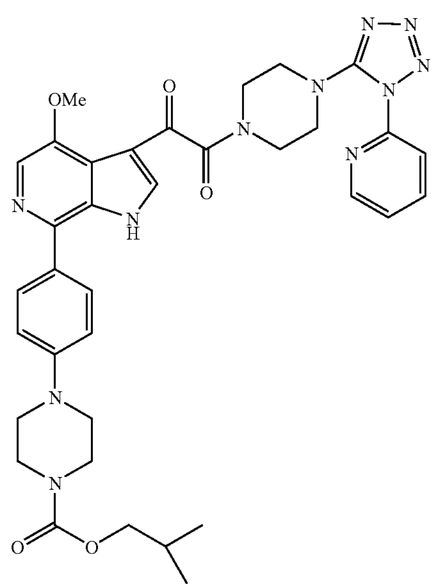 | A |

TABLE 4-continued

| Compd # | Structure | EC$_{50}$ Group from Table 3 |
|---|---|---|
| B-85 | 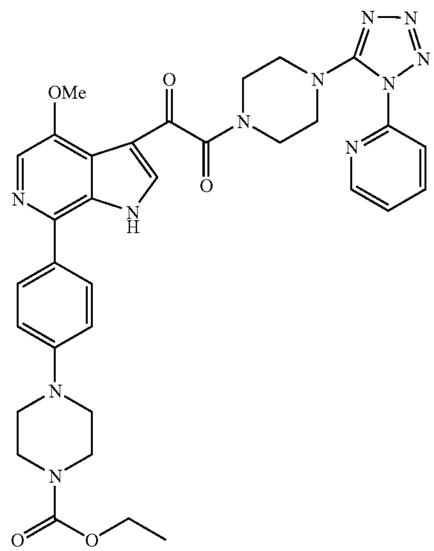 | A |
| B-86 | 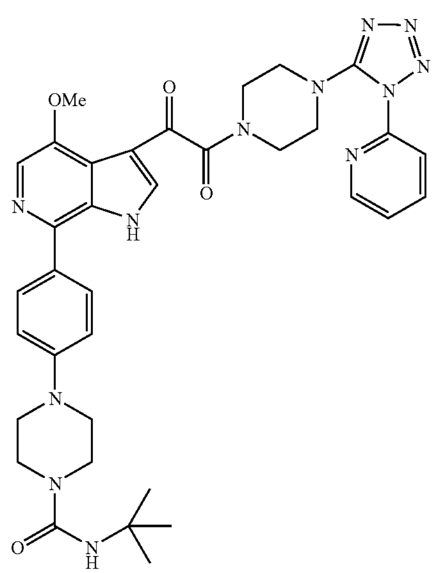 | A |

TABLE 4-continued
| Compd # | Structure | EC$_{50}$ Group from Table 3 |
|---|---|---|
| B-87 | 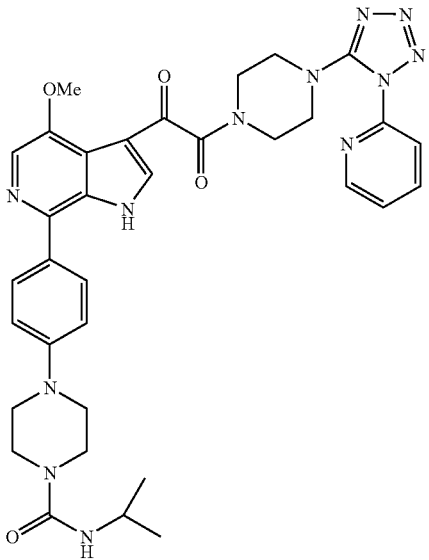 | A |
| B-88 | 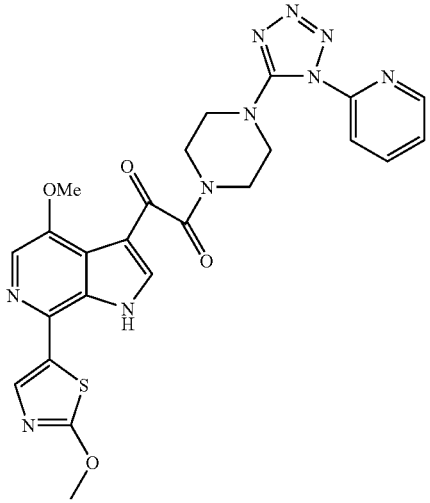 | A |

TABLE 4-continued

| Compd # | Structure | EC$_{50}$ Group from Table 3 |
|---|---|---|
| B-89 | 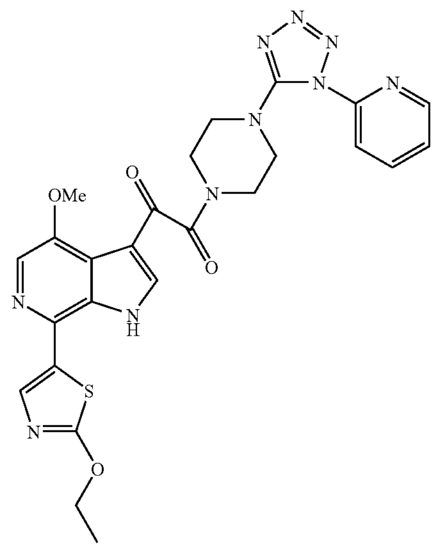 | A |
| B-90 | 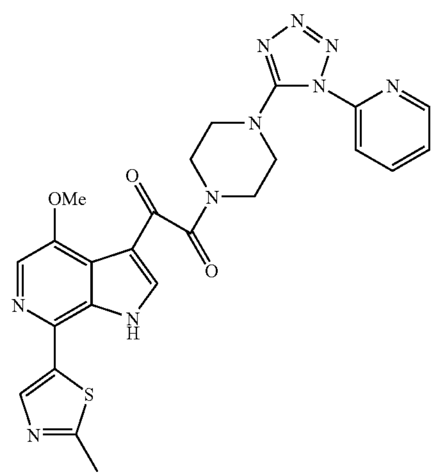 | A |
| B-91 | 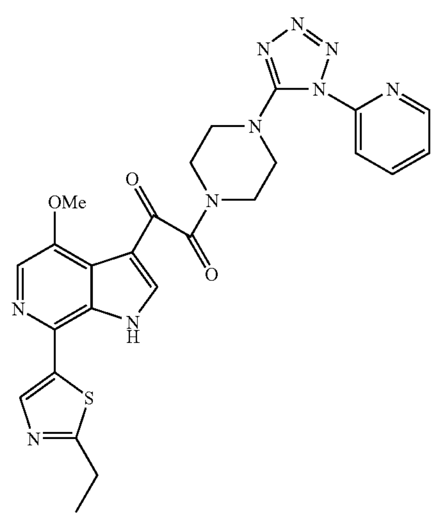 | A |

TABLE 4-continued

| Compd # | Structure | EC$_{50}$ Group from Table 3 |
|---|---|---|
| B-92 | 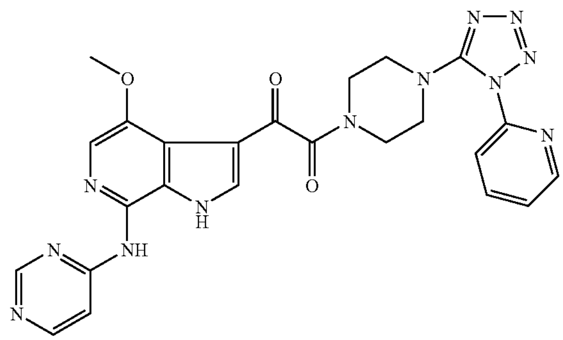 | A |
| G-1a | 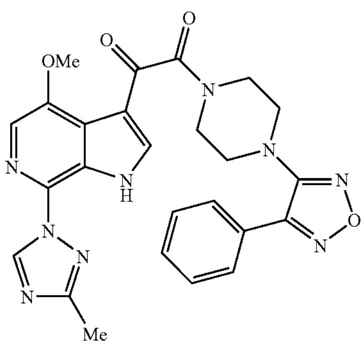 | A |
| G-1b | 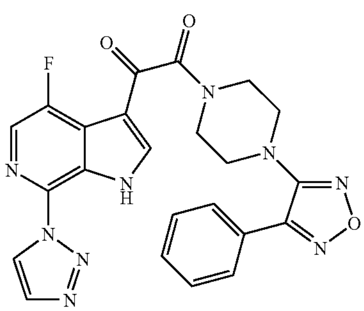 | A |
| G-2a | 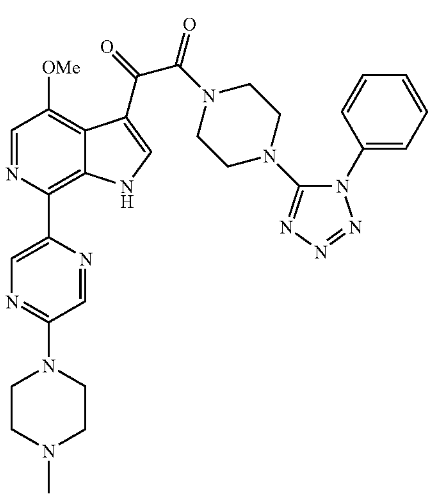 | A |

TABLE 4-continued

| Compd # | Structure | EC$_{50}$ Group from Table 3 |
|---|---|---|
| G-2b | (4-methoxy-7-(5-morpholinopyrazin-2-yl)-1H-pyrrolo[2,3-c]pyridin-3-yl) linked via oxoacetyl to 4-(1-phenyl-1H-tetrazol-5-yl)piperazine | A |
| G-2c | (4-methoxy-7-(5-(1H-imidazol-1-yl)pyrazin-2-yl)-1H-pyrrolo[2,3-c]pyridin-3-yl) linked via oxoacetyl to 4-(1-phenyl-1H-tetrazol-5-yl)piperazine | A |
| G-3a | (4-methoxy-7-(3-methyl-1H-1,2,4-triazol-1-yl)-1H-pyrrolo[2,3-c]pyridin-3-yl) linked via oxoacetyl to 4-(3-phenylpyridin-2-yl)piperazine | A |
| G-3b | (4-fluoro-7-(1H-1,2,3-triazol-1-yl)-1H-pyrrolo[2,3-c]pyridin-3-yl) linked via oxoacetyl to 4-(3-phenylpyridin-2-yl)piperazine | A |

TABLE 4-continued

| Compd # | Structure | EC$_{50}$ Group from Table 3 |
|---|---|---|
| G-4a | 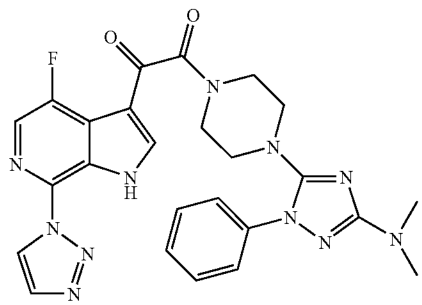 | A |
| G-4b | 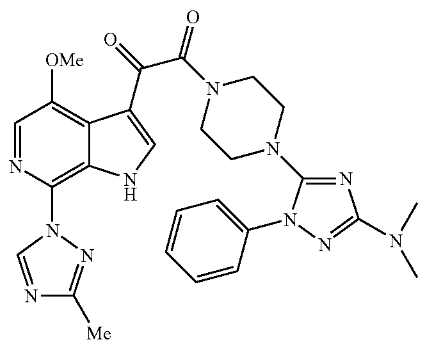 | A |
| G-4c | 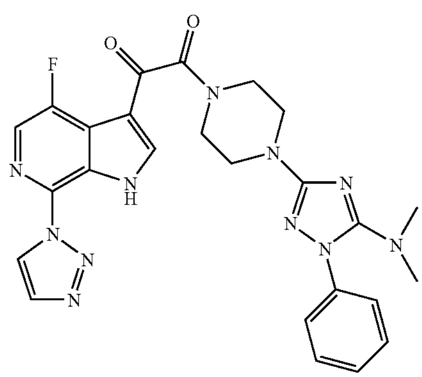 | B |
| G-4d | 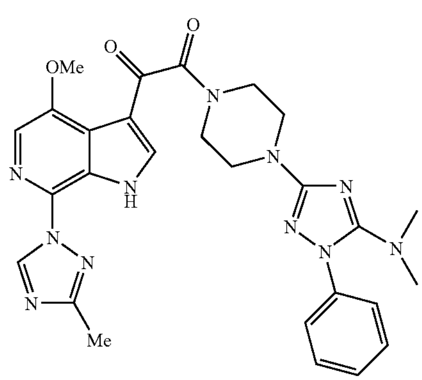 | A |

TABLE 4-continued

| Compd # | Structure | EC$_{50}$ Group from Table 3 |
|---|---|---|
| G-5a | 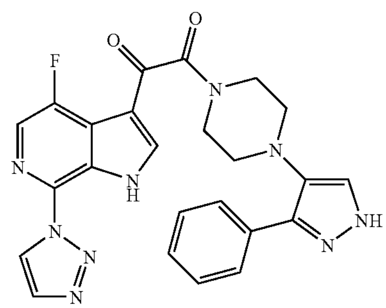 | A |
| G-5b | 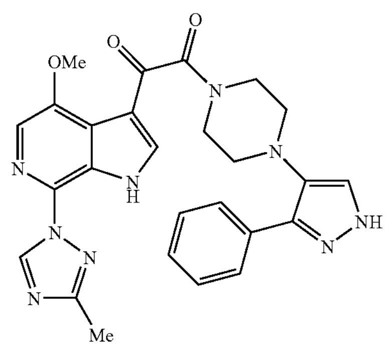 | A |
| G-6a | 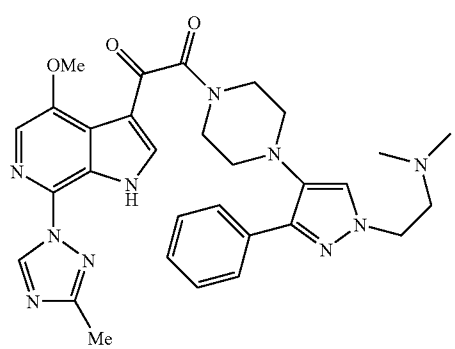 | A |
| G-6b | 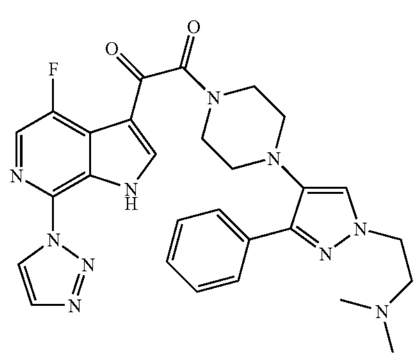 | A |

TABLE 4-continued

| Compd # | Structure | EC$_{50}$ Group from Table 3 |
|---|---|---|
| G-7a | 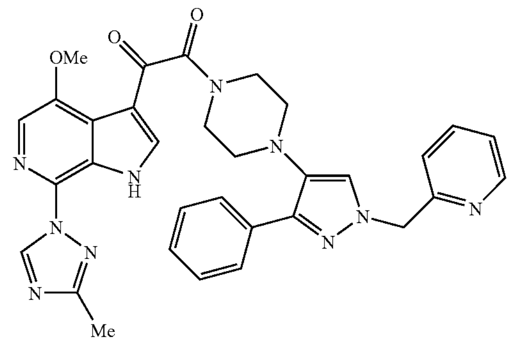 | A |
| G-7b | 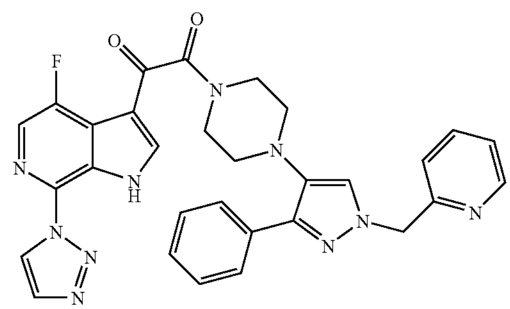 | A |
| G-8a | 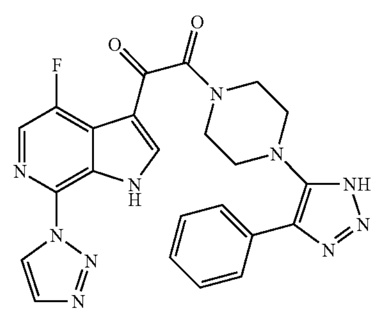 | A |
| G-8b | 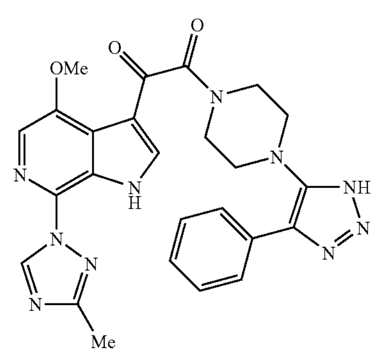 | A |

TABLE 4-continued
| Compd # | Structure | EC$_{50}$ Group from Table 3 |
|---|---|---|
| G-9a | 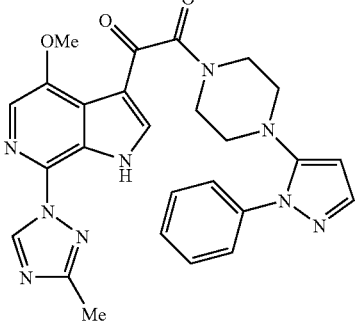 | A |
| G-9b | 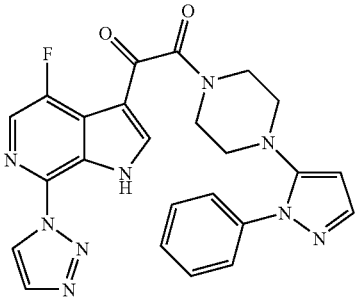 | A |
| G-10a | 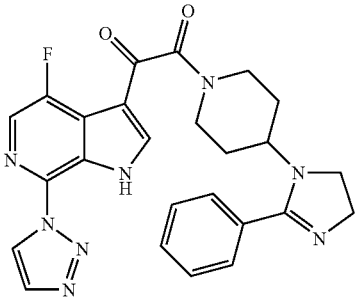 | B |
| G-10b | 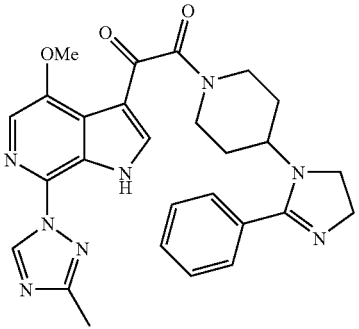 | B |

TABLE 4-continued

| Compd # | Structure | EC$_{50}$ Group from Table 3 |
|---|---|---|
| G-11a | 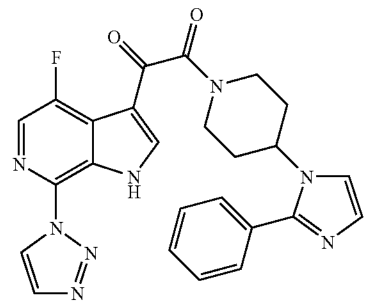 | A |
| G-11b | 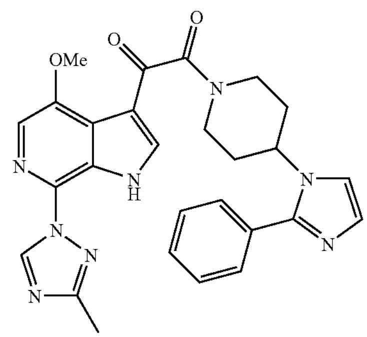 | B |
| G-12a | 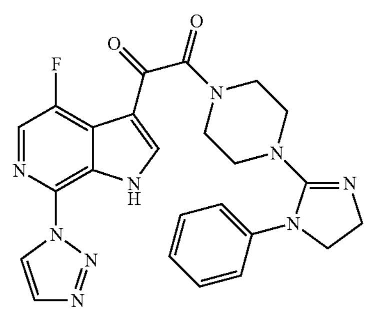 | A |
| G-12b | 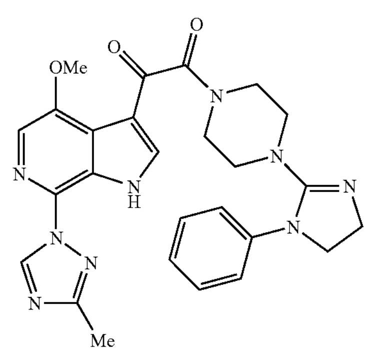 | A |

TABLE 4-continued
| Compd # | Structure | EC$_{50}$ Group from Table 3 |
|---|---|---|
| G-13a | 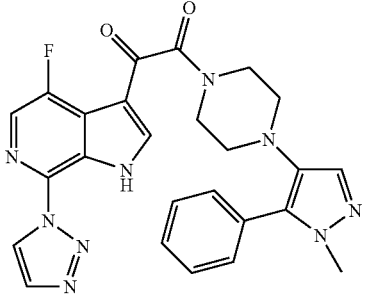 | A |
| G-13b | 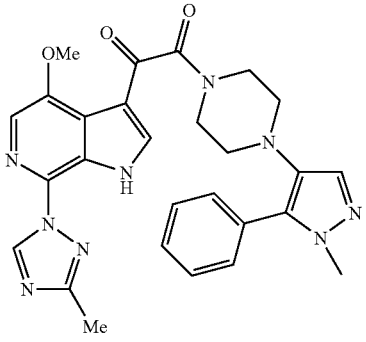 | A |
| G-14a | 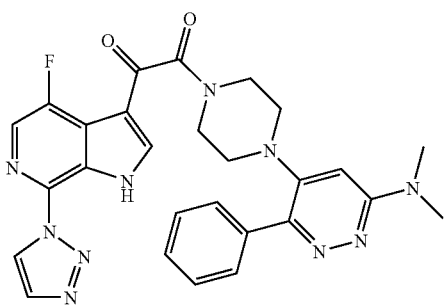 | A |
| G-14b | 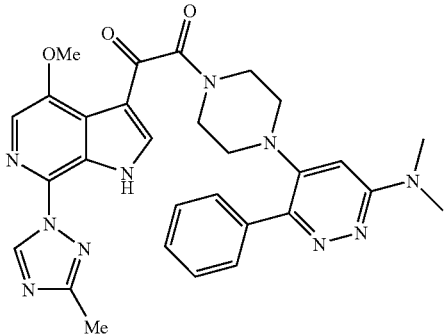 | A |

TABLE 4-continued

| Compd # | Structure | EC$_{50}$ Group from Table 3 |
|---|---|---|
| G-15a | 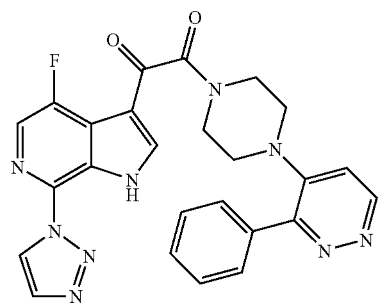 | A |
| G-15b | 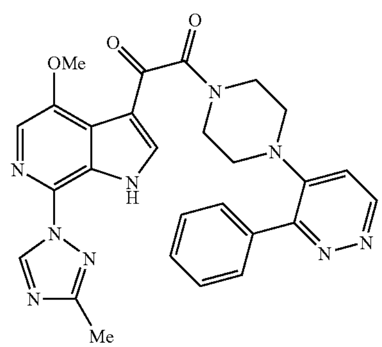 | A |
| G-16 | 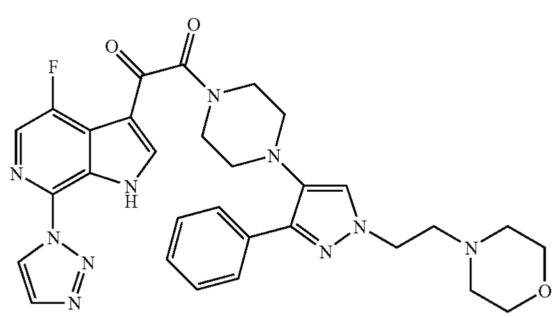 | A |
| G-17a | 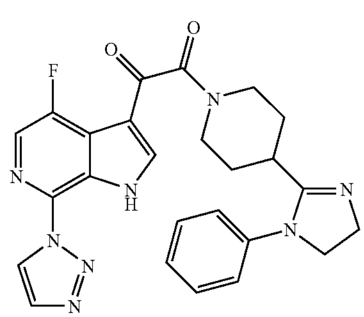 | B |

TABLE 4-continued

| Compd # | Structure | EC$_{50}$ Group from Table 3 |
|---|---|---|
| G-17b | 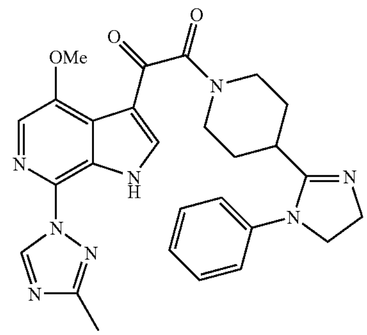 | A |
| G-18a | 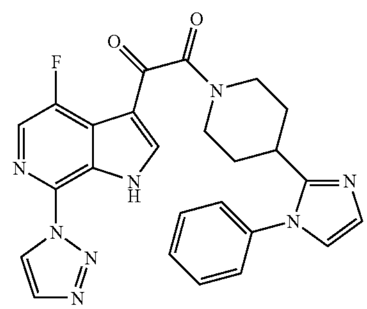 | A |
| G-18b | 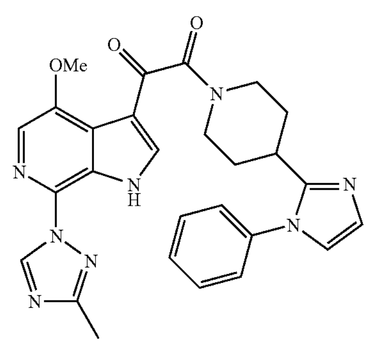 | A |
| G-19a | 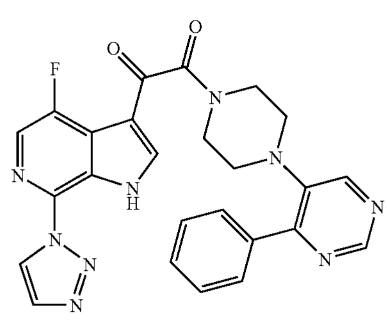 | A |

TABLE 4-continued

| Compd # | Structure | EC$_{50}$ Group from Table 3 |
|---|---|---|
| G-19b | 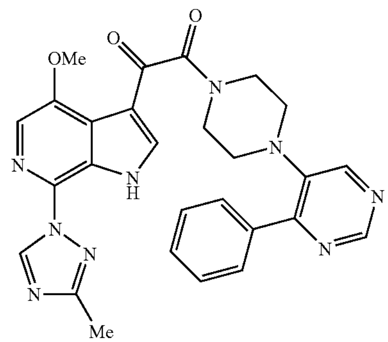 | A |
| G-20 | 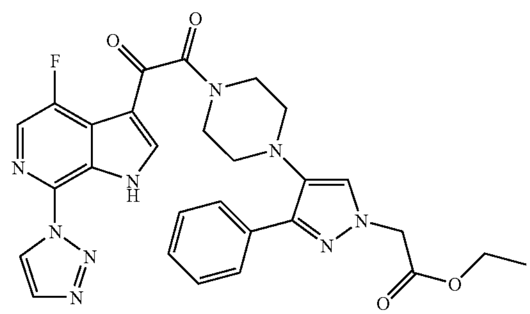 | A |
| G-21 | 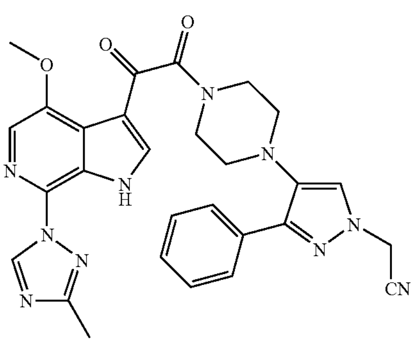 | A |
| G-22a | 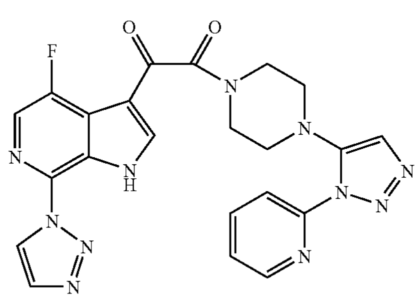 | A |

TABLE 4-continued
| Compd # | Structure | EC$_{50}$ Group from Table 3 |
|---|---|---|
| G-22b | 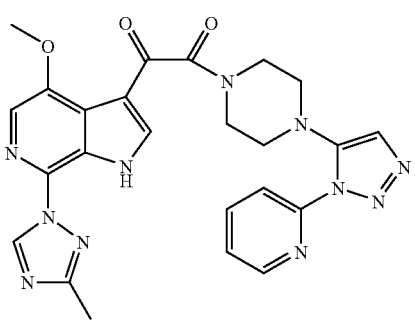 | A |
| G-23 | 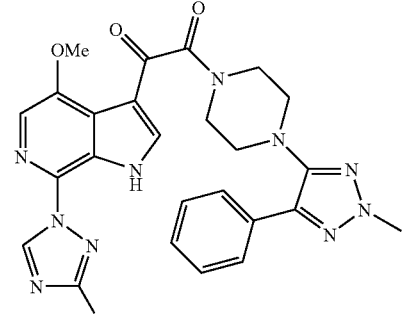 | A |
| G-24a | 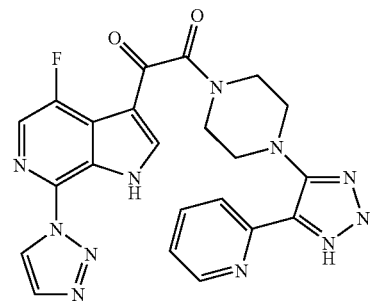 | A |
| G-24b | 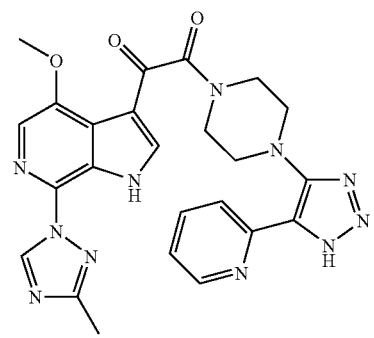 | A |

TABLE 4-continued
| Compd # | Structure | EC$_{50}$ Group from Table 3 |
|---|---|---|
| G-25a | 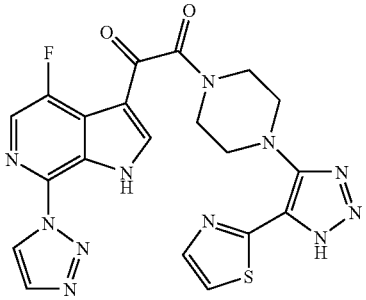 | A |
| G-25b | 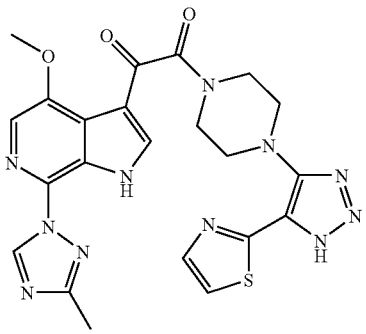 | A |
| G-26a | 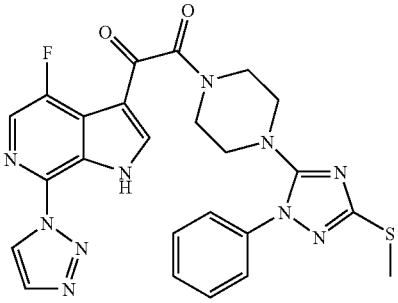 | A |
| G-26b | 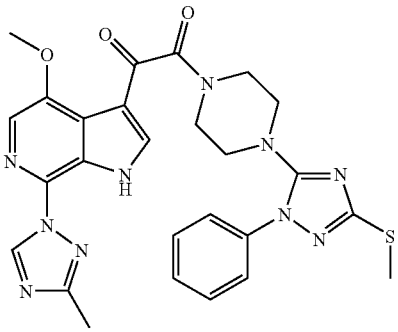 | A |

TABLE 4-continued

| Compd # | Structure | EC$_{50}$ Group from Table 3 |
|---|---|---|
| G-27a | 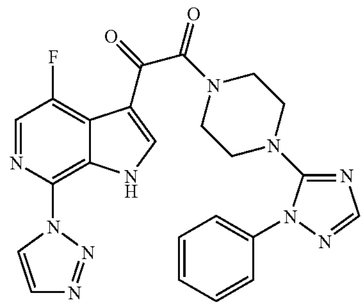 | A |
| G-27b | 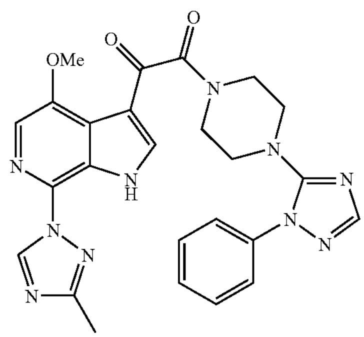 | A |
| G-28a | 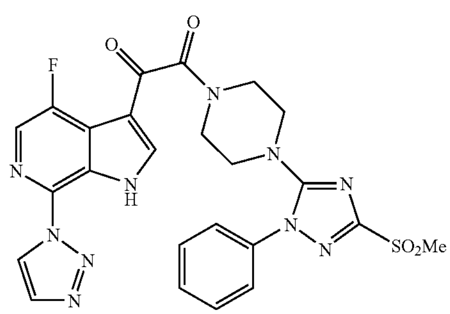 | A |
| G-28b | 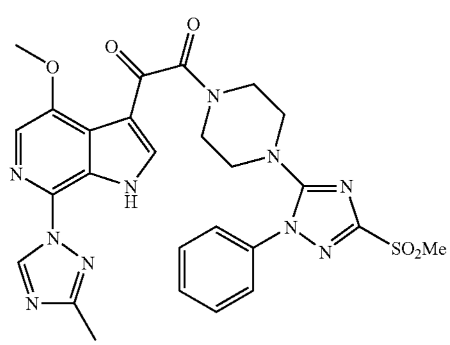 | A |

TABLE 4-continued

| Compd # | Structure | EC$_{50}$ Group from Table 3 |
|---|---|---|
| G-29a | 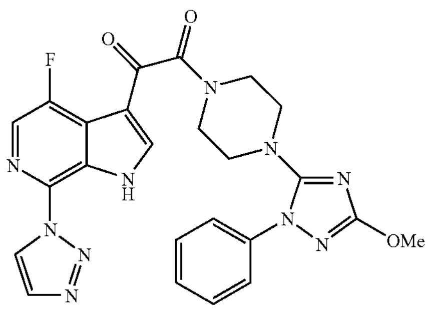 | A |
| G-29b | 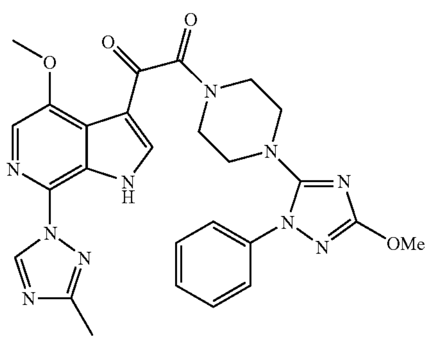 | A |
| G-30a | 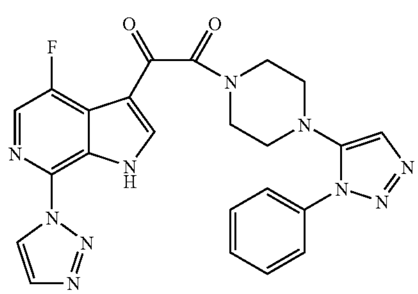 | A |
| G-30b | 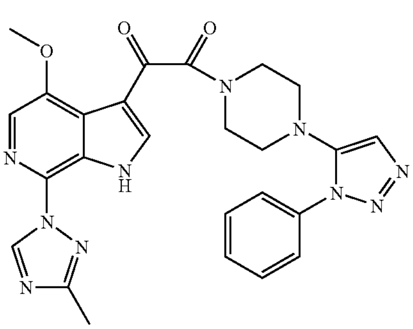 | A |

TABLE 4-continued

| Compd # | Structure | EC$_{50}$ Group from Table 3 |
|---|---|---|
| G-31 | 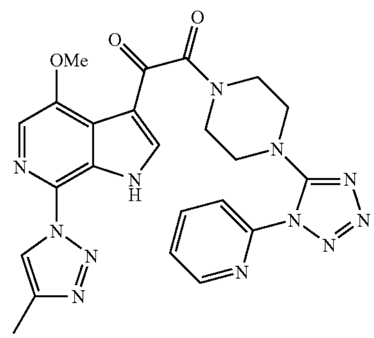 | A |
| G-32 | 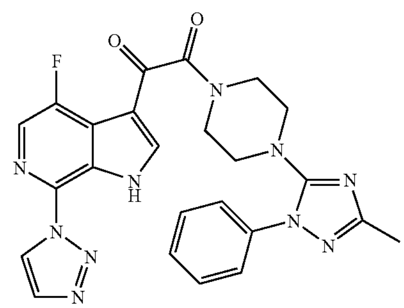 | A |
| H-1 | 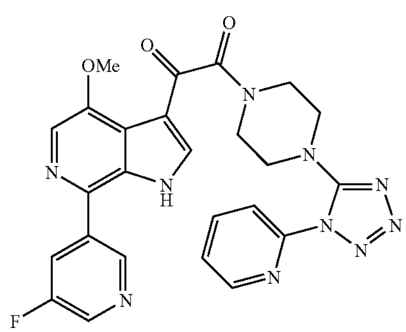 | A |
| H-2 | 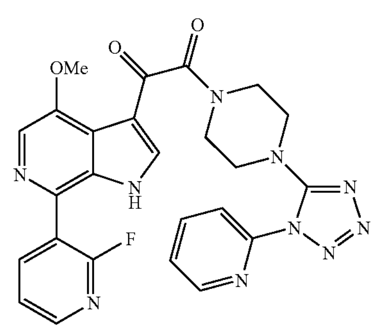 | A |

TABLE 4-continued

| Compd # | Structure | EC₅₀ Group from Table 3 |
|---|---|---|
| H-3 | 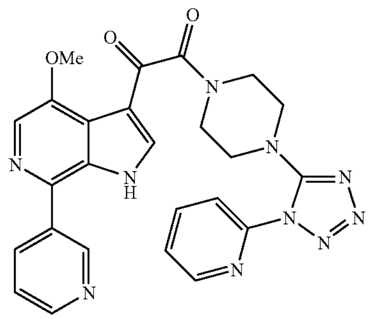 | A |
| H-4 | 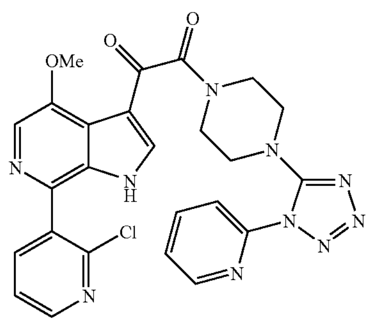 | A |
| H-5 | 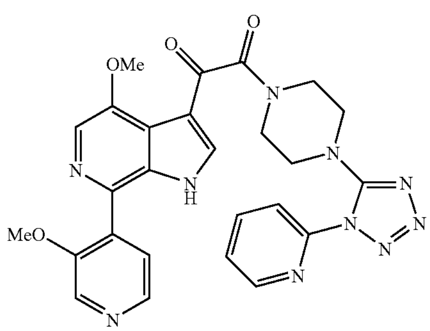 | A |
| H-6 | 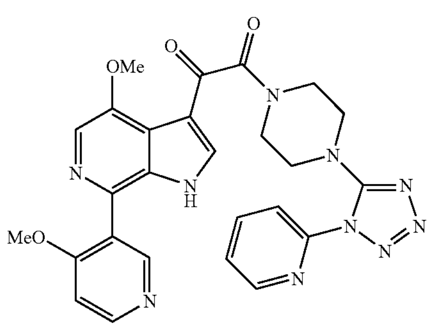 | A |

TABLE 4-continued

| Compd # | Structure | EC$_{50}$ Group from Table 3 |
|---|---|---|
| H-7 | 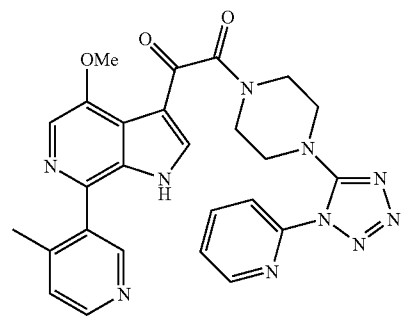 | A |
| H-8 | 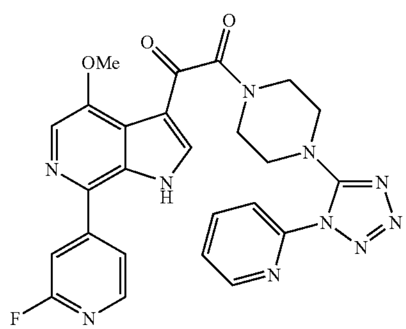 | A |
| H-9 | 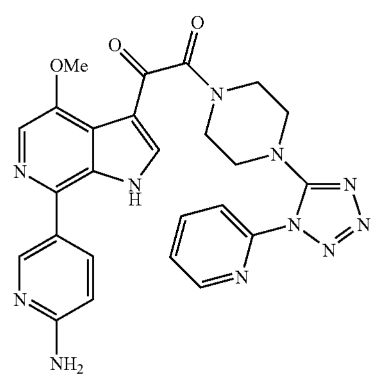 | A |
| H-10 | 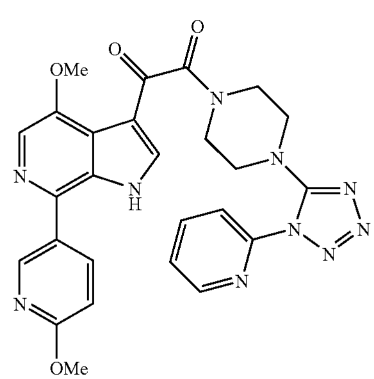 | A |

TABLE 4-continued

| Compd # | Structure | EC$_{50}$ Group from Table 3 |
|---|---|---|
| H-11 | 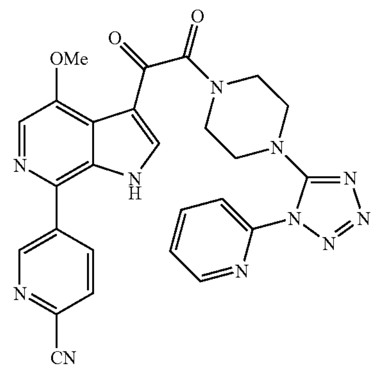 | A |
| H-12 | 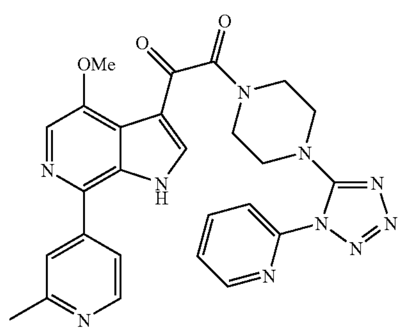 | A |
| H-13 | 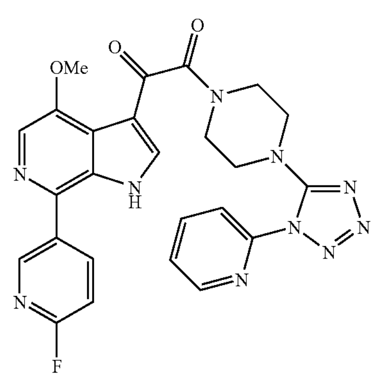 | A |

What is claimed is:
1. A compound which is selected from the group consisting of:
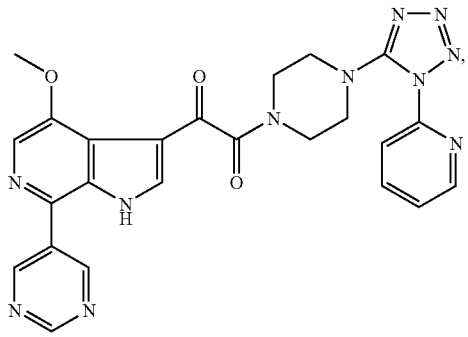
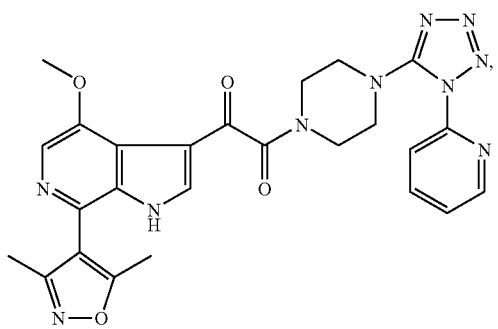
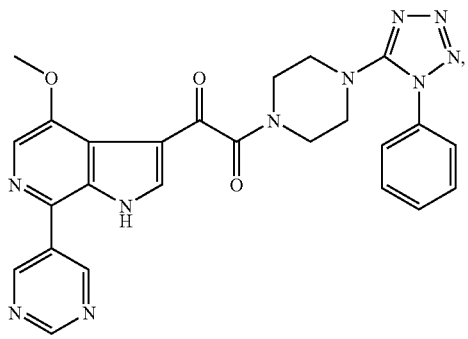
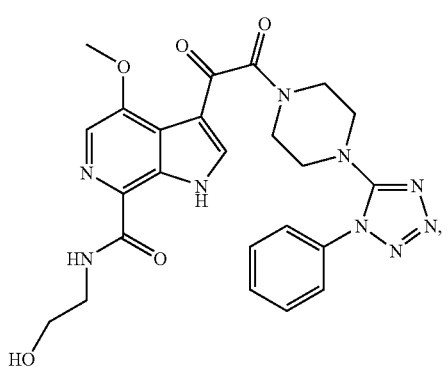
-continued
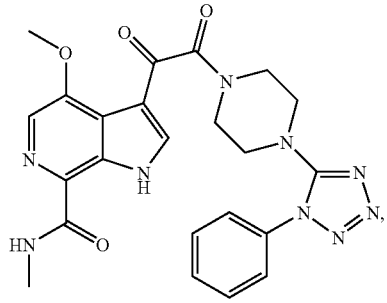
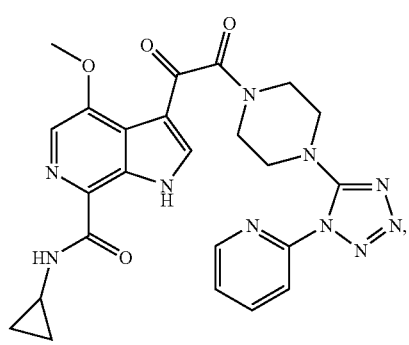
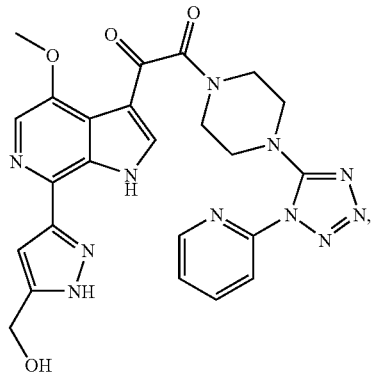
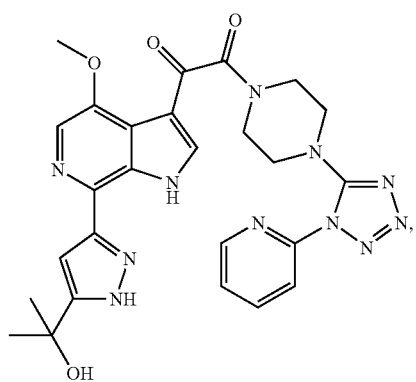

531
-continued
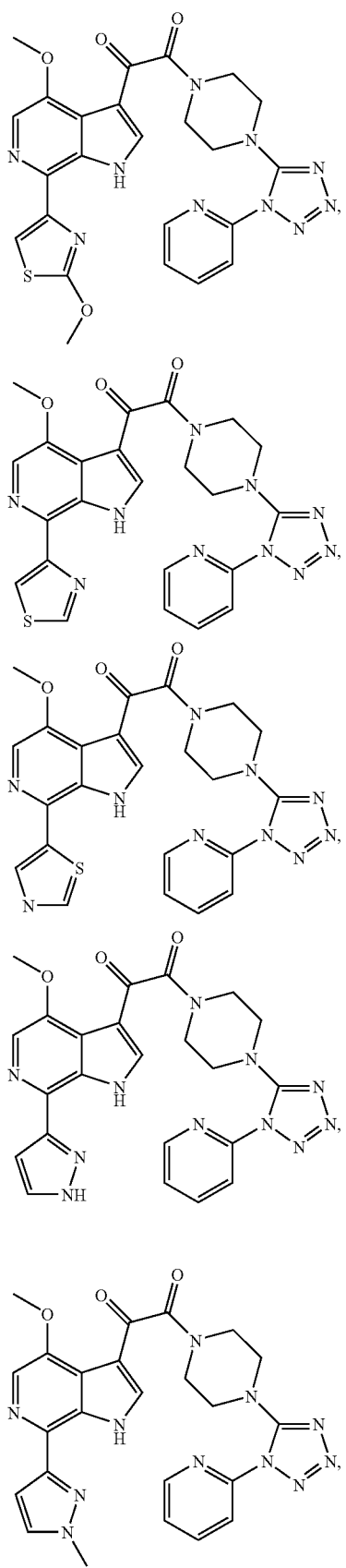
532
-continued
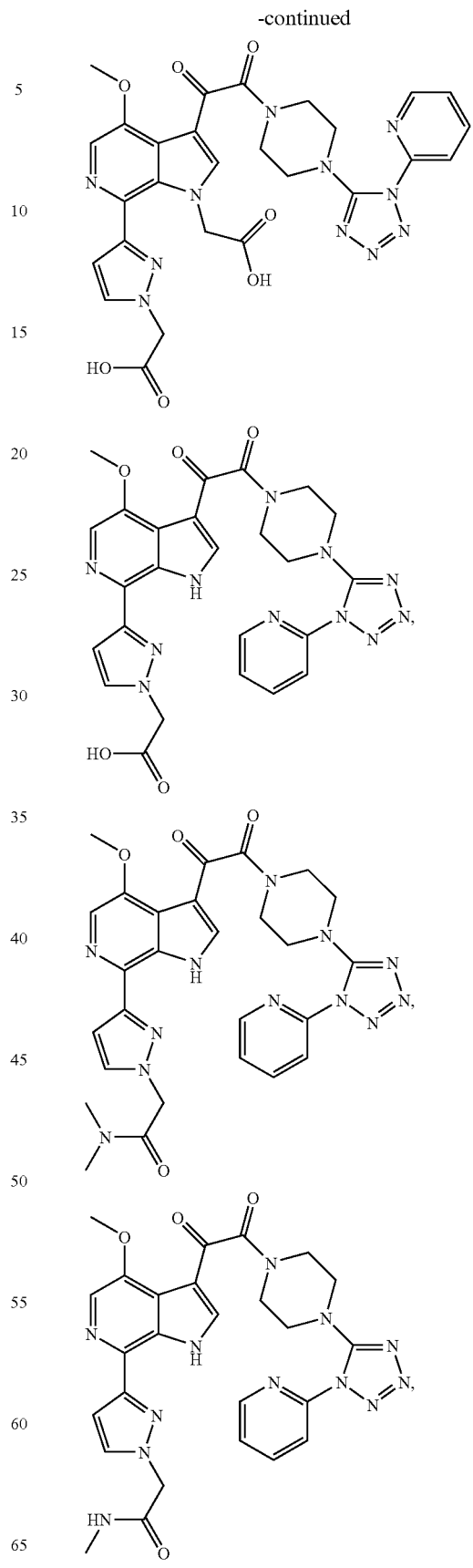

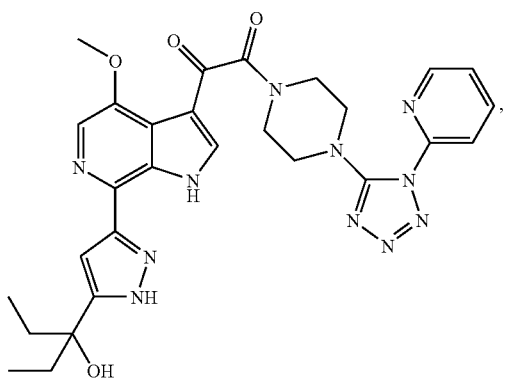
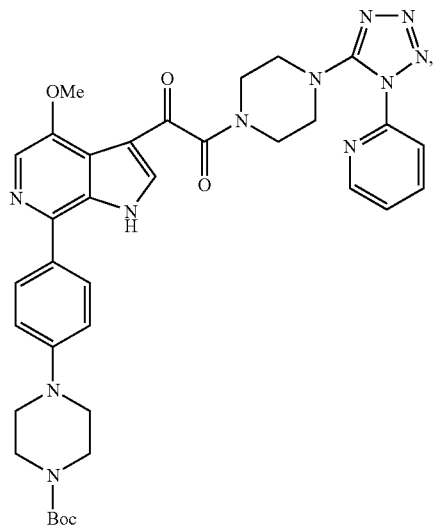
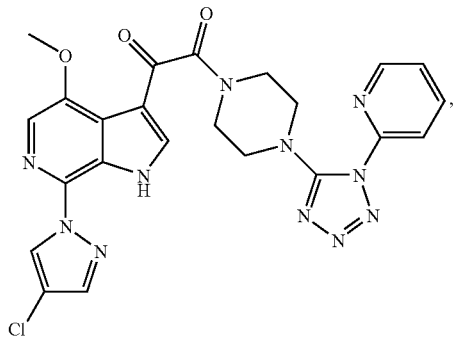
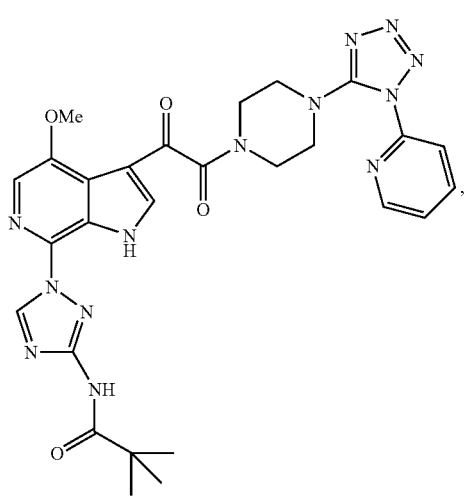
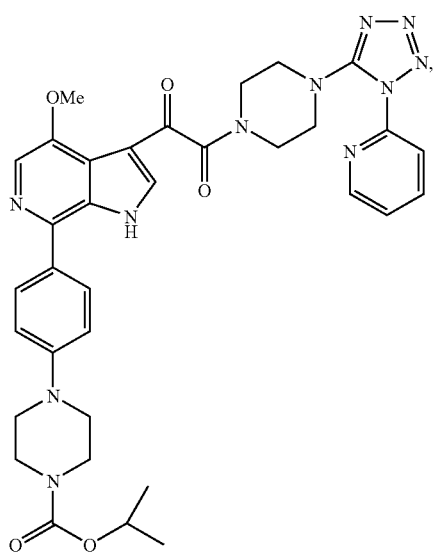

-continued
535
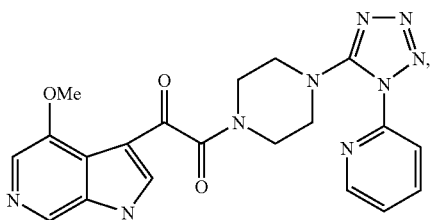
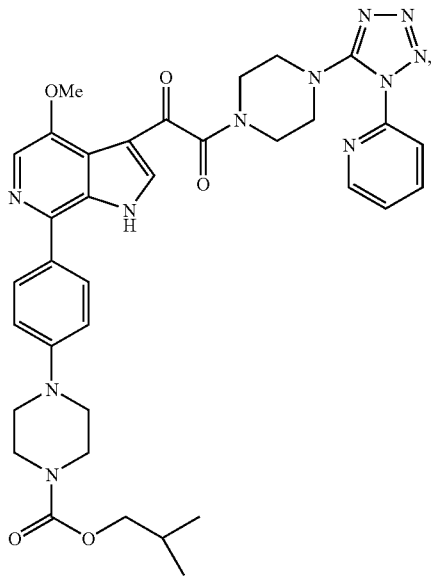
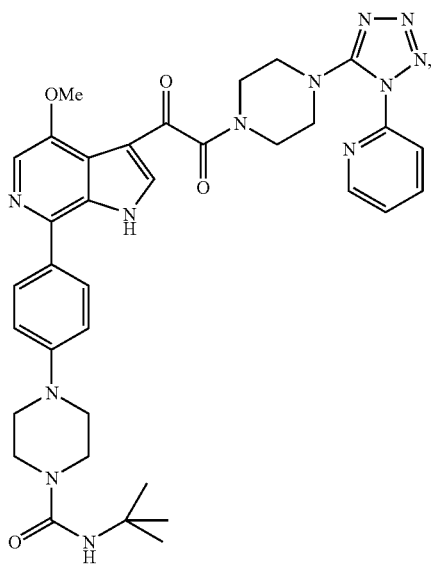
536
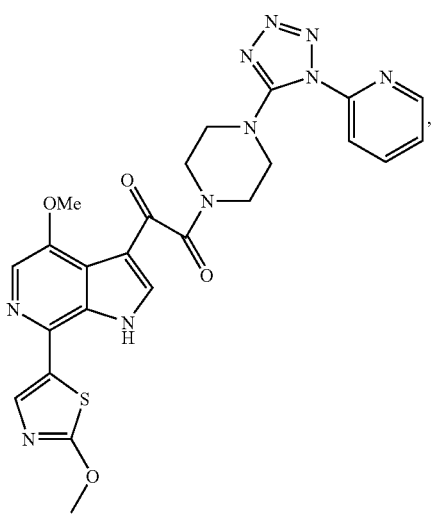
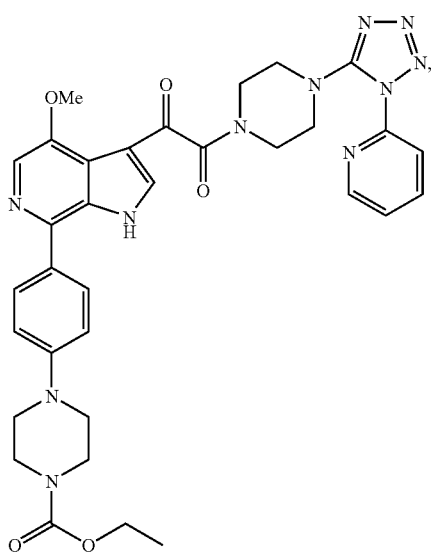
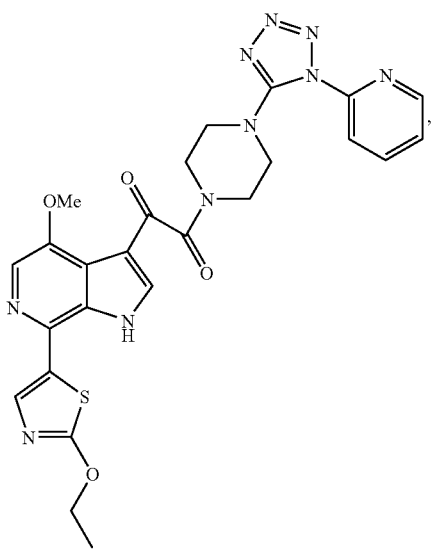

-continued
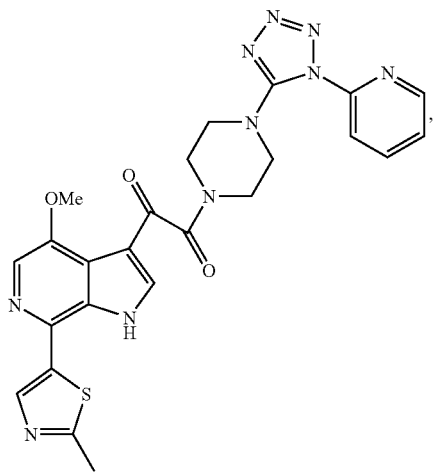
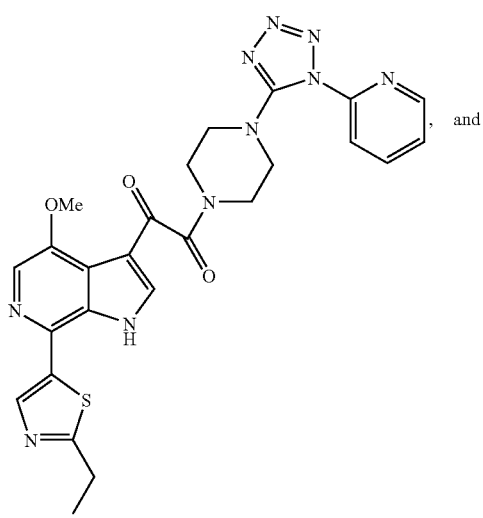
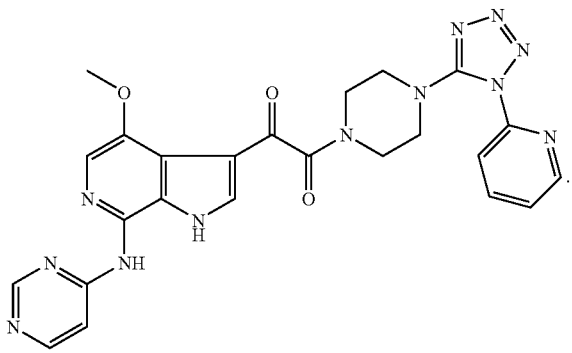
2. A compound which is selected from the group consisting of:
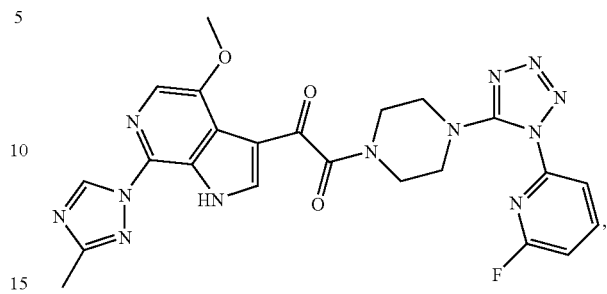
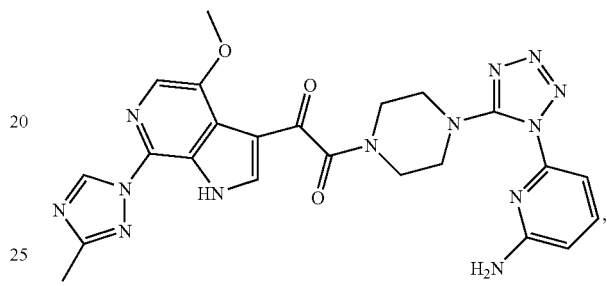
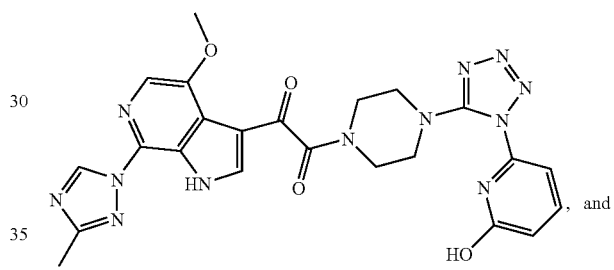
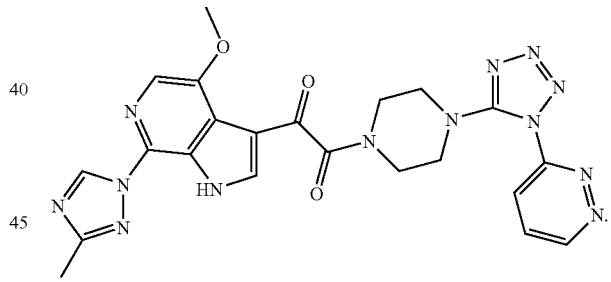
3. A compound which is selected from the group consisting of:
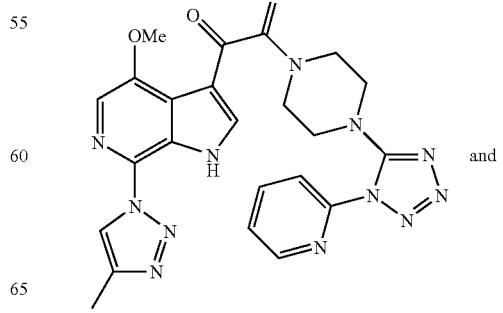

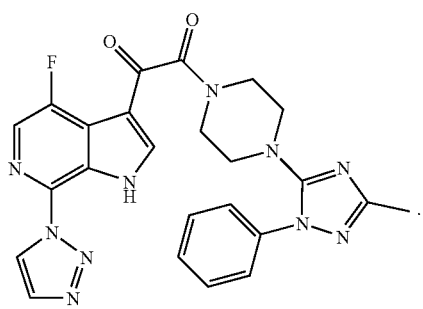
4. A compound which is selected from the group consisting of:
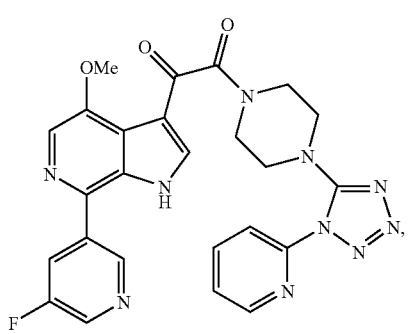
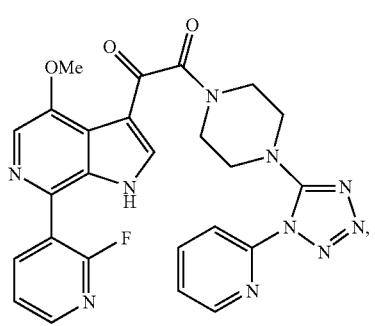
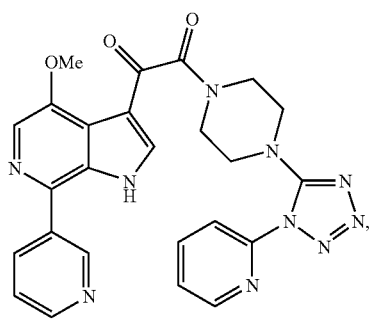
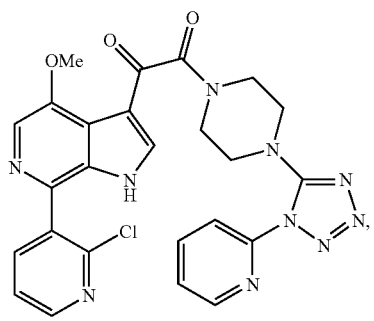
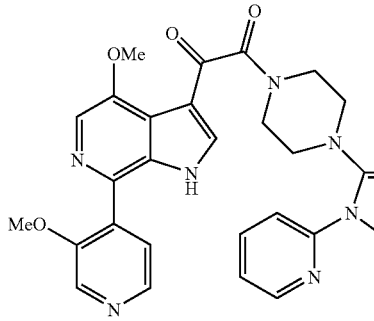
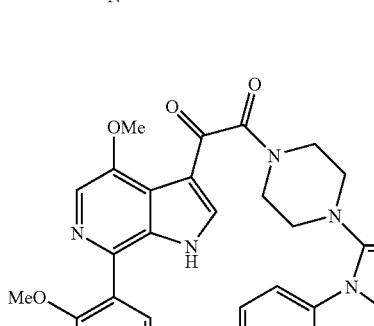
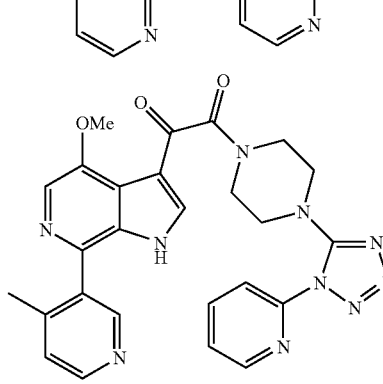
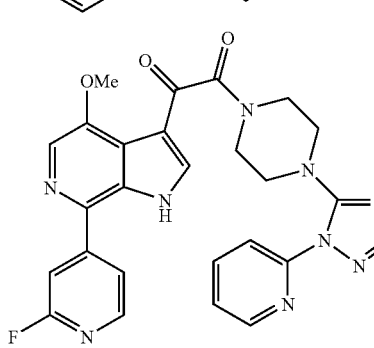

-continued

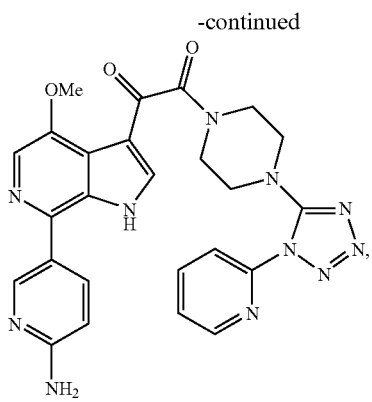

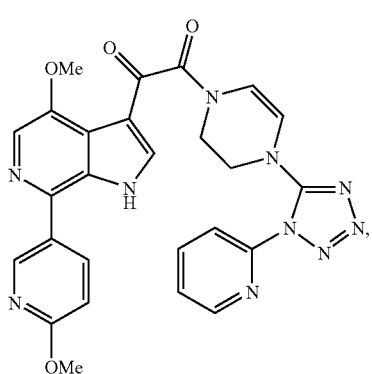

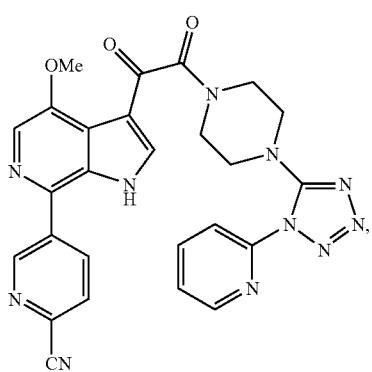

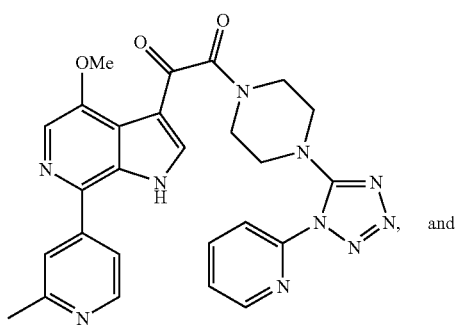 and

-continued

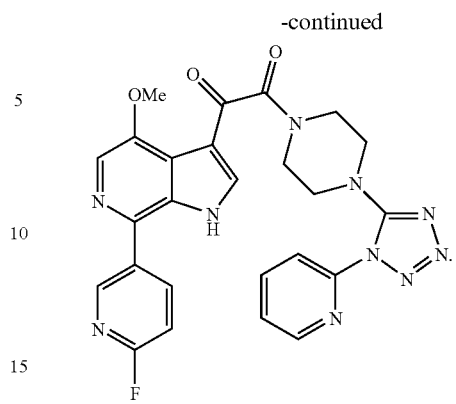

5. A pharmaceutical composition which comprises an antiviral effective amount of a compound of claim 1, or pharmaceutically acceptable salts thereof, and one or more pharmaceutically acceptable carriers, excipients or diluents.

6. A pharmaceutical composition which comprises an antiviral effective amount of a compound of claim 2, or pharmaceutically acceptable salts thereof, and one or more pharmaceutically acceptable carriers, excipients or diluents.

7. A pharmaceutical composition which comprises an antiviral effective amount of a compound of claim 3, or pharmaceutically acceptable salts thereof, and one or more pharmaceutically acceptable carriers, excipients or diluents.

8. A pharmaceutical composition which comprises an antiviral effective amount of a compound of claim 4, or pharmaceutically acceptable salts thereof, and one or more pharmaceutically acceptable carriers, excipients or diluents.

9. The composition of claim 5, further comprising a second compound having anti-HIV activity.

10. The composition of claim 6, further comprising a second compound having anti-HIV activity.

11. The composition of claim 7, further comprising a second compound having anti-HIV activity.

12. The composition of claim 8, further comprising a second compound having anti-HIV activity.

13. A method for treating a mammal infected with HIV virus comprising administering to said mammal an antiviral effective amount of a compound of claim 1, or pharmaceutically acceptable salts thereof, and one or more pharmaceutically acceptable carriers, excipients or diluents.

14. A method for treating a mammal infected with HIV virus comprising administering to said mammal an antiviral effective amount of a compound of claim 2, or pharmaceutically acceptable salts thereof, and one or more pharmaceutically acceptable carriers, excipients or diluents.

15. A method for treating a mammal infected with HIV virus comprising administering to said mammal an antiviral effective amount of a compound of claim 3, or pharmaceutically acceptable salts thereof, and one or more pharmaceutically acceptable carriers, excipients or diluents.

16. A method for treating a mammal infected with HIV virus comprising administering to said mammal an antiviral effective amount of a compound of claim 4, or pharmaceutically acceptable salts thereof, and one or more pharmaceutically acceptable carriers, excipients or diluents.

17. The method of claim 13, comprising administering to said mammal an antiviral effective amount of said compound in combination with an antiviral effective amount of an AIDS treatment agent selected from the group consisting of: an AIDS antiviral agent; an anti-infective agent; an immunomodulator; and an HIV entry inhibitor.

18. The method of claim 14, comprising administering to said mammal an antiviral effective amount of said compound in combination with an antiviral effective amount of an AIDS treatment agent selected from the group consisting of: an AIDS antiviral agent; an anti-infective agent; an immunomodulator; and an HIV entry inhibitor.

19. The method of claim 15, comprising administering to said mammal an antiviral effective amount of said compound in combination with an antiviral effective amount of an AIDS treatment agent selected from the group consisting of: an AIDS antiviral agent; an anti-infective agent; an immunomodulator; and an HIV entry inhibitor.

20. The method of claim 16, comprising administering to said mammal an antiviral effective amount of said compound in combination with an antiviral effective amount of an AIDS treatment agent selected from the group consisting of: an AIDS antiviral agent; an anti-infective agent; an immunomodulator; and an HIV entry inhibitor.

21. The compound of claim 1, wherein said compound is selected from the group

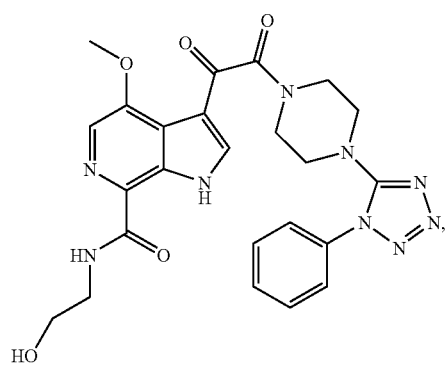

-continued

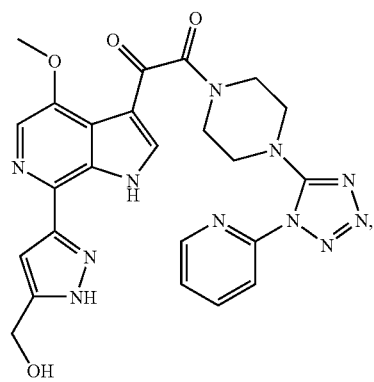

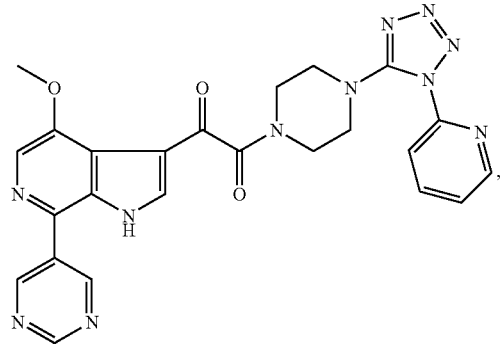

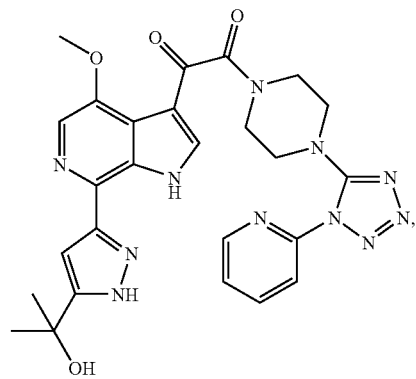

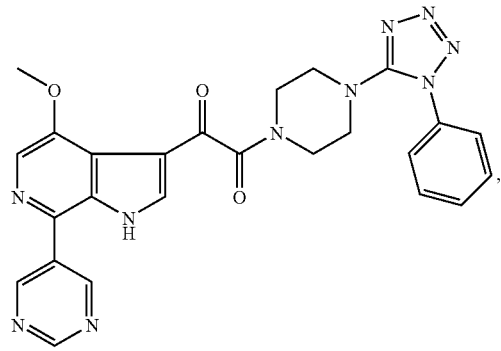

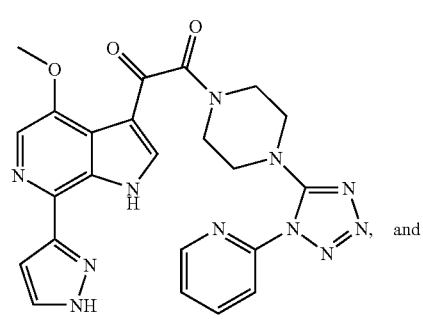

-continued
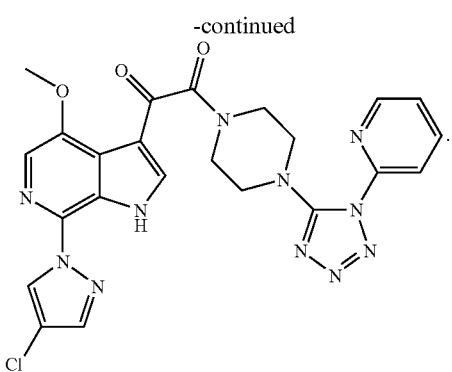
22. The compound of claim 2, wherein said compound is
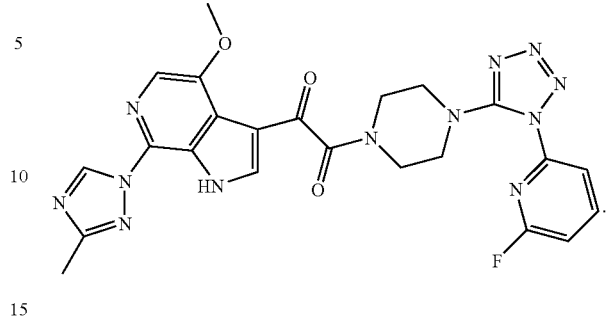
* * * * *